US011028051B2

(12) United States Patent
Guy et al.

(10) Patent No.: US 11,028,051 B2
(45) Date of Patent: Jun. 8, 2021

(54) TETRAHYDROQUINOLINE-BASED BROMODOMAIN INHIBITORS

(71) Applicant: St. Jude Children's Research Hospital, Memphis, TN (US)

(72) Inventors: R. Kip Guy, Lexington, KY (US); P. Jake Slavish, Memphis, TN (US); William Robert Shadrick, Collierville, TN (US); Brandon M. Young, Germantown, TN (US); Vincent A. Boyd, Tyler, TX (US); Nagakumar Bharatham, Bangalore (IN); Jeanine E. Price, Germantown, TN (US); Anang Shelat, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 16/468,657

(22) PCT Filed: Dec. 12, 2017

(86) PCT No.: PCT/US2017/065705
§ 371 (c)(1),
(2) Date: Jun. 11, 2019

(87) PCT Pub. No.: WO2018/111805
PCT Pub. Date: Jun. 21, 2018

(65) Prior Publication Data
US 2020/0079739 A1 Mar. 12, 2020

Related U.S. Application Data

(60) Provisional application No. 62/433,597, filed on Dec. 13, 2016.

(51) Int. Cl.
*C07D 215/42* (2006.01)
*C07D 215/44* (2006.01)
*C07D 215/46* (2006.01)
*C07D 401/10* (2006.01)
*C07D 401/12* (2006.01)
*C07D 405/10* (2006.01)
*C07D 405/12* (2006.01)
*C07D 409/10* (2006.01)
*C07D 413/12* (2006.01)

(52) U.S. Cl.
CPC ......... *C07D 215/42* (2013.01); *C07D 215/44* (2013.01); *C07D 215/46* (2013.01); *C07D 401/10* (2013.01); *C07D 401/12* (2013.01); *C07D 405/10* (2013.01); *C07D 405/12* (2013.01); *C07D 409/10* (2013.01); *C07D 413/12* (2013.01)

(58) Field of Classification Search
CPC .. C07D 215/42; C07D 215/44; C07D 215/46; C07D 401/10; C07D 401/12; C07D 405/10; C07D 405/12; C07D 409/10; C07D 413/12
See application file for complete search history.

(56) References Cited

U.S. PATENT DOCUMENTS

| | | | | |
|---|---|---|---|---|
| 6,235,771 B1 * | 5/2001 | Shiraishi | ............ | A61K 31/7068 514/431 |
| 6,949,575 B2 * | 9/2005 | Barta | ...................... | A61P 25/16 514/381 |
| 7,030,246 B2 * | 4/2006 | Bladh | ..................... | A61P 11/00 546/159 |
| 7,109,339 B2 * | 9/2006 | Lee | ......................... | A61P 25/00 546/86 |
| 8,580,957 B2 * | 11/2013 | Demont | ............... | C07D 215/44 544/128 |
| 8,697,725 B2 * | 4/2014 | Demont | ................... | A61P 37/02 514/312 |
| 8,993,554 B2 * | 3/2015 | Amans | ................. | C07D 401/04 514/210.18 |
| 9,029,395 B2 * | 5/2015 | Amans | .................... | A61P 37/02 514/313 |
| 9,315,487 B2 * | 4/2016 | Amans | ..................... | A61P 37/06 |
| 2005/0228016 A1 * | 10/2005 | Michelotti | .............. | A61P 35/00 514/313 |
| 2014/0031336 A1 | 1/2014 | Amans et al. | | |
| 2014/0371206 A1 | 12/2014 | Albrecht et al. | | |
| 2015/0148344 A1 | 5/2015 | Babaoglu et al. | | |
| 2016/0022684 A1 * | 1/2016 | Kuo | .................... | A61K 31/4745 424/133.1 |
| 2016/0256448 A1 | 9/2016 | Bair et al. | | |

FOREIGN PATENT DOCUMENTS

WO WO-2016038120 A1 * 3/2016 ........... C07D 405/14
WO WO-2018/111805 A1 6/2018

OTHER PUBLICATIONS

Atkinson; Med. Chem. Commun., 2014,5, 342-351. DOI: 10.1039/C3MD00285C (Year: 2014).*
Gosmini; J. Med. Chem. 2014, 57, 19, 8111-8131. DOI:10.1021/jm5010539 (Year: 2014).*
Haggarty; Chemistry and Biology 2003, 10, 1267-1279. DOI: 10.1016/j.chembiol.2003.11.014 (Year: 2003).*
National Center for Biotechnology Information. PubChem Database. SCHEMBL17627191, Source=SureChEMBL, SID=312986693, https://pubchem.ncbi.nlm.nih.gov/substance/312986693 Available Apr. 9, 2016 (accessed on May 27, 2020) (Year: 2016).*

(Continued)

*Primary Examiner* — Daniel R Carcanague
(74) *Attorney, Agent, or Firm* — Ballard Spahr LLP

(57) ABSTRACT

In one aspect, compounds and compositions that modulate a bromodomain and methods of making and using same are disclosed. The disclosed compounds and compositions can be useful for disorders associated with inhibition of a bromodomain such as, for example, cancer. This abstract is intended as a scanning tool for purposes of searching in the particular art and is not intended to be limiting of the present invention.

16 Claims, 7 Drawing Sheets

(56) References Cited

OTHER PUBLICATIONS

National Center for Biotechnology Information. PubChem Database. SID 123073369, Source=Thomson Pharma, SID=123073369, https://pubchem.ncbi.nlm.nih.gov/substance/123073369 Available Jun. 13, 2011 (accessed on May 27, 2020) (Year: 2011).*
Miyaura; Chem. Rev. 1995, 95, 7, 2457-2483. (Year: 1995).*
Ruiz-Castillo; Chem. Rev. 2016, 116, 19, 12564-12649. (Year: 2016).*
Slavish; Cancer Res 2020, 80, 3507-3518. (Year: 2020).*
International Search Report and Written Opinion dated Feb. 12, 2018 by the International Searching Authority for International Application No. PCT/US2017/065705, filed on Dec. 12, 2017 and published as WO 2018/111805 on Jun. 21, 2018 (Applicant—St. Jude Children's Research Hospital) (13 Pages).
International Preliminary Report on Patentability dated Jun. 18, 2019 by the International Searching Authority for International Application No. PCT/US2017/065705, filed on Dec. 12, 2017 and published as WO 2018/111805 on Jun. 21, 2018 (Applicant—St. Jude Children's Research Hospital) (12 Pages).

* cited by examiner

TETRAHYDROQUINOLINE-BASED BROMODOMAIN INHIBITORS

CROSS-REFERENCE TO RELATED APPLICATIONS

This is a U.S. National Phase Application of International Application No. PCT/US2017/065705, filed on Dec. 12, 2017, which claims the benefit of U.S. Provisional Application No. 62/433,597, filed on Dec. 13, 2016, the contents of which are incorporated herein by reference in their entireties.

BACKGROUND

Regulation of transcription in eukaryotes is tightly regulated by post-translational chemical modification of histones, specifically in the tail region (Verdin and Ott (2015) *Nat. Rev. Mol. Cell Biol.* 16: 258; Rothbart and Strahl (2014) *Biochimica et biophysica acta* 1839: 627). One critical modification is ξ-acetylation of lysine residues, which is a hallmark for transcriptional activation (Marushige, K. (1976) *Proceedings of the National Academy of Sciences of the United States of America* 73: 3937; Marmorstein, R. (2001) *Nature Reviews Molecular Cell Biology* 2: 422). Control of the lysine acetylation (Kac) state of histone tails is governed by histone acetyltransferases (HATs) and histone deacetylases (HDACs), which are tightly regulated (Johnstone, R. W. (2002) *Nature Reviews Drug Discovery* 1: 287). Upon acetylation, activated histone tails can be "read" by bromodomains (BRDs) (Wolffe and Hayes (1999) *Nucleic Acids Research* 27: 711; Zeng and Zhou (2002) *FEBS Letters* 513: 124), which act as adaptors to transcriptional factors and/or other non-histone partner(s). These complexes are integral to gene transcription and regulation (Sanchez et al. (2014) *Biochimica et Biophysica Acta. Gene Regulatory Mechanisms* 1839: 676).

All BRDs contain a left-handed bundle of four highly conserved alpha-helices (named αZ, αA, αB and αC) that are tethered together by two loop regions (ZA and BC) of variable length and sequence. The key interactions of the Kac-BRD binding event are consistent in all BRDs: the carbonyl of the acetyl group interacts directly with a conserved Asp residue and indirectly with a conserved Tyr residue through a water-mediated interaction. In a highly conserved architecture, four highly conserved water molecules form the base of the BRD binding pocket, providing a network of hydrogen bonds that afford additional stability to the BRD-histone complex (Filippakopoulos and Knapp (2014) *Nature Reviews Drug Discovery* 13: 337). Two subsets of BRDs, the BET family and the CREBBP bromodomain, utilize two additional bound water molecules, located along the ZA channel. Variations in the utilization of organized water molecules among BRD's provides a unique opportunity to increase the potency of ligands binding to BET/CREBBP, and to fine-tune the selectivity of potential BET inhibitors (Romero et al. (2016) *J. Med. Chem.* 59: 1271).

The BET family (bromodomain and extra-terminal domain), consisting of BRD2, BRD3, BRD4, and BRD6/BRDT, has received the most attention in the research community due to their reported involvement in the progression of various diseases (including cancer) (Wu et al. (2013) *Journal of Biological Chemistry* 288: 36094; Belkina and Denis (2012) *Nature Reviews Cancer* 12: 465; Xu and Shi (2011) *Zhonghua Fuchanke Zazhi* 46: 636). BET family members are distinguished from other BRDs by the presence of two bromodomains, originally referred to as N-terminal and C-terminal domains, but now commonly referred to as BD1 and BD2, respectively (Filippakopoulos et al. (2010) *Nature* (London. United Kingdom) 468: 1067). All BET members function as transcription factors. BRD2 and BRD4 regulate transcriptional elongation by recruiting the positive transcription elongation factor B (P-TEFb) complex, ultimately resulting in the activation of RNA polymerase II (Muller et al. (2011) *Expert Reviews in Molecular Medicine* 13: e29/1). The BET-BD1 domains are highly homologous (65-90%), particularly in the binding pocket, and hence recognize similar Kac patterns. Homology between BET BD1 and BD2 is much lower (<50%), although there is a high degree of residue conservation in the binding pockets of all BET BD's. Both BRD2-BD1 and BRD4-BD1 have minimal affinity towards histone 3 (H3) acetylated lysines, but high affinity for acetylated lysines on histone 4 (H4), specifically H4K5ac, H4K12ac, H4K14ac, and H4K5ac/K8ac. BET-BD2 domains also share sequence identity with each other. As opposed to BRD4-BD1, BRD4-BD2 is currently believed to have minimal affinity for any histone acetylated lysines and appears to be responsible for the recruitment of non-histone proteins and/or transcription factors (e.g., Twist) to the chromatin bound complex, which is anchored by BD1 (Shi et al. (2014) *Cancer Cell* 25: 210). BRD2-BD2 has been reported to interact with H4 acetylated lysines (H4K5ac, H4K12ac and H4K5ac/K12ac) (Umehara et al. (2010) *FEBS Letters* 584: 3901).

Given the high degree of structural and sequence similarities between the BET binding domains, it is not surprising that first generation BET-selective inhibitors, e.g., (+)-JQ1 (Filippakopoulos et al. (2010) *Nature* (London. United Kingdom) 468: 1067) and GSK525762A (Nicodeme et al. (2010) *Nature* 468: 1119), are pan-BET inhibitors. (+)-JQ1 (Filippakopoulos et al. (2010) *Nature* (London. United Kingdom) 468: 1067) has been shown to reduce oncogenic protein expression (e.g. c-Myc) (Delmore et al. (2011) Cell (Cambridge, Mass., United States) 146: 904), which leads to diminished cellular proliferation in multiple cancer cell lines (Xu and Shi (2011) *Zhonghua Fuchanke Zazhi* 46: 636; Shimamura et al. (2013) *Clinical Cancer Research* 19: 6183; Puissant et al. (2013) *Cancer Discovery* 3: 308; Pastori et al. (2014) *Epigenetics* 9: 611; Ott et al. (2012) *Blood* 120: 2843; Henssen et al. (2013) *Oncotarget* 4: 2080; Bandopadhayay et al. (2014) *Clinical Cancer Research* 20: 912; Cheng et al. (2013) *Clinical Cancer Research* 19: 1748; Fowler et al. (2014) *PLoS One* 9: e87003/1; Mertz et al. (2011) *Proceedings of the National Academy of Sciences of the United States of America* 108: 16669; Roderick et al. (2014) *Blood* 123: 1040; Wyce et al. (2013) *Oncotarget* 4: 2419). Studies with GSK525762A have revealed that pan-BET inhibition can block the transcription of key genes associated with inflammation (Nicodeme et al. (2010) *Nature* 468: 1119). All biochemical data reported for GSK525762A used full length bromodomain proteins (BRD2, 3, and 4); hence, BET subfamily domain specificity is unknown. Other BET inhibitors have also been reported (Gamier et al. (2014) *Expert Opinion on Therapeutic Patents* 24: 185; Gehling et al. (2013) *ACS Medicinal Chemistry Letters* 4: 835; Hewings et al. (2012) *J. Med. Chem.* 55: 9393; Chung et al. (2011) *J. Med. Chem.* 54: 3827; Mirguet et al. (2013) *J. Med. Chem.* 56: 7501; Fedorov et al. (2014) *J. Med. Chem.* 57: 462) and are being examined for future applications in a range of diseases and disorders including atherosclerosis (Spiltoir et al. (2013) *Journal of Molecular and Cellular Cardiology* 63: 175), HIV (Boehm et al. (2013) *Cell Cycle* 12: 452), HPV (McBride and Jang (2013) *Viruses* 5: 1374), HTLV (Wu et al. (2013) *Journal of Biological Chemistry* 288: 36094), Type 2 diabetes (Wang et al. (2010) *Biochemical Journal* 425: 71), and obesity (Belkina and Denis (2012) *Nature Reviews Cancer* 12: 465; Wang et al. (2010) *Biochemical Journal* 425: 71). Inhibition of Brd6/BrdT is considered a target for male contraception (Matzuk et al. (2012) *Cell* (Cambridge, Mass., United States) 150: 673).

While pan-BET inhibitors have been useful therapeutic leads and facilitated understanding of BET function, the lack of family member selective compounds convolutes conclusions drawn from studies with these inhibitors and clouds understanding of the function of individual BET family members. In addition, the lack of selectivity within the BET family could result in off-target effects and/or safety concerns as these compounds advance in clinical studies for specific indications. A similar situation occurred with HDAC inhibitors; while initial leads have shown promising antitumor responses in early-phase clinical trials, undesired side effects attributed to poor selectivity between the HDAC isoforms halted these initial studies (Bolden et al. (2006) *Nature Reviews Drug Discovery* 5: 769). Accordingly, there remains a need for BET-selective inhibitors and methods of making and using same.

SUMMARY

In accordance with the purpose(s) of the invention, as embodied and broadly described herein, the invention, in one aspect, relates to compositions and methods for use in the prevention and treatment of disorders associated with inhibition of a bromodomain such as, for example, cancer, an estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis. In a further aspect, the invention relates to compositions and methods for use as a male contraceptive. In a still further aspect, the invention relates to compositions and methods for use in stem cell differentiation.

Disclosed are compounds having a structure represented by a formula:

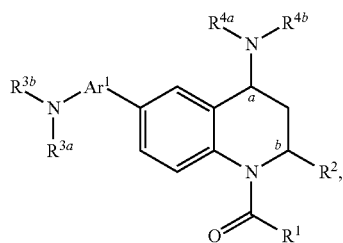

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, $Cy^2$, —(C1-C6 alkyl)$Cy^2$, —(C1-C6 alkyl)$Ar^4$, —C(O)(C1-C6 alkyl), —C(O)(CH$_2$)$_m$Cy$^2$, —C(O)(CH$_2$)$_m$Ar$^4$, —C(O)(C1-C4 alkyl)CCH, —CO$_2$(C1-C6 alkyl), and amine protecting group; wherein m, when present, is selected from 0, 1, 2, and 3; wherein $Cy^2$, when present, is selected from C3-C6 cycloalkyl and C3-C6 heterocycloalkyl and is substituted with 0-4 non-hydrogen groups independently selected from halogen, —OH, —CN, C1-C4 alkyl, C1-C4 alkoxy, and C1-C4 haloalkyl; wherein $Ar^4$, when present, is selected from aryl and heteroaryl and is substituted with 0-4 non-hydrogen groups independently selected from halogen, —OH, —CN, C1-C4 alkyl, C1-C4 alkoxy, and C1-C4 haloalkyl; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein $Ar^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group and wherein $R^{4b}$ is selected from C4-C8 alkyl, —(CH$_2$)$_n$Cy$^1$, —(CH$_2$)$_o$Ar$^2$, and —COR$^6$; wherein each of n and o, when present, is selected from 0, 1, 2, and 3; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —(CH$_2$)$_q$NR$^{22a}$R$^{22b}$, —SO$_2$NR$^{22a}$R$^{22b}$, —NR$^{23}$C(O)R$^{24}$, —NR$^{23}$(CH$_2$)$_q$(C3-C6 cycloalkyl), —NR$^{23}$(CH$_2$)$_q$(heterocycloalkyl), and 3- to 5-membered heterocycloalkyl; wherein q, when present, is selected from 0, 1, 2, 3, and 4; wherein each occurrence of $R^{21}$, when present, is independently selected from hydrogen, C1-C6 alkyl, C1-C6 hydroxyalkyl, C3-C6 cycloalkyl, C3-C6 heterocycloalkyl, —COR$^{30}$, —(C1-C4 alkyl)OC(O)(C1-C4 alkyl), and —(C1-C6 alkyl)NHC(O)A; wherein A has a structure:

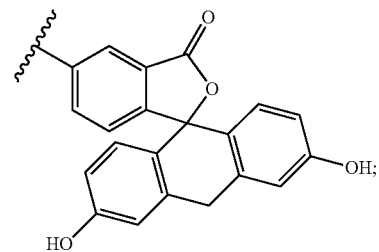

wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein each occurrence of each of $R^{22a}$ and $R^{22b}$, when present, is independently selected from hydrogen, C1-C6 alkyl, C3-C6 cycloalkyl, C3-C6 heterocycloalkyl, and —COR$^{30}$; wherein $R^{23}$, when present, is selected from hydrogen and C1-C4 alkyl; wherein $R^{24}$, when present, is selected from C1-C4 alkyl, C1-C4 hydroxyalkyl, C1-C4 alkyl(C1-C4 alkoxy), C1-C4 alkylamino, (C1-C4)C1-C4)

dialkylamino, C1-4 alkylamino(C1-C4 alkyl), (C1-C4)(C1-C4) dialkylamino(C1-C4 alkyl), —(CH₂)ᵣ(C3-C6 cycloalkyl), and —(CH₂)ₛ(C3-C6 heterocycloalkyl); wherein r, when present, is selected from 0, 1, 2, and 3; wherein $R^6$, when present, is selected from C1-C4 alkyl, C1-C4 haloalkyl, C1-C4 alkoxy, and —(CH₂)ₛCy³; wherein s, when present, is selected from 0, 1, and 2; and wherein Cy³, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl; or wherein each of $R^{4a}$ and $R^{4b}$ is hydrogen, provided that each of $R^{3a}$ and $R^{3b}$ is not hydrogen when $R^{4b}$ is —COR⁶ or when $Ar^1$ is six-membered heteroaryl, provided that each of $R^{3a}$ and $R^{3b}$ are not covalently bonded together when $Ar^1$ is six-membered heteroaryl, and provided that when n is 0 and $Ar^2$ is monoaryl then $Ar^2$ is substituted with at least one non-hydrogen group, or a pharmaceutically acceptable salt thereof.

Also disclosed are compounds having a structure represented by a formula:

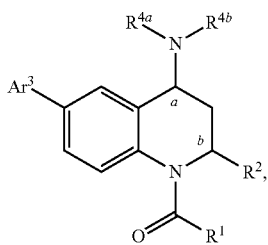

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected from —(CH₂)ₙCy¹, —(CH₂)ₒAr², —COR⁶, and amine protecting group; wherein each of n and o, when present, is selected from 0, 1, 2, and 3; wherein Cy¹, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —NO₂, C1-C4 alkyl, C1-C4 alkoxy, C1-C4 haloalkyl, C1-C4 haloalkoxy, C1-C4 aminoalkyl, C3-C6 cycloalkyl, —COR²¹, —CO₂R²¹, —CONR²²ᵃR²²ᵇ, —(CH₂)qNR²²ᵃR²²ᵇ, —SO₂NR²²ᵃR²²ᵇ, —NR²³C(O)R²⁴, —NR²³(CH₂)q(C3-C6 cycloalkyl), —NR²³(CH₂)q(heterocycloalkyl), and 3- to 5-membered heterocycloalkyl; and wherein q, when present, is selected from 0, 1, 2, 3, and 4; wherein each occurrence of $R^{21}$, when present, is independently selected from hydrogen, C1-C6 alkyl, C3-C6 cycloalkyl, C3-C6 heterocycloalkyl, —COR³⁰, —(C1-C4 alkyl)OC(O)(C1-C4 alkyl), and —(C1-C6 alkyl)NHC(O)A; wherein A has a structure:

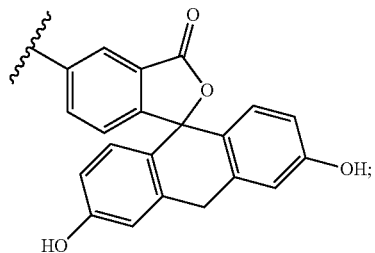

wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein each occurrence of each of $R^{22a}$ and $R^{22b}$, when present, is independently selected from hydrogen, C1-C6 alkyl, C3-C6 cycloalkyl, C3-C6 heterocycloalkyl, and —COR³⁰; wherein $R^{23}$, when present, is selected from hydrogen and C1-C4 alkyl; wherein $R^{24}$, when present, is selected from C1-C4 alkyl, C1-C4 hydroxyalkyl, C1-C4 alkyl(C1-C4 alkoxy), C1-C4 alkylamino, (C1-C4)C1-C4) dialkylamino, C1-4 alkylamino(C1-C4 alkyl), (C1-C4)(C1-C4) dialkylamino(C1-C4 alkyl), —(CH₂)ᵣ(C3-C6 cycloalkyl), and —(CH₂)ᵣ(C3-C6 heterocycloalkyl); wherein r, when present, is selected from 0, 1, 2, and 3; wherein $R^6$, when present, is selected from C1-C4 alkyl, C1-C4 haloalkyl, C1-C4 alkoxy, and (CH₂)ₛCy³; wherein s, when present, is selected from 0, 1, and 2; wherein Cy³, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl; and wherein $Ar^3$ is phenyl substituted with 1-4 non-hydrogen groups independently selected—from —NO₂, OR³¹, and —CH₂NR³²ᵃR³²ᵇ; wherein each occurrence of $R^{31}$, when present, is independently selected from hydrogen, C1-C6 alkyl, and aryl; wherein each of $R^{32a}$ and $R^{32b}$, when present, is independently selected from hydrogen, C1-C4 alkyl, and C1-C4 haloalkyl, provided that at least one of $R^{32a}$ and $R^{32b}$ is not hydrogen; or wherein $Ar^3$ is selected from:

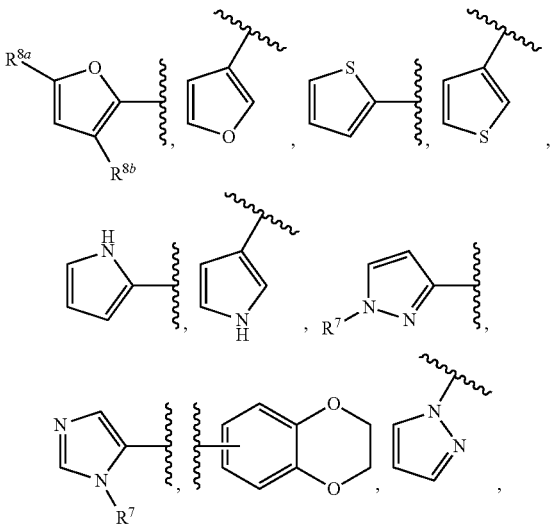

-continued

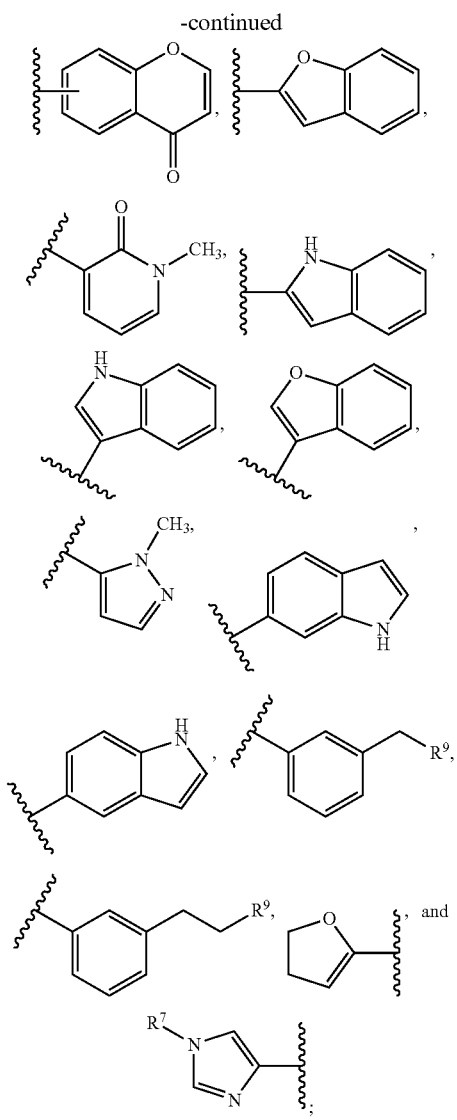

wherein $R^7$, when present, is selected from hydrogen, C1-C4 alkyl, and aryl substituted with 0-4 non-hydrogen groups independently selected from halogen, —OH, —CN, C1-C4 alkyl, C1-C4 alkoxy, and C1-C4 haloalkyl; wherein each of $R^{8a}$ and $R^{8b}$, when present, is independently selected from hydrogen and —CO$_2$(C1-C4 alkyl); and wherein $R^9$, when present, is selected from —OH, —NH$_2$, C1-C4 hydroxyalkyl, C1-C4 alkylamino, and (C1-C4)(C1-C4) dialkylamino, provided that when $R^{4b}$ is —COR$^6$, then Ar$^3$ is not

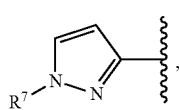

provided that when $R^7$ is hydrogen or methyl, then $R^{4b}$ is not amine protecting group, provided that when $R^{31}$ is methyl, then Ar$^3$ is phenyl substituted 1-4 non-hydrogen groups, only one of which is OR$^{31}$, and provided that when n is 0 then Ar$^2$ is substituted with at least one non-hydrogen group, or a pharmaceutically acceptable salt thereof.

Also disclosed are compounds having a structure represented by a formula:

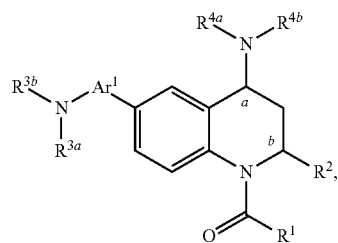

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, —(C1-C6 alkyl) C3-C6 cycloalkyl), —(C1-C6 alkyl)C3-C6 heterocycloalkyl), —C(O)C1-C6 alkyl), —C(O)C3-C4 cycloalkyl), and amine protecting group; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein Ar$^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group; wherein $R^{4b}$ is selected from Cy$^1$, Ar$^2$R$^5$, and —COR$^6$; wherein Cy$^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein Ar$^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle; and wherein $R^5$, when present, is selected from halogen, —OH, —CN, —NO$_2$, C1-C4 alkyl, C1-C4 haloalkyl, C1-C4 alkoxy, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and 3- to 5-membered heterocycle; wherein each occurrence of $R^{21}$, when present, is independently selected from hydrogen, C1-C6 alkyl, C3-C6 cycloalkyl, C3-C6 heterocycloalkyl, and —COR$^{30}$; and wherein each occurrence of each of $R^{2a}$ and $R^{2b}$, when present, is independently selected from hydrogen, C1-C6 alkyl, C3-C6 cycloalkyl, C3-C6 heterocycloalkyl, and —COR$^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein $R^6$, when present, is selected from C1-C4 alkyl, C1-C4 haloalkyl, and C1-C4 alkoxy; provided that each of $R^{3a}$ and $R^{3b}$ is not hydrogen when $R^{4b}$ is —COR$^6$ or when Ar$^1$ is six-membered heteroaryl; and provided that each of $R^{3a}$ and $R^{3b}$ are not covalently bonded together when Ar$^1$ is six-membered heteroaryl, or a pharmaceutically acceptable salt thereof.

Also disclosed are compounds having a structure represented by a formula:

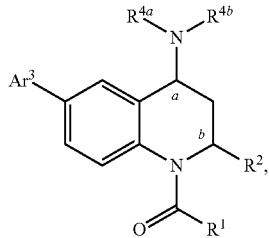

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected $Cy^1$, $Ar^2R^5$, —$COR^6$, and amine protecting group; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —$NO_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and heterocycle; and wherein $R^5$, when present, is selected from halogen, —OH, —CN, —$NO_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and 3- to 5-membered heterocycle; wherein each occurrence of $R^{21}$, when present, is independently selected from hydrogen, C1-C6 alkyl, C3-C6 cycloalkyl, C3-C6 heterocycloalkyl, and —$COR^{30}$; wherein each occurrence of each of $R^{22a}$ and $R^{22b}$, when present, is independently selected from hydrogen, C1-C6 alkyl, C3-C6 cycloalkyl, C3-C6 heterocycloalkyl, and —$COR^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein $R^6$, when present, is selected from C1-C4 alkyl, C1-C4 haloalkyl, and C1-C4 alkoxy; and wherein $Ar^3$ is phenyl substituted with 1-4 independently selected —$OR^{31}$ groups; wherein each occurrence of $R^{31}$ is independently selected from hydrogen and C2-C6 alkyl; or wherein $Ar^3$ is a five-membered heteroaryl selected from:

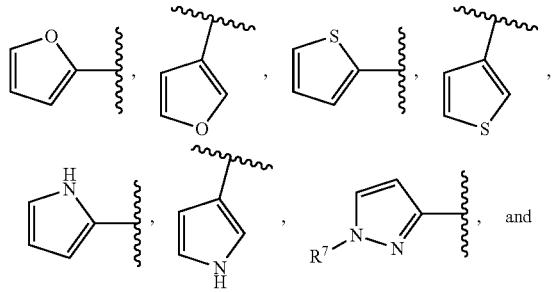

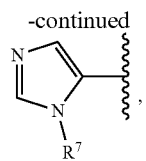

wherein $R^7$, when present, is selected from hydrogen and C1-C4 alkyl; provided that when $R^{4b}$ is —$COR^6$, then $Ar^3$ is not

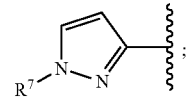

or a pharmaceutically acceptable salt thereof.

Also disclosed are compounds having a structure represented by a formula:

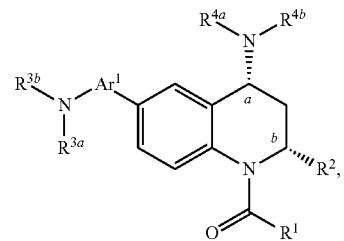

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, $Cy^2$, —(C1-C6 alkyl)$Cy^2$, —(C1-C6 alkyl)$Ar^4$, —C(O)(C1-C6 alkyl), —C(O)(CH$_2$)$_m$Cy$^2$, —C(O)(CH$_2$)$_m$Ar$^4$, —C(O)(C1-C4 alkyl)CCH, —$CO_2$(C1-C6 alkyl), and amine protecting group; wherein m, when present, is selected from 0, 1, 2, and 3; wherein $Cy^2$, when present, is selected from C3-C6 cycloalkyl and C3-C6 heterocycloalkyl and is substituted with 0-4 non-hydrogen groups independently selected from halogen, —OH, —CN, C1-C4 alkyl, C1-C4 alkoxy, and C1-C4 haloalkyl; wherein $Ar^4$, when present, is selected from aryl and heteroaryl and is substituted with 0-4 non-hydrogen groups independently selected from halogen, —OH, —CN, C1-C4 alkyl, C1-C4 alkoxy, and C1-C4 haloalkyl; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein $Ar^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group and wherein $R^{4b}$ is selected from C4-C8 alkyl, —(CH$_2$)$_n$Cy$^1$, —(CH$_2$)$_o$Ar$^2$, and —$COR^6$; wherein each of n and o, when present, is selected from 0, 1, 2, and 3; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein Ar$^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —(CH$_2$)$_q$NR$^{22a}$R$^{22b}$, —SO$_2$NR$^{22a}$R$^{22b}$, —NR$^{23}$C(O)R$^{24}$, —NR$^{23}$(CH$_2$)$_q$(C3-C6 cycloalkyl), —NR$^{23}$(CH$_2$)$_q$(heterocycloalkyl), and 3- to 5-membered heterocycloalkyl; wherein q, when present, is selected from 0, 1, 2, 3, and 4; wherein each occurrence of R$^{21}$, when present, is independently selected from hydrogen, C1-C6 alkyl, C1-C6 hydroxyalkyl, C3-C6 cycloalkyl, C3-C6 heterocycloalkyl, —COR$^{30}$, —(C1-C4 alkyl)OC(O)(C1-C4 alkyl), and —(C1-C6 alkyl)NHC(O)A; wherein A has a structure:

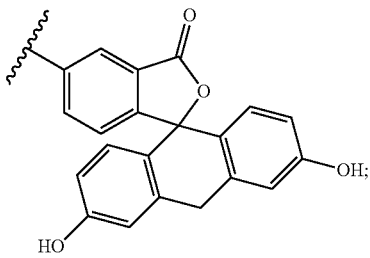

wherein each occurrence of R$^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein each occurrence of each of R$^{22a}$ and R$^{22b}$, when present, is independently selected from hydrogen, C1-C6 alkyl, C3-C6 cycloalkyl, C3-C6 heterocycloalkyl, and —COR$^{30}$; wherein R$^{23}$, when present, is selected from hydrogen and C1-C4 alkyl; wherein R$^{24}$, when present, is selected from C1-C4 alkyl, C1-C4 hydroxyalkyl, C1-C4 alkyl(C1-C4 alkoxy), C1-C4 alkylamino, (C1-C4)(C1-C4) dialkylamino, C1-4 alkylamino(C1-C4 alkyl), (C1-C4)(C1-C4) dialkylamino(C1-C4 alkyl), —(CH$_2$)$_r$(C3-C6 cycloalkyl), and —(CH$_2$)$_s$(C3-C6 heterocycloalkyl); wherein r, when present, is selected from 0, 1, 2, and 3; wherein R$^6$, when present, is selected from C1-C4 alkyl, C1-C4 haloalkyl, C1-C4 alkoxy, and —(CH$_2$)$_s$Cy$^3$; wherein s, when present, is selected from 0, 1, and 2; and wherein Cy$^3$, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl; or wherein each of R$^{4a}$ and R$^{4b}$ is hydrogen, provided that each of R$^{3a}$ and R$^{3b}$ is not hydrogen when R$^{4b}$ is —COR$^6$ or when Ar$^1$ is six-membered heteroaryl, provided that each of R$^{3a}$ and R$^{3b}$ are not covalently bonded together when Ar$^1$ is six-membered heteroaryl, and provided that when n is 0 and Ar$^2$ is monoaryl then Ar$^2$ is substituted with at least one non-hydrogen group, or a pharmaceutically acceptable salt thereof.

Also disclosed are compounds having a structure represented by a formula:

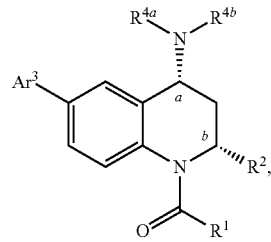

wherein R$^1$ is selected from C1-C4 alkyl, C1-C4 haloalkyl, and C1-C4 deuterated alkyl; wherein R$^2$ is C1-C4 alkyl; wherein R$^{4a}$ is selected from hydrogen, C1-C4 alkyl, and amine protecting group; wherein R$^{4b}$ is selected from —(CH$_2$)$_n$Cy$^1$, —(CH$_2$)$_o$Ar$^2$, —COR$^6$, and amine protecting group; wherein each of n and o, when present, is selected from 0, 1, 2, and 3; wherein Cy$^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein Ar$^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —(CH$_2$)$_q$NR$^{22a}$R$^{22b}$, —SO$_2$NR$^{22a}$R$^{22b}$, —NR$^{23}$C(O)R$^{24}$, —NR$^{23}$(CH$_2$)$_q$(C3-C6 cycloalkyl), —NR$^{23}$(CH$_2$)$_q$(heterocycloalkyl), and 3- to 5-membered heterocycloalkyl; and wherein q, when present, is selected from 0, 1, 2, 3, and 4; wherein each occurrence of R$^{21}$, when present, is independently selected from hydrogen, C1-C6 alkyl, C3-C6 cycloalkyl, C3-C6 heterocycloalkyl, —COR$^{30}$, —(C1-C4 alkyl)OC(O)(C1-C4 alkyl), and —(C1-C6 alkyl)NHC(O)A; wherein A has a structure:

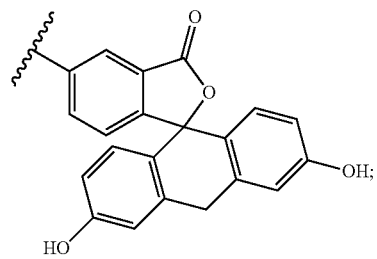

wherein each occurrence of R$^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein each occurrence of each of R$^{22a}$ and R$^{22b}$, when present, is independently selected from hydrogen, C1-C6 alkyl, C3-C6 cycloalkyl, C3-C6 heterocycloalkyl, and —COR$^{30}$; wherein R$^{23}$, when present, is selected from hydrogen and C1-C4 alkyl; wherein R$^{24}$, when present, is selected from C1-C4 alkyl, C1-C4 hydroxyalkyl, C1-C4 alkyl(C1-C4 alkoxy), C1-C4 alkylamino, (C1-C4)(C1-C4) dialkylamino, C1-4 alkylamino(C1-C4 alkyl), (C1-C4)(C1-C4) dialkylamino(C1-C4 alkyl), —(CH$_2$)$_r$(C3-C6 cycloalkyl), and —(CH$_2$)$_r$(C3-C6 heterocycloalkyl); wherein r, when present, is selected from 0, 1, 2, and 3; wherein R$^6$, when present, is selected from C1-C4 alkyl, C1-C4 haloalkyl, C1-C4 alkoxy, and (CH$_2$)$_s$Cy$^3$; wherein s, when present, is selected from 0, 1, and 2; wherein $Cy^3$, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl; and wherein $Ar^3$ is phenyl substituted with 1-4 non-hydrogen groups independently selected—from —$NO_2$, $OR^{31}$, and —$CH_2NR^{32a}R^{32b}$; wherein each occurrence of $R^{31}$, when present, is independently selected from hydrogen, C1-C6 alkyl, and aryl; wherein each of $R^{32a}$ and $R^{32b}$, when present, is independently selected from hydrogen, C1-C4 alkyl, and C1-C4 haloalkyl, provided that at least one of $R^{32a}$ and $R^{32b}$ is not hydrogen; or wherein $Ar^3$ is selected from:

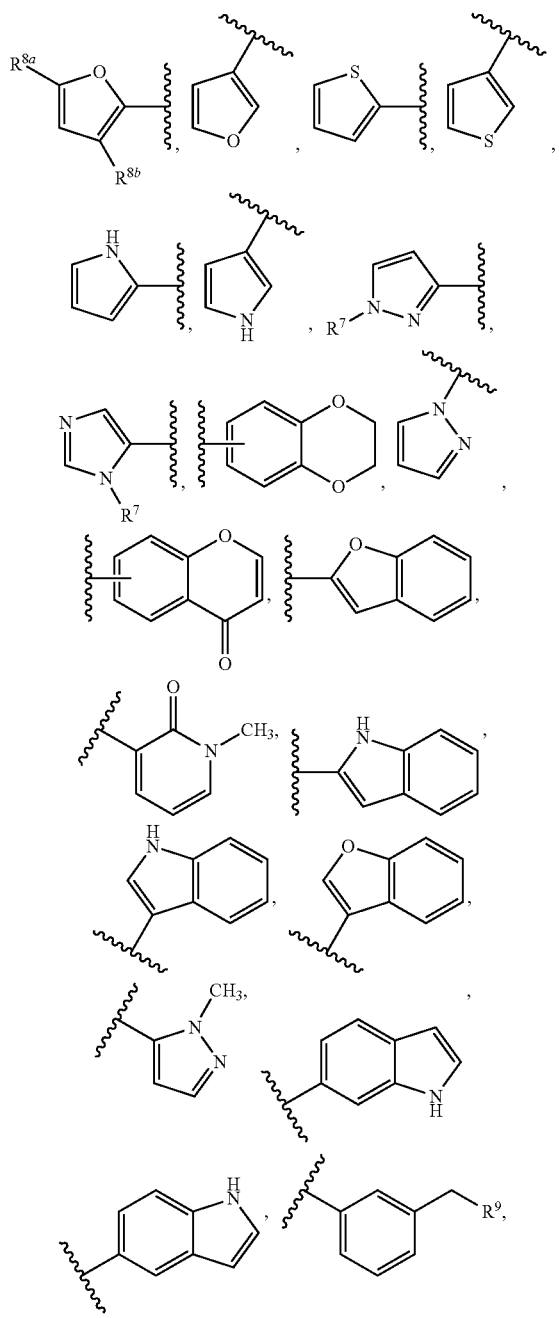

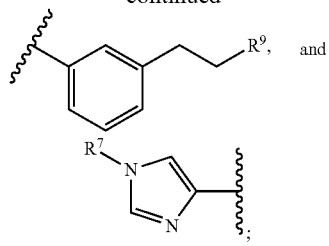

wherein $R^7$, when present, is selected from hydrogen, C1-C4 alkyl, and aryl substituted with 0-4 non-hydrogen groups independently selected from halogen, —OH, —CN, C1-C4 alkyl, C1-C4 alkoxy, and C1-C4 haloalkyl; wherein each of $R^{8a}$ and $R^{8b}$, when present, is independently selected from hydrogen and —$CO_2$(C1-C4 alkyl); and wherein $R^9$, when present, is selected from —OH, —$NH_2$, C1-C4 hydroxyalkyl, C1-C4 alkylamino, and (C1-C4)C1-C4) dialkylamino, provided that when $R^{4b}$ is —$COR^6$, then $Ar^3$ is not

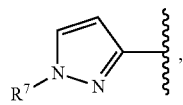

provided that when $R^7$ is hydrogen or methyl, then $R^{4b}$ is not amine protecting group, provided that when $R^{31}$ is methyl, then $Ar^3$ is phenyl substituted 1-4 non-hydrogen groups, only one of which is $OR^{31}$, and provided that when n is 0 then $Ar^2$ is substituted with at least one non-hydrogen group, or a pharmaceutically acceptable salt thereof.

Also disclosed are compounds having a structure represented by a formula:

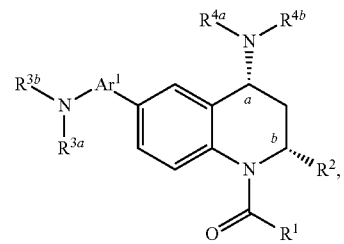

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, —(C1-C6 alkyl)C3-C6 cycloalkyl), —(C1-C6 alkyl)C3-C6 heterocycloalkyl), —C(O)C1-C6 alkyl), —C(O)C3-C4 cycloalkyl), and amine protecting group; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein $Ar^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group; wherein $R^{4b}$ is selected from $Cy^1$, $Ar^2R^5$, and —$COR^6$; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —$NO_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and heterocycle; and wherein $R^5$, when present, is selected from halogen, —OH, —CN, —$NO_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and 3- to 5-membered heterocycle; wherein each occurrence of $R^{21}$, when present, is independently selected from hydrogen, C1-C6 alkyl, C3-C6 cycloalkyl, C3-C6 heterocycloalkyl, and —$COR^{30}$; and wherein each occurrence of each of $R^{22a}$ and $R^{22b}$, when present, is independently selected from hydrogen, C1-C6 alkyl, C3-C6 cycloalkyl, C3-C6 heterocycloalkyl, and —$COR^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl, wherein $R^6$, when present, is selected from C1-C4 alkyl, C1-C4 haloalkyl, and C1-C4 alkoxy; provided that each of $R^{3a}$ and $R^{3b}$ is not hydrogen when $R^{4b}$ is —$COR^6$ or when $Ar^1$ is six-membered heteroaryl; and provided that each of $R^{3a}$ and $R^{3b}$ are not covalently bonded together when $Ar^1$ is six-membered heteroaryl, or a pharmaceutically acceptable salt thereof.

Also disclosed are compounds having a structure represented by a formula:

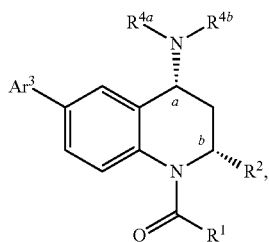

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected $Cy^1$, $Ar^2R^5$, —$COR^6$, and amine protecting group; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —$NO_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and heterocycle; and wherein $R^5$, when present, is selected from halogen, —OH, —CN, —$NO_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and 3- to 5-membered heterocycle; wherein each occurrence of $R^{21}$, when present, is independently selected from hydrogen, C1-C6 alkyl, C3-C6 cycloalkyl, C3-C6 heterocycloalkyl, and —$COR^{30}$; wherein each occurrence of each of $R^{22a}$ and $R^{22b}$, when present, is independently selected from hydrogen, C1-C6 alkyl, C3-C6 cycloalkyl, C3-C6 heterocycloalkyl, and —$COR^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein $R^6$, when present, is selected from C1-C4 alkyl, C1-C4 haloalkyl, and C1-C4 alkoxy; and wherein $Ar^3$ is phenyl substituted with 1-4 independently selected —$OR^{31}$ groups; wherein each occurrence of $R^{31}$ is independently selected from hydrogen and C2-C6 alkyl; or wherein $Ar^3$ is a five-membered heteroaryl selected from:

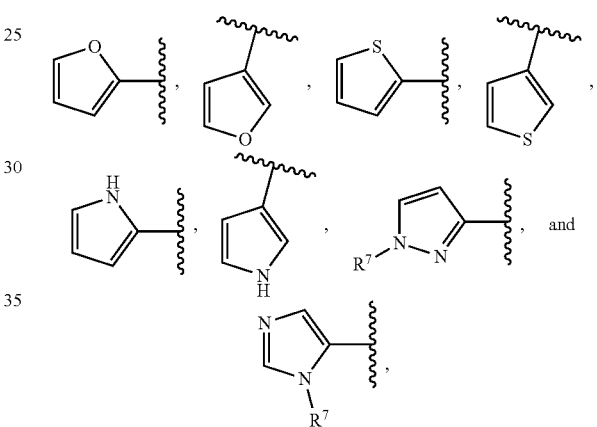

wherein $R^7$, when present, is selected from hydrogen and C1-C4 alkyl; provided that when $R^{4b}$ is —$COR^6$, then $Ar^3$ is not

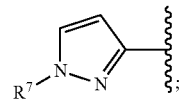

and or a pharmaceutically acceptable salt thereof.

Also disclosed are pharmaceutical compositions comprising a disclosed compound.

Also disclosed are uses of a disclosed compound as a male contraceptive.

Also disclosed are uses of a disclosed compound to suppress stem cell differentiation.

Also disclosed are methods of inhibiting a bromodomain, the method comprising contacting the bromodomain with a disclosed compound.

A method of treating a disorder for which a bromodomain is indicated in a subject in need thereof, the method comprising administering a therapeutically effective amount of a disclosed compound.

Also disclosed are methods of making a disclosed compound.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

Figures 1A, 1B:
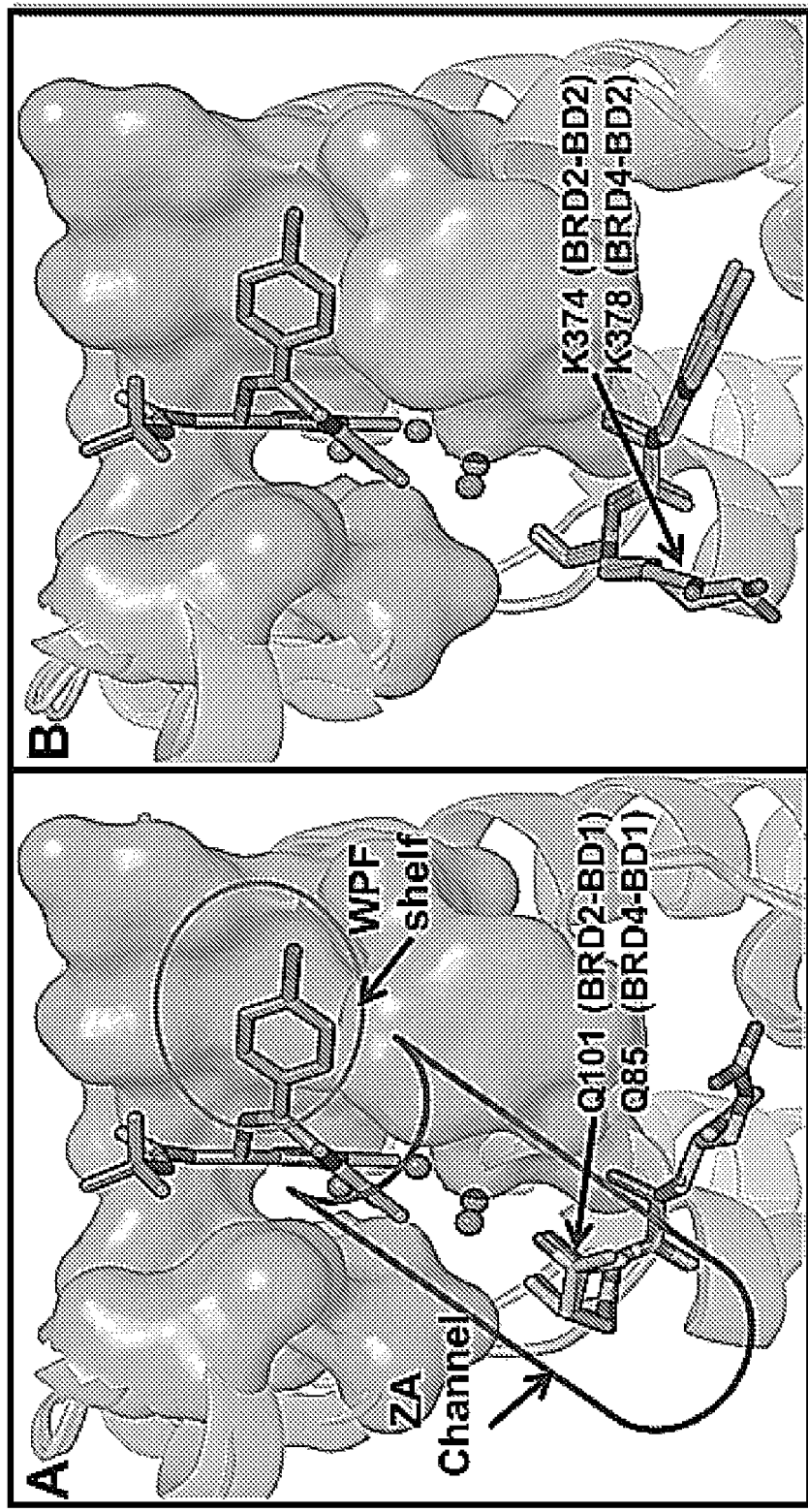
FIG. 1A and FIG. 1B show variable residues of the ZA loop. Specifically, glutamine (BD1) is shown in an "IN" orientation (1A) and lysine (BD2) is shown in an "OUT" orientation (1B). Four conserved water molecules and (+)-JQ1 are depicted as spheres and sticks, respectively. The ligand binding pocket is represented as a solid surface, with the ZA channel and WPF shelf separately outlined.
Figures 2A, 2B:
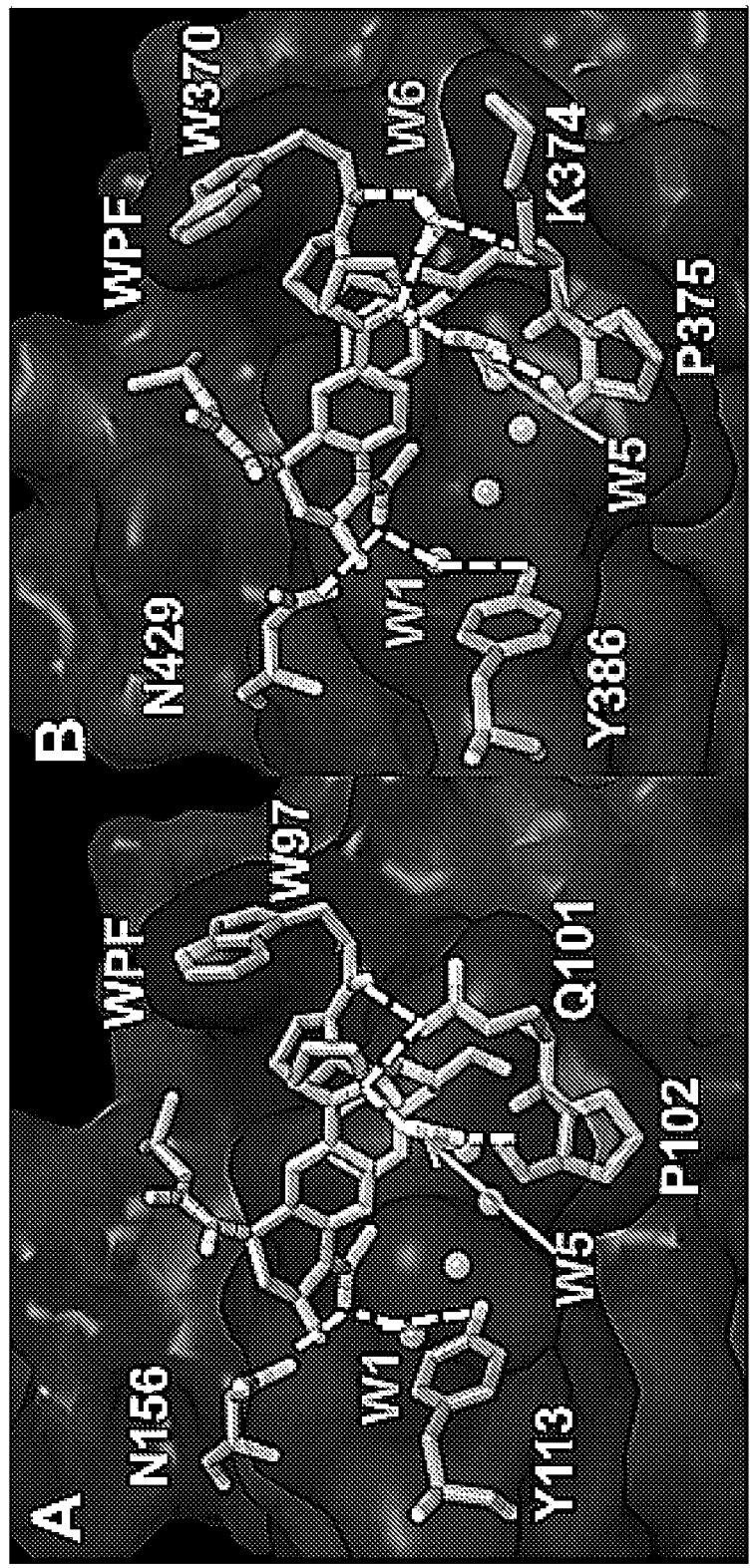
FIG. 2A-D show representative interaction patterns of compound 50 with BRD2-BD1 (2A), compound 51 with BRD2-BD1 (2B), compound 50 with BRD2-BD2 (2C), and compound 51 with BRD2-BD2 (2D). Hydrogen bond interactions are illustrated as broken dashes and all of the residues are labeled accordingly.
Figures 2C, 2D:
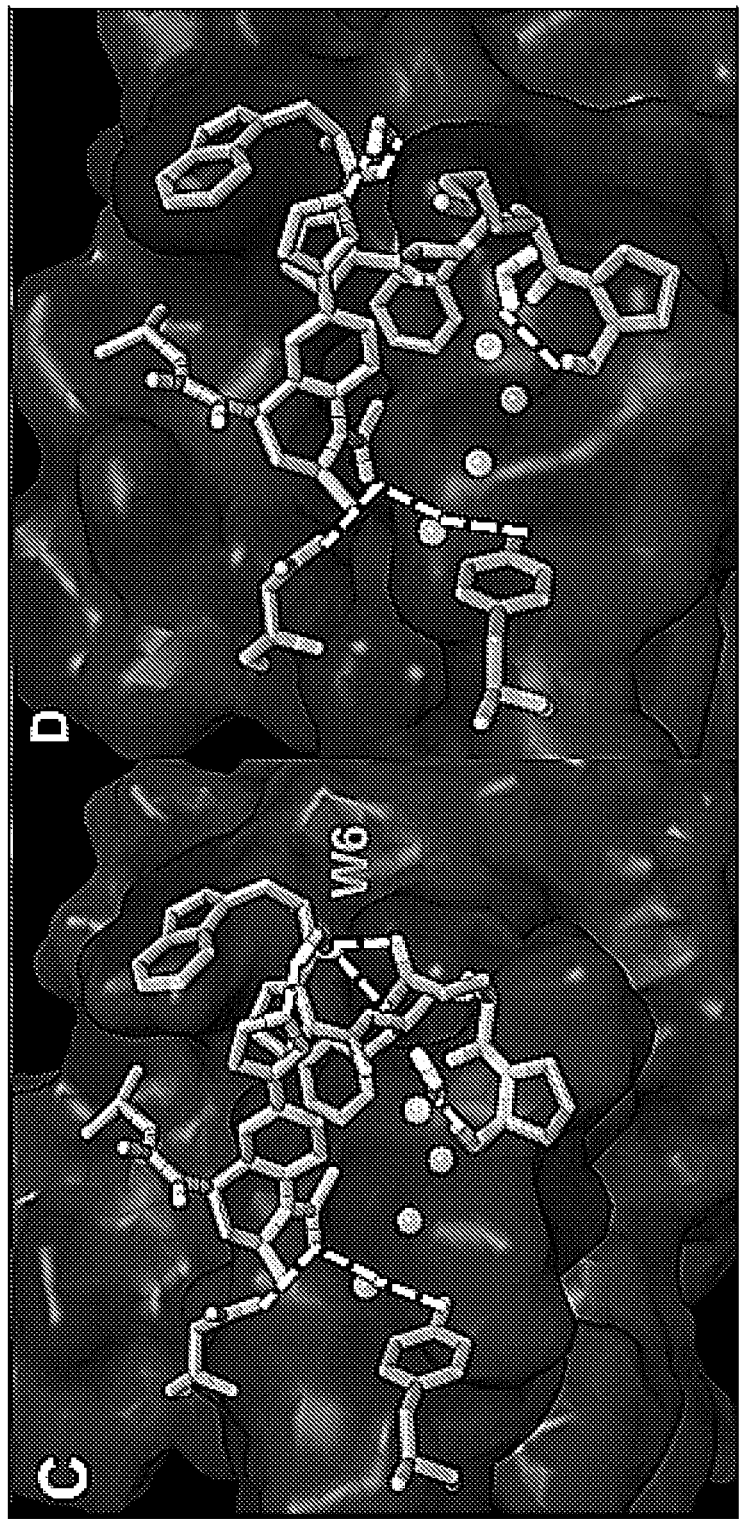
Figures 3A, 3B:
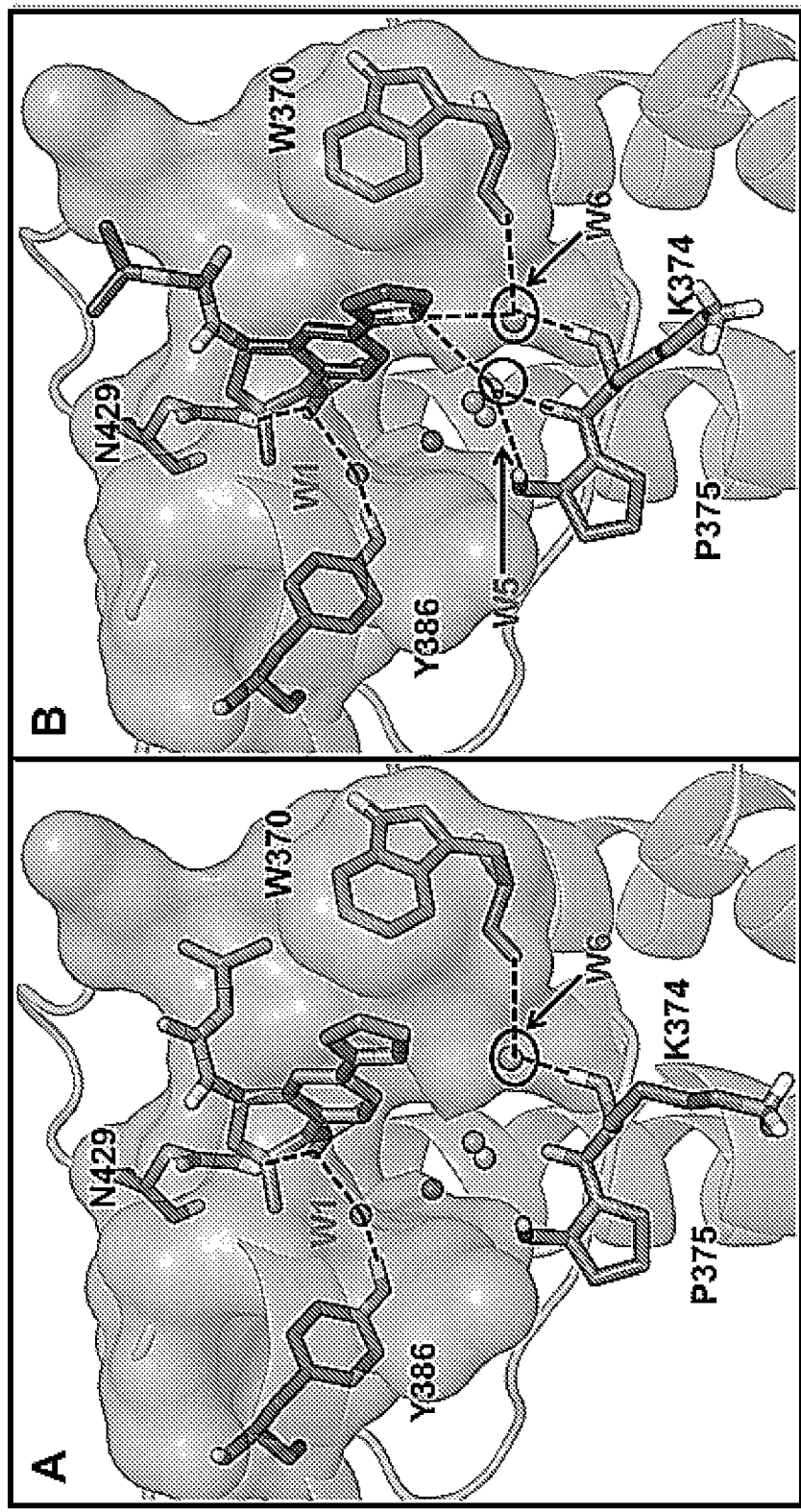
FIG. 3A and FIG. 3B show representative co-crystal structures of BRD2-BD2 with compound 50 in the ligand binding pocket of monomer chain A (3A) and monomer chain B (3B). Water mediated and direct hydrogen bond interactions are shown as broken lines.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), anti-foaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized n electrons above and below the plane of the molecule, where the a clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $-NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" is represented by the formula $A'S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A'S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-4}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, $SC(S)SR°$; —$(CH_2)_{0-4}SC(O)R°$; —$(CH_2)_{0-4}C(O)NR°_2$; —$C(S)NR°_2$; —$C(S)SR°$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●_2$, —NO$_2$, —SiR$^●_3$, —OSiR$^●_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, C(O)R$^†$, —C(O)OR$^†$, C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

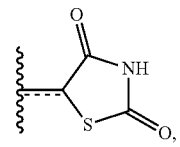

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but are not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

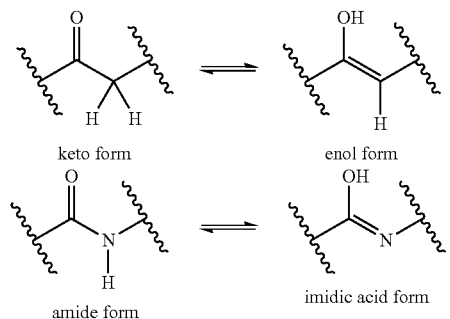

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

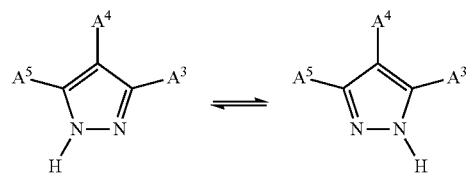

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

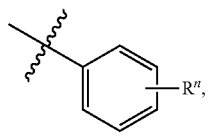

which is understood to be equivalent to a formula:

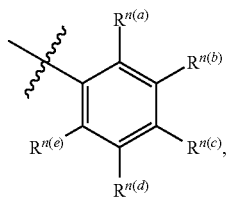

wherein n is typically an integer. That is, $R''$ is understood to represent five independent substituents, $R''^{(a)}$, $R''^{(b)}$, $R''^{(c)}$, $R''^{(d)}$, $R''^{(e)}$. By "independent substituents," it is meant that each R substituent can be independently defined. For example, if in one instance $R''^{(a)}$ is halogen, then $R''^{(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, Mass.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, disclosed are compounds useful in treating or preventing a disorder associated with inhibition of a bromodomain such as, for example, cancer, an estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis. In a further aspect, the disclosed compounds exhibit modulation of bromodomain activity. In a still further aspect, the disclosed compounds exhibit inhibition of bromodomain activity. In yet a further aspect, the disclosed compounds exhibit antagonism of bromodomain activity.

In a further aspect, the invention relates to compositions and methods for use as a male contraceptive. In a still further aspect, the invention relates to compositions and methods for use in stem cell differentiation.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

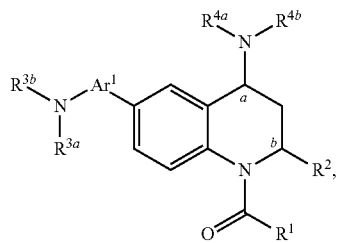

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, $Cy^2$, —(C1-C6 alkyl)$Cy^2$, —(C1-C6 alkyl)$Ar^4$, —C(O)(C1-C6 alkyl), —C(O)(CH$_2$)$_m$Cy$^2$, —C(O)(CH$_2$)$_m$Ar$^4$, —C(O)(C1-C4 alkyl)CCH, —CO$_2$(C1-C6 alkyl), and amine protecting group; wherein m, when present, is selected from 0, 1, 2, and 3; wherein $Cy^2$, when present, is selected from C3-C6 cycloalkyl and C3-C6 heterocycloalkyl and is substituted with 0-4 non-hydrogen groups independently selected from halogen, —OH, —CN, C1-C4 alkyl, C1-C4 alkoxy, and C1-C4 haloalkyl; wherein $Ar^4$, when present, is selected from aryl and heteroaryl and is substituted with 0-4 non-hydrogen groups independently selected from halogen, —OH, —CN, C1-C4 alkyl, C1-C4 alkoxy, and C1-C4 haloalkyl; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein $Ar^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group and wherein $R^{4b}$ is selected from C4-C8 alkyl, —(CH$_2$)$_n$Cy$^1$, —(CH$_2$)$_o$Ar$^2$, and —COR$^6$; wherein each of n and o, when present, is selected from 0, 1, 2, and 3; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —(CH$_2$)$_q$NR$^{22a}$R$^{22b}$, —SO$_2$NR$^{22a}$R$^{22b}$, —NR$^{23}$C(O)R$^{24}$, —NR$^{23}$(CH$_2$)$_q$(C3-C6 cycloalkyl), —NR$^{23}$(CH$_2$)$_q$(heterocycloalkyl), and 3- to 5-membered heterocycloalkyl; wherein q, when present, is selected from 0, 1, 2, 3, and 4; wherein each occurrence of $R^{21}$ is independently selected from hydrogen, C1-C6 alkyl, C1-C6 hydroxyalkyl, C3-C6 cycloalkyl, C3-C6 heterocycloalkyl, —COR$^{30}$, —(C1-C4 alkyl)OC(O)(C1-C4 alkyl), and —(C1-C6 alkyl)NHC(O)A; wherein A has a structure:

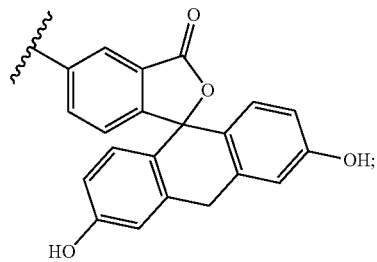

wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein each occurrence of each of $R^{22a}$ and $R^{22b}$, when present, is independently selected from hydrogen, C1-C6 alkyl, C3-C6 cycloalkyl, C3-C6 heterocycloalkyl, and —COR$^{30}$; wherein $R^{23}$, when present, is selected from hydrogen and C1-C4 alkyl; wherein $R^{24}$, when present, is selected from C1-C4 alkyl, C1-C4 hydroxyalkyl, C1-C4 alkyl(C1-C4 alkoxy), C1-C4 alkylamino, (C1-C4)C1-C4) dialkylamino, C1-4 alkylamino(C1-C4 alkyl), (C1-C4)(C1-C4) dialkylamino(C1-C4 alkyl), —(CH$_2$)$_r$(C3-C6 cycloalkyl), and —(CH$_2$)$_s$(C3-C6 heterocycloalkyl); wherein r, when present, is selected from 0, 1, 2, and 3; wherein $R^6$, when present, is selected from C1-C4 alkyl, C1-C4 haloalkyl, C1-C4 alkoxy, and —(CH$_2$)$_s$Cy$^3$; wherein s, when present, is selected from 0, 1, and 2; and wherein $Cy^3$, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl; or wherein each of $R^{4a}$ and $R^{4b}$ is hydrogen, provided that each of $R^{3a}$ and $R^{3b}$ is not hydrogen when $R^{4b}$ is —COR$^6$ or when $Ar^1$ is six-membered heteroaryl, provided that each of $R^{3a}$ and $R^{3b}$ are not covalently bonded together when $Ar^1$ is six-membered heteroaryl, and provided that when n is 0 and $Ar^2$ is monoaryl then $Ar^2$ is substituted with at least one non-hydrogen group, or a pharmaceutically acceptable salt thereof.

In one aspect, disclosed are compounds having a structure represented by a formula:

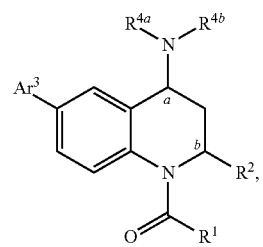

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected from —(CH$_2$)$_n$Cy$^1$, —(CH$_2$)$_o$Ar$^2$, —COR$^6$, and amine protecting group; wherein each of n and o, when present, is selected from 0, 1, 2, and 3; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein Ar², when present, is selected from aryl and 5- to 12-membered heteroaryl and is substituted with 0-4 non-hydrogen groups independently selected from halogen, —OH, —CN, —NO₂, C1-C4 alkyl, C1-C4 alkoxy, C1-C4 haloalkyl, C1-C4 haloalkoxy, C1-C4 aminoalkyl, C3-C6 cycloalkyl, —COR²¹, —CO₂R²¹, —CONR²²ᵃR²²ᵇ, —(CH₂)$_q$NR²²ᵃR²²ᵇ, —SO₂NR²²ᵃR²²ᵇ, —NR²³C(O)R²⁴, —NR²³(CH₂)$_q$(C3-C6 cycloalkyl), —NR²³(CH₂)$_q$(heterocycloalkyl), and 3- to 5-membered heterocycloalkyl; and wherein q, when present, is selected from 0, 1, 2, 3, and 4; wherein each occurrence of R²¹, when present, is independently selected from hydrogen, C1-C6 alkyl, C3-C6 cycloalkyl, C3-C6 heterocycloalkyl, —COR³⁰, —(C1-C4 alkyl)OC(O)(C1-C4 alkyl), and —(C1-C6 alkyl)NHC(O)A; wherein A has a structure:

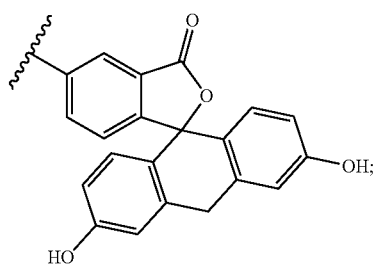

wherein each occurrence of R³⁰, when present, is independently selected from hydrogen, C1-C6 alkyl, C1-C6 alkoxy, C1-C6 aminoalkyl, C3-C6 cycloalkyl, and C3-C6 heterocycloalkyl; wherein each occurrence of each of R²²ᵃ and R²²ᵇ, when present, is independently selected from hydrogen, C1-C6 alkyl, C3-C6 cycloalkyl, C3-C6 heterocycloalkyl, and —COR³⁰; wherein R²³, when present, is selected from hydrogen and C1-C4 alkyl; wherein R²⁴, when present, is selected from C1-C4 alkyl, C1-C4 hydroxyalkyl, C1-C4 alkyl(C1-C4 alkoxy), C1-C4 alkylamino, (C1-C4)C1-C4) dialkylamino, C1-4 alkylamino(C1-C4 alkyl), (C1-C4)(C1-C4) dialkylamino(C1-C4 alkyl), —(CH₂)$_r$(C3-C6 cycloalkyl), and —(CH₂)$_r$(C3-C6 heterocycloalkyl); wherein r, when present, is selected from 0, 1, 2, and 3; wherein R⁶, when present, is selected from C1-C4 alkyl, C1-C4 haloalkyl, C1-C4 alkoxy, and (CH₂)$_s$Cy³; wherein s, when present, is selected from 0, 1, and 2; wherein Cy³, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl; and wherein Ar³ is phenyl substituted with 1-4 non-hydrogen groups independently selected from —NO₂, OR³¹, and —CH₂NR³²ᵃR³²ᵇ; wherein each occurrence of R³¹, when present, is independently selected from hydrogen, C1-C6 alkyl, and aryl; wherein each of R³²ᵃ and R³²ᵇ, when present, is independently selected from hydrogen, C1-C4 alkyl, and C1-C4 haloalkyl, provided that at least one of R³²ᵃ and R³²ᵇ is not hydrogen; or wherein Ar³ is selected from:

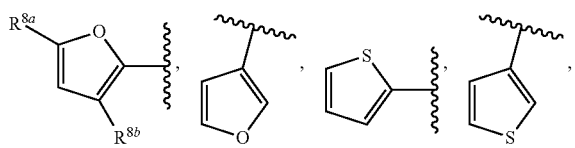

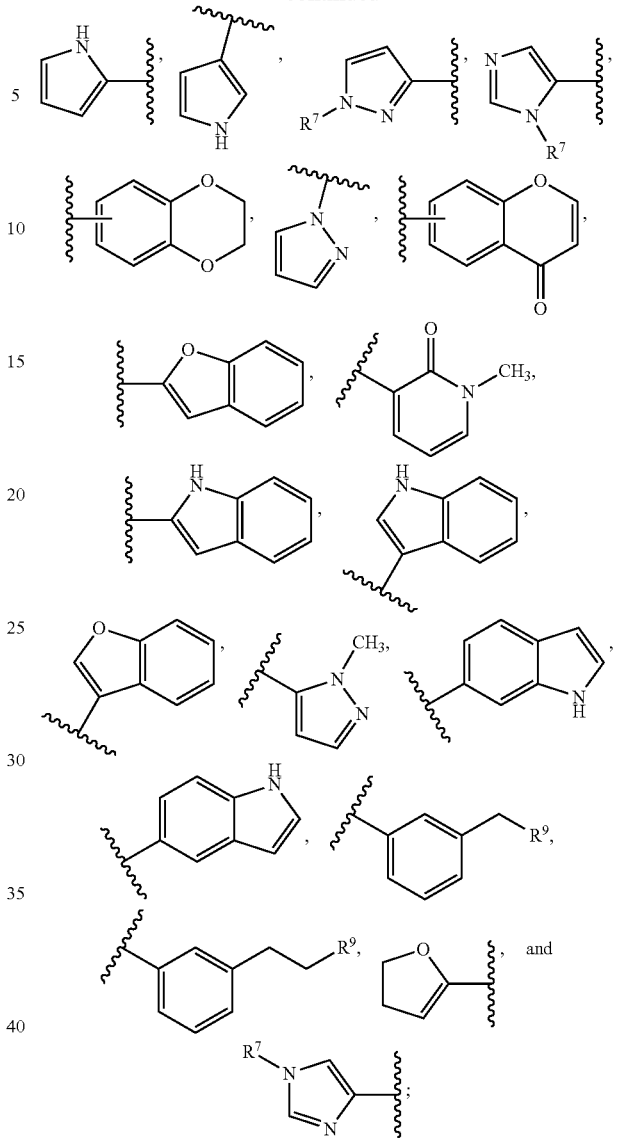

wherein R⁷, when present, is selected from hydrogen, C1-C4 alkyl, and aryl substituted with 0-4 non-hydrogen groups independently selected from halogen, —OH, —CN, C1-C4 alkyl, C1-C4 alkoxy, and C1-C4 haloalkyl; wherein each of R⁸ᵃ and R⁸ᵇ, when present, is independently selected from hydrogen and —CO₂(C1-C4 alkyl); and wherein R⁹, when present, is selected from —OH, —NH₂, C1-C4 hydroxyalkyl, C1-C4 alkylamino, and (C1-C4)C1-C4) dialkylamino, provided that when R⁴ᵇ is —COR⁶, then Ar³ is not

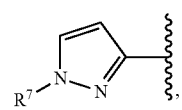

provided that when R⁷ is hydrogen or methyl, then R⁴ᵇ is not amine protecting group, provided that when R³¹ is methyl, then Ar³ is phenyl substituted 1-4 non-hydrogen groups, only one of which is OR³¹, and provided that when n is 0 then Ar² is substituted with at least one non-hydrogen group, or a pharmaceutically acceptable salt thereof.

In one aspect, disclosed are compounds having a structure represented by a formula:

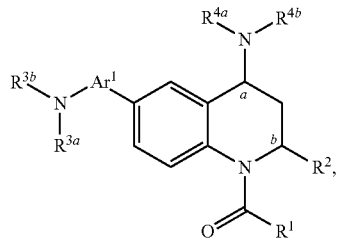

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, —(C1-C6 alkyl)(C3-C6 cycloalkyl), —C(O)(C1-C6 alkyl), —(C1-C6 alkyl)(C3-C6 heterocycloalkyl), —C(O)(C3-C4 cycloalkyl), and amine protecting group; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein $Ar^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group; wherein $R^{4b}$ is selected from $Cy^1$, $Ar^2R^5$, and —COR$^6$; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle; and wherein $R^5$, when present, is selected from halogen, —OH, —CN, —NO$_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and 3- to 5-membered heterocycle; wherein each occurrence of $R^{2'}$, when present, is independently selected from hydrogen, C1-C6 alkyl, C3-C6 cycloalkyl, C3-C6 heterocycloalkyl, and —COR$^{30}$; and wherein each occurrence of each of $R^{22a}$ and $R^{22b}$, when present, is independently selected from hydrogen, C1-C6 alkyl, C3-C6 cycloalkyl, C3-C6 heterocycloalkyl, and —COR$^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl, wherein $R^6$, when present, is selected from C1-C4 alkyl, C1-C4 haloalkyl, and C1-C4 alkoxy; provided that each of $R^{3a}$ and $R^{3b}$ is not hydrogen when $R^{4b}$ is —COR$^6$ or when $Ar^1$ is six-membered heteroaryl; and provided that each of $R^{3a}$ and $R^{3b}$ are not covalently bonded together when $Ar^1$ is six-membered heteroaryl, or a pharmaceutically acceptable salt thereof.

In one aspect, disclosed are compounds having a structure represented by a formula:

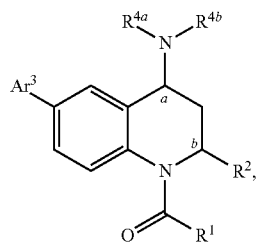

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected $Cy^1$, $Ar^2R^5$, —COR$^6$, and amine protecting group; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle; and wherein $R^5$, when present, is selected from halogen, —OH, —CN, —NO$_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and 3- to 5-membered heterocycle; wherein each occurrence of $R^{21}$, when present, is independently selected from hydrogen, C1-C6 alkyl, C3-C6 cycloalkyl, C3-C6 heterocycloalkyl, and —COR$^{30}$; wherein each occurrence of each of $R^{22a}$ and $R^{22b}$, when present, is independently selected from hydrogen, C1-C6 alkyl, C3-C6 cycloalkyl, C3-C6 heterocycloalkyl, and —COR$^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein $R^6$, when present, is selected from C1-C4 alkyl, C1-C4 haloalkyl, and C1-C4 alkoxy; and wherein $Ar^3$ is phenyl substituted with 1-4 independently selected —OR$^{31}$ groups; wherein each occurrence of $R^{31}$ is independently selected from hydrogen and C2-C6 alkyl; or wherein $Ar^3$ is a five-membered heteroaryl selected from:

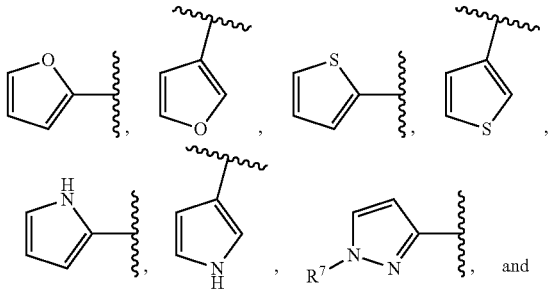

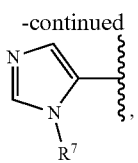

wherein R⁷, when present, is selected from hydrogen and C1-C4 alkyl; provided that when R⁴ᵇ is —COR⁶, then Ar³ is not

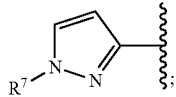

or a pharmaceutically acceptable salt thereof.

In one aspect, disclosed are compounds having a structure represented by a formula:

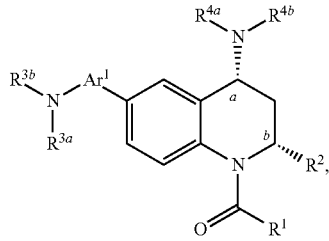

wherein R¹ is selected from C1-C4 alkyl, C1-C4 haloalkyl, and C1-C4 deuterated alkyl; wherein R² is C1-C4 alkyl; wherein each of R³ᵃ and R³ᵇ is independently selected from hydrogen, C1-C6 alkyl, C1-C6 haloalkyl, Cy², —(C1-C6 alkyl)Cy², —(C1-C6 alkyl)Ar⁴, —C(O)(C1-C6 alkyl), —C(O)(CH₂)ₘCy², —C(O)(CH₂)ₘAr⁴, —C(O)(C1-C4 alkyl)CCH, —CO₂(C1-C6 alkyl), and amine protecting group; wherein m, when present, is selected from 0, 1, 2, and 3; wherein Cy², when present, is selected from C3-C6 cycloalkyl and C3-C6 heterocycloalkyl and is substituted with 0-4 non-hydrogen groups independently selected from halogen, —OH, —CN, C1-C4 alkyl, C1-C4 alkoxy, and C1-C4 haloalkyl; wherein Ar⁴, when present, is selected from aryl and heteroaryl and is substituted with 0-4 non-hydrogen groups independently selected from halogen, —OH, —CN, C1-C4 alkyl, C1-C4 alkoxy, and C1-C4 haloalkyl; or wherein each of R³ᵃ and R³ᵇ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein Ar¹ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein R⁴ᵃ is selected from hydrogen, C1-C4 alkyl, and amine protecting group and wherein R⁴ᵇ is selected from C4-C8 alkyl, —(CH₂)ₙCy¹, —(CH₂)ₒAr², and —COR⁶; wherein each of n and o, when present, is selected from 0, 1, 2, and 3; wherein Cy¹, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein Ar², when present, is selected from aryl and 5- to 12-membered heteroaryl and is substituted with 0-4 non-hydrogen groups independently selected from halogen, —OH, —CN, —NO₂, C1-C4 alkyl, C1-C4 alkoxy, C1-C4 haloalkyl, C1-C4 haloalkoxy, C1-C4 aminoalkyl, C3-C6 cycloalkyl, —COR²¹, —CO₂R²¹, —CONR²²ᵃR²²ᵇ, —(CH₂)q NR²²ᵃR²²ᵇ, —SO₂NR²²ᵃR²²ᵇ, —NR²³C(O)R²⁴, —NR²³ (CH₂)q(C3-C6 cycloalkyl), —NR²³(CH₂)q(heterocycloalkyl), and 3- to 5-membered heterocycloalkyl; wherein q, when present, is selected from 0, 1, 2, 3, and 4; wherein each occurrence of R²¹, when present, is independently selected from hydrogen, C1-C6 alkyl, C1-C6 hydroxyalkyl, C3-C6 cycloalkyl, C3-C6 heterocycloalkyl, —COR³⁰, —(C1-C4 alkyl)OC(O)(C1-C4 alkyl), and —(C1-C6 alkyl)NHC(O)A; wherein A has a structure:

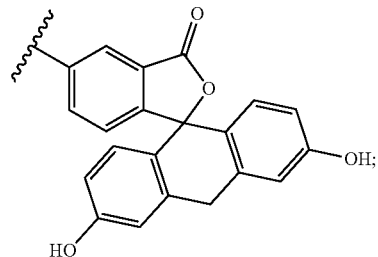

wherein each occurrence of R³⁰, when present, is independently selected from hydrogen, C1-C6 alkyl, C1-C6 alkoxy, C1-C6 aminoalkyl, C3-C6 cycloalkyl, and C3-C6 heterocycloalkyl; wherein each occurrence of each of R²²ᵃ and R²²ᵇ, when present, is independently selected from hydrogen, C1-C6 alkyl, C3-C6 cycloalkyl, C3-C6 heterocycloalkyl, and —COR³⁰; wherein R²³, when present, is selected from hydrogen and C1-C4 alkyl; wherein R²⁴, when present, is selected from C1-C4 alkyl, C1-C4 hydroxyalkyl, C1-C4 alkyl(C1-C4 alkoxy), C1—C4 alkylamino, (C1-C4)C1-C4) dialkylamino, C1-4 alkylamino(C1-C4 alkyl), (C1-C4)(C1-C4) dialkylamino(C1-C4 alkyl), —(CH₂)ᵣ(C3-C6 cycloalkyl), and —(CH₂)ₛ(C3-C6 heterocycloalkyl); wherein r, when present, is selected from 0, 1, 2, and 3; wherein R⁶, when present, is selected from C1-C4 alkyl, C1-C4 haloalkyl, C1-C4 alkoxy, and —(CH₂)ₛCy³; wherein s, when present, is selected from 0, 1, and 2; and wherein Cy³, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl; or wherein each of R⁴ᵃ and R⁴ᵇ is hydrogen, provided that each of R³ᵃ and R³ᵇ is not hydrogen when R⁴ᵇ is —COR⁶ or when Ar¹ is six-membered heteroaryl, provided that each of R³ᵃ and R³ᵇ are not covalently bonded together when Ar¹ is six-membered heteroaryl, and provided that when n is 0 and Ar² is monoaryl then Ar² is substituted with at least one non-hydrogen group, or a pharmaceutically acceptable salt thereof.

In one aspect, disclosed are compounds having a structure represented by a formula:

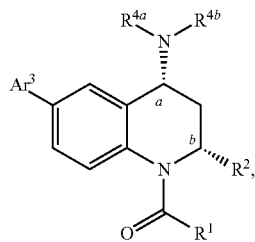

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected from —$(CH_2)_nCy^1$, —$(CH_2)_oAr^2$, —$COR^6$, and amine protecting group; wherein each of n and o, when present, is selected from 0, 1, 2, and 3; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^Z$, when present, is selected from aryl and 5- to 12-membered heteroaryl and is substituted with 0-4 non-hydrogen groups independently selected from halogen, —OH, —CN, —$NO_2$, C1-C4 alkyl, C1-C4 alkoxy, C1-C4 haloalkyl, C1-C4 haloalkoxy, C1-C4 aminoalkyl, C3-C6 cycloalkyl, —$COR^{21}$, —$CO_2R^{21}$, —$CONR^{22a}R^{22b}$, —$(CH_2)_q NR^{22a}R^{22b}$, —$SO_2NR^{22a}R^{22b}$, —$NR^{23}C(O)R^{24}$, —$NR^{23}(CH_2)_q(C3-C6$ cycloalkyl), —$NR^{23}(CH_2)_q$(heterocycloalkyl), and 3- to 5-membered heterocycloalkyl; and wherein q, when present, is selected from 0, 1, 2, 3, and 4; wherein each occurrence of $R^{21}$, when present, is independently selected from hydrogen, C1-C6 alkyl, C3-C6 cycloalkyl, C3-C6 heterocycloalkyl, —$COR^{30}$, —(C1-C4 alkyl)OC(O)(C1-C4 alkyl), and —(C1-C6 alkyl)NHC(O)A; wherein A has a structure:

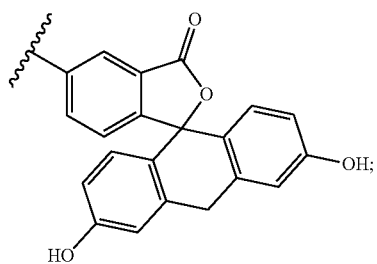

wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein each occurrence of each of $R^{22a}$ and $R^{22b}$, when present, is independently selected from hydrogen, C1-C6 alkyl, C3-C6 cycloalkyl, C3-C6 heterocycloalkyl, and —$COR^{30}$; wherein $R^{23}$, when present, is selected from hydrogen and C1-C4 alkyl; wherein $R^{24}$, when present, is selected from C1-C4 alkyl, C1-C4 hydroxyalkyl, C1-C4 alkyl(C1-C4 alkoxy), C1-C4 alkylamino, (C1-C4)C1-C4) dialkylamino, C1-4 alkylamino(C1-C4 alkyl), (C1-C4)(C1-C4) dialkylamino(C1-C4 alkyl), —$(CH_2)_r(C3-C6$ cycloalkyl), and —$(CH_2)_r(C3-C6$ heterocycloalkyl); wherein r, when present, is selected from 0, 1, 2, and 3; wherein $R^6$, when present, is selected from C1-C4 alkyl, C1-C4 haloalkyl, C1-C4 alkoxy, and $(CH_2)_sCy^3$; wherein s, when present, is selected from 0, 1, and 2; wherein $Cy^3$, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl; and wherein $Ar^3$ is phenyl substituted with 1-4 non-hydrogen groups independently selected from —$NO_2$, $OR^{31}$, and —$CH_2NR^{32a}R^{32b}$; wherein each occurrence of $R^{31}$, when present, is independently selected from hydrogen, C1-C6 alkyl, and aryl; wherein each of $R^{32a}$ and $R^{32b}$, when present, is independently selected from hydrogen, C1-C4 alkyl, and C1-C4 haloalkyl, provided that at least one of $R^{32a}$ and $R^{32b}$ is not hydrogen; or wherein $Ar^3$ is selected from:

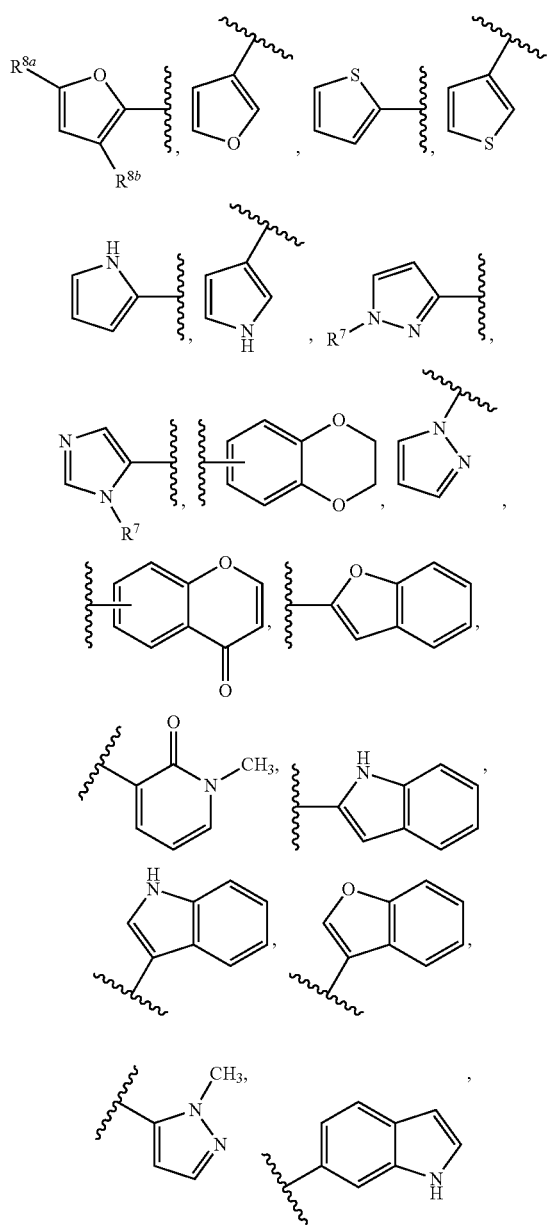

-continued

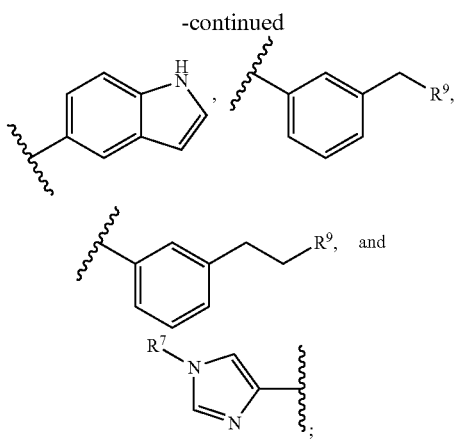

wherein $R^7$, when present, is selected from hydrogen, C1-C4 alkyl, and aryl substituted with 0-4 non-hydrogen groups independently selected from halogen, —OH, —CN, C1-C4 alkyl, C1-C4 alkoxy, and C1-C4 haloalkyl; wherein each of $R^{8a}$ and $R^{8b}$, when present, is independently selected from hydrogen and —CO$_2$(C1-C4 alkyl); and wherein $R^9$, when present, is selected from —OH, —NH$_2$, C1-C4 hydroxyalkyl, C1-C4 alkylamino, and (C1-C4)(C1-C4) dialkylamino, provided that when $R^{4b}$ is —COR$^6$, then Ar$^3$ is not

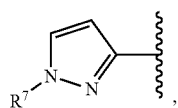

provided that when $R^7$ is hydrogen or methyl, then $R^{4b}$ is not amine protecting group, provided that when $R^{31}$ is methyl, then Ar$^3$ is phenyl substituted 1-4 non-hydrogen groups, only one of which is OR$^{31}$, and provided that when n is 0 then Ar$^2$ is substituted with at least one non-hydrogen group, or a pharmaceutically acceptable salt thereof.

In one aspect, disclosed are compounds having a structure represented by a formula:

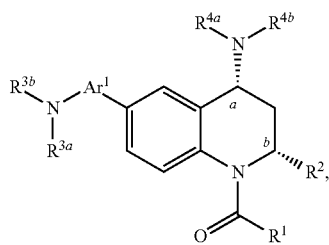

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, —(C1-C6 alkyl)(C3-C6 cycloalkyl), —(C1-C6 alkyl)(C3-C6 heterocycloalkyl), —C(O)(C1-C6 alkyl), —C(O)(C3-C4 cycloalkyl), and amine protecting group; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein Ar$^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group; wherein $R^{4b}$ is selected from Cy$^1$, Ar$^2$R$^5$, and —COR$^6$; wherein Cy$^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein Ar$^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle; and wherein $R^5$, when present, is selected from halogen, —OH, —CN, —NO$_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22}$R$^{22}$, —SO$_2$NR$^{22}$R$^{22}$, and 3- to 5-membered heterocycle; wherein each occurrence of $R^{21}$, when present, is independently selected from hydrogen, C1-C6 alkyl, C3-C6 cycloalkyl, C3-C6 heterocycloalkyl, and —COR$^{30}$; and wherein each occurrence of each of $R^{22a}$ and $R^{22b}$, when present, is independently selected from hydrogen, C1-C6 alkyl, C3-C6 cycloalkyl, C3-C6 heterocycloalkyl, and —COR$^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl, wherein $R^6$, when present, is selected from C1-C4 alkyl, C1-C4 haloalkyl, and C1-C4 alkoxy; provided that each of $R^{3a}$ and $R^{3b}$ is not hydrogen when $R^{4b}$ is —COR$^6$ or when Ar$^1$ is six-membered heteroaryl; and provided that each of $R^{3a}$ and $R^{3b}$ are not covalently bonded together when Ar$^1$ is six-membered heteroaryl, or a pharmaceutically acceptable salt thereof.

In one aspect, disclosed are compounds having a structure represented by a formula:

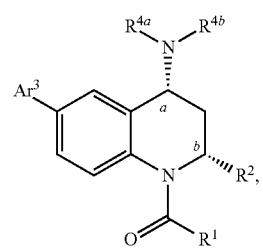

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected Cy$^1$, Ar$^2$R$^5$, —COR$^6$, and amine protecting group; wherein Cy$^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein Ar$^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle; and wherein R$^5$, when present, is selected from halogen, —OH, —CN, —NO$_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and 3- to 5-membered heterocycle; wherein each occurrence of R$^{21}$, when present, is independently selected from hydrogen, C1-C6 alkyl, C3-C6 cycloalkyl, C3-C6 heterocycloalkyl, and —COR$^{30}$; wherein each occurrence of each of R$^{22a}$ and R$^{22b}$, when present, is independently selected from hydrogen, C1-C6 alkyl, C3-C6 cycloalkyl, C3-C6 heterocycloalkyl, and —COR$^{30}$; wherein each occurrence of R$^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein R$^6$, when present, is selected from C1-C4 alkyl, C1-C4 haloalkyl, and C1-C4 alkoxy; and wherein Ar$^3$ is phenyl substituted with 1-4 independently selected —OR$^{31}$ groups; wherein each occurrence of R$^{31}$ is independently selected from hydrogen and C2-C6 alkyl; or wherein Ar$^3$ is a five-membered heteroaryl selected from:

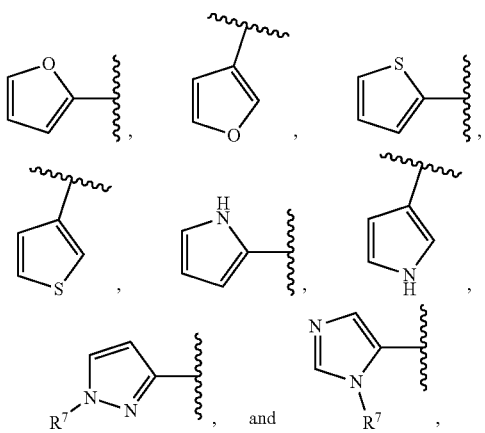

wherein R$^7$, when present, is selected from hydrogen and C1-C4 alkyl; provided that when R$^{4b}$ is —COR$^6$, then Ar$^3$ is not

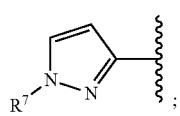

and or a pharmaceutically acceptable salt thereof.

In a further aspect, the substituents on the carbons marked "a" and "b" are in a cis configuration. In a still further aspect, the substituents on the carbons marked "a" and "b" are in a trans configuration.

In a further aspect, the compound has a structure represented by a formula:

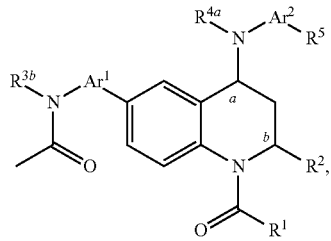

or a pharmaceutically acceptable salt thereof.

In a further aspect, the compound has a structure represented by a formula:

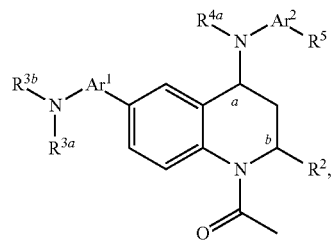

or a pharmaceutically acceptable salt thereof.

In a further aspect, the compound has a structure represented by a formula:

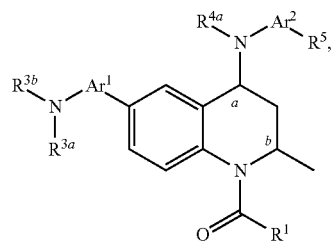

or a pharmaceutically acceptable salt thereof.

In a further aspect, the compound has a structure represented by a formula:

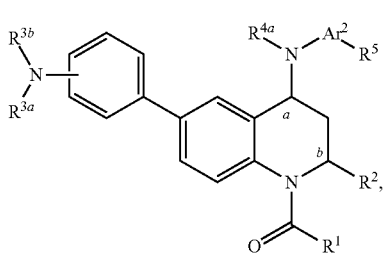

or a pharmaceutically acceptable salt thereof.

In a further aspect, the compound has a structure represented by a formula:

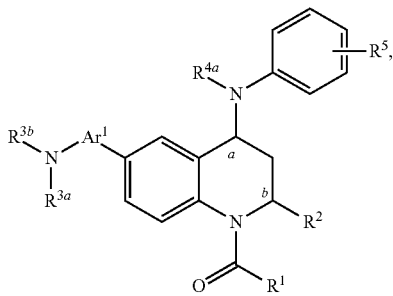

or a pharmaceutically acceptable salt thereof.

In a further aspect, the compound has a structure represented by a formula:

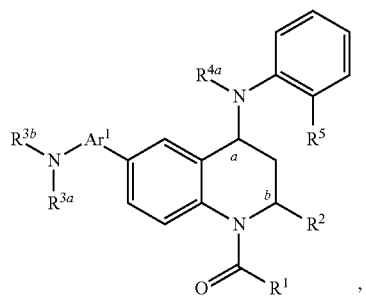

or a pharmaceutically acceptable salt thereof.

In a further aspect, the compound has a structure represented by a formula:

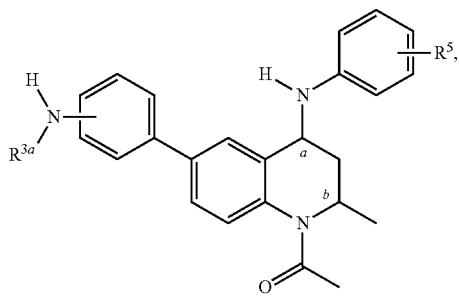

or a pharmaceutically acceptable salt thereof.

In a further aspect, the compound has a structure represented by a formula:

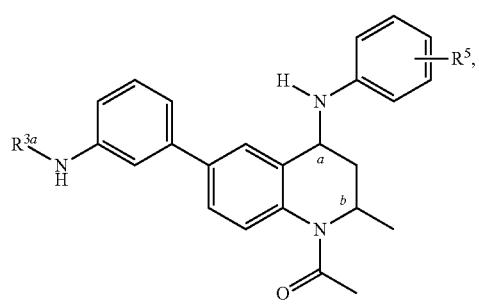

or a pharmaceutically acceptable salt thereof.

In a further aspect, the compound has a structure represented by a formula:

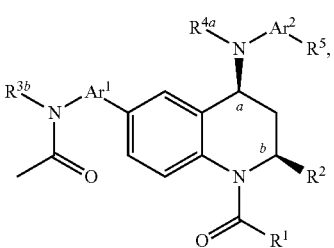

or a pharmaceutically acceptable salt thereof.

In a further aspect, the compound has a structure represented by a formula:

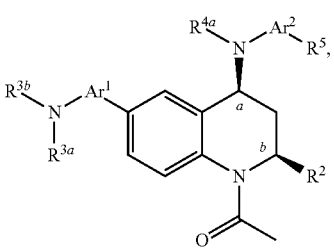

or a pharmaceutically acceptable salt thereof.

In a further aspect, the compound has a structure represented by a formula:

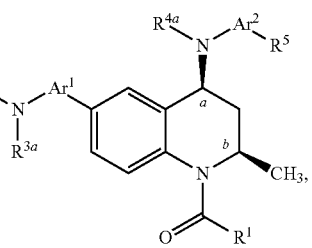

or a pharmaceutically acceptable salt thereof.

In a further aspect, the compound has a structure represented by a formula:

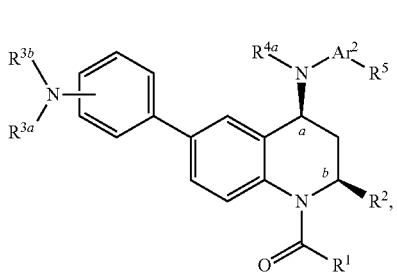

or a pharmaceutically acceptable salt thereof.

In a further aspect, the compound has a structure represented by a formula:

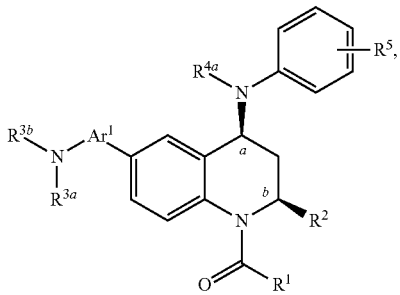

or a pharmaceutically acceptable salt thereof.

In a further aspect, the compound has a structure represented by a formula:

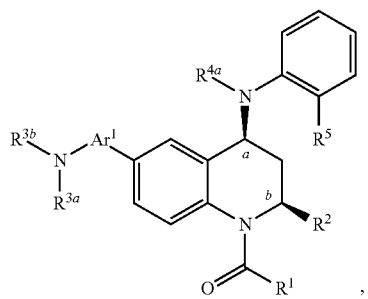

or a pharmaceutically acceptable salt thereof.

In a further aspect, the compound has a structure represented by a formula:

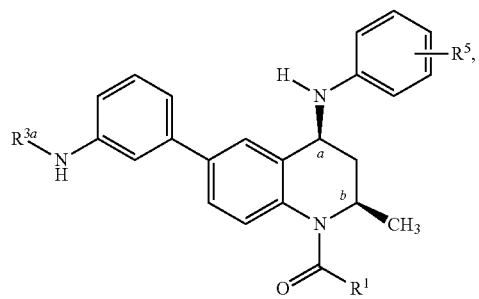

or a pharmaceutically acceptable salt thereof.

In a further aspect, the compound has a structure represented by a formula:

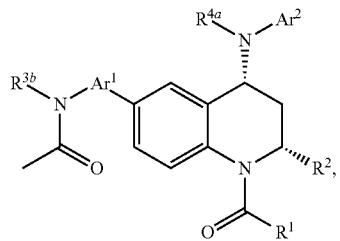

or a pharmaceutically acceptable salt thereof.

In a further aspect, the compound has a structure represented by a formula:

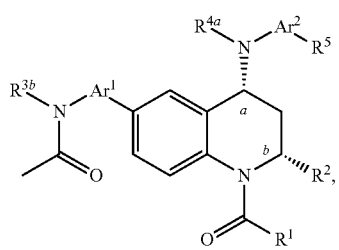

or a pharmaceutically acceptable salt thereof.

In a further aspect, the compound has a structure represented by a formula:

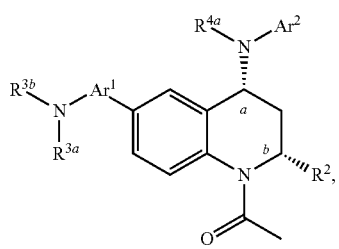

or a pharmaceutically acceptable salt thereof.

In a further aspect, the compound has a structure represented by a formula:

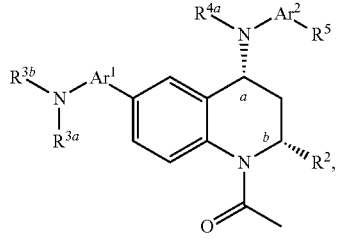

or a pharmaceutically acceptable salt thereof.

In a further aspect, the compound has a structure represented by a formula:

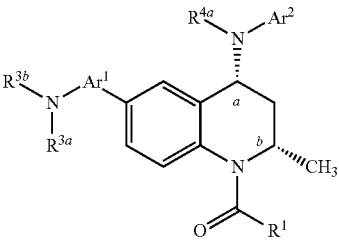

or a pharmaceutically acceptable salt thereof.

In a further aspect, the compound has a structure represented by a formula:

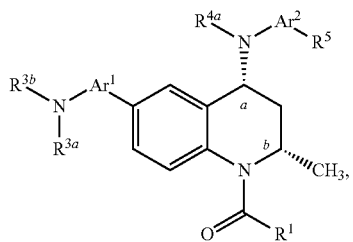

or a pharmaceutically acceptable salt thereof.

In a further aspect, the compound has a structure represented by a formula:

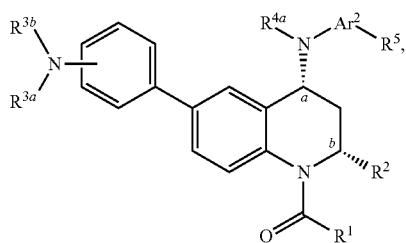

or a pharmaceutically acceptable salt thereof.

In a further aspect, the compound has a structure represented by a formula:

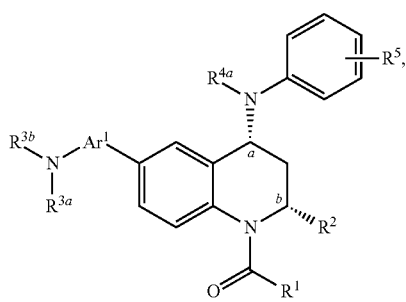

or a pharmaceutically acceptable salt thereof.

In a further aspect, the compound has a structure represented by a formula:

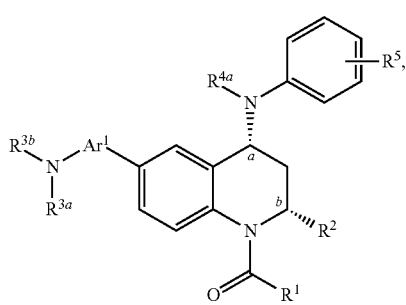

or a pharmaceutically acceptable salt thereof.

wherein $R^5$ is selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —NR$^{22a}$R$^{22b}$, —SO$_2$NR$^{22a}$R$^{22b}$, and 3- to 5-membered heterocycloalkyl or a pharmaceutically acceptable salt thereof.

In a further aspect, the compound has a structure represented by a formula:

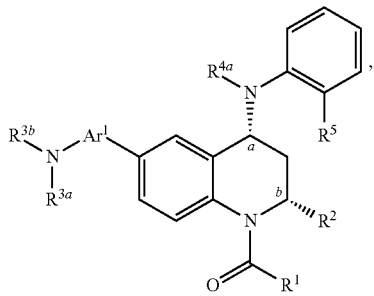

or a pharmaceutically acceptable salt thereof.

In a further aspect, the compound has a structure represented by a formula:

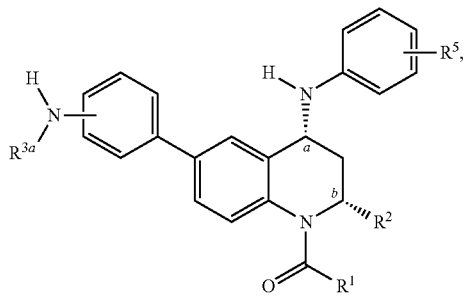

or a pharmaceutically acceptable salt thereof.

In a further aspect, the compound has a structure represented by a formula:

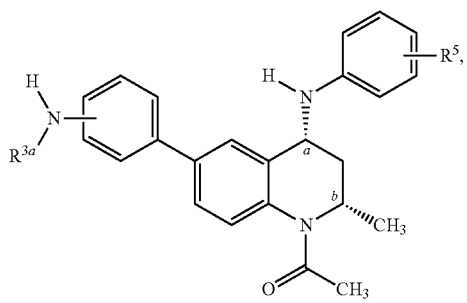

or a pharmaceutically acceptable salt thereof.

In a further aspect, the compound has a structure represented by a formula:

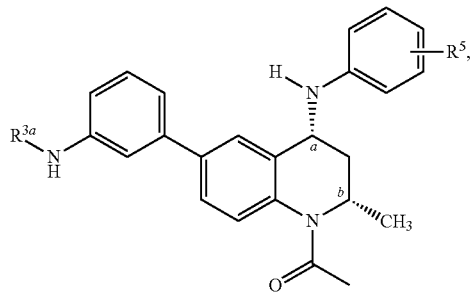

or a pharmaceutically acceptable salt thereof.

In a further aspect, the compound has a structure represented by a formula selected from:

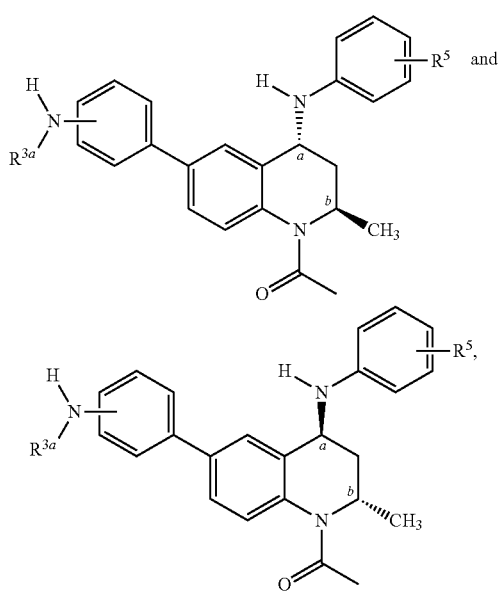

or a pharmaceutically acceptable salt thereof.

In a further aspect, the compound has a structure represented by a formula:

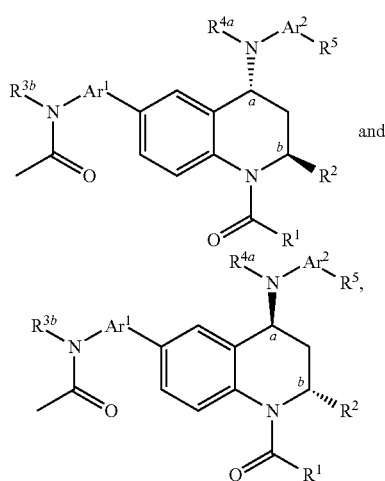

In a further aspect, the compound has a structure represented by a formula selected from:

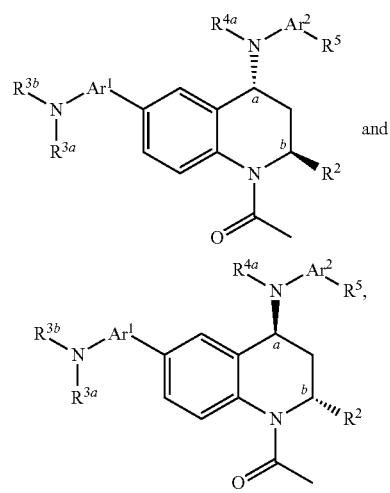

or a pharmaceutically acceptable salt thereof.

In a further aspect, the compound has a structure represented by a formula selected from:

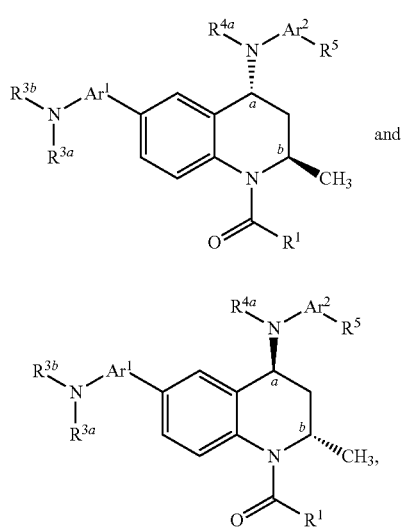

or a pharmaceutically acceptable salt thereof.

In a further aspect, the compound has a structure represented by a formula selected from:

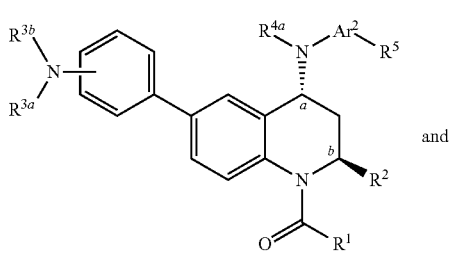

-continued

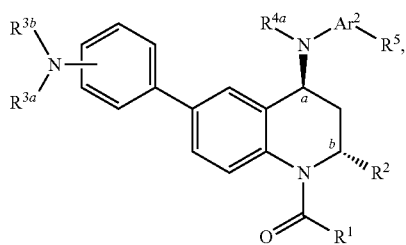

or a pharmaceutically acceptable salt thereof.

In a further aspect, the compound has a structure represented by a formula selected from:

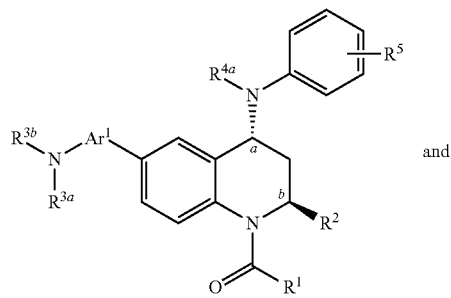

and

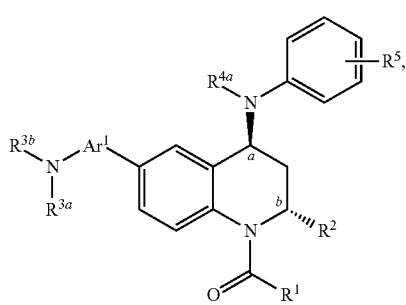

or a pharmaceutically acceptable salt thereof.

In a further aspect, the compound has a structure represented by a formula selected from:

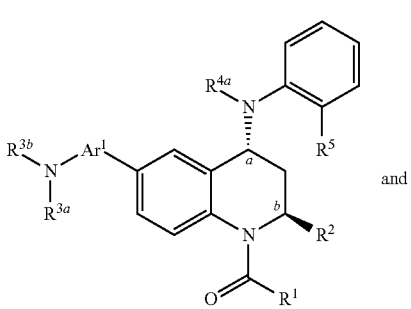

-continued

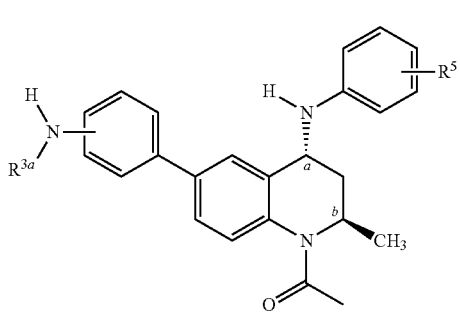

or a pharmaceutically acceptable salt thereof.

In a further aspect, the compound has a structure represented by a formula selected from:

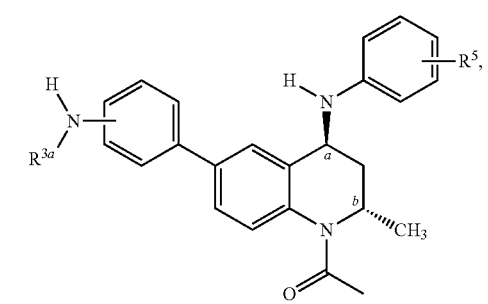

and or a pharmaceutically acceptable salt thereof.

In a further aspect, the compound has a structure represented by a formula selected from:

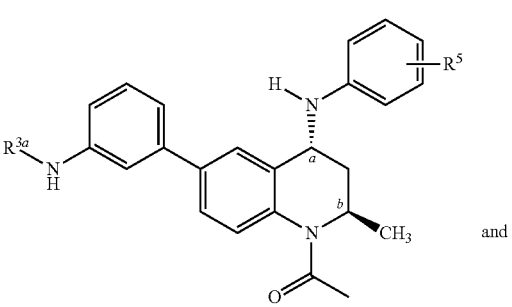

and

-continued

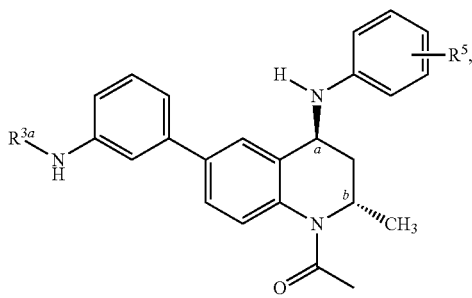

or a pharmaceutically acceptable salt thereof.

In a further aspect, the compound has a structure represented by a formula:

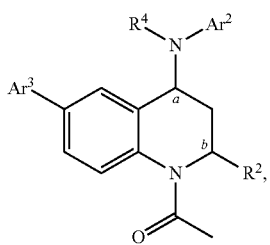

or a pharmaceutically acceptable salt thereof.

In a further aspect, the compound has a structure represented by a formula:

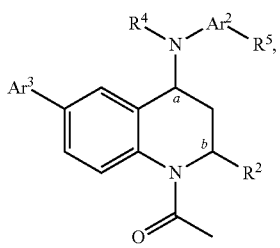

or a pharmaceutically acceptable salt thereof.

In a further aspect, the compound has a structure represented by a formula:

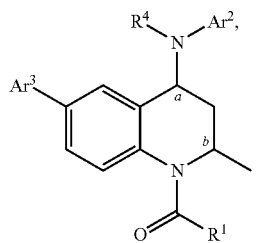

or a pharmaceutically acceptable salt thereof.

In a further aspect, the compound has a structure represented by a formula:

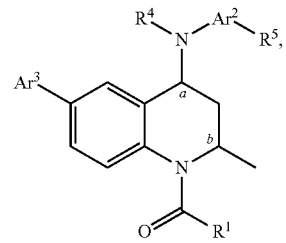

or a pharmaceutically acceptable salt thereof.

In a further aspect, the compound has a structure represented by a formula:

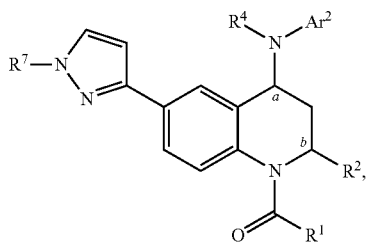

or a pharmaceutically acceptable salt thereof.

In a further aspect, the compound has a structure represented by a formula:

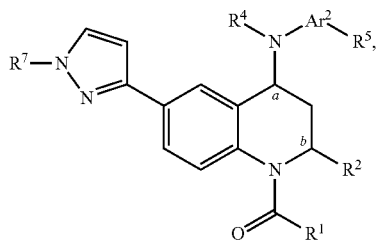

or a pharmaceutically acceptable salt thereof.

In a further aspect, the compound has a structure represented by a formula selected from:

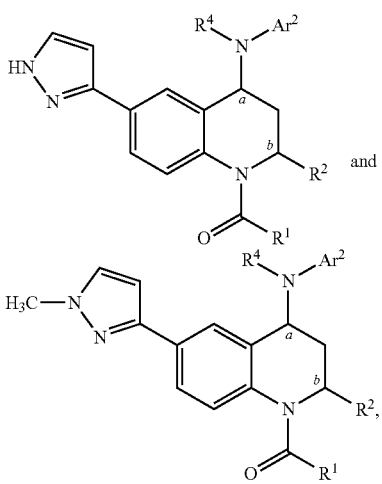

or a pharmaceutically acceptable salt thereof.

In a further aspect, the compound has a structure represented by a formula selected from:

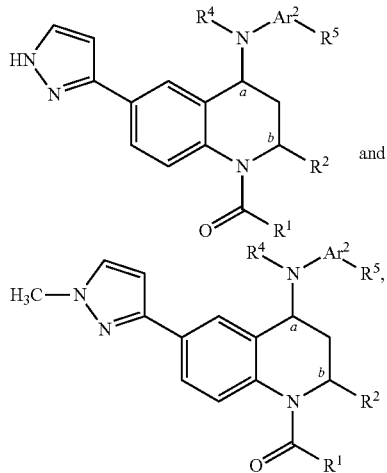

and or a pharmaceutically acceptable salt thereof.

In a further aspect, the compound has a structure represented by a formula:

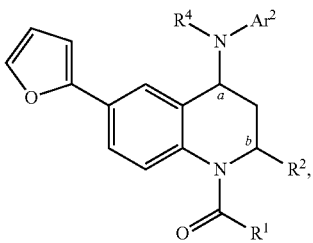

or a pharmaceutically acceptable salt thereof.

In a further aspect, the compound has a structure represented by a formula:

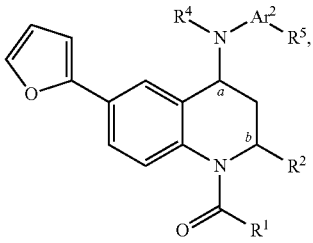

or a pharmaceutically acceptable salt thereof.

In a further aspect, the compound has a structure represented by a formula:

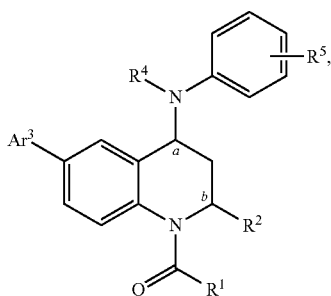

or a pharmaceutically acceptable salt thereof.

In a further aspect, the compound has a structure represented by a formula:

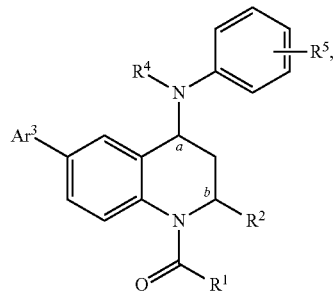

wherein $R^5$ is selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —NR$^{22a}$R$^{22b}$, —SO$_2$NR$^{22a}$R$^{22b}$, and 3- to 5-membered heterocycloalkyl or a pharmaceutically acceptable salt thereof.

In a further aspect, the compound has a structure represented by a formula:

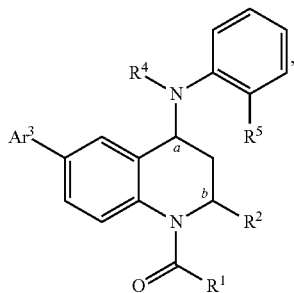

or a pharmaceutically acceptable salt thereof.

In a further aspect, the compound has a structure represented by a formula:

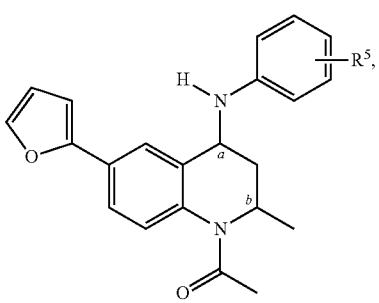

or a pharmaceutically acceptable salt thereof.

In a further aspect, the compound has a structure represented by a formula:

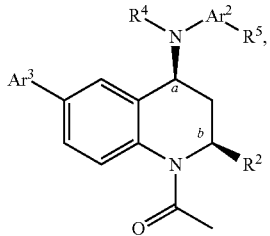

or a pharmaceutically acceptable salt thereof.

In a further aspect, the compound has a structure represented by a formula:

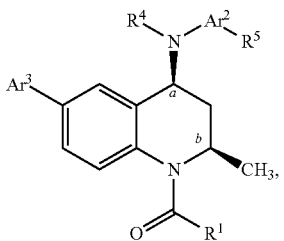

or a pharmaceutically acceptable salt thereof.

In a further aspect, the compound has a structure represented by a formula:

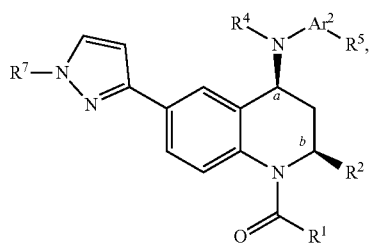

or a pharmaceutically acceptable salt thereof.

In a further aspect, the compound has a structure represented by a formula selected from:

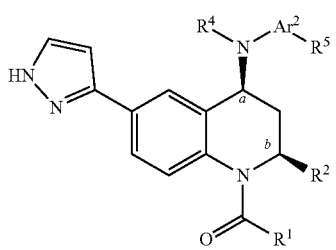

and

-continued

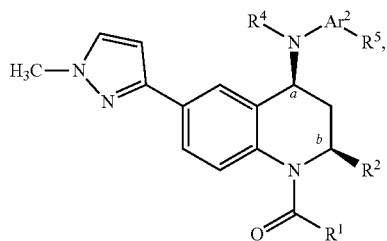

or a pharmaceutically acceptable salt thereof.

In a further aspect, the compound has a structure represented by a formula:

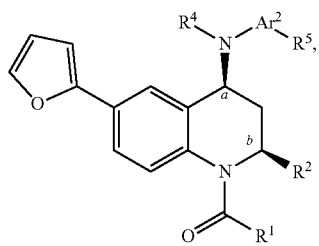

or a pharmaceutically acceptable salt thereof.

In a further aspect, the compound has a structure represented by a formula:

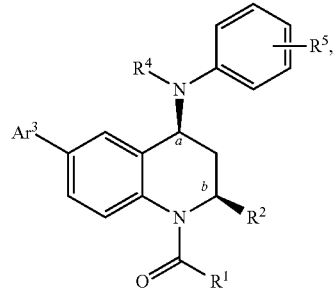

or a pharmaceutically acceptable salt thereof.

In a further aspect, the compound has a structure represented by a formula:

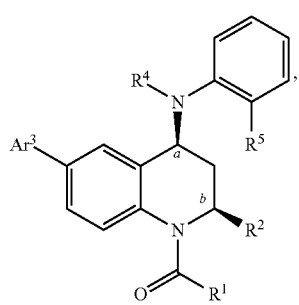

or a pharmaceutically acceptable salt thereof.

In a further aspect, the compound has a structure represented by a formula:

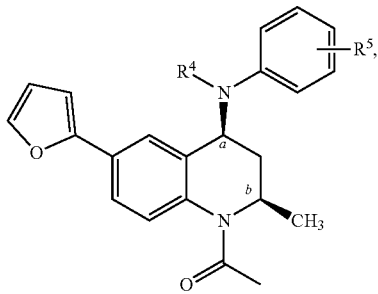

or a pharmaceutically acceptable salt thereof.

In a further aspect, the compound has a structure represented by a formula:

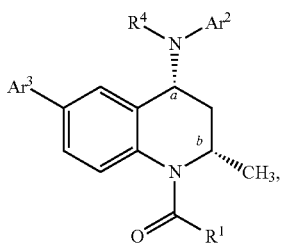

or a pharmaceutically acceptable salt thereof.

In a further aspect, the compound has a structure represented by a formula:

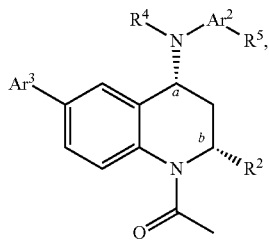

or a pharmaceutically acceptable salt thereof.

In a further aspect, the compound has a structure represented by a formula:

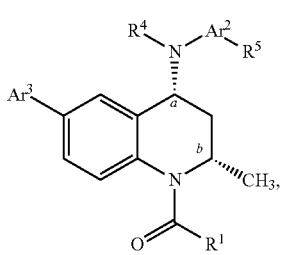

or a pharmaceutically acceptable salt thereof.

In a further aspect, the compound has a structure represented by a formula:

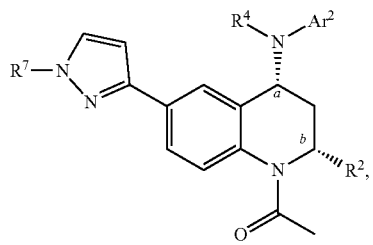

or a pharmaceutically acceptable salt thereof.

In a further aspect, the compound has a structure represented by a formula:

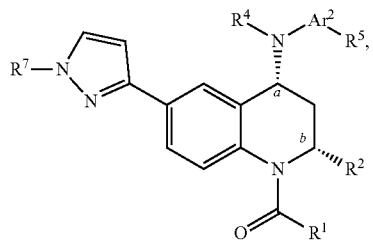

or a pharmaceutically acceptable salt thereof.

In a further aspect, the compound has a structure represented by a formula selected from:

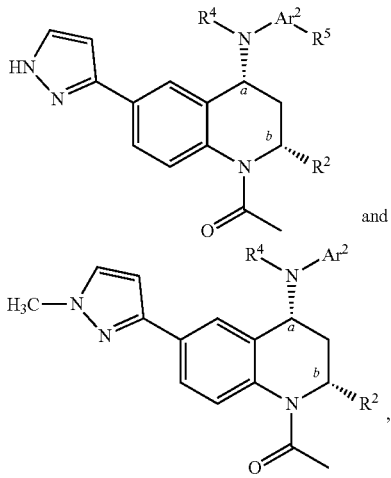

or a pharmaceutically acceptable salt thereof.

In a further aspect, the compound has a structure represented by a formula selected from:

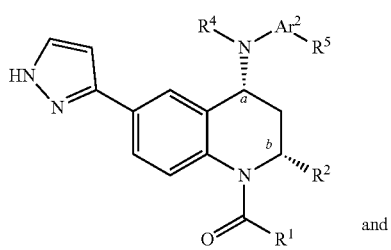

-continued

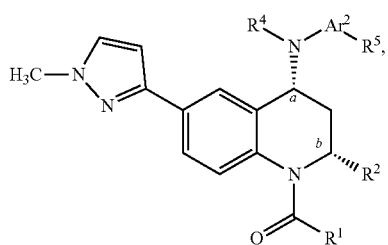

or a pharmaceutically acceptable salt thereof.

In a further aspect, the compound has a structure represented by a formula:

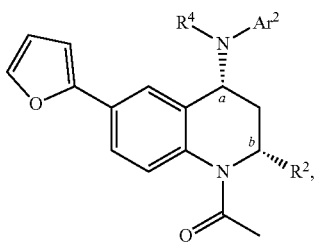

or a pharmaceutically acceptable salt thereof.

In a further aspect, the compound has a structure represented by a formula:

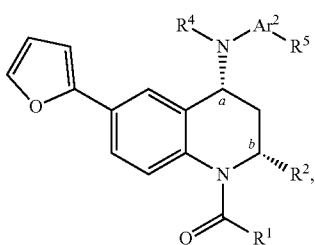

or a pharmaceutically acceptable salt thereof.

In a further aspect, the compound has a structure represented by a formula:

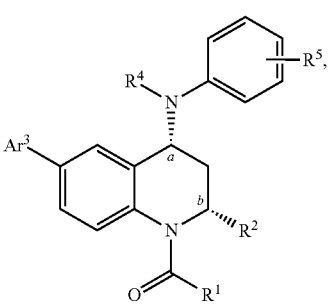

or a pharmaceutically acceptable salt thereof.

In a further aspect, the compound has a structure represented by a formula:

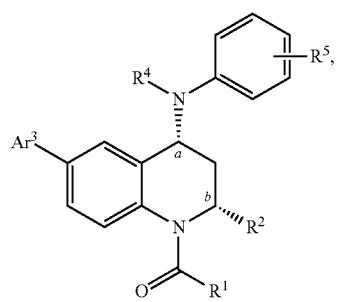

wherein $R^5$ is selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —NR$^{22a}$R$^{22b}$, —SO$_2$NR$^{22a}$R$^{22b}$, and 3- to 5-membered heterocycloalkyl or a pharmaceutically acceptable salt thereof.

In a further aspect, the compound has a structure represented by a formula:

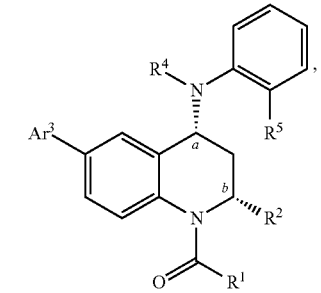

or a pharmaceutically acceptable salt thereof.

In a further aspect, the compound has a structure represented by a formula:

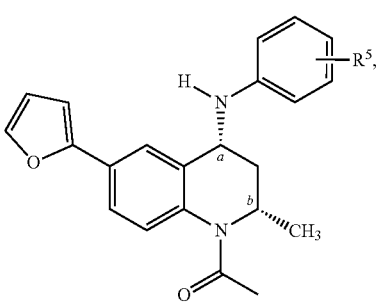

or a pharmaceutically acceptable salt thereof.

In a further aspect, the compound has a structure represented by a formula selected from:

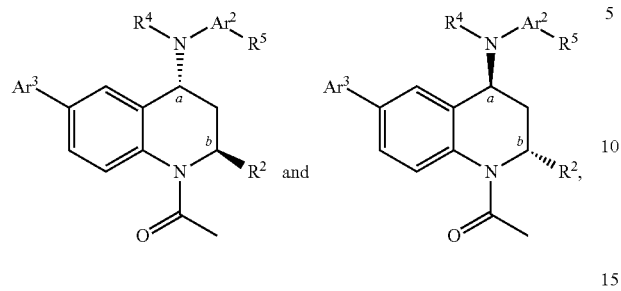

or a pharmaceutically acceptable salt thereof.

In a further aspect, the compound has a structure represented by a formula selected from:

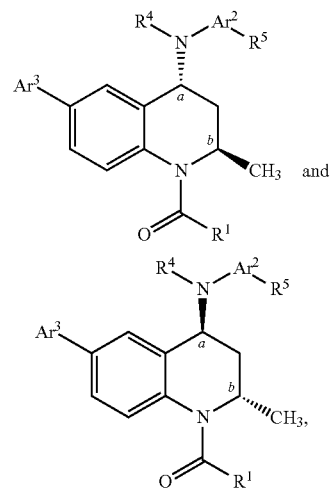

or a pharmaceutically acceptable salt thereof.

In a further aspect, the compound has a structure represented by a formula selected from:

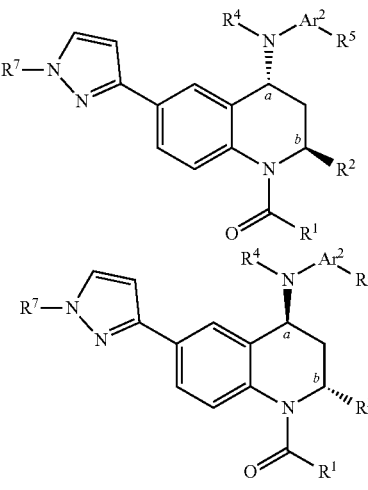

or a pharmaceutically acceptable salt thereof.

In a further aspect, the compound has a structure represented by a formula selected from:

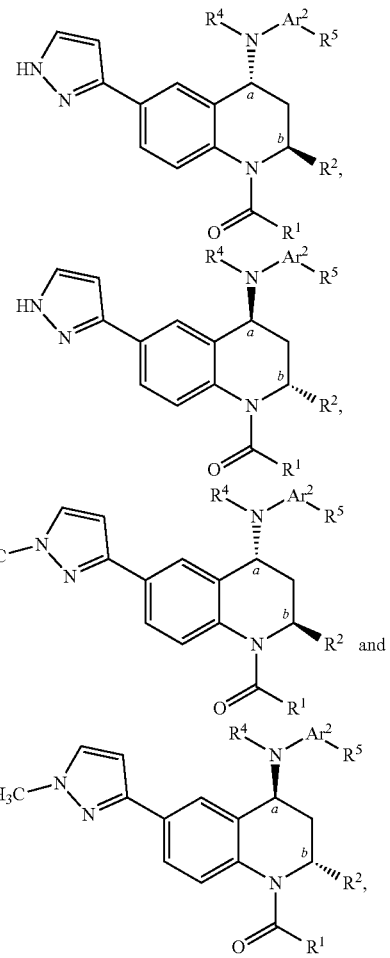

or a pharmaceutically acceptable salt thereof.

In a further aspect, the compound has a structure represented by a formula selected from:

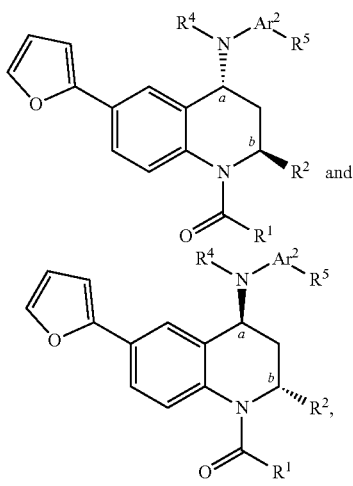

or a pharmaceutically acceptable salt thereof.

In a further aspect, the compound has a structure represented by a formula selected from:

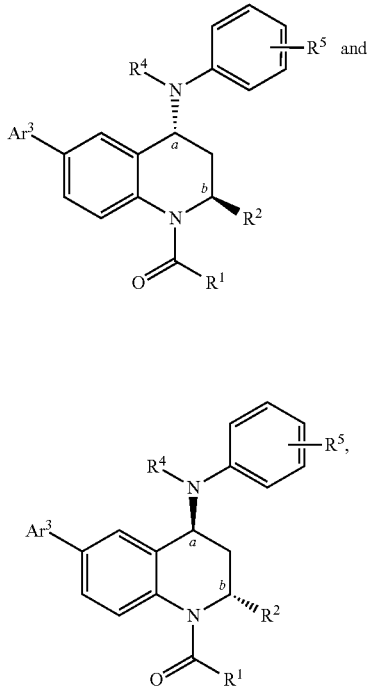

or a pharmaceutically acceptable salt thereof.

In a further aspect, the compound has a structure represented by a formula selected from:

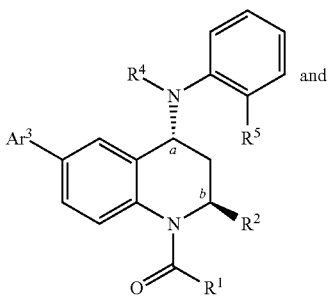

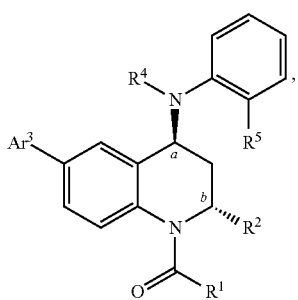

or a pharmaceutically acceptable salt thereof.

In a further aspect, the compound has a structure represented by a formula selected from:

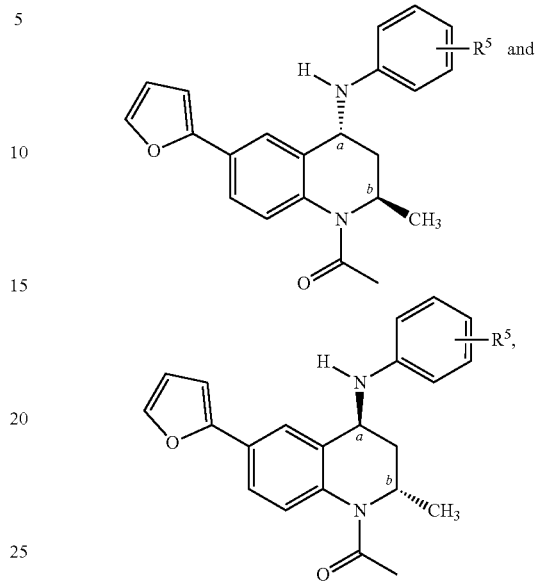

or a pharmaceutically acceptable salt thereof.

In a further aspect, each of $R^{3a}$ and $R^{3b}$ is independently selected from hydrogen, C1-C6 alkyl, C1-C6 haloalkyl, —(C1-C6 alkyl)$Cy^2$, —C(O)(C1-C6 alkyl), —C(O)$Cy^2$, and amine protecting group; wherein $Cy^2$, when present, is selected from C3-C6 cycloalkyl and C3-C6 heterocycloalkyl and is substituted with 0-4 non-hydrogen groups independently selected from halogen, —OH, —CN, C1-C4 alkyl, C1-C4 alkoxy, and C1-C4 haloalkyl; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group and wherein $R^{4b}$ is selected from $Cy^1$, $Ar^2$, and —$COR^6$; wherein $Ar^2$, when present, is selected from aryl and 5- to 12-membered heteroaryl and is substituted with 1-4 non-hydrogen groups independently selected from halogen, —OH, —CN, —$NO_2$, C1-C4 alkyl, C1-C4 alkoxy, C1-C4 haloalkyl, C1-C4 haloalkoxy, C1-C4 aminoalkyl, C3-C6 cycloalkyl, —$COR^{21}$, —$CO_2R^{21}$, —$CONR^{22a}R^{22b}$, —$NR^{22a}R^{22b}$, —$SO_2NR^{22a}R^{22b}$, and 3- to 5-membered heterocycloalkyl; wherein each occurrence of $R^{21}$, when present, is independently selected from hydrogen, C1-C6 alkyl, C3-C6 cycloalkyl, C3-C6 heterocycloalkyl, and —$COR^{30}$; and wherein $R^6$, when present, is selected from C1-C4 alkyl, C1-C4 haloalkyl, and C1-C4 alkoxy.

In a further aspect, $Ar^3$ is phenyl substituted with 1-4 non-hydrogen groups independently selected—from —$NO_2$ and $OR^{31}$; wherein each occurrence of $R^{31}$, when present, is independently selected from hydrogen, C2-C6 alkyl, and aryl; or wherein $Ar^3$ is selected from:

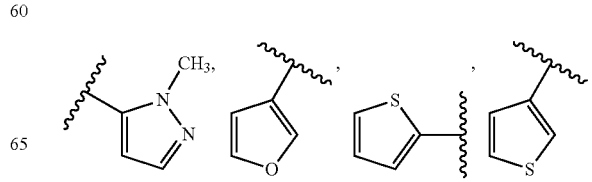

-continued

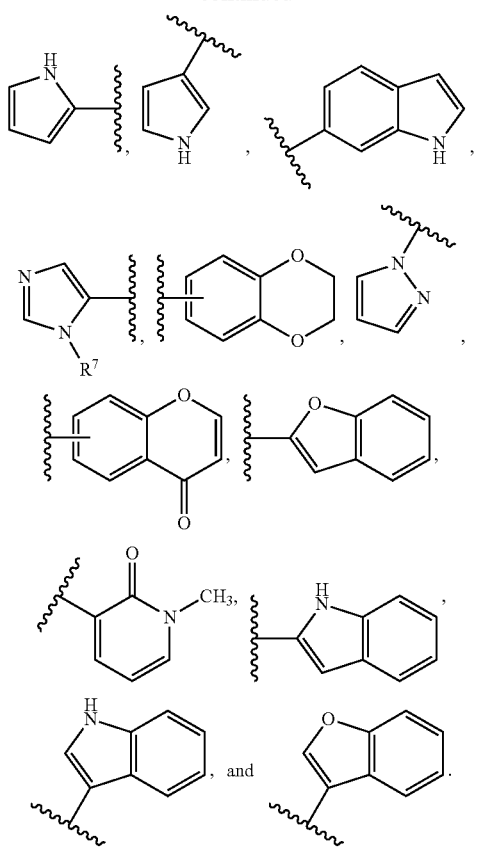

In a further aspect, $R^{4b}$ is selected from $Cy^1$, $Ar^2$, —$COR^6$, and amine protecting group; wherein $Ar^2$, when present, is selected from aryl and 5- to 12-membered heteroaryl and is substituted with 1-4 non-hydrogen groups independently selected from halogen, —OH, —CN, —$NO_2$, C1-C4 alkyl, C1-C4 alkoxy, C1-C4 haloalkyl, C1-C4 haloalkoxy, C1-C4 aminoalkyl, C3-C6 cycloalkyl, —$COR^{21}$, —$CO_2R^{21}$, —$CONR^{22a}R^{22b}$, —$NR^{22a}R^{22b}$, —$SO_2NR^{22a}R^{22b}$, and 3- to 5-membered heterocycloalkyl; and wherein each occurrence of $R^{21}$, when present, is independently selected from hydrogen, C1-C6 alkyl, C3-C6 cycloalkyl, C3-C6 heterocycloalkyl, and —$COR^{30}$; wherein $R^6$, when present, is selected from C1-C4 alkyl, C1-C4 haloalkyl, and C1-C4 alkoxy; wherein $Ar^3$ is phenyl substituted with 1-4 $OR^{31}$ groups; wherein each occurrence of $R^3$ is independently selected from hydrogen and C2-C6 alkyl; or wherein $Ar^3$ is selected from:

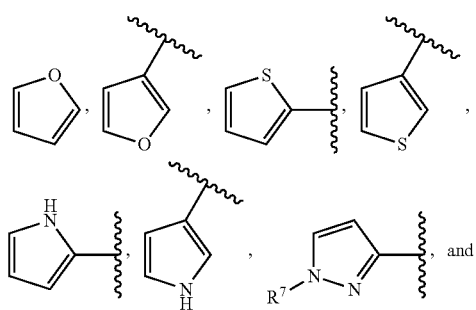

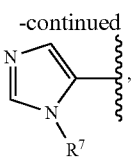

wherein $R^7$, when present, is selected from hydrogen and C1-C4 alkyl; provided that when $R^{4b}$ is —$COR^6$, then $Ar^3$ is not

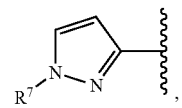

or a pharmaceutically acceptable salt thereof.

In a further aspect, $Ar^3$ is phenyl substituted with 1-4 non-hydrogen groups independently selected—from —$NO_2$ and $OR^{31}$; wherein each occurrence of $R^{31}$, when present, is independently selected from hydrogen, C2-C6 alkyl, and aryl; or wherein $Ar^3$ is selected from:

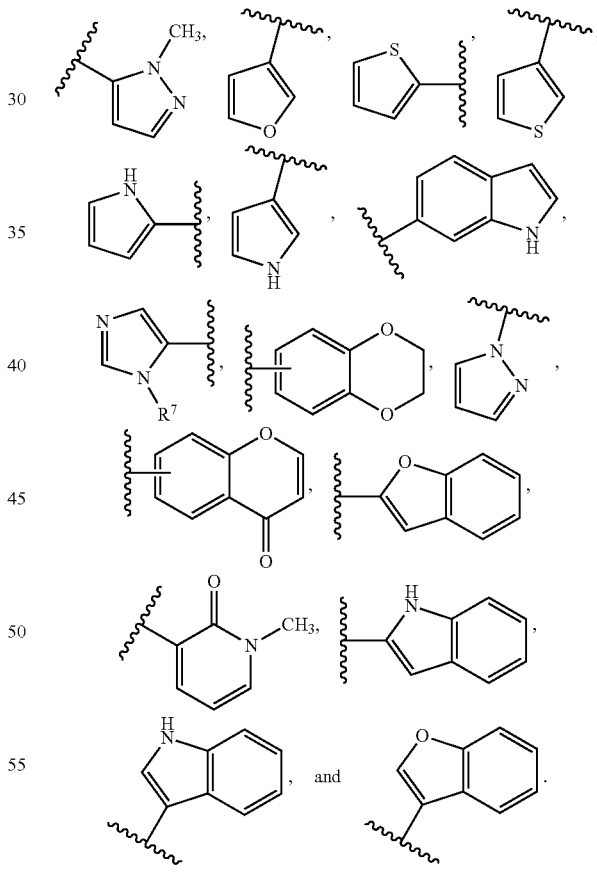

In one aspect, m, when present, is selected from 0, 1, 2, and 3. In a further aspect, m, when present, is selected from 0, 1, and 2. In a still further aspect, m, when present, is selected from 0 and 1. In yet a further aspect, m, when present, is 3. In an even further aspect, m, when present, is 2. In a still further aspect, m, when present, is 1. In yet a further aspect, m, when present, is 0.

In one aspect, each of n and o, when present, is selected from 0, 1, 2, and 3. In a further aspect, each of n and o, when present, is selected from 0, 1, and 2. In a still further aspect, each of n and o, when present, is selected from 0 and 1. In yet a further aspect, each of n and o, when present, is 3. In an even further aspect, each of n and o, when present, is 2. In a still further aspect, each of n and o, when present, is 1. In yet a further aspect, each of n and o, when present, is 0.

In one aspect, q, when present, is selected from 0, 1, 2, 3, and 4. In a further aspect, q, when present, is selected from 0, 1, 2, and 3. In a still further aspect, q, when present, is selected from 0, 1, and 2. In yet a further aspect, q, when present, is selected from 0 and 1. In an even further aspect, q, when present, is 4. In a still further aspect, q, when present, is 3. In yet a further aspect, q, when present, is 2. In an even further aspect, q, when present, is 1. In a still further aspect, q, when present, is 0.

In one aspect, r, when present, is selected from 0, 1, 2, and 3. In a further aspect, r, when present, is selected from 0, 1, and 2. In a still further aspect, r, when present, is selected from 0 and 1. In yet a further aspect, r, when present, is 3. In an even further aspect, r, when present, is 2. In a still further aspect, r, when present, is 1. In yet a further aspect, r, when present, is 0.

In one aspect, s, when present, is selected from 0, 1, and 2. In a further aspect, s, when present, is selected from 0 and 1. In a still further aspect, s, when present, is 2. In yet a further aspect, s, when present, is 1. In an even further aspect, s, when present, is 0.

In one aspect, A has a structure:

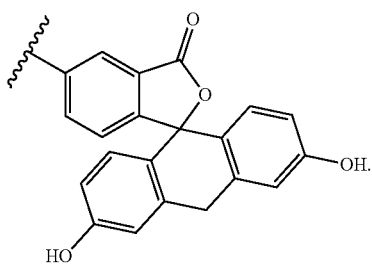 [SMILES: *c1ccc2c(c1)C(=O)OC21c2ccc(O)cc2Cc2cc(O)ccc21]

a. $R^1$ Groups

In one aspect, $R^1$ is selected from C1-C4 alkyl, C1-C4 haloalkyl, and C1-C4 deuterated alkyl.

In a further aspect, $R^1$ is selected from C1-C4 alkyl and C1-C4 haloalkyl. In a still further aspect, $R^1$ is selected from methyl, ethyl, n-propyl, i-propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, and —$CCl_3$. In yet a further aspect, $R^1$ is selected from methyl, ethyl, —$CH_2F$, —$CH_2Cl$, —$CH_2CH_2F$, —$CH_2CH_2Cl$, —$CHF_2$, —$CF_3$, —$CHCl_2$, and —$CCl_3$. In an even further aspect, $R^1$ is selected from methyl, —$CH_2F$, —$CH_2Cl$, —$CHF_2$, —$CF_3$, —$CHCl_2$, and —$CCl_3$.

In a further aspect, $R^1$ is C1-C4 haloalkyl. In a still further aspect, $R^1$ is selected from —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, and —$CCl_3$. In yet a further aspect, $R^1$ is selected from —$CH_2F$, —$CH_2Cl$, —$CH_2CH_2F$, —$CH_2CH_2Cl$, —$CHF_2$, —$CF_3$, —$CHCl_2$, and —$CCl_3$. In an even further aspect, $R^1$ is selected from —$CH_2F$, —$CH_2Cl$, —$CHF_2$, —$CF_3$, —$CHCl_2$, and —$CCl_3$.

In a further aspect, $R^1$ is C1-C4 alkyl. In a still further aspect, $R^1$ is selected from methyl, ethyl, n-propyl, i-propyl, n-butyl, sec-butyl, i-butyl, and t-butyl. In yet a further aspect, $R^1$ is selected from methyl, ethyl, n-propyl, and i-propyl. In an even further aspect, $R^1$ is selected from methyl and ethyl. In a still further aspect, $R^1$ is ethyl. In yet a further aspect, $R^1$ is methyl. In yet a further aspect, $R^1$ is C1-C4 deuterated alkyl.

b. $R^2$ Groups

In one aspect, $R^2$ is C1-C4 alkyl. In a still further aspect, $R^2$ is selected from methyl, ethyl, n-propyl, i-propyl, n-butyl, sec-butyl, i-butyl, and t-butyl. In yet a further aspect, $R^2$ is selected from methyl, ethyl, n-propyl, and i-propyl. In an even further aspect, $R^2$ is selected from methyl and ethyl. In a still further aspect, $R^2$ is ethyl. In yet a further aspect, $R^2$ is methyl.

In a further aspect, $R^2$ is C1-C4 alkyl and optionally substituted with 1, 2, or 3 groups independently selected halogen groups. In a further aspect, $R^2$ is selected from methyl, ethyl, n-propyl, i-propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, and —$CCl_3$. In a still further aspect, $R^2$ is selected from methyl, ethyl, —$CH_2F$, —$CH_2Cl$, —$CH_2CH_2F$, —$CH_2CH_2Cl$, —$CHF_2$, —$CF_3$, —$CHCl_2$, and —$CCl_3$. In yet a further aspect, $R^2$ is selected from methyl, —$CH_2F$, —$CH_2Cl$, —$CHF_2$, —$CF_3$, —$CHCl_2$, and —$CCl_3$.

In a further aspect, $R^2$ is C1-C4 alkyl and optionally substituted with 1 or 2 groups independently selected halogen groups. In a still further aspect, $R^2$ is C1-C4 alkyl and optionally monosubstituted with a halogen group. In yet a further aspect, $R^2$ is selected from unsubstituted C1-C4 alkyl.

c. $R^{3a}$ and $R^{3b}$ Groups

In one aspect, each of $R^{3a}$ and $R^{3b}$ is independently selected from hydrogen, C1-C6 alkyl, C1-C6 haloalkyl, $Cy^2$, —(C1-C6 alkyl)$Cy^2$, —(C1-C6 alkyl)$Ar^4$, —C(O)(C1-C6 alkyl), —C(O)$(CH_2)_m Cy^2$, —C(O)$(CH_2)_m Ar^4$, —C(O)(C1-C4 alkyl)CCH, —$CO_2$(C1-C6 alkyl), and amine protecting group.

In one aspect, each of $R^{3a}$ and $R^{3b}$ is independently selected from hydrogen, C1-C6 alkyl, C1-C6 haloalkyl, —(C1-C6 alkyl)(C3-C6 cycloalkyl), —(C1-C6 alkyl)(C3-C6 heterocycloalkyl), —C(O)(C1-C6 alkyl), —C(O)(C3-C4 cycloalkyl), and amine protecting group; or each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl, provided that each of $R^{3a}$ and $R^{3b}$ is not hydrogen when $R^{4b}$ is —$COR^6$ or when $Ar^1$ is six-membered heteroaryl; and provided that each of $R^{3a}$ and $R^{3b}$ are not covalently bonded together when $Ar^1$ is six-membered heteroaryl.

In a further aspect, each of $R^{3a}$ and $R^{3b}$ is independently selected from hydrogen, $Cy^2$, —(C1-C6 alkyl)$Cy^2$, —(C1-C6 alkyl)$Ar^4$, and amine protecting group. In a still further aspect, each of $R^{3a}$ and $R^{3b}$ is independently selected from hydrogen, $Cy^2$, —(C1-C3 alkyl)$Cy^2$, —(C1-C3 alkyl)$Ar^4$, and amine protecting group. In yet a further aspect, each of $R^{3a}$ and $R^{3b}$ is independently selected from hydrogen and $Cy^2$. In an even further aspect, each of $R^{3a}$ and $R^{3b}$ is independently selected from hydrogen and —(C1-C3 alkyl)$Cy^2$. In a still further aspect, each of $R^{3a}$ and $R^{3b}$ is independently selected from hydrogen and —(C1-C3 alkyl)$Ar^4$.

In a further aspect, each of $R^{3a}$ and $R^{3b}$ is independently selected from hydrogen, —C(O)(C1-C6 alkyl), —C(O)$(CH_2)_m Cy^2$, —C(O)$(CH_2)_m Ar^4$, —C(O)(C1-C4 alkyl)CCH, —and —CO$_2$(C1-C6 alkyl). In a still further aspect, each of R$^{3a}$ and R$^{3b}$ is independently selected from hydrogen, —C(O)(C1-C6 alkyl), —C(O)(CH$_2$)$_m$Cy$^2$, —C(O)(CH$_2$)$_m$Ar$^4$, and —C(O)(C1-C4 alkyl)CCH. In yet a further aspect, each of R$^{3a}$ and R$^{3b}$ is independently selected from hydrogen, —C(O)(C1-C6 alkyl), —C(O)(CH$_2$)$_m$Cy$^2$, and —C(O)(CH$_2$)$_m$Ar$^4$. In an even further aspect, each of R$^{3a}$ and R$^{3b}$ is independently selected from hydrogen, —C(O)(CH$_2$)$_m$Cy$^2$, and —C(O)(CH$_2$)$_m$Ar$^4$. In a still further aspect, each of R$^{3a}$ and R$^{3b}$ is independently selected from hydrogen and —C(O)(C1-C6 alkyl). In yet a further aspect, each of R$^{3a}$ and R$^{3b}$ is independently selected from hydrogen and —C(O)(CH$_2$)$_m$Cy$^2$. In an even further aspect, each of R$^{3a}$ and R$^{3b}$ is independently selected from hydrogen and —C(O)(CH$_2$)$_m$Ar$^4$. In a still further aspect, each of R$^{3a}$ and R$^{3b}$ is independently selected from hydrogen and —C(O)(C1-C4 alkyl)CCH.

In a further aspect, each of R$^{3a}$ and R$^{3b}$ is independently selected from hydrogen, C1-C6 alkyl, C1-C6 haloalkyl, —(C1-C6 alkyl)(C3-C6 cycloalkyl), —(C1-C6 alkyl)(C3-C6 heterocycloalkyl), —C(O)(C1-C6 alkyl), —C(O)(C3-C4 cycloalkyl), and amine protecting group. In a still further aspect, each of R$^{3a}$ and R$^{3b}$ is hydrogen.

In a further aspect, each of R$^{3a}$ and R$^{3b}$ is independently selected from hydrogen and amine protecting group. Examples of amine protecting groups include, but are not limited to, carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, and 4-nitrobenzenesulfonyl. In a still further aspect, each of R$^{3a}$ and R$^{3b}$ is independently selected from hydrogen and t-butyloxycarbonyl.

In a further aspect, each of R$^{3a}$ and R$^{3b}$ is independently selected from hydrogen, C1-C6 alkyl, C1-C6 haloalkyl, —(C1-C6 alkyl)(C3-C6 cycloalkyl), —(C1-C6 alkyl)(C3-C6 heterocycloalkyl), —C(O)(C1-C6 alkyl), —C(O)(C3-C4 cycloalkyl). In still further aspect, each of R$^{3a}$ and R$^{3b}$ is independently selected from hydrogen, C1-C3 alkyl, C1-C3 haloalkyl, —(C1-C3 alkyl)(C3-C6 cycloalkyl), —(C1-C3 alkyl)(C3-C6 heterocycloalkyl), —C(O)(C1-C3 alkyl), —C(O)(C3-C4 cycloalkyl). In yet a further aspect, each of R$^{3a}$ and R$^{3b}$ is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CH$_2$(cyclopropyl), —CH$_2$CH$_2$(cyclobutyl), —CH$_2$CH$_2$(cyclopentyl), —CH$_2$CH$_2$(cyclohexyl), —CH$_2$(cyclopropyl), —CH$_2$(cyclobutyl), —CH$_2$(cyclopentyl), —CH$_2$(cyclohexyl), —CH$_2$CH$_2$(morpholinyl), —CH$_2$(morpholinyl), —C(O)CH$_2$CH$_3$, —C(O)CH$_3$, —C(O)cyclopropyl, and —C(O)cyclobutyl. In an even further aspect, each of R$^{3a}$ and R$^{3b}$ is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CH$_2$(cyclopropyl), —CH$_2$CH$_2$(cyclobutyl), —CH$_2$(cyclopropyl), —CH$_2$(cyclobutyl), —C(O)CH$_2$CH$_3$, —C(O)CH$_3$, —C(O)cyclopropyl, and —C(O)cyclobutyl. In a still further aspect, each of R$^{3a}$ and R$^{3b}$ is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$(cyclopropyl), —C(O)CH$_2$CH$_3$, —C(O)CH$_3$, and —C(O)cyclopropyl. In yet a further aspect, each of R$^{3a}$ and R$^{3b}$ is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —C(O)CH$_2$CH$_3$, and —C(O)CH$_3$. In an even further aspect, each of R$^{3a}$ and R$^{3b}$ is independently selected from hydrogen, methyl, —CH$_2$F, —CH$_2$Cl, —CHF$_2$, —CF$_3$, —CHCl$_2$, —CCl$_3$, and —C(O)CH$_3$.

In a further aspect, each of R$^{3a}$ and R$^{3b}$ is independently selected from hydrogen and C1-C6 alkyl. In a still further aspect, each of R$^{3a}$ and R$^{3b}$ is independently selected from hydrogen and C1-C6 alkyl. In yet a further aspect, each of R$^{3a}$ and R$^{3b}$ is independently selected from hydrogen, methyl, ethyl, n-propyl, and i-propyl. In an even further aspect, each of R$^{3a}$ and R$^{3b}$ is independently selected from hydrogen, methyl, and ethyl. In a still further aspect, each of R$^{3a}$ and R$^{3b}$ is independently selected from hydrogen and ethyl. In yet a further aspect, each of R$^{3a}$ and R$^{3b}$ is independently selected from hydrogen and methyl.

In a further aspect, each of R$^{3a}$ and R$^{3b}$ is independently selected from C1-C6 alkyl, C1-C6 haloalkyl, —(C1-C6 alkyl)(C3-C6 cycloalkyl), —(C1-C6 alkyl)(C3-C6 heterocycloalkyl), —C(O)(C1-C6 alkyl), —C(O)(C3-C4 cycloalkyl), and amine protecting group.

In a further aspect, each of R$^{3a}$ and R$^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl. In a still further aspect, each of R$^{3a}$ and R$^{3b}$ are optionally covalently bonded together and, together with the intermediate atoms, comprise a 3- to 7-membered heterocycloalkyl, or a 5- to 7-membered heteroaryl and are substituted with 0-3 non-hydrogen groups independently selected from halogen, —OH, —CN, C1-C4 alkyl, C1-C4 alkoxy, and C1-C4 haloalkyl. In yet a further aspect, each of R$^{3a}$ and R$^{3b}$ are optionally covalently bonded together and, together with the intermediate atoms, comprise a 3- to 7-membered heterocycloalkyl, or a 5- to 7-membered heteroaryl and are substituted with 0-2 non-hydrogen groups independently selected from halogen, —OH, —CN, C1-C4 alkyl, C1-C4 alkoxy, and C1-C4 haloalkyl. In an even further aspect, each of R$^{3a}$ and R$^{3b}$ are optionally covalently bonded together and, together with the intermediate atoms, comprise a 3- to 7-membered heterocycloalkyl, or a 5- to 7-membered heteroaryl and are substituted with 0-1 non-hydrogen groups independently selected from halogen, —OH, —CN, C1-C4 alkyl, C1-C4 alkoxy, and C1-C4 haloalkyl. In a still further aspect, each of R$^{3a}$ and R$^{3b}$ are optionally covalently bonded together and, together with the intermediate atoms, comprise a 3- to 7-membered heterocycloalkyl, or a 5- to 7-membered heteroaryl and are substituted with a non-hydrogen group selected from halogen, —OH, —CN, C1-C4 alkyl, C1-C4 alkoxy, and C1-C4 haloalkyl. In yet a further aspect, each of R$^{3a}$ and R$^{3b}$ are optionally covalently bonded together and, together with the intermediate atoms, comprise a 3- to 7-membered heterocycloalkyl, or a 5- to 7-membered heteroaryl and are unsubstituted.

In a further aspect, each of R$^{3a}$ and R$^{3b}$ are optionally covalently bonded together and, together with the intermediate atoms, comprise a 3- to 7-membered heterocycloalkyl substituted with 0-4 non-hydrogen groups independently selected from halogen, —OH, —CN, C1-C4 alkyl, C1-C4 alkoxy, and C1-C4 haloalkyl. In a still further aspect, each of R$^{3a}$ and R$^{3b}$ are optionally covalently bonded together and, together with the intermediate atoms, comprise a 3- to 7-membered heterocycloalkyl substituted with 0-3 non-hydrogen groups independently selected from halogen, —OH, —CN, C1-C4 alkyl, C1-C4 alkoxy, and C1-C4 haloalkyl. In yet a further aspect, each of R$^{3a}$ and R$^{3b}$ are optionally covalently bonded together and, together with the intermediate atoms, comprise a 3- to 7-membered heterocycloalkyl substituted with 0-2 non-hydrogen groups independently selected from halogen, —OH, —CN, C1-C4 alkyl, C1-C4 alkoxy, and C1-C4 haloalkyl. In an even further aspect, each of $R^{3a}$ and $R^{3b}$ are optionally covalently bonded together and, together with the intermediate atoms, comprise a 3- to 7-membered heterocycloalkyl substituted with 0-1 non-hydrogen groups independently selected from halogen, —OH, —CN, C1-C4 alkyl, C1-C4 alkoxy, and C1-C4 haloalkyl. In a still further aspect, each of $R^{3a}$ and $R^{3b}$ are optionally covalently bonded together and, together with the intermediate atoms, comprise a 3- to 7-membered heterocycloalkyl substituted with a non-hydrogen group selected from halogen, —OH, —CN, C1-C4 alkyl, C1-C4 alkoxy, and C1-C4 haloalkyl. In yet a further aspect, each of $R^{3a}$ and $R^{3b}$ are optionally covalently bonded together and, together with the intermediate atoms, comprise an unsubstituted 3- to 7-membered heterocycloalkyl.

In a further aspect, each of $R^{3a}$ and $R^{3b}$ are optionally covalently bonded together and, together with the intermediate atoms, comprise a 5- to 7-membered heteroaryl substituted with 0-4 non-hydrogen groups independently selected from halogen, —OH, —CN, C1-C4 alkyl, C1-C4 alkoxy, and C1-C4 haloalkyl. In a still further aspect, each of $R^{3a}$ and $R^{3b}$ are optionally covalently bonded together and, together with the intermediate atoms, comprise a 5- to 7-membered heteroaryl substituted with 0-3 non-hydrogen groups independently selected from halogen, —OH, —CN, C1-C4 alkyl, C1-C4 alkoxy, and C1-C4 haloalkyl. In yet a further aspect, each of $R^{3a}$ and $R^{3b}$ are optionally covalently bonded together and, together with the intermediate atoms, comprise a 5- to 7-membered heteroaryl substituted with 0-2 non-hydrogen groups independently selected from halogen, —OH, —CN, C1-C4 alkyl, C1-C4 alkoxy, and C1-C4 haloalkyl. In an even further aspect, each of $R^{3a}$ and $R^{3b}$ are optionally covalently bonded together and, together with the intermediate atoms, comprise a 5- to 7-membered heteroaryl substituted with 0-1 non-hydrogen groups independently selected from halogen, —OH, —CN, C1-C4 alkyl, C1-C4 alkoxy, and C1-C4 haloalkyl. In a still further aspect, each of $R^{3a}$ and $R^{3b}$ are optionally covalently bonded together and, together with the intermediate atoms, comprise a 5- to 7-membered heteroaryl substituted with a non-hydrogen group selected from halogen, —OH, —CN, C1-C4 alkyl, C1-C4 alkoxy, and C1-C4 haloalkyl. In yet a further aspect, each of $R^{3a}$ and $R^{3b}$ are optionally covalently bonded together and, together with the intermediate atoms, comprise an unsubstituted 5- to 7-membered heteroaryl.

In a further aspect, each of $R^{3a}$ and $R^{3b}$ are optionally covalently bonded together and, together with the intermediate atoms, comprise a morpholinyl substituted with 0-4 non-hydrogen groups independently selected from halogen, —OH, —CN, C1-C4 alkyl, C1-C4 alkoxy, and C1-C4 haloalkyl. In a still further aspect, each of $R^{3a}$ and $R^{3b}$ are optionally covalently bonded together and, together with the intermediate atoms, comprise a morpholinyl substituted with 0-3 non-hydrogen groups independently selected from halogen, —OH, —CN, C1-C4 alkyl, C1-C4 alkoxy, and C1-C4 haloalkyl. In yet a further aspect, each of $R^{3a}$ and $R^{3b}$ are optionally covalently bonded together and, together with the intermediate atoms, comprise a morpholinyl substituted with 0-2 non-hydrogen groups independently selected from halogen, —OH, —CN, C1-C4 alkyl, C1-C4 alkoxy, and C1-C4 haloalkyl. In an even further aspect, each of $R^{3a}$ and $R^{3b}$ are optionally covalently bonded together and, together with the intermediate atoms, comprise a morpholinyl substituted with 0-1 non-hydrogen groups independently selected from halogen, —OH, —CN, C1-C4 alkyl, C1-C4 alkoxy, and C1-C4 haloalkyl. In a still further aspect, each of $R^{3a}$ and $R^{3b}$ are optionally covalently bonded together and, together with the intermediate atoms, comprise a morpholinyl substituted with a non-hydrogen group selected from halogen, —OH, —CN, C1-C4 alkyl, C1-C4 alkoxy, and C1-C4 haloalkyl. In yet a further aspect, each of $R^{3a}$ and $R^{3b}$ are optionally covalently bonded together and, together with the intermediate atoms, comprise an unsubstituted morpholinyl.

d. $R^{4a}$ and $R^{4b}$ Groups

In one aspect, $R^{4a}$ is selected from hydrogen, C1-C4 alkyl, and amine protecting group and $R^{4b}$ is selected from C4-C8 alkyl, —$(CH_2)_nCy^1$, —$(CH_2)_oAr^2$, and —$COR^6$; or wherein each of $R^{4a}$ and $R^{4b}$ is hydrogen. In a further aspect, $R^{4a}$ is selected from hydrogen, C1-C4 alkyl, and amine protecting group and $R^{4b}$ is selected from C4-C8 alkyl, —$(CH_2)_nCy^1$, —$(CH_2)_oAr^2$, and —$COR^6$. In a still further aspect, each of $R^{4a}$ and $R^{4b}$ is hydrogen.

In one aspect, $R^{4a}$ is selected from hydrogen, C1-C4 alkyl, and amine protecting group and $R^{4b}$ is selected from $Cy^1$, $Ar^2R^5$, and —$COR^6$. Examples of amine protecting groups include, but are not limited to, carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, and 4-nitrobenzenesulfonyl. Thus, in a further aspect, $R^{4a}$ is selected from hydrogen, C1-C4 alkyl, and t-butyloxycarbonyl and $R^{4b}$ is selected from $Cy^1$, $Ar^2R^5$, and —$COR^6$. In a still further aspect, $R^{4a}$ is selected from hydrogen, methyl, ethyl, n-propyl, i-propyl, and t-butyloxycarbonyl and $R^{4b}$ is selected from $Cy^1$, $Ar^2R^5$, and —$COR^6$. In yet a further aspect, $R^{4a}$ is selected from hydrogen, methyl, ethyl, and t-butyloxycarbonyl and $R^{4b}$ is selected from $Cy^1$, $Ar^2R^5$, and —$COR^6$. In an even further aspect, $R^{4a}$ is selected from hydrogen, methyl, and t-butyloxycarbonyl, and $R^{4b}$ is selected from $Cy^1$, $Ar^2R^5$, and —$COR^6$. In a still further aspect, $R^{4a}$ is t-butyloxycarbonyl and $R^{4b}$ is selected from $Cy^1$, $Ar^2R^5$, and —$COR^6$. In yet a further aspect, $R^{4a}$ is methyl and $R^{4b}$ is selected from $Cy^1$, $Ar^2R^5$, and —$COR^6$. In an even further aspect, $R^{4a}$ is hydrogen and $R^{4b}$ is selected from $Cy^1$, $Ar^2R^5$, and —$COR^6$.

In one aspect, $R^{4a}$ is selected from hydrogen, C1-C4 alkyl, and amine protecting group; and $R^{4b}$ is selected from —$(CH_2)_nCy^1$, —$(CH_2)_oAr^2$, —$COR^6$, and amine protecting group.

In one aspect, $R^{4a}$ is selected from hydrogen, C1-C4 alkyl, and amine protecting group and $R^{4b}$ is selected $Cy^1$, $Ar^2R^5$, —$COR^6$, and amine protecting group, provided that when $R^{4b}$ is —$COR^6$, then $Ar^3$ is not

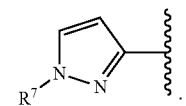

Examples of amine protecting groups include, but are not limited to, carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, and 4-nitrobenzenesulfonyl. Thus, in a further aspect, $R^{4a}$ is selected from hydrogen, C1-C4 alkyl, and t-butyloxycarbonyl and $R^{4b}$ is selected from $Cy^1$, $Ar^2R^5$, —$COR^6$, and amine protecting group. In a still further aspect, $R^{4a}$ is selected from hydrogen, methyl, ethyl, n-propyl, i-propyl, and t-butyloxycarbonyl and $R^{4b}$ is selected from $Cy^1$, $Ar^2R^5$, —$COR^6$, and amine protecting group. In yet a further aspect, $R^{4a}$ is selected from hydrogen, methyl, ethyl, and t-butyloxycarbonyl and $R^{4b}$ is selected from $Cy^1$, $Ar^2R^5$, —$COR^6$, and amine protecting group. In an even further aspect, $R^{4a}$ is selected from hydrogen, methyl, and t-butyloxycarbonyl, and $R^{4b}$ is selected from $Cy^1$, $Ar^2R^5$, —$COR^6$, and amine protecting group. In a still further aspect, $R^{4a}$ is t-butyloxycarbonyl and $R^{4b}$ is selected from $Cy^1$, $Ar^2R^5$, —$COR^6$, and amine protecting group. In yet a further aspect, $R^{4a}$ is methyl and $R^{4b}$ is selected from $Cy^1$, $Ar^2R^5$, —$COR^6$, and amine protecting group. In an even further aspect, $R^{4a}$ is hydrogen and $R^{4b}$ is selected from $Cy^1$, $Ar^2R^5$, —$COR^6$, and amine protecting group.

In a further aspect, $R^{4a}$ is selected from hydrogen, C1-C4 alkyl, and amine protecting group and $R^{4b}$ is selected from $Cy^1$ and $Ar^2R^5$. In a still further aspect, $R^{4a}$ is selected from hydrogen, C1-C4 alkyl, and amine protecting group and $R^{4b}$ is selected from $Cy^1$ and —$COR^6$. In yet a further aspect, $R^{4a}$ is selected from hydrogen, C1-C4 alkyl, and amine protecting group and $R^{4b}$ is selected from $Ar^2R^5$ and —$COR^6$. In an even further aspect, $R^{4a}$ is selected from hydrogen, C1-C4 alkyl, and amine protecting group and $R^{4b}$ is $Cy^1$. In a still further aspect, $R^{4a}$ is selected from hydrogen, C1-C4 alkyl, and amine protecting group and $R^{4b}$ is $Ar^2R^5$. In yet a further aspect, $R^{4a}$ is selected from hydrogen, C1-C4 alkyl, and amine protecting group and $R^{4b}$ is —$COR^6$.

In a further aspect, $R^{4a}$ is selected from hydrogen, C1-C4 alkyl, and amine protecting group and $R^{4b}$ is selected from $Ar^2R^5$, —$COR^6$, and amine protecting group. In a still further aspect, $R^{4a}$ is selected from hydrogen, C1-C4 alkyl, and amine protecting group and $R^{4b}$ is selected from $Cy^1$, —$COR^6$, and amine protecting group. In yet a further aspect, $R^{4a}$ is selected from hydrogen, C1-C4 alkyl, and amine protecting group and $R^{4b}$ is selected from $Cy^1$, $Ar^2R^5$, and amine protecting group. In an even further aspect, $R^{4a}$ is selected from hydrogen, C1-C4 alkyl, and amine protecting group and $R^{4b}$ is selected from $Cy^1$ and amine protecting group. In a still further aspect, $R^{4a}$ is selected from hydrogen, C1-C4 alkyl, and amine protecting group and $R^{4b}$ is selected from $Ar^2R^5$ and amine protecting group. In yet a further aspect, $R^{4a}$ is selected from hydrogen, C1-C4 alkyl, and amine protecting group and $R^{4b}$ is selected from —$COR^6$ and amine protecting group. In an even further aspect, $R^{4a}$ is selected from hydrogen, C1-C4 alkyl, and amine protecting group and $R^{4b}$ is amine protecting group.

In a further aspect, $R^{4a}$ is hydrogen and $R^{4b}$ is $Ar^2R^5$. In a further aspect, $R^{4a}$ is hydrogen and $R^{4b}$ is $Ar^2$.

In a further aspect, $R^{4a}$ is hydrogen and $R^{4b}$ is amine protecting group.

In a further aspect, $R^{4b}$ is selected from C4-C8 alkyl, —$(CH_2)_nCy^1$, and —$(CH_2)_oAr^2$. In a still further aspect, $R^{4b}$ is selected from C4-C8 alkyl, —$CH_2Cy^1$, and —$CH_2Ar^2$. In yet a further aspect, $R^{4b}$ is selected from C4-C8 alkyl, —$Cy^1$, and —$Ar^2$.

In a further aspect, $R^{4b}$ is C4-C8 alkyl. In a still further aspect, $R^{4b}$ is selected from C4-C6 alkyl. In an even further aspect, $R^{4b}$ is selected from C4-C6 alkyl. In a still further aspect, $R^{4b}$ is selected from n-butyl, i-butyl, sec-butyl, and t-butyl. In yet a further aspect, $R^{4b}$ is i-butyl.

In a further aspect, $R^{4b}$ is selected from —$(CH_2)_nCy^1$ and —$(CH_2)_oAr^2$. In a still further aspect, $R^{4b}$ is selected from —$CH_2Cy^1$ and —$CH_2Ar^2$. In yet a further aspect, $R^{4b}$ is selected from —$Cy^1$ and -$A^2$.

In a further aspect, $R^{4a}$ is selected from hydrogen, C1-C4 alkyl, and amine protecting group and wherein $R^{4b}$ is selected from C4-C8 alkyl, —$(CH_2)_nCy^1$, —$(CH_2)_oAr^2$, and —$COR^6$.

In a further aspect, $R^{4b}$ is selected from —$(CH_2)_nCy^1$, —$(CH_2)_oAr^2$, and —$COR^6$.

e. $R^5$ Groups

In one aspect, $R^5$, when present, is selected from halogen, —OH, —CN, —$NO_2$, C1-C4 alkyl, C1-C4 haloalkyl, C1-C4 alkoxy, C1-C4 haloalkoxy, C1-C4 alkylamino, (C1-C4)(C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and 3- to 5-membered heterocycle.

In a further aspect, $R^5$, when present, is selected from halogen, —OH, —CN, —$NO_2$, C1-C4 alkyl, C1-C4 haloalkyl, C1-C4 alkoxy, C1-C4 haloalkoxy, C1-C4 alkylamino, (C1-C4)(C1-C4) dialkylamino, C1-C4 aminoalkyl, —$COR^{21}$, —$CO_2R^{21}$, —$CONR^{22a}R^{22b}$, and —$SO_2NR^{22a}R^{22b}$. In a still further aspect, $R^5$, when present, is selected from halogen, —OH, —CN, —$NO_2$, methyl, ethyl, n-propyl, i-propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$OCH_3$, —$OCH_2CH_3$, —$OCH(CH_3)_2$, —$OCH_2CH_2CH_3$, —$OCH_2F$, —$OCH_2Cl$, —$OCH_2CH_2F$, —$OCH_2CH_2Cl$, —$OCH_2CH_2CH_2F$, —$OCH_2CH_2CH_2Cl$, —$OCHF_2$, —$OCF_3$, —$NHCH_3$, —$NHCH_2CH_3$, —$NHCH(CH_3)_2$, —$NHCH_2CH_2CH_3$, —$N(CH_3)_2$, —$N(CH_2CH_3)_2$, —$N(CH(CH_3)_2)_2$, —$N(CH_2CH_2CH_3)_2$, —$CH_2NH_2$, —$CH_2CH_2NH_2$, —$CH_2CH_2CH_2NH_2$, —$COR^{21}$, —$CO_2R^{21}$, —$CONR^{22a}R^{22b}$, and —$SO_2NR^{22a}R^{22b}$. In yet a further aspect, $R^5$, when present, is selected from halogen, —OH, —CN, —$NO_2$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$OCH_3$, —$OCH_2CH_3$, —$OCH_2F$, —$OCH_2Cl$, —$OCH_2CH_2F$, —$OH_2CH_2CH$, —$OCHF_2$, —$OCF_3$, —$NHCH_3$, —$NHCH_2CH_3$, —$N(CH_3)_2$, —$N(CH_2CH_3)_2$, —$CH_2NH_2$, —$CH_2CH_2NH_2$, —$COR^{21}$, —$CO_2R^{21}$, —$CONR^{22a}R^{22b}$, and —$SO_2NR^{22a}R^{22b}$. In an even further aspect, $R^5$, when present, is selected from halogen, —OH, —CN, —$NO_2$, methyl, —$CH_2F$, —$CH_2Cl$, —$CHF_2$, —$CF_3$, —$CHCl_2$, —$CCl_3$, —$OCH_3$, —$OCH_2F$, —$OCH_2Cl$, —$OCHF_2$, —$OCF_3$, —$NHCH_3$, —$N(CH_3)_2$, —$CH_2NH_2$, —$COR^{21}$, —$CO_2R^{21}$, —$CONR^{22a}R^{22b}$, and —$SO_2NR^{22a}R^{22b}$.

In a further aspect, $R^5$, when present, is selected from halogen, —OH, —CN, —$NO_2$, C1-C4 alkyl, C1-C4 haloalkyl, C1-C4 alkoxy, C1-C4 haloalkoxy, C3-C6 cycloalkyl, —$COR^{21}$, —$CO_2R^{21}$, —$CONR^{22a}R^{22b}$, —$SO_2NR^{22a}R^{22b}$, and 3- to 5-membered heterocycle. In a still further aspect, $R^5$, when present, is selected from halogen, —OH, —CN, —$NO_2$, methyl, ethyl, n-propyl, i-propyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CHF_2$, —$CF_3$, —$CHCl_2$, —$CCl_3$, —$OCH_3$, —$OCH_2CH_3$, —$OCH(CH_3)_2$, —$OCH_2CH_2CH_3$, —$OCH_2F$, —$OCH_2Cl$, —$OCH_2CH_2F$, —$OCH_2CH_2Cl$, —$OCH_2CH_2CH_2F$, —$OCH_2CH_2CH_2Cl$, —$OCHF_2$, —$OCF_3$, —$COR^{21}$, —$CO_2R^{21}$, —$CONR^{22a}R^{22b}$, —$SO_2NR^{22a}R^{22}$, and 3- to 5-membered heterocycle. In yet a further aspect, $R^5$, when present, is selected from halogen, —OH, —CN, —$NO_2$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$OCH_3$, —$OCH_2CH_3$, —$OCH_2F$, —$OCH_2Cl$, —$OCHF_2$, —$OCF_3$, —$COR^{21}$, —$CO_2R^{21}$, —$CONR^{22a}R^{22b}$, —$SO_2NR^{22a}R^{22b}$, and 3- to 5-membered heterocycle. In an even further aspect, $R^5$, when present, is selected from halogen, —OH, —CN, —NO$_2$, methyl, —CH$_2$F, —CH$_2$Cl, —CHF$_2$, —CF$_3$, —CHCl$_2$, —CCl$_3$, —OCH$_3$, —OCH$_2$F, —OCH$_2$Cl, —OCHF$_2$, —OCF$_3$, —COR$^{21}$, —CO$_2$R$^{21}$, —CONR$^{22a}$R$^{22b}$, —SO$_2$NR$^{22a}$R$^{22b}$, and 3- to 5-membered heterocycle.

In a further aspect, R$^5$, when present, is selected from halogen, —OH, —CN, —NO$_2$, C1-C4 alkyl, C1-C4 haloalkyl, —COR$^{21}$, —CO$_2$R$^{21}$, —CONR$^{22a}$R$^{22b}$, and —SO$_2$NR$^{22a}$R$^{22b}$. In a still further aspect, R$^5$, when present, is selected from halogen, —OH, —CN, —NO$_2$, methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —COR$^{21}$, —CO$_2$R$^{21}$, —CONR$^{22a}$R$^{22b}$, and —SO$_2$NR$^{22a}$R$^{22b}$. In yet a further aspect, R$^5$, when present, is selected from halogen, —OH, —CN, —NO$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —COR$^{21}$, —CO$_2$R$^{21}$, —CONR$^{22a}$R$^{22b}$, and —SO$_2$NR$^{22a}$R$^{22b}$. In an even further aspect, R$^5$, when present, is selected from halogen, —OH, —CN, —NO$_2$, methyl, —CH$_2$F, —CH$_2$Cl, —CHF$_2$, —CF$_3$, —CHCl$_2$, —CCl$_3$, —COR$^{21}$, —CO$_2$R$^{21}$, —CONR$^{22a}$R$^{22b}$, and —SO$_2$NR$^{22a}$R$^{22b}$.

In a further aspect, R$^5$, when present, is selected from halogen, —OH, —CN, —NO$_2$, C1-C4 alkyl, C1-C4 alkoxy, C1-C4 haloalkoxy, —COR$^{21}$, —CO$_2$R$^{21}$, —CONR$^{22a}$R$^{22b}$, and —SO$_2$NR$^{22a}$R$^{22b}$. In a still further aspect, R$^5$, when present, is selected from halogen, —OH, —CN, —NO$_2$, methyl, ethyl, n-propyl, i-propyl, —OCH$_3$, —OCH$_2$CH$_3$, —OCH(CH$_3$)$_2$, —OCH$_2$CH$_2$CH$_3$, —OCH$_2$F, —OCH$_2$Cl, —OCH$_2$CH$_2$F, —OCH$_2$CH$_2$C, —OCH$_2$CH$_2$CH$_2$F, —OCH$_2$CH$_2$CH$_2$C, —OCHF$_2$, —OCF$_3$, —COR$^{21}$, —CO$_2$R$^{21}$, —CONR$^{22a}$R$^{22}$, and —SO$_2$NR$^{22a}$R$^{22b}$. In yet a further aspect, R$^5$, when present, is selected from halogen, —OH, —CN, —NO$_2$, methyl, ethyl, —OCH$_3$, —OCH$_2$CH$_3$, —OCH$_2$F, —OCH$_2$Cl, —OCH$_2$CH$_2$F, —OCH$_2$CH$_2$C, —OCHF$_2$, —OCF$_3$, —COR$^{21}$, —CO$_2$R$^{21}$, —CONR$^{22a}$R$^{22b}$, and —SO$_2$NR$^{22a}$R$^{22b}$. In an even further aspect, R$^5$, when present, is selected from halogen, —OH, —CN, —NO$_2$, methyl, —OCH$_3$, —OCH$_2$F, —OCH$_2$Cl, —OCHF$_2$, —OCF$_3$, —COR$^{21}$, —CO$_2$R$^{21}$, —CONR$^{22a}$R$^{22b}$, and —SO$_2$NR$^{22a}$R$^{22b}$.

In a further aspect, R$^5$, when present, is selected from halogen, —OH, —CN, —NO$_2$, C1-C4 alkyl, C1-C4 alkylamino, (C1-C4)C1-C4) dialkylamino, C1-C4 aminoalkyl, —COR$^{21}$, —CO$_2$R$^{21}$, —CONR$^{22a}$R$^{22b}$, and —SO$_2$NR$^{22a}$R$^{22b}$. In a still further aspect, R$^5$, when present, is selected from halogen, —OH, —CN, —NO$_2$, methyl, ethyl, n-propyl, i-propyl, —NHCH$_3$, —NHCH$_2$CH$_3$, —NHCH(CH$_3$)$_2$, —NHCH$_2$CH$_2$CH$_3$, —N(CH$_3$)$_2$, —N(CH$_2$CH$_3$)$_2$, —N(CH(CH$_3$)$_2$)$_2$, —N(CH$_2$CH$_2$CH$_3$)$_2$, —CH$_2$NH$_2$, —CH$_2$CH$_2$NH$_2$, —CH$_2$CH$_2$CH$_2$NH$_2$, —COR$^{21}$, —CO$_2$R$^{21}$, —CONR$^{22a}$R$^{22b}$, and —SO$_2$NR$^{22a}$R$^{22b}$. In yet a further aspect, R$^5$, when present, is selected from halogen, —OH, —CN, —NO$_2$, methyl, ethyl, —NHCH$_3$, —NHCH$_2$CH$_3$, —N(CH$_3$)$_2$, —N(CH$_2$CH$_3$)$_2$, —CH$_2$NH$_2$, —CH$_2$CH$_2$NH$_2$, —COR$^{21}$, —CO$_2$R$^{21}$, —CONR$^{22a}$R$^{22b}$, and —SO$_2$NR$^{22a}$R$^{22b}$. In an even further aspect, R$^5$, when present, is selected from halogen, —OH, —CN, —NO$_2$, methyl, —NHCH$_3$, —N(CH$_3$)$_2$, —CH$_2$NH$_2$, —COR$^{21}$, —CO$_2$R$^{21}$, —CONR$^{22a}$R$^{22b}$, and —SO$_2$NR$^{22a}$R$^{22b}$.

In a further aspect, R$^5$, when present, is selected from halogen and C1-C4 alkyl. In a still further aspect, R$^5$, when present, is selected from halogen, methyl, ethyl, n-propyl, and i-propyl. In yet a further aspect, R$^5$, when present, is selected from halogen, methyl, and ethyl. In an even further aspect, R$^5$, when present, is selected from halogen and methyl.

f. R$^6$ Groups

In one aspect, R$^6$, when present, is selected from C1-C4 alkyl, C1-C4 haloalkyl, C1-C4 alkoxy, and —(CH$_2$)$_s$Cy$^3$.

In one aspect, R$^6$, when present, is selected from C1-C4 alkyl, C1-C4 haloalkyl, and C1-C4 alkoxy. In a further aspect, R$^6$, when present, is selected from methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, —CCl$_3$, —OCH$_3$, —OCH$_2$CH$_3$, —OCH(CH$_3$)$_2$, and —OCH$_2$CH$_2$CH$_3$. In a still further aspect, R$^6$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, and —OCH$_2$CH$_3$. In yet a further aspect, R$^6$, when present, is selected from methyl, —CH$_2$F, —CH$_2$Cl, —CHF$_2$, —CF$_3$, —CHCl$_2$, —CCl$_3$, and —OCH$_3$.

In a further aspect, R$^6$, when present, is —(CH$_2$)$_s$Cy$^3$. In a still further aspect, R$^6$, when present, is —(CH$_2$)$_2$Cy$^3$. In yet a further aspect, R$^6$, when present, is —CH$_2$Cy$^3$. In an even further aspect, R$^6$, when present, is —Cy$^3$.

In a further aspect, R$^6$, when present, is selected from C1-C4 alkyl and C1-C4 haloalkyl. In a still further aspect, R$^6$, when present, is selected from methyl, ethyl, n-propyl, i-propyl, —CH$_2$F, —CH$_2$Cl, —CH$_2$CH$_2$F, —CH$_2$CH$_2$C, —CH$_2$CH$_2$CH$_2$F, —CH$_2$CH$_2$CH$_2$Cl, —CHF$_2$, —CF$_3$, —CHCl$_2$, and —CCl$_3$. In yet a further aspect, R$^6$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, and —CCl$_3$. In an even further aspect, R$^6$, when present, is selected from methyl, —CH$_2$F, —CH$_2$Cl, —CHF$_2$, —CF$_3$, —CHCl$_2$, and —CCl$_3$.

In a further aspect, R$^6$, when present, is selected from C1-C4 alkyl and C1-C4 alkoxy. In a still further aspect, R$^6$, when present, is selected from methyl, ethyl, n-propyl, i-propyl, —OCH$_3$, —OCH$_2$CH$_3$, —OCH(CH$_3$)$_2$, and —OCH$_2$CH$_3$. In yet a further aspect, R$^6$, when present, is selected from methyl, ethyl, —OCH$_3$, and —OCH$_2$CH$_3$. In an even further aspect, R$^6$, when present, is selected from methyl and —OCH$_3$.

In a further aspect, R$^6$, when present, is C1-C4 haloalkyl. In a still further aspect, R$^6$, when present, is selected from —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, and —CCl$_3$. In yet a further aspect, R$^6$, when present, is selected from —CH$_2$F, —CH$_2$Cl, —CH$_2$CH$_2$F, —CH$_2$CH$_2$Cl, —CHF$_2$, —CF$_3$, —CHCl$_2$, and —CCl$_3$. In an even further aspect, R$^6$, when present, is selected from —CH$_2$F, —CH$_2$Cl, —CHF$_2$, —CF$_3$, —CHCl$_2$, and —CCl$_3$.

In a further aspect, R$^6$, when present, is C1-C4 alkoxy. In a still further aspect, R$^6$, when present, is selected from —OCH$_3$, —OCH$_2$CH$_3$, —OCH(CH$_3$)$_2$, and —OCH$_2$CH$_3$. In yet a further aspect, R$^6$, when present, is selected from —CH$_3$ and —OCH$_2$CH$_3$. In an even further aspect, R$^6$, when present, is —OCH$_2$CH$_3$. In a still further aspect, R$^6$, when present, is —OCH$_3$.

In a further aspect, R$^6$, when present, is C1-C4 alkyl. In a still further aspect, R$^6$, when present, is selected from methyl, ethyl, n-propyl, and i-propyl. In yet a further aspect, R$^6$, when present, is selected from methyl and ethyl. In an even further aspect, R$^6$, when present, is ethyl. In a still further aspect, R$^6$, when present, is methyl.

g. R$^7$ Groups

In one aspect, R$^7$, when present, is selected from hydrogen, C1-C4 alkyl, and aryl substituted with 0-4 non-hydrogen groups independently selected from halogen, —OH, —CN, C1-C4 alkyl, C1-C4 alkoxy, and C1-C4 haloalkyl, provided that when $R^7$ is hydrogen or methyl, then $R^{4b}$ is not amine protecting group. In a further aspect, $R^7$, when present, is selected from hydrogen, C1-C4 alkyl, and aryl substituted with 0-3 non-hydrogen groups independently selected from halogen, —OH, —CN, C1-C4 alkyl, C1-C4 alkoxy, and C1-C4 haloalkyl. In a still further aspect, $R^7$, when present, is selected from hydrogen, C1-C4 alkyl, and aryl substituted with 0-2 non-hydrogen groups independently selected from halogen, —OH, —CN, C1-C4 alkyl, C1-C4 alkoxy, and C1-C4 haloalkyl. In yet a further aspect, $R^7$, when present, is selected from hydrogen, C1-C4 alkyl, and aryl substituted with 0-1 non-hydrogen groups independently selected from halogen, —OH, —CN, C1-C4 alkyl, C1-C4 alkoxy, and C1-C4 haloalkyl. In an even further aspect, $R^7$, when present, is selected from hydrogen, C1-C4 alkyl, and aryl monosubstituted with a non-hydrogen group selected from halogen, —OH, —CN, C1-C4 alkyl, C1-C4 alkoxy, and C1-C4 haloalkyl. In a still further aspect, $R^7$, when present, is selected from hydrogen, C1-C4 alkyl, and unsubstituted aryl.

In one aspect, $R^7$, when present, is selected from hydrogen and C1-C4 alkyl. In a further aspect, $R^7$, when present, is hydrogen.

In a further aspect, $R^7$, when present, is aryl substituted with 0-4 non-hydrogen groups independently selected from halogen, —OH, —CN, C1-C4 alkyl, C1-C4 alkoxy, and C1-C4 haloalkyl. In a further aspect, $R^7$, when present, is aryl substituted with 0-3 non-hydrogen groups independently selected from halogen, —OH, —CN, C1-C4 alkyl, C1-C4 alkoxy, and C1-C4 haloalkyl. In a still further aspect, $R^7$, when present, is aryl substituted with 0-2 non-hydrogen groups independently selected from halogen, —OH, —CN, C1-C4 alkyl, C1-C4 alkoxy, and C1-C4 haloalkyl. In yet a further aspect, $R^7$, when present, is aryl substituted with 0-1 non-hydrogen groups independently selected from halogen, —OH, —CN, C1-C4 alkyl, C1-C4 alkoxy, and C1-C4 haloalkyl. In an even further aspect, $R^7$, when present, is aryl monosubstituted with a non-hydrogen group selected from halogen, —OH, —CN, C1-C4 alkyl, C1-C4 alkoxy, and C1-C4 haloalkyl. In a still further aspect, $R^7$, when present, is unsubstituted aryl.

In a further aspect, $R^7$, when present, is selected from hydrogen, methyl, ethyl, n-propyl, i-propyl, n-butyl, s-butyl, i-butyl, and t-butyl. In a still further aspect, $R^7$, when present, is selected from hydrogen, methyl, ethyl, n-propyl, and i-propyl. In yet a further aspect, $R^7$, when present, is selected from hydrogen, methyl, and ethyl. In an even further aspect, $R^7$, when present, is selected from hydrogen and ethyl. In a still further aspect, $R^7$, when present, is selected from hydrogen and methyl.

In a further aspect, $R^7$, when present, is C1-C4 alkyl. In a still further aspect, $R^7$, when present, is selected from methyl, ethyl, n-propyl, and i-propyl. In yet a further aspect, $R^7$, when present, is selected from methyl and ethyl. In an even further aspect, $R^7$, when present, is ethyl. In a still further aspect, $R^7$, when present, is methyl.

h. $R^{8a}$ and $R^{8b}$ Groups

In one aspect, each of $R^{8a}$ and $R^{8b}$, when present, is independently selected from hydrogen and —CO$_2$(C1-C4 alkyl). In a further aspect, each of $R^{8a}$ and $R^{8b}$, when present, is hydrogen.

In a further aspect, each of $R^{8a}$ and $R^{8b}$, when present, is independently selected from hydrogen, —CO$_2$CH$_3$, —CO$_2$CH$_2$CH$_3$, —CO$_2$CH(CH$_3$)$_2$, —CO$_2$CH$_2$CH$_2$CH$_3$, —CO$_2$CH(CH$_3$)CH$_2$CH$_3$, —CO$_2$CH$_2$CH(CH$_3$)$_2$, —CO$_2$C(CH$_3$)$_3$, and —CO$_2$(CH$_2$)$_3$CH$_3$. In a still further aspect, each of $R^{8a}$ and $R^{8b}$, when present, is independently selected from hydrogen, —CO$_2$CH$_3$, —CO$_2$CH$_2$CH$_3$, —CO$_2$CH(CH$_3$)$_2$, and —CO$_2$CH$_2$CH$_2$CH$_3$. In yet a further aspect, each of $R^{8a}$ and $R^{8b}$, when present, is independently selected from hydrogen, —CO$_2$CH$_3$, and —CO$_2$CH$_2$CH$_3$. In an even further aspect, each of $R^{8a}$ and $R^{8b}$, when present, is independently selected from hydrogen and —CO$_2$CH$_2$CH$_3$. In a still further aspect, each of $R^{8a}$ and $R^{8b}$, when present, is independently selected from hydrogen and —CO$_2$CH$_3$.

a. $R^9$ Groups

In one aspect, $R^9$, when present, is selected from —OH, —NH$_2$, C1-C4 hydroxyalkyl, C1-C4 alkylamino, and (C1-C4)(C1-C4) dialkylamino. In a further aspect, $R^9$, when present, is —OH. In a still further aspect, $R^9$, when present, is —NH$_2$.

In a further aspect, $R^9$, when present, is selected from C1-C4 hydroxyalkyl, C1-C4 alkylamino, and (C1-C4)(C1-C4) dialkylamino. In a still further aspect, $R^9$, when present, is selected from —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_2$CH$_3$)$_2$, —N((CH$_2$)$_2$CH$_3$)$_2$, —N(CH(CH$_3$)$_2$), and —N(CH$_3$)(CH$_2$CH$_3$). In yet a further aspect, $R^9$, when present, is selected from —OCH$_3$, —OCH$_2$CH$_3$, —NHCH$_3$, —NHCH$_2$CH$_3$, —N(CH$_3$)$_2$, —N(CH$_2$CH$_3$)$_2$, and —N((CH$_2$)$_2$CH$_3$)$_2$. In an even further aspect, $R^9$, when present, is selected from —OCH$_3$, —NHCH$_3$, and —N(CH$_3$)$_2$.

b. $R^{21}$ Groups

In one aspect, each occurrence of $R^2$, when present, is independently selected from hydrogen, C1-C6 alkyl, C1-C6 hydroxyalkyl, C3-C6 cycloalkyl, C3-C6 heterocycloalkyl, —COR$^{30}$, —(C1-C4 alkyl)OC(O)(C1-C4 alkyl), and —(C1-C6 alkyl)NHC(O)A.

In one aspect, each occurrence of $R^{21}$, when present, is independently selected from hydrogen, C1-C6 alkyl, C3-C6 cycloalkyl, C3-C6 heterocycloalkyl, and —COR$^{30}$. In a further aspect, each occurrence of $R^{21}$, when present, is independently selected from hydrogen, C1-C3 alkyl, C3-C6 cycloalkyl, C3-C6 heterocycloalkyl, and —COR$^{30}$. In a still further aspect, each occurrence of $R^{21}$, when present, is hydrogen.

In a further aspect, each occurrence of $R^{21}$, when present, is independently selected from hydrogen, C1-C6 alkyl, and —COR$^{30}$. In a still further aspect, each occurrence of $R^{21}$, when present, is independently selected from hydrogen, C1-C3 alkyl, and —COR$^{30}$. In yet a further aspect, each occurrence of $R^{21}$, when present, is independently selected from hydrogen, methyl, ethyl, and —COR$^{30}$. In an even further aspect, each occurrence of $R^{21}$, when present, is independently selected from hydrogen, methyl, and —COR$^{30}$.

In a further aspect, each occurrence of $R^{21}$, when present, is independently selected from hydrogen, C3-C6 cycloalkyl, C3-C6 heterocycloalkyl, and —COR$^{30}$. In a still further aspect, each occurrence of $R^{21}$, when present, is independently selected from hydrogen, C3-C6 cycloalkyl, C3-C6 heterocycloalkyl, and —COR$^{30}$. In yet a further aspect, each occurrence of $R^{21}$, when present, is independently selected from hydrogen, cyclopropyl, cyclobutyl, morpholinyl, and —COR$^{30}$. In an even further aspect, each occurrence of $R^{21}$, when present, is independently selected from hydrogen, cyclopropyl, morpholinyl, and —COR$^{30}$.

In a further aspect, each occurrence of $R^{21}$, when present, is independently selected from hydrogen and C1-C6 alkyl. In a still further aspect, each occurrence of $R^{21}$, when present, is independently selected from hydrogen and C1-C3 alkyl. In yet a further aspect, each occurrence of $R^2$, when present, is independently selected from hydrogen, methyl, and ethyl. In an even further aspect, each occurrence of $R^2$, when present, is independently selected from hydrogen and ethyl. In a still further aspect, each occurrence of $R^{21}$, when present, is independently selected from hydrogen and methyl.

c. $R^{22a}$ and $R^{22b}$ Groups

In one aspect, each occurrence of each of $R^{22a}$ and $R^{22b}$, when present, is independently selected from hydrogen, C1-C6 alkyl, C3-C6 cycloalkyl, C3-C6 heterocycloalkyl, and —$COR^{30}$. In a further aspect, each occurrence of each of $R^{22a}$ and $R^{22b}$, when present, is independently selected from hydrogen, C1-C3 alkyl, C3-C6 cycloalkyl, C3—C6 heterocycloalkyl, and —$COR^{30}$. In a still further aspect, each occurrence of each of $R^2$ and $R^{22}$, when present, is hydrogen.

In a further aspect, each occurrence of each of $R^{22a}$ and $R^{22b}$, when present, is independently selected from hydrogen, C1-C6 alkyl, and —$COR^{30}$. In a still further aspect, each occurrence of each of $R^{22a}$ and $R^{22b}$, when present, is independently selected from hydrogen, C1-C3 alkyl, and —$COR^{30}$. In yet a further aspect, each occurrence of each of $R^{22}$ and $R^{22b}$, when present, is independently selected from hydrogen, methyl, ethyl, and —$COR^3$. In an even further aspect, each occurrence of each of $R^{22a}$ and $R^{22b}$, when present, is independently selected from hydrogen, methyl, and —$COR^3$.

In a further aspect, each occurrence of each of $R^{22a}$ and $R^{22b}$, when present, is independently selected from hydrogen, C3-C6 cycloalkyl, C3-C6 heterocycloalkyl, and —$COR^{30}$. In a still further aspect, each occurrence of each of $R^{22a}$ and $R^{22b}$, when present, is independently selected from hydrogen, C3-C6 cycloalkyl, C3-C6 heterocycloalkyl, and —$COR^{30}$. In yet a further aspect, each occurrence of each of $R^{22a}$ and $R^{22b}$, when present, is independently selected from hydrogen, cyclopropyl, cyclobutyl, morpholinyl, and —$COR^{30}$. In an even further aspect, each occurrence of each of $R^{22a}$ and $R^{22b}$, when present, is independently selected from hydrogen, cyclopropyl, morpholinyl, and —$COR^{30}$.

In a further aspect, each occurrence of each of $R^{22a}$ and $R^{22b}$, when present, is independently selected from hydrogen and C1-C6 alkyl. In a still further aspect, each occurrence of $R^{22a}$ and $R^{22b}$, when present, is independently selected from hydrogen and C1-C3 alkyl. In yet a further aspect, each occurrence of each of $R^{22a}$ and $R^{22b}$, when present, is independently selected from hydrogen, methyl, and ethyl. In an even further aspect, each occurrence of each of $R^{22a}$ and $R^{22b}$, when present, is independently selected from hydrogen and ethyl. In a still further aspect, each occurrence of each of $R^{22a}$ and $R^{22b}$, when present, is independently selected from hydrogen and methyl.

d. $R^{23}$ Groups

In one aspect, $R^{23}$, when present, is selected from hydrogen and C1-C4 alkyl. In a further aspect, $R^{23}$, when present, is hydrogen.

In a further aspect, $R^{23}$, when present, is selected from C1-C4 alkyl. In a still further aspect, $R^{23}$, when present, is selected from methyl, ethyl, n-propyl, and i-propyl. In yet a further aspect, $R^{23}$, when present, is selected from methyl and ethyl. In an even further aspect, $R^{23}$, when present, is ethyl. In a still further aspect, $R^{23}$, when present, is methyl.

e. $R^{24}$ Groups

In one aspect, $R^{24}$, when present, is selected from C1-C4 alkyl, C1-C4 hydroxyalkyl, C1-C4 alkyl(C1-C4 alkoxy), C1-C4 alkylamino, (C1-C4)C1-C4) dialkylamino, C1-4 alkylamino(C1-C4 alkyl), (C1-C4)C1-C4) dialkylamino (C1-C4 alkyl), —$(CH_2)_r$(C3-C6 cycloalkyl), and —$(CH_2)_r$(C3-C6 heterocycloalkyl).

In a further aspect, $R^{24}$, when present, is selected from C1-C4 alkyl, C1-C4 hydroxyalkyl, C1-C4 alkyl(C1-C4 alkoxy), C1-C4 alkylamino, (C1-C4)C1-C4) dialkylamino, C1-4 alkylamino(C1-C4 alkyl), and (C1-C4)C1-C4) dialkylamino(C1-C4 alkyl). In a further aspect, $R^{24}$, when present, is selected from C1-C3 alkyl, C1-C3 hydroxyalkyl, C1-C3 alkyl(C1-C3 alkoxy), C1-C3 alkylamino, (C1-C3)C1-C3) dialkylamino, C1-3 alkylamino(C1-C3 alkyl), and (C1-C3) C1-C3) dialkylamino(C1-C3 alkyl). In a still further aspect, $R^{24}$, when present, is selected from methyl, ethyl, —$CH_2OH$, —$CH(OH)CH_3$, —$CH_2CH_2OH$, —$CH_2OCH_3$, —$CH_2OCH_2CH_3$, —$CH_2CH_2OCH_3$, —$NHCH_3$, —$NHCH_2CH_3$, —$N(CH_3)_2$, —$N(CH_2CH_3)_2$, —$CH_2NHCH_3$, —$CH_2NHCH_2CH_3$, —$CH_2CH_2NHCH_3$, —$CH_2N(CH_3)_2$, —$CH_2N(CH_2CH_3)$, —$CH_2CH_2N(CH_3)$.

In a further aspect, $R^{24}$, when present, is selected from —$(CH_2)_r$(C3-C6 cycloalkyl) and —$(CH_2)_r$(C3-C6 heterocycloalkyl). In a still further aspect, $R^{24}$, when present, is selected from —$CH_2$(C3-C6 cycloalkyl) and —$CH_2$(C3-C6 heterocycloalkyl). In yet a further aspect, $R^{24}$, when present, is selected from C3-C6 cycloalkyl and C3-C6 heterocycloalkyl.

f. $R^{30}$ Groups

In one aspect, each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl. In a further aspect, each occurrence of $R^{30}$, when present, is independently selected from hydrogen, C1-C3 alkyl, C1-C3 alkoxy, C1-C3 aminoalkyl, C3-C6 cycloalkyl, C3-C6 heterocycloalkyl, and —$COR^{30}$. In a still further aspect, each occurrence of $R^{30}$, when present, is hydrogen.

In a further aspect, each occurrence of $R^{30}$, when present, is independently selected from hydrogen, C1-C6 alkyl, C1-C6 alkoxy, and C1-C6 aminoalkyl. In a still further aspect, each occurrence of $R^{30}$, when present, is independently selected from hydrogen, C1-C3 alkyl, C1-C3 alkoxy, and C1-C3 aminoalkyl. In yet a further aspect, each occurrence of $R^{30}$, when present, is independently selected from hydrogen, methyl, ethyl, —$OCH_3$, —$OCH_2CH_3$, —$NHCH_3$, and —$NHCH_2CH_3$. In an even further aspect, each occurrence of $R^3$, when present, is independently selected from hydrogen, methyl, —$OCH_3$, and —$NHCH_3$.

In a further aspect, each occurrence of $R^{30}$, when present, is independently selected from hydrogen, C3-C6 cycloalkyl, and C3-C6 heterocycloalkyl. In a still further aspect, each occurrence of $R^{30}$, when present, is independently selected from hydrogen, C3-C6 cycloalkyl, and C3-C6 heterocycloalkyl. In yet a further aspect, each occurrence of $R^{30}$, when present, is independently selected from hydrogen, cyclopropyl, cyclobutyl, and morpholinyl. In an even further aspect, each occurrence of $R^{30}$, when present, is independently selected from hydrogen, cyclopropyl and morpholinyl.

In a further aspect, each occurrence of $R^{30}$, when present, is independently selected from hydrogen and C1-C6 alkyl. In a still further aspect, each occurrence of $R^{30}$, when present, is independently selected from hydrogen and C1-C3 alkyl. In yet a further aspect, each occurrence of $R^{30}$, when present, is independently selected from hydrogen, methyl, and ethyl. In an even further aspect, each occurrence of $R^{30}$, when present, is independently selected from hydrogen and ethyl. In a still further aspect, each occurrence of $R^{30}$, when present, is independently selected from hydrogen and methyl.

g. $R^{31}$ Groups

In one aspect, each occurrence of $R^{31}$, when present, is independently selected from hydrogen, C1-C6 alkyl, and aryl, provided that when $R^{31}$ is methyl, then $Ar^3$ is phenyl substituted 1-4 non-hydrogen groups, only one of which is $OR^{31}$.

In one aspect, each occurrence of $R^3$ is independently selected from hydrogen and C2-C6 alkyl. In a further aspect, each occurrence of $R^3$ is hydrogen.

In a further aspect, each occurrence of $R^3$ is independently selected from hydrogen, C2-C6 alkyl, and aryl.

In a further aspect, each occurrence of $R^{31}$, when present, is independently selected from hydrogen and C1-C6 alkyl. In a still further aspect, each occurrence of $R^{31}$, when present, is independently selected from hydrogen and C1-C4 alkyl. In yet a further aspect, each occurrence of $R^{31}$, when present, is independently selected from hydrogen, methyl, ethyl, n-propyl, and iso-propyl. In an even further aspect, each occurrence of $R^{31}$, when present, is independently selected from hydrogen, methyl, and ethyl. In a still further aspect, each occurrence of $R^{31}$, when present, is independently selected from hydrogen and methyl.

In a further aspect, each occurrence of $R^{31}$, when present, is independently selected from hydrogen and aryl. In a still further aspect, each occurrence of $R^3$, when present, is aryl.

In a further aspect, each occurrence of $R^3$ is independently selected from hydrogen and C2-C4 alkyl. In a still further aspect, each occurrence of $R^{31}$ is independently selected from hydrogen, ethyl, n-propyl, and iso-propyl. In yet a further aspect, each occurrence of $R^3$ is independently selected from hydrogen and ethyl. In an even further aspect, each occurrence of $R^3$ is independently selected from hydrogen and n-propyl. In a still further aspect, each occurrence of $R^3$ is independently selected from hydrogen and iso-propyl.

In a further aspect, each occurrence of $R^3$ is independently selected from C2-C6 alkyl. In a still further aspect, each occurrence of $R^3$ is independently selected from ethyl, n-propyl, and iso-propyl. In yet a further aspect, each occurrence of $R^3$ is ethyl. In an even further aspect, each occurrence of $R^3$ is n-propyl. In a still further aspect, each occurrence of $R^{31}$ is iso-propyl.

h. $R^{32a}$ and $R^{32b}$ Groups

In one aspect, each of $R^{32a}$ and $R^{32b}$, when present, is independently selected from hydrogen, C1-C4 alkyl, and C1-C4 haloalkyl, provided that at least one of $R^{32a}$ and $R^{32b}$ is not hydrogen.

In a further aspect, each of $R^{32a}$ and $R^{32b}$, when present, is independently selected from hydrogen and C1-C4 alkyl. In a still further aspect, each of $R^{32a}$ and $R^{32b}$, when present, is independently selected from hydrogen, methyl, ethyl, n-propyl, and i-propyl. In yet a further aspect, each of $R^{32a}$ and $R^{32b}$, when present, is independently selected from hydrogen, methyl, and ethyl. In an even further aspect, each of $R^{32a}$ and $R^{32b}$, when present, is independently selected from hydrogen and ethyl. In a still further aspect, each of $R^{32a}$ and $R^{32b}$, when present, is independently selected from hydrogen and methyl.

In a further aspect, each of $R^{32a}$ and $R^{32b}$, when present, is independently selected from hydrogen and C1-C4 haloalkyl. In a still further aspect, each of $R^{32a}$ and $R^{32b}$, when present, is independently selected from hydrogen, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CHF$_2$, —CF$_3$, —CHCl$_2$, and —CCl$_3$.

In yet a further aspect, each of $R^{3a}$ and $R'^{32}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, and —CCl$_3$. In an even further aspect, each of $R^{32a}$ and $R^{32b}$, when present, is independently selected from hydrogen, —CH$_2$F, —CH$_2$Cl, —CHF$_2$, —CF$_3$, —CHCl$_2$, and —CCl$_3$.

i. $Ar^1$ Groups

In one aspect, $Ar^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl. In a further aspect, $Ar^1$ is selected from aryl, five-membered heteroaryl, and six-membered heteroaryl and is substituted with 0-3 non-hydrogen groups independently selected from halogen, —OH, —CN, C1-C4 alkyl, C1-C4 alkoxy, and C1-C4 haloalkyl. In a still further aspect, $Ar^1$ is selected from aryl, five-membered heteroaryl, and six-membered heteroaryl and is substituted with 0-2 non-hydrogen groups independently selected from halogen, —OH, —CN, C1-C4 alkyl, C1-C4 alkoxy, and C1-C4 haloalkyl. In yet a further aspect, $Ar^1$ is selected from aryl, five-membered heteroaryl, and six-membered heteroaryl and is substituted with 0-1 non-hydrogen groups independently selected from halogen, —OH, —CN, C1-C4 alkyl, C1-C4 alkoxy, and C1-C4 haloalkyl. In an even further aspect, $Ar^1$ is selected from aryl, five-membered heteroaryl, and six-membered heteroaryl and is substituted with a non-hydrogen group selected from halogen, —OH, —CN, C1-C4 alkyl, C1-C4 alkoxy, and C1-C4 haloalkyl. In a still further aspect, $Ar^1$ is selected from aryl, five-membered heteroaryl, and six-membered heteroaryl and is unsubstituted.

In a further aspect, $Ar^1$ is selected from aryl and five-membered heteroaryl and is substituted with 0-4 non-hydrogen groups independently selected from halogen, —OH, —CN, C1-C4 alkyl, C1-C4 alkoxy, and C1-C4 haloalkyl. In a still further aspect, $Ar^1$ is selected from aryl and five-membered heteroaryl and is substituted with 0-3 non-hydrogen groups independently selected from halogen, —OH, —CN, C1-C4 alkyl, C1-C4 alkoxy, and C1-C4 haloalkyl. In yet a further aspect, $Ar^1$ is selected from aryl and five-membered heteroaryl and is substituted with 0-2 non-hydrogen groups independently selected from halogen, —OH, —CN, C1-C4 alkyl, C1-C4 alkoxy, and C1-C4 haloalkyl. In an even further aspect, $Ar^1$ is selected from aryl and five-membered heteroaryl and is substituted with 0-1 non-hydrogen groups independently selected from halogen, —OH, —CN, C1-C4 alkyl, C1-C4 alkoxy, and C1-C4 haloalkyl. In a still further aspect, $Ar^1$ is selected from aryl and five-membered heteroaryl and is substituted with a non-hydrogen group selected from halogen, —OH, —CN, C1-C4 alkyl, C1-C4 alkoxy, and C1-C4 haloalkyl. In yet a further aspect, $Ar^1$ is selected from aryl and five-membered heteroaryl and is unsubstituted.

In a further aspect, $Ar^1$ is five-membered heteroaryl substituted with 0-4 non-hydrogen groups independently selected from halogen, —OH, —CN, C1-C4 alkyl, C1-C4 alkoxy, and C1-C4 haloalkyl. In a still further aspect, $Ar^1$ is five-membered heteroaryl substituted with 0-3 non-hydrogen groups independently selected from halogen, —OH, —CN, C1-C4 alkyl, C1-C4 alkoxy, and C1-C4 haloalkyl. In yet a further aspect, $Ar^1$ is five-membered heteroaryl substituted with 0-2 non-hydrogen groups independently selected from halogen, —OH, —CN, C1-C4 alkyl, C1-C4 alkoxy, and C1-C4 haloalkyl. In an even further aspect, $Ar^1$ is five-membered heteroaryl substituted with 0-1 non-hydrogen groups independently selected from halogen, —OH, —CN, C1-C4 alkyl, C1-C4 alkoxy, and C1-C4 haloalkyl. In a still further aspect, Ar$^1$ is five-membered heteroaryl substituted with a non-hydrogen group selected from halogen, —OH, —CN, C1-C4 alkyl, C1-C4 alkoxy, and C1-C4 haloalkyl. In yet a further aspect, Ar$^1$ is unsubstituted five-membered heteroaryl.

In a further aspect, Ar$^1$ is six-membered heteroaryl substituted with 0-4 non-hydrogen groups independently selected from halogen, —OH, —CN, C1-C4 alkyl, C1-C4 alkoxy, and C1-C4 haloalkyl. In a still further aspect, Ar$^1$ is six-membered heteroaryl substituted with 0-3 non-hydrogen groups independently selected from halogen, —OH, —CN, C1-C4 alkyl, C1-C4 alkoxy, and C1-C4 haloalkyl. In yet a further aspect, Ar$^1$ is six-membered heteroaryl substituted with 0-2 non-hydrogen groups independently selected from halogen, —OH, —CN, C1-C4 alkyl, C1-C4 alkoxy, and C1-C4 haloalkyl. In an even further aspect, Ar$^1$ is six-membered heteroaryl substituted with 0-1 non-hydrogen groups independently selected from halogen, —OH, —CN, C1-C4 alkyl, C1-C4 alkoxy, and C1-C4 haloalkyl. In a still further aspect, Ar$^1$ is six-membered heteroaryl substituted with a non-hydrogen group selected from halogen, —OH, —CN, C1-C4 alkyl, C1-C4 alkoxy, and C1-C4 haloalkyl. In yet a further aspect, Ar$^1$ is unsubstituted six-membered heteroaryl.

In a further aspect, Ar$^1$ is pyridinyl substituted with 0-4 non-hydrogen groups independently selected from halogen, —OH, —CN, C1-C4 alkyl, C1-C4 alkoxy, and C1-C4 haloalkyl. In a still further aspect, Ar$^1$ is pyridinyl substituted with 0-3 non-hydrogen groups independently selected from halogen, —OH, —CN, C1-C4 alkyl, C1-C4 alkoxy, and C1-C4 haloalkyl. In yet a further aspect, Ar$^1$ is pyridinyl substituted with 0-2 non-hydrogen groups independently selected from halogen, —OH, —CN, C1-C4 alkyl, C1-C4 alkoxy, and C1-C4 haloalkyl. In an even further aspect, Ar$^1$ is pyridinyl substituted with 0-1 non-hydrogen groups independently selected from halogen, —OH, —CN, C1-C4 alkyl, C1-C4 alkoxy, and C1-C4 haloalkyl. In a still further aspect, Ar$^1$ is pyridinyl substituted with a non-hydrogen group selected from halogen, —OH, —CN, C1-C4 alkyl, C1-C4 alkoxy, and C1-C4 haloalkyl. In yet a further aspect, Ar$^1$ is unsubstituted pyridinyl.

In a further aspect, Ar$^1$ is aryl substituted with 0-4 non-hydrogen groups independently selected from halogen, —OH, —CN, C1-C4 alkyl, C1-C4 alkoxy, and C1-C4 haloalkyl. In a still further aspect, Ar$^1$ is aryl substituted with 0-3 non-hydrogen groups independently selected from halogen, —OH, —CN, C1-C4 alkyl, C1-C4 alkoxy, and C1-C4 haloalkyl. In yet a further aspect, Ar$^1$ is aryl substituted with 0-2 non-hydrogen groups independently selected from halogen, —OH, —CN, C1-C4 alkyl, C1-C4 alkoxy, and C1-C4 haloalkyl. In an even further aspect, Ar$^1$ is aryl substituted with 0-1 non-hydrogen groups independently selected from halogen, —OH, —CN, C1-C4 alkyl, C1-C4 alkoxy, and C1-C4 haloalkyl. In a still further aspect, Ar$^1$ is aryl substituted with a non-hydrogen group selected from halogen, —OH, —CN, C1-C4 alkyl, C1-C4 alkoxy, and C1-C4 haloalkyl. In yet a further aspect, Ar$^1$ is unsubstituted aryl.

In a further aspect, Ar$^1$ is phenyl substituted with 0-4 non-hydrogen groups independently selected from halogen, —OH, —CN, C1-C4 alkyl, C1-C4 alkoxy, and C1-C4 haloalkyl. In a still further aspect, Ar$^1$ is phenyl substituted with 0-3 non-hydrogen groups independently selected from halogen, —OH, —CN, C1-C4 alkyl, C1-C4 alkoxy, and C1-C4 haloalkyl. In yet a further aspect, Ar$^1$ is phenyl substituted with 0-2 non-hydrogen groups independently selected from halogen, —OH, —CN, C1-C4 alkyl, C1-C4 alkoxy, and C1-C4 haloalkyl. In an even further aspect, Ar$^1$ is phenyl substituted with 0-1 non-hydrogen groups independently selected from halogen, —OH, —CN, C1-C4 alkyl, C1-C4 alkoxy, and C1-C4 haloalkyl. In a still further aspect, Ar$^1$ is phenyl substituted with a non-hydrogen group selected from halogen, —OH, —CN, C1-C4 alkyl, C1-C4 alkoxy, and C1-C4 haloalkyl. In yet a further aspect, Ar$^1$ is unsubstituted phenyl.

j. Ar$^2$ Groups

In one aspect, Ar$^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —(CH$_2$)$_q$NR$^{22a}$R$^{22b}$, —SO$_2$NR$^{22a}$R$^{2'}$, —NR$^{23}$C(O)R$^{24}$, —NR$^{23}$(CH$_2$)$_q$(C3-C6 cycloalkyl), —NR$^{23}$(CH$_2$)$_q$(heterocycloalkyl), and 3- to 5-membered heterocycloalkyl, provided that when n is 0 and Ar$^2$ is monoaryl then Ar$^2$ is substituted with at least one non-hydrogen group.

In one aspect, Ar$^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a further aspect, Ar$^2$, when present, is selected from aryl and 5- to 12-membered heteroaryl and is substituted with 2 non-hydrogen groups that are optionally covalently bonded together and, together with the intermediate atoms, comprise a 5- to 6-membered heterocycloalkyl.

In a further aspect, Ar$^2$, when present, is selected from aryl and 5- to 12-membered heteroaryl and is substituted with 0-3 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, Ar$^2$, when present, is selected from aryl and 5- to 12-membered heteroaryl and is substituted with 0-2 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In yet a further aspect, Ar$^2$, when present, is selected from aryl and 5- to 12-membered heteroaryl and is substituted with 0-1 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In an even further aspect, Ar$^2$, when present, is selected from aryl and 5- to 12-membered heteroaryl and is substituted with a non-hydrogen group selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, Ar$^2$, when present, is selected from aryl and 5- to 12-membered heteroaryl and is unsubstituted.

In a further aspect, $Ar^2$, when present, is aryl substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, $Ar^2$, when present, is aryl substituted with 0-3 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In yet a further aspect, $Ar^2$, when present, is aryl substituted with 0-2 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In an even further aspect, $Ar^2$, when present, is aryl substituted with 0-1 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, $Ar^2$, when present, is aryl substituted with a non-hydrogen group selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In yet a further aspect, $Ar^2$, when present, is unsubstituted aryl.

In a further aspect, $Ar^2$, when present, is phenyl substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, $Ar^2$, when present, is phenyl substituted with 0-3 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In yet a further aspect, $Ar^2$, when present, is phenyl substituted with 0-2 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In an even further aspect, $Ar^2$, when present, is phenyl substituted with 0-1 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, $Ar^2$, when present, is phenyl substituted with a non-hydrogen group selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In yet a further aspect, $Ar^2$, when present, is unsubstituted phenyl.

In a further aspect, $Ar^2$, when present, is selected from isobenzofuran-1(3H)-only and benzo[d][1,3]dioxolyl, and substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, $Ar^2$, when present, is selected from isobenzofuran-1(3H)-only and benzo[d][1,3]dioxolyl, and substituted with 0-3 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In yet a further aspect, $Ar^2$, when present, is selected from isobenzofuran-1(3H)-only and benzo[d][1,3]dioxolyl, and substituted with 0-2 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In an even further aspect, $Ar^2$, when present, is selected from isobenzofuran-1(3H)-only and benzo[d][1,3]dioxolyl, and substituted with 0-1 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, $Ar^2$, when present, is selected from isobenzofuran-1(3H)-only and benzo[d][1,3]dioxolyl, and substituted with a non-hydrogen group selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In yet a further aspect, $Ar^2$, when present, is selected from isobenzofuran-1(3H)-only and benzo[d][1,3]dioxolyl, and unsubstituted.

In a further aspect, $Ar^2$, when present, is 5- to 12-membered heteroaryl substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In a still further aspect, $Ar^2$, when present, is 5- to 12-membered heteroaryl substituted with 0-3 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In yet a further aspect, $Ar^2$, when present, is 5- to 12-membered heteroaryl substituted with 0-2 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle. In an even further aspect, Ar², when present, is 5- to 12-membered heteroaryl substituted with 0-1 non-hydrogen groups independently selected from halogen, —OH, —CN, —NO₂, C1-C4 alkyl, C1-C4 alkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR²¹, —CO₂R²¹, —CONR²²ᵃR²²ᵇ, —SO₂NR²²ᵃR²²ᵇ, and heterocycle. In a still further aspect, Ar², when present, is 5- to 12-membered heteroaryl substituted with a non-hydrogen group selected from halogen, —OH, —CN, —NO₂, C1-C4 alkyl, C1-C4 alkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR²¹, —CO₂R²¹, —CONR²²ᵃR²²ᵇ, —SO₂NR²²ᵃR²²ᵇ, and heterocycle. In yet a further aspect, Ar², when present, is unsubstituted 5- to 12-membered heteroaryl.

In a further aspect, Ar², when present, is selected from quinolinyl, pyridinyl, pyrimidinyl, imidazolyl, triazolyl, and tetrazolyl, and substituted with 0-4 non-hydrogen groups independently selected from halogen, —OH, —CN, —NO₂, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR²¹, —CO₂R²¹, —CONR²²ᵃR²²ᵇ, —SO₂NR²²ᵃR²²ᵇ, and heterocycle. In a still further aspect, Ar², when present, is selected from quinolinyl, pyridinyl, pyrimidinyl, imidazolyl, triazolyl, and tetrazolyl, and substituted with 0-3 non-hydrogen groups independently selected from halogen, —OH, —CN, —NO₂, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR²¹, —CO₂R²¹, —CONR²²ᵃR²²ᵇ, —SO₂NR²²ᵃR²²ᵇ, and heterocycle. In yet a further aspect, Ar², when present, is selected from quinolinyl, pyridinyl, pyrimidinyl, imidazolyl, triazolyl, and tetrazolyl, and substituted with 0-2 non-hydrogen groups independently selected from halogen, —OH, —CN, —NO₂, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR²¹, —CO₂R²¹, —CONR²²ᵃR²²ᵇ, —SO₂NR²²ᵃR²²ᵇ, and heterocycle. In an even further aspect, Ar², when present, is selected from quinolinyl, pyridinyl, pyrimidinyl, imidazolyl, triazolyl, and tetrazolyl, and substituted with 0-1 non-hydrogen groups independently selected from halogen, —OH, —CN, —NO₂, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR²¹, —CO₂R²¹, —CONR²²ᵃR²²ᵇ, —SO₂NR²²ᵃR²²ᵇ, and heterocycle. In a still further aspect, Ar², when present, is selected from quinolinyl, pyridinyl, pyrimidinyl, imidazolyl, triazolyl, and tetrazolyl, and substituted with a non-hydrogen group selected from halogen, —OH, —CN, —NO₂, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR²¹, —CO₂R²¹, —CONR²²ᵃR²²ᵇ, —SO₂NR²²ᵃR²²ᵇ, and heterocycle. In yet a further aspect, Ar², when present, is selected from quinolinyl, pyridinyl, pyrimidinyl, imidazolyl, triazolyl, and tetrazolyl, and unsubstituted.

k. Ar³ Groups

In one aspect, Ar³ is phenyl substituted with 1-4 non-hydrogen groups independently selected—from —NO₂, OR³¹, and —CH₂NR³²ᵃR³²ᵇ. In a further aspect, Ar³ is phenyl substituted with 1-4-NO₂ groups. In a still further aspect, Ar³ is phenyl substituted with 1-4 OR³¹ groups. In yet a further aspect, Ar³ is phenyl substituted with 1-4-CH₂NR³²ᵃR³²ᵇ groups.

In one aspect, Ar³ is selected from:

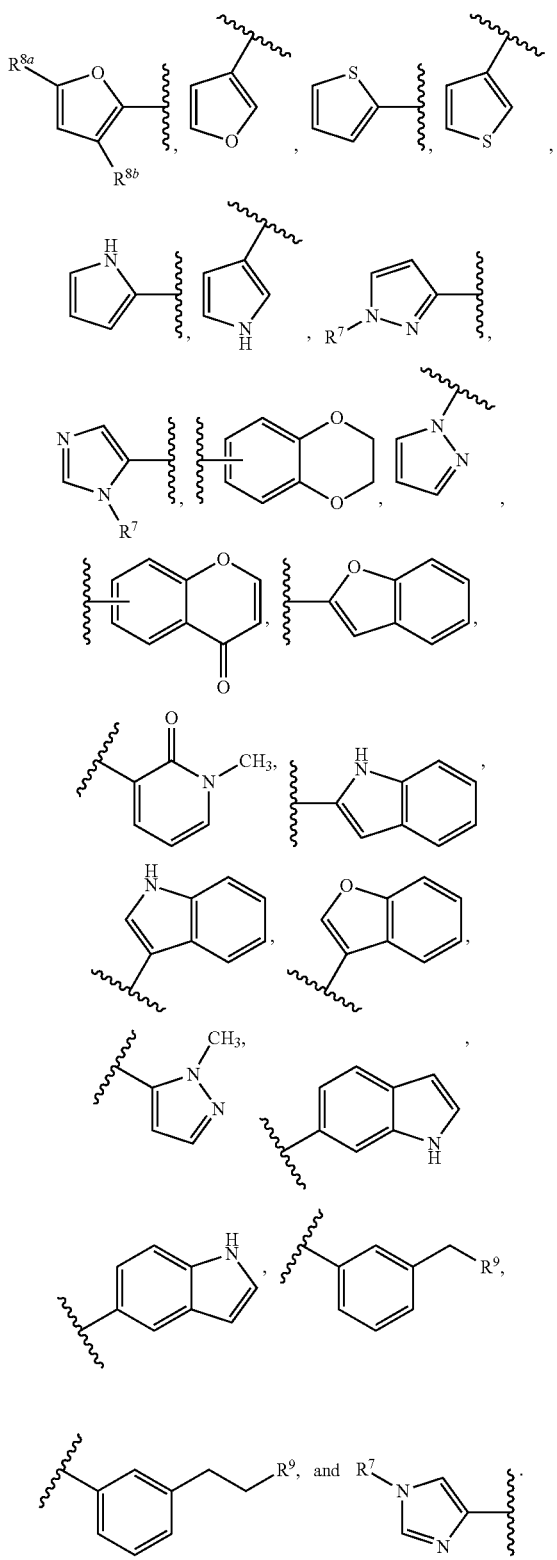

In one aspect, $Ar^3$ is phenyl substituted with 1-4 independently selected $—OR^{31}$ groups; or $Ar^3$ is a five-membered heteroaryl selected from:

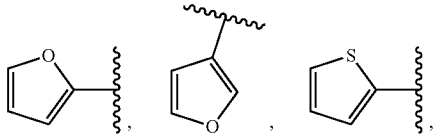

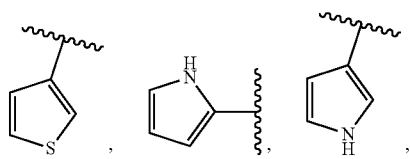

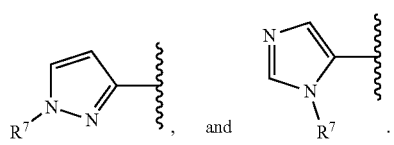

In a further aspect, $Ar^3$ is a five-membered heteroaryl selected from:

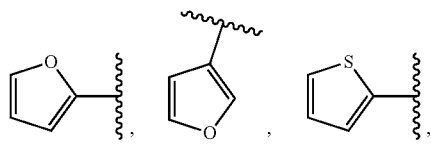

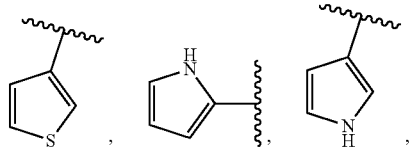

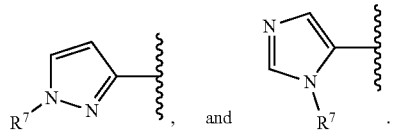

In a further aspect, $Ar^3$ is a five-membered heteroaryl selected from:

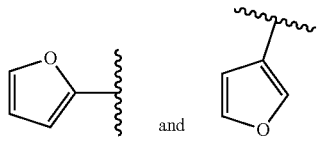

In a further aspect, $Ar^3$ is a five-membered heteroaryl selected from:

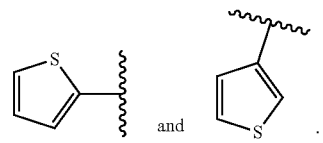 [SMILES: *c1cccs1 ; *c1ccsc1]

In a further aspect, $Ar^3$ is:

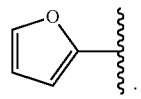

In a further aspect, $Ar^3$ is a five-membered heteroaryl selected from:

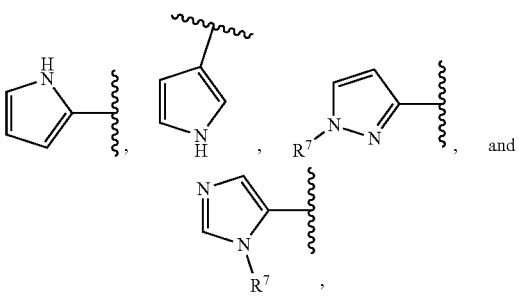

In a further aspect, $Ar^3$ is a five-membered heteroaryl selected from:

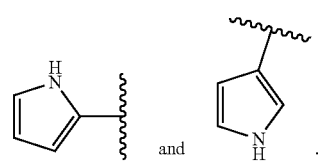 [SMILES: *c1ccc[nH]1 ; *c1cc[nH]c1]

In a further aspect, $Ar^3$ is a five-membered heteroaryl selected from:

[structures: pyrazole with $R^7$ on N, and imidazole with $R^7$ on N]

, and .

In a further aspect, $Ar^3$ is:

[structure: pyrazole with $R^7$ on N]

.

In a further aspect, $Ar^3$ is phenyl substituted with 1-4 independently selected —$OR^3$ groups. In a still further aspect, $Ar^3$ is phenyl substituted with 1-3 independently selected —$OR^{31}$ groups. In yet a further aspect, $Ar^3$ is phenyl substituted with 1-2 independently selected —$OR^{31}$ groups. In an even further aspect, $Ar^3$ is phenyl monosubstituted with a —$OR^{31}$ group.

In a further aspect, $Ar^3$ is phenyl substituted with 1-4-$OCH_2CH_2CH_3$ groups. In a still further aspect, $Ar^3$ is phenyl substituted with 1-3-$OCH_2CH_2CH_3$ groups. In yet a further aspect, $Ar^3$ is phenyl substituted with —$OCH_2CH_2CH_3$ groups. In an even further aspect, $Ar^3$ is phenyl monosubstituted with a —$OCH_2CH_2CH_3$ group.

l. $Ar^4$ Groups

In one aspect, $Ar^4$, when present, is selected from aryl and heteroaryl and is substituted with 0-4 non-hydrogen groups independently selected from halogen, —OH, —CN, C1-C4 alkyl, C1-C4 alkoxy, and C1-C4 haloalkyl. In a further aspect, $Ar^4$, when present, is selected from aryl and heteroaryl and is substituted with 0-3 non-hydrogen groups independently selected from halogen, —OH, —CN, C1-C4 alkyl, C1-C4 alkoxy, and C1-C4 haloalkyl. In a still further aspect, $Ar^4$, when present, is selected from aryl and heteroaryl and is substituted with 0-2 non-hydrogen groups independently selected from halogen, —OH, —CN, C1-C4 alkyl, C1-C4 alkoxy, and C1-C4 haloalkyl. In yet a further aspect, $Ar^4$, when present, is selected from aryl and heteroaryl and is substituted with 0-1 non-hydrogen groups independently selected from halogen, —OH, —CN, C1-C4 alkyl, C1-C4 alkoxy, and C1-C4 haloalkyl. In an even further aspect, $Ar^4$, when present, is selected from aryl and heteroaryl and is substituted with a non-hydrogen group selected from halogen, —OH, —CN, C1-C4 alkyl, C1-C4 alkoxy, and C1-C4 haloalkyl. In a still further aspect, $Ar^4$, when present, is selected from aryl and heteroaryl and is unsubstituted.

In a further aspect, $Ar^4$, when present, is heteroaryl substituted with 0-4 non-hydrogen groups independently selected from halogen, —OH, —CN, C1-C4 alkyl, C1-C4 alkoxy, and C1-C4 haloalkyl. In a still further aspect, $Ar^4$, when present, is heteroaryl substituted with 0-3 non-hydrogen groups independently selected from halogen, —OH, —CN, C1-C4 alkyl, C1-C4 alkoxy, and C1-C4 haloalkyl. In yet a further aspect, $Ar^4$, when present, is heteroaryl substituted with 0-2 non-hydrogen groups independently selected from halogen, —OH, —CN, C1-C4 alkyl, C1-C4 alkoxy, and C1-C4 haloalkyl. In an even further aspect, $Ar^4$, when present, is heteroaryl substituted with 0-1 non-hydrogen groups independently selected from halogen, —OH, —CN, C1-C4 alkyl, C1-C4 alkoxy, and C1-C4 haloalkyl. In a still further aspect, $Ar^4$, when present, is heteroaryl substituted with a non-hydrogen group selected from halogen, —OH, —CN, C1-C4 alkyl, C1-C4 alkoxy, and C1-C4 haloalkyl. In yet a further aspect, $Ar^4$, when present, is unsubstituted heteroaryl.

In a further aspect, $Ar^4$, when present, is pyridinyl substituted with 0-4 non-hydrogen groups independently selected from halogen, —OH, —CN, C1-C4 alkyl, C1-C4 alkoxy, and C1-C4 haloalkyl. In a still further aspect, $Ar^4$, when present, is pyridinyl substituted with 0-3 non-hydrogen groups independently selected from halogen, —OH, —CN, C1-C4 alkyl, C1-C4 alkoxy, and C1-C4 haloalkyl. In yet a further aspect, $Ar^4$, when present, is pyridinyl substituted with 0-2 non-hydrogen groups independently selected from halogen, —OH, —CN, C1-C4 alkyl, C1-C4 alkoxy, and C1-C4 haloalkyl. In an even further aspect, $Ar^4$, when present, is pyridinyl substituted with 0-1 non-hydrogen groups independently selected from halogen, —OH, —CN, C1-C4 alkyl, C1-C4 alkoxy, and C1-C4 haloalkyl. In a still further aspect, $Ar^4$, when present, is pyridinyl substituted with a non-hydrogen group selected from halogen, —OH, —CN, C1-C4 alkyl, C1-C4 alkoxy, and C1-C4 haloalkyl. In yet a further aspect, $Ar^4$, when present, is unsubstituted pyridinyl.

In a further aspect, $Ar^4$, when present, is aryl substituted with 0-4 non-hydrogen groups independently selected from halogen, —OH, —CN, C1-C4 alkyl, C1-C4 alkoxy, and C1-C4 haloalkyl. In a still further aspect, $Ar^4$, when present, is aryl substituted with 0-3 non-hydrogen groups independently selected from halogen, —OH, —CN, C1-C4 alkyl, C1-C4 alkoxy, and C1-C4 haloalkyl. In yet a further aspect, $Ar^4$, when present, is aryl substituted with 0-2 non-hydrogen groups independently selected from halogen, —OH, —CN, C1-C4 alkyl, C1-C4 alkoxy, and C1-C4 haloalkyl. In an even further aspect, $Ar^4$, when present, is aryl substituted with 0-1 non-hydrogen groups independently selected from halogen, —OH, —CN, C1-C4 alkyl, C1-C4 alkoxy, and C1-C4 haloalkyl. In a still further aspect, $Ar^4$, when present, is aryl substituted with a non-hydrogen group selected from halogen, —OH, —CN, C1-C4 alkyl, C1-C4 alkoxy, and C1-C4 haloalkyl. In yet a further aspect, $Ar^4$, when present, is unsubstituted aryl.

In a further aspect, $Ar^4$, when present, is phenyl substituted with 0-4 non-hydrogen groups independently selected from halogen, —OH, —CN, C1-C4 alkyl, C1-C4 alkoxy, and C1-C4 haloalkyl. In a still further aspect, $Ar^4$, when present, is phenyl substituted with 0-3 non-hydrogen groups independently selected from halogen, —OH, —CN, C1-C4 alkyl, C1-C4 alkoxy, and C1-C4 haloalkyl. In yet a further aspect, $Ar^4$, when present, is phenyl substituted with 0-2 non-hydrogen groups independently selected from halogen, —OH, —CN, C1-C4 alkyl, C1-C4 alkoxy, and C1-C4 haloalkyl. In an even further aspect, $Ar^4$, when present, is phenyl substituted with 0-1 non-hydrogen groups independently selected from halogen, —OH, —CN, C1-C4 alkyl, C1-C4 alkoxy, and C1-C4 haloalkyl. In a still further aspect, $Ar^4$, when present, is phenyl substituted with a non-hydrogen group selected from halogen, —OH, —CN, C1-C4 alkyl, C1-C4 alkoxy, and C1-C4 haloalkyl. In yet a further aspect, $Ar^4$, when present, is unsubstituted phenyl.

m. $Cy^1$ Groups

In one aspect, $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl. In a further aspect, $Cy^1$, when present, is selected from cycloalkyl, five-membered heterocycle, and six-membered heterocycle and is substituted with 0-3 non-hydrogen groups independently selected from halogen, —OH, —CN, C1-C4 alkyl, C1-C4 alkoxy, and C1-C4 haloalkyl. In a still further aspect, $Cy^1$, when present, is selected from cycloalkyl, five-membered heterocycle, and six-membered heterocycle and is substituted with 0-2 non-hydrogen groups independently selected from halogen, —OH, —CN, C1-C4 alkyl, C1-C4 alkoxy, and C1-C4 haloalkyl. In yet a further aspect, $Cy^1$, when present, is selected from cycloalkyl, five-membered heterocycle, and six-membered heterocycle and is substituted with 0-1 non-hydrogen groups independently selected from halogen, —OH, —CN, C1-C4 alkyl, C1-C4 alkoxy, and C1-C4 haloalkyl. In an even further aspect, $Cy^1$, when present, is selected from cycloalkyl, five-membered heterocycle, and six-membered heterocycle and is substituted with a non-hydrogen group selected from halogen, —OH, —CN, C1-C4 alkyl, C1-C4 alkoxy, and C1-C4 haloalkyl. In a still further aspect, $Cy^1$, when present, is selected from cycloalkyl, five-membered heterocycle, and six-membered heterocycle and is unsubstituted.

In a further aspect, $Cy^1$, when present, is cycle substituted with 0-4 non-hydrogen groups independently selected from halogen, —OH, —CN, C1-C4 alkyl, C1-C4 alkoxy, and C1-C4 haloalkyl. In a still further aspect, $Cy^1$, when present, is cycle substituted with 0-3 non-hydrogen groups independently selected from halogen, —OH, —CN, C1-C4 alkyl, C1-C4 alkoxy, and C1-C4 haloalkyl. In yet a further aspect, $Cy^1$, when present, is cycle substituted with 0-2 non-hydrogen groups independently selected from halogen, —OH, —CN, C1-C4 alkyl, C1-C4 alkoxy, and C1-C4 haloalkyl. In an even further aspect, $Cy^1$, when present, is cycle substituted with 0-1 non-hydrogen groups independently selected from halogen, —OH, —CN, C1-C4 alkyl, C1-C4 alkoxy, and C1-C4 haloalkyl. In a still further aspect, $Cy^1$, when present, is cycle substituted with a non-hydrogen group selected from halogen, —OH, —CN, C1-C4 alkyl, C1-C4 alkoxy, and C1-C4 haloalkyl. In a still further aspect, $Cy^1$, when present, is unsubstituted cycle.

In a further aspect, $Cy^1$, when present, is cyclopentyl substituted with 0-4 non-hydrogen groups independently selected from halogen, —OH, —CN, C1-C4 alkyl, C1-C4 alkoxy, and C1-C4 haloalkyl. In a still further aspect, $Cy^1$, when present, is cyclopentyl substituted with 0-3 non-hydrogen groups independently selected from halogen, —OH, —CN, C1-C4 alkyl, C1-C4 alkoxy, and C1-C4 haloalkyl. In yet a further aspect, $Cy^1$, when present, is cyclopentyl substituted with 0-2 non-hydrogen groups independently selected from halogen, —OH, —CN, C1-C4 alkyl, C1-C4 alkoxy, and C1-C4 haloalkyl. In an even further aspect, $Cy^1$, when present, is cyclopentyl substituted with 0-1 non-hydrogen groups independently selected from halogen, —OH, —CN, C1-C4 alkyl, C1-C4 alkoxy, and C1-C4 haloalkyl. In a still further aspect, $Cy^1$, when present, is cyclopentyl substituted with a non-hydrogen group selected from halogen, —OH, —CN, C1-C4 alkyl, C1-C4 alkoxy, and C1-C4 haloalkyl. In a still further aspect, $Cy^1$, when present, is unsubstituted cyclopentyl.

In a further aspect, $Cy^1$, when present, is cycloheptyl substituted with 0-4 non-hydrogen groups independently selected from halogen, —OH, —CN, C1-C4 alkyl, C1-C4 alkoxy, and C1-C4 haloalkyl. In a still further aspect, $Cy^1$, when present, is cycloheptyl substituted with 0-3 non-hydrogen groups independently selected from halogen, —OH, —CN, C1-C4 alkyl, C1-C4 alkoxy, and C1-C4 haloalkyl. In yet a further aspect, $Cy^1$, when present, is cycloheptyl substituted with 0-2 non-hydrogen groups independently selected from halogen, —OH, —CN, C1-C4 alkyl, C1-C4 alkoxy, and C1-C4 haloalkyl. In an even further aspect, $Cy^1$, when present, is cycloheptyl substituted with 0-1 non-hydrogen groups independently selected from halogen, —OH, —CN, C1-C4 alkyl, C1-C4 alkoxy, and C1-C4 haloalkyl. In a still further aspect, $Cy^1$, when present, is cycloheptyl substituted with a non-hydrogen group selected from halogen, —OH, —CN, C1-C4 alkyl, C1-C4 alkoxy, and C1-C4 haloalkyl. In a still further aspect, $Cy^1$, when present, is unsubstituted cycloheptyl.

In a further aspect, $Cy^1$, when present, is selected from five-membered heterocycle and six-membered heterocycle and is substituted with 0-4 non-hydrogen groups independently selected from halogen, —OH, —CN, C1-C4 alkyl, C1-C4 alkoxy, and C1-C4 haloalkyl. In a still further aspect, $Cy^1$, when present, is selected from five-membered heterocycle and six-membered heterocycle and is substituted with 0-3 non-hydrogen groups independently selected from halogen, —OH, —CN, C1-C4 alkyl, C1-C4 alkoxy, and C1-C4 haloalkyl. In yet a further aspect, $Cy^1$, when present, is selected from five-membered heterocycle and six-membered heterocycle and is substituted with 0-2 non-hydrogen groups independently selected from halogen, —OH, —CN, C1-C4 alkyl, C1-C4 alkoxy, and C1-C4 haloalkyl. In an even further aspect, $Cy^1$, when present, is selected from five-membered heterocycle and six-membered heterocycle and is substituted with 0-1 non-hydrogen groups independently selected from halogen, —OH, —CN, C1-C4 alkyl, C1-C4 alkoxy, and C1-C4 haloalkyl. In a still further aspect, $Cy^1$, when present, is selected from five-membered heterocycle and six-membered heterocycle and is substituted with a non-hydrogen group selected from halogen, —OH, —CN, C1-C4 alkyl, C1-C4 alkoxy, and C1-C4 haloalkyl. In a still further aspect, $Cy^1$, when present, is selected from five-membered heterocycle and six-membered heterocycle and is unsubstituted.

In a further aspect, $Cy^1$, when present, is five-membered heterocycle substituted with 0-4 non-hydrogen groups independently selected from halogen, —OH, —CN, C1-C4 alkyl, C1-C4 alkoxy, and C1-C4 haloalkyl. In a still further aspect, $Cy^1$, when present, is five-membered heterocycle substituted with 0-3 non-hydrogen groups independently selected from halogen, —OH, —CN, C1-C4 alkyl, C1-C4 alkoxy, and C1-C4 haloalkyl. In yet a further aspect, $Cy^1$, when present, is five-membered heterocycle substituted with 0-2 non-hydrogen groups independently selected from halogen, —OH, —CN, C1-C4 alkyl, C1-C4 alkoxy, and C1-C4 haloalkyl. In an even further aspect, $Cy^1$, when present, is five-membered heterocycle substituted with 0-1 non-hydrogen groups independently selected from halogen, —OH, —CN, C1-C4 alkyl, C1-C4 alkoxy, and C1-C4 haloalkyl. In a still further aspect, $Cy^1$, when present, is five-membered heterocycle substituted with a non-hydrogen group selected from halogen, —OH, —CN, C1-C4 alkyl, C1-C4 alkoxy, and C1-C4 haloalkyl. In a still further aspect, $Cy^1$, when present, is unsubstituted five-membered heterocycle.

In a further aspect, $Cy^1$, when present, is six-membered heterocycle substituted with 0-4 non-hydrogen groups independently selected from halogen, —OH, —CN, C1-C4 alkyl, C1-C4 alkoxy, and C1-C4 haloalkyl. In a still further aspect, $Cy^1$, when present, is six-membered heterocycle substituted with 0-3 non-hydrogen groups independently selected from halogen, —OH, —CN, C1-C4 alkyl, C1-C4 alkoxy, and C1-C4 haloalkyl. In yet a further aspect, $Cy^1$, when present, is six-membered heterocycle substituted with 0-2 non-hydrogen groups independently selected from halogen, —OH, —CN, C1-C4 alkyl, C1-C4 alkoxy, and C1-C4 haloalkyl. In an even further aspect, $Cy^1$, when present, is six-membered heterocycle substituted with 0-1 non-hydrogen groups independently selected from halogen, —OH, —CN, C1-C4 alkyl, C1-C4 alkoxy, and C1-C4 haloalkyl. In a still further aspect, $Cy^1$, when present, is six-membered heterocycle substituted with a non-hydrogen group selected from halogen, —OH, —CN, C1-C4 alkyl, C1-C4 alkoxy, and C1-C4 haloalkyl. In a still further aspect, $Cy^1$, when present, is unsubstituted six-membered heterocycle.

In a further aspect, $Cy^1$, when present, is tetrahydro-2H-pyranyl substituted with 0-4 non-hydrogen groups independently selected from halogen, —OH, —CN, C1-C4 alkyl, C1-C4 alkoxy, and C1-C4 haloalkyl. In a still further aspect, $Cy^1$, when present, is tetrahydro-2H-pyranyl substituted with 0-3 non-hydrogen groups independently selected from halogen, —OH, —CN, C1-C4 alkyl, C1-C4 alkoxy, and C1-C4 haloalkyl. In yet a further aspect, $Cy^1$, when present, is tetrahydro-2H-pyranyl substituted with 0-2 non-hydrogen groups independently selected from halogen, —OH, —CN, C1-C4 alkyl, C1-C4 alkoxy, and C1-C4 haloalkyl. In an even further aspect, $Cy^1$, when present, is tetrahydro-2H-pyranyl substituted with 0-1 non-hydrogen groups independently selected from halogen, —OH, —CN, C1-C4 alkyl, C1-C4 alkoxy, and C1-C4 haloalkyl. In a still further aspect, $Cy^1$, when present, is tetrahydro-2H-pyranyl substituted with a non-hydrogen group selected from halogen, —OH, —CN, C1-C4 alkyl, C1-C4 alkoxy, and C1-C4 haloalkyl. In a still further aspect, $Cy^1$, when present, is unsubstituted tetrahydro-2H-pyranyl.

n. $Cy^2$ Groups

In one aspect, $Cy^2$, when present, is selected from C3-C6 cycloalkyl and C3-C6 heterocycloalkyl and is substituted with 0-4 non-hydrogen groups independently selected from halogen, —OH, —CN, C1-C4 alkyl, C1-C4 alkoxy, and C1-C4 haloalkyl. In a further aspect, $Cy^2$, when present, is selected from C3-C6 cycloalkyl and C3-C6 heterocycloalkyl and is substituted with 0-3 non-hydrogen groups independently selected from halogen, —OH, —CN, C1-C4 alkyl, C1-C4 alkoxy, and C1-C4 haloalkyl. In a still further aspect, $Cy^2$, when present, is selected from C3-C6 cycloalkyl and C3-C6 heterocycloalkyl and is substituted with 0-2 non-hydrogen groups independently selected from halogen, —OH, —CN, C1-C4 alkyl, C1-C4 alkoxy, and C1-C4 haloalkyl. In yet a further aspect, $Cy^2$, when present, is selected from C3-C6 cycloalkyl and C3-C6 heterocycloalkyl and is substituted with 0-1 non-hydrogen groups independently selected from halogen, —OH, —CN, C1-C4 alkyl, C1-C4 alkoxy, and C1-C4 haloalkyl. In an even further aspect, $Cy^2$, when present, is selected from C3-C6 cycloalkyl and C3-C6 heterocycloalkyl and is substituted with a non-hydrogen group selected from halogen, —OH, —CN, C1-C4 alkyl, C1-C4 alkoxy, and C1-C4 haloalkyl. In a still further aspect, $Cy^2$, when present, is selected from C3-C6 cycloalkyl and C3-C6 heterocycloalkyl and is unsubstituted.

In a further aspect, $Cy^2$, when present, is C3-C6 cycloalkyl substituted with 0-4 non-hydrogen groups independently selected from halogen, —OH, —CN, C1-C4 alkyl, C1-C4 alkoxy, and C1-C4 haloalkyl. In a still further aspect, $Cy^2$, when present, is C3-C6 cycloalkyl substituted with 0-3 non-hydrogen groups independently selected from halogen, —OH, —CN, C1-C4 alkyl, C1-C4 alkoxy, and C1-C4 haloalkyl. In yet a further aspect, $Cy^2$, when present, is C3-C6 cycloalkyl substituted with 0-2 non-hydrogen groups independently selected from halogen, —OH, —CN, C1-C4 alkyl, C1-C4 alkoxy, and C1-C4 haloalkyl. In an even further aspect, $Cy^2$, when present, is C3-C6 cycloalkyl substituted with 0-1 non-hydrogen groups independently selected from halogen, —OH, —CN, C1-C4 alkyl, C1-C4 alkoxy, and C1-C4 haloalkyl. In a still further aspect, $Cy^2$, when present, is C3-C6 cycloalkyl substituted with a non-hydrogen group selected from halogen, —OH, —CN, C1-C4 alkyl, C1-C4 alkoxy, and C1-C4 haloalkyl. In a still further aspect, $Cy^2$, when present, is unsubstituted C3-C6 cycloalkyl.

In a further aspect, $Cy^2$, when present, is cyclopentyl substituted with 0-4 non-hydrogen groups independently selected from halogen, —OH, —CN, C1-C4 alkyl, C1-C4 alkoxy, and C1-C4 haloalkyl. In a still further aspect, $Cy^2$, when present, is cyclopentyl substituted with 0-3 non-hydrogen groups independently selected from halogen, —OH, —CN, C1-C4 alkyl, C1-C4 alkoxy, and C1-C4 haloalkyl. In yet a further aspect, $Cy^2$, when present, is cyclopentyl substituted with 0-2 non-hydrogen groups independently selected from halogen, —OH, —CN, C1-C4 alkyl, C1-C4 alkoxy, and C1-C4 haloalkyl. In an even further aspect, $Cy^2$, when present, is cyclopentyl substituted with 0-1 non-hydrogen groups independently selected from halogen, —OH, —CN, C1-C4 alkyl, C1-C4 alkoxy, and C1-C4 haloalkyl. In a still further aspect, $Cy^2$, when present, is cyclopentyl substituted with a non-hydrogen group selected from halogen, —OH, —CN, C1-C4 alkyl, C1-C4 alkoxy, and C1-C4 haloalkyl. In a still further aspect, $Cy^2$, when present, is unsubstituted cyclopentyl.

In a further aspect, $Cy^2$, when present, is cycloheptyl substituted with 0-4 non-hydrogen groups independently selected from halogen, —OH, —CN, C1-C4 alkyl, C1-C4 alkoxy, and C1-C4 haloalkyl. In a still further aspect, $Cy^2$, when present, is cycloheptyl substituted with 0-3 non-hydrogen groups independently selected from halogen, —OH, —CN, C1-C4 alkyl, C1-C4 alkoxy, and C1-C4 haloalkyl. In yet a further aspect, $Cy^2$, when present, is cycloheptyl substituted with 0-2 non-hydrogen groups independently selected from halogen, —OH, —CN, C1-C4 alkyl, C1-C4 alkoxy, and C1-C4 haloalkyl. In an even further aspect, $Cy^2$, when present, is cycloheptyl substituted with 0-1 non-hydrogen groups independently selected from halogen, —OH, —CN, C1-C4 alkyl, C1-C4 alkoxy, and C1-C4 haloalkyl. In a still further aspect, $Cy^2$, when present, is cycloheptyl substituted with a non-hydrogen group selected from halogen, —OH, —CN, C1-C4 alkyl, C1-C4 alkoxy, and C1-C4 haloalkyl. In a still further aspect, $Cy^2$, when present, is unsubstituted cycloheptyl.

In a further aspect, $Cy^2$, when present, is C3-C6 heterocycloalkyl substituted with 0-4 non-hydrogen groups independently selected from halogen, —OH, —CN, C1-C4 alkyl, C1-C4 alkoxy, and C1-C4 haloalkyl. In a still further aspect, $Cy^2$, when present, is C3-C6 heterocycloalkyl substituted with 0-3 non-hydrogen groups independently selected from halogen, —OH, —CN, C1-C4 alkyl, C1-C4 alkoxy, and C1-C4 haloalkyl. In yet a further aspect, $Cy^2$, when present, is C3-C6 heterocycloalkyl substituted with 0-2 non-hydrogen groups independently selected from halogen, —OH, —CN, C1-C4 alkyl, C1-C4 alkoxy, and C1-C4 haloalkyl. In an even further aspect, $Cy^2$, when present, is C3-C6 heterocycloalkyl substituted with 0-1 non-hydrogen groups independently selected from halogen, —OH, —CN, C1-C4 alkyl, C1-C4 alkoxy, and C1-C4 haloalkyl. In a still further aspect, $Cy^2$, when present, is C3-C6 heterocycloalkyl substituted with a non-hydrogen group selected from halogen, —OH, —CN, C1-C4 alkyl, C1-C4 alkoxy, and C1-C4 haloalkyl. In a still further aspect, $Cy^2$, when present, is unsubstituted C3-C6 heterocycloalkyl.

In a further aspect, $Cy^2$, when present, is tetrahydro-2H-pyranyl substituted with 0-4 non-hydrogen groups independently selected from halogen, —OH, —CN, C1-C4 alkyl, C1-C4 alkoxy, and C1-C4 haloalkyl. In a still further aspect, $Cy^2$, when present, is tetrahydro-2H-pyranyl substituted with 0-3 non-hydrogen groups independently selected from halogen, —OH, —CN, C1-C4 alkyl, C1-C4 alkoxy, and C1-C4 haloalkyl. In yet a further aspect, $Cy^2$, when present, is tetrahydro-2H-pyranyl substituted with 0-2 non-hydrogen groups independently selected from halogen, —OH, —CN, C1-C4 alkyl, C1-C4 alkoxy, and C1-C4 haloalkyl. In an even further aspect, $Cy^2$, when present, is tetrahydro-2H-pyranyl substituted with 0-1 non-hydrogen groups independently selected from halogen, —OH, —CN, C1-C4 alkyl, C1-C4 alkoxy, and C1-C4 haloalkyl. In a still further aspect, $Cy^2$, when present, is tetrahydro-2H-pyranyl substituted with a non-hydrogen group selected from halogen, —OH, —CN, C1-C4 alkyl, C1-C4 alkoxy, and C1-C4 haloalkyl. In a still further aspect, $Cy^2$, when present, is unsubstituted tetrahydro-2H-pyranyl.

o. $Cy^3$ Groups

In one aspect, $Cy^3$, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl. In a further aspect, $Cy^3$, when present, is selected from cycloalkyl, heterocycloalkyl, aryl, and heteroaryl and is substituted with 0-3 non-hydrogen groups independently selected from halogen, —OH, —CN, C1-C4 alkyl, C1-C4 alkoxy, and C1-C4 haloalkyl. In a still further aspect, $Cy^3$, when present, is selected from cycloalkyl, heterocycloalkyl, aryl, and heteroaryl and is substituted with 0-2 non-hydrogen groups independently selected from halogen, —OH, —CN, C1-C4 alkyl, C1-C4 alkoxy, and C1-C4 haloalkyl. In yet a further aspect, $Cy^3$, when present, is selected from cycloalkyl, heterocycloalkyl, aryl, and heteroaryl and is substituted with 0-1 non-hydrogen groups independently selected from halogen, —OH, —CN, C1-C4 alkyl, C1-C4 alkoxy, and C1-C4 haloalkyl. In an even further aspect, $Cy^3$, when present, is selected from cycloalkyl, heterocycloalkyl, aryl, and heteroaryl and is monosubstituted with a non-hydrogen group selected from halogen, —OH, —CN, C1-C4 alkyl, C1-C4 alkoxy, and C1-C4 haloalkyl. In a still further aspect, $Cy^3$, when present, is selected from cycloalkyl, heterocycloalkyl, aryl, and heteroaryl and is unsubstituted.

In a further aspect, $Cy^3$, when present, is selected from cycloalkyl and heterocycloalkyl and is substituted with 0-4 non-hydrogen groups independently selected from halogen, —OH, —CN, C1-C4 alkyl, C1-C4 alkoxy, and C1-C4 haloalkyl. In a further aspect, $Cy^3$, when present, is selected from cycloalkyl and heterocycloalkyl and is substituted with 0-3 non-hydrogen groups independently selected from halogen, —OH, —CN, C1-C4 alkyl, C1-C4 alkoxy, and C1-C4 haloalkyl. In a still further aspect, $Cy^3$, when present, is selected from cycloalkyl and heterocycloalkyl and is substituted with 0-2 non-hydrogen groups independently selected from halogen, —OH, —CN, C1-C4 alkyl, C1-C4 alkoxy, and C1-C4 haloalkyl. In yet a further aspect, $Cy^3$, when present, is selected from cycloalkyl and heterocycloalkyl and is substituted with 0-1 non-hydrogen groups independently selected from halogen, —OH, —CN, C1-C4 alkyl, C1-C4 alkoxy, and C1-C4 haloalkyl. In an even further aspect, $Cy^3$, when present, is selected from cycloalkyl and heterocycloalkyl and is substituted with a non-hydrogen group selected from halogen, —OH, —CN, C1-C4 alkyl, C1-C4 alkoxy, and C1-C4 haloalkyl. In a still further aspect, $Cy^3$, when present, is selected from cycloalkyl and heterocycloalkyl and is unsubstituted.

In a further aspect, $Cy^3$, when present, is cycloalkyl substituted with 0-4 non-hydrogen groups independently selected from halogen, —OH, —CN, C1-C4 alkyl, C1-C4 alkoxy, and C1-C4 haloalkyl. In a still further aspect, $Cy^3$, when present, is cycloalkyl substituted with 0-3 non-hydrogen groups independently selected from halogen, —OH, —CN, C1-C4 alkyl, C1-C4 alkoxy, and C1-C4 haloalkyl. In yet a further aspect, $Cy^3$, when present, is cycloalkyl substituted with 0-2 non-hydrogen groups independently selected from halogen, —OH, —CN, C1-C4 alkyl, C1-C4 alkoxy, and C1-C4 haloalkyl. In an even further aspect, $Cy^3$, when present, is cycloalkyl substituted with 0-1 non-hydrogen groups independently selected from halogen, —OH, —CN, C1-C4 alkyl, C1-C4 alkoxy, and C1-C4 haloalkyl. In a still further aspect, $Cy^3$, when present, is cycloalkyl substituted with a non-hydrogen group selected from halogen, —OH, —CN, C1-C4 alkyl, C1-C4 alkoxy, and C1-C4 haloalkyl. In a still further aspect, $Cy^3$, when present, is unsubstituted cycloalkyl.

In a further aspect, $Cy^3$, when present, is heterocycloalkyl substituted with 0-4 non-hydrogen groups independently selected from halogen, —OH, —CN, C1-C4 alkyl, C1-C4 alkoxy, and C1-C4 haloalkyl. In a still further aspect, $Cy^3$, when present, is heterocycloalkyl substituted with 0-3 non-hydrogen groups independently selected from halogen, —OH, —CN, C1-C4 alkyl, C1-C4 alkoxy, and C1-C4 haloalkyl. In yet a further aspect, $Cy^3$, when present, is heterocycloalkyl substituted with 0-2 non-hydrogen groups independently selected from halogen, —OH, —CN, C1-C4 alkyl, C1-C4 alkoxy, and C1-C4 haloalkyl. In an even further aspect, $Cy^3$, when present, is heterocycloalkyl substituted with 0-1 non-hydrogen groups independently selected from halogen, —OH, —CN, C1-C4 alkyl, C1-C4 alkoxy, and C1-C4 haloalkyl. In a still further aspect, $Cy^3$, when present, is heterocycloalkyl substituted with a non-hydrogen group selected from halogen, —OH, —CN, C1-C4 alkyl, C1-C4 alkoxy, and C1-C4 haloalkyl. In a still further aspect, $Cy^3$, when present, is unsubstituted heterocycloalkyl.

In a further aspect, $Cy^3$, when present, is selected from aryl and heteroaryl and is substituted with 0-4 non-hydrogen groups independently selected from halogen, —OH, —CN, C1-C4 alkyl, C1-C4 alkoxy, and C1-C4 haloalkyl. In a further aspect, $Cy^3$, when present, is selected from aryl and heteroaryl and is substituted with 0-3 non-hydrogen groups independently selected from halogen, —OH, —CN, C1-C4 alkyl, C1-C4 alkoxy, and C1-C4 haloalkyl. In a still further aspect, $Cy^3$, when present, is selected from aryl and heteroaryl and is substituted with 0-2 non-hydrogen groups independently selected from halogen, —OH, —CN, C1-C4 alkyl, C1-C4 alkoxy, and C1-C4 haloalkyl. In yet a further aspect, $Cy^3$, when present, is selected from aryl and heteroaryl and is substituted with 0-1 non-hydrogen groups independently selected from halogen, —OH, —CN, C1-C4 alkyl, C1-C4 alkoxy, and C1-C4 haloalkyl. In an even further aspect, $Cy^3$, when present, is selected from aryl and heteroaryl and is substituted with a non-hydrogen group selected from halogen, —OH, —CN, C1-C4 alkyl, C1-C4 alkoxy, and C1-C4 haloalkyl. In a still further aspect, $Cy^3$, when present, is selected from aryl and heteroaryl and is unsubstituted.

In a further aspect, $Cy^3$, when present, is heteroaryl substituted with 0-4 non-hydrogen groups independently selected from halogen, —OH, —CN, C1-C4 alkyl, C1-C4 alkoxy, and C1-C4 haloalkyl. In a still further aspect, $Cy^3$, when present, is heteroaryl substituted with 0-3 non-hydrogen groups independently selected from halogen, —OH, —CN, C1-C4 alkyl, C1-C4 alkoxy, and C1-C4 haloalkyl. In yet a further aspect, Cy³, when present, is heteroaryl substituted with 0-2 non-hydrogen groups independently selected from halogen, —OH, —CN, C1-C4 alkyl, C1-C4 alkoxy, and C1-C4 haloalkyl. In an even further aspect, Cy³, when present, is heteroaryl substituted with 0-1 non-hydrogen groups independently selected from halogen, —OH, —CN, C1-C4 alkyl, C1-C4 alkoxy, and C1-C4 haloalkyl. In a still further aspect, Cy³, when present, is heteroaryl substituted with a non-hydrogen group selected from halogen, —OH, —CN, C1-C4 alkyl, C1-C4 alkoxy, and C1-C4 haloalkyl. In yet a further aspect, Cy³, when present, is unsubstituted heteroaryl.

In a further aspect, Cy³, when present, is aryl substituted with 0-4 non-hydrogen groups independently selected from halogen, —OH, —CN, C1-C4 alkyl, C1-C4 alkoxy, and C1-C4 haloalkyl. In a still further aspect, Cy³, when present, is aryl substituted with 0-3 non-hydrogen groups independently selected from halogen, —OH, —CN, C1-C4 alkyl, C1-C4 alkoxy, and C1-C4 haloalkyl. In yet a further aspect, Cy³, when present, is aryl substituted with 0-2 non-hydrogen groups independently selected from halogen, —OH, —CN, C1-C4 alkyl, C1-C4 alkoxy, and C1-C4 haloalkyl. In an even further aspect, Cy³, when present, is aryl substituted with 0-1 non-hydrogen groups independently selected from halogen, —OH, —CN, C1-C4 alkyl, C1-C4 alkoxy, and C1-C4 haloalkyl. In a still further aspect, Cy³, when present, is aryl substituted with a non-hydrogen group selected from halogen, —OH, —CN, C1-C4 alkyl, C1-C4 alkoxy, and C1-C4 haloalkyl. In yet a further aspect, Cy³, when present, is unsubstituted aryl.

2. Example Compounds

In one aspect, a compound can be present as one or more of the following structures:

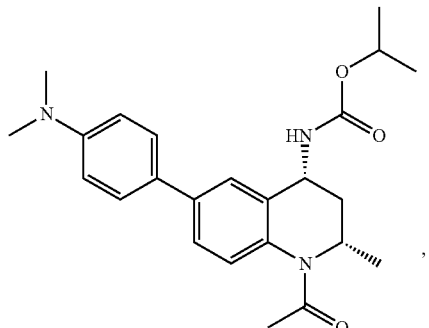

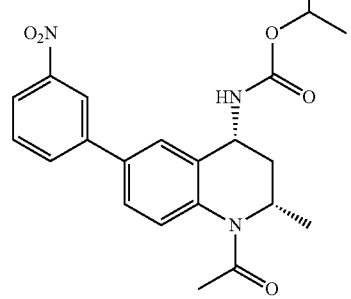

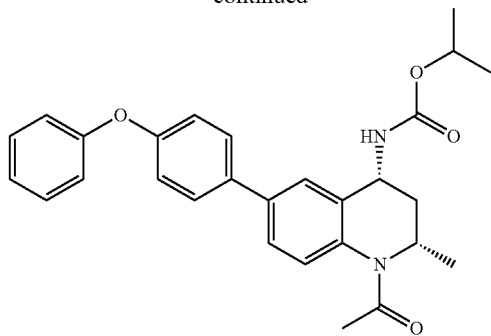

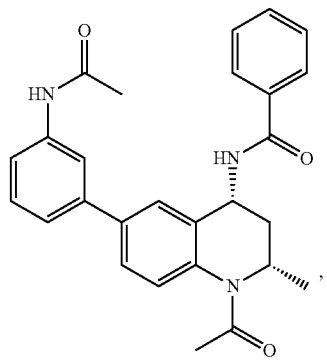

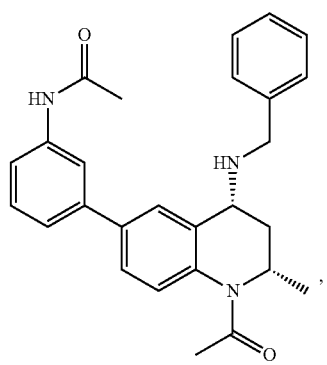

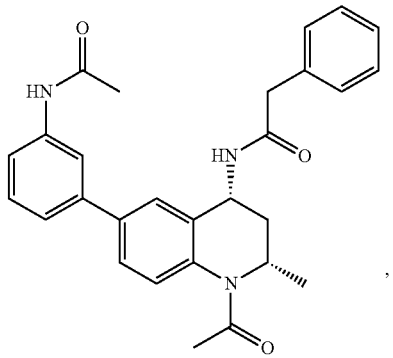

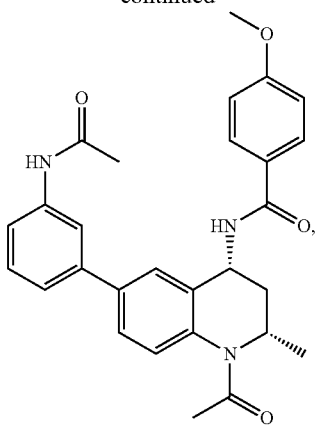
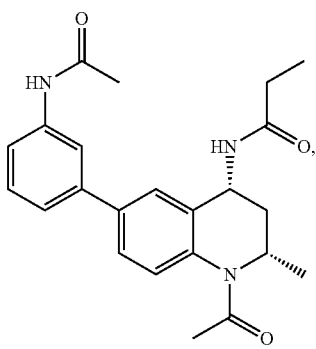
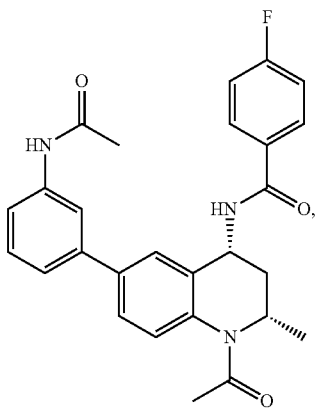
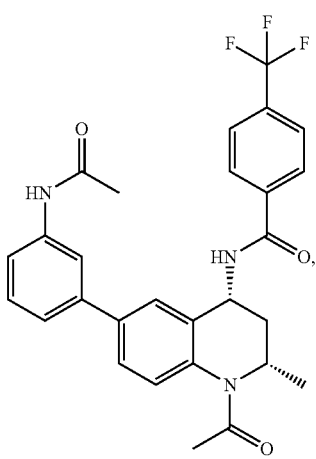
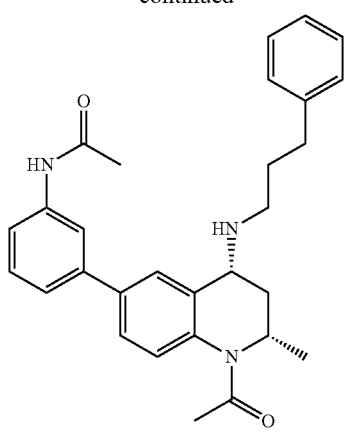
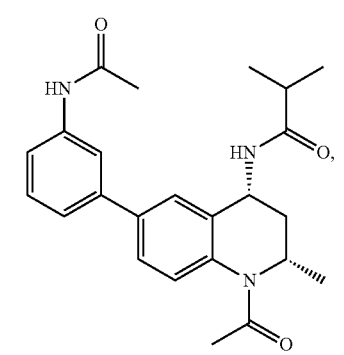
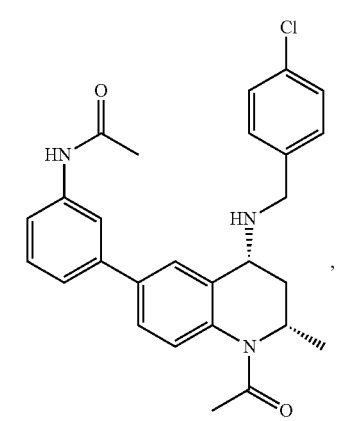
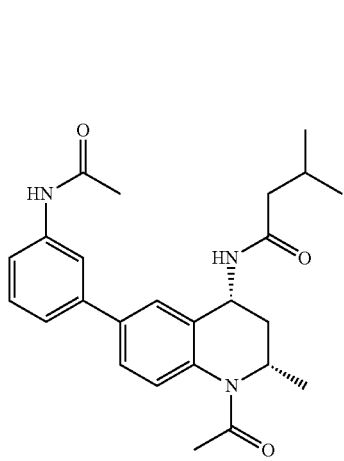

115
-continued
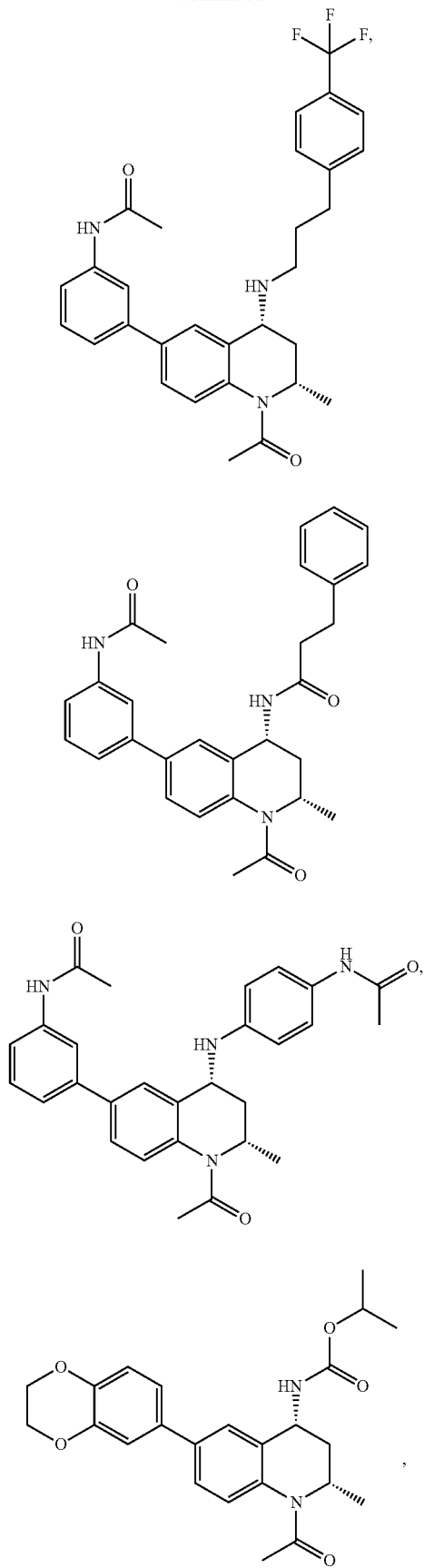
116
-continued
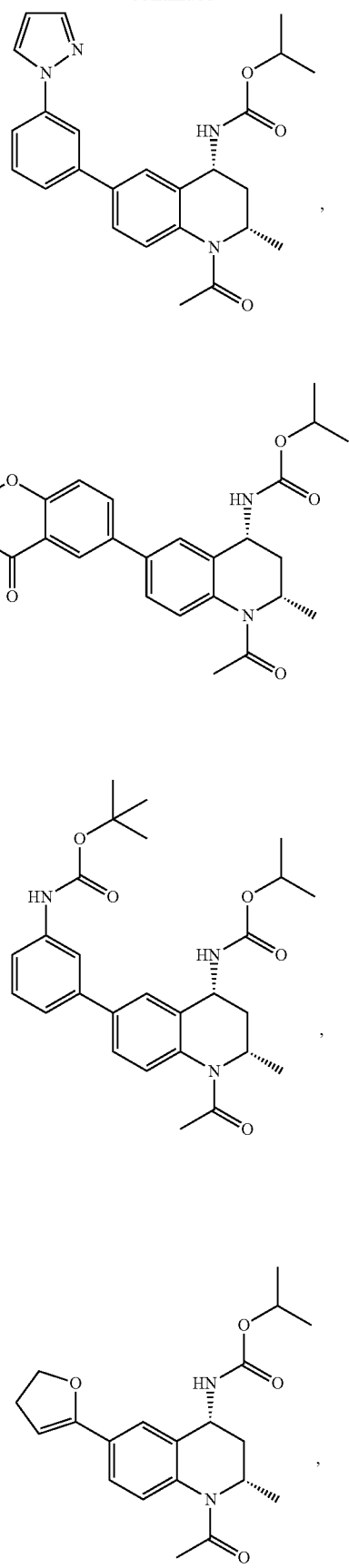

117
-continued
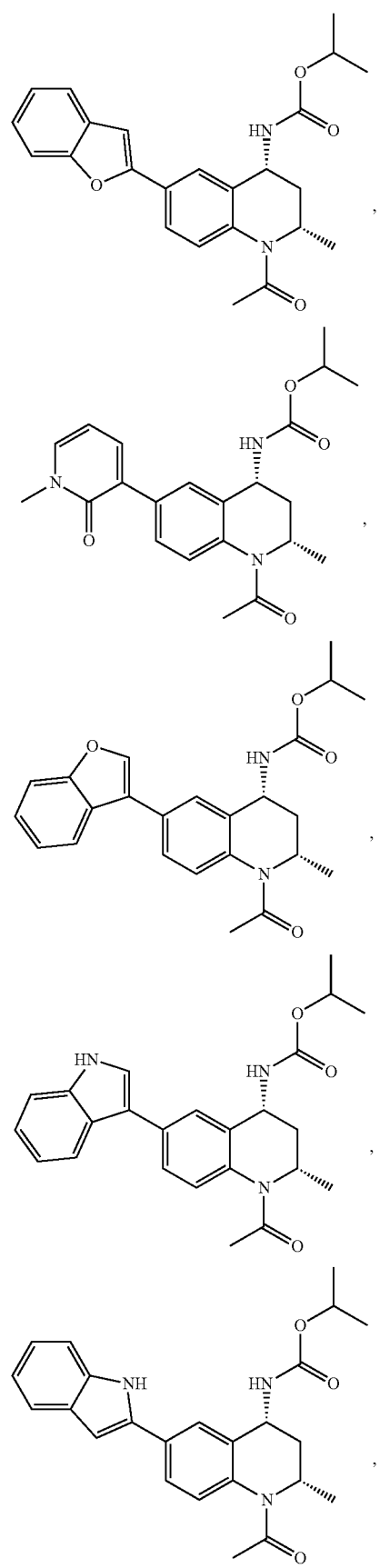
118
-continued
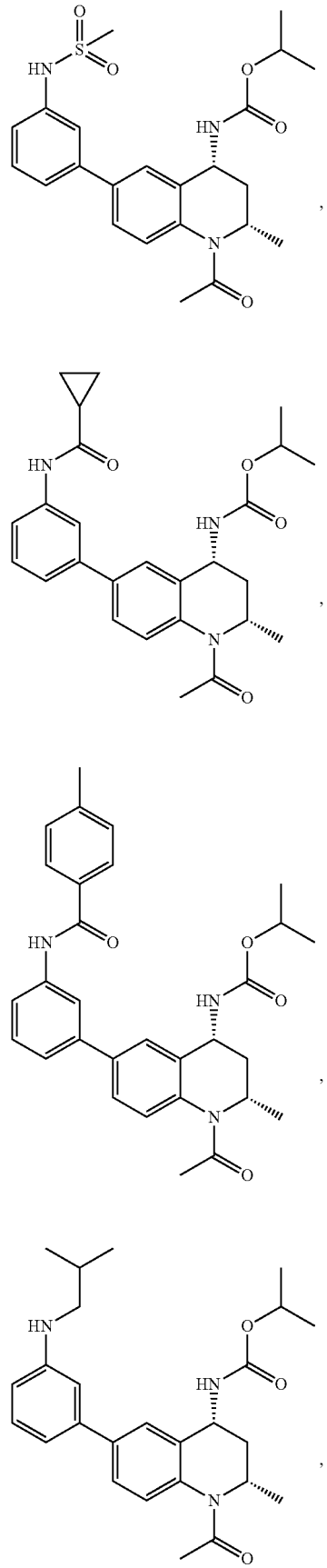

-continued
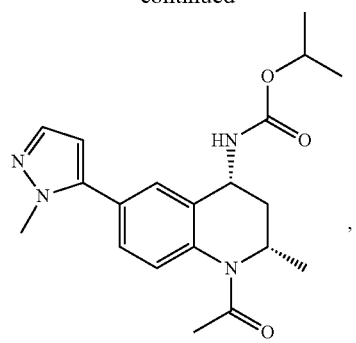
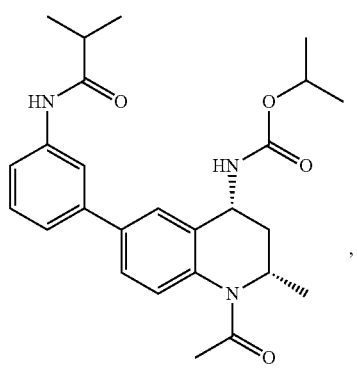
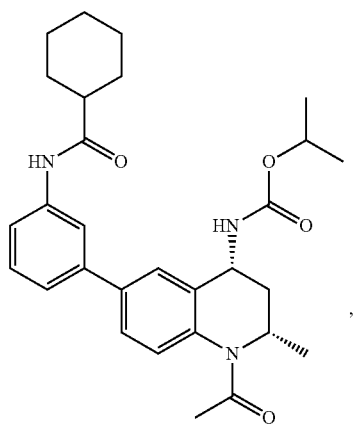
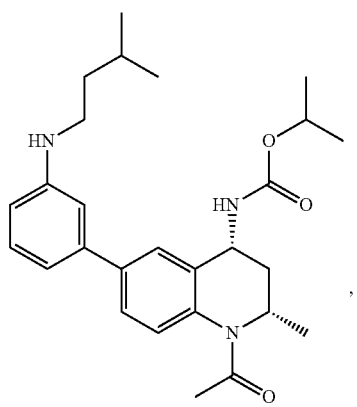
-continued
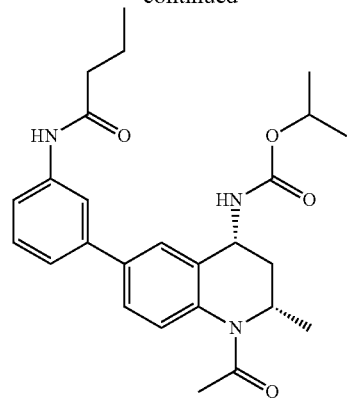
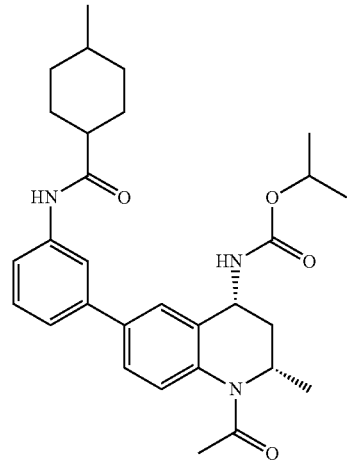
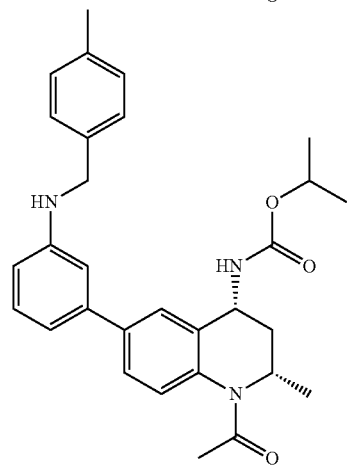
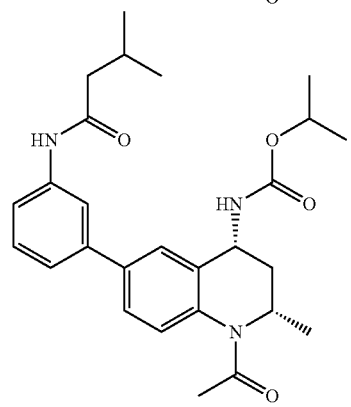

121
-continued
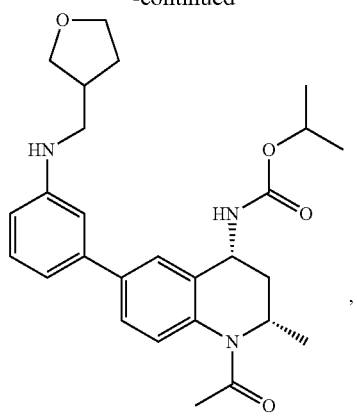
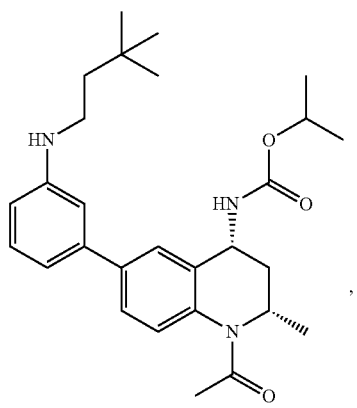
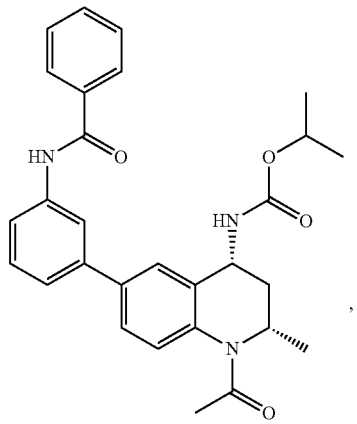
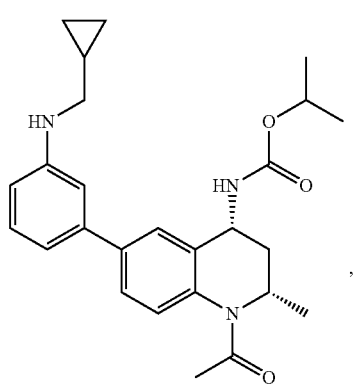
122
-continued
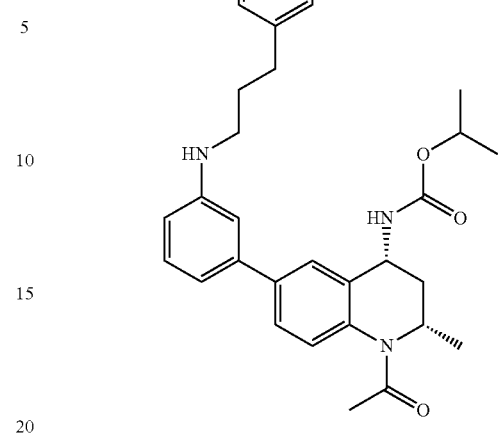
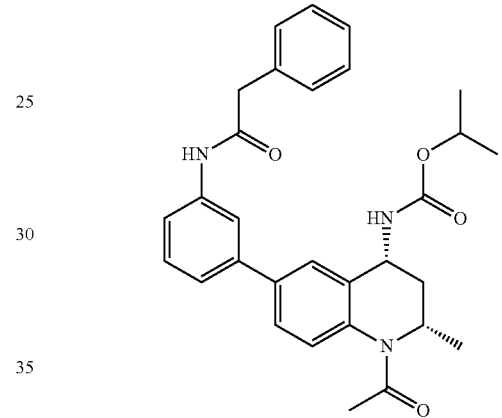
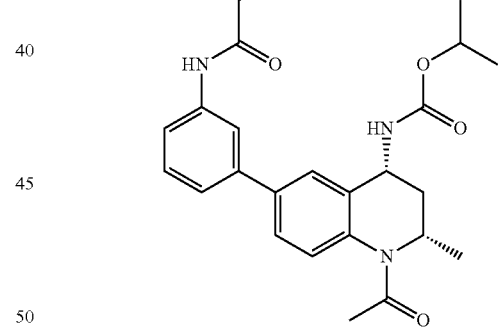
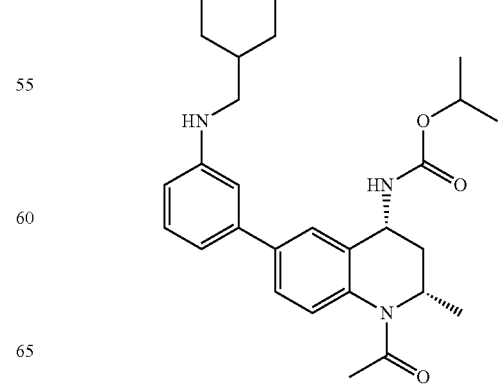

123
-continued
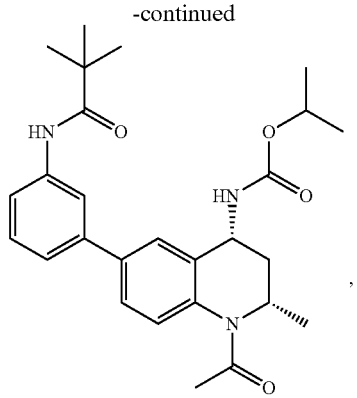
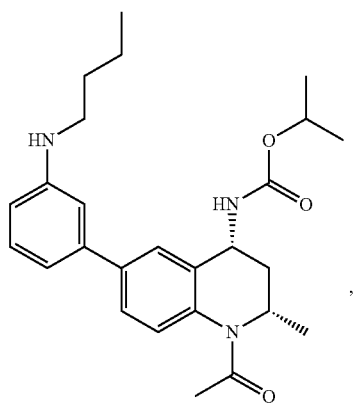
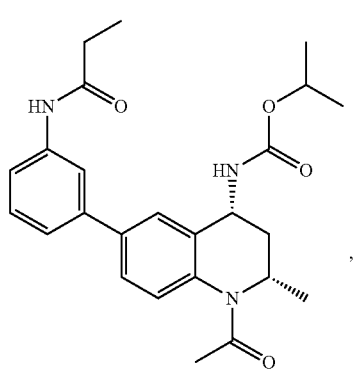
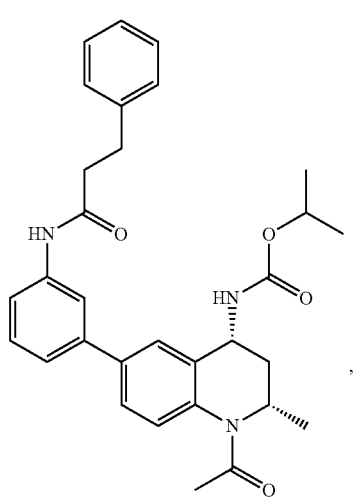
124
-continued
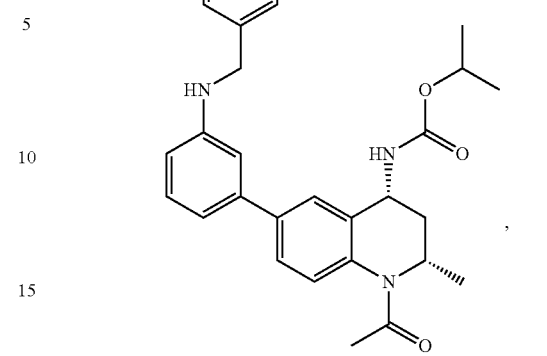
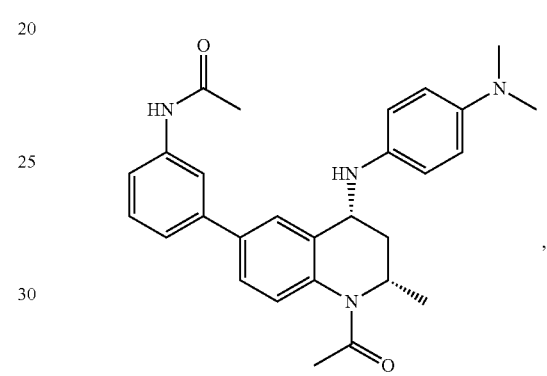
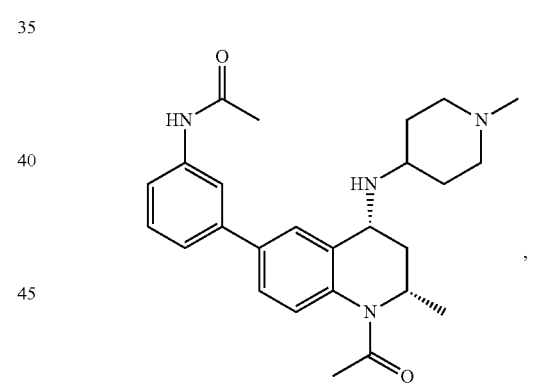
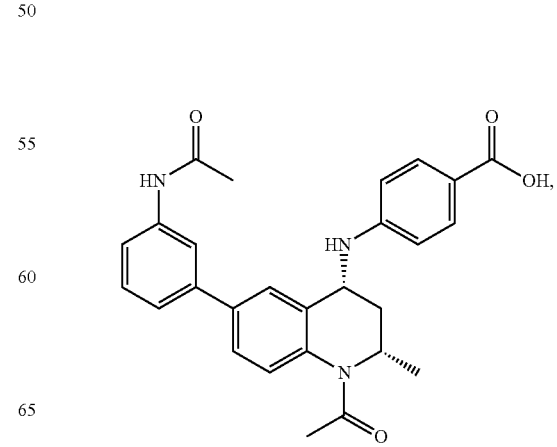

125
-continued
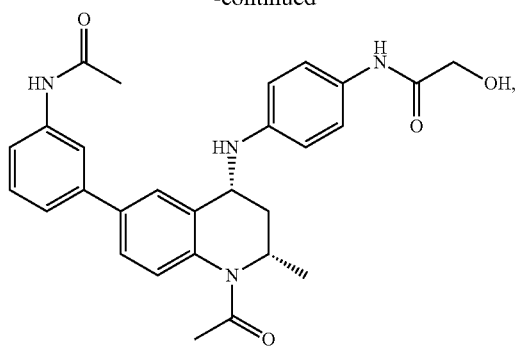
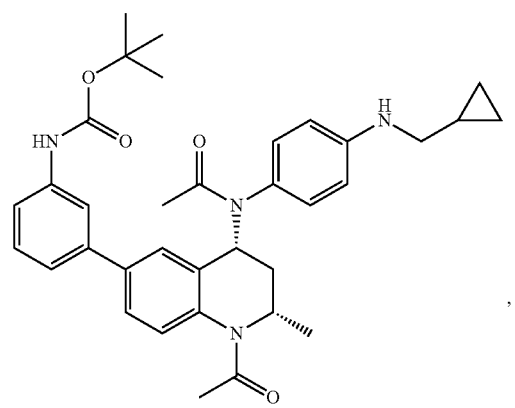
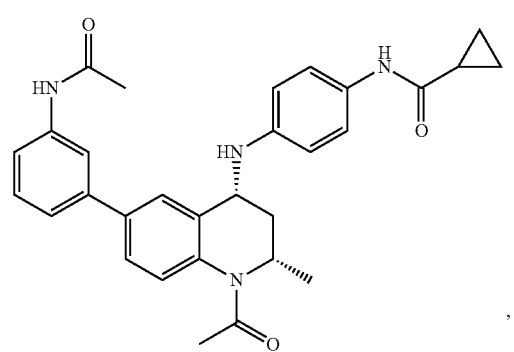
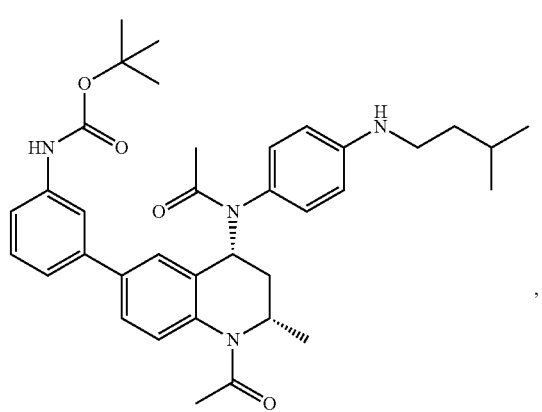
126
-continued
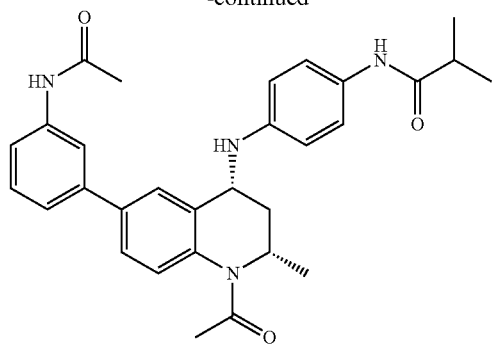
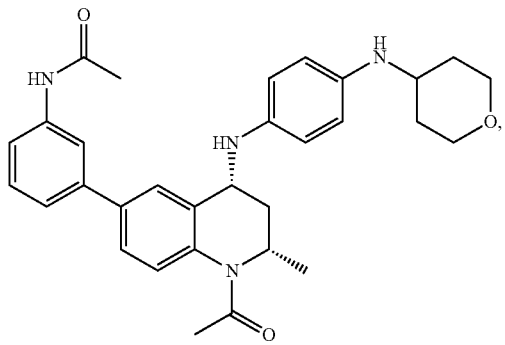
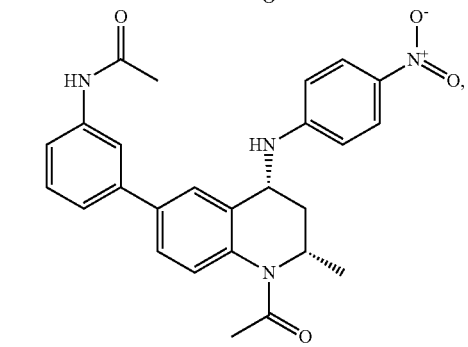
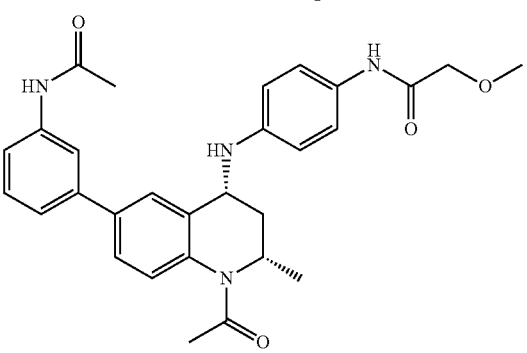
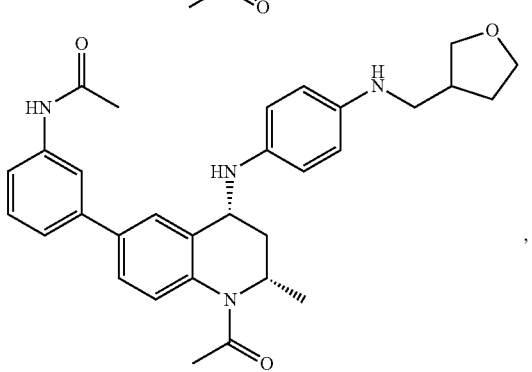

127
-continued
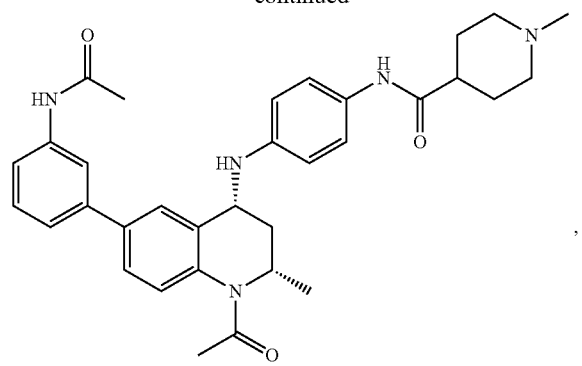
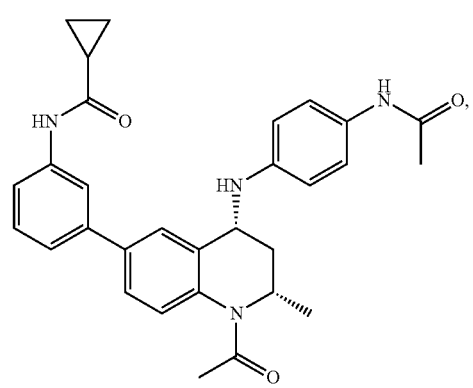
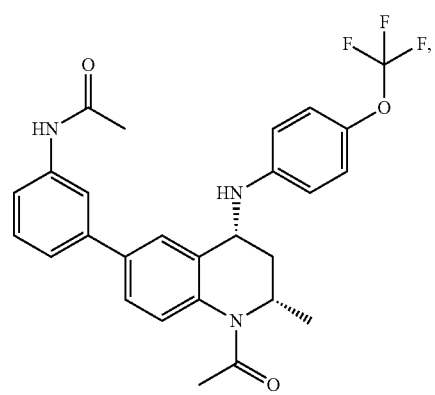
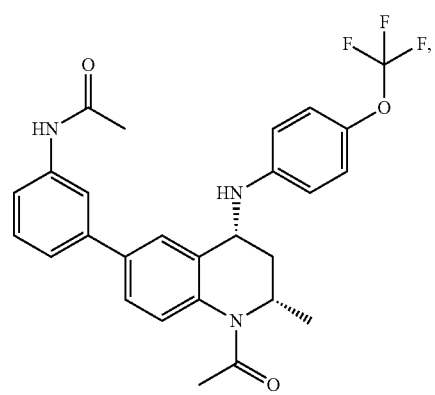
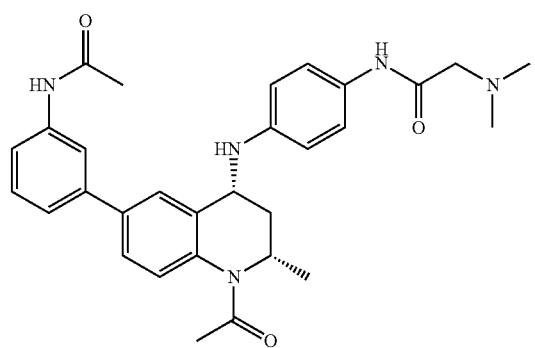
128
-continued
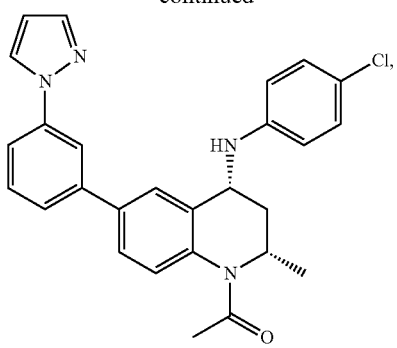
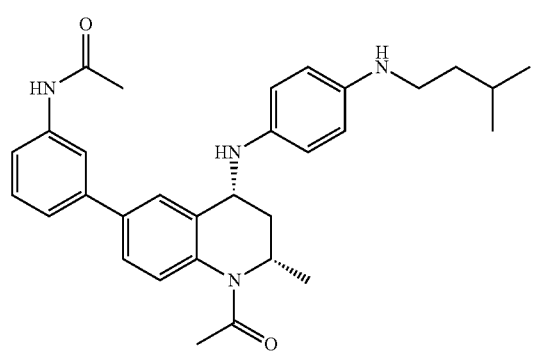
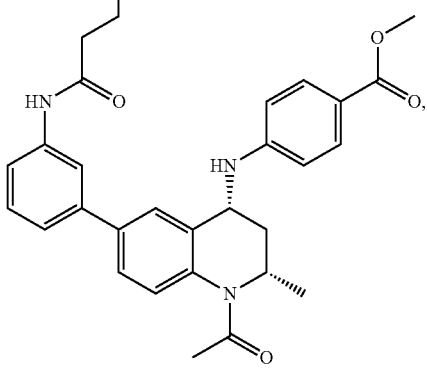
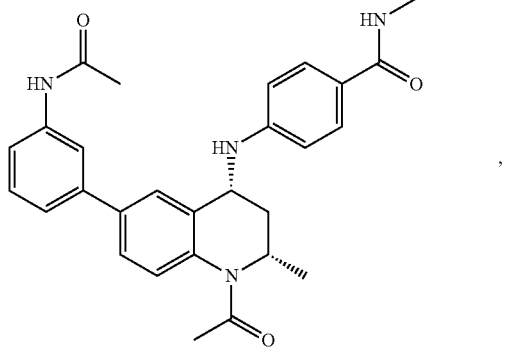

129
-continued
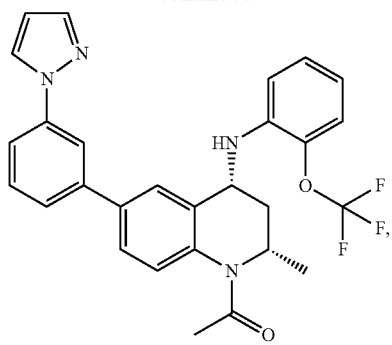
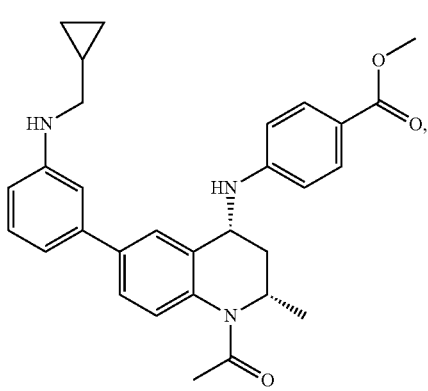
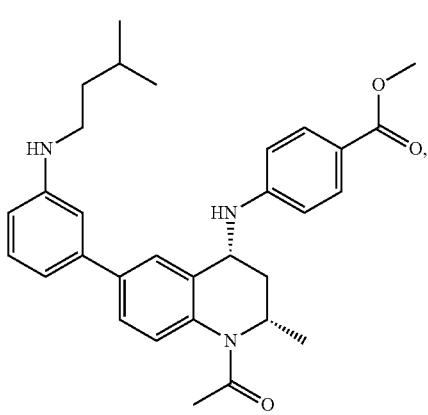
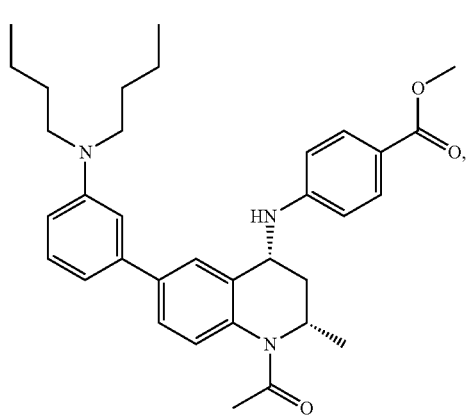
130
-continued
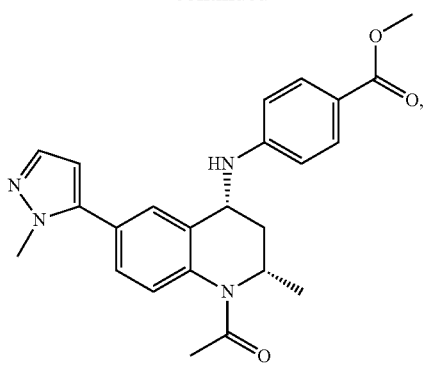
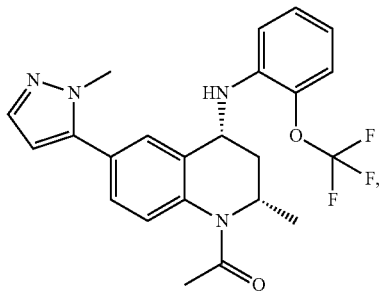
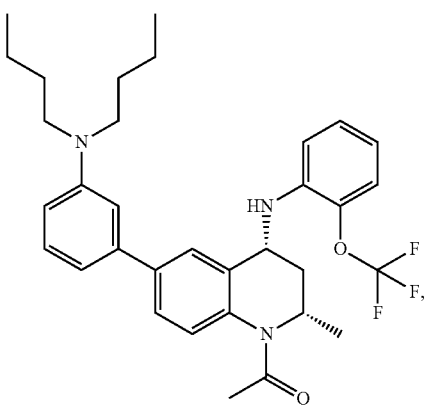
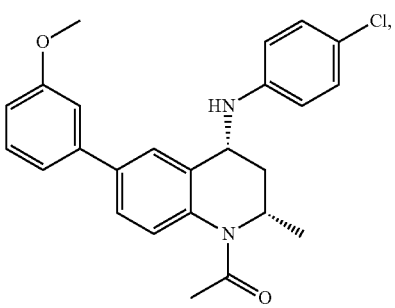

131
-continued
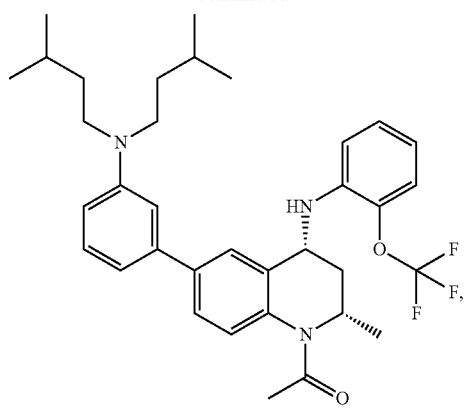
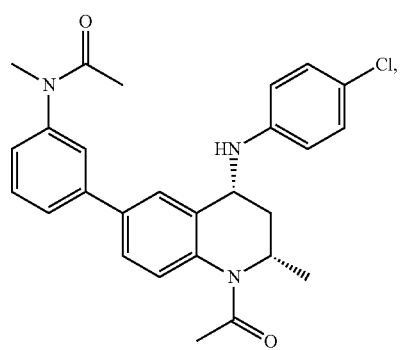
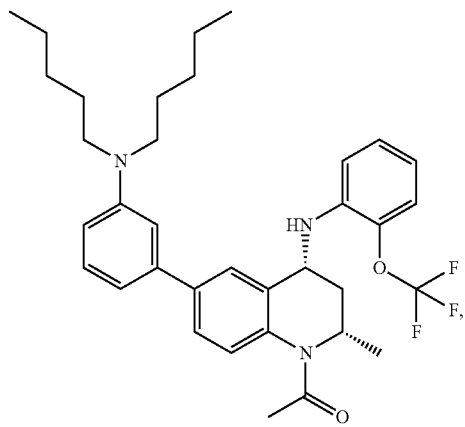
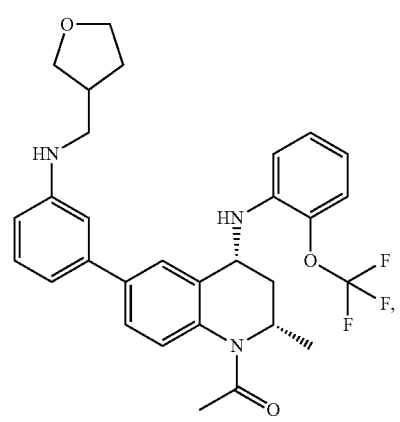
132
-continued
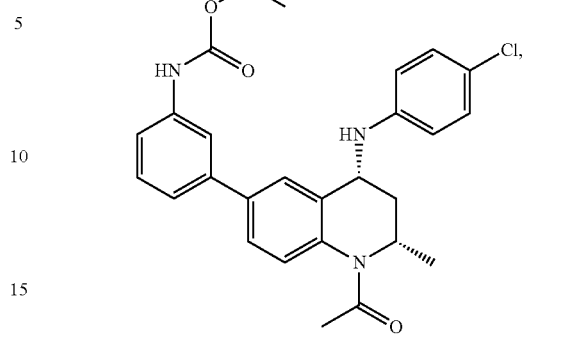
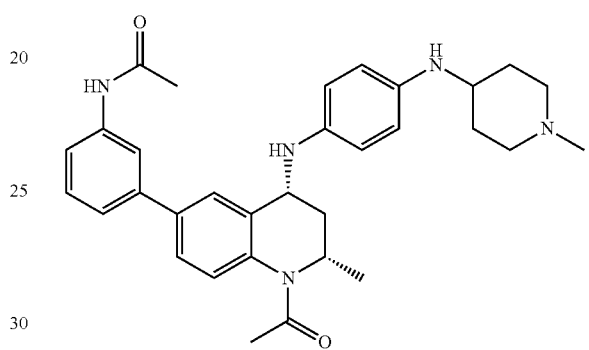
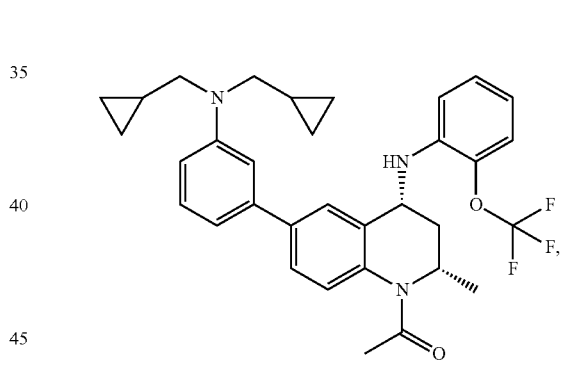
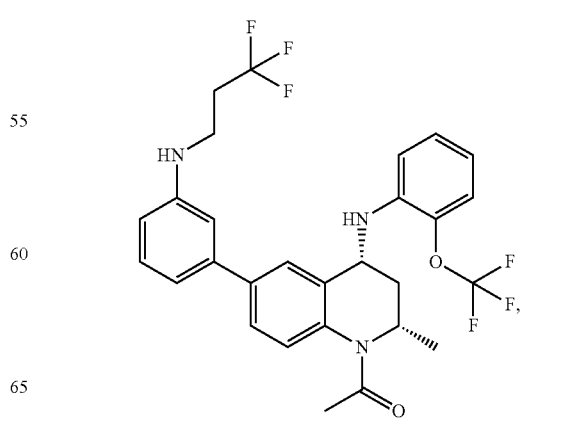

133
-continued
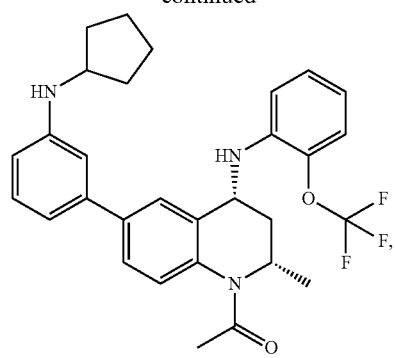
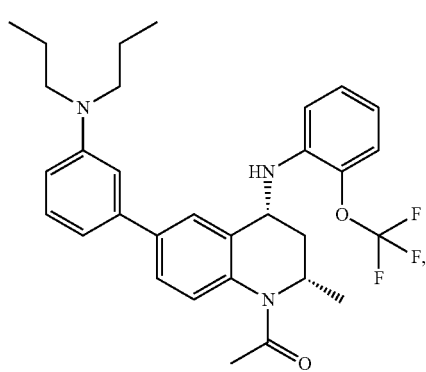
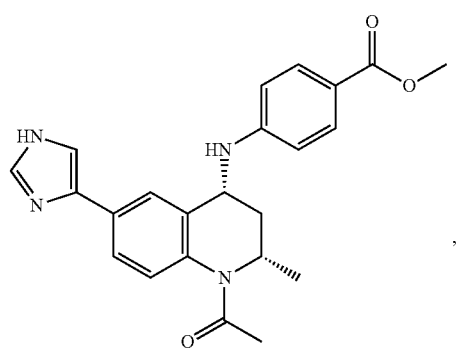
,
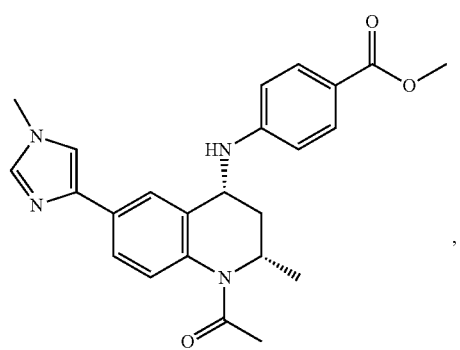
,
134
-continued
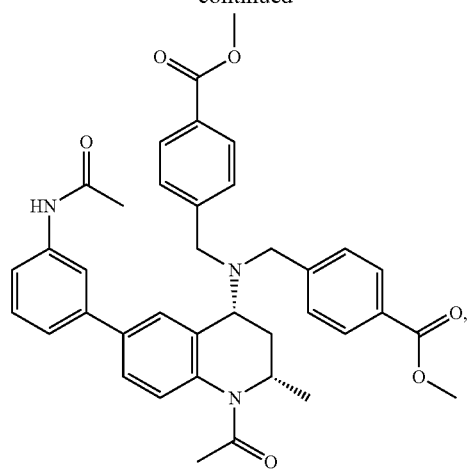
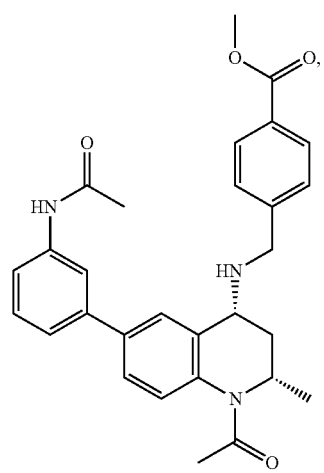
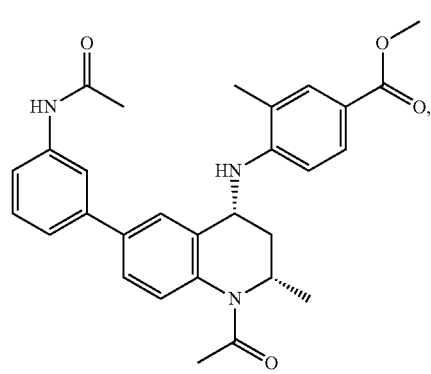
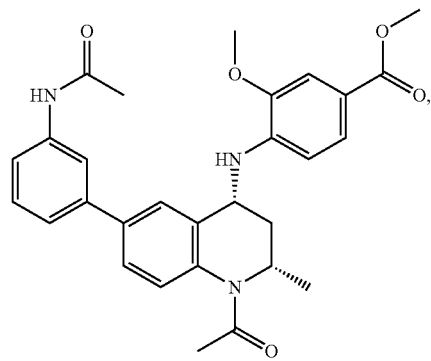

135
-continued
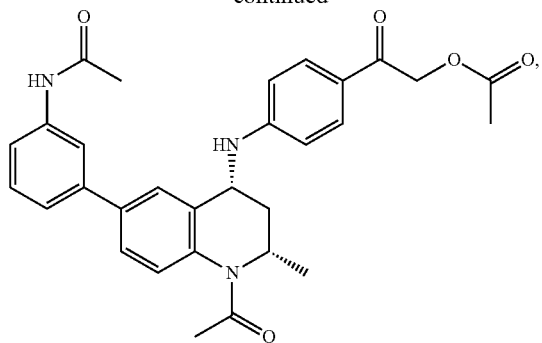
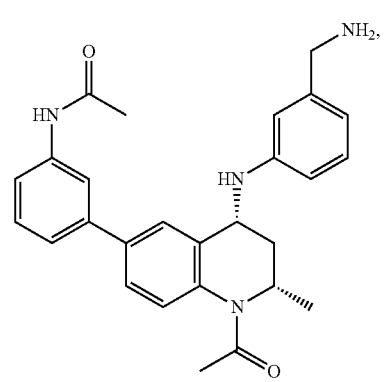
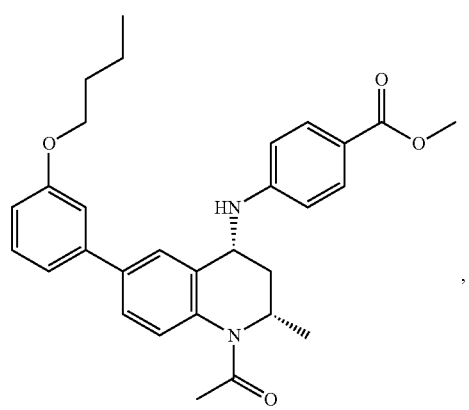
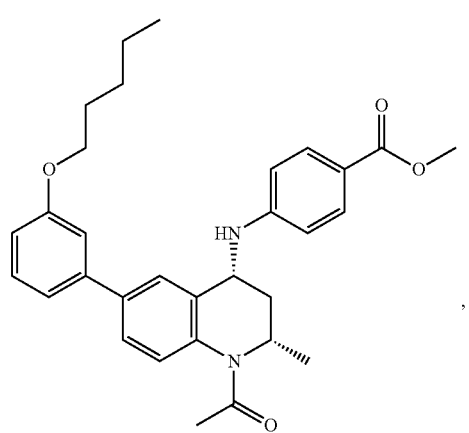
136
-continued
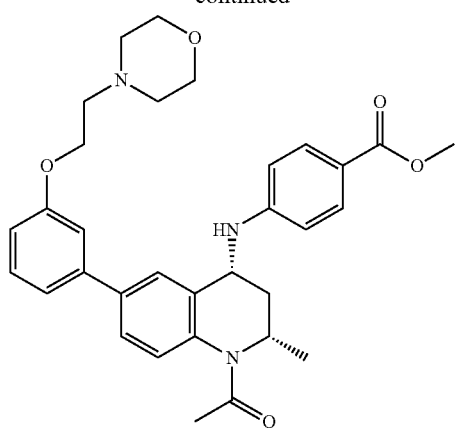
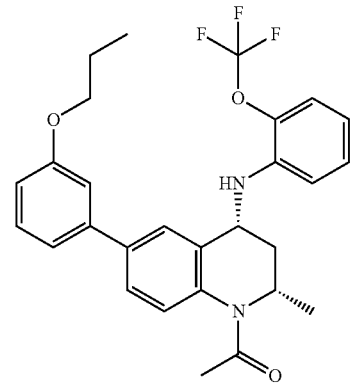
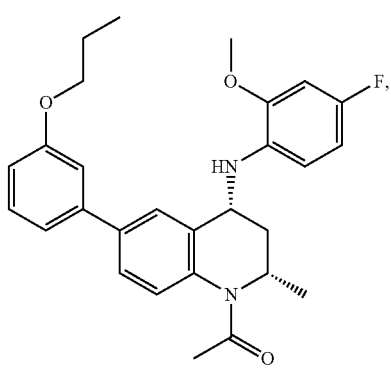
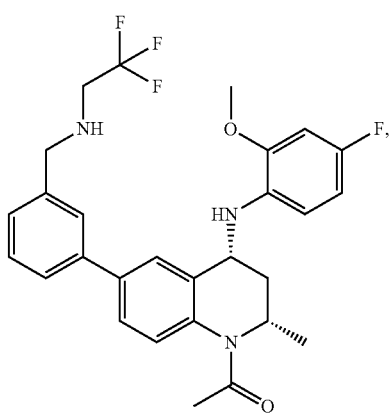

-continued
| 137 | 138 |
|---|---|
| 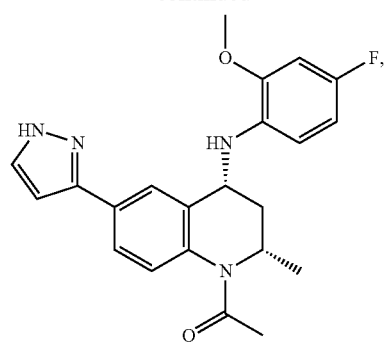 | 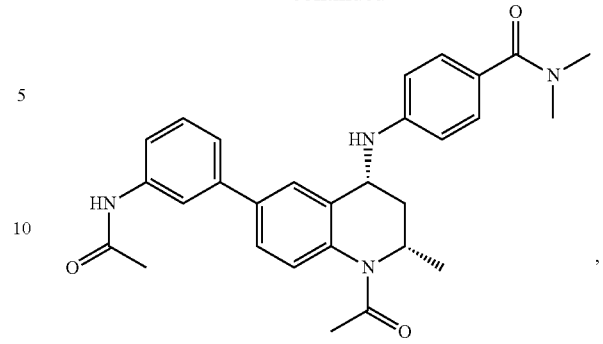 |
| 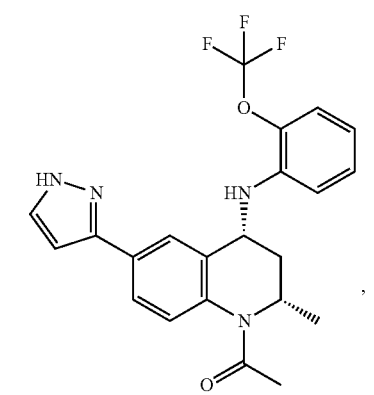 | 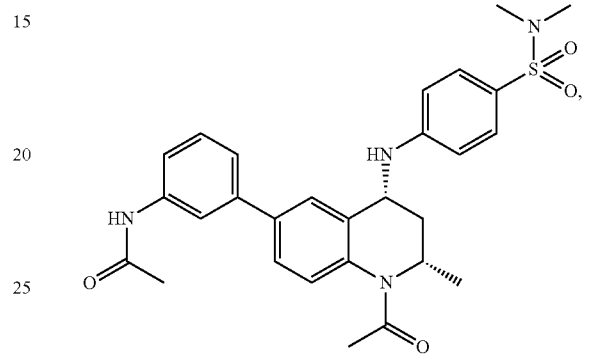 |
| 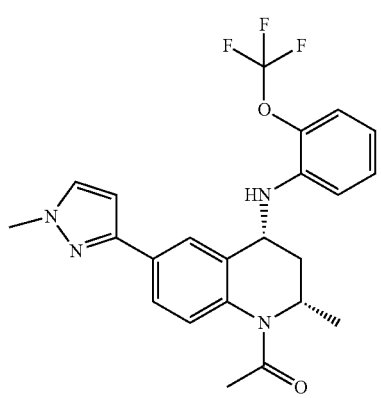 | 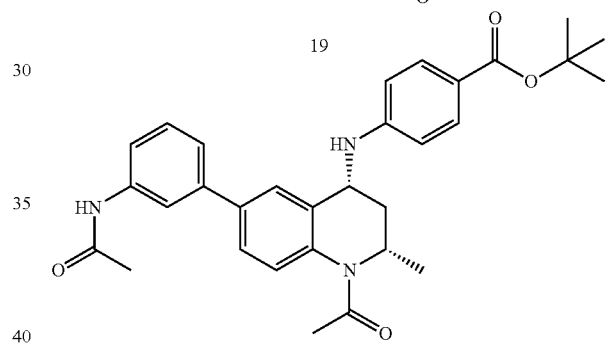 |
| 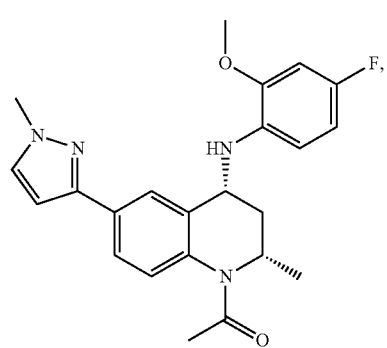 | 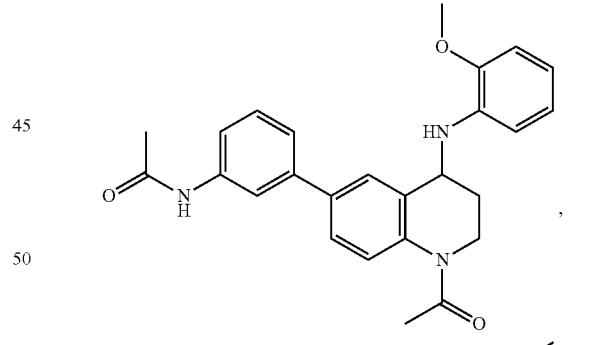 |
|  | 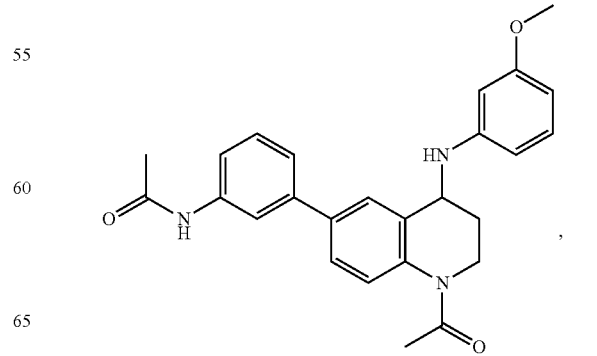 |

139
-continued
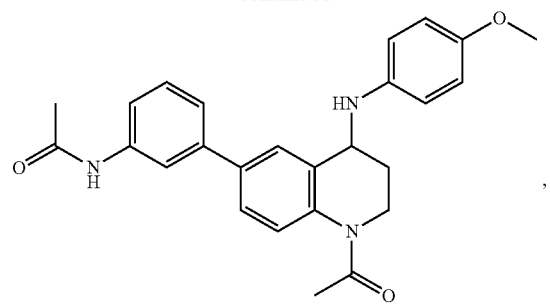
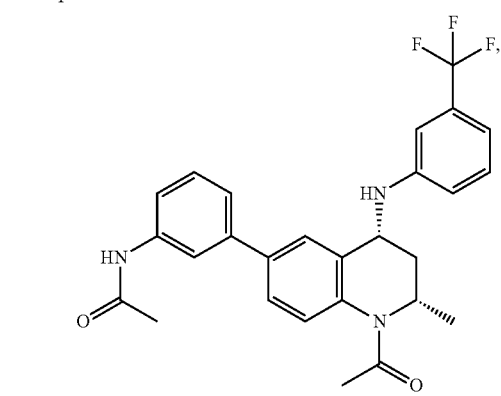
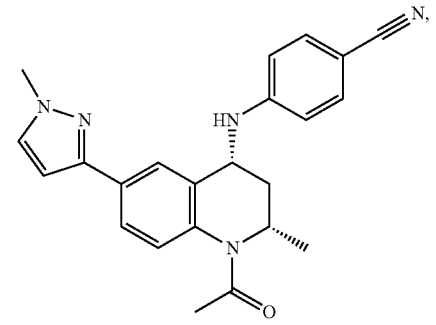
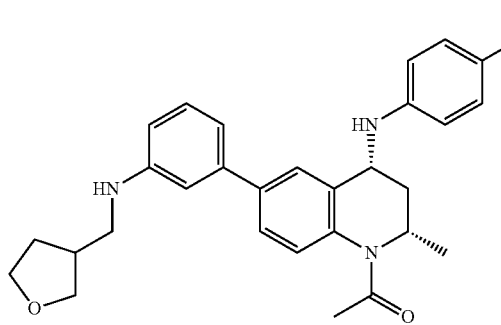
140
-continued
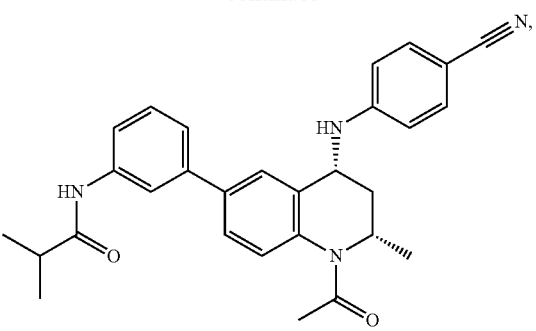
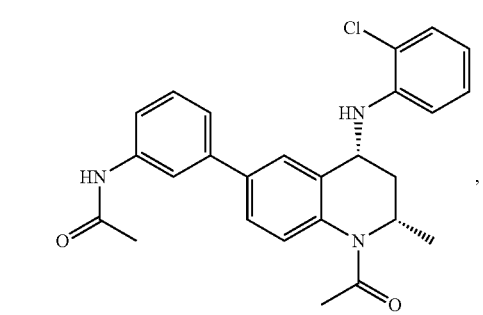
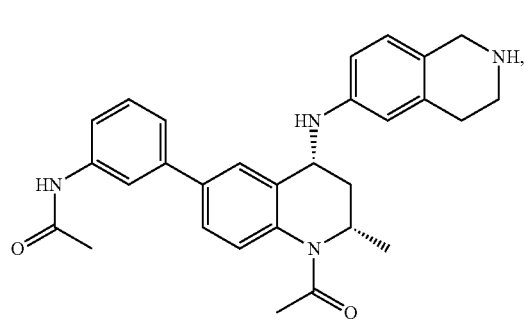

| 141 -continued | 142 -continued |
|---|---|
| 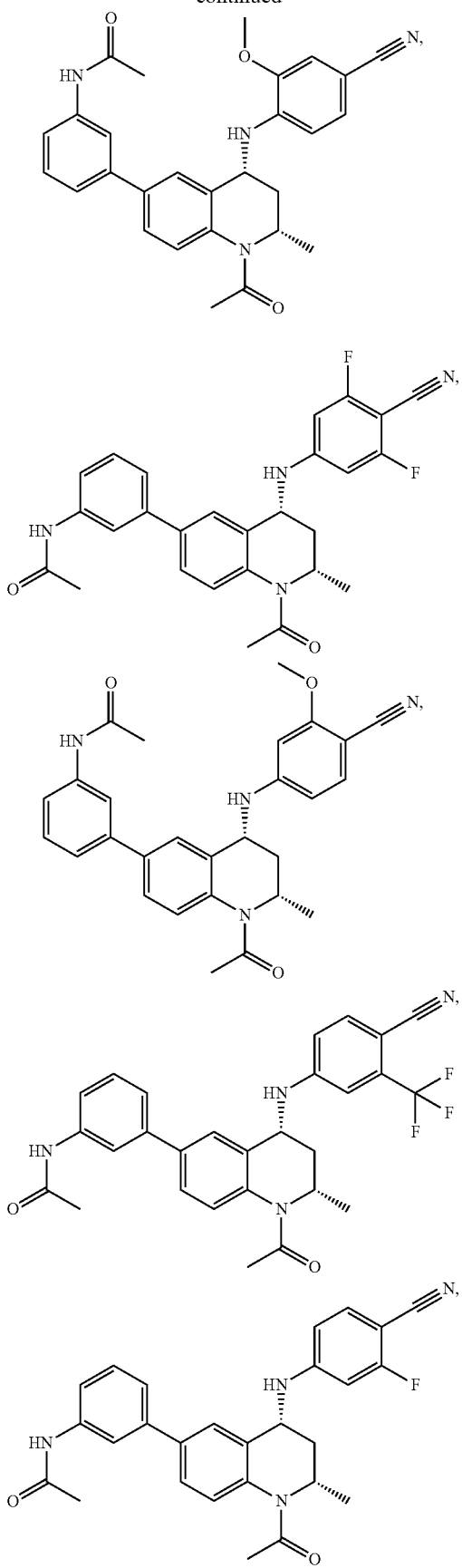 | 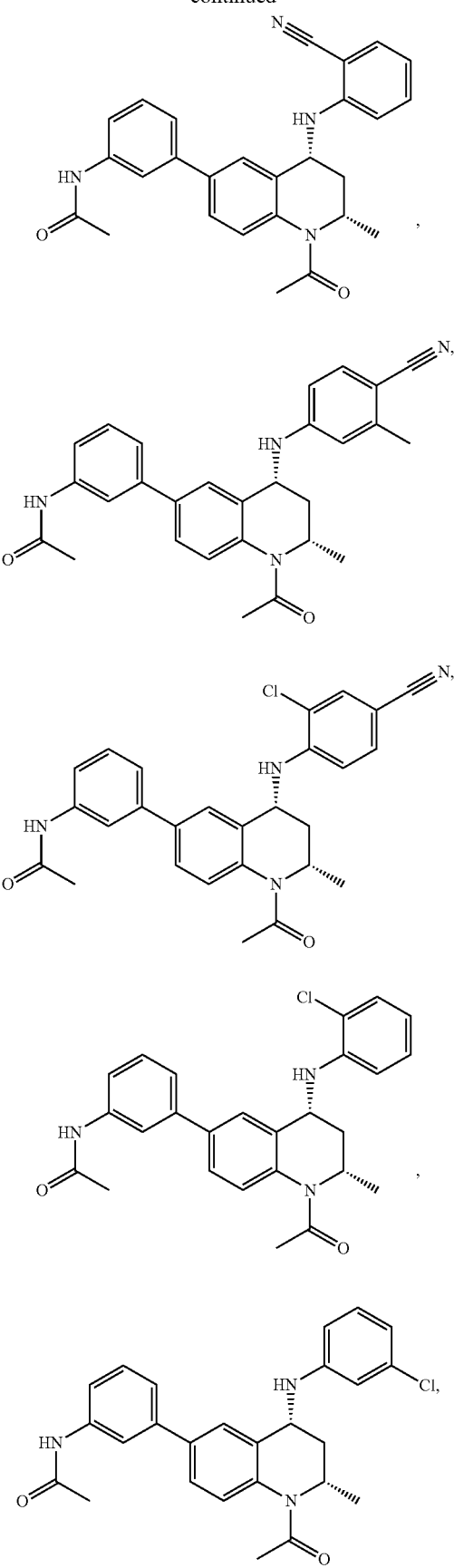 |

143
-continued
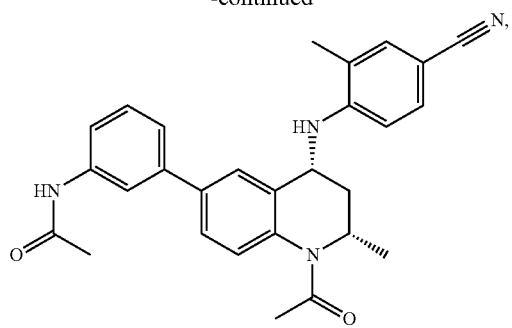
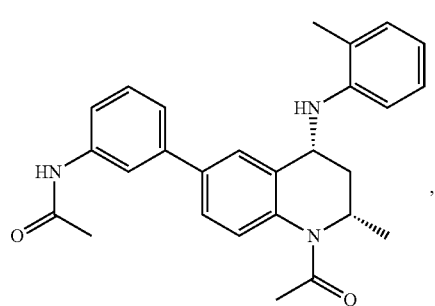
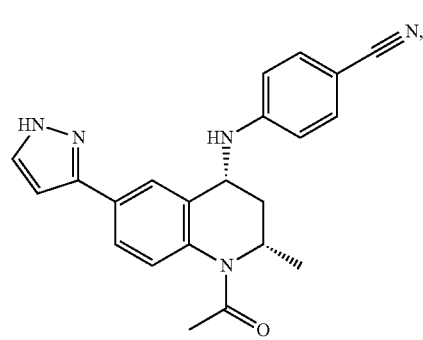
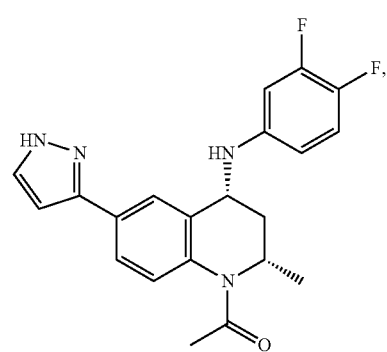
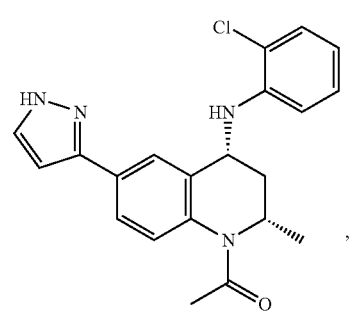
144
-continued
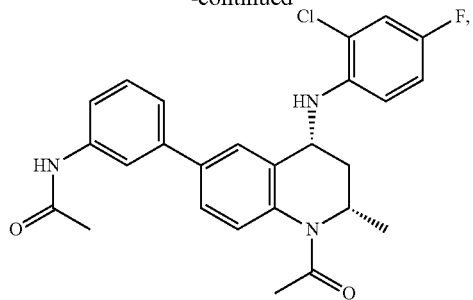
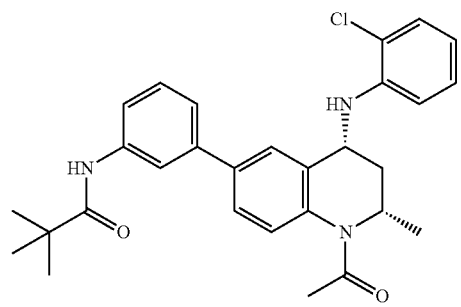
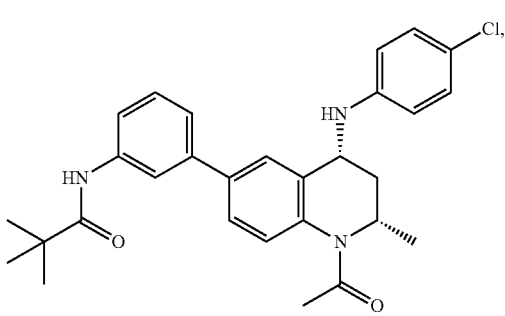
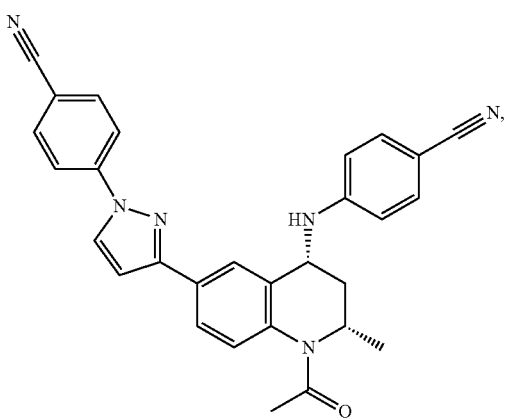
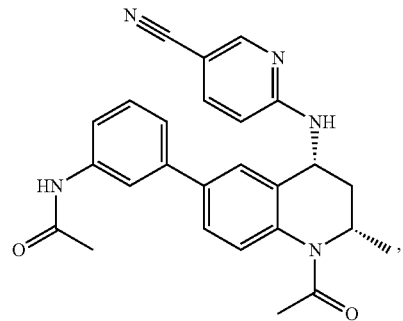

145
-continued
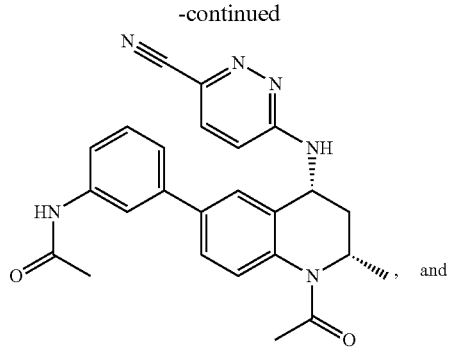, and
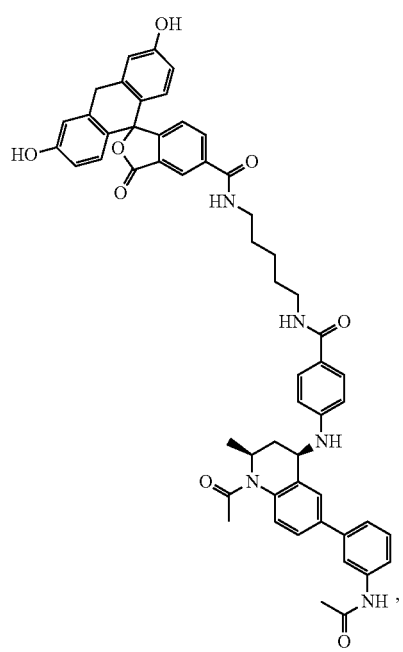 [SMILES: CC(=O)Nc1cccc(-c2ccc3c(c2)[C@H](Nc2ccc(C(=O)NCCCCCNC(=O)c4ccc5c(c4)C(=O)OC54c5ccc(O)cc5Cc5cc(O)ccc54)cc2)C[C@H](C)N3C(C)=O)c1]
or a pharmaceutically acceptable salt thereof.
In one aspect, a compound can be present as one or more of the following structures:
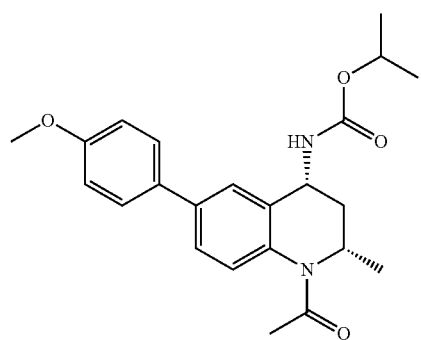
146
-continued
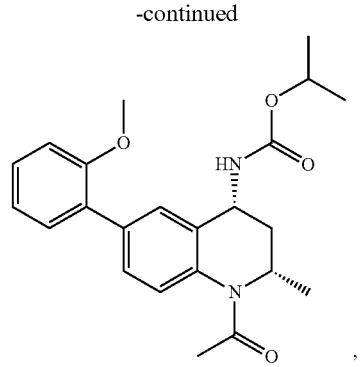,
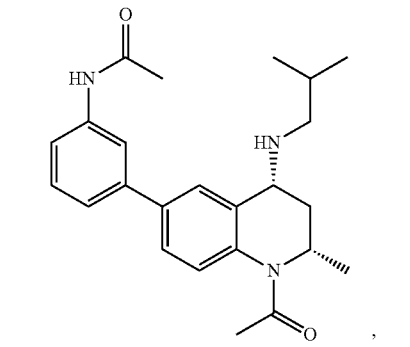,
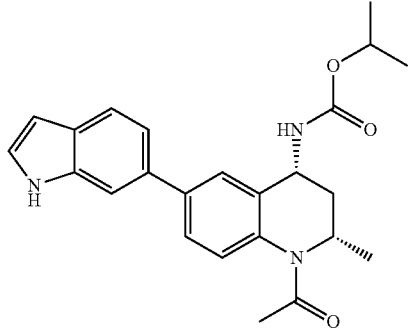,
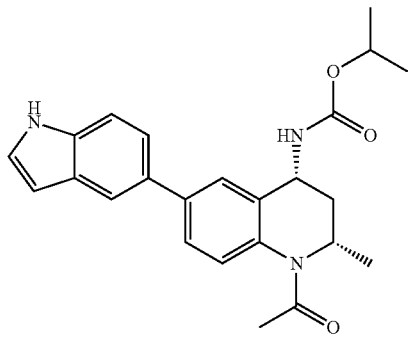,
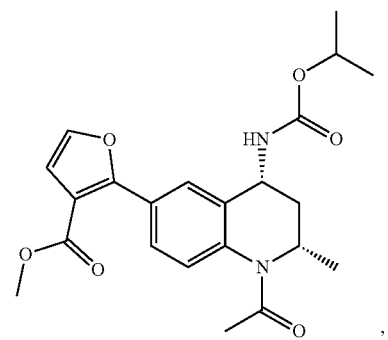,

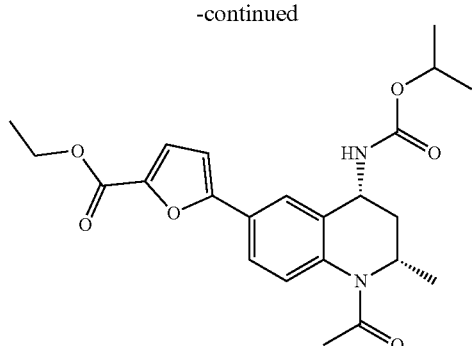
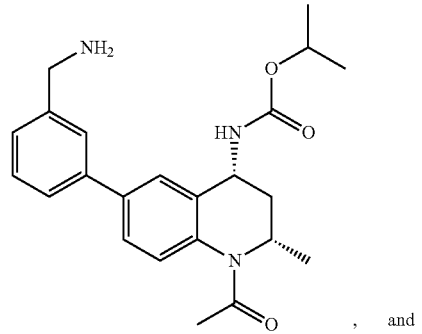, and
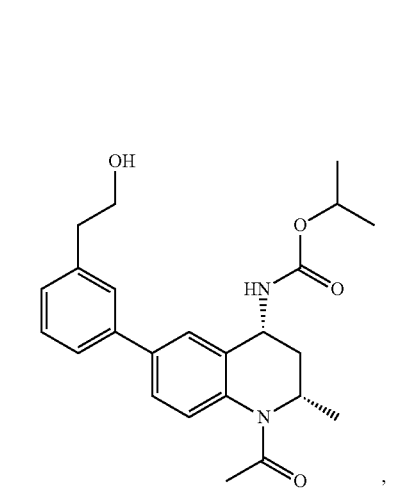,
or a pharmaceutically acceptable salt thereof.
In one aspect, a compound can be present as one or more of the following structures:
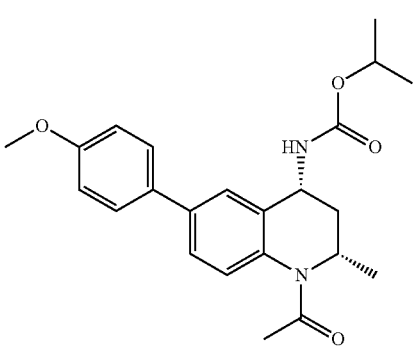,
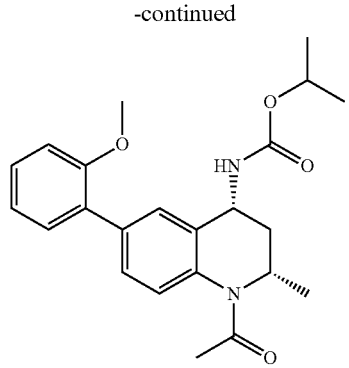,
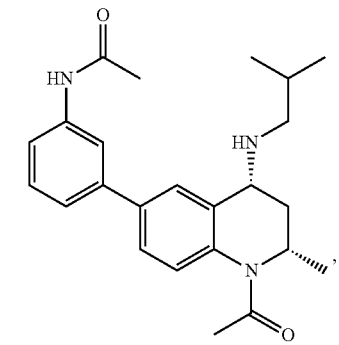,
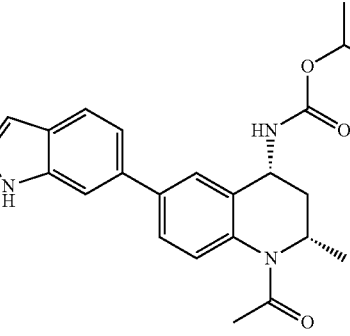,
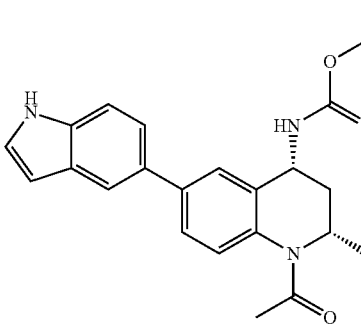,
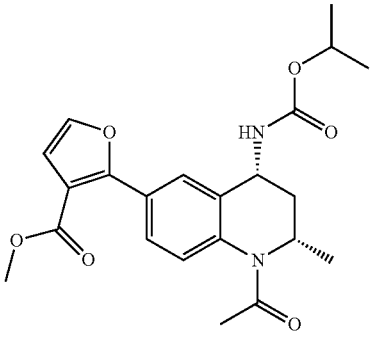, -continued
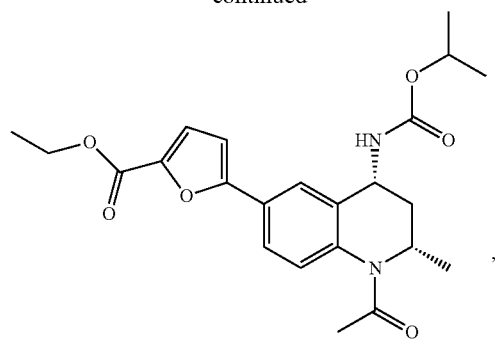
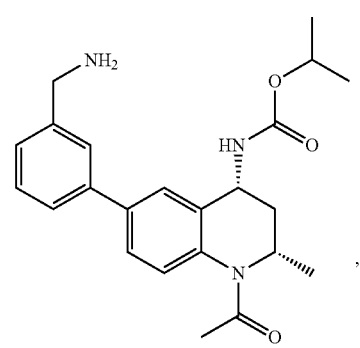
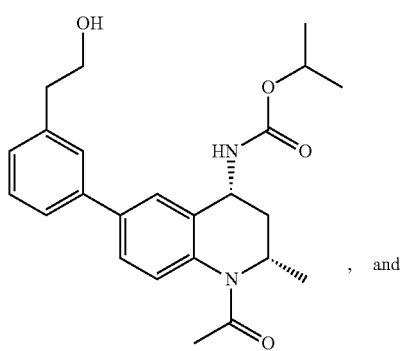
, and
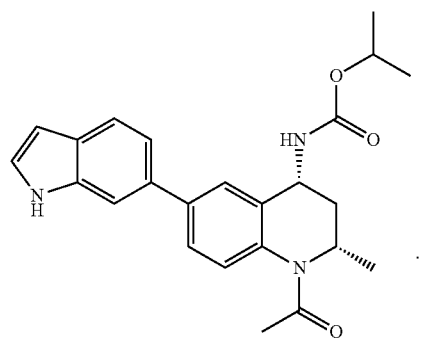
or a pharmaceutically acceptable salt thereof.
In one aspect, a compound can be present as one or more of the following structures:
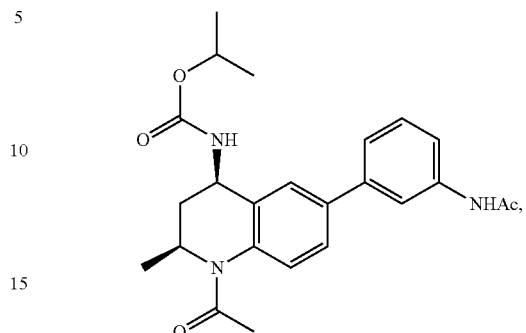
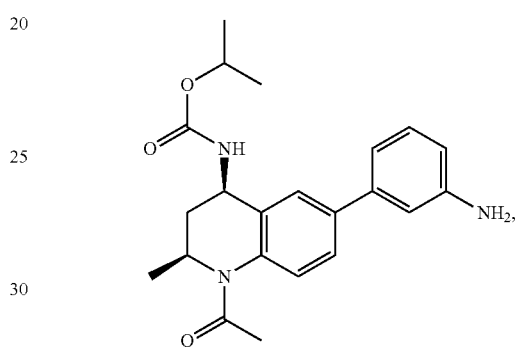
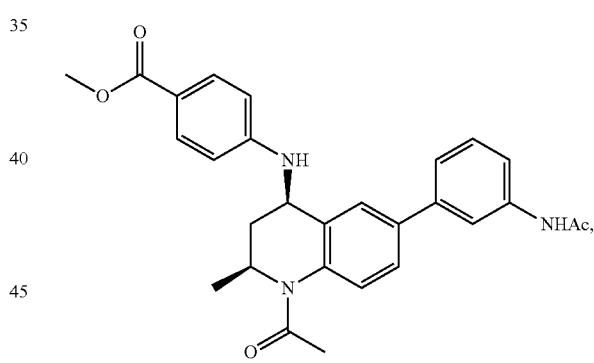
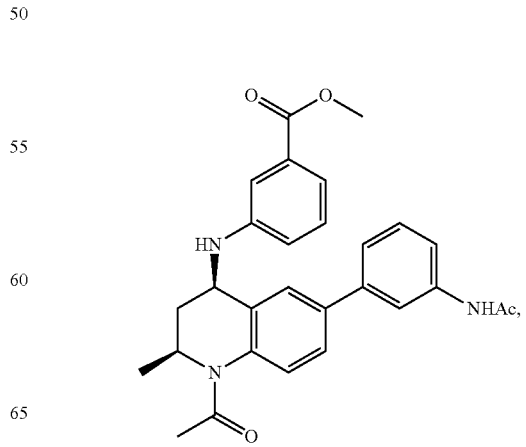

151
-continued
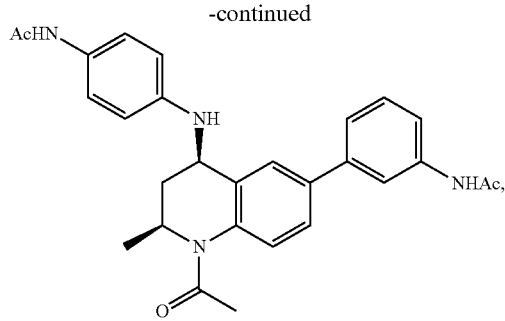
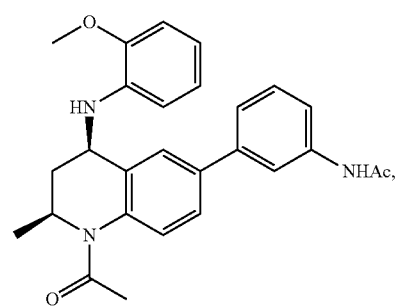
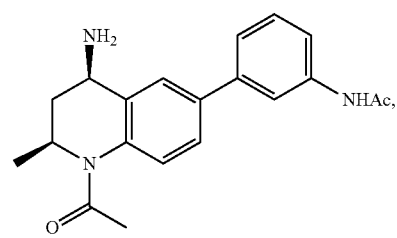
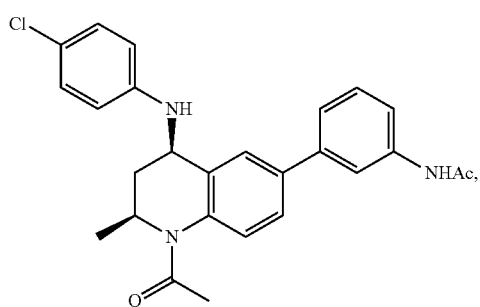
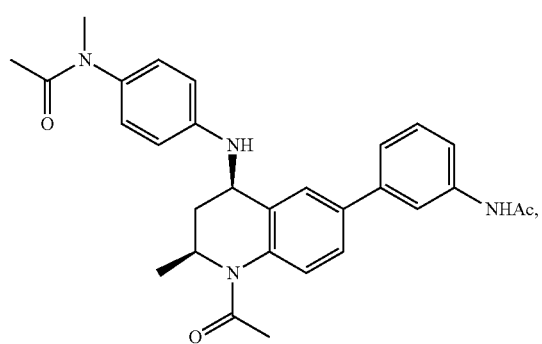
152
-continued
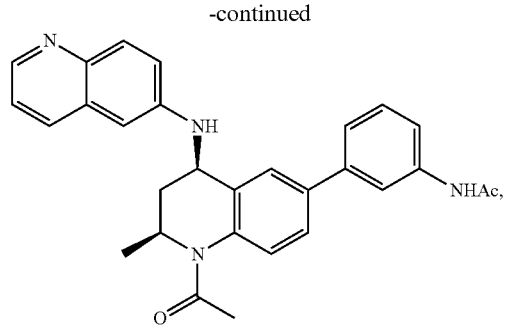
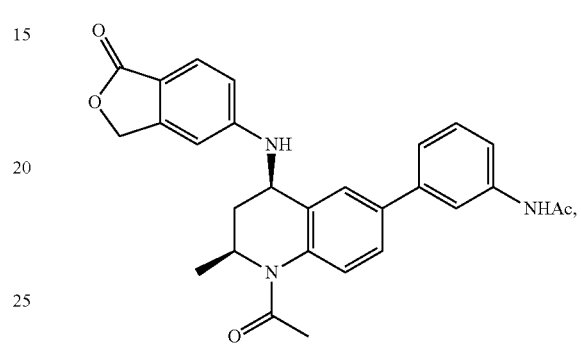
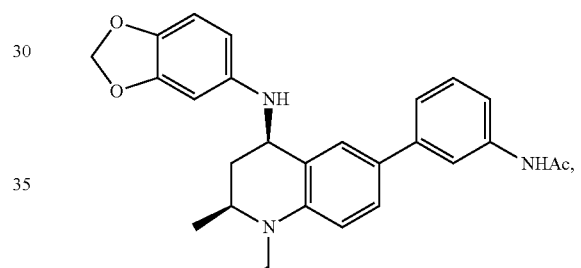
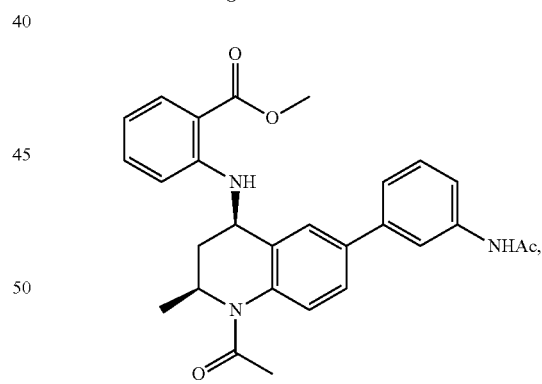
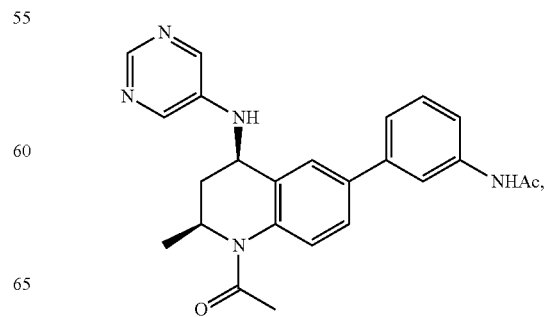

153
-continued
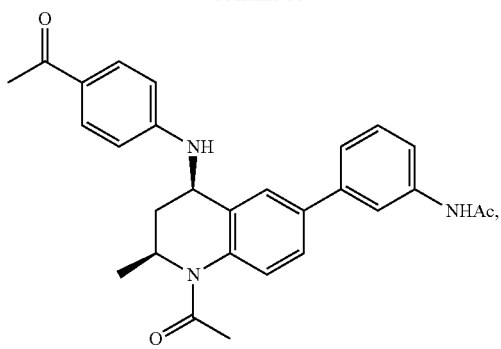
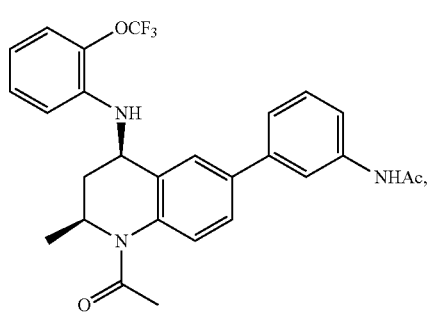
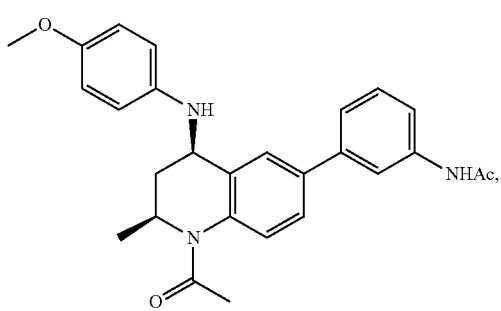
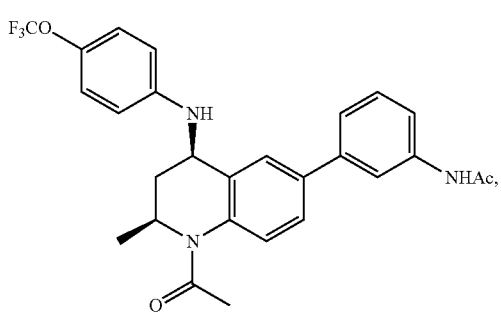
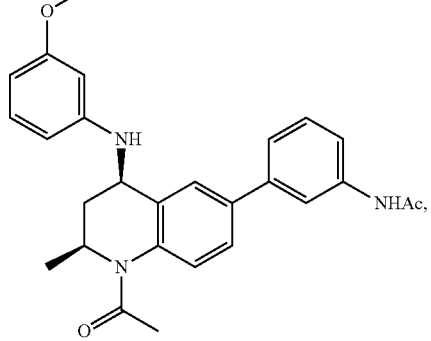
154
-continued
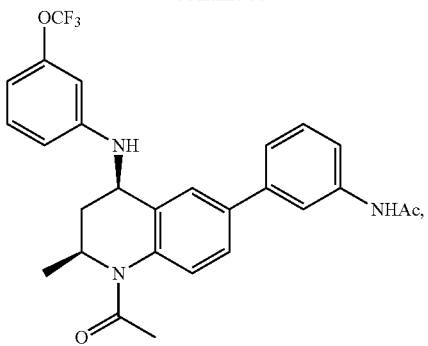
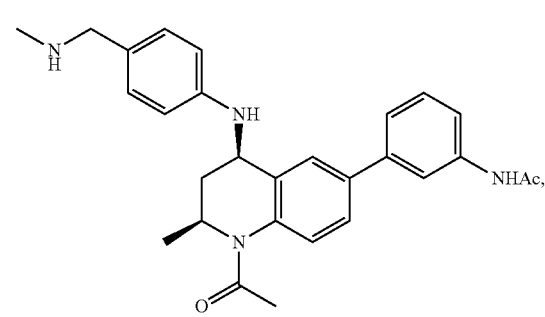

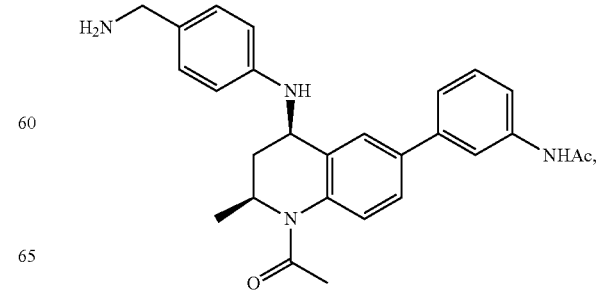

155
-continued
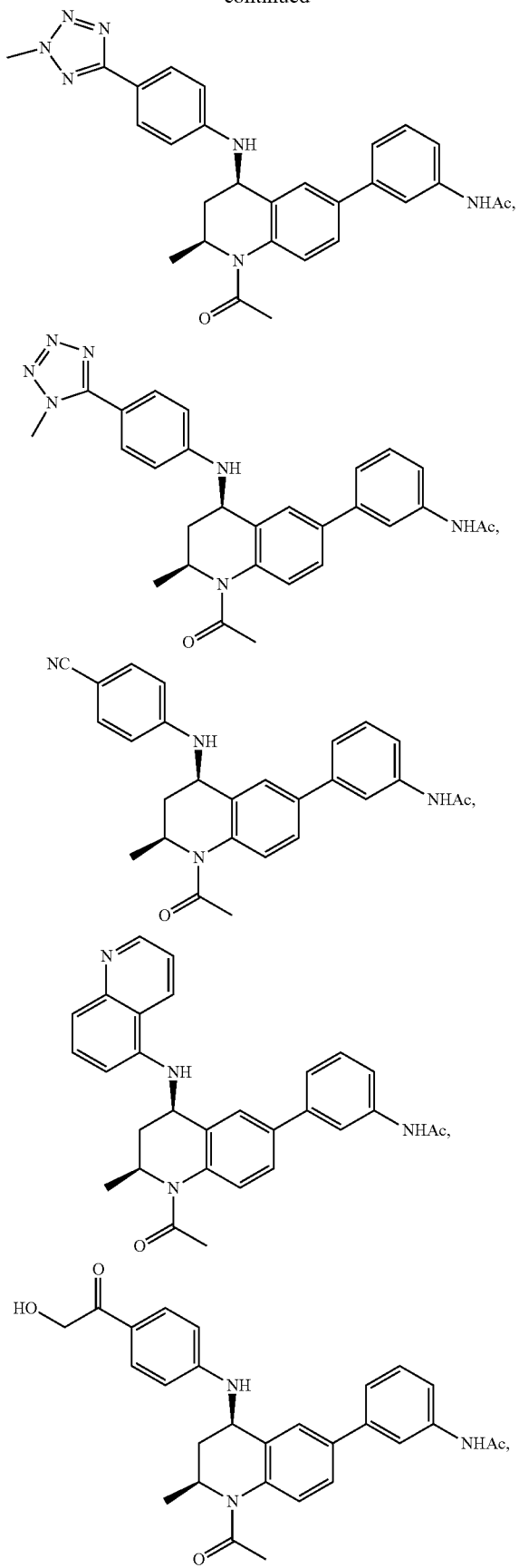
156
-continued
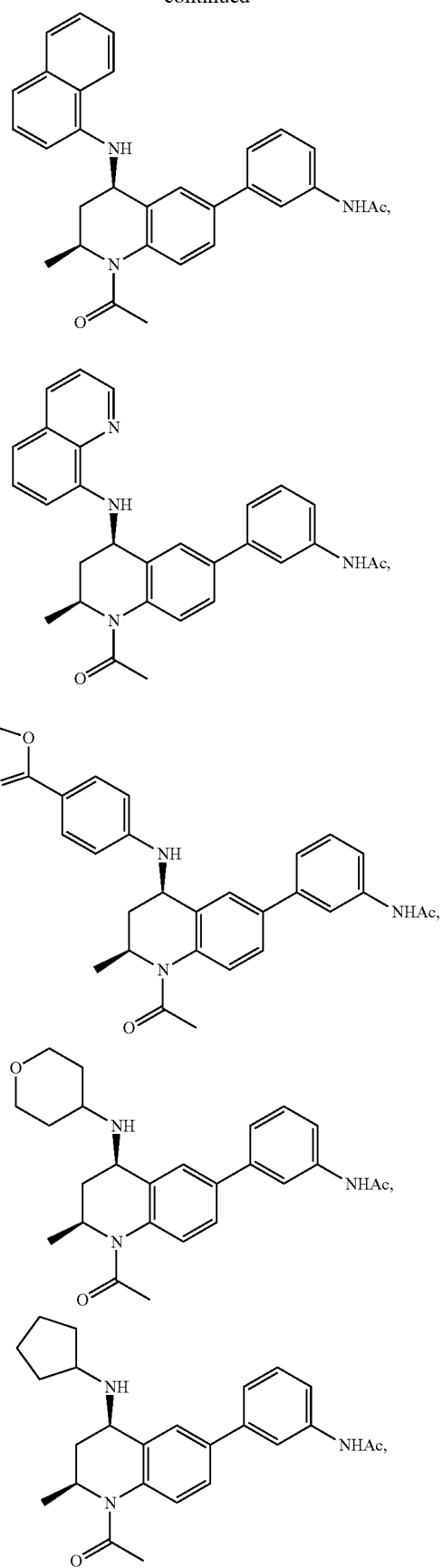

157
-continued
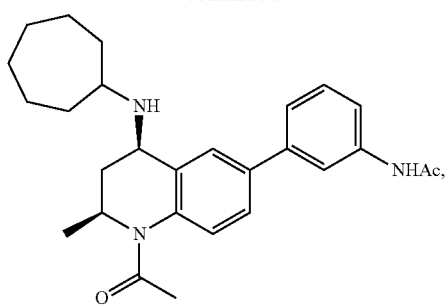
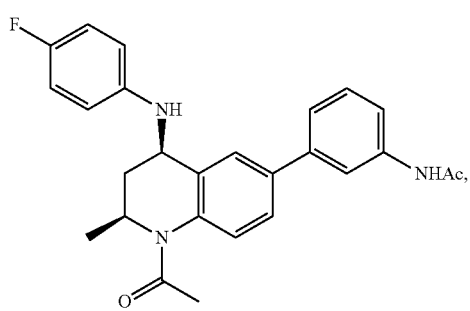
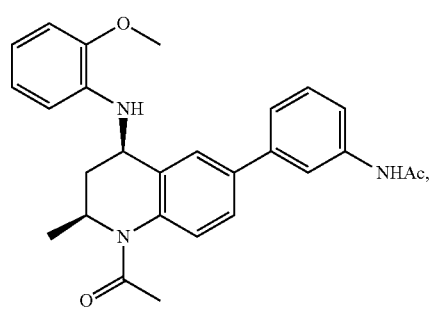
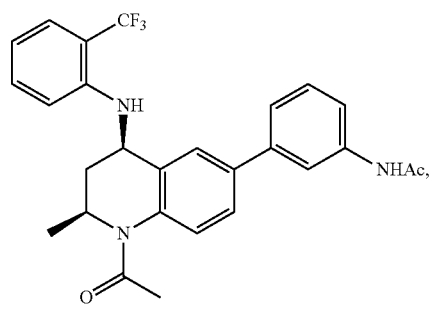
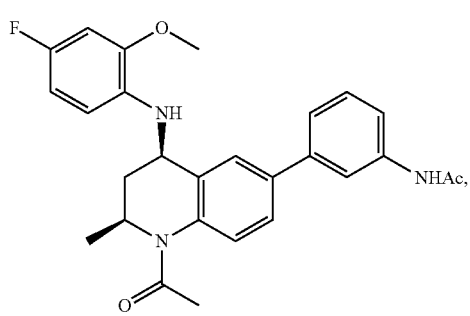
158
-continued
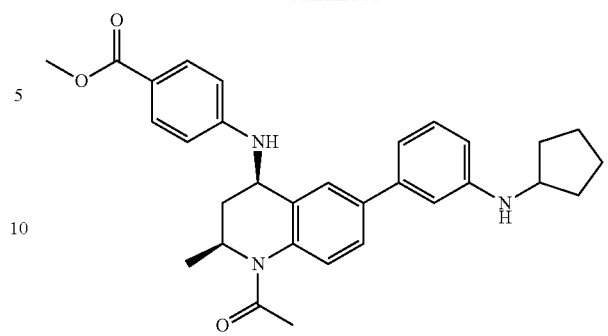
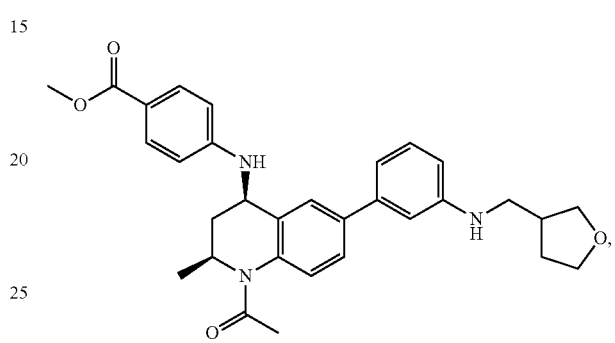
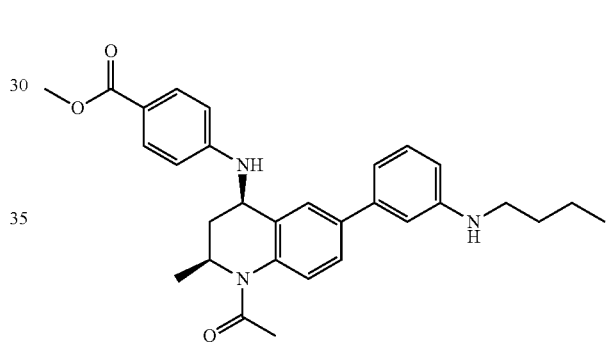
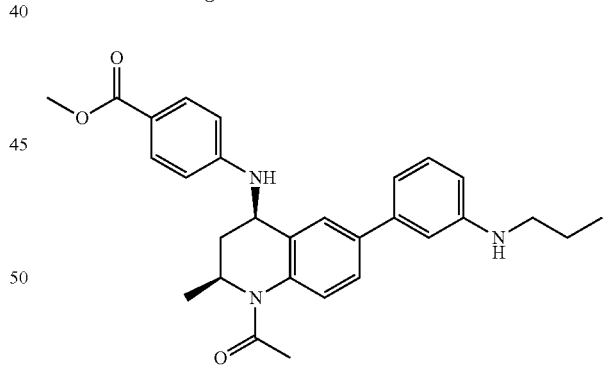
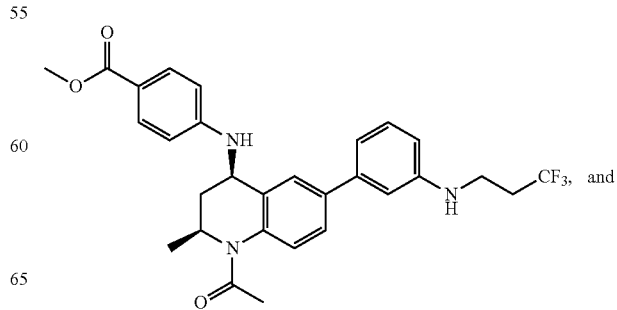

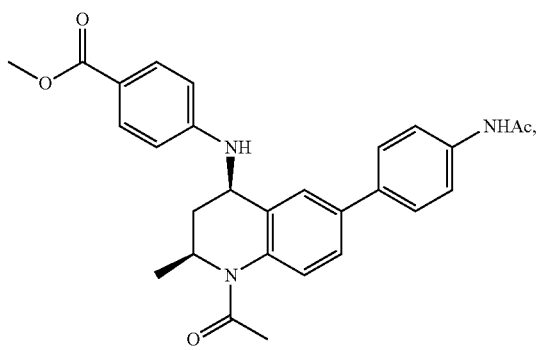 [SMILES: COC(=O)c1ccc(N[C@@H]2C[C@H](C)N(C(C)=O)c3ccc(-c4ccc(NC(C)=O)cc4)cc32)cc1]

or a pharmaceutically acceptable salt thereof.

In one aspect, a compound can be present as one or more of the following structures:

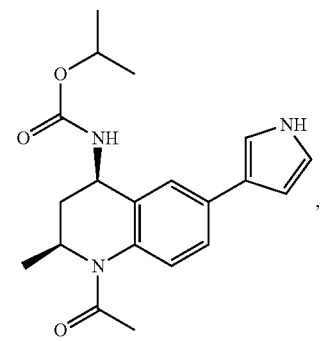

,

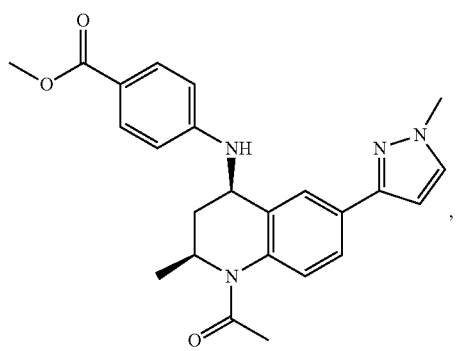

,

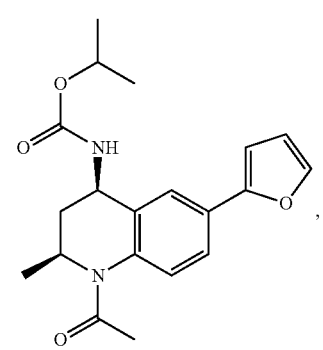

,

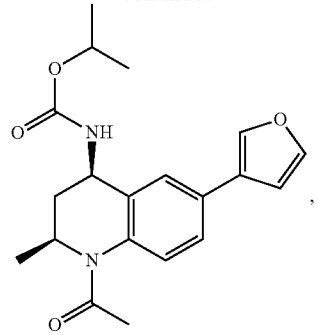

,

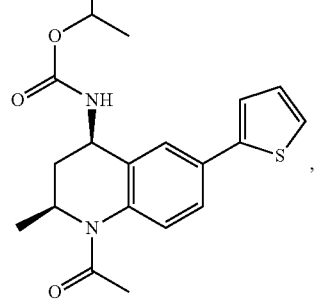

,

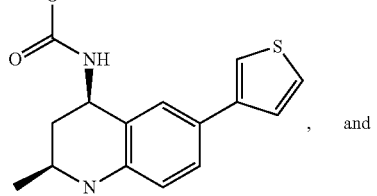

,

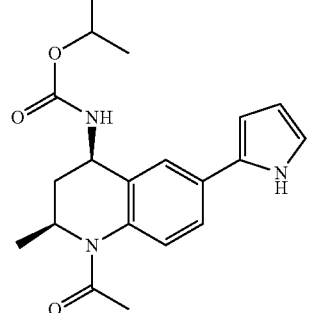

, and

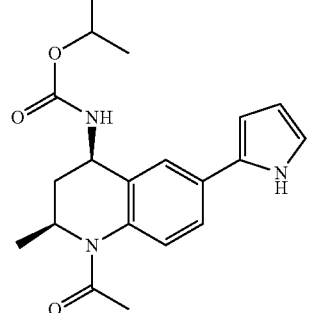

, or a pharmaceutically acceptable salt thereof.

C. Methods of Making a Compound

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-IV, as described and exemplified below. The following examples are provided so that the invention might be more fully understood, are illustrative only, and should not be construed as limiting.

1. Route I

In one aspect, substituted tetrahydroquinoline derivatives can be prepared as shown below.

SCHEME 1A.

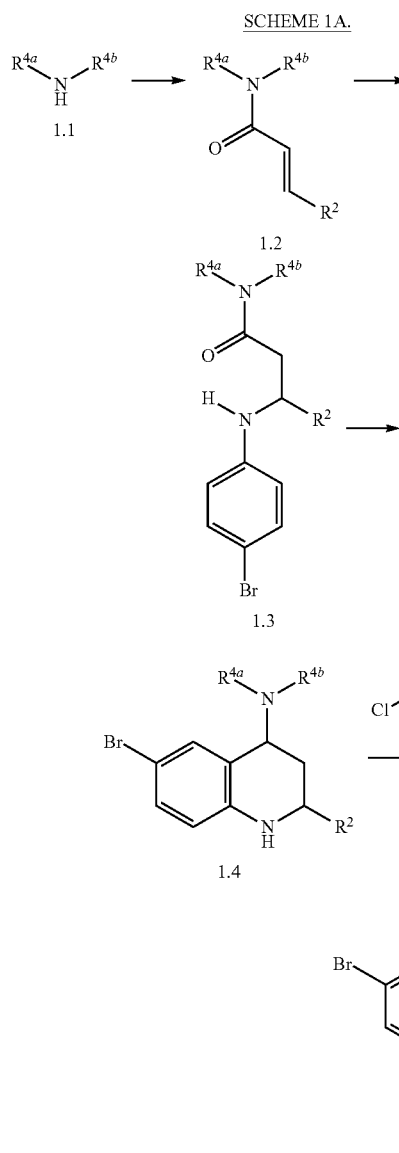

Compounds are represented in generic form, with substituents as noted in compound descriptions elsewhere herein. A more specific example is set forth below.

SCHEME 1B.

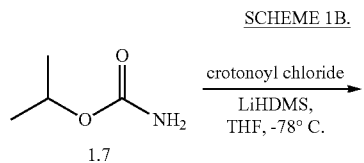

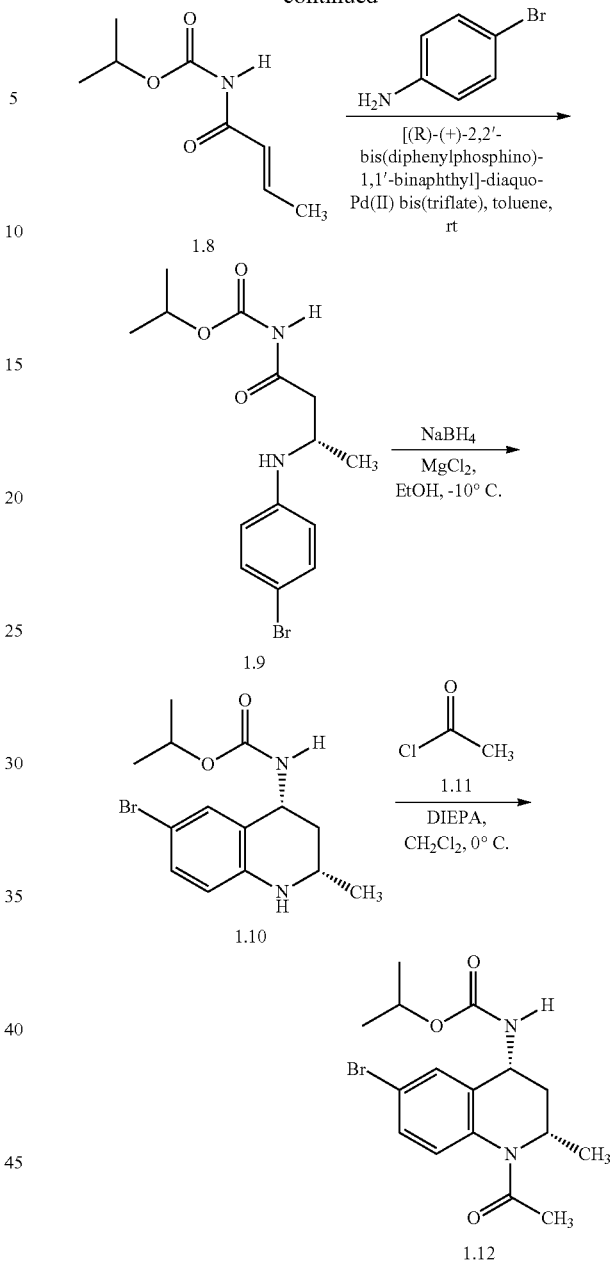

In one aspect, compounds of type 1.12, and similar compounds, can be prepared according to reaction Scheme 1B above. Thus, compounds of type 1.8 can be prepared by acylation of an appropriate carbamate, e.g., 1.7 as shown above, and an appropriate acyl halide, e.g., crotonoyl chloride as shown above. Appropriate carbamates and appropriate acyl halides are commercially available or prepared by methods known to one skilled in the art. The acylation is carried out in the presence of an appropriate base, e.g., lithium bis(trimethylsilyl)amide (LiHDMS), in an appropriate solvent, e.g., tetrahydrofuran (THF), at an appropriate temperature, e.g., −78° C. Compounds of type 1.9 can be prepared by nucleophilic addition to an appropriate alkene, e.g., 1.8 as shown above, with an appropriate amine, e.g., 4-bromoaniline as shown above. Appropriate amines are commercially available or prepared by methods known to one skilled in the art. The nucleophilic addition is carried out in the presence of an appropriate catalyst, e.g., [(R)-(+)-2,2'-bis(diphenylphosphino)-1,1'-binaphthyl]-diaquo-Pd(II) bis(triflate), in an appropriate solvent, e.g., toluene, at an appropriate temperature, e.g., room temperature (rt). Compounds of type 1.10 can be prepared by cyclization of an appropriate imide, e.g., 1.9 as shown above. The cyclization is carried out in the presence of an appropriate base, e.g., sodium borohydride (NaBH$_4$), and an appropriate salt, e.g., magnesium chloride (MgCl$_2$), in an appropriate solvent, e.g., ethanol (EtOH), at an appropriate temperature, e.g., −10° C. Compounds of type 1.12 can be prepared by acylation of an appropriate amine, e.g., 1.10 as shown above, and an appropriate acyl halide, e.g., 1.11 as shown above. Appropriate acyl halides are commercially available or prepared by methods known to one skilled in the art. The acylation is carried out in the presence of an appropriate base, e.g., N,N'-diisopropylethylamine (DIPEA), in an appropriate solvent, e.g., dichloromethane (CH$_2$Cl$_2$), at an appropriate temperature, e.g., 0° C. As can be appreciated by one skilled in the art, the above reaction provides an example of a generalized approach wherein compounds similar in structure to the specific reactants above (compounds similar to compounds of type 1.1, 1.2, 1.3, 1.4, and 1.5), can be substituted in the reaction to provide substituted tetrahydroquinoline derivatives similar to Formula 1.6.

2. Route II

In one aspect, substituted tetrahydroquinoline derivatives can be prepared as shown below.

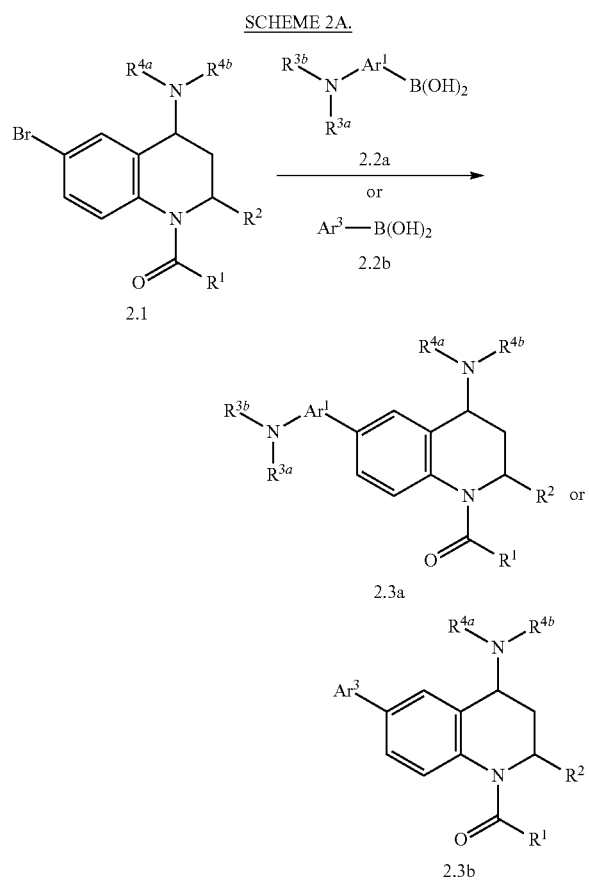

Compounds are represented in generic form, with substituents as noted in compound descriptions elsewhere herein. A more specific example is set forth below.

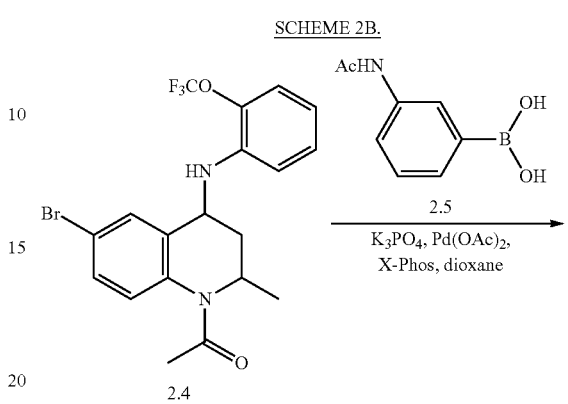

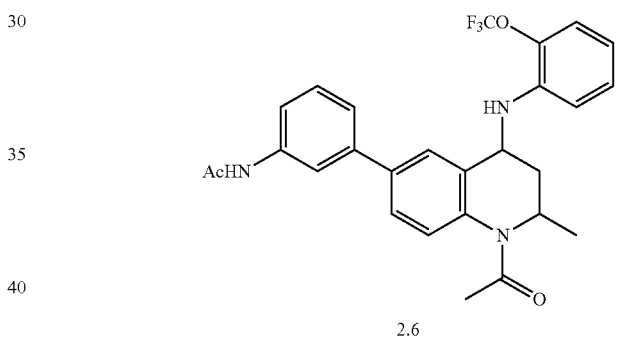

In one aspect, compounds of type 2.6, and similar compounds, can be prepared according to reaction Scheme 2B above. Thus, compounds of type 2.6 can be prepared by coupling of an appropriate aryl halide, e.g., 2.4 as shown above, and an appropriate boronic acid, e.g., 2.5 as shown above. Appropriate aryl halides and appropriate boronic acids are commercially available or prepared by methods known to one skilled in the art. The coupling reaction is carried out in the presence of an appropriate base, e.g., tripotassium phosphate, an appropriate catalyst, e.g., palladium II acetate, and an appropriate ligand, e.g., X-Phos, in an appropriate solvent, e.g., dioxane. As can be appreciated by one skilled in the art, the above reaction provides an example of a generalized approach wherein compounds similar in structure to the specific reactants above (compounds similar to compounds of type 2.1, 2.2a, and 2.2b), can be substituted in the reaction to provide substituted tetrahydroquinoline derivatives similar to Formula 2.3a and 2.3b.

3. Route III

In one aspect, substituted tetrahydroquinoline derivatives can be prepared as shown below.

SCHEME 3A.

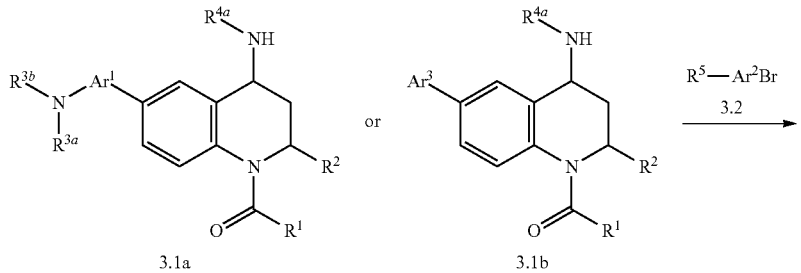

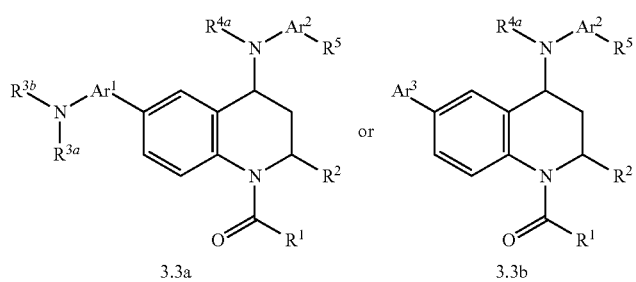

Compounds are represented in generic form, with substituents as noted in compound descriptions elsewhere herein. A more specific example is set forth below.

-continued

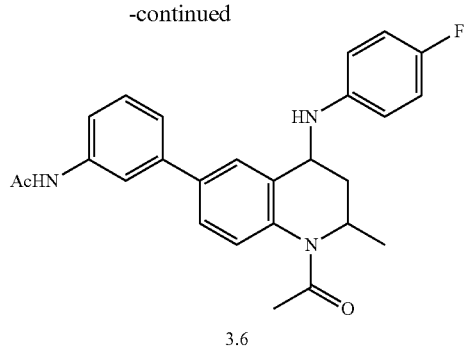

SCHEME 3B.

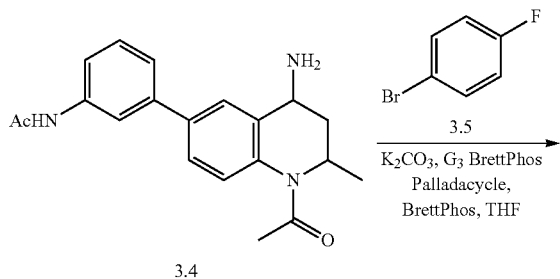

In one aspect, compounds of type 3.6, and similar compounds, can be prepared according to reaction Scheme 3B above. Thus, compounds of type 3.6 can be prepared by coupling of an appropriate amine, e.g., 3.4 as shown above, and an appropriate aryl halides, e.g., 3.5 as shown above. Appropriate amines and appropriate aryl halides are commercially available or prepared by methods known to one skilled in the art. The coupling reaction is carried out in the presence of an appropriate base, e.g., potassium carbonate, an appropriate catalyst, e.g., Gen3 Brettphos palladacycle, and an appropriate ligand, e.g., BrettPhos, in an appropriate solvent, e.g., tetrahydrofuran. As can be appreciated by one skilled in the art, the above reaction provides an example of a generalized approach wherein compounds similar in structure to the specific reactants above (compounds similar to compounds of type 3.1a, 3.1b, and 3.2), can be substituted in the reaction to provide substituted tetrahydroquinoline derivatives similar to Formula 3.3a and 3.3b.

4. Route IV

In one aspect, substituted tetrahydroquinoline derivatives can be prepared as shown below.

SCHEME 4A.

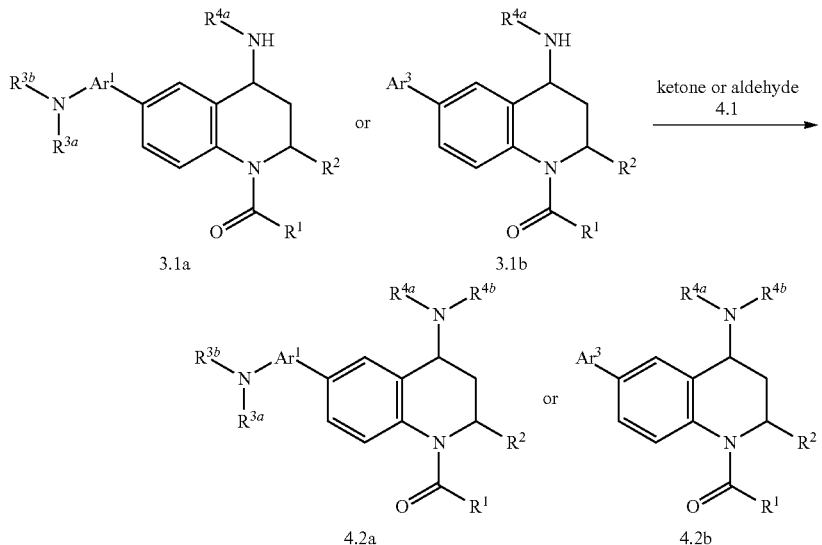

Compounds are represented in generic form, with substituents as noted in compound descriptions elsewhere herein. A more specific example is set forth below.

SCHEME 4B.

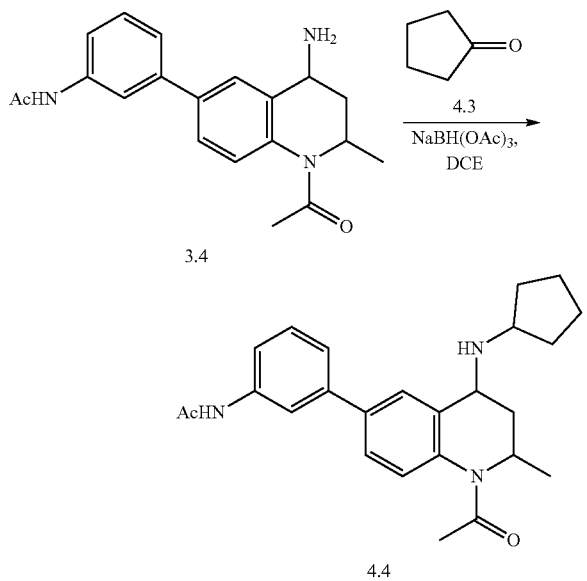

In one aspect, compounds of type 4.2a and 4.2b, and similar compounds, can be prepared according to reaction Scheme 4B above. Thus, compounds of type 4.4 can be prepared by reductive amination of an appropriate amine, e.g., 3.4 as shown above, and an appropriate aldehyde or ketone, e.g., 4.3 as shown above. Appropriate amines and appropriate aldehydes or ketones are commercially available or prepared by methods known to one skilled in the art. The reductive amination is carried out in the presence of an appropriate reducing agent, e.g., sodium triacetyoxyborohydride, in an appropriate solvent, e.g., 1,2-dichloroethane. As can be appreciated by one skilled in the art, the above reaction provides an example of a generalized approach wherein compounds similar in structure to the specific reactants above (compounds similar to compounds of type 3.1a, 3.1b, and 4.1), can be substituted in the reaction to provide substituted tetrahydroquinoline derivatives similar to Formula 4.2a and 4.2b.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

5. Route V

In one aspect, substituted tetrahydroquinoline derivatives can be prepared as shown below.

SCHEME 5A.

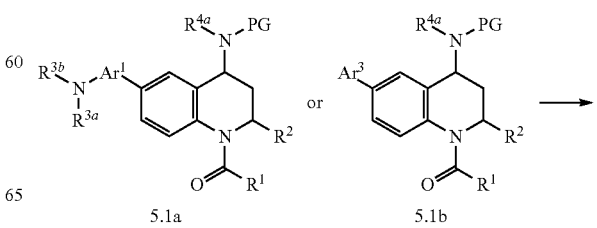

-continued

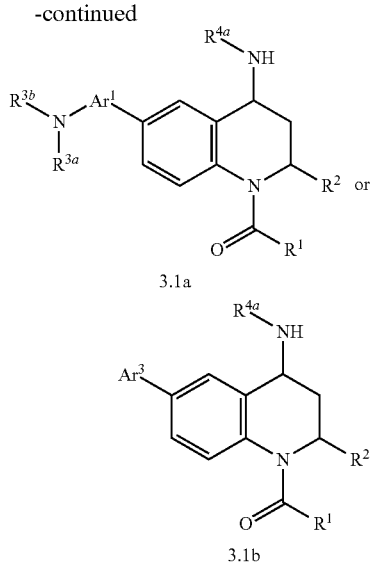

3.1a 3.1b

Compounds are represented in generic form, with substituents as noted in compound descriptions elsewhere herein and wherein PG is a protecting group. A more specific example is set forth below.

SCHEME 5B.

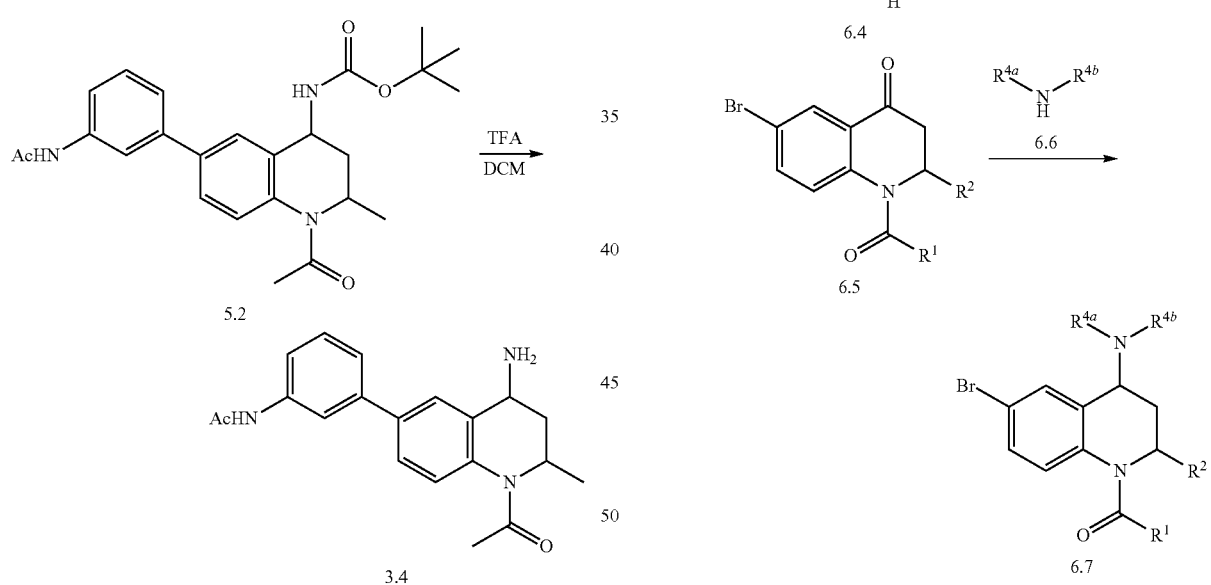

5.2

3.4

In one aspect, compounds of type 3.4, and similar compounds, can be prepared according to reaction Scheme 5B above. Thus, compounds of type 3.4 can be prepared by deprotection of an appropriate amine, e.g., 5.2 as shown above. Appropriate amines are commercially available or prepared by methods known to one skilled in the art. The deprotection is carried out in the presence of an appropriate acid, e.g., trifluoroacetic acid, in an appropriate solvent, e.g., dichloromethane (DCM). As can be appreciated by one skilled in the art, the above reaction provides an example of a generalized approach wherein compounds similar in structure to the specific reactants above (compounds similar to compounds of type 5.1a and 5.1b), can be substituted in the reaction to provide substituted tetrahydroquinoline derivatives similar to Formula 3.1a and 3.1b.

6. Route VI

In one aspect, substituted tetrahydroquinoline derivatives can be prepared as shown below.

SCHEME 6A.

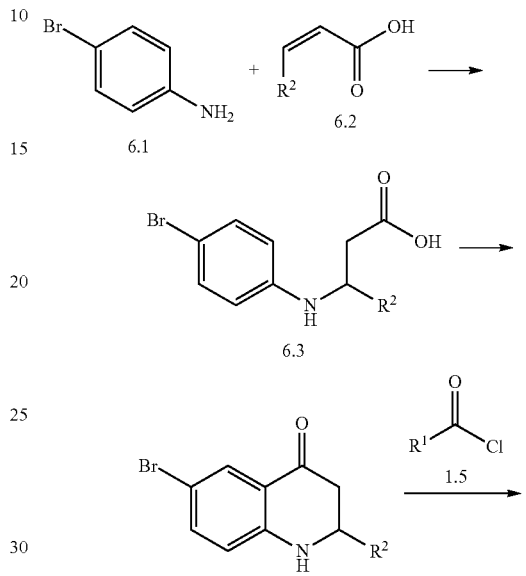

6.1  6.2

6.3

6.4

6.5

6.7

Compounds are represented in generic form, with substituents as noted in compound descriptions elsewhere herein. A more specific example is set forth below.

SCHEME 6B.

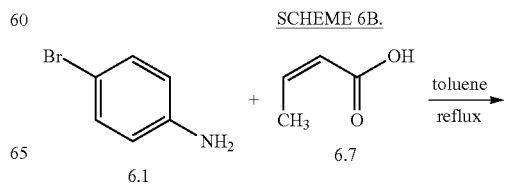

6.1  6.7

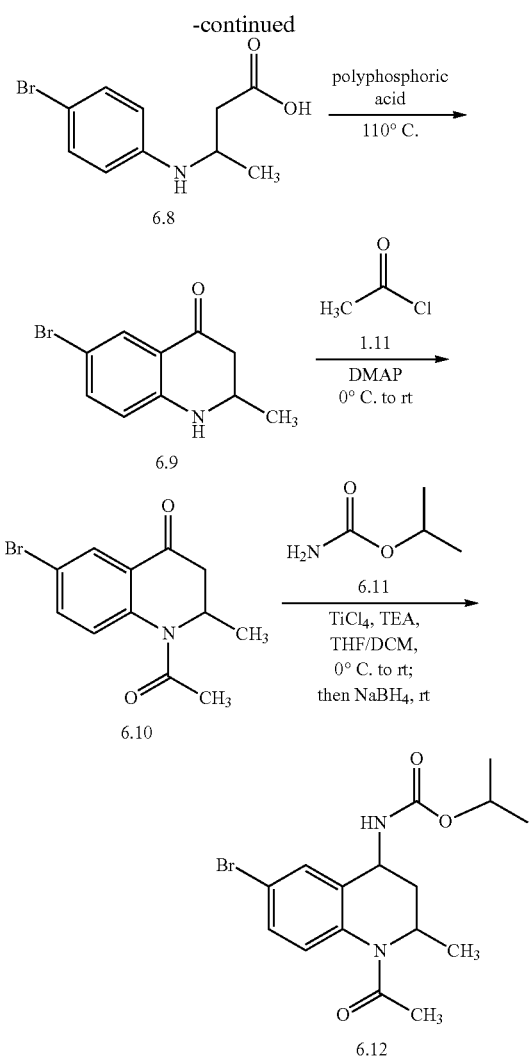

In one aspect, compounds of type 6.13, and similar compounds, can be prepared according to reaction Scheme 6B above. Thus, compounds of type 6.9 can be prepared by Michael addition of an appropriate amine, e.g., 6.1 as shown above, and an appropriate alkene, e.g., 6.7 as shown above. Appropriate amines and appropriate alkenes are commercially available or prepared by methods known to one skilled in the art. The Michael addition is carried out in the presence of an appropriate solvent, e.g., toluene. Compounds of type 6.9 can be prepared by cyclization of an appropriate carboxylic acid, e.g., 6.8 as shown above. The cyclization is carried out in the presence of an appropriate acid, e.g., polyphosphoric acid, at an appropriate temperature, e.g., 110° C. Compounds of type 6.10 can be prepared by acylation of an appropriate amine, e.g., 6.9 as shown above. The acylation is carried out in the presence of an appropriate acyl halide, e.g., 1.11 as shown above, and an appropriate base, e.g., dimethylaminopyridine (DMAP). Compounds of type 6.12 can be prepared by reductive amination of an appropriate ketone, e.g., 6.10 as shown above, and an appropriate amine, e.g., 6.11 as shown above. Appropriate amines are commercially available or prepared by methods known to one skilled in the art. The reductive amination is carried out in the presence of an appropriate catalyst, e.g., titanium tetrachloride, and an appropriate base, e.g., triethylamine, in an appropriate solvent, e.g., THF/DCM, followed by addition of an appropriate reducing agent, e.g., sodium borohydride. As can be appreciated by one skilled in the art, the above reaction provides an example of a generalized approach wherein compounds similar in structure to the specific reactants above (compounds similar to compounds of type 1.5, 6.1, 6.2, 6.3, 6.4, 6.5, and 6.6), can be substituted in the reaction to provide substituted tetrahydroquinoline derivatives similar to Formula 6.7.

D. Pharmaceutical Compositions

In one aspect, disclosed are pharmaceutical compositions comprising a disclosed compound, or a pharmaceutically acceptable salt thereof and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with bromodomain activity such as, for example, an estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis.

In a further aspect, the pharmaceutical composition is used as a male contraceptive. In a still further aspect, the pharmaceutical composition is used to suppress stem cell differentiation.

In a further aspect, the pharmaceutical composition is used to treat cancer. In a further aspect, the cancer is selected from leukemia, breast cancer, prostate cancer, Ewing sarcoma, gastric cancer, melanoma, multiple myeloma, blastic plasmacytoid dendritic cell neoplasm, human squamous carcinoma, NUT midline carcinoma, lymphoma, angiogenesis, bladder cancer, thyroid cancer, childhood rhabdomyosarcoma, ovarian cancer, neurofibromatosis, lung cancer, colorectal cancer, IDH1-mutant glioma, uveal melanoma, pancreatic cancer, glioblastoma, neuroblastoma, advanced systemic mastocytosis, osteosarcoma, Merkel cell carcinoma, medulloblastoma, and malignant peripheral nerve sheath tumors.

It is understood that the disclosed compositions can be prepared from the disclosed compounds. It is also understood that the disclosed compositions can be employed in the disclosed methods of using.

E. Methods of Treating a Disorder Associated with Bromodomain Activity

In various aspects, the compounds and compositions disclosed herein are useful for treating, preventing, ameliorating, controlling or reducing the risk of a variety of disorders associated with bromodomain activity, including, for example, cancer. Thus, in one aspect, disclosed are methods of treating a disorder associated with bromodomain activity in a subject, the method comprising administering to the subject an effective amount of at least one disclosed compound or a pharmaceutically acceptable salt thereof.

In one aspect, disclosed are methods of treating a disorder for which a bromodomain is indicated in a subject in need thereof, the method comprising administering a therapeutically effective amount of a compound having a structure represented by a formula:

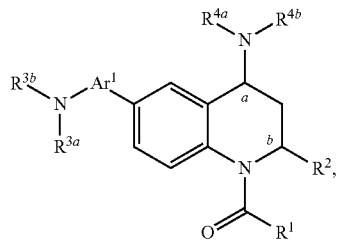

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, —(C1-C6 alkyl)C3-C6 cycloalkyl), —(C1-C6 alkyl)(C3-C6 heterocycloalkyl), —C(O)(C1-C6 alkyl), —C(O)(C3-C4 cycloalkyl), and amine protecting group; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein $Ar^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group; wherein $R^{4b}$ is selected from $Cy^1$, $Ar^2R^5$, and —$COR^6$; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —$NO_2$, C1-C4 alkyl, C1-C4 alkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —$COR^{21}$, —$CO_2R^{21}$, —$CONR^{22}R^{22b}$, —$SO_2NR^{22a}R^{22b}$, and heterocycle; and wherein $R^5$, when present, is selected from halogen, —OH, —CN, —$NO_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and 3- to 5-membered heterocycle; wherein each occurrence of $R^{21}$, when present, is independently selected from hydrogen, C1-C6 alkyl, C3-C6 cycloalkyl, C3-C6 heterocycloalkyl, and —$COR^{30}$; and wherein each occurrence of each of $R^{22a}$ and $R^{22b}$, when present, is independently selected from hydrogen, C1-C6 alkyl, C3-C6 cycloalkyl, C3-C6 heterocycloalkyl, and —$COR^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl, wherein $R^6$, when present, is selected from C1-C4 alkyl, C1-C4 haloalkyl, and C1-C4 alkoxy; provided that each of $R^{3a}$ and $R^{3b}$ is not hydrogen when $R^{4b}$ is —$COR^6$ or when $Ar^1$ is six-membered heteroaryl; and provided that each of $R^{3a}$ and $R^{3b}$ are not covalently bonded together when $Ar^1$ is six-membered heteroaryl, or a pharmaceutically acceptable salt thereof.

In one aspect, disclosed are methods of treating a disorder for which a bromodomain is indicated in a subject in need thereof, the method comprising administering a therapeutically effective amount of a compound having a structure represented by a formula:

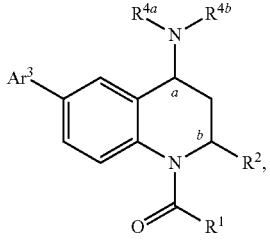

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected $Cy^1$, $Ar^2R^5$, —$COR^6$, and amine protecting group; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —$NO_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —$COR^{21}$, —$CO_2R^{21}$, —$CONR^{22a}R^{22b}$, —$SO_2NR^{22a}R^{22b}$, and heterocycle; and wherein $R^5$, when present, is selected from halogen, —OH, —CN, —$NO_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and 3- to 5-membered heterocycle; wherein each occurrence of R$^{21}$, when present, is independently selected from hydrogen, C1-C6 alkyl, C3-C6 cycloalkyl, C3-C6 heterocycloalkyl, and —COR$^{30}$; wherein each occurrence of each of R$^{22a}$ and R$^{22b}$, when present, is independently selected from hydrogen, C1-C6 alkyl, C3-C6 cycloalkyl, C3-C6 heterocycloalkyl, and —COR$^{30}$; wherein each occurrence of R$^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein R$^6$, when present, is selected from C1-C4 alkyl, C1-C4 haloalkyl, and C1-C4 alkoxy; and wherein Ar$^3$ is phenyl substituted with 1-4 independently selected —OR$^{31}$ groups; wherein each occurrence of R$^{31}$ is independently selected from hydrogen and C2-C6 alkyl; or wherein Ar$^3$ is a five-membered heteroaryl selected from:

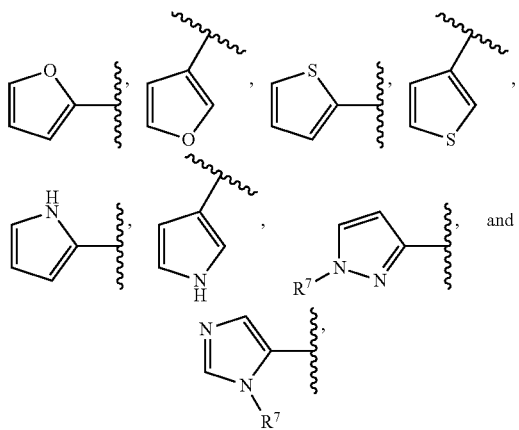

wherein R$^7$, when present, is selected from hydrogen and C1-C4 alkyl; provided that when R$^{4b}$ is —COR$^6$, then Ar$^3$ is not

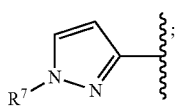

or a pharmaceutically acceptable salt thereof.

In a further aspect, the disorder is selected from an estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis.

In a further aspect, the disorder is cancer. In a further aspect, the cancer is selected from leukemia, breast cancer, prostate cancer, Ewing sarcoma, gastric cancer, melanoma, multiple myeloma, blastic plasmacytoid dendritic cell neoplasm, human squamous carcinoma, NUT midline carcinoma, lymphoma, angiogenesis, bladder cancer, thyroid cancer, childhood rhabdomyosarcoma, ovarian cancer, neurofibromatosis, lung cancer, colorectal cancer, IDH1-mutant glioma, uveal melanoma, pancreatic cancer, glioblastoma, neuroblastoma, advanced systemic mastocytosis, osteosarcoma, Merkel cell carcinoma, medulloblastoma, and malignant peripheral nerve sheath tumors.

In various aspects, the disclosed compounds can be used in combination with one or more other drugs in the treatment, prevention, control, amelioration, or reduction of risk of disorders associated with bromodomain activity for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In a further aspect, the compound exhibits inhibition of bromodomain activity. In a still further aspect, the compound exhibits a decrease in bromodomain activity.

In a further aspect, the compound exhibits inhibition of bromodomain activity with an IC$_{50}$ of from about 0.001 µM to about 25 µM. In a still further aspect, the compound exhibits inhibition of bromodomain activity with an IC$_{50}$ of from about 0.001 µM to about 15 µM. In yet a further aspect, the compound exhibits inhibition of bromodomain activity with an IC$_{50}$ of from about 0.001 µM to about 10 µM. In an even further aspect, the compound exhibits inhibition of bromodomain activity with an IC$_{50}$ of from about 0.001 µM to about 5 µM. In a still further aspect, the compound exhibits inhibition of bromodomain activity with an IC$_{50}$ of from about 0.001 µM to about 1 µM. In yet a further aspect, the compound exhibits inhibition of bromodomain activity with an IC$_{50}$ of from about 0.001 µM to about 0.5 µM. In an even further aspect, the compound exhibits inhibition of bromodomain activity with an IC$_{50}$ of from about 0.001 µM to about 0.1 µM. In a still further aspect, the compound exhibits inhibition of bromodomain activity with an IC$_{50}$ of from about 0.001 µM to about 0.05 µM. In yet a further aspect, the compound exhibits inhibition of bromodomain activity with an IC$_{50}$ of from about 0.001 µM to about 0.01 µM. In an even further aspect, the compound exhibits inhibition of bromodomain activity with an IC$_{50}$ of from about 0.001 µM to about 0.005 µM. In a still further aspect, the compound exhibits inhibition of bromodomain activity with an IC$_{50}$ of from about 0.005 µM to about 25 µM. In yet a further aspect, the compound exhibits inhibition of bromodomain activity with an IC$_{50}$ of from about 0.01 µM to about 25 µM. In an even further aspect, the compound exhibits inhibition of bromodomain activity with an IC$_{50}$ of from about 0.05 µM to about 25 µM. In a still further aspect, the compound exhibits inhibition of bromodomain activity with an IC$_{50}$ of from about 0.1 µM to about 25 µM. In yet a further aspect, the compound exhibits inhibition of bromodomain activity with an IC$_{50}$ of from about 0.5 μM to about 25 μM. In an even further aspect, the compound exhibits inhibition of bromodomain activity with an IC$_{50}$ of from about 1 μM to about 25 μM. In a still further aspect, the compound exhibits inhibition of bromodomain activity with an IC$_{50}$ of from about 5 μM to about 25 μM. In yet a further aspect, the compound exhibits inhibition of bromodomain activity with an IC$_{50}$ of from about 10 μM to about 25 μM. In an even further aspect, the compound exhibits inhibition of bromodomain activity with an IC$_{50}$ of from about 15 μM to about 25 μM.

In a further aspect, the subject is a mammal. In a still further aspect, the mammal is human.

In a further aspect, the subject has been diagnosed with a need for treatment of the disorder prior to the administering step. In a still further aspect, the subject is at risk for developing the disorder prior to the administering step.

In a further aspect, the method further comprises identifying a subject at risk for developing the disorder prior to the administering step.

F. Methods of Inhibiting a Bromodomain in at Least One Cell

In one aspect, disclosed are methods of inhibiting a bromodomain in at least one cell, the method comprising the step of contacting the at least one cell with an effective amount of at least one disclosed compound, or a pharmaceutically acceptable salt thereof.

In one aspect, disclosed are methods of inhibiting a bromodomain comprising contacting the bromodomain with a compound having a structure represented by a formula:

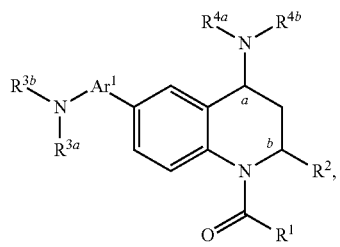

wherein $R^1$ is selected from C1-C4 alkyl, C1-C4 haloalkyl, and C1-C4 deuterated alkyl; wherein $R^2$ is C1-C4 alkyl; wherein each of $R^{3a}$ and $R^{3b}$ is independently selected from hydrogen, C1-C6 alkyl, C1-C6 haloalkyl, —(C1-C6 alkyl)(C3-C6 cycloalkyl), —(C1-C6 alkyl)(C3-C6 heterocycloalkyl), —C(O)(C1-C6 alkyl), —C(O)(C3-C4 cycloalkyl), and amine protecting group; or wherein each of $R^{3a}$ and $R^{3b}$ are optionally covalently bonded together and, together with the intermediate atoms, comprise a 3- to 7-membered heterocycloalkyl, or a 5- to 7-membered heteroaryl and are substituted with 0-4 non-hydrogen groups independently selected from halogen, —OH, —CN, C1-C4 alkyl, C1-C4 alkoxy, and C1-C4 haloalkyl; wherein $Ar^1$ is selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl; wherein $R^{4a}$ is selected from hydrogen, C1-C4 alkyl, and amine protecting group; wherein $R^{4b}$ is selected from $Cy^1$, $Ar^2R^5$, and —COR$^6$; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle; and wherein $R^5$, when present, is selected from halogen, —OH, —CN, —NO$_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and 3- to 5-membered heterocycle; wherein each occurrence of $R^{21}$, when present, is independently selected from hydrogen, C1-C6 alkyl, C3-C6 cycloalkyl, C3-C6 heterocycloalkyl, and —COR$^{30}$; and wherein each occurrence of each of $R^{22a}$ and $R^{22b}$, when present, is independently selected from hydrogen, C1-C6 alkyl, C3-C6 cycloalkyl, C3-C6 heterocycloalkyl, and —COR$^{30}$; wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl, wherein $R^6$, when present, is selected from C1-C4 alkyl, C1-C4 haloalkyl, and C1-C4 alkoxy; provided that each of $R^{3a}$ and $R^{3b}$ is not hydrogen when $R^{4b}$ is —COR$^6$ or when $Ar^1$ is six-membered heteroaryl; and provided that each of $R^{3a}$ and $R^{3b}$ are not covalently bonded together when $Ar^1$ is six-membered heteroaryl, or a pharmaceutically acceptable salt thereof.

In one aspect, disclosed are methods of inhibiting a bromodomain comprising contacting the bromodomain with a compound having a structure represented by a formula:

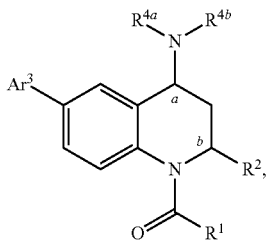

wherein $R^1$ is selected from C1-C4 alkyl, C1-C4 haloalkyl, and C1-C4 deuterated alkyl; wherein $R^2$ is C1-C4 alkyl; wherein $R^{4a}$ is selected from hydrogen, C1-C4 alkyl, and amine protecting group; wherein $R^{4b}$ is selected $Cy^1$, $Ar^2R^5$, —COR$^6$, and amine protecting group; wherein $Cy^1$, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl; wherein $Ar^2$, when present, is selected from aryl and 5- to 12-membered heteroaryl and is substituted with 0-4 non-hydrogen groups independently selected from halogen, —OH, —CN, —NO$_2$, C1-C4 alkyl, C1-C4 alkoxy, C1-C4 haloalkyl, C1-C4 haloalkoxy, C1-C4 alkylamino, (C1-C4)(C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and heterocycle; and wherein $R^5$, when present, is selected from halogen, —OH, —CN, —NO$_2$, C1-C4 alkyl, C1-C4 haloalkyl, C1-C4 alkoxy, C1-C4 haloalkoxy, C1-C4 haloalkyl, C1-C4 haloalkoxy, C1-C4 alkylamino, (C1-C4)C1-C4) dialkylamino, C1-C4 aminoalkyl, C3-C6 cycloalkyl, —COR$^{21}$, —CO$_2$R$^{21}$, —CONR$^{22a}$R$^{22b}$, —SO$_2$NR$^{22a}$R$^{22b}$, and 3- to 5-membered heterocycle; wherein each occurrence of R$^{21}$, when present, is independently selected from hydrogen, C1-C6 alkyl, C3-C6 cycloalkyl, C3-C6 heterocycloalkyl, and —COR$^{30}$; wherein each occurrence of each of R$^{22a}$ and R$^{22b}$, when present, is independently selected from hydrogen, C1-C6 alkyl, C3-C6 cycloalkyl, C3-C6 heterocycloalkyl, and —COR$^{30}$; wherein each occurrence of R$^{30}$, when present, is independently selected from hydrogen, C1-C6 alkyl, C1-C6 alkoxy, C1-C6 aminoalkyl, C3-C6 cycloalkyl, and C3-C6 heterocycloalkyl; wherein R$^6$, when present, is selected from C1-C4 alkyl, C1-C4 haloalkyl, and C1-C4 alkoxy; and wherein Ar$^3$ is phenyl substituted with 1-4 independently selected —OR$^{31}$ groups; wherein each occurrence of R$^{31}$ is independently selected from hydrogen and C2-C6 alkyl; or wherein Ar$^3$ is a five-membered heteroaryl selected from:

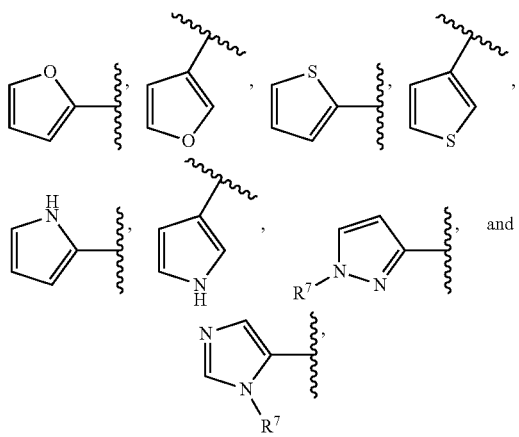

wherein R$^7$, when present, is selected from hydrogen and C1-C4 alkyl; provided that when R$^{4b}$ is —COR$^6$, then Ar$^3$ is not

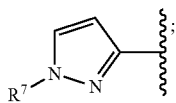

or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal.

G. Methods of Using the Compositions

Provided are methods of using of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, the invention relates to a method for the manufacture of a medicament for treating a disorder associated with bromodomain dysfunction in a mammal, the method comprising combining a therapeutically effective amount of a disclosed compound or product of a disclosed method with a pharmaceutically acceptable carrier or diluent.

In a further aspect, the disorder is selected from an estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis.

In a further aspect, the disorder is cancer. In a further aspect, the cancer is selected from leukemia, breast cancer, prostate cancer, Ewing sarcoma, gastric cancer, melanoma, multiple myeloma, blastic plasmacytoid dendritic cell neoplasm, human squamous carcinoma, NUT midline carcinoma, lymphoma, angiogenesis, bladder cancer, thyroid cancer, childhood rhabdomyosarcoma, ovarian cancer, neurofibromatosis, lung cancer, colorectal cancer, IDH1-mutant glioma, uveal melanoma, pancreatic cancer, glioblastoma, neuroblastoma, advanced systemic mastocytosis, osteosarcoma, Merkel cell carcinoma, medulloblastoma, and malignant peripheral nerve sheath tumors.

As regards these applications, the present method includes the administration to an animal, particularly a mammal, and more particularly a human, of a therapeutically effective amount of the compound effective in the inhibition of protein and especially bromodomain. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the disorder.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

2. Use of Compounds and Compositions

Also provided are the uses of the disclosed compounds and compositions. Thus, in one aspect, the invention relates to the uses of inhibitors of a bromodomain. In a further aspect, the use is as a male contraceptive. In a still further aspect, the use is to suppress stem cell differentiation.

In a further aspect, the invention relates to the use of a disclosed compound or product of a disclosed method in the manufacture of a medicament for the treatment of a disorder associated with bromodomain activity such as, for example, cancer.

In a further aspect, the disorder is selected from an estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis.

In a further aspect, the disorder is cancer. In a further aspect, the cancer is selected from leukemia, breast cancer, prostate cancer, Ewing sarcoma, gastric cancer, melanoma, multiple myeloma, blastic plasmacytoid dendritic cell neoplasm, human squamous carcinoma, NUT midline carcinoma, lymphoma, angiogenesis, bladder cancer, thyroid cancer, childhood rhabdomyosarcoma, ovarian cancer, neurofibromatosis, lung cancer, colorectal cancer, IDH1-mutant glioma, uveal melanoma, pancreatic cancer, glioblastoma, neuroblastoma, advanced systemic mastocytosis, osteosarcoma, Merkel cell carcinoma, medulloblastoma, and malignant peripheral nerve sheath tumors.

In a further aspect, the use relates to a process for preparing a pharmaceutical composition comprising a therapeutically effective amount of a disclosed compound or a product of a disclosed method, and a pharmaceutically acceptable carrier, for use as a medicament.

In a further aspect, the use relates to a process for preparing a pharmaceutical composition comprising a therapeutically effective amount of a disclosed compound or a product of a disclosed method, wherein a pharmaceutically acceptable carrier is intimately mixed with a therapeutically effective amount of the disclosed compound or the product of a disclosed method.

In various aspects, the use relates to the treatment of a disorder in a vertebrate animal. In a further aspect, the use relates to the treatment of a disorder in a human subject.

It is understood that the disclosed uses can be employed in connection with the disclosed compounds, methods, compositions, and kits. In a further aspect, the invention relates to the use of a disclosed compound or composition of a medicament for the treatment of a disorder associated with bromodomain activity in a mammal.

3. Kits

In one aspect, disclosed are kits comprising a disclosed compound and one or more of: (a) at least one chemotherapeutic agent; (b) at least one agent known to treat a disorder selected from estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis; (c) at least one birth control agent; (d) at least one agent known to differentiate stem cells; (e) at least one agent known to suppress stem cell differentiation; (f) instructions for treating cancer; (g) instructions for treating a disorder selected from estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis; (h) instructions for using a birth control agent; and (i) instructions for suppressing stem cell differentiation.

In various aspects, the agents and pharmaceutical compositions described herein can be provided in a kit. The kit can also include combinations of the agents and pharmaceutical compositions described herein.

In various aspects, the informational material can be descriptive, instructional, marketing or other material that relates to the methods described herein and/or to the use of the agents for the methods described herein. For example, the informational material may relate to the use of the agents herein to treat a subject who has, or who is at risk for developing, a disorder associated with bromodomain activity. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, a disorder associated with Bromodomain activity.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the compound and the at least one agent known are co-formulated. In a still further aspect, the compound and the at least one agent are co-packaged.

In a further aspect, the kit further comprises a plurality of dosage forms, the plurality comprising one or more doses; wherein each dose comprises an effective amount of the compound and the at least one agent. In a still further aspect, the effective amount is a therapeutically effective amount. In yet a further aspect, the effective amount is a prophylactically effective amount. In an even further aspect, each dose of the compound and the at least one agent are co-packaged. In a still further aspect, each dose of the compound and the at least one agent are co-formulated.

4. Subjects

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In some aspects of the disclosed methods, the subject has been diagnosed with a need for treatment prior to the administering step. In some aspects of the disclosed method, the subject has been diagnosed with a disorder associated with Bromodomain activity prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, Pa.). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, N.Y.).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

H. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals

All solvents were purchased from Sigma-Aldrich (anhydrous grade). All reagents and control compounds were used as purchased at the highest grade available. All melting points were recorded with Buchi MP B-545 instrument and were not corrected. All reactions were performed under an atmosphere of nitrogen. All reactions were monitored via ultra-performance liquid chromatography (UPLC) analysis. UPLC analysis was performed on a Waters Acquity instrument and was carried out with a BEH C18 2.1×50 mm column using gradient elution with stationary phase: BEH C18, 1.7 mm, solvents: A: 0.1% formic acid in water, B: 0.1% formic acid in acetonitrile, detector types: PDA (210 to 400 nm) and ELS (evaporating light scattering). Chiral purity was ascertained via Waters UPC$^2$ supercritical fluid chromatography (SFC); column: ADH, method: 15-40% methanol:liquid carbon dioxide gradient, time=11 minutes. High-resolution mass spectrometric (HRMS) analyses were accomplished using a UPLC/Q-ToF MS with stationary phase: BEH C18, 1.7 mm, solvents: A: 0.1% formic acid in water, B: 0.1% formic acid in acetonitrile. All single runs, normal phase flash chromatography or reverse phase purifications employed automated chromatography using a Biotage Isolera One or Four (Biotoage SNAP® Ultra cartridges, solvent system for normal phase: EtOAc in hexane; for reverse phase; 0.1% aqueous formic acid in acetonitrile). Nuclear magnetic resonance (NMR) experiments were conducted using a 400 MHz II instrument (Bruker Avance II). Abbreviations for multiplicities observed in NMR spectra: s; singlet; br s, broad singlet; d, doublet; t, triplet; q, quadruplet; m, multiplet. The purity of all compounds was determined by UPLC (UV and ELSD purity average). QC for control compounds was conducted on the aforementioned UPLC instrument (method: formate). (+)-JQ1 retention time 1.32 min, [M+H]$^+$=456.87 and IBET-726 retention time 1.16 min, [M+H]$^+$=435.36. All were used at >95% purity (UV & ELSD).

a. Synthesis of Isopropyl ((2S,4R)-1-acetyl-6-bromo-2-methyl-1,2,3,4-tetrahydroquinolin-4-yl) carbamate

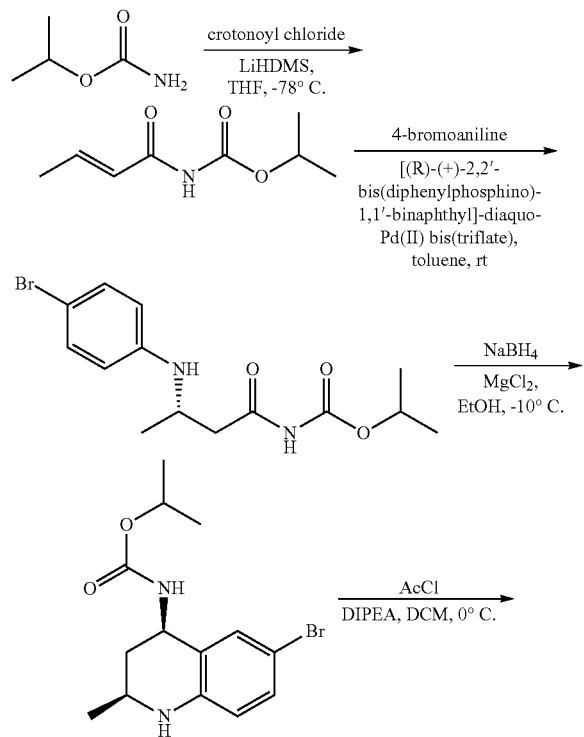

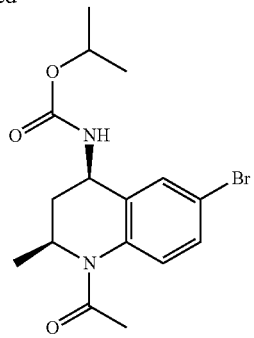

i. Preparation of Isopropyl (E)-but-2-enoylcarbamate

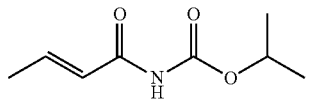

To a solution of isopropyl carbamate (15.85 g, 154 mmol) in anhydrous THF (150 mL) in a flame-dried flask at −78° C. was added crotonoyl chloride (14.16 mL, 146 mmol), followed by LiHMDS (300 mL, 1.0 M in THF). After 30 minutes of stirring at −78° C., solution was permitted to warm to RT and stir at RT overnight. Reaction was quenched via addition of sat. aq. NH$_4$Cl (200 mL). Solution was extracted with EtOAc (3×75 mL). Combined organics were washed with sat NaCl and dried with MgSO$_4$, filtered and concentrated under reduced pressure. Crude product was purified via automated normal phase chromatography (23% EtOAc in hexanes) to provide the desired imide as a white solid (12.3 g, 64% yield). mp 91° C. LCMS/UPLC (method: formate) retention time 0.82 min, [M+H]+=172.27. $^1$H NMR (400 MHz, CDCl$_3$) δ 7.55 (s, 1H), 7.14 (dq, J=15.3, 6.9 Hz, 1H), 6.86 (dq, J=15.2, 1.7 Hz, 1H), 4.99 (p, J=6.3 Hz, 1H), 1.94 (dd, J=6.9, 1.7 Hz, 3H), 1.30 (d, J=6.3 Hz, 6H). $^{13}$C NMR (126 MHz, CDCl$_3$) δ 166.03, 151.36, 146.34, 122.94, 70.23, 21.78, 18.40.

ii. Preparation of Isopropyl (S)-(3-((4-bromophenyl) amino)butanoyl)carbamate

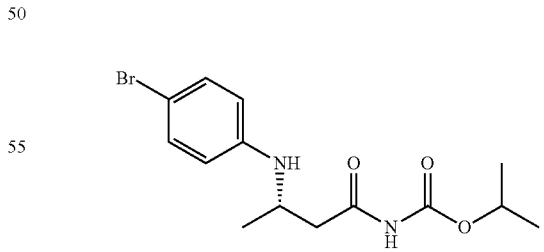

To a suspension of ene-imide (5.0 g, 29.2 mmol) and (R)-BINAP-Pd(OH)$_2$(OTf)$_2$ (1.45 g, 1.36 mmol) in anhydrous toluene (80 mL) in a round bottom flask (rbf) at 45° C. was added a solution of 4-bromo aniline (3.35 g, 19.47 mmol, dissolved in 100 mL of anhydrous toluene) dropwise over 3 h. Resulting reaction was permitted to stir at 25° C. for 48 h. Reaction was then permitted to return to RT and concentrated in vaccuo. Residual was purified via automated normal phase chromatography (25% EtOAc in hexanes) to provide the desired Michael adduct as an off-white solid (6.12 g, 92% yield). mp 131° C. LCMS/UPLC (method: formate) retention time 1.15 min, [M+H]$^+$=342.79. Chiral SFC (method: methanol:liquid CO$_2$) retention time 7.40 min (major enantiomer, 92.2% UV), 10.58 min (minor enantiomer, 7.8% UV). $^1$H NMR (400 MHz, CDCl$_3$) δ 7.42 (s, 1H), 7.25-7.21 (m, 2H), 6.54-6.46 (m, 2H), 4.97 (hept, J=6.3 Hz, 1H), 3.99 (q, J=6.3 Hz, 1H), 3.90 (s, 1H), 3.09 (dd, J=16.0, 5.7 Hz, 1H), 2.90 (dd, J=16.0, 6.0 Hz, 1H), 1.29 (m, 9H). $^{13}$C NMR (126 MHz, CDCl$_3$) δ 172.71, 151.28, 145.87, 132.02, 115.21, 109.22, 70.56, 45.98, 41.94, 21.76, 20.69.

iii. Preparation of Isopropyl ((2S,4R)-6-bromo-2-methyl-1,2,3,4-tetrahydroquinolin-4-yl)carbamate

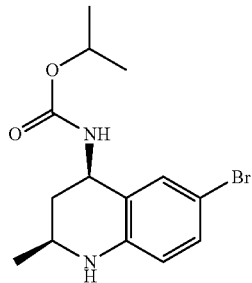 [SMILES: CC(C)OC(=O)N[C@@H]1C[C@H](C)Nc2ccc(Br)cc21]

To a solution of amino imide (6.12 g, 17.83 mmol) in EtOH (90 mL) at −20° C. was added NaBH$_4$ (0.51 g, 13.37 mmol) in one portion, followed by an aqueous solution of MgCl$_2$.6H$_2$O (3.99 g, 19.61 mmol, dissolved in 12 mL water) added dropwise such that the internal temperature did not exceed −10° C. The resulting solution was permitted to stir at 0° C. for 1 h, followed by 1 h at RT. The reaction was quenched via addition of citric acid (6.5 g, 2.5 eq) dissolved in aq 1M HCl (54 mL), followed by treatment of CH$_2$Cl$_2$ (50 mL). After 1 h of heterogeneous stirring, organic solution was collected, followed by aqueous extractions with CH$_2$Cl$_2$ (2×30 mL). Combined organics were washed with sat aq NaCl, dried over MgSO$_4$, filtered and concentrated. Crude product was purified via automated normal phase chromatography (22% EtOAc in hexanes) to provide cyclized amine as a white solid (2.1 g, 91% yield). mp 167° C. LCMS/UPLC (method: formate) retention time 1.19 min, [M+H]$^+$=327.01. $^1$H NMR (400 MHz, CDCl$_3$) δ 7.26 (d, J=1.1 Hz, 1H), 7.08 (dd, J=8.5, 0.9 Hz, 1H), 6.34 (dd, J=8.5, 0.9 Hz, 1H), 4.98 (m, J=5.4 Hz, 2H), 4.70 (d, J=9.5 Hz, 1H), 3.74 (s, 1H), 3.62-3.48 (m, 1H), 2.26 (ddd, J=12.6, 6.0, 2.3 Hz, 1H), 1.43 (q, J=11.7 Hz, 1H), 1.28 (dd, J=14.6, 6.3 Hz, 6H), 1.20 (d, J=6.2 Hz, 3H). $^{13}$C NMR (126 MHz, CDCl$_3$) δ 156.26, 143.96, 130.94, 129.44, 123.73, 115.67, 109.04, 68.49, 47.72, 46.74, 37.97, 22.20, 22.14.

iv. Preparation of Isopropyl ((2S,4R)-1-acetyl-6-bromo-2-methyl-1,2,3,4-tetrahydroquinolin-4-yl)carbamate

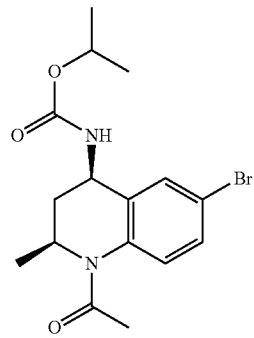 [SMILES: CC(=O)N1c2ccc(Br)cc2[C@H](NC(=O)OC(C)C)C[C@@H]1C]

To a solution of amine (5.32 g, 16.26 mmol) in CH$_2$Cl$_2$ (35 mL) and DIPEA (2.93 mL) under nitrogen at RT was added dropwise acetyl chloride (1.89 mL, 24.39 mmol). Reaction was permitted to stir at RT until complete by TLC. Reaction was then treated with CH$_2$Cl$_2$ (50 mL) and sat aq. NaHCO$_3$ (50 mL). The phases were separated; aqueous solution was extracted with CH$_2$Cl$_2$ (2×20 mL). Combined organics were washed with sat. NaCl, dried over MgSO$_4$, filtered and concentrated. Residual was purified via automated normal phase chromatography (29% EtOAc in hexanes) to provide amide product as a white solid (1.8 g, 95% yield). mp 163° C. LCMS/UPLC (method: formate) retention time 1.11 min, [M+H]$^+$=368.88. $^1$H NMR (400 MHz, Methanol-d$_4$) δ 7.49 (dd, J=8.4, 2.2 Hz, 1H), 7.37 (s, 1H), 7.24 (d, J=8.4 Hz, 1H), 4.95 (dq, J=12.5, 6.1 Hz, 1H), 4.81 (d, J=7.2 Hz, 1H), 4.48 (dd, J=12.5, 4.1 Hz, 1H), 2.55 (ddd, J=12.8, 8.7, 4.4 Hz, 1H), 2.15 (s, 3H), 1.39-1.21 (m, 7H), 1.13 (d, J=6.4 Hz, 3H). $^{13}$C NMR (126 MHz, Acetone) δ 169.22, 155.78, 138.21, 133.75, 128.64, 126.59, 124.46, 118.09, 67.08, 46.79, 46.62, 38.39, 20.07, 19.74, 18.76.

b. Synthesis of Tert-butyl ((2S,4R)-1-acetyl-6-bromo-2-methyl-1,2,3,4-tetrahydroquinolin-4-yl) carbamate (Z-038-2)

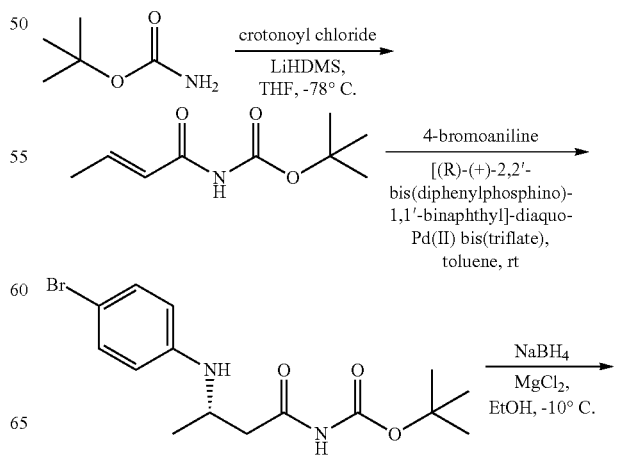

-continued

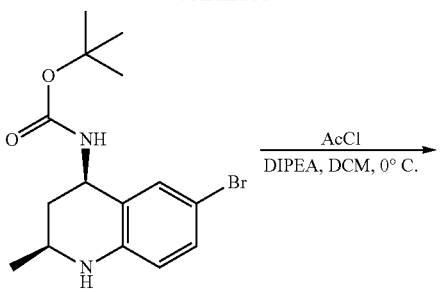

i. Preparation OF Tert-butyl (E)-but-2-enoylcarbamate

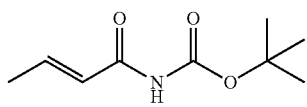

To a solution of tert-butyl carbamate (8.8 g, 75 mmol) in anhydrous THF (100 mL) in a flame-dried flask at −78° C. was added crotonoyl chloride (7.9 mL, 83 mmol), followed by LiHMDS (150 mL, 1.0 M in THF). Reaction was permitted to warm to RT and stir at RT overnight. Reaction was quenched via addition of sat. aq NH$_4$Cl (100 mL). Solution was extracted with EtOAc (3×75 mL). Combined organics were washed with sat NaCl and dried with MgSO$_4$, filtered and concentrated under reduced pressure. Crude product was purified via automated normal phase chromatography (23% EtOAc in hexanes) to provide the desired imide as a white solid (8.7 g, 63% yield). mp. 124° C. LCMS/UPLC (method: formate) retention time 0.91 min, [M+H-Boc]$^+$=129.65. $^1$H NMR (400 MHz, Acetone-d$_6$) δ 5.73 (dq, J=15.4, 6.9 Hz, 1H), 5.01-4.79 (m, 1H), 0.60 (dd, J=6.9, 1.7 Hz, 3H), 0.21 (s, 9H). $^{13}$C NMR (126 MHz, Acetone) δ 164.49, 149.76, 143.12, 122.56, 80.08, 25.62, 15.43.

ii. Preparation of Tert-butyl (S)-(3-((4-bromophenyl)amino)butanoyl)carbamate

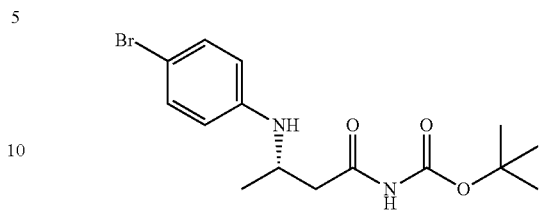

To a suspension of ene-imide (5.0 g, 27.0 mmol) and (R)-BINAP-Pd(OH)$_2$(OTf)$_2$ (0.77 g, 0.72 mmol) in anhydrous toluene (150 mL) at RT was added 4-bromo aniline (3.1 g, 18.0 mmol) dropwise. Resulting reaction was permitted to stir at RT for 48 h. Reaction was concentrated in vaccuo. Residual was purified via automated normal phase chromatography (25% EtOAc in hexanes) to provide the desired Michael adduct as an off-white solid (4.4 g, 68.4% yield) mp 116° C. LCMS/UPLC (method: formate) retention time 1.21 min, [M+H]+=356.86. SFC (method: methanol: liquid CO$_2$) retention time 5.88 min (major enantiomer, 93.4% UV), 7.93 min (minor enantiomer, 6.6% UV). $^1$H NMR (400 MHz, Acetone-d$_6$) δ 9.11 (s, 1H), 7.30-7.15 (m, 2H), 6.70-6.56 (m, 2H), 5.01 (d, J=9.0 Hz, 1H), 4.11-3.89 (m, 1H), 2.99 (dd, J=16.0, 5.5 Hz, 1H), 2.75 (dd, J=16.0, 7.3 Hz, 1H), 1.47 (s, 9H), 1.26 (d, J=6.4 Hz, 3H). $^{13}$C NMR (126 MHz, Acetone) δ 171.64, 150.82, 147.10, 131.63, 114.73, 107.15, 80.87, 45.17, 42.49, 27.26, 19.85.

iii. Preparation of Tert-butyl ((2S,4R)-6-bromo-2-methyl-1,2,3,4-tetrahydroquinolin-4-yl)carbamate

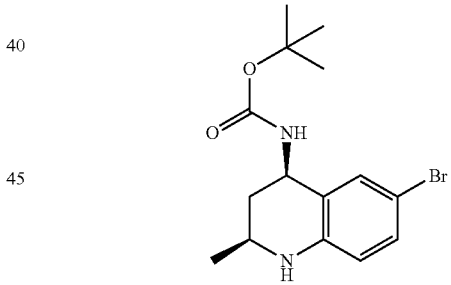

To a solution of amino imide (1.80 g, 5.04 mmol) in EtOH (20 mL) at −10° C. was added NaBH$_4$ (0.19 g, 5.04 mmol) in one portion, followed by an aqueous solution of MgCl$_2$.6H$_2$O (1.13 g, 5.54 mmol, dissolved in 5 mL water) added dropwise such that the internal temperature did not exceed −10° C. The resulting solution was permitted to stir at 0° C. for 1 h, followed by 1 h at RT. The reaction was quenched via addition of citric acid (2.5 g, 12.6 mmol) dissolved in aq 1M NH$_4$Cl (5 mL), followed by treatment of CH$_2$Cl$_2$ (20 mL). After 1 h of heterogeneous stirring, organic solution was collected, followed by aqueous extractions with CH$_2$Cl$_2$ (2×30 mL). Combined organics were washed with sat aq NaCl, dried over MgSO$_4$, filtered and concentrated. Crude product was purified via automated normal phase chromatography (22% EtOAc in hexanes) to provide cyclized amine as a white solid (1.5 g, 84% yield) mp 129° C. LCMS/UPLC (method: formate) retention time 1.26 min,

[M+H]⁺=341.08. ¹H NMR (400 MHz, CDCl₃) δ 7.26 (d, J=1.1 Hz, 1H), 7.08 (dd, J=8.5, 0.9 Hz, 1H), 6.34 (dd, J=8.5, 0.9 Hz, 1H), 4.98 (m, J=5.4 Hz, 2H), 4.70 (d, J=9.5 Hz, 1H), 3.74 (s, 1H), 3.62-3.48 (m, 1H), 2.26 (ddd, J=12.6, 6.0, 2.3 Hz, 1H), 1.43 (q, J=11.7 Hz, 1H), 1.28 (dd, J=14.6, 6.3 Hz, 6H), 1.20 (d, J=6.2 Hz, 3H). ¹³C NMR (126 MHz, CDCl₃) δ 156.26, 143.96, 130.94, 129.44, 123.73, 115.67, 109.04, 68.49, 47.72, 46.74, 37.97, 22.20, 22.14.

iv. Preparation of Tert-butyl ((2S,4R)-1-acetyl-6-bromo-2-methyl-1,2,3,4-tetrahydroquinolin-4-yl)carbamate

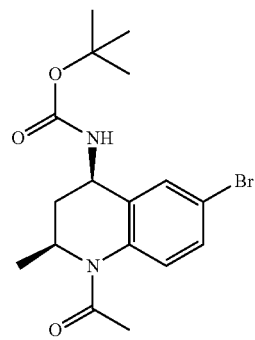 [SMILES: CC(=O)N1c2ccc(Br)cc2[C@H](NC(=O)OC(C)(C)C)C[C@@H]1C]

To a solution of amine (1.45 g, 4.25 mmol) in CH₂Cl₂ (10 mL) and DIPEA (3.66 mL) under nitrogen at RT was added dropwise acetyl chloride (0.758 mL, 10.62 mmol). Reaction was permitted to stir at RT for 4-17 h. Reaction was then treated with CH₂Cl₂ (20 mL) and sat aq. NaHCO₃ (20 mL). The phases were separated; aqueous solution was extracted with CH₂Cl₂ (2×20 mL). Combined organics were washed with sat. NaCl, dried over MgSO₄, filtered and concentrated. Residual product was purified via automated normal phase chromatography (29% EtOAc in hexanes) to provide amide product as a white solid (1.0 g, 61.4% yield). mp 178° C. LCMS/UPLC (method: formate) retention time 1.18 min, [M+H]⁺=383.11. ¹H NMR (400 MHz, Methanol-d₄) δ 7.49 (dd, J=8.4, 2.2 Hz, 1H), 7.37 (s, 1H), 7.24 (d, J=8.4 Hz, 1H), 4.95 (dq, J=12.5, 6.1 Hz, 1H), 4.81 (d, J=7.2 Hz, 1H), 4.48 (dd, J=12.5, 4.1 Hz, 1H), 2.55 (ddd, J=12.8, 8.7, 4.4 Hz, 1H), 2.15 (s, 3H), 1.39-1.21 (m, 7H), 1.13 (d, J=6.4 Hz, 3H). ¹³C NMR (126 MHz, Acetone) δ 169.22, 155.78, 138.21, 133.75, 128.64, 126.59, 124.46, 118.09, 67.08, 46.79, 46.62, 38.39, 20.07, 19.74, 18.76.

c. Synthesis of Tert-butyl ((2R,4S)-1-acetyl-6-bromo-2-methyl-1,2,3,4-tetrahydroquinolin-4-yl)carbamate

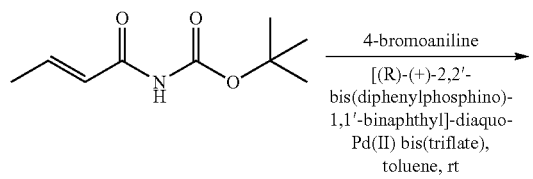

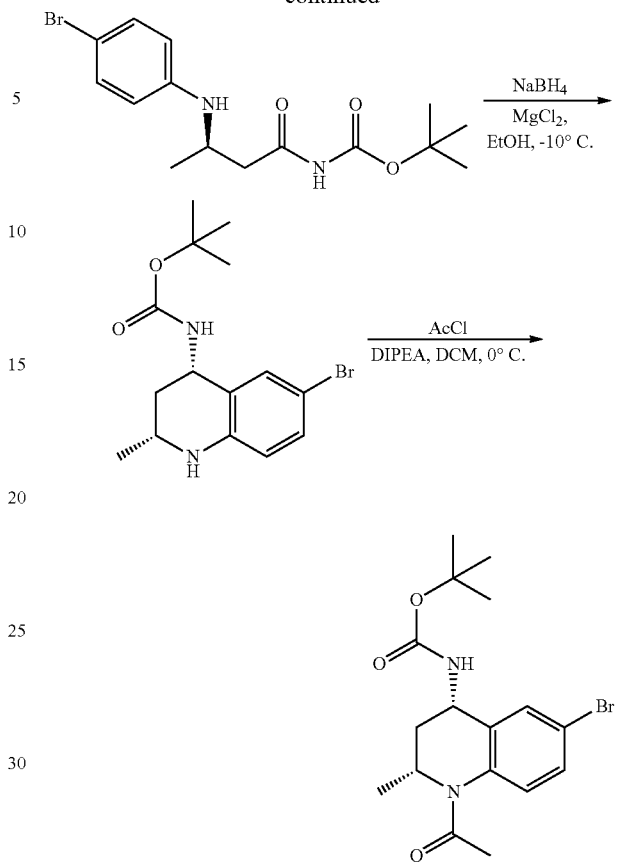

i. Preparation of Tert-butyl (R)-(3-((4-bromophenyl)amino)butanoyl)carbamate

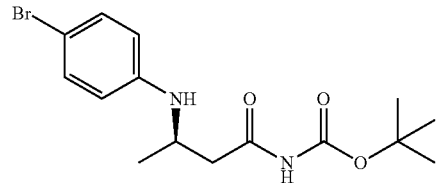 [SMILES: C[C@H](CC(=O)NC(=O)OC(C)(C)C)Nc1ccc(Br)cc1]

To a suspension of ene-imide (5.6 g, 30.0 mmol) and (S)-BINAP-Pd(OH)₂(OTf)₂ (0.85 g, 0.8 mmol) in anhydrous toluene (200 mL) at RT was added 4-bromo aniline (3.4 g, 20.0 mmol) dropwise. Resulting reaction was permitted to stir at RT for 48 h. Reaction was concentrated in vaccuo. Residual was purified via automated normal phase chromatography (25% EtOAc in hexanes) to provide the desired Michael adduct as an off-white solid (4.0 g, 56.0% yield). LCMS/UPLC (method: formate) retention time 1.21 min, [M+H]⁺=356.86. ¹H NMR (400 MHz, Acetone-d₆) δ 9.11 (s, 1H), 7.30-7.15 (m, 2H), 6.70-6.56 (m, 2H), 5.01 (d, J=9.0 Hz, 1H), 4.11-3.89 (m, 1H), 2.99 (dd, J=16.0, 5.5 Hz, 1H), 2.75 (dd, J=16.0, 7.3 Hz, 1H), 1.47 (s, 9H), 1.26 (d, J=6.4 Hz, 3H). ¹³C NMR (126 MHz, Acetone) δ 171.64, 150.82, 147.10, 131.63, 114.73, 107.15, 80.87, 45.17, 42.49, 27.26, 19.85.

ii. Preparation of Tert-butyl ((2R,4S)-6-bromo-2-methyl-1,2,3,4-tetrahydroquinolin-4-yl)carbamate

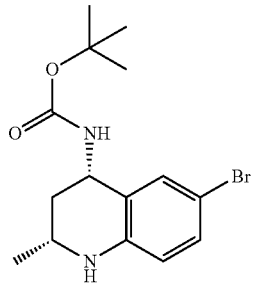 [SMILES: C[C@@H]1C[C@H](NC(=O)OC(C)(C)C)c2cc(Br)ccc2N1]

To a solution of amino imide (4.0 g, 11.2 mmol) in EtOH (20 mL) at −10° C. was added NaBH$_4$ (0.42 g, 11.2 mmol) in one portion, followed by an aqueous solution of MgCl$_2$.6H$_2$O (2.3 g, 11.2 mmol, dissolved in 5 mL water) added dropwise such that the internal temperature did not exceed −10° C. The resulting solution was permitted to stir at 0° C. for 1 h, followed by 1 h at RT. The reaction was quenched via addition of citric acid (5.4 g, 28.0 mmol) dissolved in aq 1M NH$_4$Cl (5 mL), followed by treatment of CH$_2$Cl$_2$ (20 mL). After 1 h of heterogeneous stirring, organic solution was collected, followed by aqueous extractions with CH$_2$Cl$_2$ (2×30 mL). Combined organics were washed with sat aq NaCl, dried over MgSO$_4$, filtered and concentrated. Crude product was purified via automated normal phase chromatography (22% EtOAc in hexanes) to provide cyclized amine as a white solid (1.0 g, 26% yield). LCMS/UPLC (method: formate) retention time 1.26 min, [M+H]$^+$= 341.08. $^1$H NMR (400 MHz, CDCl$_3$) δ 7.26 (d, J=1.1 Hz, 1H), 7.08 (dd, J=8.5, 0.9 Hz, 1H), 6.34 (dd, J=8.5, 0.9 Hz, 1H), 4.98 (m, J=5.4 Hz, 2H), 4.70 (d, J=9.5 Hz, 1H), 3.74 (s, 1H), 3.62-3.48 (m, 1H), 2.26 (ddd, J=12.6, 6.0, 2.3 Hz, 1H), 1.43 (q, J=11.7 Hz, 1H), 1.28 (dd, J=14.6, 6.3 Hz, 6H), 1.20 (d, J=6.2 Hz, 3H). $^{13}$C NMR (126 MHz, CDCl$_3$) δ 156.26, 143.96, 130.94, 129.44, 123.73, 115.67, 109.04, 68.49, 47.72, 46.74, 37.97, 22.20, 22.14.

iii. Preparation of Tert-butyl ((2R,4S)-1-acetyl-6-bromo-2-methyl-1,2,3,4-tetrahydroquinolin-4-yl)carbamate

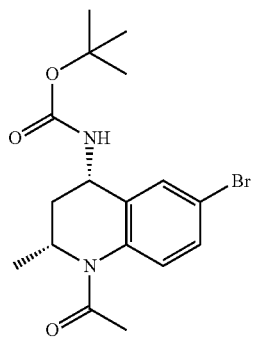 [SMILES: CC(=O)N1c2ccc(Br)cc2[C@@H](NC(=O)OC(C)(C)C)C[C@H]1C]

To a solution of amine (1.0 g, 2.9 mmol) in CH$_2$Cl$_2$ (10 mL) and DIPEA (2.37 mL) under nitrogen at RT was added dropwise acetyl chloride (0.575 mL, 7.33 mmol). Reaction was permitted to stir at RT for 4-17 h. Reaction was then treated with CH$_2$Cl$_2$ (20 mL) and sat aq. NaHCO$_3$ (20 mL). The phases were separated; aqueous solution was extracted with CH$_2$Cl$_2$ (2×20 mL). Combined organics were washed with sat. NaCl, dried over MgSO$_4$, filtered and concentrated. Residual product was purified via automated normal phase chromatography (29% EtOAc in hexanes) to provide amide product as a white solid (0.3 g, 26.7% yield). LCMS/UPLC (method: formate) retention time 1.18 min, [M+H]$^+$=383.11. $^1$H NMR (400 MHz, Methanol-d$_4$) δ 7.49 (dd, J=8.4, 2.2 Hz, 1H), 7.37 (s, 1H), 7.24 (d, J=8.4 Hz, 1H), 4.95 (dq, J=12.5, 6.1 Hz, 1H), 4.81 (d, J=7.2 Hz, 1H), 4.48 (dd, J=12.5, 4.1 Hz, 1H), 2.55 (ddd, J=12.8, 8.7, 4.4 Hz, 1H), 2.15 (s, 3H), 1.39-1.21 (m, 7H), 1.13 (d, J=6.4 Hz, 3H). $^{13}$C NMR (126 MHz, Acetone) δ 169.22, 155.78, 138.21, 133.75, 128.64, 126.59, 124.46, 118.09, 67.08, 46.79, 46.62, 38.39, 20.07, 19.74, 18.76.

d. General Procedure for Parallel Suzuki Couplings (Method A)

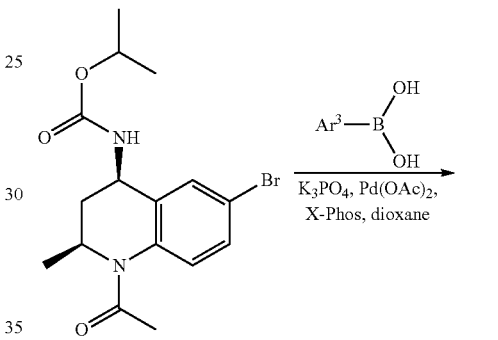

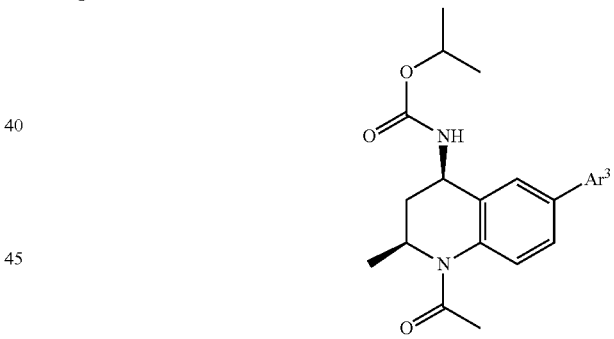

To a reaction vessel under nitrogen was added aryl bromide (37 mgs, 0.10 mmol), boronic acid (20-40 mgs, 0.30 mmol), followed by K$_3$PO$_4$ (69 mgs, 0.50 mmol). The vessel(s) were then sealed under inert atmosphere. Vessels were treated with anhydrous dioxane (0.2 mL). In a separate microwave vial under nitrogen was added Pd(OAc)$_2$ (0.0025 mmol/# of reactions) and X-Phos (0.0075 mmol/# of reactions). Upon sealing, the vessel is evacuated and charged with nitrogen. After treatment with anhydrous dioxanes (0.3 mL/# of reactions), the solution turned orange. Vial was then treated with degassed water (0.18 μL/# of reactions), resulting in a vibrant red solution. Solution was heated to 110° C. for 90 seconds prior to use. A solution of the activated catalyst (0.30 mL) was transferred to each reaction; resulting solutions were heated to 60° C. overnight. Reactions were quenched via addition of EtOAc (0.5 mL). Reactions were treated with Si—SH (0.025 g) and Si-Diol (0.025 g) and permitted to stir at RT for 2 h. Suspensions were filtered through Celite® and concentrated. Crude products were purified via automated normal phase chromatography (EtOAc: hexane). Reactions can also be purified in an automated reverse phase (acetonitrile: 0.1% aqueous formic acid) manner as well (singular or parallel format). Masses and yields for each example are reported separately. The yields of the reported compounds vary from 30-89%.

i. Preparation of Isopropyl ((2S,4R)-6-(3-acetamidophenyl)-1-acetyl-2-methyl-1,2,3,4-tetrahydroquinolin-4-yl)carbamate

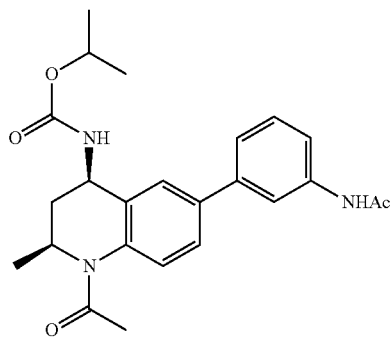 [SMILES: CC(=O)Nc1cccc(-c2ccc3c(c2)[C@H](NC(=O)OC(C)C)C[C@H](C)N3C(C)=O)c1]

68% yield. mp >250° C. LCMS/UPLC (method: formate) retention time 1.01 min, [M+H]$^+$=424.24. >95% UV & ELSD purity. $^1$H NMR (400 MHz, DMSO-d$_6$) δ 10.09 (s, 1H), 7.99 (s, 1H), 7.71 (d, J=8.6 Hz, 1H), 7.44 (dd, J=14.8, 6.4 Hz, 3H), 7.35 (d, J=7.6 Hz, 1H), 4.91 (p, J=6.2 Hz, 1H), 4.72 (d, J=6.2 Hz, 1H), 4.48 (s, 1H), 2.57-2.44 (m, 1H), 2.14 (d, J=11.4 Hz, 6H), 1.27 (dt, J=26.4, 7.6 Hz, 7H), 1.12 (d, J=6.2 Hz, 3H). $^{13}$C NMR (126 MHz, DMSO) δ 170.80, 168.97, 168.85, 156.36, 140.86, 140.38, 137.63, 137.53, 136.03, 129.78, 126.94, 125.46, 121.73, 121.48, 118.57, 117.71, 67.70, 60.22, 47.44, 24.53, 23.19, 22.52, 21.81, 21.23, 14.55.

ii. Preparation of Isopropyl ((2S,4R)-1-acetyl-6-(3-aminophenyl)-2-methyl-1,2,3,4-tetrahydroquinolin-4-yl)carbamate

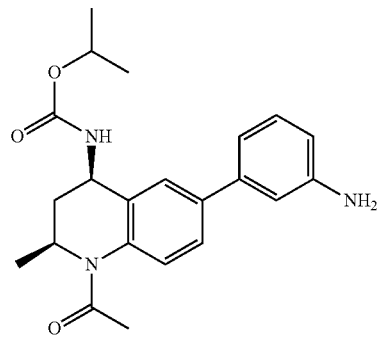 [SMILES: CC(=O)N1c2ccc(-c3cccc(N)c3)cc2[C@H](NC(=O)OC(C)C)C[C@@H]1C]

58% yield. LCMS/UPLC (method: formate) retention time 0.95 min, [M+H]$^+$=381.96. >95% UV & ELSD purity. $^1$H NMR (400 MHz, DMSO-d$_6$) δ 7.69 (d, J=8.7 Hz, 1H), 7.50 (d, J=8.2 Hz, 1H), 7.44-7.31 (m, 2H), 7.17 (t, J=7.8 Hz, 1H), 6.87 (s, 1H), 6.81 (d, J=7.6 Hz, 1H), 6.62 (d, J=7.9 Hz, 1H), 5.23 (s, 2H), 4.91 (p, J=6.2 Hz, 1H), 4.74 (m, 1H), 4.52 (m, 1H), 2.53 (m, 1H), 2.14 (s, 3H), 1.40-1.19 (m, 7H), 1.11 (d, J=6.2 Hz, 3H). $^{13}$C NMR (126 MHz, DMSO) δ 168.92, 156.34, 149.62, 141.09, 138.53, 137.29, 135.59, 129.89, 126.72, 125.22, 121.29, 114.63, 113.62, 112.39, 67.66, 47.43, 23.17, 22.56, 22.51, 21.81.

iii. Preparation of Isopropyl ((2S,4R)-1-acetyl-6-(3-methoxyphenyl)-2-methyl-1,2,3,4-tetrahydroquinolin-4-yl) carbamate

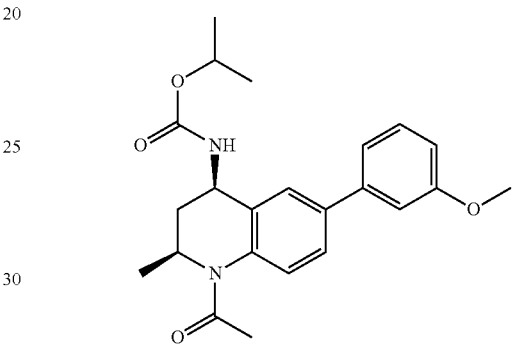

70% yield. LCMS/UPLC (method: formate) retention time 1.18 min, [M+H]$^+$=397.01. >95% UV & ELSD purity. $^1$H NMR (500 MHz, Chloroform-d) δ 7.48 (d, J=8.4 Hz, 1H), 7.45 (s, 1H), 7.37 (t, J=7.9 Hz, 1H), 7.17 (td, J=9.0, 7.6, 4.4 Hz, 2H), 7.10 (t, J=2.1 Hz, 1H), 6.92 (dd, J=8.2, 2.6 Hz, 1H), 5.00 (p, J=6.2 Hz, 1H), 4.89 (d, J=9.1 Hz, 1H), 4.75 (dd, J=24.1, 10.2 Hz, 2H), 3.87 (s, 3H), 2.62 (ddd, J=12.5, 8.5, 4.4 Hz, 1H), 2.17 (s, 3H), 1.30 (dd, J=12.3, 6.2 Hz, 7H), 1.18 (d, J=6.4 Hz, 3H). $^{13}$C NMR (126 MHz, MeOD) δ 165.54, 156.06, 151.83, 138.05, 134.97, 125.95, 122.37, 122.06, 117.52, 115.64, 109.01, 108.84, 64.85, 51.40, 43.32, 43.17, 37.14, 19.08, 18.20, 17.33.

e. General Procedure for Suzuki Coupling (Method B)

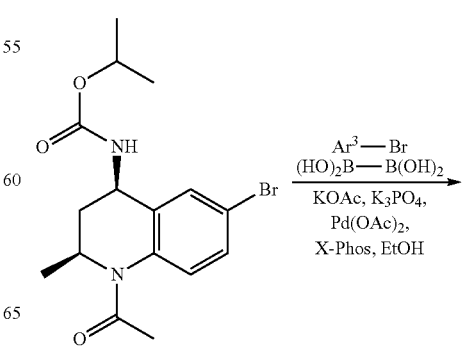

-continued

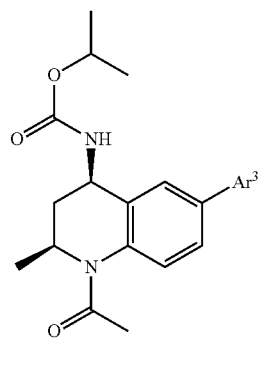

Alternatively, a Suzuki coupling can be performed as described by Molander, et al. (2015) *Tetrahedron* 71: 5758-5764. To a reaction vessel under nitrogen was added aryl bromide (74 mgs, 0.20 mmol), hypodiboric acid (54 mgs, 0.60 mmol), followed by KOAc (59 mgs, 0.60 mmol), XPhos Palladacycle G2, CAS number: 1310584-14-5 purchased from Strem, (18 mgs, 0.02 mmol) and XPhos, CAS number: 564483-18-7 purchased from Strem, (11 mgs, 0.02 mmol). The vessel(s) were then sealed under inert atmosphere. Vessels were treated with anhydrous EtOH (2 mL). Solution was heated to 80° C. for 2 h. A solution of the $Ar^3$ bromide (0.20 mmol) in 1 mL EtOH was transferred to each reaction, followed by a solution $K_3PO_4$ (127 mg, 0.6 mmol) in 1 mL water. The resulting solutions were heated to 80° C. overnight. Reactions were concentrated. Residual aqueous solution was extracted with EtOAc 3×. Organic extracts were concentrated. Crude products were purified via automated normal phase chromatography (EtOAc: hexane). Reactions can also be purified in an automated reverse phase (acetonitrile: 0.1% aqueous formic acid) manner as well (singular or parallel format). Masses and yields for each example are reported separately.

i. Preparation of Tert-butyl ((2S,4R)-1-acetyl-2-methyl-6-(1-tosyl-1H-pyrazol-3-yl)-1,2,3,4-tetrahydroquinolin-4-yl)carbamate

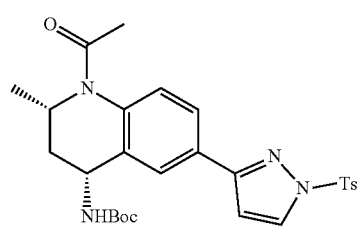 [SMILES: CC(=O)N1c2ccc(-c3ccn(S(=O)(=O)c4ccc(C)cc4)n3)cc2[C@H](NC(=O)OC(C)(C)C)C[C@@H]1C]

$^1$H NMR (400 MHz, Acetone-$d_6$) δ 8.40 (d, J=2.8 Hz, 1H), 7.95 (d, J=8.4 Hz, 2H), 7.86-7.72 (m, 2H), 7.49 (d, J=8.0 Hz, 2H), 7.37 (d, J=8.1 Hz, 1H), 6.99 (d, J=2.8 Hz, 1H), 6.52 (d, J=8.8 Hz, 1H), 4.92-4.70 (m, 1H), 4.61-4.40 (m, 1H), 2.59 (ddd, J=12.8, 8.5, 4.2 Hz, 1H), 2.44 (s, 3H), 2.10 (s, 6H), 1.62-1.31 (m, 10H), 1.11 (d, J=6.3 Hz, 3H). $^{13}$C NMR (101 MHz, Acetone) 169.18, 157.27, 156.44, 147.13, 138.78, 138.59, 135.31, 134.37, 131.08, 129.47, 128.78, 127.21, 125.79, 121.46, 107.51, 79.34, 48.21, 47.93, 41.08, 28.71, 22.97, 21.70, 21.57.

ii. Preparation of Tert-butyl ((2S,4R)-1-acetyl-6-bromo-2-methyl-1,2,3,4-tetrahydroquinolin-4-yl)carbamate

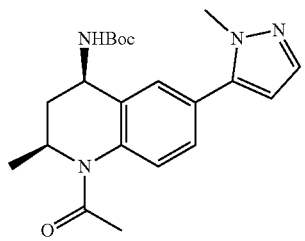

43% yield. $^1$H NMR (400 MHz, Acetone-$d_6$) δ 7.39-7.27 (m, 3H), 7.24 (s, 1H), 6.41 (d, J=8.5 Hz, 1H), 6.20 (d, J=1.8 Hz, 1H), 4.68 (h, J=6.3 Hz, 1H), 4.41 (ddd, J=12.7, 8.8, 4.3 Hz, 1H), 3.75 (s, 3H), 2.46 (ddd, J=12.8, 8.7, 4.4 Hz, 1H), 2.00 (s, 3H), 1.39-1.19 (m, 10H), 1.00 (d, J=6.3 Hz, 3H). $^{13}$C NMR (126 MHz, Acetone) δ 168.34, 155.53, 142.70, 137.92, 137.69, 136.75, 126.93, 126.30, 123.04, 105.48, 78.43, 47.39, 47.01, 40.26, 37.05, 27.71, 24.36, 22.09, 20.84.

ii. Preparation of Tert-butyl ((2S,4R)-1-acetyl-2-methyl-6-(1-methyl-1H-pyrazol-3-yl)-1,2,3,4-tetrahydroquinolin-4-yl)carbamate

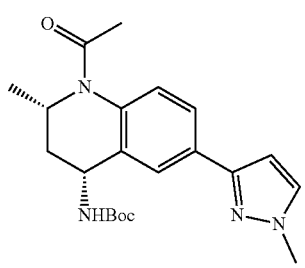 [SMILES: CC(=O)N1c2ccc(-c3ccn(C)n3)cc2[C@H](NC(=O)OC(C)(C)C)C[C@@H]1C]

61% yield. $^1$H NMR (400 MHz, Acetone-$d_6$) δ 7.65 (s, 1H), 7.59 (dd, J=8.1, 1.4 Hz, 1H), 7.49 (d, J=2.2 Hz, 1H), 7.15 (d, J=8.1 Hz, 1H), 6.46 (d, J=2.2 Hz, 1H), 6.34 (d, J=9.0 Hz, 1H), 4.68 (h, J=6.4 Hz, 1H), 4.49-4.33 (m, 1H), 3.80 (s, 3H), 2.44 (ddt, J=12.7, 8.7, 3.7 Hz, 1H), 1.96 (d, J=1.3 Hz, 3H), 1.36 (d, J=7.6 Hz, 9H), 1.20-1.10 (m, 1H), 0.97 (d, J=6.3 Hz, 3H). $^{13}$C NMR (101 MHz, Acetone) δ 169.15, 156.48, 151.22, 138.36, 136.62, 132.57, 132.26, 126.97, 124.46, 120.58, 103.01, 79.23, 47.98, 41.31, 39.11, 28.68, 22.94, 21.67.

iv. Preparation of Tert-butyl ((2S,4R)-1-acetyl-6-(1H-imidazol-4-yl)-2-methyl-1,2,3,4-tetrahydroquinolin-4-yl)carbamate

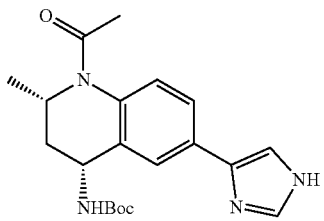 [SMILES: CC(=O)N1c2ccc(-c3c[nH]cn3)cc2[C@H](NC(=O)OC(C)(C)C)C[C@@H]1C]

43% yield. 1H NMR (400 MHz, Acetone-d6) δ 7.70-7.53 (m, 3H), 7.37 (s, 1H), 7.12 (d, J=8.2 Hz, 1H), 6.35 (d, J=8.7 Hz, 1H), 4.78-4.56 (m, 1H), 4.40 (s, 1H), 2.42 (ddd, J=12.7, 8.7, 4.3 Hz, 1H), 1.83 (s, 3H), 1.34 (d, J=6.8 Hz, 11H), 1.20 (ddd, J=28.3, 15.0, 5.8 Hz, 3H), 0.95 (d, J=6.3 Hz, 4H). $^{13}$C NMR (101 MHz, Acetone) δ 172.36, 169.30, 156.48, 138.34, 136.78, 135.78, 127.03, 123.90, 120.13, 79.24, 48.00, 41.45, 28.70, 22.95, 21.65, 20.75.

v. Preparation of Tert-butyl ((2S,4R)-1-acetyl-2-methyl-6-(1-methyl-1H-imidazol-4-yl)-1,2,3,4-tetrahydroquinolin-4-yl)carbamate

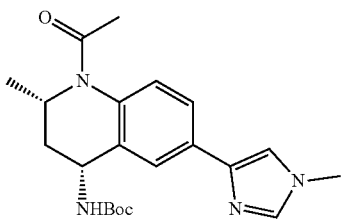

23% yield. $^1$H NMR (400 MHz, Acetone-d$_6$) δ 9.21 (s, 1H), 8.42-8.27 (m, 1H), 7.92 (s, 1H), 7.88-7.75 (m, 1H), 7.66-7.40 (m, 6H), 7.26 (dt, J=14.0, 8.0 Hz, 3H), 7.13 (d, J=8.1 Hz, 1H), 6.69 (d, J=7.4 Hz, 1H), 5.85 (d, J=7.2 Hz, 1H), 4.75 (m, 1H), 4.44 (s, 1H), 2.89 (td, J=8.5, 4.2 Hz, 1H), 2.21 (s, 3H), 2.05 (s, 3H), 1.77-1.53 (m, 1H), 1.20 (d, J=6.3 Hz, 3H). $^{13}$C NMR (126 MHz, Acetone) δ 168.44, 168.01, 143.36, 141.19, 140.11, 138.19, 138.05, 136.54, 134.69, 129.08, 128.33, 126.64, 125.64, 125.32, 124.38, 123.63, 122.35, 121.50, 121.23, 117.90, 117.41, 117.08, 105.24, 50.32, 47.43, 40.93, 23.40, 22.28, 20.81.

f. Synthesis of N-(3-(1-acetyl-4-amino-2-methyl-1,2,3,4-tetrahydroquinolin-6-yl)phenyl)acetamide

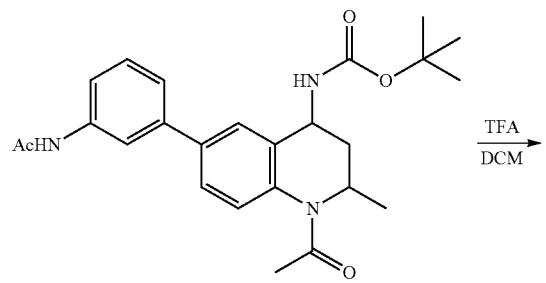

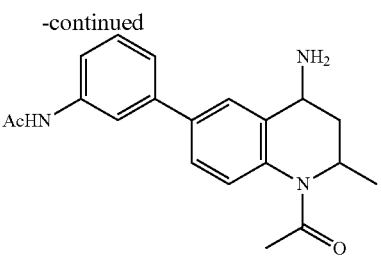

In a 100 mL round bottom flask under nitrogen, tert-butyl (6-(3-acetamidophenyl)-1-acetyl-2-methyl-1,2,3,4-tetrahydroquinolin-4-yl)carbamate (2.56 g, 5.87 mmol) was dissolved in 15 mL of DCM at 25° C. TFA (4.47 mL, 58.7 mmol, 10 eq) was added and the reaction stirred overnight. The reaction was diluted with 20 mL of DCM and washed with 1M HCl (2×25 mL). The aqueous layers were combined and neutralized with solid K$_2$CO$_3$. The aqueous layer was then extracted with EtOAc (3×30 mL). The combined organics were washed with saturated NaCl, dried with MgSO$_4$, filtered, and concentrated. The residue was dried to give N-(3-(1-acetyl-4-amino-2-methyl-1,2,3,4-tetrahydroquinolin-6-yl)phenyl)acetamide (1.90 g, 5.62 mmol) as a yellow oil in 96% yield. LCMS/UPLC (method: formate) retention time 1.13 min, [M+H]$^+$=339.36, [M+H-NH$_2$]$^+$= 320.79. >95% UV & ELSD purity. $^1$H NMR (400 MHz, Methanol-d$_4$) δ 7.93 (t, J=1.8 Hz, 1H), 7.75 (dd, J=2.1, 1.1 Hz, 1H), 7.60 (ddd, J=8.2, 2.2, 0.8 Hz, 1H), 7.53 (dt, J=7.5, 1.8 Hz, 1H), 7.49-7.38 (m, 2H), 7.35 (d, J=8.1 Hz, 1H), 4.86-4.76 (m, 1H), 3.81 (dd, J=12.2, 4.2 Hz, 1H), 2.69-2.53 (m, 1H), 2.17 (d, J=3.9 Hz, 6H), 1.37-1.02 (m, 4H). $^{13}$C NMR (126 MHz, MeOD) δ 170.62, 170.34, 141.11, 139.31, 139.08, 135.10, 128.96, 126.19, 125.08, 122.38, 120.83, 118.82, 118.31, 42.39, 22.48, 21.43, 20.08.

g. General Procedure for Parallel Buchwald Couplings (Method C)

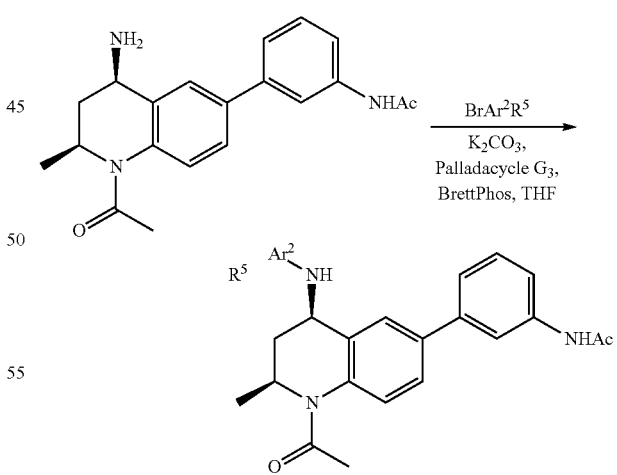

To a previously flame-dried microwave vessel purged with nitrogen was added aryl bromide (0.15 mmol), K$_2$CO$_3$ (0.5 mmol), Brettphos palladacycle G3 (0.01 mmol), BrettPhos (0.01 mmol) followed by amine (0.1 mmol) and THF (0.2 mL). Reaction vessels were sealed and heated to 100° C. for 5-17 h. Reactions were then permitted to return to RT. In a single reaction format, crude products were diluted in EtOAc, applied to a SNAP column and purified via automated normal phase chromatography (EtOAc: hexane). In a parallel format, the crude concentrated reactions were diluted in DMSO (1 mL) and were purified in an automated reverse phase (acetonitrile: 0.1% aqueous formic acid). Yields are reported for each example.

i. Preparation of Methyl 4-(((2S,4R)-6-(3-acetamidophenyl)-1-acetyl-2-methyl-1,2,3,4-tetrahydroquinolin-4-yl) amino) benzoate

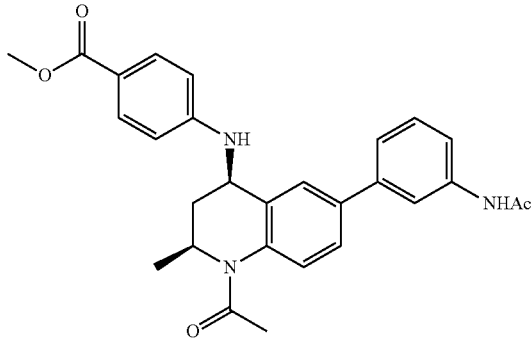 [SMILES: COC(=O)c1ccc(N[C@@H]2C[C@H](C)N(C(C)=O)c3ccc(-c4cccc(NC(C)=O)c4)cc32)cc1]

mp 157° C. 23% yield. LCMS/UPLC (method: formate) retention time 1.07 min, [M+H]$^+$=472.08, [M+H-OCH$_3$]$^+$=440.19. >95% UV & ELSD purity. HRMS [M+H]+=472.2236 (calc.), found: 472.2233. SFC (method: methanol: liquid CO$_2$) retention time 8.19 min (minor enantiomer, 4.0% UV), 9.22 min (major enantiomer, 96.0% UV). [α]$_D$=381.0° C., (temp.=26.4° C., 3.4 mg dissolved in 3 mL EtOH, cell length=0.5 dm). CHN analysis (mono-hydrate): theoretical: C, 68.69; H, 6.38; N, 8.58. found: C, 68.52; H, 6.40, N, 8.6. $^1$H NMR (400 MHz, Methanol-d$_4$) δ 7.74 (d, J=8.6 Hz, 2H), 7.65 (s, 1H), 7.49 (d, J=8.4 Hz, 1H), 7.44-7.35 (m, 2H), 7.30 (d, J=7.7 Hz, 1H), 7.24 (t, J=7.9 Hz, 1H), 7.13 (d, J=7.7 Hz, 1H), 6.65 (d, J=8.6 Hz, 2H), 4.81 (m, 1H) 4.40-4.24 (m, 1H), 3.74 (s, 3H), 2.72-2.56 (m, 1H), 2.17 (s, 3H), 2.04 (s, 3H), 1.42-1.25 (m, 1H), 1.12 (d, J=6.3 Hz, 3H). $^{13}$C NMR (126 MHz, MeOD) δ 170.74, 170.33, 167.82, 152.55, 141.00, 139.01, 131.22, 128.94, 126.49, 125.40, 122.22, 122.00, 118.87, 118.16, 117.37, 111.44, 50.59, 48.89, 48.21, 40.14, 22.41, 21.58, 20.03.

ii. Preparation of Methyl 4-(((2R,4S)-6-(3-acetamidophenyl)-1-acetyl-2-methyl-1,2,3,4-tetrahydroquinolin-4-yl)amino)benzoate

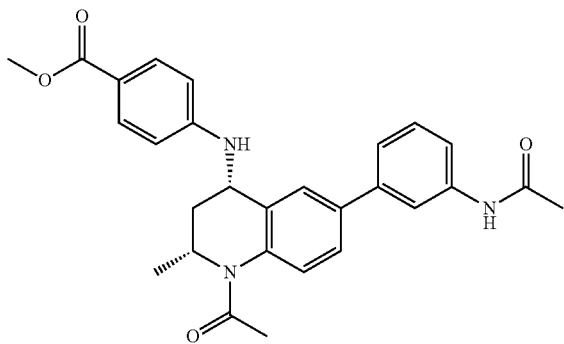 [SMILES: COC(=O)c1ccc(N[C@H]2C[C@@H](C)N(C(C)=O)c3ccc(-c4cccc(NC(C)=O)c4)cc32)cc1]

22% yield. LCMS/UPLC (method: formate) retention time 1.07 min, [M+H]$^+$=472.08, [M+H-OCH$_3$]$^+$=440.19. >95% UV & ELSD purity. [α]$_D$=−367.3° C., (temp.=26.5° C., 2.2 mg dissolved in 2 mL EtOH, cell length=0.5 dm). $^1$H NMR (400 MHz, Acetone-d$_6$) δ 9.15 (s, 1H), 7.91 (s, 1H), 7.83-7.69 (m, 2H), 7.57-7.43 (m, 3H), 7.39 (d, J=8.1 Hz, 1H), 7.26 (t, J=7.9 Hz, 1H), 7.15 (d, J=8.1 Hz, 1H), 6.86-6.70 (m, 2H), 6.14 (d, J=7.8 Hz, 1H), 4.82 (h, J=6.4 Hz, 1H), 4.52 (ddd, J=12.0, 7.9, 4.1 Hz, 1H), 3.73 (s, 3H), 2.72 (ddd, J=12.6, 8.6, 4.2 Hz, 1H), 2.12 (s, 3H), 1.37 (td, J=12.1, 9.1 Hz, 1H), 1.11 (d, J=6.3 Hz, 3H). $^{13}$C NMR (126 MHz, Acetone) δ 168.39, 168.04, 166.36, 152.33, 141.08, 140.18, 138.09, 137.59, 136.47, 131.25, 129.14, 126.66, 125.42, 121.93, 121.50, 118.12, 117.42, 111.90, 50.62, 49.21, 48.88, 40.70, 23.41, 22.24, 20.70.

iii. Preparation of N-(4-(((2S,4R)-6-(3-acetamidophenyl)-1-acetyl-2-methyl-1,2,3,4-tetrahydroquinolin-4-yl) amino) phenyl) acetamide

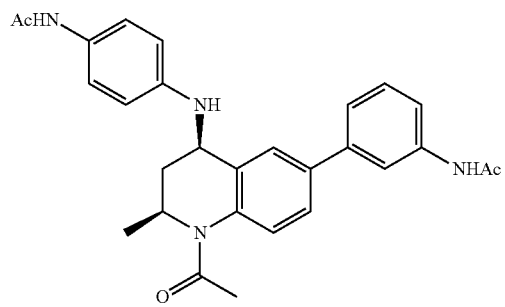 [SMILES: CC(=O)Nc1ccc(N[C@@H]2C[C@H](C)N(C(C)=O)c3ccc(-c4cccc(NC(C)=O)c4)cc32)cc1]

9% yield. LCMS/UPLC (method: formate) retention time 0.95 min, [M+H]$^+$=471.18, [M+H-NHPhCO$_2$CH$_3$]$^+$=320.88. >95% UV & ELSD purity. HRMS [M+H]$^+$=471.2396 (calc.), found: 471.2406. $^1$H NMR (400 MHz, Methanol-d$_4$) δ 7.73 (t, J=1.9 Hz, 1H), 7.62-7.49 (m, 3H), 7.40-7.18 (m, 5H), 6.78-6.65 (m, 2H), 4.81 (m, 1H), 4.25 (dd, J=12.2, 4.1 Hz, 1H), 2.70 (ddd, J=12.6, 8.6, 4.3 Hz, 1H), 2.25 (s, 3H), 2.14 (s, 3H), 2.09 (s, 3H), 1.34 (q, J=10.9, 10.3 Hz, 2H), 1.19 (d, J=6.3 Hz, 3H). $^{13}$C NMR (126 MHz, DMSO) δ 169.06, 158.38, 158.14, 144.77, 140.96, 140.34, 138.96, 137.55, 136.42, 129.76, 126.93, 125.28, 122.30, 121.67, 121.31, 118.92, 118.43, 117.55, 116.54, 113.15, 49.72, 47.63, 40.83, 24.52, 24.17, 23.42, 21.79.

iv. Preparation of Methyl 3-(((2S,4R)-6-(3-acetamidophenyl)-1-acetyl-2-methyl-1,2,3,4-tetrahydroquinolin-4-yl)amino) benzoate

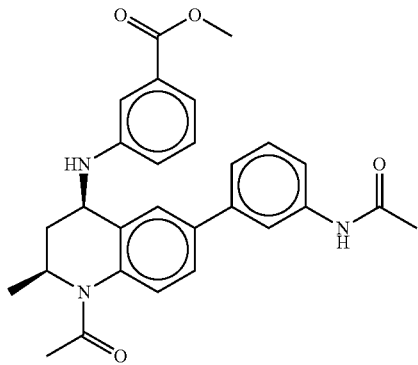

35% yield. LCMS/UPLC (method: formate) retention time 1.09 min, [M+H]$^+$=472.41, [M+H-NHPhCO$_2$CH$_3$]$^+$= 320.96. >95% UV & ELSD purity. HRMS [M+H]$^+$= 472.2236 (calc.), found: 472.2240. $^1$H NMR (400 MHz, Methanol-d$_4$) δ 7.75 (s, 1H), 7.64-7.45 (m, 3H), 7.45-7.18 (m, 6H), 6.96 (ddd, J=8.1, 2.6, 1.1 Hz, 1H), 4.81 (m, 1H), 4.33 (dd, J=12.2, 4.1 Hz, 1H), 3.87 (s, 3H), 2.73 (m, 1H), 2.26 (s, 3H), 2.13 (s, 3H), 1.38 (q, J=11.8 Hz, 1H), 1.20 (d, J=6.3 Hz, 3H). $^{13}$C NMR (126 MHz, MeOD) δ 170.75, 170.33, 167.83, 148.38, 141.06, 139.00, 138.84, 130.74, 128.98, 126.43, 125.27, 122.24, 122.13, 118.84, 118.16, 117.76, 117.24, 113.09, 51.11, 49.32, 40.25, 39.01, 22.42, 21.59, 20.05.

v. Preparation of N-(3-((2S,4R)-1-acetyl-4-((2-methoxyphenyl)amino)-2-methyl-1,2,3,4-tetrahydroquinolin-6-yl) phenyl) acetamide

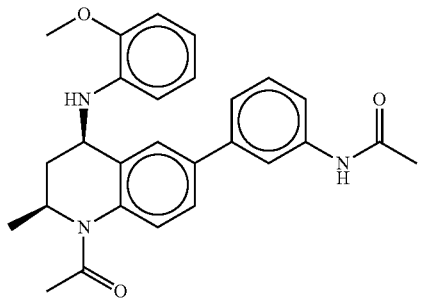

52% yield. LCMS/UPLC (method: formate) retention time 1.13 min, [M+H]$^+$=444.28, [M+H-NHPhOCH$_3$]$^+$= 320.88. >95% UV & ELSD purity. HRMS [M+H]$^+$= 444.2287 (calc.), found: 444.2291. $^1$H NMR (400 MHz, Methanol-d$_4$) δ 7.73 (t, J=1.9 Hz, 1H), 7.62-7.48 (m, 3H), 7.44-7.27 (m, 2H), 7.26-7.15 (m, 1H), 6.91 (dd, J=8.0, 1.4 Hz, 1H), 6.80 (td, J=7.7, 1.4 Hz, 1H), 6.69 (td, J=7.7, 1.5 Hz, 1H), 6.62 (dd, J=7.9, 1.6 Hz, 1H), 4.81 (m, 1H), 4.29 (dd, J=12.2, 4.1 Hz, 1H), 3.92 (s, 3H), 2.77-2.69 (m, 1H), 2.24 (s, 3H), 2.14 (s, 3H), 1.48-1.34 (m, 1H), 1.20 (d, J=6.3 Hz, 3H). $^{13}$C NMR (126 MHz, MeOD) δ 170.71, 170.32, 146.98, 141.11, 139.01, 137.20, 132.83, 128.90, 128.38, 126.29, 125.18, 122.25, 122.17, 120.93, 118.82, 118.15, 117.07, 110.90, 109.57, 54.68, 49.76, 40.48, 39.01, 22.43, 21.56, 20.03.

vi. Preparation of N-(3-((2S,4R)-1-acetyl-4-((4-chlorophenyl)amino)-2-methyl-1,2,3,4-tetrahydroquinolin-6-yl) phenyl) acetamide

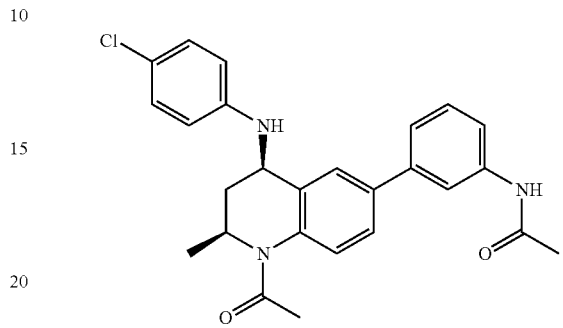

28% yield. LCMS/UPLC (method: formate) retention time 1.16 min, [M+H-NHPhCl]$^+$=320.96. >95% UV & ELSD purity. HRMS [M+H]$^+$=448.1792 (calc.), found: 448.1790. $^1$H NMR (400 MHz, Methanol-d$_4$) δ 7.76 (s, 1H), 7.62-7.44 (m, 3H), 7.42-7.18 (m, 3H), 7.18-6.99 (m, 2H), 6.83-6.58 (m, 2H), 4.81 (m, 1H), 4.24 (dd, J=12.2, 4.1 Hz, 1H), 2.69 (ddd, J=12.6, 8.6, 4.2 Hz, 1H), 2.24 (s, 3H), 2.14 (s, 3H), 1.44-1.24 (m, 1H), 1.19 (d, J=6.3 Hz, 3H). $^{13}$C NMR (126 MHz, MeOD) δ 170.70, 170.35, 146.94, 141.06, 139.00, 138.82, 128.94, 128.60, 126.36, 125.21, 122.25, 122.20, 121.17, 118.86, 118.20, 113.86, 49.48, 48.45, 40.22, 22.44, 21.57, 20.04.

vii. Preparation of N-(4-(((2S,4R)-6-(3-acetamidophenyl)-1-acetyl-2-methyl-1,2,3,4-tetrahydroquinolin-4-yl)amino) phenyl)-n-methyl acetamide

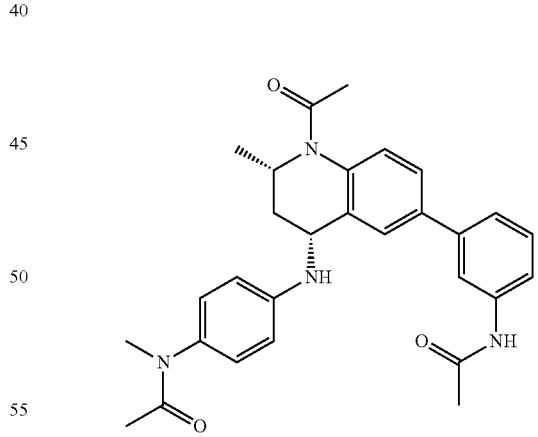

29% yield. LCMS/UPLC (method: formate) retention time 0.98 min, [M+H]$^+$=485.00. >95% UV & ELSD purity. HRMS [M+H]$^+$=485.2552 (calc.), found: 485.2560. $^1$H NMR (400 MHz, Methanol-d$_4$) δ 7.82 (s, 1H), 7.61-7.52 (m, 2H), 7.52-7.42 (m, 1H), 7.39 (d, J=8.1 Hz, 1H), 7.32 (t, J=7.9 Hz, 1H), 7.27-7.19 (m, 1H), 7.14-6.98 (m, 2H), 6.79 (d, J=8.8 Hz, 2H), 4.81 (m, 1H), 4.32 (dd, J=12.0, 4.1 Hz, 1H), 3.21 (s, 3H), 2.80-2.68 (m, 1H), 2.25 (s, 3H), 2.14 (s, 3H), 1.86 (s, 3H), 1.39 (q, J=11.5 Hz, 1H), 1.21 (d, J=6.3 Hz, 3H). $^{13}$C NMR (126 MHz, MeOD) δ 172.35, 170.72, 170.28, 148.04, 141.10, 139.04, 138.83, 133.45, 128.86, 127.39, 126.38, 125.22, 122.18, 118.77, 118.19, 113.25, 49.39, 40.22, 36.36, 22.44, 21.56, 20.76, 20.03.

viii. Preparation of N-(3-((2S,4R)-1-acetyl-2-methyl-4-((1-oxo-1,3-dihydroisobenzofuran-5-yl)amino)-1,2,3,4-tetrahydroquinolin-6-yl) phenyl) acetamide

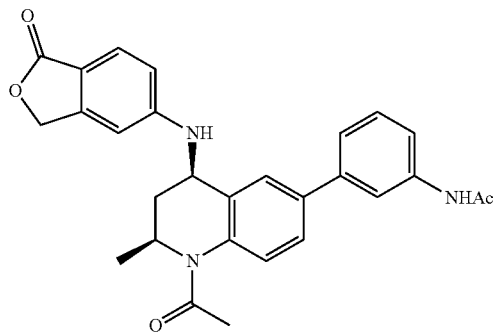 [SMILES: CC(=O)Nc1cccc(-c2ccc3c(c2)[C@H](Nc2ccc4c(c2)COC4=O)C[C@H](C)N3C(C)=O)c1]

13% yield. LCMS/UPLC (method: formate) retention time 0.97 min, [M+H]$^+$=470.28. >95% UV & ELSD purity. HRMS [M+H]$^+$=470.2080 (calc.), found: 470.2079. $^1$H NMR (400 MHz, Methanol-d$_4$) δ 7.78 (t, J=1.9 Hz, 1H), 7.68-7.54 (m, 2H), 7.50-7.38 (m, 3H), 7.33 (t, J=7.9 Hz, 1H), 7.23 (dt, J=7.8, 1.4 Hz, 1H), 6.94 (dd, J=8.5, 2.0 Hz, 1H), 6.75 (s, 1H), 5.22 (s, 2H), 4.82 (m, 1H), 4.48 (dd, J=12.2, 4.1 Hz, 1H), 2.75 (ddd, J=12.6, 8.6, 4.2 Hz, 1H), 2.26 (s, 3H), 2.13 (s, 3H), 1.58-1.35 (m, 1H), 1.22 (d, J=6.3 Hz, 3H). $^{13}$C NMR (126 MHz, MeOD) δ 173.06, 170.73, 170.28, 154.04, 150.91, 140.94, 139.06, 135.51, 128.94, 126.60, 126.14, 125.51, 122.13, 121.89, 118.79, 118.23, 114.58, 112.50, 102.70, 69.53, 49.05, 40.06, 22.41, 21.58, 20.02.

ix. Preparation of N-(3-((2S,4R)-1-acetyl-2-methyl-4-(quinolin-6-ylamino)-1,2,3,4-tetrahydroquinolin-6-yl)phenyl) acetamide

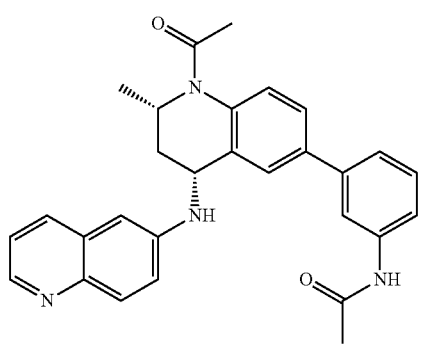 [SMILES: CC(=O)Nc1cccc(-c2ccc3c(c2)[C@H](Nc2ccc4ncccc4c2)C[C@H](C)N3C(C)=O)c1]

12% yield. LCMS/UPLC (method: formate) retention time 0.78 min, [M+H]$^+$=464.80. >95% UV & ELSD purity. HRMS [M+H]$^+$=465.2290 (calc.), found: 465.2279. $^1$H NMR (400 MHz, Methanol-d$_4$) δ 8.49 (dd, J=4.4, 1.6 Hz, 1H), 8.17 (s, 1H), 8.09 (dt, J=8.4, 1.2 Hz, 1H), 7.85 (d, J=9.1 Hz, 1H), 7.75 (t, J=1.9 Hz, 1H), 7.65-7.52 (m, 2H), 7.52-7.33 (m, 4H), 7.28 (t, J=7.9 Hz, 1H), 7.20 (dt, J=7.8, 1.3 Hz, 1H), 6.87 (d, J=2.6 Hz, 1H), 4.83 (s, 1H), 4.49 (dd, J=12.1, 4.1 Hz, 1H), 2.79 (ddd, J=12.5, 8.5, 4.1 Hz, 1H), 2.30 (s, 3H), 2.10 (s, 3H), 1.45 (q, J=12.0 Hz, 1H), 1.23 (d, J=6.3 Hz, 3H). $^{13}$C NMR (126 MHz, MeOD) 170.78, 170.29, 163.92, 146.86, 144.18, 140.99, 138.98, 138.87, 135.40, 130.77, 128.91, 127.67, 126.54, 125.36, 122.28, 122.17, 122.04, 121.19, 118.82, 118.14, 102.73, 49.29, 40.17, 22.39, 21.64, 20.05.

x. Preparation of N-(3-((2S,4R)-1-acetyl-4-(benzo[d][1,3]dioxol-5-ylamino)-2-methyl-1,2,3,4-tetrahydroquinolin-6-yl)phenyl)acetamide

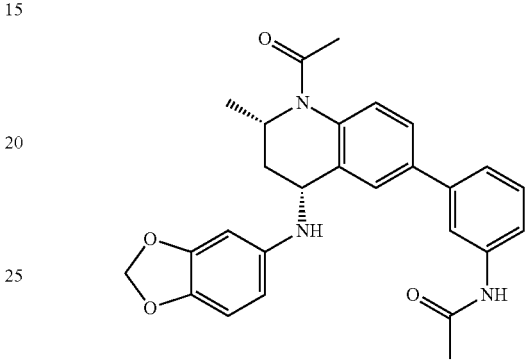

7% yield. LCMS/UPLC (method: formate) retention time 0.78 min, [M+H]$^+$=458.34, [M+H-NHPhO$_2$CH$_2$]$^+$=320.88. >95% UV & ELSD purity. $^1$H NMR (400 MHz, Methanol-d$_4$) δ 7.78 (t, J=1.9 Hz, 1H), 7.70-7.46 (m, 3H), 7.44-7.31 (m, 2H), 7.28 (dt, J=7.9, 1.3 Hz, 1H), 6.64 (d, J=8.3 Hz, 1H), 6.40 (d, J=2.3 Hz, 1H), 6.17 (dd, J=8.4, 2.3 Hz, 1H), 5.82 (q, J=1.2 Hz, 2H), 4.84 (s, 1H), 4.18 (dd, J=12.1, 4.1 Hz, 1H), 2.81-2.62 (m, 1H), 2.24 (s, 3H), 2.15 (s, 3H), 1.42-1.24 (m, 1H), 1.18 (d, J=6.4 Hz, 3H). $^{13}$C NMR (126 MHz, MeOD) 170.72, 170.35, 148.42, 143.74, 141.14, 139.58, 139.00, 128.92, 126.25, 125.06, 122.40, 122.28, 118.83, 118.20, 108.08, 104.44, 100.30, 95.94, 50.33, 48.21, 40.28, 39.01, 22.43, 21.54, 20.04.

xi. Preparation of Methyl 2-(((2S,4R)-6-(3-acetamidophenyl)-1-acetyl-2-methyl-1,2,3,4-tetrahydroquinolin-4-yl)amino) benzoate

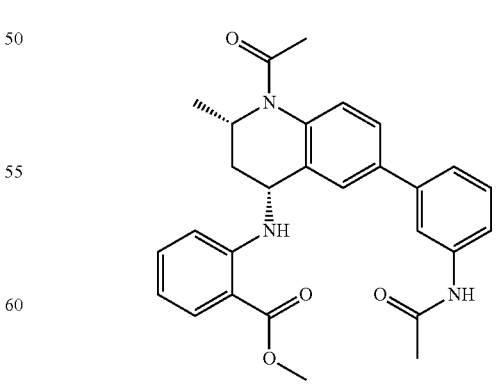

19% yield. LCMS/UPLC (method: formate) retention time 1.19 min, [M+H]$^+$=472.33, >95% UV & ELSD purity. $^1$H NMR (400 MHz, Methanol-d$_4$) δ 7.98 (dd, J=8.0, 1.7 Hz, 1H), 7.72 (t, J=1.9 Hz, 1H), 7.65-7.51 (m, 2H), 7.51-7.29 (m, 4H), 7.27-7.18 (m, 1H), 6.79 (d, J=8.5 Hz, 1H), 6.68 (ddd, J=8.1, 7.1, 1.0 Hz, 1H), 4.81 (s, 1H), 4.49 (dd, J 12.1, 4.2 Hz, 1H), 3.91 (s, 3H), 2.79 (ddd, J=12.5, 8.5, 4.2 Hz, 1H), 2.27 (s, 3H), 2.13 (s, 3H), 1.44 (q, J=11.4 Hz, 1H), 1.23 (d, J=6.4 Hz, 3H). $^{13}$C NMR (126 MHz, MeOD) δ 170.75, 170.32, 169.14, 150.36, 140.97, 139.05, 134.60, 131.33, 128.95, 126.62, 125.55, 122.22, 121.79, 118.92, 118.13, 115.31, 112.11, 110.11, 50.73, 48.92, 40.52, 22.40, 21.57, 19.94.

xii. Preparation of N-(3-((2S,4R)-1-acetyl-2-methyl-4-(pyrimidin-5-ylamino)-1,2,3,4-tetrahydroquinolin-6-yl)phenyl) acetamide

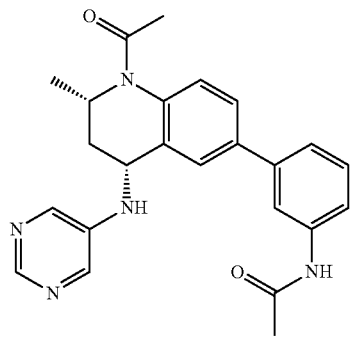 [SMILES: CC(=O)Nc1cccc(-c2ccc3c(c2)[C@H](Nc2cncnc2)C[C@H](C)N3C(C)=O)c1]

13% yield. LCMS/UPLC (method: formate) retention time 0.88 min, [M+H]$^+$=415.90, [M+H-NHC$_4$H$_3$N$_2$]$^+$= 320.96. >95% UV & ELSD purity. $^1$H NMR (400 MHz, Methanol-d$_4$) δ 8.47 (s, 1H), 8.28 (s, 2H), 7.81 (t, J=1.9 Hz, 1H), 7.61 (dd, J=8.2, 2.1 Hz, 1H), 7.56-7.39 (m, 3H), 7.35 (t, J=7.9 Hz, 1H), 7.31-7.20 (m, 1H), 4.85 (s, 1H), 4.57-4.33 (m, 1H), 2.75 (ddd, J=12.6, 8.5, 4.2 Hz, 1H), 2.26 (s, 3H), 2.14 (s, 3H), 1.42 (q, J=11.6 Hz, 1H), 1.21 (d, J=6.3 Hz, 3H). $^{13}$C NMR (126 MHz, MeOD) δ 170.72, 170.34, 148.42, 143.74, 141.14, 139.58, 139.03, 139.00, 128.92, 126.28, 126.25, 125.06, 122.40, 122.28, 118.83, 118.20, 108.08, 104.44, 100.30, 95.94, 50.33, 40.28, 39.01, 22.43, 21.54, 20.05.

xiii. Preparation of N-(3-((2S,4R)-1-acetyl-4-((4-acetylphenyl)amino)-2-methyl-1,2,3,4-tetrahydroquinolin-6-yl)phenyl) acetamide

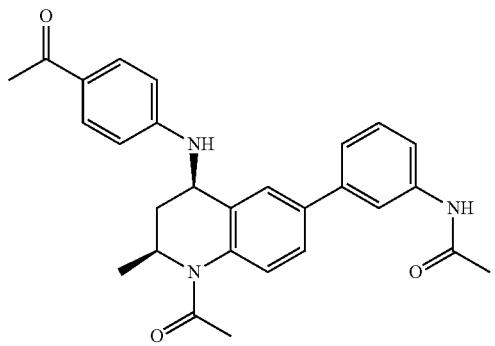 [SMILES: CC(=O)Nc1cccc(-c2ccc3c(c2)[C@H](Nc2ccc(C(C)=O)cc2)C[C@H](C)N3C(C)=O)c1]

21% yield. LCMS/UPLC (method: formate) retention time 1.02 min, [M+H]$^+$=456.13, [M+H-NHPhCOCH$_3$]$^+$= 321.12. >95% UV & ELSD purity. HRMS [M+H]$^+$= 456.2287 (calc.), found: 456.2294. $^1$H NMR (400 MHz, Methanol-d$_4$) δ 7.95-7.81 (m, 2H), 7.76 (t, J=2.0 Hz, 1H), 7.58 (dd, J=8.2, 2.2 Hz, 1H), 7.53-7.42 (m, 2H), 7.39 (d, J=8.2 Hz, 1H), 7.32 (t, J=7.9 Hz, 1H), 7.21 (dt, J=7.9, 1.3 Hz, 1H), 6.82-6.68 (m, 2H), 4.85 (m, 1H), 4.44 (dd, J=12.1, 4.1 Hz, 1H), 2.81-2.62 (m, 1H), 2.49 (s, 3H), 2.26 (s, 3H), 2.13 (s, 3H), 1.53-1.36 (m, 1H), 1.21 (d, J=6.3 Hz, 3H). $^{13}$C NMR (126 MHz, MeOD) δ 197.82, 170.73, 170.30, 152.99, 140.99, 139.03, 130.85, 128.93, 126.53, 125.79, 125.45, 122.20, 121.97, 118.83, 118.16, 111.40, 48.85, 40.10, 24.56, 22.43, 21.59, 20.03.

xiv. Preparation of N-(3-((2S,4R)-1-acetyl-4-((4-methoxyphenyl)amino)-2-methyl-1,2,3,4-tetrahydroquinolin-6-yl)phenyl)acetamide

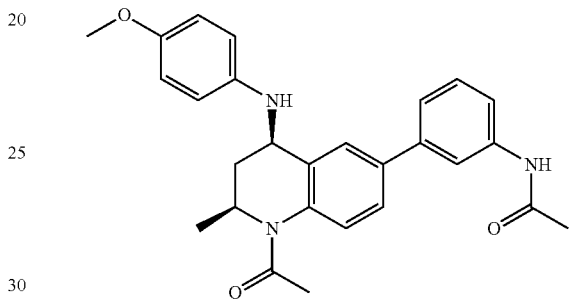

11% yield. LCMS/UPLC (method: formate) retention time 1.07 min, [M+H]$^+$=444.36, [M+H-NHPhOCH$_3$]$^+$= 320.79. >95% UV & ELSD purity. HRMS [M+H]$^+$= 444.2287 (calc.), found: 444.2278. $^1$H NMR (400 MHz, Methanol-d$_4$) δ 7.77 (t, J=1.9 Hz, 1H), 7.62 (dd, J=2.2, 1.1 Hz, 1H), 7.57 (dd, J=8.1, 2.2 Hz, 1H), 7.52 (ddd, J=8.0, 2.1, 1.1 Hz, 1H), 7.34 (t, J=8.0 Hz, 2H), 7.26 (dt, J=7.9, 1.3 Hz, 1H), 6.83-6.76 (m, 2H), 6.75-6.68 (m, 2H), 4.81 (m, 1H), 4.20 (dd, J=12.2, 4.0 Hz, 1H), 3.73 (s, 3H), 2.77-2.63 (m, 1H), 2.19 (m, 7H), 1.30 (q, J=11.9 Hz, 1H), 1.19 (d, J=6.3 Hz, 3H). $^{13}$C NMR (126 MHz, MeOD) δ 170.70, 170.33, 152.21, 142.11, 141.13, 139.20, 138.99, 138.77, 135.38, 128.90, 126.23, 125.01, 122.43, 122.27, 118.82, 118.20, 114.55, 114.31, 54.76, 50.32, 40.32, 22.43, 21.55, 20.03.

xv. Preparation of N-(3-((2S,4R)-1-acetyl-2-methyl-4-((2-(trifluoromethoxy)phenyl)amino)-1,2,3,4-tetrahydroquinolin-6-yl)phenyl) acetamide

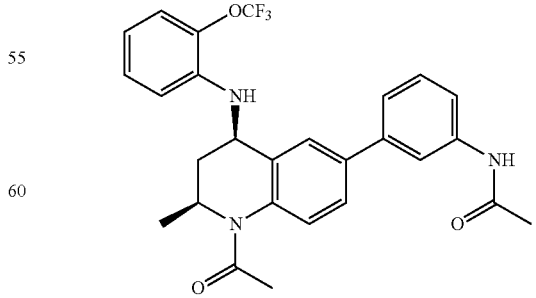

6% yield. LCMS/UPLC (method: formate) retention time 1.22 min, [M+H]$^+$=496.37, [M+H-NHPhOCF$_3$]$^+$=

321.04. >95% UV & ELSD purity. HRMS [M+H]⁺= 498.2004 (calc.), found: 498.2007. ¹H NMR (400 MHz, Methanol-$d_4$) δ 7.75 (t, J=2.0 Hz, 1H), 7.58 (dd, J=8.2, 2.1 Hz, 1H), 7.55-7.36 (m, 3H), 7.33 (t, J=7.9 Hz, 1H), 7.27-7.07 (m, 3H), 6.86-6.67 (m, 2H), 4.81 (m, 1H), 4.40 (dd, J=12.2, 4.2 Hz, 1H), 2.71 (ddd, J=12.6, 8.6, 4.2 Hz, 1H), 2.26 (s, 3H), 2.14 (s, 3H), 1.63-1.42 (m, 1H), 1.22 (d, J=6.3 Hz, 3H). ¹³C NMR (126 MHz, MeOD) δ 170.75, 170.33, 141.06, 140.25, 139.00, 138.88, 135.88, 128.90, 127.83, 126.44, 125.36, 122.18, 121.93, 121.13, 118.90, 118.24, 116.43, 112.79, 49.20, 40.14, 22.39, 21.57, 20.03.

xvi. Preparation of N-(3-((2S,4R)-1-acetyl-2-methyl-4-((4-(trifluoromethoxy)phenyl)amino)-1,2,3,4-tetrahydroquinolin-6-yl)phenyl) acetamide

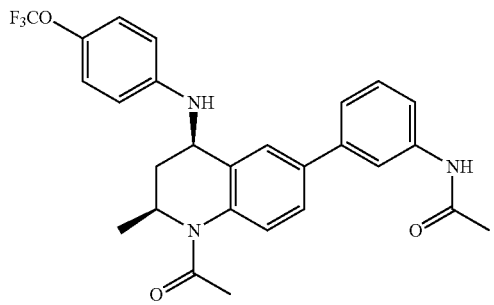 [SMILES: CC(=O)Nc1cccc(-c2ccc3c(c2)[C@H](Nc2ccc(OC(F)(F)F)cc2)C[C@H](C)N3C(C)=O)c1]

17% yield. LCMS/UPLC (method: formate) retention time 1.20 min, [M+H-NHPhOCF₃]⁺=320.96. >95% UV & ELSD purity. ¹H NMR (400 MHz, Methanol-$d_4$) δ 7.78 (t, J=1.9 Hz, 1H), 7.65-7.44 (m, 3H), 7.44-7.28 (m, 2H), 7.28-7.19 (m, 1H), 7.11-7.00 (m, 2H), 6.82-6.67 (m, 2H), 4.81 (m, 1H), 4.29 (dd, J=12.1, 4.1 Hz, 1H), 2.71 (ddd, J=12.6, 8.6, 4.2 Hz, 1H), 2.24 (s, 3H), 2.14 (s, 3H), 1.44-1.28 (m, 1H), 1.20 (d, J=6.3 Hz, 3H). ¹³C NMR (126 MHz, MeOD) δ 170.72, 170.34, 147.33, 141.06, 140.02, 138.99, 138.82, 138.39, 135.45, 128.91, 126.37, 125.22, 122.18, 121.95, 119.78, 118.87, 118.23, 113.02, 49.55, 40.22, 22.41, 21.57, 20.04.

xvii. Preparation of N-(3-((2S,4R)-1-acetyl-4-((3-methoxyphenyl)amino)-2-methyl-1,2,3,4-tetrahydroquinolin-6-yl)phenyl) acetamide

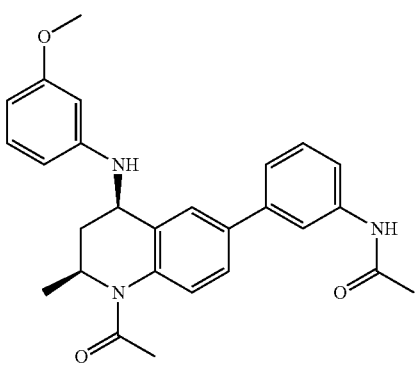 [SMILES: COc1cccc(N[C@@H]2C[C@H](C)N(C(C)=O)c3ccc(-c4cccc(NC(C)=O)c4)cc32)c1]

12% yield. LCMS/UPLC (method: formate) retention time 1.09 min, [M+H]⁺=444.11, [M+H-NHPhOCH₃]⁺=320.88. >95% UV & ELSD purity. HRMS [M+H]⁺= 444.2287 (calc.), found: 444.2293. ¹H NMR (400 MHz, Methanol-$d_4$) δ 7.76 (t, J=1.9 Hz, 1H), 7.66-7.46 (m, 3H), 7.41-7.19 (m, 3H), 7.05 (t, J=8.1 Hz, 1H), 6.41-6.21 (m, 2H), 4.81 (m, 1H), 4.26 (dd, J=12.2, 4.1 Hz, 1H), 3.74 (s, 3H), 2.70 (ddd, J=12.6, 8.6, 3.2 Hz, 1H), 2.24 (s, 3H), 2.14 (s, 3H), 1.44-1.25 (m, 1H), 1.19 (d, J=6.3 Hz, 3H). ¹³C NMR (126 MHz, MeOD) 170.73, 170.34, 160.92, 149.50, 141.12, 138.98, 138.78, 129.57, 129.55, 128.90, 126.28, 125.11, 122.38, 118.83, 118.17, 105.70, 102.33, 102.29, 98.91, 54.03, 49.49, 40.29, 22.42, 21.55, 20.04.

iviii. Preparation of N-(3-((2S,4R)-1-acetyl-2-methyl-4-((3-(trifluoromethoxy)phenyl)amino)-1,2,3,4-tetrahydroquinolin-6-yl)phenyl) acetamide

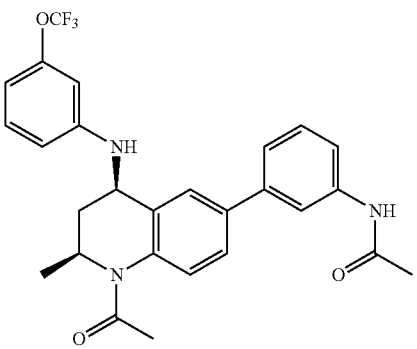 [SMILES: CC(=O)Nc1cccc(-c2ccc3c(c2)[C@H](Nc2cccc(OC(F)(F)F)c2)C[C@H](C)N3C(C)=O)c1]

15% yield. LCMS/UPLC (method: formate) retention time 1.20 min, [M+H-NHPhOCF₃]⁺=321.04. HRMS [M+H]⁺=498.2004 (calc.), found: 498.2002. >95% UV & ELSD purity. ¹H NMR (400 MHz, Methanol-$d_4$) δ 7.77 (t, J=1.9 Hz, 1H), 7.65-7.45 (m, 3H), 7.45-7.28 (m, 2H), 7.28-7.13 (m, 2H), 6.69 (ddd, J=8.3, 2.3, 0.8 Hz, 1H), 6.61 (td, J=2.3, 1.1 Hz, 1H), 6.53 (ddq, J=8.1, 2.2, 1.1 Hz, 1H), 4.82 (m, 1H), 4.31 (dd, J=12.2, 4.2 Hz, 1H), 2.71 (ddt, J=12.9, 8.5, 4.2 Hz, 1H), 2.25 (s, 3H), 2.14 (s, 3H), 1.37 (q, J=11.9 Hz, 1H), 1.20 (d, J=6.3 Hz, 3H). ¹³C NMR (126 MHz, MeOD) δ 170.75, 170.35, 150.38, 149.94, 141.04, 139.00, 138.85, 130.04, 128.91, 126.41, 125.28, 122.12, 121.58, 118.88, 118.19, 110.94, 108.26, 105.03, 49.32, 40.16, 22.41, 21.55, 20.04.

xix. Preparation of N-(3-((2S,4R)-1-acetyl-2-methyl-4-((4-((methylamino)methyl)phenyl)amino)-1,2,3,4-tetrahydroquinolin-6-yl) phenyl) acetamide

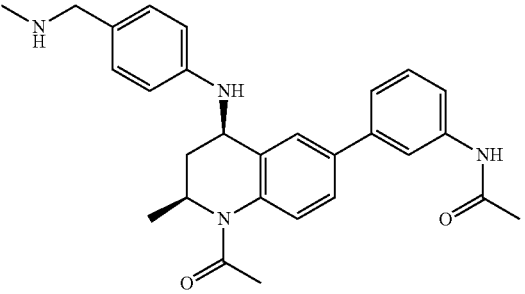 [SMILES: CNCc1ccc(N[C@@H]2C[C@H](C)N(C(C)=O)c3ccc(-c4cccc(NC(C)=O)c4)cc32)cc1]

5% yield. LCMS/UPLC (method: formate) retention time 0.77 min, [M+H]⁺=444.11, [M+H-NHCH₃]⁺=425.88. ¹H NMR (400 MHz, Methanol-d₄) δ 8.53 (s, 1H), 7.82 (t, J=2.0 Hz, 1H), 7.56 (dd, J=8.1, 2.1 Hz, 1H), 7.50-7.14 (m, 6H), 6.87-6.71 (m, 2H), 4.32 (dd, J=12.2, 4.1 Hz, 1H), 4.03 (s, 2H), 2.77-2.69 (m, 1H), 2.26 (s, 3H), 2.14 (s, 3H), 1.27 (m, 1H), 1.21 (d, J=6.4 Hz, 3H). ¹³C NMR (126 MHz, MeOD) δ 170.72, 170.30, 149.39, 141.18, 139.07, 130.77, 128.84, 125.34, 122.25, 122.21, 118.66, 118.10, 112.80, 52.33, 49.13, 40.18, 39.01, 31.22, 22.48, 21.54, 20.08.

xx. Preparation of Methyl 4-(((2S,4R)-6-(3-acetamidophenyl)-1-acetyl-2-methyl-1,2,3,4-tetrahydroquinolin-4-yl)amino)-3-methylbenzoate

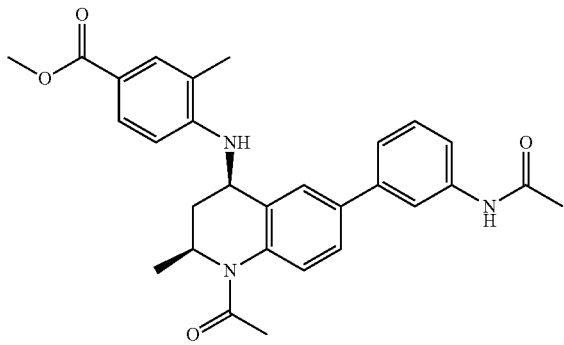 [SMILES: COC(=O)c1ccc(N[C@@H]2C[C@H](C)N(C(C)=O)c3ccc(-c4cccc(NC(C)=O)c4)cc32)c(C)c1]

24% yield. LCMS/UPLC (method: formate) retention time 1.14 min, [M+H]⁺=485.89. ¹H NMR (400 MHz, DMSO-d₆) δ 10.01 (s, 1H), 7.87 (s, 1H), 7.68 (d, J=1.4 Hz, 1H), 7.62 (dd, J=8.5, 2.0 Hz, 1H), 7.54-7.44 (m, 3H), 7.34 (t, J=7.9 Hz, 1H), 7.27 (s, 1H), 7.12 (d, J=7.9 Hz, 1H), 6.68 (d, J=8.8 Hz, 1H), 5.91 (d, J=8.2 Hz, 1H), 4.75 (m, 1H), 4.5 (m, 1H), 3.76 (s, 3H), 2.73-2.56 (m, 1H), 2.31 (s, 3H), 2.18 (s, 3H), 2.11 (s, 3H), 1.65-1.51 (m, 1H), 1.21-1.09 (m, 3H). ¹³C NMR (126 MHz, Acetone) δ 168.68, 168.39, 166.39, 150.18, 140.44, 139.91, 131.24, 129.36, 129.18, 126.68, 125.12, 121.51, 121.12, 117.95, 117.08, 116.64, 109.36, 51.26, 48.85, 30.72, 29.62, 24.10, 23.06, 21.42, 17.97.

xxi. Preparation of Methyl 4-(((2S,4R)-6-(3-acetamidophenyl)-1-acetyl-2-methyl-1,2,3,4-tetrahydroquinolin-4-yl)amino)-3-methoxybenzoate

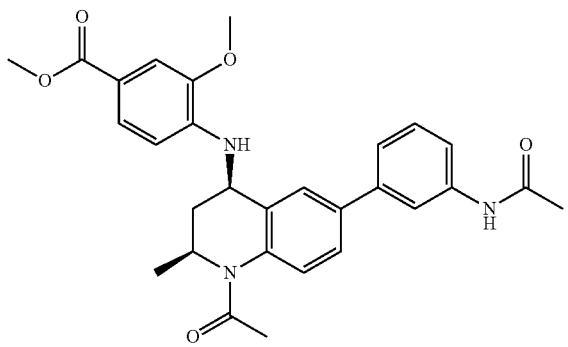 [SMILES: COC(=O)c1ccc(N[C@@H]2C[C@H](C)N(C(C)=O)c3ccc(-c4cccc(NC(C)=O)c4)cc32)c(OC)c1]

32% yield. LCMS/UPLC (method: formate) retention time 1.14 min, [M+H]⁺=501.92. ¹H NMR (400 MHz, DMSO-d₆) δ 10.05 (s, 1H), 7.85 (s, 1H), 7.59-7.46 (m, 4H), 7.44 (d, J=1.8 Hz, 1H), 7.38 (t, J=7.9 Hz, 1H), 7.28 (s, 1H), 7.16 (d, J=8.1 Hz, 1H), 6.73 (d, J=8.6 Hz, 1H), 6.05 (d, J=8.0 Hz, 1H), 4.75 (m, 1H), 4.5 (m, 1H), 3.98 (s, 3H), 3.85 (s, 3H), 2.64 (ddd, J=12.4, 8.5, 4.0 Hz, 1H), 2.21 (s, 3H), 2.15 (s, 3H), 1.68-1.53 (m, 1H), 1.16 (d, J=6.3 Hz, 3H). ¹³C NMR (126 MHz, Acetone) δ 168.67, 168.38, 166.34, 145.47, 142.03, 140.46, 139.88, 136.02, 129.35, 126.65, 125.18, 124.15, 121.20, 117.97, 117.10, 116.65, 110.02, 109.08, 55.69, 51.45, 48.83, 30.72, 29.62, 24.08, 23.04, 21.33.

xxii. Preparation of N-(3-((2S,4R)-1-acetyl-4-((4-(aminomethyl)phenyl)amino)-2-methyl-1,2,3,4-tetrahydroquinolin-6-yl)phenyl)acetamide

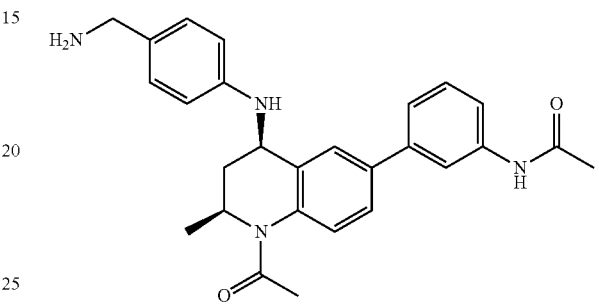

57% yield. LCMS/UPLC (method: formate) retention time 1.19 min, [M+H-NH₂]⁺=425.81. ¹H NMR (400 MHz, Acetone-d₆) δ 8.11 (s, 1H, 7.71 (s, 1H), 7.62-7.40 (m, 3H), 7.31 (d, J=8.1 Hz, 1H), 7.23 (t, J=7.9 Hz, 1H), 7.14 (d, J=8.0 Hz, 1H), 7.02 (d, J=8.6 Hz, 2H), 6.66 (d, J=8.5 Hz, 2H), 4.75 (m, 1H), 4.24 (s, 1H), 2.65 (ddd, J=12.5, 8.6, 4.2 Hz, 2H), 2.07 (s, 1H), 1.33-1.15 (m, 1H), 1.05 (d, J=6.3 Hz, 3H).

xxiii. Preparation of N-(3-((2S,4R)-1-acetyl-2-methyl-4-((4-(2-methyl-2H-tetrazol-5-yl)phenyl)amino)-1,2,3,4-tetrahydroquinolin-6-yl)phenyl)acetamide

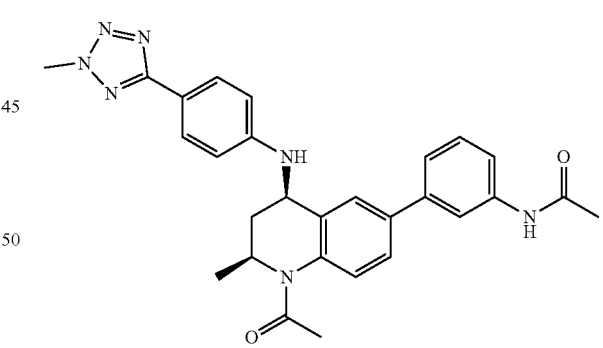

59% yield. LCMS/UPLC (method: formate) retention time 1.07 min, [M+H]⁺=495.87. ¹H NMR (500 MHz, Methanol-d₄) δ 7.88 (d, J=8.7 Hz, 2H), 7.75 (s, 1H), 7.58 (dd, J=8.1, 1.9 Hz, 1H), 7.54 (s, 1H), 7.50 (d, J=8.9 Hz, 1H), 7.39 (d, J=7.4 Hz, 1H), 7.32 (t, J=7.9 Hz, 1H), 7.24 (d, J=7.8 Hz, 1H), 6.84 (d, J=8.7 Hz, 2H), 4.98-4.89 (m, 1H), 4.46-4.31 (m, 3H), 2.74 (ddd, J=12.5, 8.6, 4.2 Hz, 1H), 2.27 (s, 3H), 2.11 (s, 2H), 1.50-1.35 (m, 2H), 1.21 (d, J=6.3 Hz, 3H). ¹³C NMR (126 MHz, MeOD) δ 170.75, 170.32, 165.45, 150.21, 141.05, 138.99, 128.92, 127.69, 126.42, 125.30, 122.24, 118.85, 118.16, 115.36, 112.48, 49.10, 48.44, 40.23, 38.32, 22.39, 21.59, 20.04.

xiv. Preparation of N-(3-((2S,4R)-1-acetyl-2-methyl-4-((4-(1-methyl-1H-tetrazol-5-yl)phenyl)amino)-1,2,3,4-tetrahydroquinolin-6-yl)phenyl)acetamide

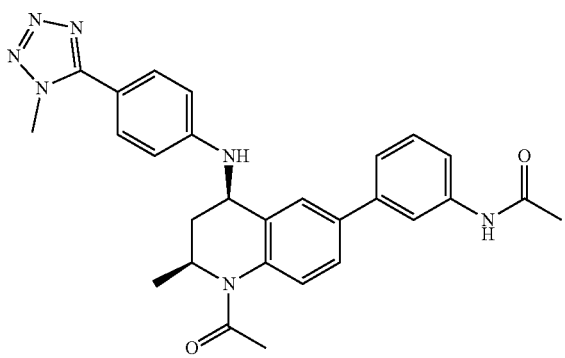 [SMILES: CC(=O)Nc1cccc(-c2ccc3c(c2)[C@H](Nc2ccc(-c4nnnn4C)cc2)C[C@H](C)N3C(C)=O)c1]

44% yield. LCMS/UPLC (method: formate) retention time 1.02 min, [M+H]$^+$=495.79. $^1$H NMR (400 MHz, Acetone-d$_6$) δ 9.08 (s, 1H) 7.88 (s, 1H), 7.64-7.52 (m, 2H), 7.50-7.43 (m, 2H), 7.38 (d, J=7.9 Hz, 1H), 7.32 (d, J=8.7 Hz, 1H), 7.20 (t, J=7.8 Hz, 1H), 7.11 (d, J=7.8 Hz, 1H), 6.87 (d, J=8.8 Hz, 2H), 5.98 (d, J=7.7 Hz, 1H), 4.77 (d, J=6.2 Hz, 1H), 4.51-4.37 (m, 1H), 4.10 (s, 3H), 2.64 (ddd, J=12.4, 8.5, 4.0 Hz, 1H), 2.06 (s, 3H), 1.41-1.24 (m, 1H), 1.05 (d, J=6.3 Hz, 3H). $^{13}$C NMR (126 MHz, DMSO) δ 169.12, 168.85, 154.59, 150.97, 140.92, 140.34, 137.93, 137.70, 136.49, 130.24, 129.79, 127.12, 125.61, 122.06, 121.72, 118.44, 117.60, 112.98, 110.99, 99.98, 79.64, 49.06, 35.56, 24.48, 23.46, 21.75.

xxv. Preparation of N-(3-((2S,4R)-1-acetyl-4-((4-cyanophenyl)amino)-2-methyl-1,2,3,4-tetrahydroquinolin-6-yl)phenyl)acetamide

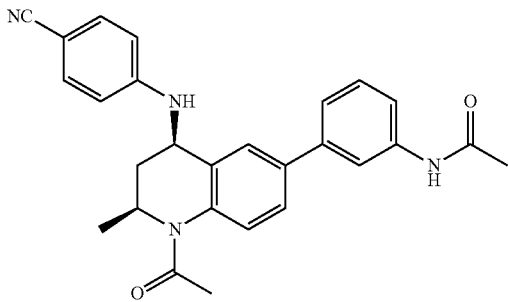 [SMILES: CC(=O)Nc1cccc(-c2ccc3c(c2)[C@H](Nc2ccc(C#N)cc2)C[C@H](C)N3C(C)=O)c1]

41% yield. LCMS/UPLC (method: formate) retention time 1.07 min, [M+H]$^+$=439.21. $^1$H NMR (400 MHz, Acetone-d$_6$) δ 9.16 (s, 1H), 7.94 (s, 1H), 7.61-7.35 (m, 5H), 7.27 (t, J=7.9 Hz, 1H), 7.16 (d, J=7.8 Hz, 1H), 6.97-6.78 (m, 2H), 6.33 (d, J=7.6 Hz, 1H), 4.94-4.70 (m, 1H), 4.53 (ddd, J=11.8, 7.8, 4.1 Hz, 1H), 2.64 (ddd, J=12.4, 8.5, 4.0 Hz, 1H), 2.11 (s, 3H), 1.38 (td, J=12.1, 9.1 Hz, 1H), 1.11 (d, J=6.3 Hz, 3H). $^{13}$C NMR (126 MHz, Acetone) 168.38, 168.04, 151.79, 141.03, 140.20, 138.14, 136.49, 133.49, 129.15, 126.73, 125.51, 121.82, 121.48, 119.83, 117.97, 117.46, 112.84, 98.43, 49.14, 47.20, 40.59, 23.41, 22.23, 20.67.

xxvi. Preparation of N-(3-((2S,4R)-1-acetyl-4-((4-(2-hydroxyacetyl)phenyl)amino)-2-methyl-1,2,3,4-tetrahydroquinolin-6-yl)phenyl)acetamide

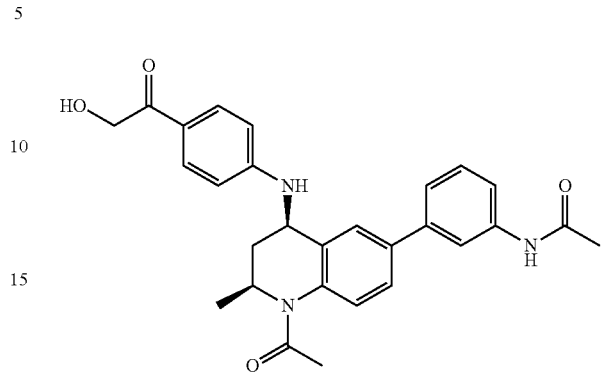

8% yield. LCMS/UPLC (method: formate) retention time 1.19 min, [M+H—OH]$^+$=456.22, [M+H-NHPhC(O)CH$_2$OH]$^+$=321.16. $^1$H NMR (400 MHz, Acetone-d$_6$) δ 9.20 (s, 1H), 7.97 (s, 1H), 7.82 (d, J=8.8 Hz, 2H), 7.63-7.49 (m, 3H), 7.45 (d, J=8.2 Hz, 1H), 7.32 (t, J=7.9 Hz, 1H), 7.21 (d, J=7.9 Hz, 1H), 6.84 (d, J=8.9 Hz, 2H), 6.24 (d, J=7.8 Hz, 1H), 4.98-4.79 (m, 1H), 4.59 (t, J=8.0 Hz, 1H), 2.61 (ddd, J=12.4, 8.5, 4.0 Hz, 1H), 2.43 (s, 3H), 2.18 (s, 3H), 2.08 (s, 2H), 1.56-1.37 (m, 1H), 1.17 (d, J=6.3 Hz, 3H). $^{13}$C NMR (126 MHz, Acetone) 196.58, 169.51, 169.06, 167.57, 151.74, 139.74, 137.77, 129.59, 127.67, 125.31, 124.53, 124.19, 120.94, 120.71, 117.58, 116.90, 110.13, 47.59, 38.84, 28.00, 23.29, 21.15, 20.32, 18.77.

xxvii. Preparation of N-(3-((2S,4R)-1-acetyl-2-methyl-4-(quinolin-5-ylamino)-1,2,3,4-tetrahydroquinolin-6-yl)phenyl) acetamide

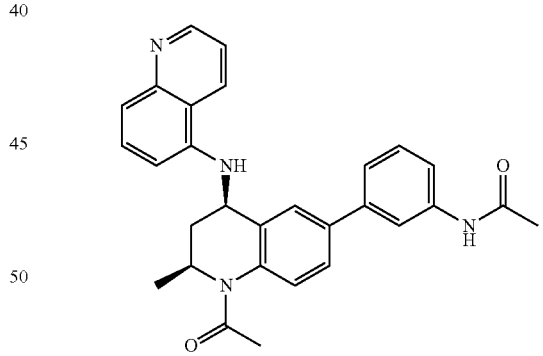

26% yield. LCMS/UPLC (method: formate) retention time 0.81 min, [M+H]$^+$=464.56. $^1$H NMR (400 MHz, Acetone-d$_6$) δ 9.08 (s, 1H), 8.71 (dd, J=10.1, 6.4 Hz, 2H), 7.80 (s, 1H), 7.50-7.20 (m, 8H), 7.08 (t, J=7.9 Hz, 1H), 6.98 (d, J=7.8 Hz, 1H), 6.60 (d, J=7.7 Hz, 1H), 5.98 (d, J=7.2 Hz, 1H), 4.76 (dt, J=15.1, 7.6 Hz, 1H), 4.48 (dt, J=11.4, 5.4 Hz, 1H), 2.72 (ddd, J=12.5, 8.6, 4.1 Hz, 1H), 2.06 (s, 3H), 1.95 (s, 3H), 1.47 (td, J=12.2, 9.3 Hz, 1H), 1.04 (d, J=6.3 Hz, 3H). $^{13}$C NMR (126 MHz, Acetone) δ 168.74, 168.20, 149.61, 149.16, 143.84, 141.07, 140.08, 138.13, 137.76, 136.45, 130.34, 129.10, 126.67, 125.40, 122.23, 121.51, 119.28, 118.60, 117.99, 117.77, 117.49, 105.42, 50.26, 47.46, 40.74, 23.39, 22.27, 20.77.

xxviii. Preparation of N-(3-((2S,4R)-1-acetyl-2-methyl-4 (naphthalen-1-ylamino)-1,2,3,4-tetrahydroquinolin-6-yl)phenyl)acetamide

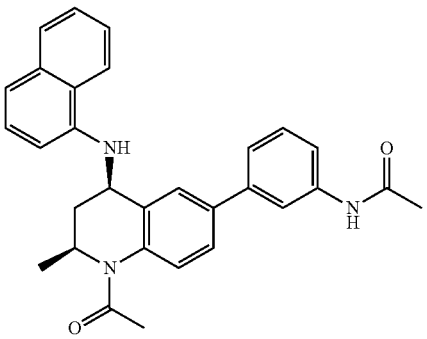 [SMILES: CC(=O)Nc1cccc(-c2ccc3c(c2)[C@H](Nc2cccc4ccccc24)C[C@H](C)N3C(C)=O)c1]

36% yield. LCMS/UPLC (method: formate) retention time 1.21 min, [M+H]+=464.07, [M+H-NHC$_{10}$H$_7$]+= 320.63. $^1$H NMR (400 MHz, Acetone-d$_6$) δ 9.01 (s, 1H), 8.25-8.12 (m, 1H), 7.77 (s, 1H), 7.73-7.62 (m, 1H), 7.48-7.26 (m, 6H), 7.19-7.04 (m, 3H), 6.98 (d, J=7.8 Hz, 1H), 6.53 (d, J=7.2 Hz, 1H), 5.70 (d, J=7.2 Hz, 1H), 4.64 (m, 1H), 4.44 (ddd, J=11.8, 7.0, 4.4 Hz, 1H), 2.06 (s, 3H), 1.90 (s, 3H), 1.49 (td, J=12.2, 9.2 Hz, 1H), 1.05 (d, J=6.3 Hz, 3H). $^{13}$C NMR (126 MHz, Acetone) δ 168.44, 168.01, 143.36, 141.19, 140.11, 138.19, 138.05, 136.54, 134.69, 129.08, 128.33, 126.64, 125.64, 125.32, 124.38, 123.63, 122.35, 121.50, 121.23, 117.90, 117.41, 117.08, 105.24, 50.32, 47.43, 40.93, 23.40, 22.28, 20.81.

xxix. Preparation of N-(3-((2S,4R)-1-acetyl-2-methyl-4-(quinolin-8-ylamino)-1,2,3,4-tetrahydroquinolin-6-yl)phenyl)acetamide

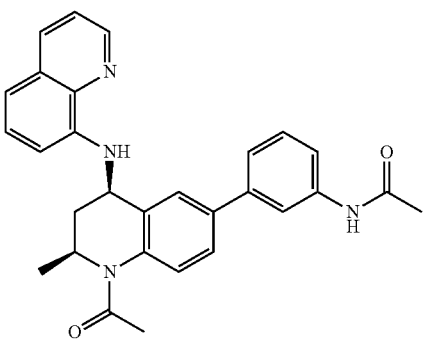 [SMILES: CC(=O)Nc1cccc(-c2ccc3c(c2)[C@H](Nc2cccc4cccnc24)C[C@H](C)N3C(C)=O)c1]

25% yield. LCMS/UPLC (method: formate) retention time 1.16 min, [M+H]+=464.80, [M+H-NHC$_{10}$H$_7$]+= 320.71. $^1$H NMR (400 MHz, Acetone-d$_6$) 9.01 (s, 1H), 8.67 (dd, J=4.2, 1.7 Hz, 1H), 8.10 (dd, J=8.3, 1.7 Hz, 1H), 7.74 (s, 1H), 7.49-7.35 (m, 4H), 7.35-7.29 (m, 1H), 7.22 (t, J=7.9 Hz, 1H), 7.11 (t, J=7.9 Hz, 1H), 7.06-6.97 (m, 2H), 6.69 (d, J=7.4 Hz, 1H), 6.52 (d, J=7.5 Hz, 1H), 4.86-4.70 (m, 1H), 4.47 (ddd, J=11.8, 7.4, 4.3 Hz, 1H), 2.06 (s, 3H), 1.90 (s, 3H), 1.48 (td, J=12.1, 9.1 Hz, 1H), 1.06 (d, J=3.0 Hz, 3H). $^{13}$C NMR (126 MHz, Acetone) δ 168.41, 167.97, 147.22, 144.23, 141.12, 140.15, 138.07, 136.51, 136.01, 129.11, 128.76, 127.73, 126.66, 125.44, 121.91, 121.71, 121.48, 117.91, 117.35, 114.59, 105.92, 49.90, 47.35, 40.93, 23.39, 22.26, 20.74.

xxx. Preparation of N-(3-((2S,4R)-4-((4-(1,3,4-oxadiazol-2-yl)phenyl)amino)-1-acetyl-2-methyl-1,2,3,4-tetrahydroquinolin-6-yl)phenyl)acetamide

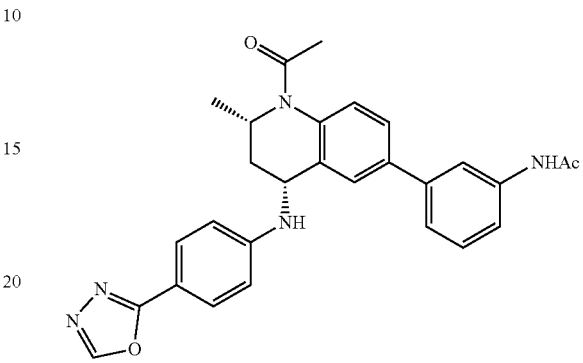

21% yield. $^1$H NMR (400 MHz, Acetone-d$_6$) δ 9.15 (s, 1H), 8.75 (s, 1H), 7.93 (s, 1H), 7.80 (d, J=8.8 Hz, 2H), 7.59-7.45 (m, 3H), 7.40 (d, J=7.9 Hz, 1H), 7.26 (t, J=7.9 Hz, 1H), 7.17 (d, J=7.7 Hz, 1H), 6.92 (d, J=8.9 Hz, 2H), 6.14 (d, J=7.8 Hz, 1H), 4.93-4.74 (m, 1H), 4.51 (m, 1H), 2.72 (m, 1H), 2.13 (s, 3H), 1.48-1.33 (m, 1H), 1.12 (d, J=6.3 Hz, 3H). $^{13}$C NMR (126 MHz, Acetone) δ 168.36, 167.99, 164.64, 152.40, 151.34, 141.09, 140.19, 138.11, 137.61, 136.50, 129.14, 128.36, 126.68, 125.43, 121.96, 121.49, 117.95, 117.43, 112.85, 111.95, 49.28, 47.27, 40.72, 23.40, 22.24, 20.71.

xxxi. Preparation of N-(3-((2S,4R)-1-acetyl-2-methyl-4-((4-(5-methyl-1,3,4-oxadiazol-2-yl)phenyl)amino)-1,2,3,4-tetrahydroquinolin-6-yl)phenyl)acetamide

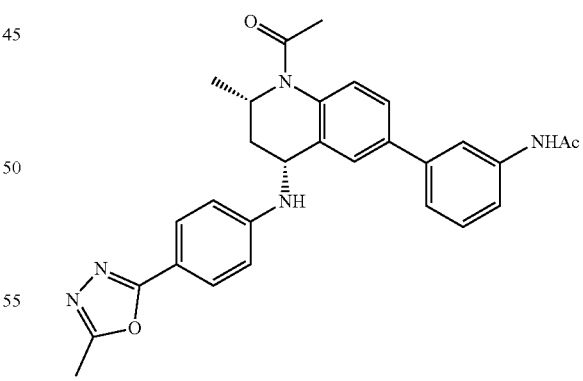

44% yield. $^1$H NMR (400 MHz, Acetone-d$_6$) δ 9.21 (s, 1H), 7.98 (s, 1H), 7.85-7.72 (m, 2H), 7.63-7.51 (m, 3H), 7.45 (d, J=8.6 Hz, 1H), 7.32 (t, J=7.9 Hz, 1H), 7.22 (d, J=7.7 Hz, 1H), 6.95 (d, J=8.9 Hz, 2H), 6.13 (d, J=7.8 Hz, 1H), 4.96-4.81 (m, 1H), 4.67-4.47 (m, 1H), 2.86-2.77 (m, 1H), 2.53 (s, 3H), 2.18 (s, 3H), 2.08 (s, 3H), 1.53-1.38 (m, 1H), 1.17 (d, J=6.3 Hz, 3H). $^{13}$C NMR (126 MHz, Acetone) δ 168.36, 168.00, 164.84, 162.26, 151.02, 141.09, 140.19, 138.09, 136.50, 129.14, 127.94, 126.66, 125.40, 121.98, 121.49, 117.95, 117.42, 112.82, 112.48, 49.28, 47.28, 40.73, 23.40, 22.25, 20.72, 9.88.

xxxii. Preparation of Methyl 4-(((2S,4R)-1-acetyl-2-methyl-6-(1-methyl-1H-pyrazol-3-yl)-1,2,3,4-tetrahydroquinolin-4-yl)amino)benzoate

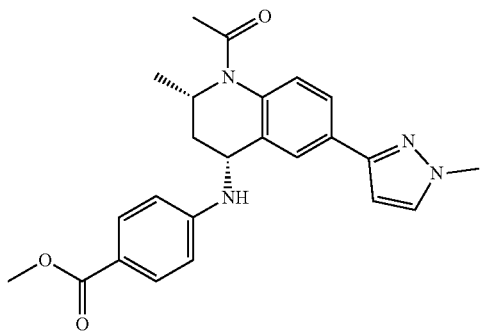

26% yield. LCMS/UPLC (method: formate) retention time 1.07 min, [M+H]⁺=418.77. ¹H NMR (400 MHz, Acetone-d₆) δ 7.86-7.80 (m, 2H), 7.74 (d, J=0.8 Hz, 1H), 7.58 (d, J=2.3 Hz, 1H), 7.35 (d, J=8.0 Hz, 1H), 6.85 (d, J=8.9 Hz, 2H), 6.48 (d, J=2.3 Hz, 1H), 6.14 (d, J=8.0 Hz, 1H), 4.95-4.80 (m, 1H), 4.54 (td, J=7.8, 3.9 Hz, 1H), 3.88 (s, 3H), 3.80 (d, J=4.2 Hz, 3H), 2.75 (ddd, J=12.5, 8.6, 4.2 Hz, 1H), 2.15 (s, 3H), 1.40 (td, J=12.2, 9.1 Hz, 2H), 1.15 (d, J=6.3 Hz, 3H). ¹³C NMR (126 MHz, Acetone) δ 168.31, 166.38, 152.39, 150.29, 137.39, 136.04, 131.65, 131.25, 126.33, 123.85, 120.24, 118.01, 111.87, 102.18, 50.62, 49.20, 47.12, 40.73, 38.17, 22.20, 20.68.

xxxiii. Preparation of 4-(((2S,4R)-1-acetyl-2-methyl-6-(1-methyl-1H-pyrazol-3-yl)-1,2,3,4-tetrahydroquinolin-4-yl)amino)benzonitrile

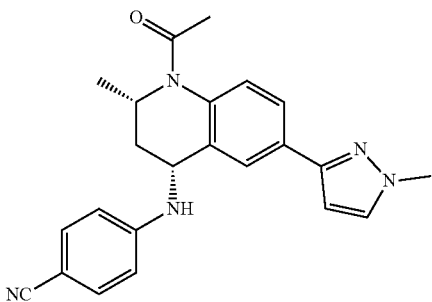 [SMILES: CC(=O)N1c2ccc(-c3ccn(C)n3)cc2[C@H](Nc2ccc(C#N)cc2)C[C@@H]1C]

21% yield. LCMS/UPLC (method: formate) retention time 1.14 min, [M+H]⁺=385.83. ¹H NMR (500 MHz, Methanol-d₄) δ 7.79-7.70 (m, 1H), 7.61 (s, 1H), 7.57 (d, J=2.3 Hz, 1H), 7.47 (d, J=8.9 Hz, 2H), 7.35 (d, J=8.0 Hz, 2H), 6.80 (d, J=8.8 Hz, 2H), 6.47 (d, J=2.3 Hz, 1H), 4.75 (m, 1H), 4.39 (dd, J=12.1, 4.0 Hz, 1H), 3.90 (s, 3H), 2.70 (ddd, J=12.6, 8.6, 4.2 Hz, 1H), 2.24 (s, 3H), 1.49-1.36 (m, 1H), 1.25-1.12 (m, 3H). ¹³C NMR (126 MHz, MeOD) 170.71, 151.99, 150.85, 135.45, 133.38, 132.22, 131.50, 126.41, 124.14, 120.40, 120.05, 112.35, 102.55, 97.39, 48.78, 48.21, 40.05, 37.48, 21.54, 19.97.

xxxiv. Preparation of 1-((2S,4R)-2-methyl-6-(1-methyl-1H-pyrazol-3-yl)-4-((2-(trifluoromethoxy)phenyl)amino)-3,4-dihydroquinolin-1(2H)-yl)ethanone

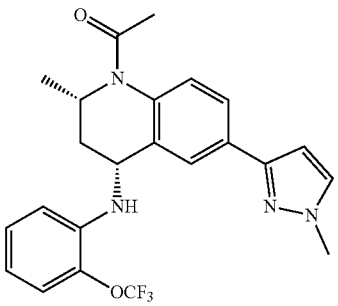 [SMILES: CC(=O)N1c2ccc(-c3ccn(C)n3)cc2[C@H](Nc2ccccc2OC(F)(F)F)C[C@@H]1C]

12.8% yield. LCMS/UPLC (method: formate) retention time 1.32 min, [M+H]⁺=444.69. ¹H NMR (400 MHz, Methanol-d₄) δ 7.66 (dd, J=8.2, 1.5 Hz, 1H), 7.53 (s, 1H), 7.47 (d, J=2.3 Hz, 1H), 7.25 (d, J=8.1 Hz, 1H), 7.14 (dt, J=8.1, 1.6 Hz, 1H), 7.05 (t, J=7.3 Hz, 1H), 6.73-6.66 (m, 1H), 6.62 (td, J=8.1, 1.4 Hz, 1H), 6.32 (d, J=2.3 Hz, 1H), 5.21 (d, J=7.7 Hz, 1H), 4.36-4.21 (m, 1H), 3.81 (s, 3H), 2.60 (ddd, J=12.6, 8.7, 4.2 Hz, 1H), 2.24 (s, 3H), 1.52-1.34 (m, 1H), 1.11 (d, J=6.4 Hz, 3H).

xxxv. Preparation of 1-((2S,4R)-4-((4-fluoro-2-methoxyphenyl)amino)-2-methyl-6-(1-methyl-1H-pyrazol-3-yl)-3,4-dihydroquinolin-1(2H)-yl)ethanone

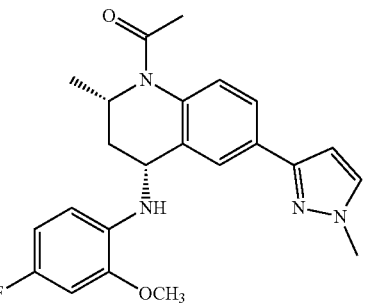

3.6% yield. LCMS/UPLC (method: formate) retention time 1.23 min, [M+H]⁺=409.37. ¹H NMR (400 MHz, Acetone-d₆) δ 7.75-7.61 (m, 2H), 7.51 (d, J=2.2 Hz, 1H), 7.25 (d, J=8.0 Hz, 1H), 6.72 (dd, J=10.5, 2.7 Hz, 1H), 6.60-6.51 (m, 1H), 6.51-6.38 (m, 2H), 4.77 (h, J=6.4 Hz, 1H), 4.58 (d, J=7.7 Hz, 1H), 4.24 (ddd, J=11.8, 7.6, 4.1 Hz, 1H), 3.89 (s, 3H), 3.81 (s, 3H), 2.63 (ddd, J=12.5, 8.6, 4.2 Hz, 1H), 2.06 (s, 3H), 1.33 (td, J=12.1, 9.1 Hz, 1H), 1.06 (d, J=6.3 Hz, 3H). ¹³C NMR (126 MHz, Acetone) δ 168.26, 156.31, 154.46, 150.38, 147.49, 138.35, 135.96, 134.23, 131.62, 131.51, 126.16, 123.68, 120.29, 110.63, 110.56, 106.02, 105.85, 102.15, 98.80, 98.58, 55.47, 50.31, 47.21, 41.04, 38.16, 22.16, 20.69.

xxxvi. Preparation of Methyl 4-(((2S,4R)-1-acetyl-2-methyl-6-(1-methyl-1H-pyrazol-5-yl)-1,2,3,4-tetrahydroquinolin-4-yl)amino)benzoate

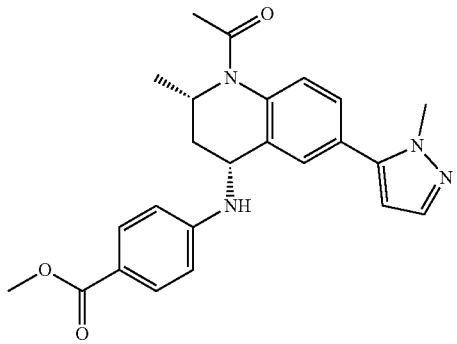 [SMILES: COC(=O)c1ccc(N[C@@H]2C[C@H](C)N(C(C)=O)c3ccc(-c4ccnn4C)cc32)cc1]

31% yield. LCMS/UPLC (method: formate) retention time 1.06 min, [M+H]$^+$=418.77. $^1$H NMR (400 MHz, Acetone-d$_6$) δ 7.87-7.75 (m, 2H), 7.48 (s, 2H), 7.35 (dd, J=13.5, 1.5 Hz, 2H), 6.90-6.78 (m, 2H), 6.26 (d, J=1.9 Hz, 1H), 6.19 (d, J=7.8 Hz, 1H), 4.95-4.80 (m, 1H), 4.60 (ddd, J=12.0, 7.9, 4.2 Hz, 1H), 3.79 (s, 3H), 3.71 (s, 3H), 2.79 (ddd, J=12.6, 8.6, 4.2 Hz, 4H), 2.19 (s, 3H), 1.45 (td, J=12.2, 9.2 Hz, 1H), 1.18 (d, J=6.3 Hz, 3H). $^{13}$C NMR (126 MHz, Acetone) δ 168.40, 166.30, 152.23, 142.52, 137.84, 137.47, 137.16, 131.23, 127.71, 127.04, 126.56, 123.70, 118.19, 111.89, 105.40, 50.65, 48.89, 47.46, 40.59, 36.95, 22.24, 20.80.

xxxvii. Preparation of 1-((2S,4R)-2-methyl-6-(1-methyl-1H-pyrazol-5-yl)-4-((2-(trifluoromethoxy)phenyl)amino)-3,4-dihydroquinolin-1(2H)-yl)ethanone

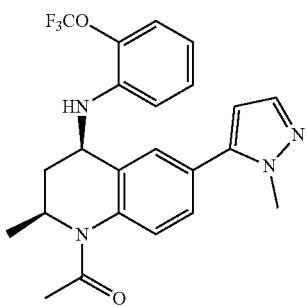 [SMILES: CC(=O)N1c2ccc(-c3ccnn3C)cc2[C@H](Nc2ccccc2OC(F)(F)F)C[C@@H]1C]

11% yield. LCMS/UPLC (method: formate) retention time 1.23 min, [M+H]$^+$=444.69. $^1$H NMR (400 MHz, Acetone-d$_6$) δ 7.33 (d, J=1.1 Hz, 2H), 7.23 (d, J=1.8 Hz, 1H), 7.11 (dt, J=8.1, 1.5 Hz, 1H), 7.05-6.95 (m, 1H), 6.75 (d, J=8.3 Hz, 1H), 6.58 (td, J=8.1, 1.4 Hz, 1H), 6.11 (d, J=1.9 Hz, 1H), 5.33 (d, J=7.8 Hz, 1H), 4.73 (td, J=8.9, 4.4 Hz, 1H), 4.43 (ddd, J=12.0, 8.0, 4.1 Hz, 1H), 2.63 (ddd, J=12.6, 8.7, 4.2 Hz, 1H), 2.04 (s, 3H), 1.44 (td, J=12.3, 9.4 Hz, 1H), 1.03 (d, J=6.3 Hz, 3H). $^{13}$C NMR (126 MHz, Acetone) δ 168.39, 142.55, 140.38, 137.86, 137.57, 137.17, 135.68, 128.15, 127.66, 126.99, 126.53, 123.53, 122.10, 121.42, 120.06, 116.59, 113.10, 105.34, 49.00, 47.54, 40.51, 36.91, 29.69, 22.24, 20.84.

xxxviii. Preparation of 1-((2S,4R)-4-((4-fluoro-2-methoxyphenyl)amino)-2-methyl-6-(1H-pyrazol-3-yl)-3,4-dihydroquinolin-1(2H)-yl)ethanone

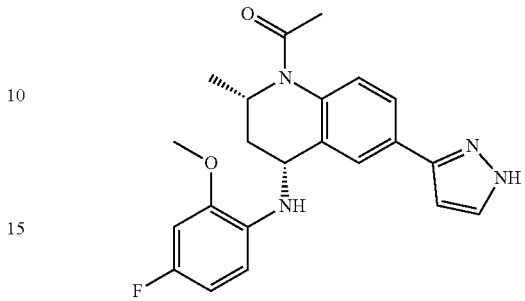

LCMS/UPLC (method: formate) retention time 1.13 min, [M+H]$^+$=395.31. $^1$H NMR (400 MHz, Acetone-d$_6$) δ 12.15 (bs, 1H), 7.77 (dd, J=7.9, 1.1 Hz, 2H), 7.69 (d, J=2.3 Hz, 1H), 7.34 (d, J=8.7 Hz, 1H), 6.78 (dd, J=10.5, 2.7 Hz, 1H), 6.65-6.44 (m, 3H), 4.91-4.75 (m, 1H), 4.66 (d, J=7.8 Hz, 1H), 4.32 (ddd, J=12.0, 7.4, 4.2 Hz, 1H), 3.95 (s, 3H), 2.70 (ddd, J=12.5, 8.6, 4.2 Hz, 1H), 2.14 (s, 3H), 1.40 (td, J=12.2, 9.2 Hz, 1H), 1.13 (d, J=6.3 Hz, 3H). $^{13}$C NMR (101 MHz, Acetone) δ 169.18, 148.35, 137.06, 135.04, 127.13, 124.72, 121.48, 111.46, 111.37, 106.92, 106.70, 102.52, 99.72, 99.45, 56.35, 51.00, 47.11, 41.88, 23.07, 21.60.

xxxix. Preparation of 1-((2S,4R)-2-methyl-6-(1H-pyrazol-3-yl)-4-((2-(trifluoromethoxy)phenyl)amino)-3,4-dihydroquinolin-1(2H)-yl)ethanone

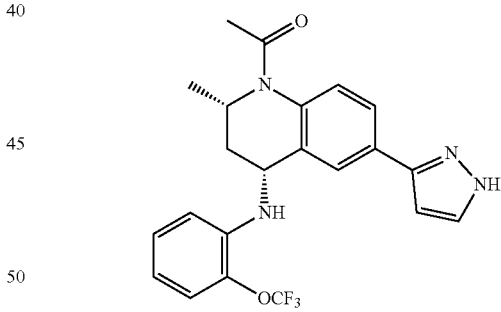

LCMS/UPLC (method: formate) retention time 1.23 min, [M+H]$^+$=430.55. $^1$H NMR (400 MHz, Acetone-d$_6$) δ 12.05 (bs, 1H), 7.75 (dd, J=8.1, 1.4 Hz, 1H), 7.70 (s, 1H), 7.64 (d, J=2.2 Hz, 1H), 7.31 (d, J=8.2 Hz, 1H), 7.22 (dt, J=8.1, 1.6 Hz, 1H), 6.85 (d, J=8.3 Hz, 1H), 6.77-6.62 (m, 1H), 6.46 (d, J=2.3 Hz, 1H), 5.30 (d, J=7.7 Hz, 1H), 4.82 (d, J=6.4 Hz, 2H), 4.53-4.32 (m, 1H), 2.68 (td, J=8.5, 4.3 Hz, 1H), 2.10 (d, J=3.3 Hz, 3H), 1.50 (td, J=12.2, 9.1 Hz, 2H), 1.10 (d, J=6.3 Hz, 3H). $^{13}$C NMR (126 MHz, Acetone) δ 168.32, 140.54, 137.61, 136.26, 135.77, 128.18, 126.35, 123.86, 121.32, 120.48, 116.41, 113.04, 101.49, 49.27, 47.22, 40.64, 22.21, 20.73.

xl. Preparation of 4-(((2S,4R)-1-acetyl-2-methyl-6-(1H-pyrazol-3-yl)-1,2,3,4-tetrahydroquinolin-4-yl)amino)benzonitrile

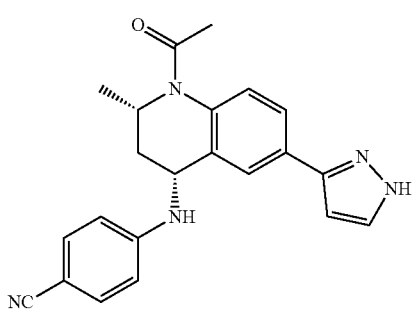 [SMILES: CC(=O)N1c2ccc(-c3cc[nH]n3)cc2[C@H](Nc2ccc(C#N)cc2)C[C@@H]1C]

13.5% yield. LCMS/UPLC (method: formate) retention time 0.64 min, [M+H]$^+$=371.96. $^1$H NMR (400 MHz, Methanol-$d_4$) δ 7.88 (s, 1H), 7.72 (s, 2H), 7.45 (d, J=8.9 Hz, 2H), 7.36 (s, 1H), 6.78 (d, J=8.9 Hz, 2H), 6.50 (s, 1H), 4.48-4.30 (m, 1H), 2.68 (ddd, J=12.7, 8.6, 4.2 Hz, 1H), 2.22 (s, 3H), 1.49-1.31 (m, 1H), 1.18 (d, J=6.4 Hz, 3H). $^{13}$C NMR (126 MHz, MeOD) δ 170.71, 151.97, 133.38, 129.79, 126.46, 124.26, 120.65, 120.04, 112.37, 101.88, 97.39, 48.72, 40.04, 21.55, 20.00.

xli. Preparation of 1-((2S,4R)-4-((3,4-difluorophenyl)amino)-2-methyl-6-(1H-pyrazol-3-yl)-3,4-dihydroquinolin-1(2H)-yl)ethanone

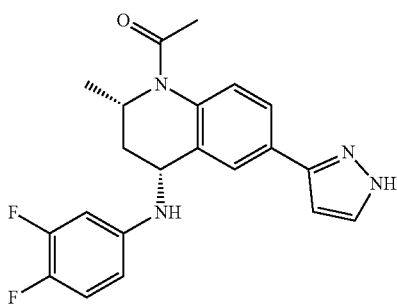 [SMILES: CC(=O)N1c2ccc(-c3cc[nH]n3)cc2[C@H](Nc2ccc(F)c(F)c2)C[C@@H]1C]

14.9% yield. LCMS/UPLC (method: formate) retention time 0.78 min, [M+H]$^+$=383.03. $^1$H NMR (400 MHz, Methanol-$d_4$) δ 7.82-7.59 (m, 3H), 7.34 (d, J=7.9 Hz, 1H), 7.01 (dt, J=10.6, 9.1 Hz, 1H), 6.59 (ddd, J=13.3, 6.8, 2.8 Hz, 1H), 6.46 (ddt, J=8.9, 4.5, 3.1 Hz, 1H), 4.22 (dd, J=12.1, 3.8 Hz, 1H), 2.68 (ddd, J=12.5, 8.5, 4.1 Hz, 1H), 2.23 (s, 3H), 1.32 (m, 1H), 1.17 (d, J=6.4 Hz, 3H). $^{13}$C NMR (126 MHz, MeOD) δ 170.73, 151.67, 149.85, 145.53, 143.36, 141.50, 138.37, 135.60, 132.21, 126.40, 124.01, 120.92, 117.07, 107.75, 101.95, 101.15, 100.98, 49.60, 48.44, 40.18, 21.54, 20.01.

xlii. Preparation of 1-((2S,4R)-4-((2-chlorophenyl)amino)-2-methyl-6-(1H-pyrazol-3-yl)-3,4-dihydroquinolin-1(2H)-yl)ethanone

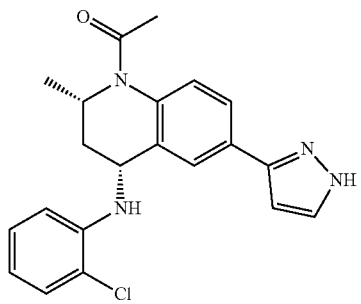 [SMILES: CC(=O)N1c2ccc(-c3cc[nH]n3)cc2[C@H](Nc2ccccc2Cl)C[C@@H]1C]

17.1% yield. LCMS/UPLC (method: formate) retention time 0.91 min, [M+H]$^+$=381.21. $^1$H NMR (400 MHz, Methanol-$d_4$) δ 7.65 (s, 1H), 7.55 (s, 2H), 7.28 (d, J=7.7 Hz, 1H), 7.24 (dd, J=7.9, 1.5 Hz, 1H), 7.03 (ddd, J=8.8, 7.4, 1.5 Hz, 1H), 6.68-6.63 (m, 1H), 6.60 (td, J=7.8, 1.4 Hz, 1H), 6.41 (d, J=2.2 Hz, 1H), 4.31 (dd, J=12.2, 4.1 Hz, 1H), 2.65 (ddd, J=12.6, 8.6, 4.2 Hz, 1H), 2.16 (s, 3H), 1.50-1.33 (m, 1H), 1.12 (d, J=6.4 Hz, 3H). $^{13}$C NMR (126 MHz, MeOD) δ 170.73, 143.44, 128.93, 127.70, 126.42, 124.14, 120.81, 118.82, 117.55, 112.32, 101.96, 49.59, 48.44, 40.30, 21.55, 20.01.

h. General Procedure for Parallel Reductive-Aminations (Method D)

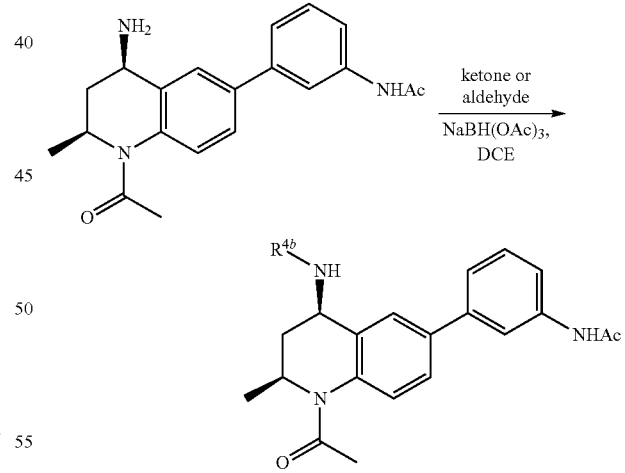

To a solution of amine (0.1 mmol) in DCE (1 mL) was added at RT aldehyde or ketone (0.125 mmol), followed by sodium triacetoxyborohydride (0.25 mmol). The resulting reaction was permitted to stir at RT overnight. Reactions were diluted with DCM and quenched via addition of sat. aq. NaHCO$_3$. The organic solution was concentrated and diluted in DMSO (1 mL) and were purified in an automated reverse phase parallel format (acetonitrile: 0.1% aqueous formic acid.)

i. Preparation of N-(3-((2S,4R)-1-acetyl-2-methyl-4-((tetrahydro-2H-pyran-4-yl)amino)-1,2,3,4-tetrahydroquinolin-6-yl) phenyl) acetamide

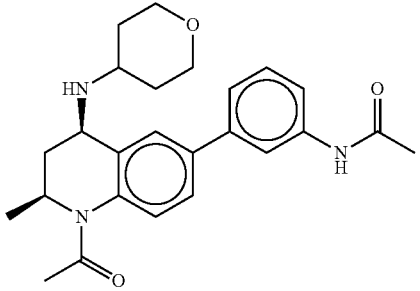

37% yield. LCMS/UPLC (method: formate) retention time 0.69 min, [M+H]$^+$=422.20. >95% UV & ELSD purity. HRMS [M+H]$^+$=422.2443 (calc.), found: 422.2445. $^1$H NMR (400 MHz, Methanol-d$_4$) δ 7.93 (d, J=2.0 Hz, 1H), 7.78 (t, J=1.5 Hz, 1H), 7.58 (dd, J=8.2, 2.2 Hz, 1H), 7.53 (dt, J=6.8, 2.2 Hz, 1H), 7.45-7.38 (m, 2H), 7.34 (d, J=8.2 Hz, 1H), 4.81 (m, 1H), 4.01 (d, J=11.6 Hz, 2H), 3.74 (dd, J=12.2, 3.9 Hz, 1H), 3.60-3.40 (m, 2H), 3.11-2.98 (m, 1H), 2.74 (ddd, J=12.6, 8.7, 4.1 Hz, 1H), 2.18 (s, 6H), 2.01 (s, 1H), 1.96 (d, J=12.2 Hz, 1H), 1.57 (m, 2H), 1.16 (d, J=6.3 Hz, 3H), 1.10 (s, 1H). $^{13}$C NMR (126 MHz, MeOD) 170.58, 170.32, 141.22, 139.12, 128.97, 126.24, 124.84, 122.28, 121.53, 118.74, 118.25, 66.53, 51.33, 49.58, 39.92, 39.01, 33.48, 32.94, 22.48, 21.45, 20.02.

ii. Preparation of N-(3-((2S,4R)-1-acetyl-4-(cycloheptylamino)-2-methyl-1,2,3,4-tetrahydroquinolin-6-yl) phenyl) acetamide

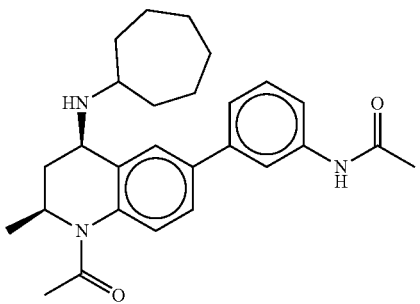

32% yield. LCMS/UPLC (method: formate) retention time 0.79 min, [M+H]$^+$=434.06. >95% UV & ELSD purity. HRMS [M+H]$^+$=434.2807 (calc.), found: 434.2813. $^1$H NMR (400 MHz, Methanol-d$_4$) δ 7.92 (m, 1H), 7.82-7.70 (m, 1H), 7.64-7.50 (m, 2H), 7.48-7.39 (m, 2H), 7.34 (d, J=8.1 Hz, 1H), 4.81 (s, 1H), 3.64 (dd, J=12.3, 3.8 Hz, 1H), 2.98 (dd, J=8.7, 4.4 Hz, 1H), 2.78-2.69 (m, 1H), 2.18 (s, 6H), 2.10 (m, 1H), 2.03-1.92 (m, 1H), 1.78 (s, 2H), 1.71-1.44 (m, 8H), 1.15 (d, J=6.4 Hz, 3H), 1.05 (q, J=11.7 Hz, 1H). $^{13}$C NMR (126 MHz, MeOD) 170.61, 170.34, 141.25, 139.11, 128.98, 126.27, 124.84, 122.29, 121.55, 118.80, 118.27, 56.62, 50.63, 39.87, 39.01, 34.80, 34.09, 27.98, 27.77, 24.29, 24.14, 22.46, 21.44, 19.93.

iii. Preparation of N-(3-((2S,4R)-1-acetyl-4-(cyclopentylamino)-2-methyl-1,2,3,4-tetrahydroquinolin-6-yl)phenyl)acetamide

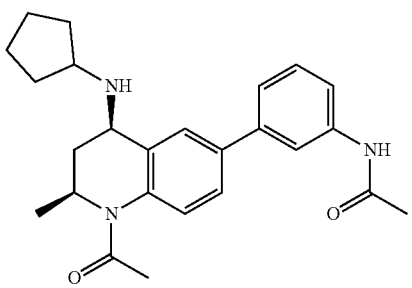 [SMILES: CC(=O)Nc1cccc(-c2ccc3c(c2)[C@H](NC2CCCC2)C[C@H](C)N3C(C)=O)c1]

6% yield. LCMS/UPLC (method: formate) retention time 0.74 min, [M+H]$^+$=406.01. >95% UV & ELSD purity. $^1$H NMR (400 MHz, Methanol-d$_4$) δ 8.41 (s, 1H), 8.08 (dt, J=2.7, 1.2 Hz, 1H), 7.69 (m, 2H), 7.55-7.43 (m, 4H), 4.82 (s, 1H), 4.16 (dd, J=12.6, 3.8 Hz, 1H), 3.84 (q, J=7.5 Hz, 1H), 3.09-2.93 (m, 1H), 2.20 (d, J=9.2 Hz, 7H), 1.82 (d, J=64.7 Hz, 6H), 1.41-1.12 (m, 4H). $^{13}$C NMR (126 MHz, MeOD) δ 170.55, 170.41, 166.76, 140.52, 139.24, 135.25, 133.55, 129.12, 127.05, 126.34, 122.31, 120.35, 119.05, 118.36, 57.08, 52.08, 39.01, 36.75, 30.68, 29.48, 23.67, 22.49, 21.46, 19.95.

2. Characterization of Exemplary Compounds

The compounds below in Table 1 were synthesized with methods identical or analogous to those described herein. The requisite starting materials were commercially available, described in the literature, or readily synthesized by one skilled in the art of organic synthesis.

TABLE 1

| No. | Structure |
|---|---|
| 1 | ![structure](isopropyl carbamate tetrahydroquinoline with NHAc phenyl) |

TABLE 1-continued
| No. | Structure |
|---|---|
| 2 | 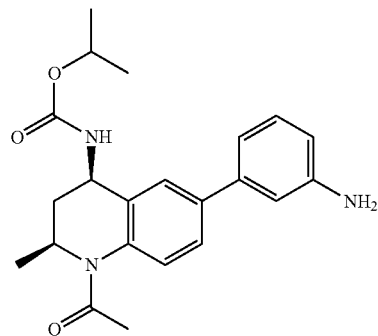 [SMILES: CC(=O)N1c2ccc(-c3cccc(N)c3)cc2[C@H](NC(=O)OC(C)C)C[C@@H]1C] |
| 3 | 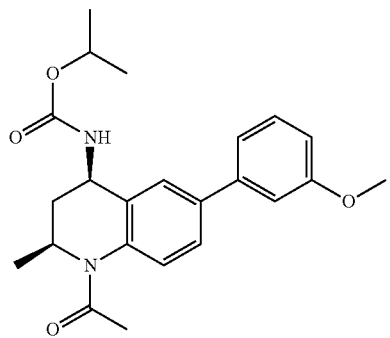 [SMILES: COc1cccc(-c2ccc3c(c2)[C@H](NC(=O)OC(C)C)C[C@H](C)N3C(C)=O)c1] |
| 4 | 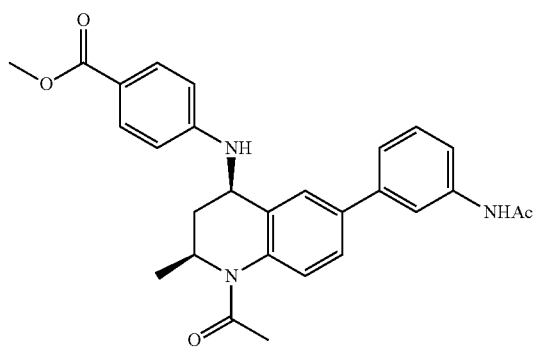 [SMILES: COC(=O)c1ccc(N[C@@H]2C[C@H](C)N(C(C)=O)c3ccc(-c4cccc(NC(C)=O)c4)cc32)cc1] |
| 5 | 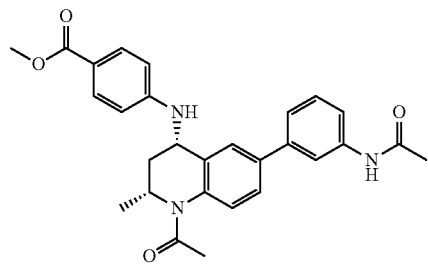 [SMILES: COC(=O)c1ccc(N[C@H]2C[C@@H](C)N(C(C)=O)c3ccc(-c4cccc(NC(C)=O)c4)cc32)cc1] |

TABLE 1-continued

| No. | Structure |
|---|---|
| 6 | 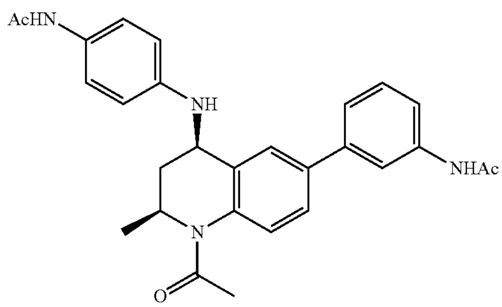 [SMILES: CC(=O)Nc1ccc(N[C@@H]2C[C@H](C)N(C(C)=O)c3ccc(-c4cccc(NC(C)=O)c4)cc32)cc1] |
| 7 | 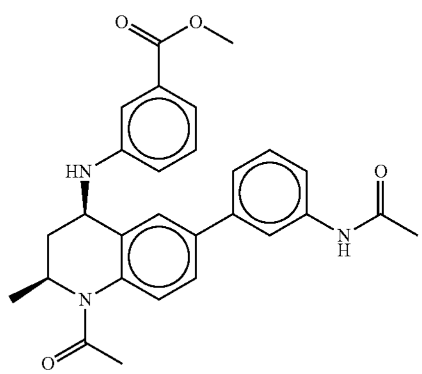 |
| 8 | 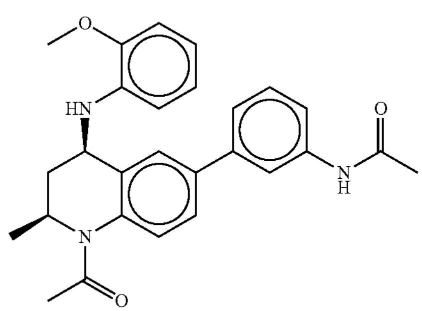 |
| 9 | 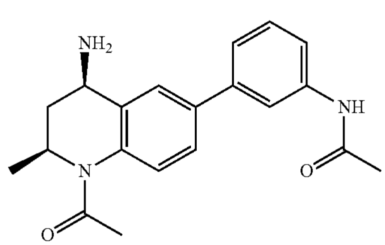 [SMILES: CC(=O)Nc1cccc(-c2ccc3c(c2)[C@H](N)C[C@H](C)N3C(C)=O)c1] |
| 10 | 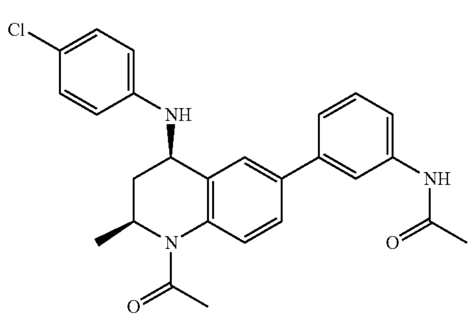 [SMILES: CC(=O)Nc1cccc(-c2ccc3c(c2)[C@H](Nc2ccc(Cl)cc2)C[C@H](C)N3C(C)=O)c1] |

TABLE 1-continued

| No. | Structure |
|-----|-----------|
| 11  | 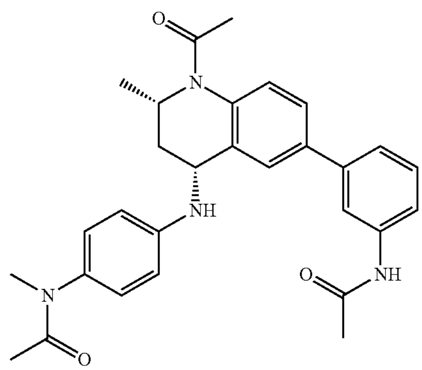 [SMILES: CC(=O)Nc1cccc(-c2ccc3c(c2)[C@H](Nc2ccc(N(C)C(C)=O)cc2)C[C@H](C)N3C(C)=O)c1] |
| 12  | 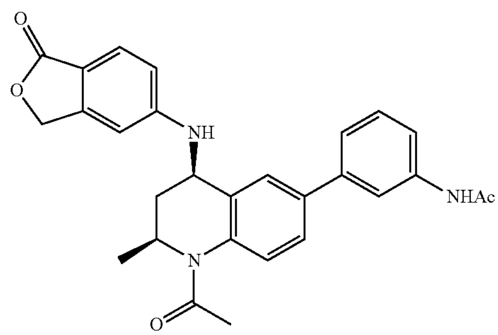 [SMILES: CC(=O)Nc1cccc(-c2ccc3c(c2)[C@H](Nc2ccc4c(c2)COC4=O)C[C@H](C)N3C(C)=O)c1] |
| 13  | 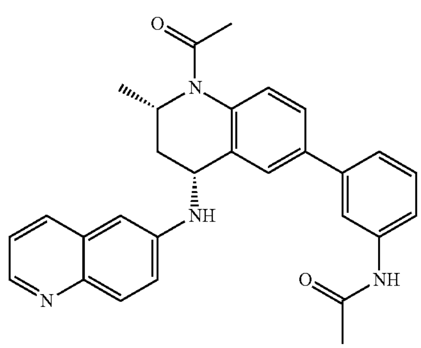 [SMILES: CC(=O)Nc1cccc(-c2ccc3c(c2)[C@H](Nc2ccc4ncccc4c2)C[C@H](C)N3C(C)=O)c1] |
| 14  | 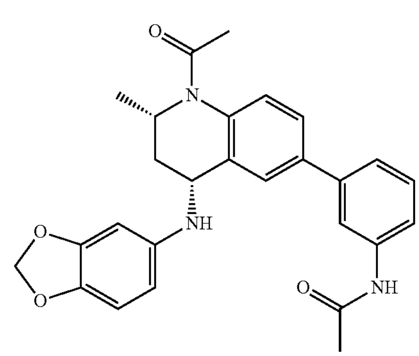 [SMILES: CC(=O)Nc1cccc(-c2ccc3c(c2)[C@H](Nc2ccc4c(c2)OCO4)C[C@H](C)N3C(C)=O)c1] |

TABLE 1-continued

| No. | Structure |
|---|---|
| 15 | 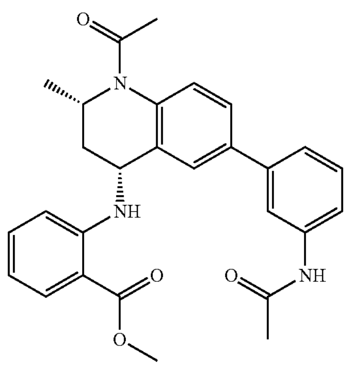 [SMILES: COC(=O)c1ccccc1N[C@@H]1C[C@H](C)N(C(C)=O)c2ccc(-c3cccc(NC(C)=O)c3)cc21] |
| 16 | 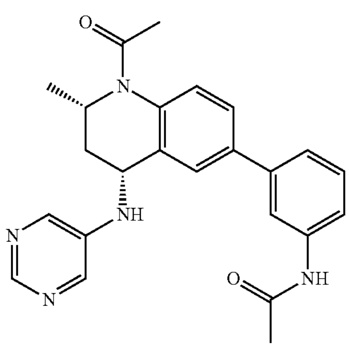 [SMILES: CC(=O)Nc1cccc(-c2ccc3c(c2)[C@H](Nc2cncnc2)C[C@H](C)N3C(C)=O)c1] |
| 17 | 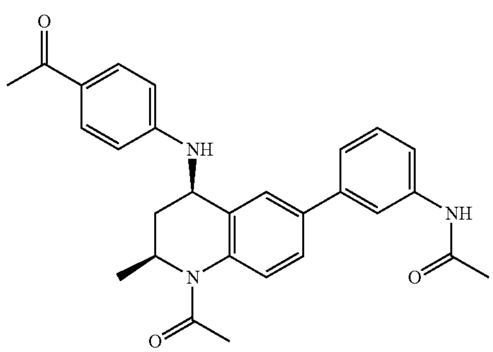 [SMILES: CC(=O)Nc1cccc(-c2ccc3c(c2)[C@H](Nc2ccc(C(C)=O)cc2)C[C@H](C)N3C(C)=O)c1] |
| 18 | 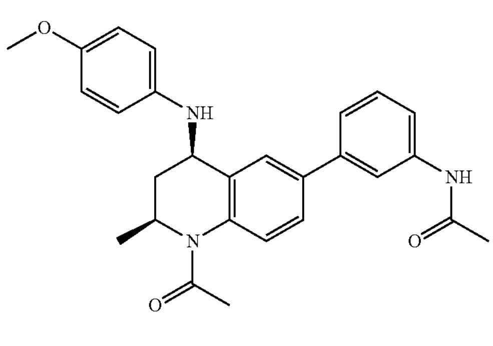 [SMILES: COc1ccc(N[C@@H]2C[C@H](C)N(C(C)=O)c3ccc(-c4cccc(NC(C)=O)c4)cc32)cc1] |

TABLE 1-continued

| No. | Structure |
|---|---|
| 19 | 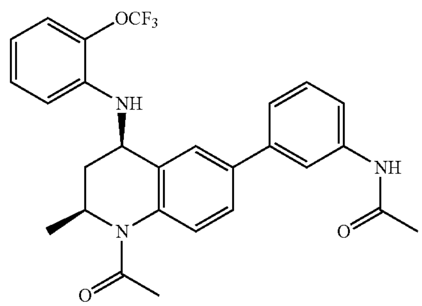 [SMILES: CC(=O)Nc1cccc(-c2ccc3c(c2)[C@H](Nc2ccccc2OC(F)(F)F)C[C@H](C)N3C(C)=O)c1] |
| 20 | 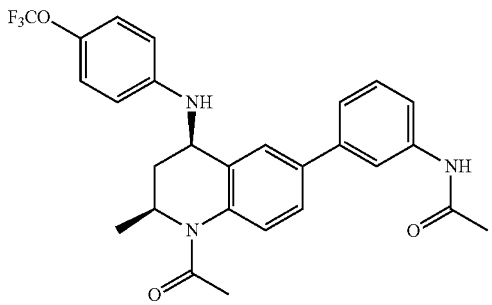 [SMILES: CC(=O)Nc1cccc(-c2ccc3c(c2)[C@H](Nc2ccc(OC(F)(F)F)cc2)C[C@H](C)N3C(C)=O)c1] |
| 21 | 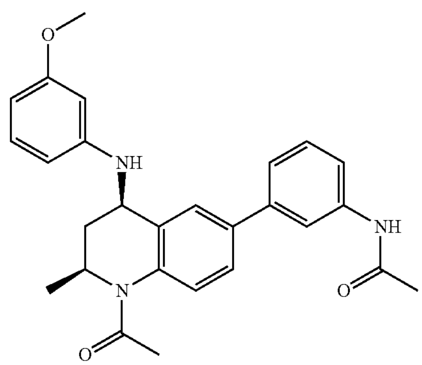 [SMILES: COc1cccc(N[C@@H]2C[C@H](C)N(C(C)=O)c3ccc(-c4cccc(NC(C)=O)c4)cc32)c1] |
| 22 | 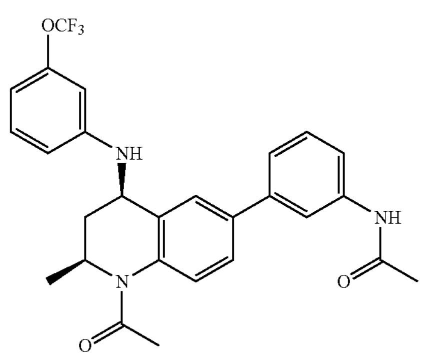 [SMILES: CC(=O)Nc1cccc(-c2ccc3c(c2)[C@H](Nc2cccc(OC(F)(F)F)c2)C[C@H](C)N3C(C)=O)c1] |

TABLE 1-continued
| No. | Structure |
|---|---|
| 23 | 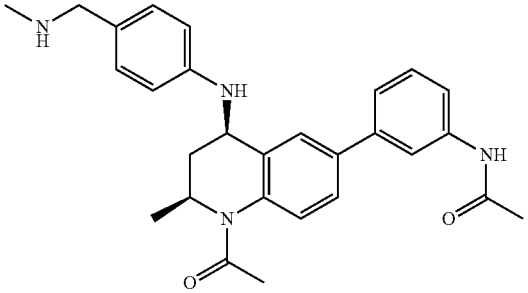 [SMILES: CNCc1ccc(N[C@@H]2C[C@H](C)N(C(C)=O)c3ccc(-c4cccc(NC(C)=O)c4)cc32)cc1] |
| 24 | 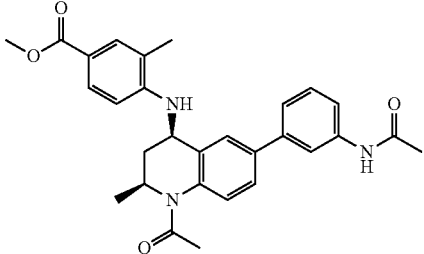 [SMILES: COC(=O)c1ccc(N[C@@H]2C[C@H](C)N(C(C)=O)c3ccc(-c4cccc(NC(C)=O)c4)cc32)c(C)c1] |
| 25 | 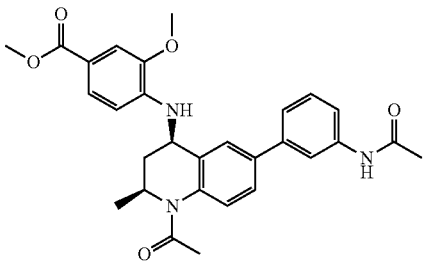 [SMILES: COC(=O)c1ccc(N[C@@H]2C[C@H](C)N(C(C)=O)c3ccc(-c4cccc(NC(C)=O)c4)cc32)c(OC)c1] |
| 26 | 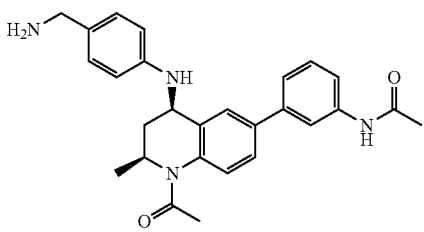 [SMILES: CC(=O)Nc1cccc(-c2ccc3c(c2)[C@H](Nc2ccc(CN)cc2)C[C@H](C)N3C(C)=O)c1] |
| 27 | 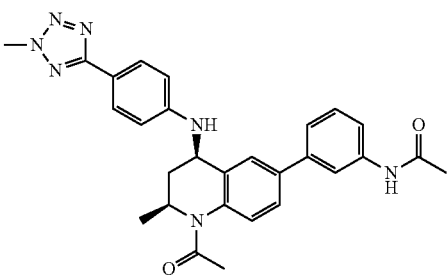 [SMILES: CC(=O)Nc1cccc(-c2ccc3c(c2)[C@H](Nc2ccc(-c4nnn(C)n4)cc2)C[C@H](C)N3C(C)=O)c1] |

TABLE 1-continued
| No. | Structure |
|-----|-----------|
| 28 | 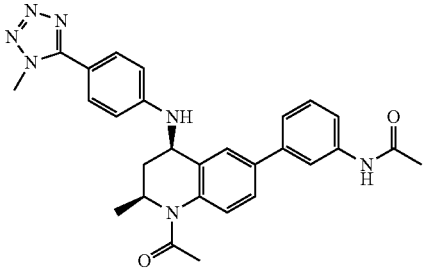 [SMILES: CC(=O)Nc1cccc(-c2ccc3c(c2)[C@H](Nc2ccc(-c4nnnn4C)cc2)C[C@H](C)N3C(C)=O)c1] |
| 29 | 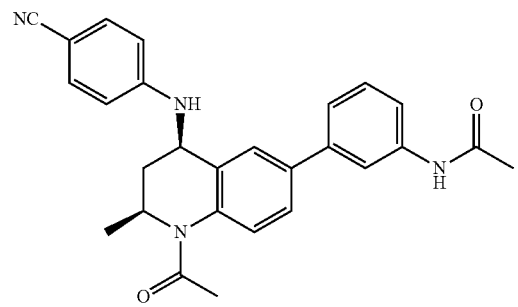 [SMILES: CC(=O)Nc1cccc(-c2ccc3c(c2)[C@H](Nc2ccc(C#N)cc2)C[C@H](C)N3C(C)=O)c1] |
| 30 | 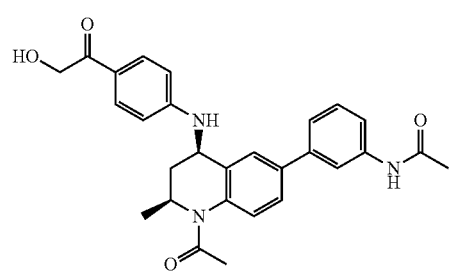 [SMILES: CC(=O)Nc1cccc(-c2ccc3c(c2)[C@H](Nc2ccc(C(=O)CO)cc2)C[C@H](C)N3C(C)=O)c1] |
| 31 | 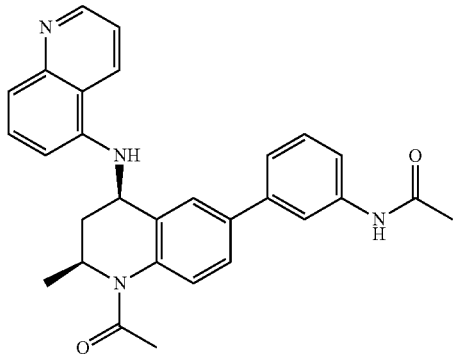 |
| 32 | 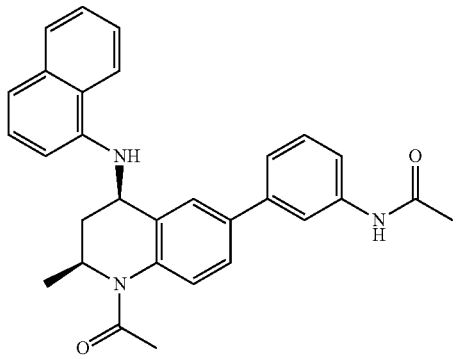 |

TABLE 1-continued

| No. | Structure |
|---|---|
| 33 | 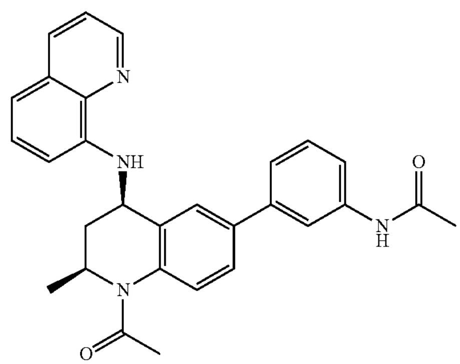 |
| 34 | 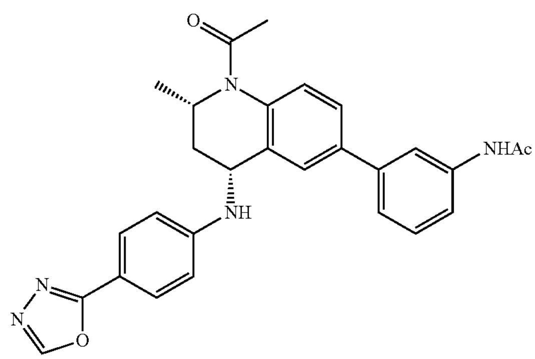 [SMILES: CC(=O)Nc1cccc(-c2ccc3c(c2)[C@H](Nc2ccc(-c4nnco4)cc2)C[C@H](C)N3C(C)=O)c1] |
| 35 | 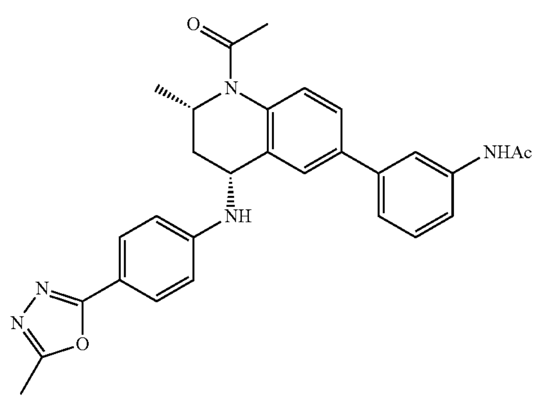 [SMILES: CC(=O)Nc1cccc(-c2ccc3c(c2)[C@H](Nc2ccc(-c4nnc(C)o4)cc2)C[C@H](C)N3C(C)=O)c1] |
| 36 | 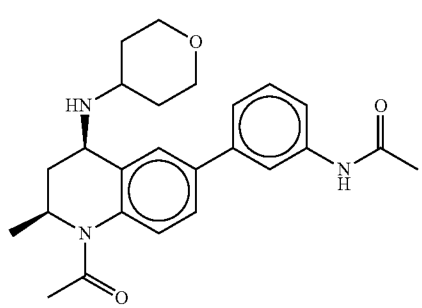 |

TABLE 1-continued

| No. | Structure |
|---|---|
| 37 | 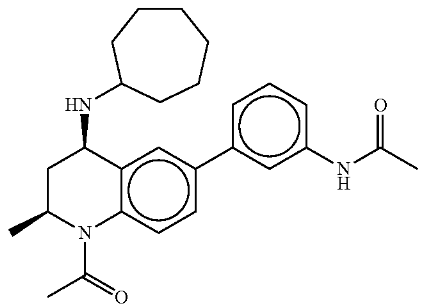 |
| 38 | 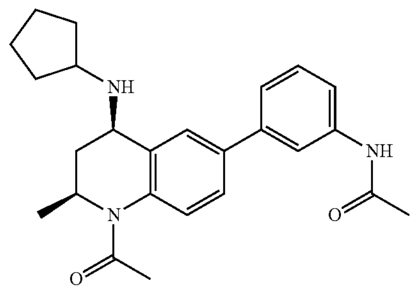 [SMILES: CC(=O)Nc1cccc(-c2ccc3c(c2)[C@H](NC2CCCC2)C[C@H](C)N3C(C)=O)c1] |
| 39 | 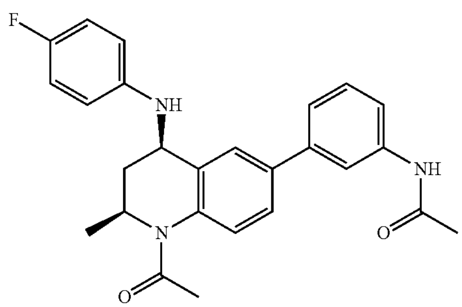 [SMILES: CC(=O)Nc1cccc(-c2ccc3c(c2)[C@H](Nc2ccc(F)cc2)C[C@H](C)N3C(C)=O)c1] |
| 40 | 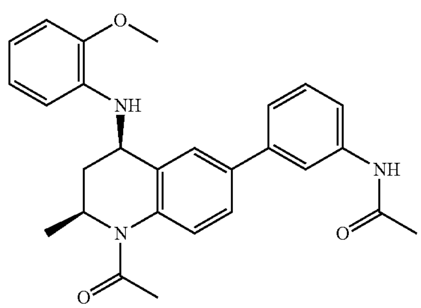 [SMILES: COc1ccccc1N[C@@H]1C[C@H](C)N(C(C)=O)c2ccc(-c3cccc(NC(C)=O)c3)cc21] |
| 41 | 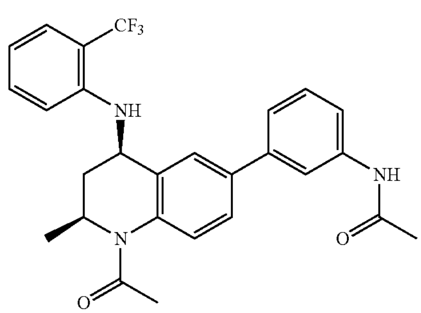 [SMILES: CC(=O)Nc1cccc(-c2ccc3c(c2)[C@H](Nc2ccccc2C(F)(F)F)C[C@H](C)N3C(C)=O)c1] |

TABLE 1-continued
| No. | Structure |
|---|---|
| 42 | 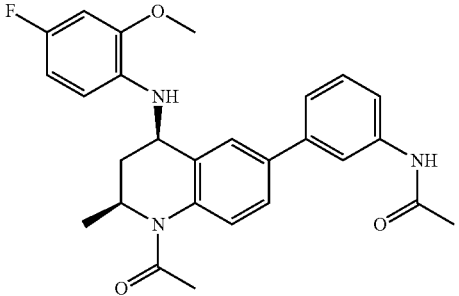 [SMILES: COc1cc(F)ccc1N[C@@H]1C[C@H](C)N(C(C)=O)c2ccc(-c3cccc(NC(C)=O)c3)cc21] |
| 43 | 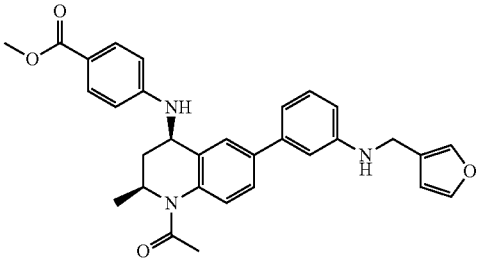 [SMILES: COC(=O)c1ccc(N[C@@H]2C[C@H](C)N(C(C)=O)c3ccc(-c4cccc(NCc5ccoc5)c4)cc32)cc1] |
| 44 | 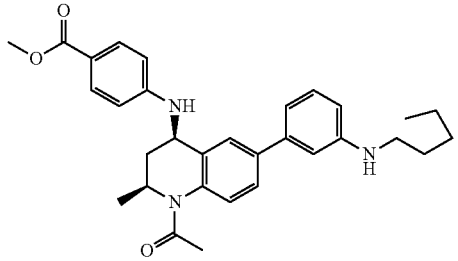 [SMILES: CCCCCNc1cccc(-c2ccc3c(c2)[C@H](Nc2ccc(C(=O)OC)cc2)C[C@H](C)N3C(C)=O)c1] |
| 45 | 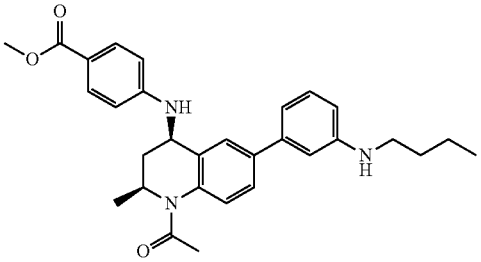 [SMILES: CCCCNc1cccc(-c2ccc3c(c2)[C@H](Nc2ccc(C(=O)OC)cc2)C[C@H](C)N3C(C)=O)c1] |
| 46 | 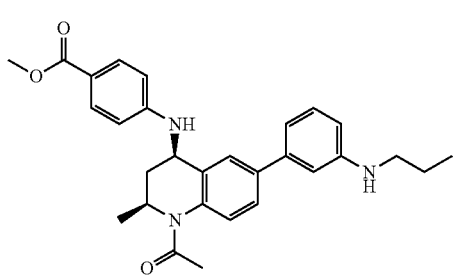 [SMILES: CCCNc1cccc(-c2ccc3c(c2)[C@H](Nc2ccc(C(=O)OC)cc2)C[C@H](C)N3C(C)=O)c1] |

TABLE 1-continued
| No. | Structure |
|---|---|
| 47 | 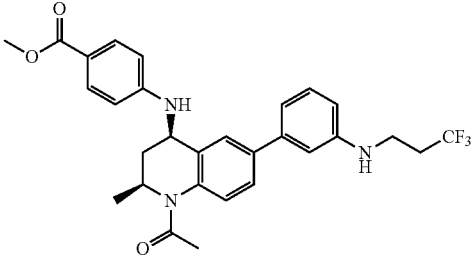 [SMILES: COC(=O)c1ccc(N[C@@H]2C[C@H](C)N(C(C)=O)c3ccc(-c4cccc(NCCC(F)(F)F)c4)cc32)cc1] |
| 48 | 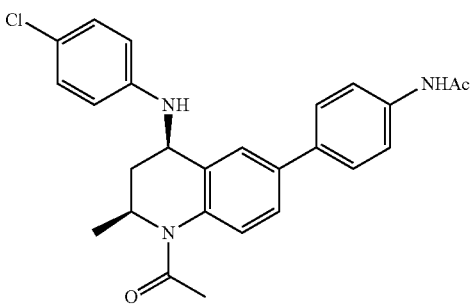 [SMILES: CC(=O)Nc1ccc(-c2ccc3c(c2)[C@H](Nc2ccc(Cl)cc2)C[C@H](C)N3C(C)=O)cc1] |
| 49 | 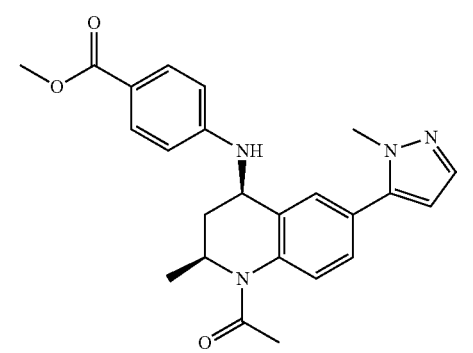 [SMILES: COC(=O)c1ccc(N[C@@H]2C[C@H](C)N(C(C)=O)c3ccc(-c4ccnn4C)cc32)cc1] |
| 50 | 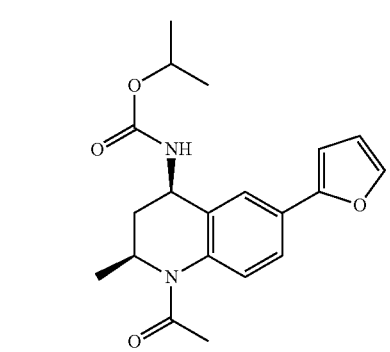 [SMILES: CC(=O)N1c2ccc(-c3cccs3)cc2[C@H](NC(=O)OC(C)C)C[C@@H]1C] |
| 51 | 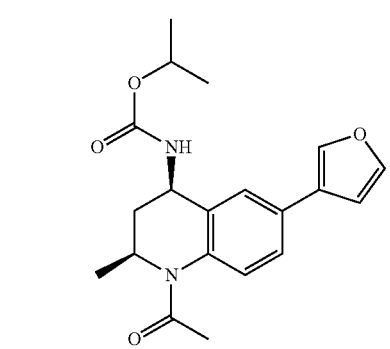 [SMILES: CC(=O)N1c2ccc(-c3ccsc3)cc2[C@H](NC(=O)OC(C)C)C[C@@H]1C] |

TABLE 1-continued
| No. | Structure |
|---|---|
| 52 | 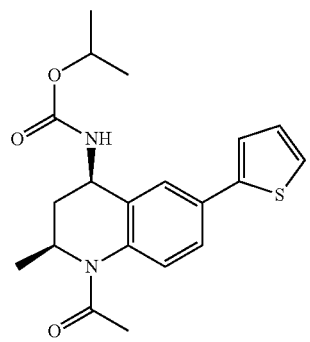 |
| 53 | 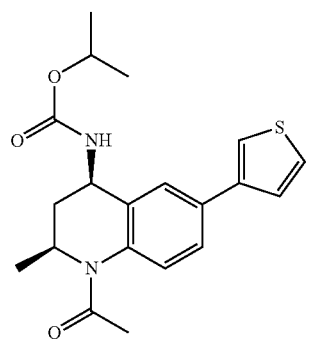 |
| 54 | 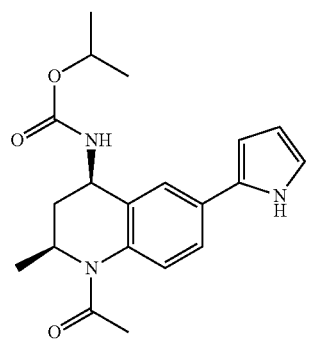 |
| 55 | 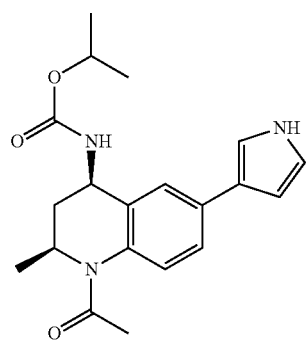 |

TABLE 1-continued

| No. | Structure |
|-----|-----------|
| 56 | 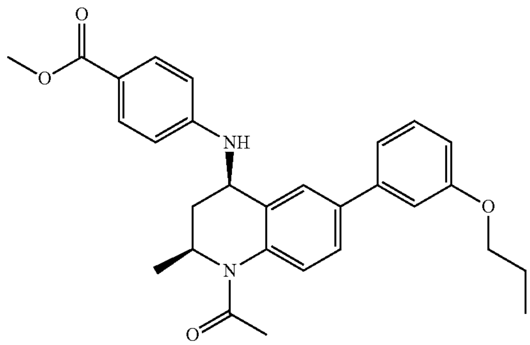 [SMILES: CCCOc1cccc(-c2ccc3c(c2)[C@H](Nc2ccc(C(=O)OC)cc2)C[C@H](C)N3C(C)=O)c1] |
| 57 | 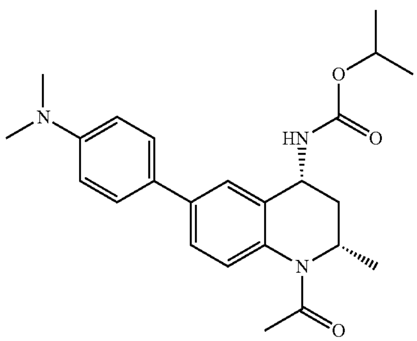 [SMILES: CC(=O)N1c2ccc(-c3ccc(N(C)C)cc3)cc2[C@H](NC(=O)OC(C)C)C[C@@H]1C] |
| 58 | 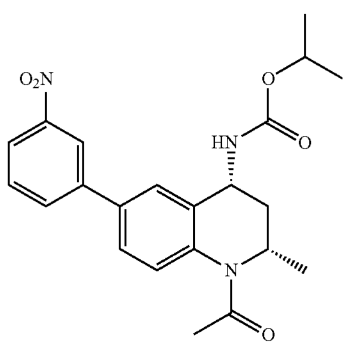 [SMILES: CC(=O)N1c2ccc(-c3cccc([N+](=O)[O-])c3)cc2[C@H](NC(=O)OC(C)C)C[C@@H]1C] |
| 59 | 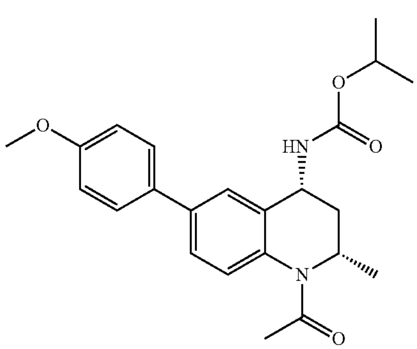 [SMILES: COc1ccc(-c2ccc3c(c2)[C@H](NC(=O)OC(C)C)C[C@H](C)N3C(C)=O)cc1] |

TABLE 1-continued
| No. | Structure |
|---|---|
| 60 | 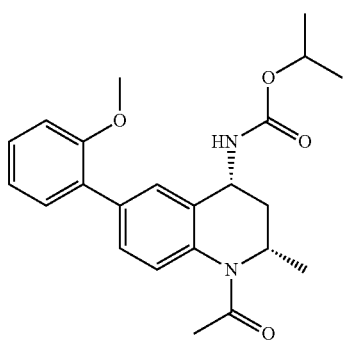 [SMILES: COc1ccccc1-c1ccc2c(c1)[C@H](NC(=O)OC(C)C)C[C@H](C)N2C(C)=O] |
| 61 | 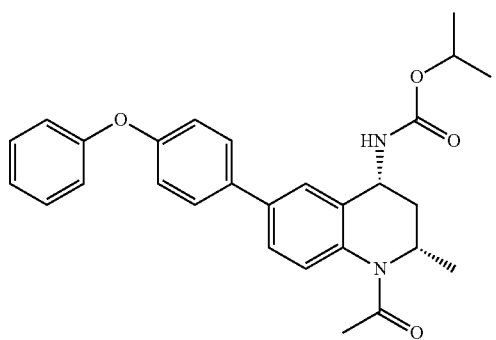 [SMILES: CC(=O)N1c2ccc(-c3ccc(Oc4ccccc4)cc3)cc2[C@H](NC(=O)OC(C)C)C[C@@H]1C] |
| 62 | 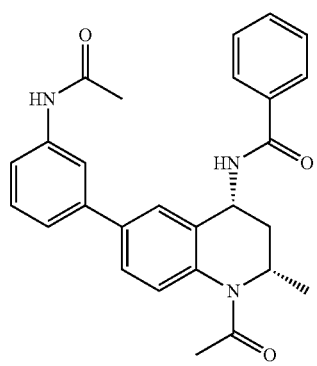 [SMILES: CC(=O)Nc1cccc(-c2ccc3c(c2)[C@H](NC(=O)c2ccccc2)C[C@H](C)N3C(C)=O)c1] |
| 63 | 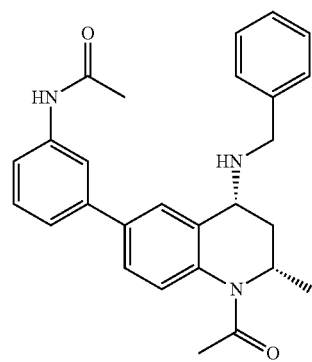 [SMILES: CC(=O)Nc1cccc(-c2ccc3c(c2)[C@H](NCc2ccccc2)C[C@H](C)N3C(C)=O)c1] |

TABLE 1-continued

| No. | Structure |
|-----|-----------|
| 64  | 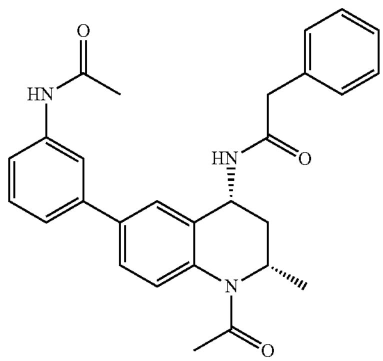 [SMILES: CC(=O)Nc1cccc(-c2ccc3c(c2)[C@H](NC(=O)Cc2ccccc2)C[C@H](C)N3C(C)=O)c1]          |
| 65  | 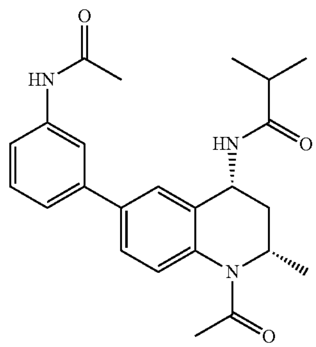 [SMILES: CC(=O)Nc1cccc(-c2ccc3c(c2)[C@H](NC(=O)C(C)C)C[C@H](C)N3C(C)=O)c1]          |
| 66  | 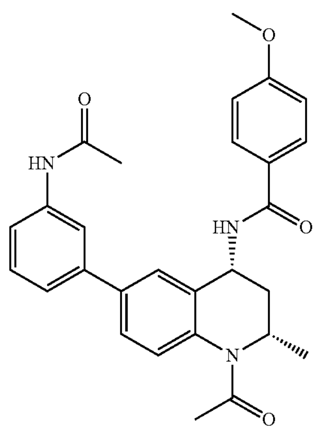 [SMILES: COc1ccc(C(=O)N[C@@H]2C[C@H](C)N(C(C)=O)c3ccc(-c4cccc(NC(C)=O)c4)cc32)cc1]          |
| 67  | 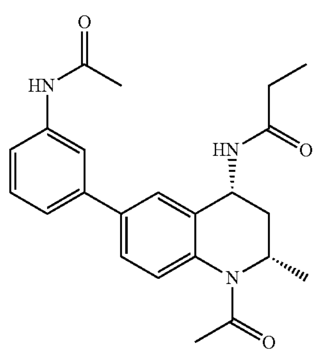 [SMILES: CCC(=O)N[C@@H]1C[C@H](C)N(C(C)=O)c2ccc(-c3cccc(NC(C)=O)c3)cc21]          |

TABLE 1-continued
| No. | Structure |
|---|---|
| 68 | 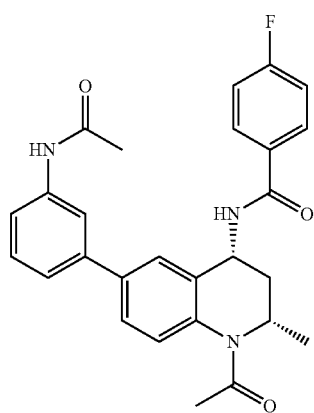 [SMILES: CC(=O)Nc1cccc(-c2ccc3c(c2)[C@H](NC(=O)c2ccc(F)cc2)C[C@H](C)N3C(C)=O)c1] |
| 69 | 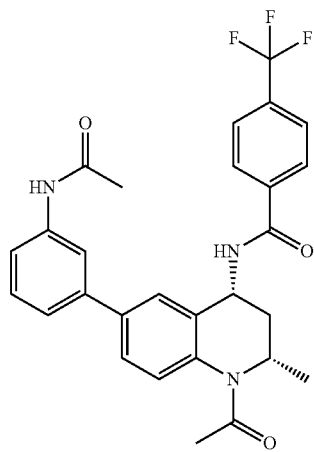 [SMILES: CC(=O)Nc1cccc(-c2ccc3c(c2)[C@H](NC(=O)c2ccc(C(F)(F)F)cc2)C[C@H](C)N3C(C)=O)c1] |
| 70 | 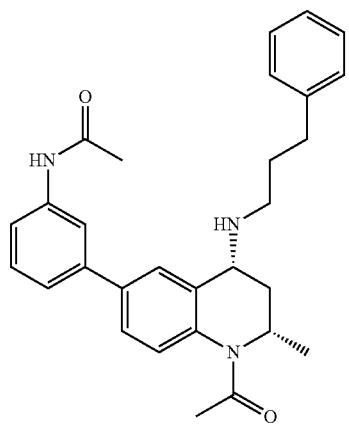 [SMILES: CC(=O)Nc1cccc(-c2ccc3c(c2)[C@H](NCCCc2ccccc2)C[C@H](C)N3C(C)=O)c1] |

TABLE 1-continued

| No. | Structure |
|---|---|
| 71 | 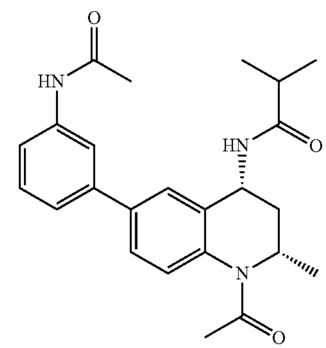 [SMILES: CC(=O)Nc1cccc(-c2ccc3c(c2)[C@H](NC(=O)C(C)C)C[C@H](C)N3C(C)=O)c1] |
| 72 | 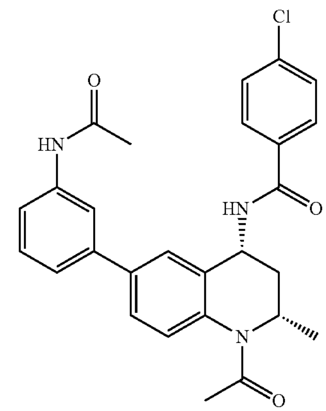 [SMILES: CC(=O)Nc1cccc(-c2ccc3c(c2)[C@H](NC(=O)c2ccc(Cl)cc2)C[C@H](C)N3C(C)=O)c1] |
| 73 | 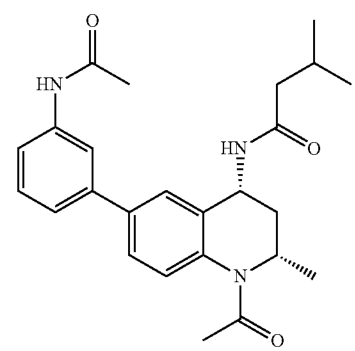 [SMILES: CC(=O)Nc1cccc(-c2ccc3c(c2)[C@H](NC(=O)CC(C)C)C[C@H](C)N3C(C)=O)c1] |
| 74 | 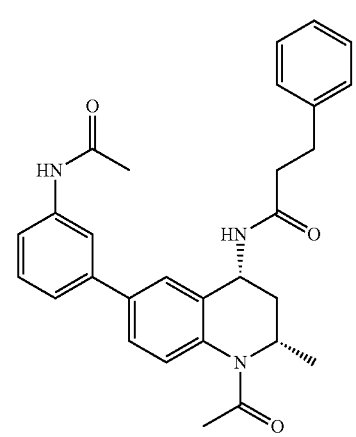 [SMILES: CC(=O)Nc1cccc(-c2ccc3c(c2)[C@H](NC(=O)CCc2ccccc2)C[C@H](C)N3C(C)=O)c1] |

TABLE 1-continued

| No. | Structure |
|---|---|
| 75 | 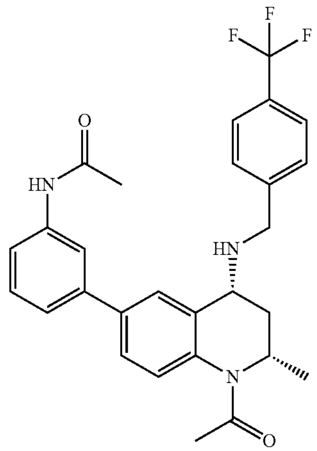 [SMILES: CC(=O)Nc1cccc(-c2ccc3c(c2)[C@H](NCc2ccc(C(F)(F)F)cc2)C[C@H](C)N3C(C)=O)c1] |
| 76 | 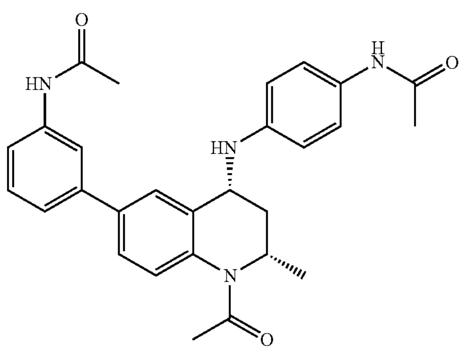 [SMILES: CC(=O)Nc1ccc(N[C@@H]2C[C@H](C)N(C(C)=O)c3ccc(-c4cccc(NC(C)=O)c4)cc32)cc1] |
| 77 | 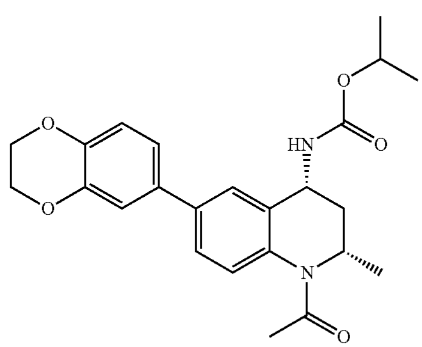 [SMILES: CC(=O)N1c2ccc(-c3ccc4c(c3)OCCO4)cc2[C@H](NC(=O)OC(C)C)C[C@@H]1C] |
| 78 | 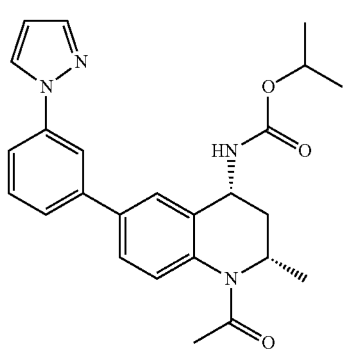 [SMILES: CC(=O)N1c2ccc(-c3cccc(-n4cccn4)c3)cc2[C@H](NC(=O)OC(C)C)C[C@@H]1C] |

TABLE 1-continued
| No. | Structure |
|---|---|
| 79 | 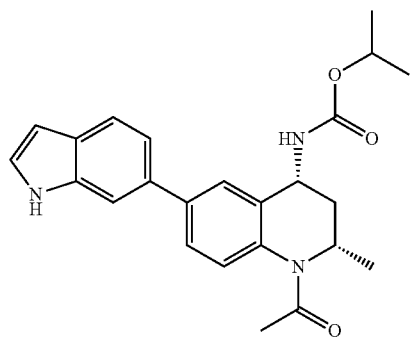 [SMILES: CC(=O)N1c2ccc(-c3ccc4cc[nH]c4c3)cc2[C@H](NC(=O)OC(C)C)C[C@@H]1C] |
| 80 | 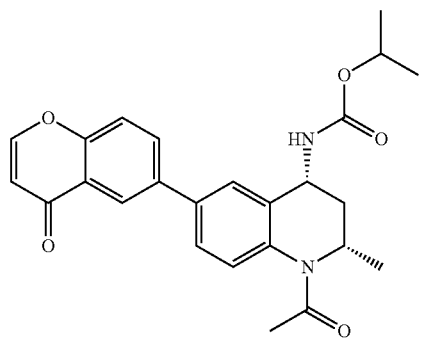 [SMILES: CC(=O)N1c2ccc(-c3ccc4occc(=O)c4c3)cc2[C@H](NC(=O)OC(C)C)C[C@@H]1C] |
| 81 | 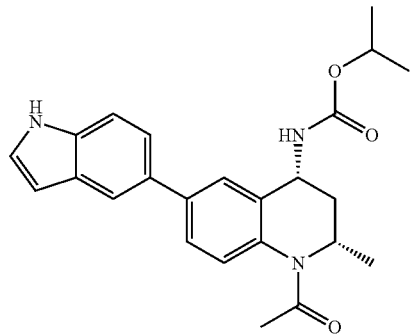 [SMILES: CC(=O)N1c2ccc(-c3ccc4[nH]ccc4c3)cc2[C@H](NC(=O)OC(C)C)C[C@@H]1C] |
| 82 | 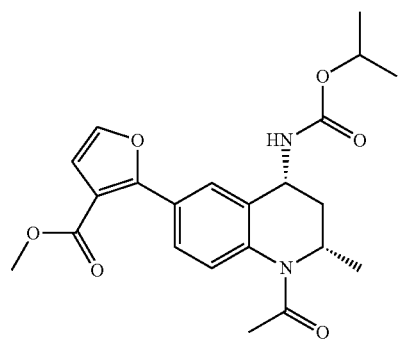 [SMILES: COC(=O)c1ccoc1-c1ccc2c(c1)[C@H](NC(=O)OC(C)C)C[C@H](C)N2C(C)=O] |

TABLE 1-continued

| No. | Structure |
|---|---|
| 83 | 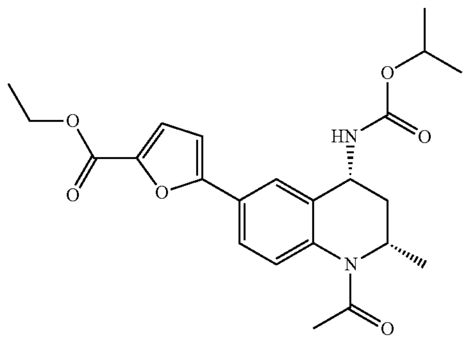 [SMILES: CCOC(=O)c1ccc(-c2ccc3c(c2)[C@H](NC(=O)OC(C)C)C[C@H](C)N3C(C)=O)o1] |
| 84 | 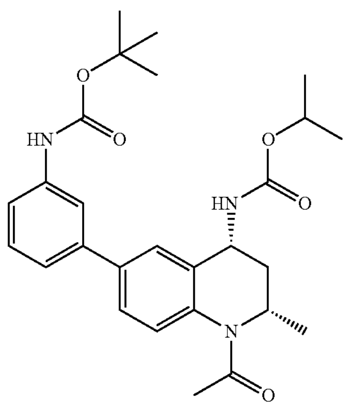 [SMILES: CC(=O)N1c2ccc(-c3cccc(NC(=O)OC(C)(C)C)c3)cc2[C@H](NC(=O)OC(C)C)C[C@@H]1C] |
| 85 | 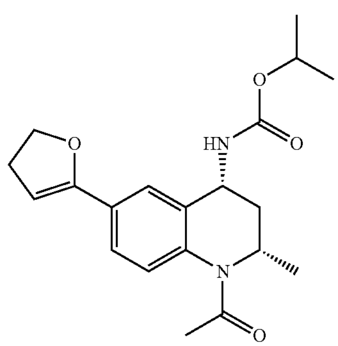 [SMILES: CC(=O)N1c2ccc(C3=CCCO3)cc2[C@H](NC(=O)OC(C)C)C[C@@H]1C] |
| 86 | 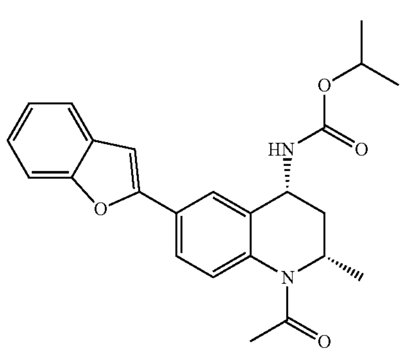 [SMILES: CC(=O)N1c2ccc(-c3cc4ccccc4o3)cc2[C@H](NC(=O)OC(C)C)C[C@@H]1C] |

TABLE 1-continued

| No. | Structure |
|---|---|
| 87 | 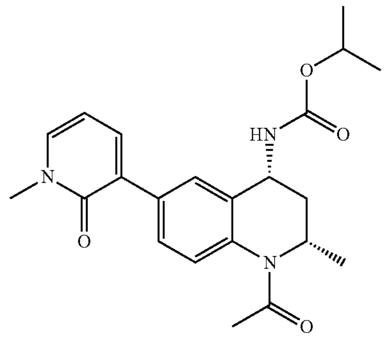 [SMILES: CC(=O)N1c2ccc(-c3cccn(C)c3=O)cc2[C@H](NC(=O)OC(C)C)C[C@@H]1C] |
| 88 | 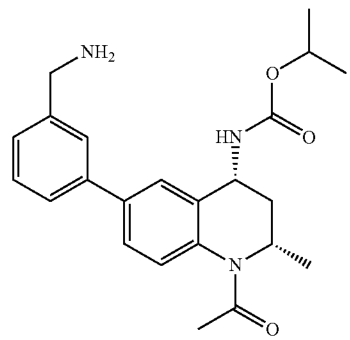 [SMILES: CC(=O)N1c2ccc(-c3cccc(CN)c3)cc2[C@H](NC(=O)OC(C)C)C[C@@H]1C] |
| 89 | 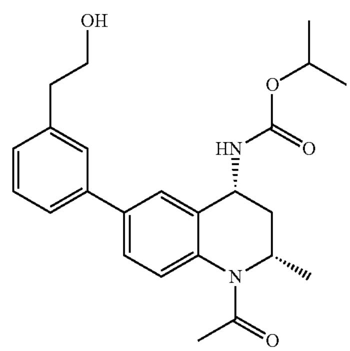 [SMILES: CC(=O)N1c2ccc(-c3cccc(CCO)c3)cc2[C@H](NC(=O)OC(C)C)C[C@@H]1C] |
| 90 | 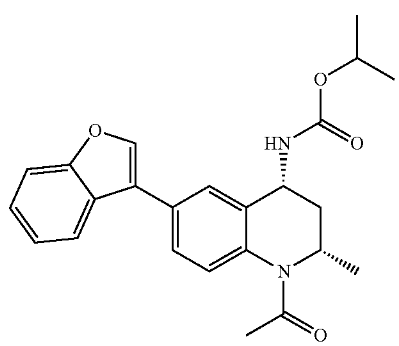 [SMILES: CC(=O)N1c2ccc(-c3coc4ccccc34)cc2[C@H](NC(=O)OC(C)C)C[C@@H]1C] |

TABLE 1-continued

| No. | Structure |
|---|---|
| 91 | 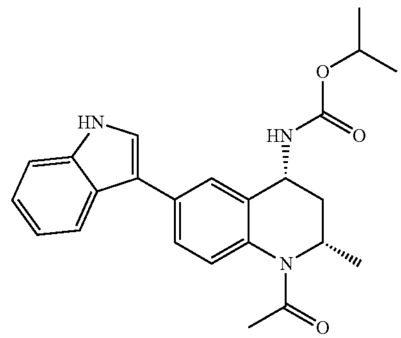 [SMILES: CC(=O)N1c2ccc(-c3c[nH]c4ccccc34)cc2[C@H](NC(=O)OC(C)C)C[C@@H]1C] |
| 92 | 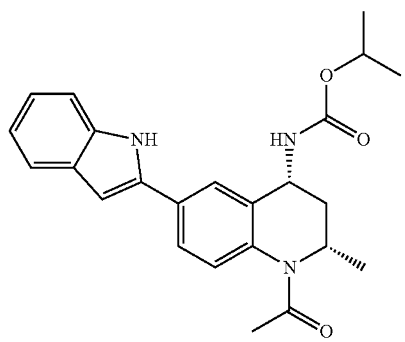 [SMILES: CC(=O)N1c2ccc(-c3cc4ccccc4[nH]3)cc2[C@H](NC(=O)OC(C)C)C[C@@H]1C] |
| 93 | 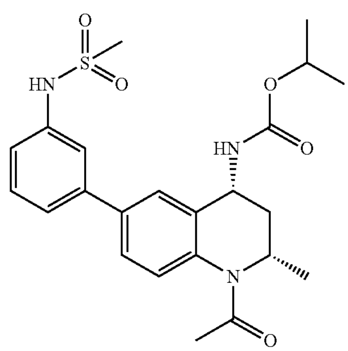 [SMILES: CC(=O)N1c2ccc(-c3cccc(NS(C)(=O)=O)c3)cc2[C@H](NC(=O)OC(C)C)C[C@@H]1C] |
| 94 | 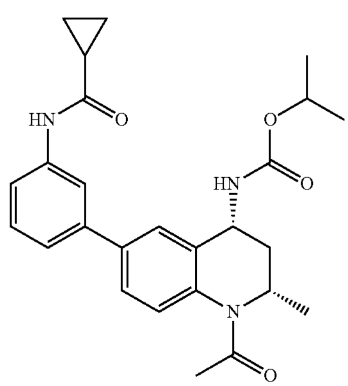 [SMILES: CC(=O)N1c2ccc(-c3cccc(NC(=O)C4CC4)c3)cc2[C@H](NC(=O)OC(C)C)C[C@@H]1C] |

TABLE 1-continued

| No. | Structure |
|---|---|
| 95 | 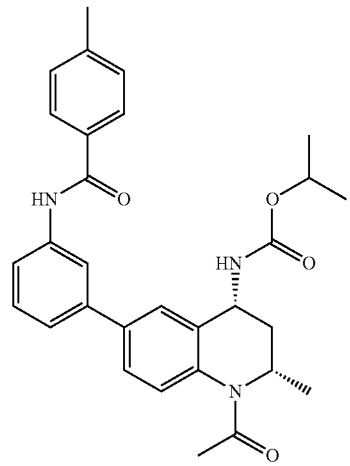 [SMILES: CC(=O)N1c2ccc(-c3cccc(NC(=O)c4ccc(C)cc4)c3)cc2[C@H](NC(=O)OC(C)C)C[C@@H]1C] |
| 96 | 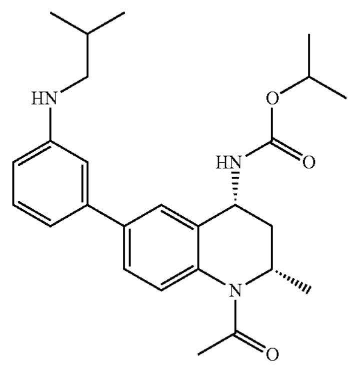 [SMILES: CC(=O)N1c2ccc(-c3cccc(NCC(C)C)c3)cc2[C@H](NC(=O)OC(C)C)C[C@@H]1C] |
| 97 | 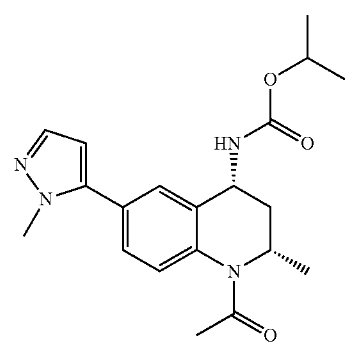 [SMILES: CC(=O)N1c2ccc(-c3ccnn3C)cc2[C@H](NC(=O)OC(C)C)C[C@@H]1C] |
| 98 | 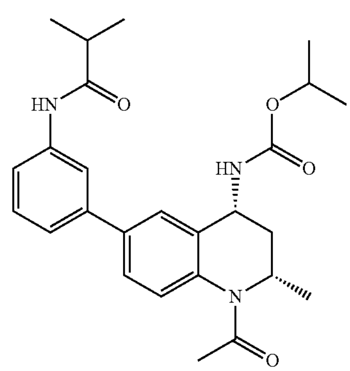 [SMILES: CC(=O)N1c2ccc(-c3cccc(NC(=O)C(C)C)c3)cc2[C@H](NC(=O)OC(C)C)C[C@@H]1C] |

TABLE 1-continued

| No. | Structure |
|---|---|
| 99 | 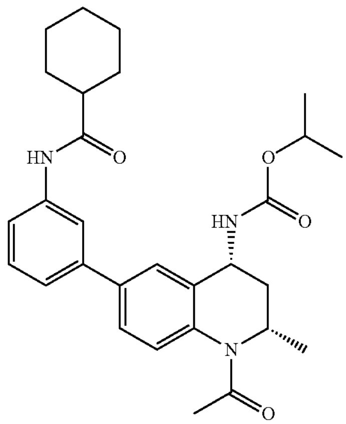 [SMILES: CC(=O)N1c2ccc(-c3cccc(NC(=O)C4CCCCC4)c3)cc2[C@H](NC(=O)OC(C)C)C[C@@H]1C] |
| 100 | 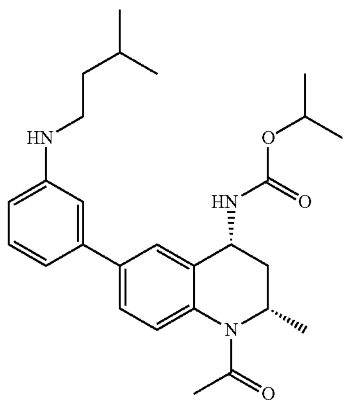 [SMILES: CC(=O)N1c2ccc(-c3cccc(NCCC(C)C)c3)cc2[C@H](NC(=O)OC(C)C)C[C@@H]1C] |
| 101 | 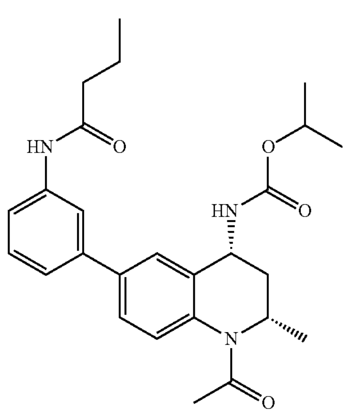 [SMILES: CCCC(=O)Nc1cccc(-c2ccc3c(c2)[C@H](NC(=O)OC(C)C)C[C@H](C)N3C(C)=O)c1] |

TABLE 1-continued

| No. | Structure |
|---|---|
| 102 | 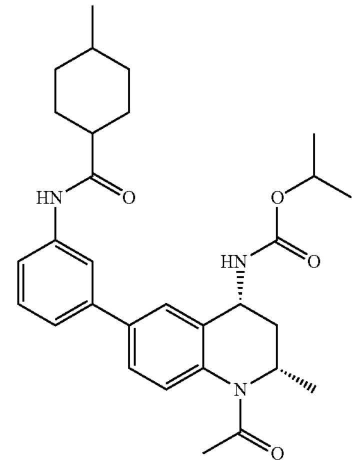 [SMILES: CC(=O)N1c2ccc(-c3cccc(NC(=O)C4CCC(C)CC4)c3)cc2[C@H](NC(=O)OC(C)C)C[C@@H]1C] |
| 103 | 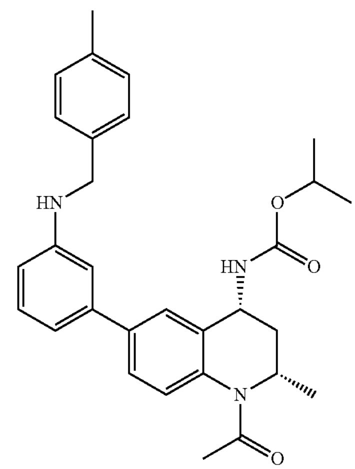 [SMILES: CC(=O)N1c2ccc(-c3cccc(NCc4ccc(C)cc4)c3)cc2[C@H](NC(=O)OC(C)C)C[C@@H]1C] |
| 104 | 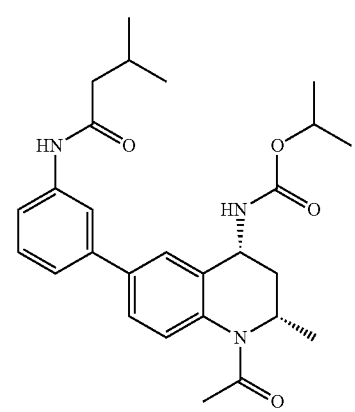 [SMILES: CC(=O)N1c2ccc(-c3cccc(NC(=O)CC(C)C)c3)cc2[C@H](NC(=O)OC(C)C)C[C@@H]1C] |

TABLE 1-continued

| No. | Structure |
|---|---|
| 105 | 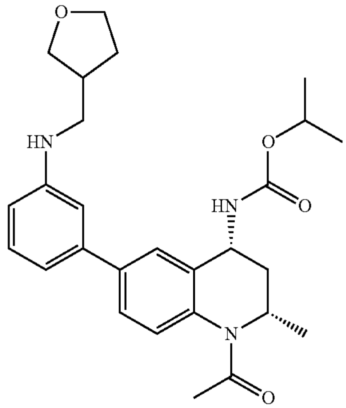 [SMILES: CC(=O)N1c2ccc(-c3cccc(NCC4CCOC4)c3)cc2[C@H](NC(=O)OC(C)C)C[C@@H]1C] |
| 106 | 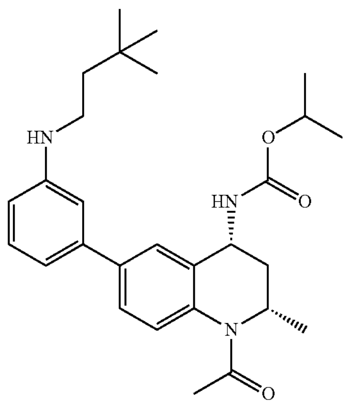 [SMILES: CC(=O)N1c2ccc(-c3cccc(NCCC(C)(C)C)c3)cc2[C@H](NC(=O)OC(C)C)C[C@@H]1C] |
| 107 | 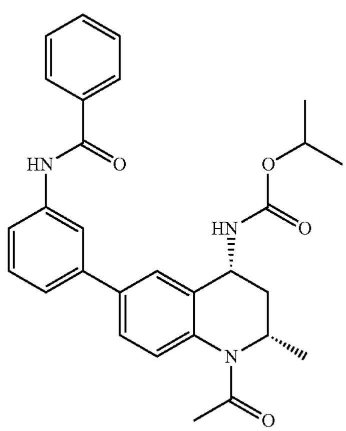 [SMILES: CC(=O)N1c2ccc(-c3cccc(NC(=O)c4ccccc4)c3)cc2[C@H](NC(=O)OC(C)C)C[C@@H]1C] |
| 108 | 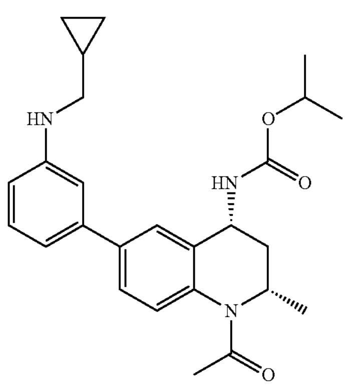 [SMILES: CC(=O)N1c2ccc(-c3cccc(NCC4CC4)c3)cc2[C@H](NC(=O)OC(C)C)C[C@@H]1C] |

TABLE 1-continued
| No. | Structure |
|-----|-----------|
| 109 | 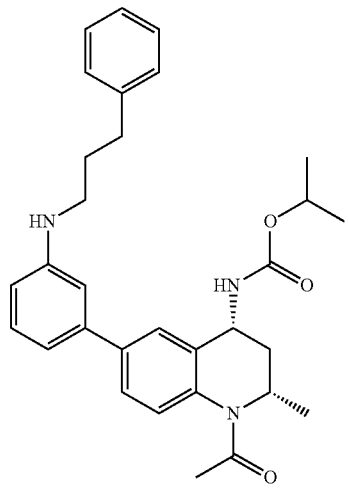 [SMILES: CC(=O)N1c2ccc(-c3cccc(NCCCc4ccccc4)c3)cc2[C@H](NC(=O)OC(C)C)C[C@@H]1C] |
| 110 | 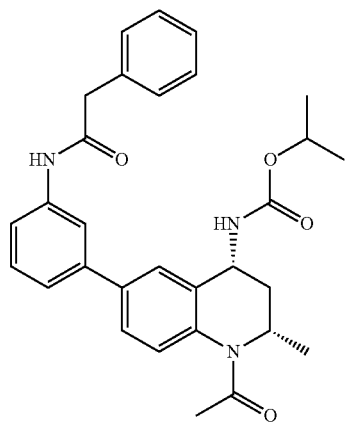 [SMILES: CC(=O)N1c2ccc(-c3cccc(NC(=O)Cc4ccccc4)c3)cc2[C@H](NC(=O)OC(C)C)C[C@@H]1C] |
| 111 | 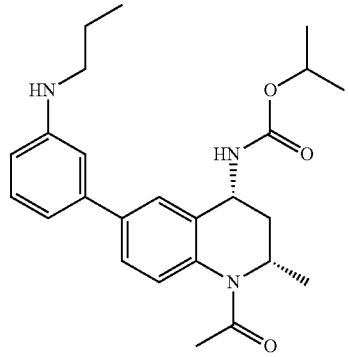 [SMILES: CCCNc1cccc(-c2ccc3c(c2)[C@H](NC(=O)OC(C)C)C[C@H](C)N3C(C)=O)c1] |

TABLE 1-continued
| No. | Structure |
|---|---|
| 112 | 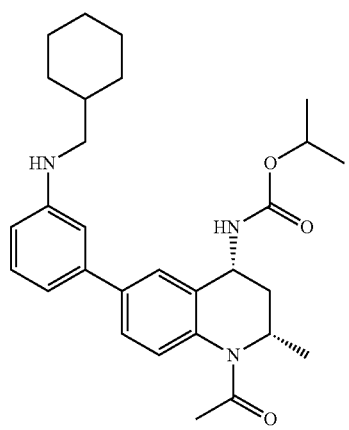 [SMILES: CC(=O)N1c2ccc(-c3cccc(NCC4CCCCC4)c3)cc2[C@H](NC(=O)OC(C)C)C[C@@H]1C] |
| 113 | 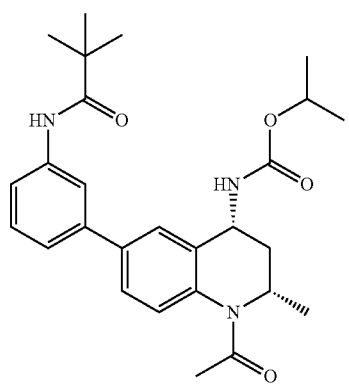 [SMILES: CC(=O)N1c2ccc(-c3cccc(NC(=O)C(C)(C)C)c3)cc2[C@H](NC(=O)OC(C)C)C[C@@H]1C] |
| 114 | 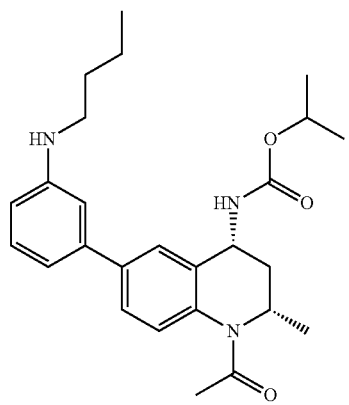 [SMILES: CCCCNc1cccc(-c2ccc3c(c2)[C@H](NC(=O)OC(C)C)C[C@H](C)N3C(C)=O)c1] |
| 115 | 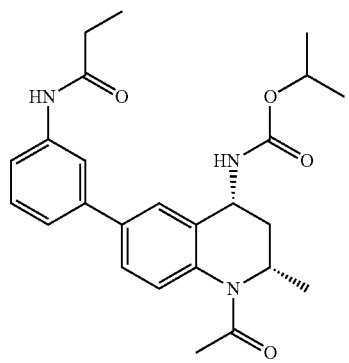 [SMILES: CCC(=O)Nc1cccc(-c2ccc3c(c2)[C@H](NC(=O)OC(C)C)C[C@H](C)N3C(C)=O)c1] |

TABLE 1-continued
| No. | Structure |
|---|---|
| 116 | 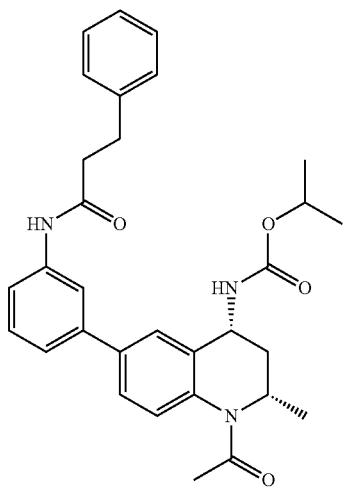 [SMILES: CC(=O)N1c2ccc(-c3cccc(NC(=O)CCc4ccccc4)c3)cc2[C@H](NC(=O)OC(C)C)C[C@@H]1C] |
| 117 | 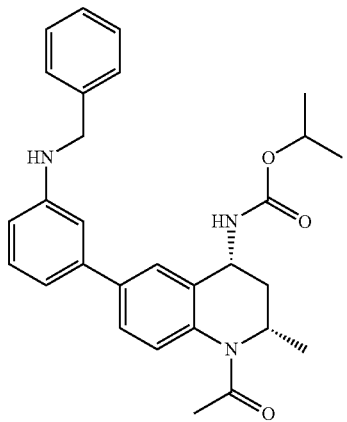 [SMILES: CC(=O)N1c2ccc(-c3cccc(NCc4ccccc4)c3)cc2[C@H](NC(=O)OC(C)C)C[C@@H]1C] |
| 118 | 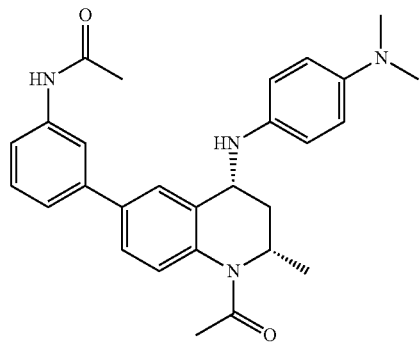 [SMILES: CC(=O)Nc1cccc(-c2ccc3c(c2)[C@H](Nc2ccc(N(C)C)cc2)C[C@H](C)N3C(C)=O)c1] |
| 119 | 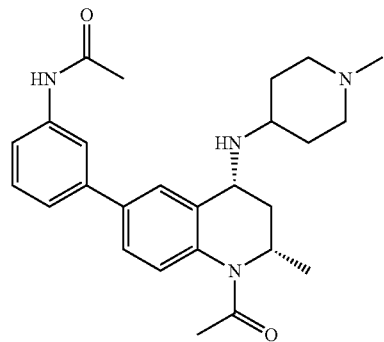 [SMILES: CC(=O)Nc1cccc(-c2ccc3c(c2)[C@H](NC2CCN(C)CC2)C[C@H](C)N3C(C)=O)c1] |

TABLE 1-continued

| No. | Structure |
|-----|-----------|
| 120 | 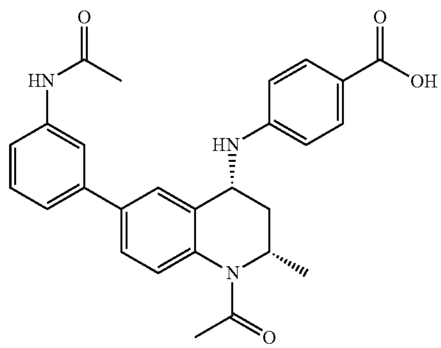 [SMILES: CC(=O)Nc1cccc(-c2ccc3c(c2)[C@H](Nc2ccc(C(=O)O)cc2)C[C@H](C)N3C(C)=O)c1] |
| 121 | 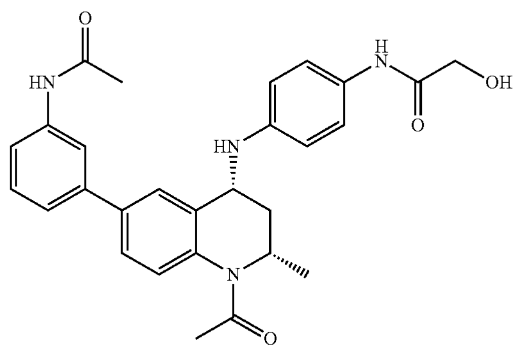 [SMILES: CC(=O)Nc1cccc(-c2ccc3c(c2)[C@H](Nc2ccc(NC(=O)CO)cc2)C[C@H](C)N3C(C)=O)c1] |
| 122 | 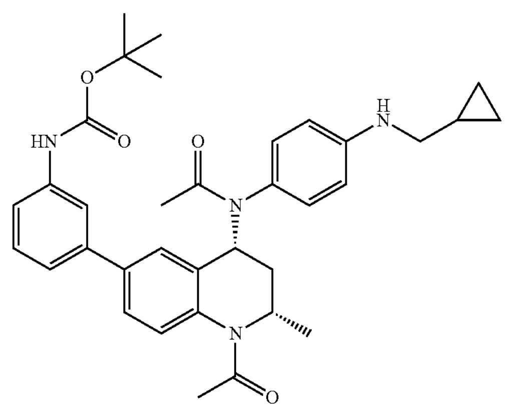 [SMILES: CC(=O)N(c1ccc(NCC2CC2)cc1)[C@@H]1C[C@H](C)N(C(C)=O)c2ccc(-c3cccc(NC(=O)OC(C)(C)C)c3)cc21] |
| 123 | 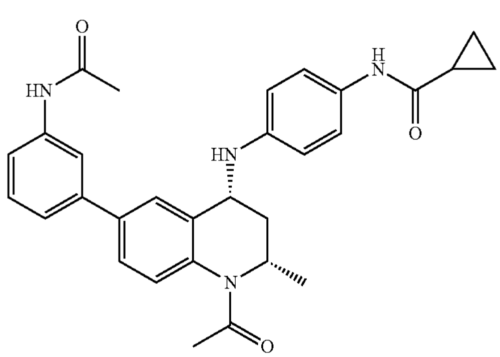 [SMILES: CC(=O)Nc1cccc(-c2ccc3c(c2)[C@H](Nc2ccc(NC(=O)C4CC4)cc2)C[C@H](C)N3C(C)=O)c1] |

TABLE 1-continued

| No. | Structure |
|---|---|
| 124 | 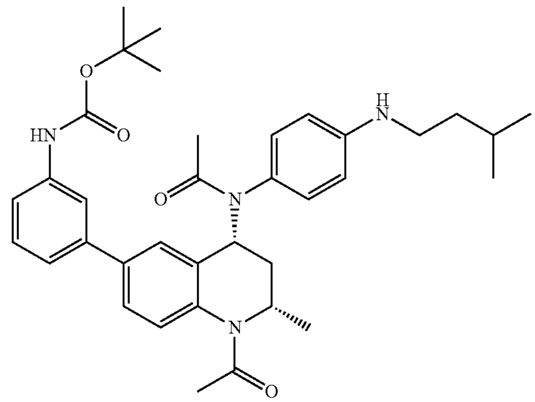 [SMILES: CC(=O)N(c1ccc(NCCC(C)C)cc1)[C@@H]1C[C@H](C)N(C(C)=O)c2ccc(-c3cccc(NC(=O)OC(C)(C)C)c3)cc21] |
| 125 | 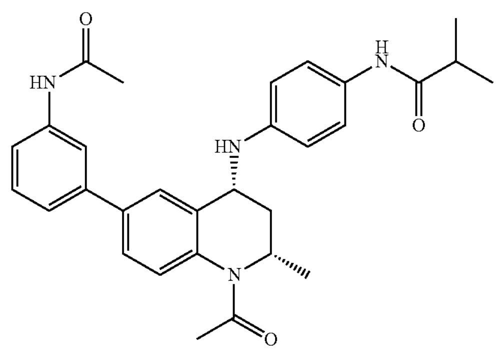 [SMILES: CC(=O)Nc1cccc(-c2ccc3c(c2)[C@H](Nc2ccc(NC(=O)C(C)C)cc2)C[C@H](C)N3C(C)=O)c1] |
| 126 | 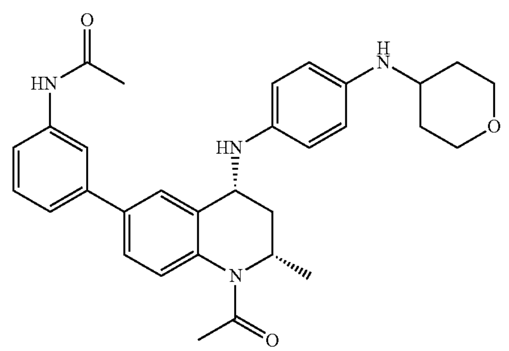 [SMILES: CC(=O)Nc1cccc(-c2ccc3c(c2)[C@H](Nc2ccc(NC4CCOCC4)cc2)C[C@H](C)N3C(C)=O)c1] |
| 127 | 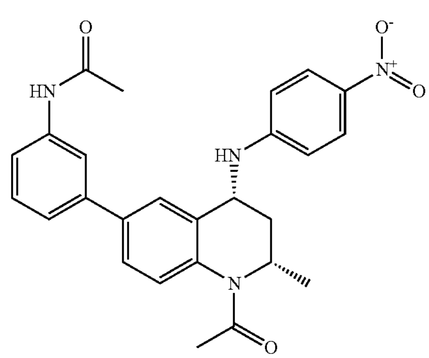 [SMILES: CC(=O)Nc1cccc(-c2ccc3c(c2)[C@H](Nc2ccc([N+](=O)[O-])cc2)C[C@H](C)N3C(C)=O)c1] |

TABLE 1-continued

| No. | Structure |
|---|---|
| 128 | 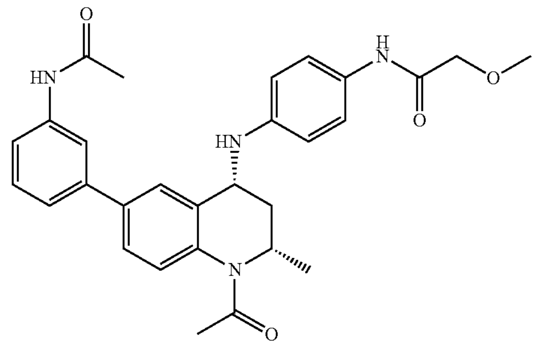 [SMILES: COCC(=O)Nc1ccc(N[C@@H]2C[C@H](C)N(C(C)=O)c3ccc(-c4cccc(NC(C)=O)c4)cc32)cc1] |
| 129 | 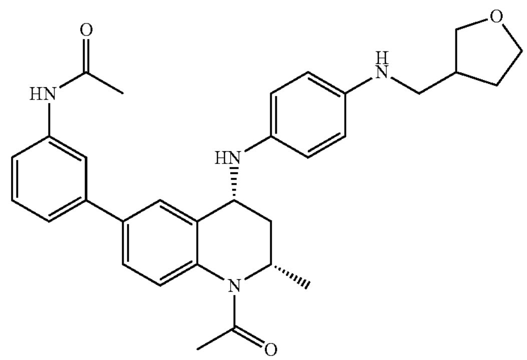 [SMILES: CC(=O)Nc1cccc(-c2ccc3c(c2)[C@H](Nc2ccc(NCC4CCOC4)cc2)C[C@H](C)N3C(C)=O)c1] |
| 130 | 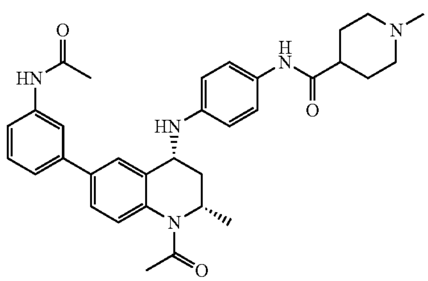 [SMILES: CC(=O)Nc1cccc(-c2ccc3c(c2)[C@H](Nc2ccc(NC(=O)C4CCN(C)CC4)cc2)C[C@H](C)N3C(C)=O)c1] |
| 131 | 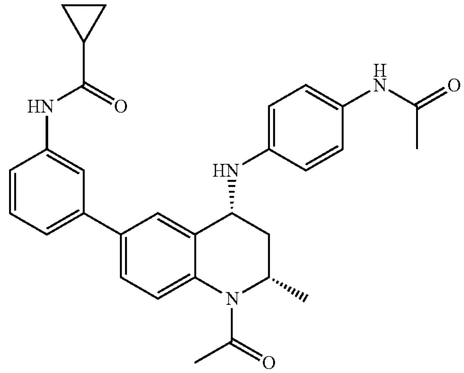 [SMILES: CC(=O)Nc1ccc(N[C@@H]2C[C@H](C)N(C(C)=O)c3ccc(-c4cccc(NC(=O)C5CC5)c4)cc32)cc1] |

TABLE 1-continued
| No. | Structure |
|---|---|
| 132 | 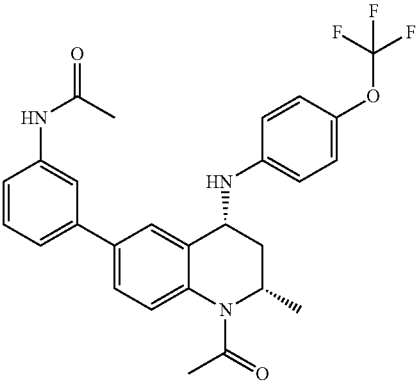 [SMILES: CC(=O)Nc1cccc(-c2ccc3c(c2)[C@H](Nc2ccc(OC(F)(F)F)cc2)C[C@H](C)N3C(C)=O)c1] |
| 133 | 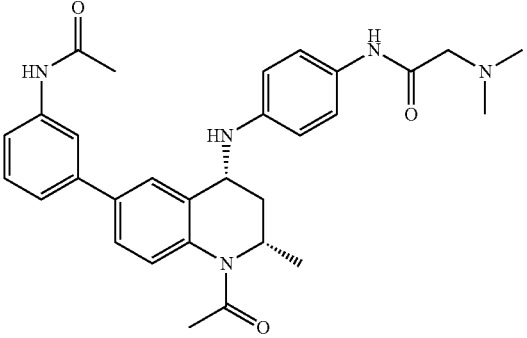 [SMILES: CC(=O)Nc1cccc(-c2ccc3c(c2)[C@H](Nc2ccc(NC(=O)CN(C)C)cc2)C[C@H](C)N3C(C)=O)c1] |
| 134 | 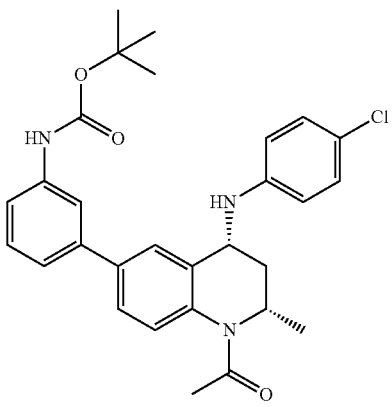 [SMILES: CC(=O)N1c2ccc(-c3cccc(NC(=O)OC(C)(C)C)c3)cc2[C@H](Nc2ccc(Cl)cc2)C[C@@H]1C] |
| 135 | 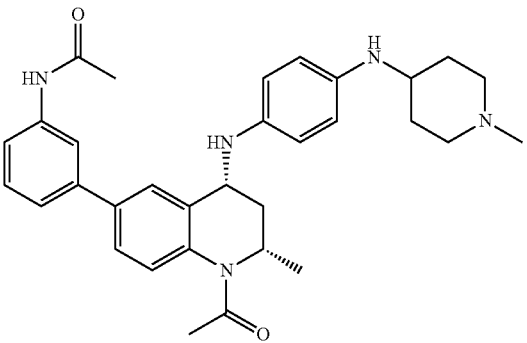 [SMILES: CC(=O)Nc1cccc(-c2ccc3c(c2)[C@H](Nc2ccc(NC4CCN(C)CC4)cc2)C[C@H](C)N3C(C)=O)c1] |

TABLE 1-continued

| No. | Structure |
|-----|-----------|
| 136 | 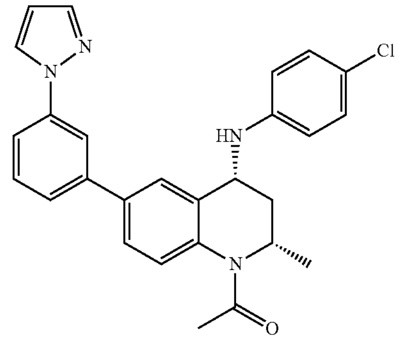 [SMILES: CC(=O)N1c2ccc(-c3cccc(-n4cccn4)c3)cc2[C@H](Nc2ccc(Cl)cc2)C[C@@H]1C] |
| 137 | 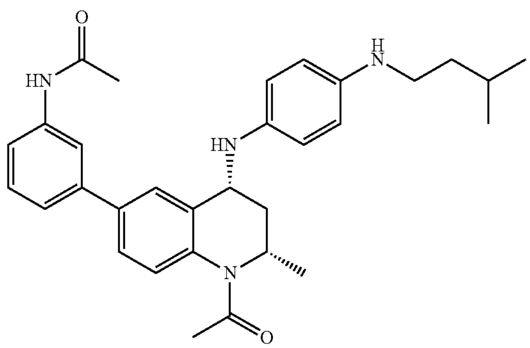 [SMILES: CC(=O)Nc1cccc(-c2ccc3c(c2)[C@H](Nc2ccc(NCCC(C)C)cc2)C[C@H](C)N3C(C)=O)c1] |
| 138 | 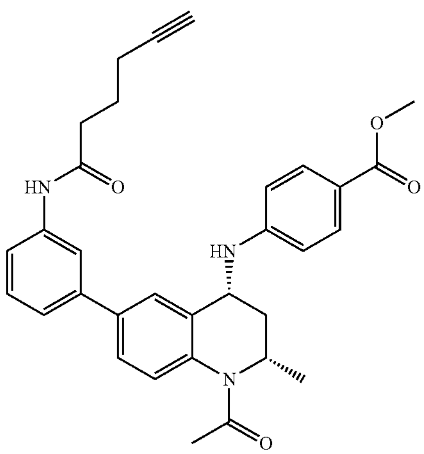 [SMILES: C#CCCCC(=O)Nc1cccc(-c2ccc3c(c2)[C@H](Nc2ccc(C(=O)OC)cc2)C[C@H](C)N3C(C)=O)c1] |
| 139 | 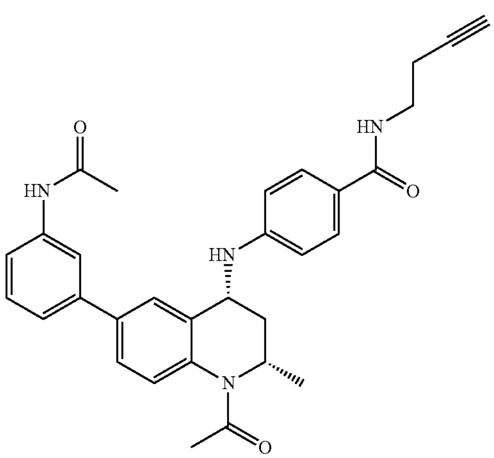 [SMILES: C#CCCNC(=O)c1ccc(N[C@@H]2C[C@H](C)N(C(C)=O)c3ccc(-c4cccc(NC(C)=O)c4)cc32)cc1] |

TABLE 1-continued

| No. | Structure |
|---|---|
| 140 | 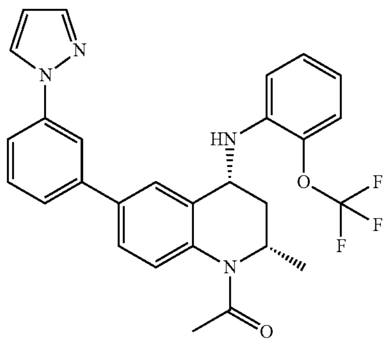 [SMILES: CC(=O)N1c2ccc(-c3cccc(-n4cccn4)c3)cc2[C@H](Nc2ccccc2OC(F)(F)F)C[C@@H]1C] |
| 141 | 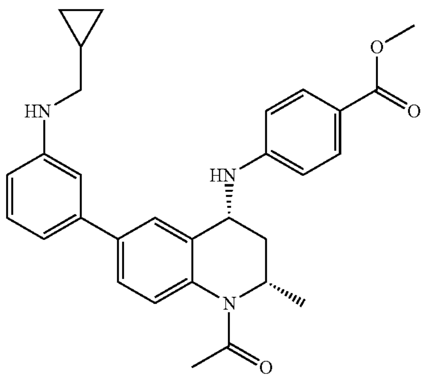 [SMILES: COC(=O)c1ccc(N[C@@H]2C[C@H](C)N(C(C)=O)c3ccc(-c4cccc(NCC5CC5)c4)cc32)cc1] |
| 142 | 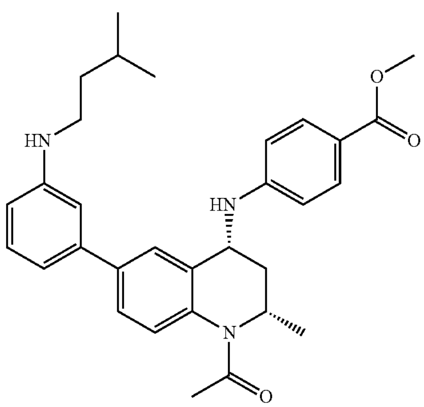 [SMILES: COC(=O)c1ccc(N[C@@H]2C[C@H](C)N(C(C)=O)c3ccc(-c4cccc(NCCC(C)C)c4)cc32)cc1] |
| 143 | 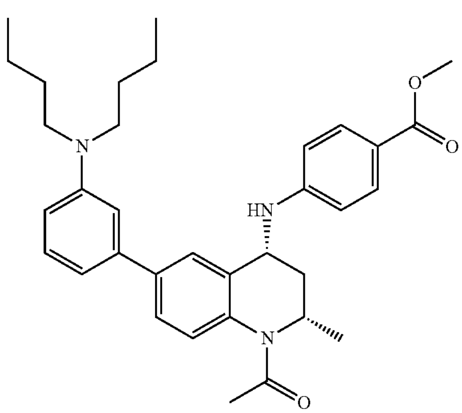 [SMILES: CCCCN(CCCC)c1cccc(-c2ccc3c(c2)[C@H](Nc2ccc(C(=O)OC)cc2)C[C@H](C)N3C(C)=O)c1] |

TABLE 1-continued
| No. | Structure |
|---|---|
| 144 | 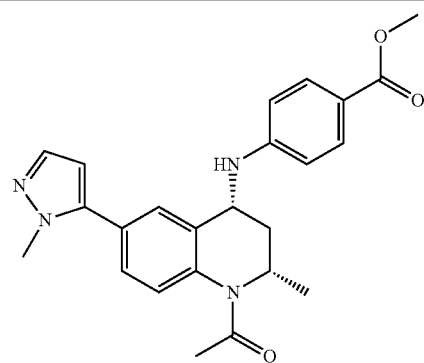 [SMILES: COC(=O)c1ccc(N[C@@H]2C[C@H](C)N(C(C)=O)c3ccc(-c4ccnn4C)cc32)cc1] |
| 145 | 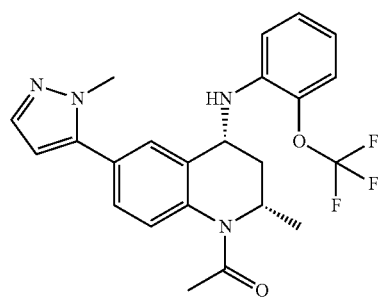 [SMILES: CC(=O)N1c2ccc(-c3ccnn3C)cc2[C@H](Nc2ccccc2OC(F)(F)F)C[C@@H]1C] |
| 146 | 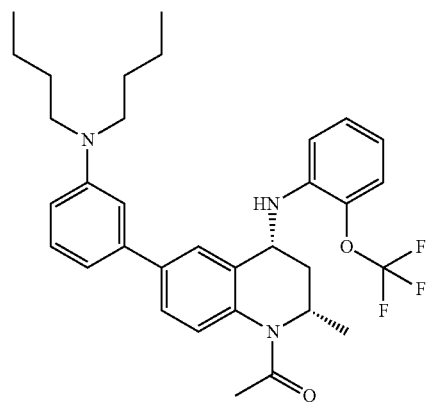 [SMILES: CCCCN(CCCC)c1cccc(-c2ccc3c(c2)[C@H](Nc2ccccc2OC(F)(F)F)C[C@H](C)N3C(C)=O)c1] |
| 147 | 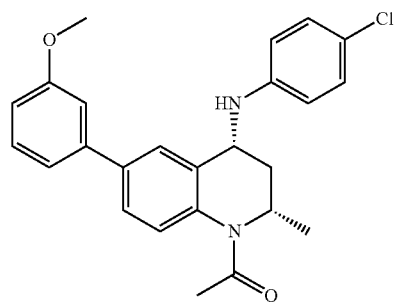 [SMILES: COc1cccc(-c2ccc3c(c2)[C@H](Nc2ccc(Cl)cc2)C[C@H](C)N3C(C)=O)c1] |

TABLE 1-continued

| No. | Structure |
|---|---|
| 148 | 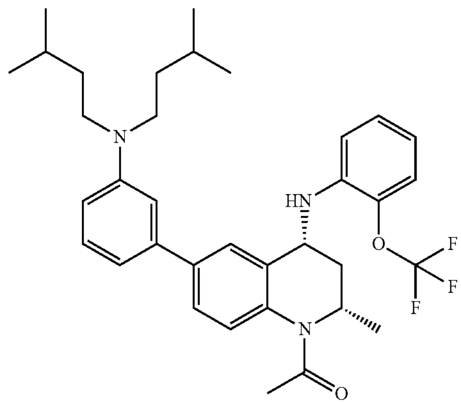 [SMILES: CC(=O)N1c2ccc(-c3cccc(N(CCC(C)C)CCC(C)C)c3)cc2[C@H](Nc2ccccc2OC(F)(F)F)C[C@@H]1C] |
| 149 | 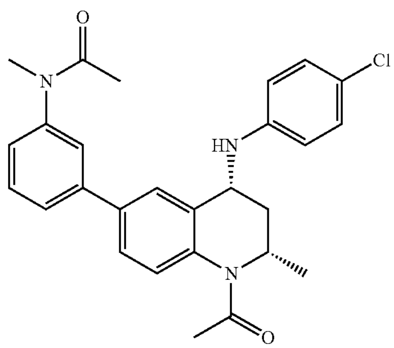 [SMILES: CC(=O)N(C)c1cccc(-c2ccc3c(c2)[C@H](Nc2ccc(Cl)cc2)C[C@H](C)N3C(C)=O)c1] |
| 150 | 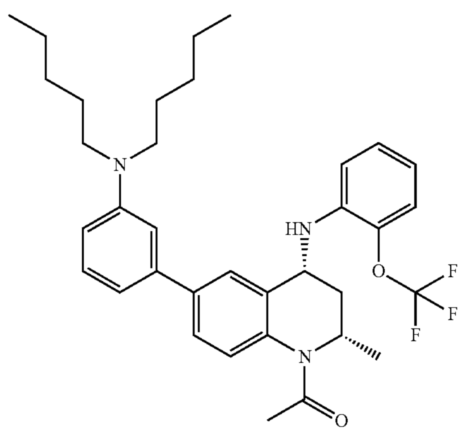 [SMILES: CCCCCN(CCCCC)c1cccc(-c2ccc3c(c2)[C@H](Nc2ccccc2OC(F)(F)F)C[C@H](C)N3C(C)=O)c1] |
| 151 | 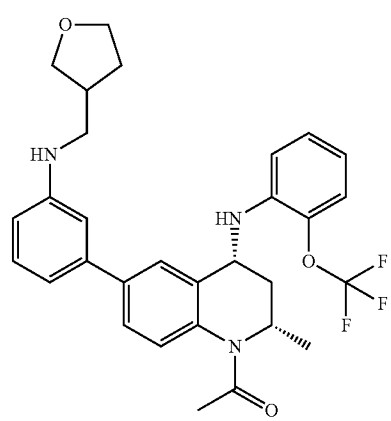 [SMILES: CC(=O)N1c2ccc(-c3cccc(NCC4CCOC4)c3)cc2[C@H](Nc2ccccc2OC(F)(F)F)C[C@@H]1C] |

TABLE 1-continued
| No. | Structure |
|---|---|
| 152 | 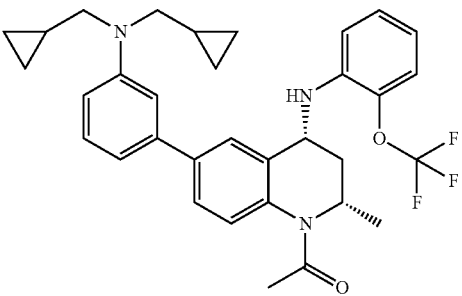 [SMILES: CC(=O)N1c2ccc(-c3cccc(N(CC4CC4)CC4CC4)c3)cc2[C@H](Nc2ccccc2OC(F)(F)F)C[C@@H]1C] |
| 153 | 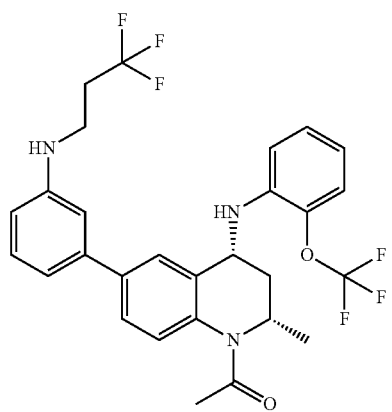 [SMILES: CC(=O)N1c2ccc(-c3cccc(NCCC(F)(F)F)c3)cc2[C@H](Nc2ccccc2OC(F)(F)F)C[C@@H]1C] |
| 154 | 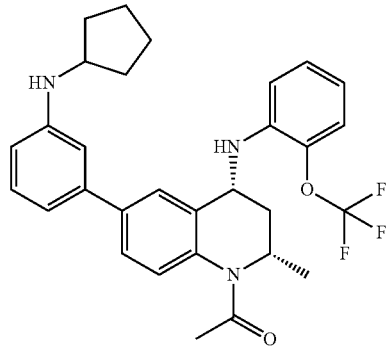 [SMILES: CC(=O)N1c2ccc(-c3cccc(NC4CCCC4)c3)cc2[C@H](Nc2ccccc2OC(F)(F)F)C[C@@H]1C] |
| 155 | 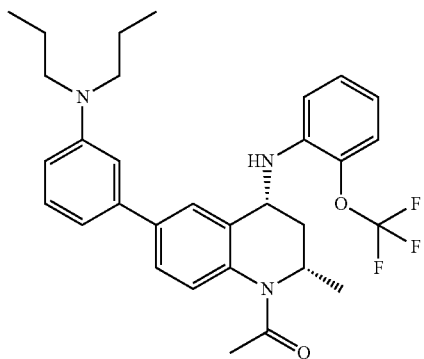 [SMILES: CCCN(CCC)c1cccc(-c2ccc3c(c2)[C@H](Nc2ccccc2OC(F)(F)F)C[C@H](C)N3C(C)=O)c1] |

TABLE 1-continued
| No. | Structure |
|---|---|
| 156 | 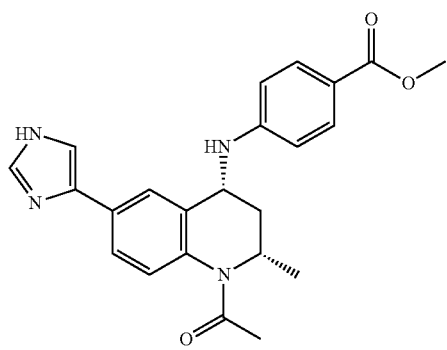 [SMILES: COC(=O)c1ccc(N[C@@H]2C[C@H](C)N(C(C)=O)c3ccc(-c4c[nH]cn4)cc32)cc1] |
| 157 | 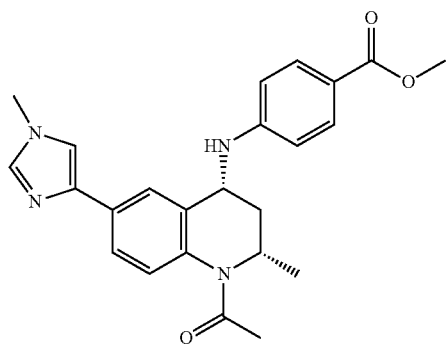 [SMILES: COC(=O)c1ccc(N[C@@H]2C[C@H](C)N(C(C)=O)c3ccc(-c4cn(C)cn4)cc32)cc1] |
| 158 | 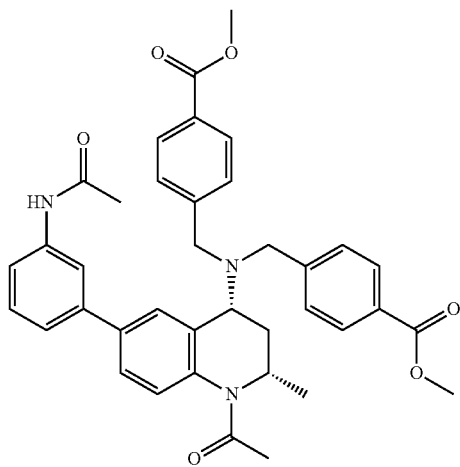 [SMILES: COC(=O)c1ccc(CN(Cc2ccc(C(=O)OC)cc2)[C@@H]2C[C@H](C)N(C(C)=O)c3ccc(-c4cccc(NC(C)=O)c4)cc32)cc1] |

TABLE 1-continued

| No. | Structure |
|---|---|
| 159 | 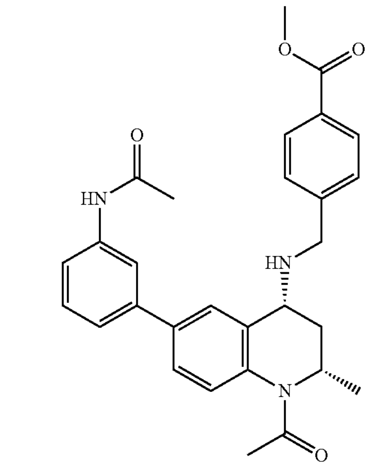 [SMILES: COC(=O)c1ccc(CN[C@@H]2C[C@H](C)N(C(C)=O)c3ccc(-c4cccc(NC(C)=O)c4)cc32)cc1] |
| 160 | 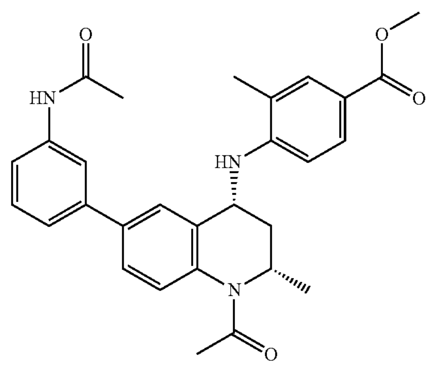 [SMILES: COC(=O)c1ccc(N[C@@H]2C[C@H](C)N(C(C)=O)c3ccc(-c4cccc(NC(C)=O)c4)cc32)c(C)c1] |
| 161 | 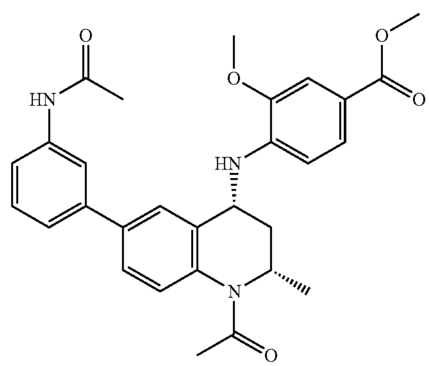 [SMILES: COC(=O)c1ccc(N[C@@H]2C[C@H](C)N(C(C)=O)c3ccc(-c4cccc(NC(C)=O)c4)cc32)c(OC)c1] |
| 162 | 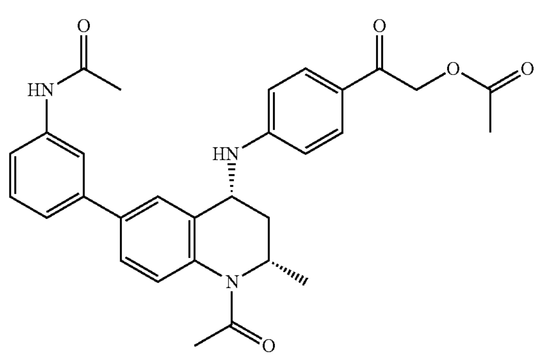 [SMILES: CC(=O)Nc1cccc(-c2ccc3c(c2)[C@H](Nc2ccc(C(=O)COC(C)=O)cc2)C[C@H](C)N3C(C)=O)c1] |

TABLE 1-continued
| No. | Structure |
|---|---|
| 163 | 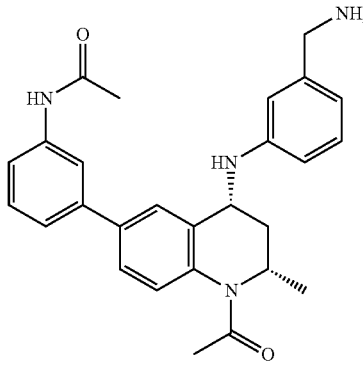 |
| 164 | 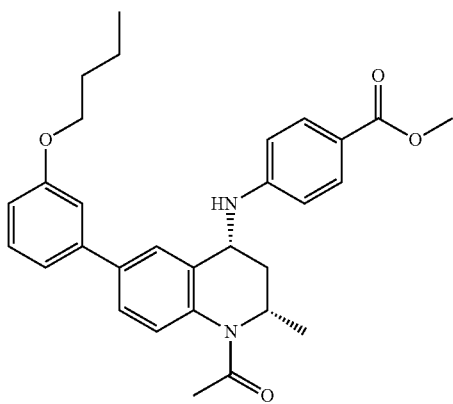 [SMILES: CCCCOc1cccc(-c2ccc3c(c2)[C@H](Nc2ccc(C(=O)OC)cc2)C[C@H](C)N3C(C)=O)c1] |
| 165 | 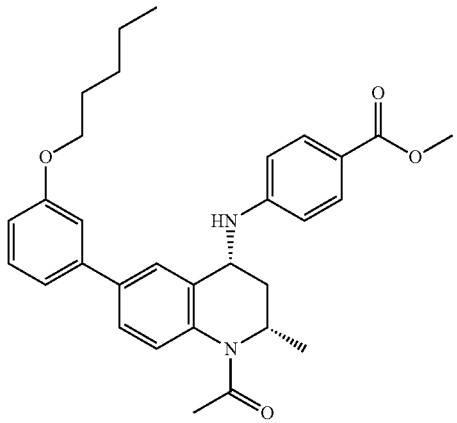 [SMILES: CCCCCOc1cccc(-c2ccc3c(c2)[C@H](Nc2ccc(C(=O)OC)cc2)C[C@H](C)N3C(C)=O)c1] |

TABLE 1-continued

| No. | Structure |
| --- | --- |
| 166 | 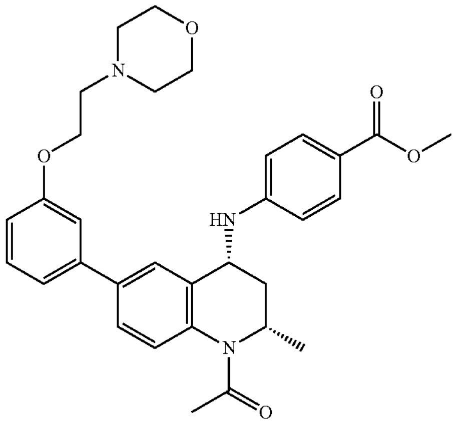 [SMILES: COC(=O)c1ccc(N[C@@H]2C[C@H](C)N(C(C)=O)c3ccc(-c4cccc(OCCN5CCOCC5)c4)cc32)cc1] |
| 167 | 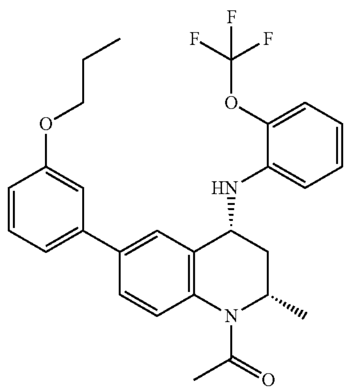 [SMILES: CCCOc1cccc(-c2ccc3c(c2)[C@H](Nc2ccccc2OC(F)(F)F)C[C@H](C)N3C(C)=O)c1] |
| 168 | 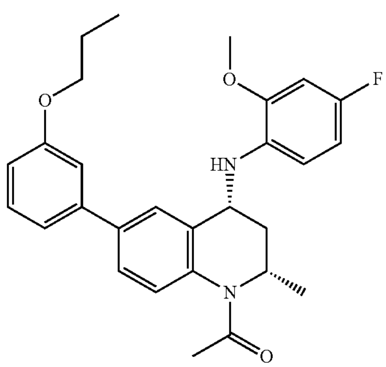 [SMILES: CCCOc1cccc(-c2ccc3c(c2)[C@H](Nc2ccc(F)cc2OC)C[C@H](C)N3C(C)=O)c1] |
| 169 | 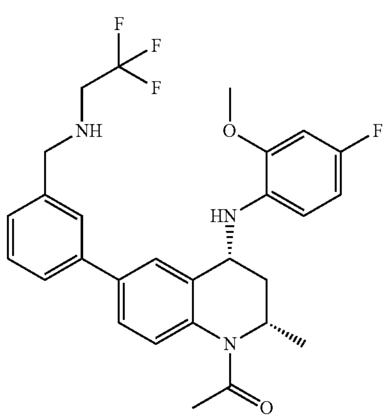 [SMILES: COc1cc(F)ccc1N[C@@H]1C[C@H](C)N(C(C)=O)c2ccc(-c3cccc(CNCC(F)(F)F)c3)cc21] |

TABLE 1-continued

| No. | Structure |
|---|---|
| 170 | 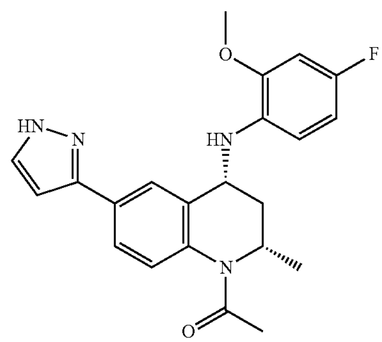 [SMILES: COc1cc(F)ccc1N[C@@H]1C[C@H](C)N(C(C)=O)c2ccc(-c3cc[nH]n3)cc21] |
| 171 | 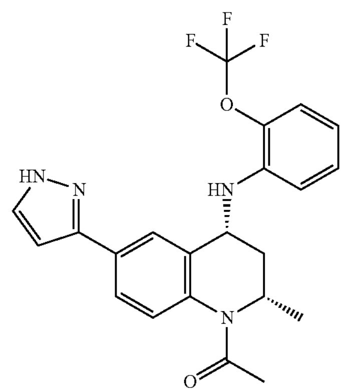 [SMILES: CC(=O)N1c2ccc(-c3cc[nH]n3)cc2[C@H](Nc2ccccc2OC(F)(F)F)C[C@@H]1C] |
| 172 | 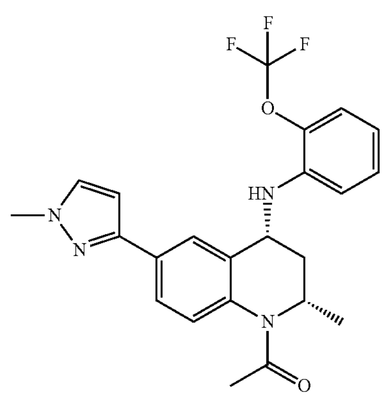 [SMILES: CC(=O)N1c2ccc(-c3ccn(C)n3)cc2[C@H](Nc2ccccc2OC(F)(F)F)C[C@@H]1C] |
| 173 | 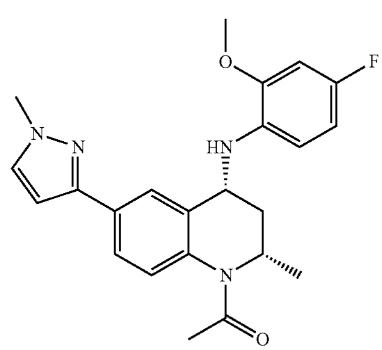 [SMILES: COc1cc(F)ccc1N[C@@H]1C[C@H](C)N(C(C)=O)c2ccc(-c3ccn(C)n3)cc21] |

TABLE 1-continued

| No. | Structure |
|---|---|
| 174 | 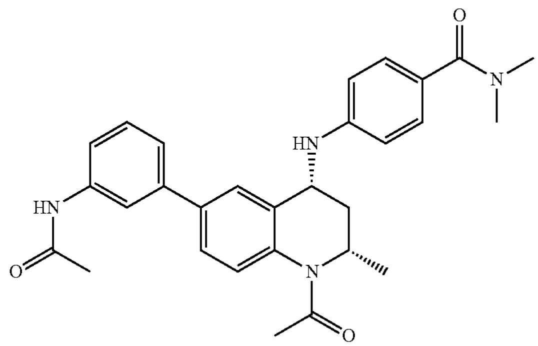 [SMILES: CC(=O)Nc1cccc(-c2ccc3c(c2)[C@H](Nc2ccc(C(=O)N(C)C)cc2)C[C@H](C)N3C(C)=O)c1] |
| 175 | 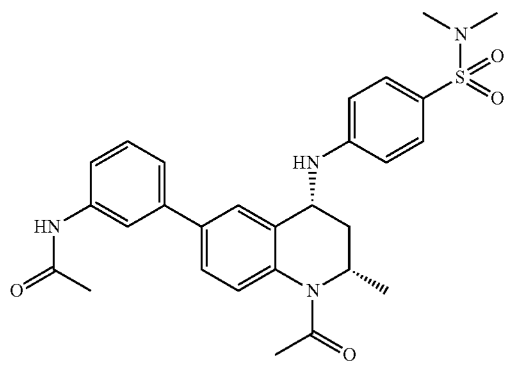 [SMILES: CC(=O)Nc1cccc(-c2ccc3c(c2)[C@H](Nc2ccc(S(=O)(=O)N(C)C)cc2)C[C@H](C)N3C(C)=O)c1] |
| 176 | 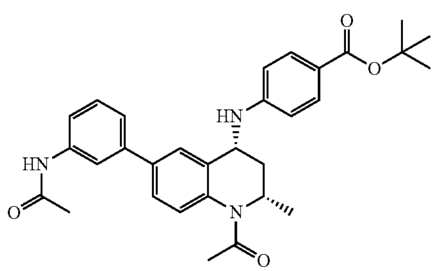 [SMILES: CC(=O)Nc1cccc(-c2ccc3c(c2)[C@H](Nc2ccc(C(=O)OC(C)(C)C)cc2)C[C@H](C)N3C(C)=O)c1] |
| 177 | 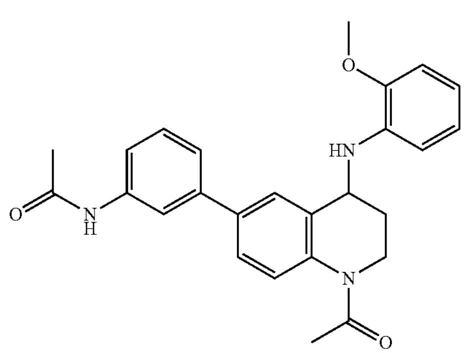 [SMILES: COc1ccccc1NC1CCN(C(C)=O)c2ccc(-c3cccc(NC(C)=O)c3)cc21] |

TABLE 1-continued
| No. | Structure |
|---|---|
| 178 | 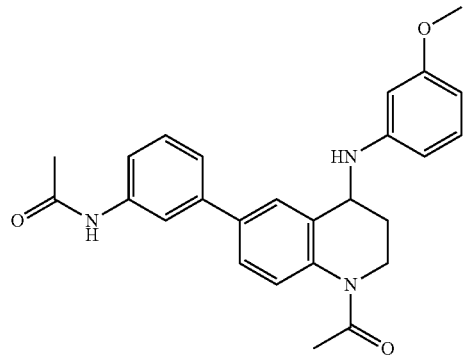 [SMILES: COc1cccc(NC2CCN(C(C)=O)c3ccc(-c4cccc(NC(C)=O)c4)cc32)c1] |
| 179 | 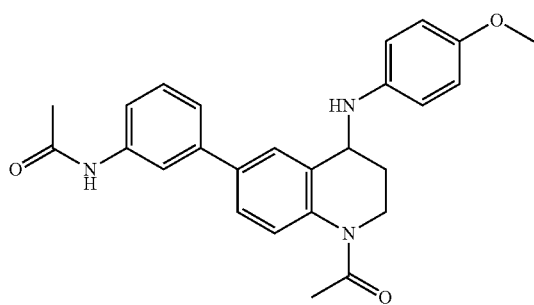 [SMILES: COc1ccc(NC2CCN(C(C)=O)c3ccc(-c4cccc(NC(C)=O)c4)cc32)cc1] |
| 180 | 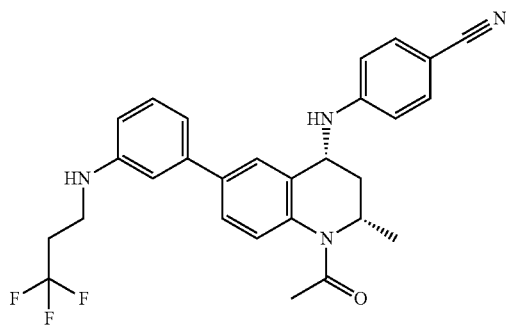 [SMILES: CC(=O)N1c2ccc(-c3cccc(NCCC(F)(F)F)c3)cc2[C@H](Nc2ccc(C#N)cc2)C[C@@H]1C] |
| 181 | 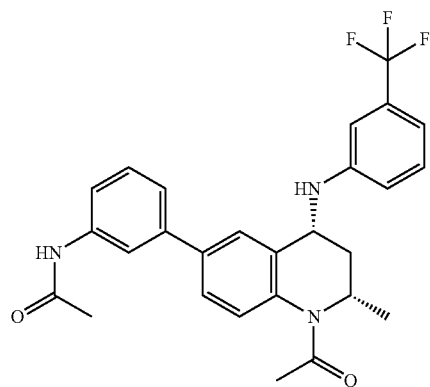 [SMILES: CC(=O)Nc1cccc(-c2ccc3c(c2)[C@H](Nc2cccc(C(F)(F)F)c2)C[C@H](C)N3C(C)=O)c1] |

TABLE 1-continued

| No. | Structure |
|---|---|
| 182 | 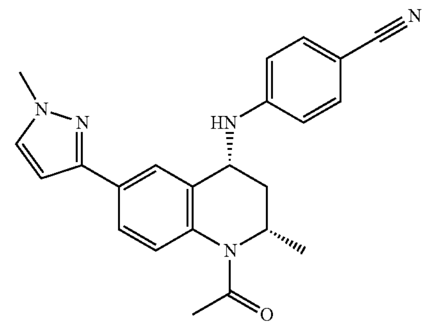 [SMILES: CC(=O)N1c2ccc(-c3ccn(C)n3)cc2[C@H](Nc2ccc(C#N)cc2)C[C@@H]1C] |
| 183 | 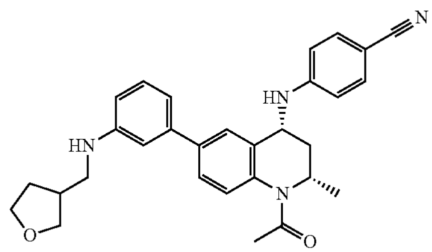 [SMILES: CC(=O)N1c2ccc(-c3cccc(NCC4CCOC4)c3)cc2[C@H](Nc2ccc(C#N)cc2)C[C@@H]1C] |
| 184 | 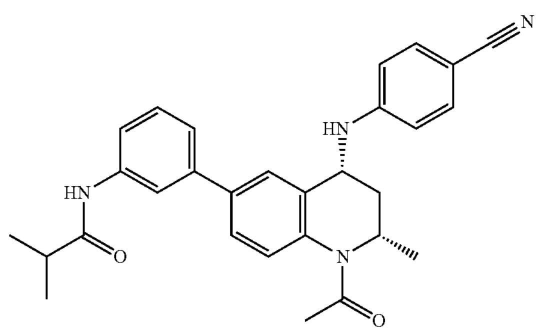 [SMILES: CC(=O)N1c2ccc(-c3cccc(NC(=O)C(C)C)c3)cc2[C@H](Nc2ccc(C#N)cc2)C[C@@H]1C] |
| 185 | 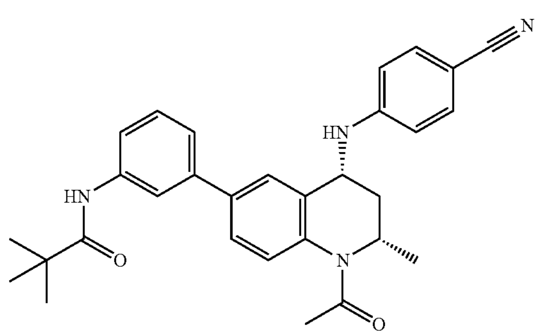 [SMILES: CC(=O)N1c2ccc(-c3cccc(NC(=O)C(C)(C)C)c3)cc2[C@H](Nc2ccc(C#N)cc2)C[C@@H]1C] |
| 186 | 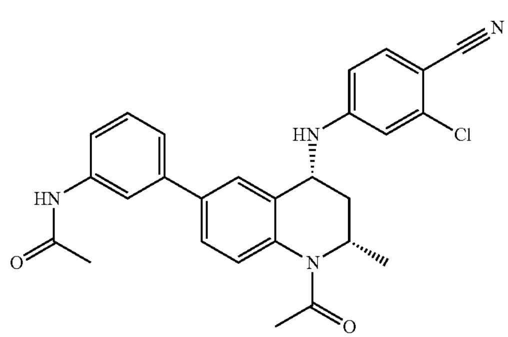 [SMILES: CC(=O)Nc1cccc(-c2ccc3c(c2)[C@H](Nc2ccc(C#N)c(Cl)c2)C[C@H](C)N3C(C)=O)c1] |

TABLE 1-continued

| No. | Structure |
|-----|-----------|
| 187 | 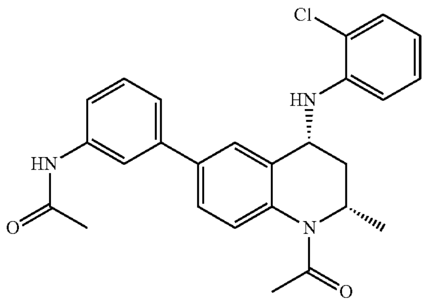 [SMILES: CC(=O)Nc1cccc(-c2ccc3c(c2)[C@H](Nc2ccccc2Cl)C[C@H](C)N3C(C)=O)c1] |
| 188 | 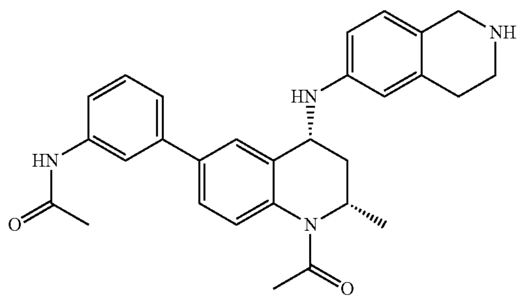 [SMILES: CC(=O)Nc1cccc(-c2ccc3c(c2)[C@H](Nc2ccc4c(c2)CCNC4)C[C@H](C)N3C(C)=O)c1] |
| 189 | 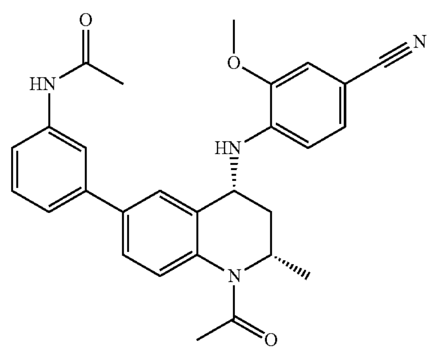 [SMILES: COc1cc(C#N)ccc1N[C@@H]1C[C@H](C)N(C(C)=O)c2ccc(-c3cccc(NC(C)=O)c3)cc21] |
| 190 | 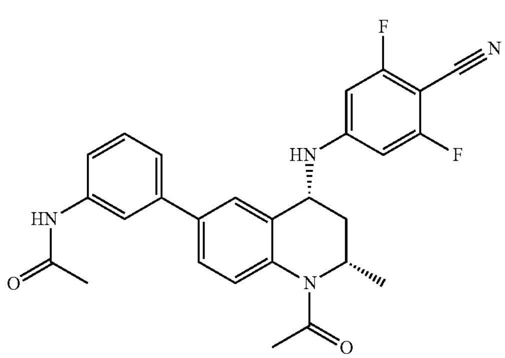 [SMILES: CC(=O)Nc1cccc(-c2ccc3c(c2)[C@H](Nc2cc(F)c(C#N)c(F)c2)C[C@H](C)N3C(C)=O)c1] |

TABLE 1-continued

| No. | Structure |
|---|---|
| 191 | 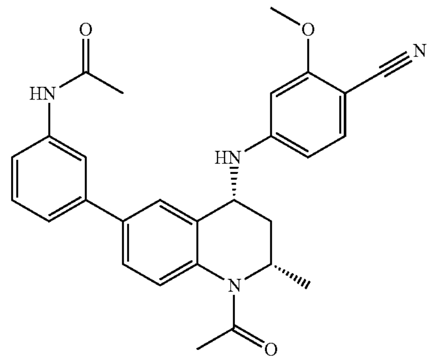 [SMILES: COc1cc(N[C@@H]2C[C@H](C)N(C(C)=O)c3ccc(-c4cccc(NC(C)=O)c4)cc32)ccc1C#N] |
| 192 | 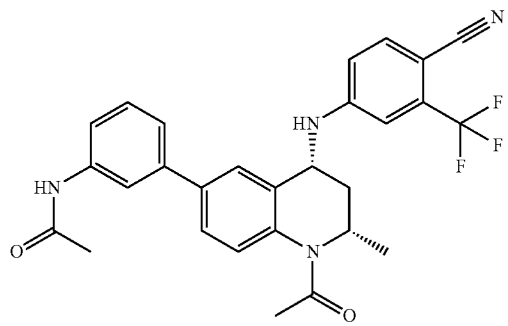 [SMILES: CC(=O)Nc1cccc(-c2ccc3c(c2)[C@H](Nc2ccc(C#N)c(C(F)(F)F)c2)C[C@H](C)N3C(C)=O)c1] |
| 193 | 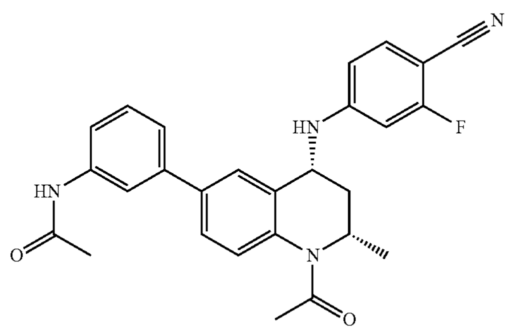 |
| 194 | 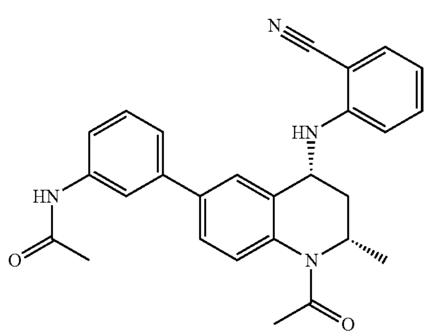 [SMILES: CC(=O)Nc1cccc(-c2ccc3c(c2)[C@H](Nc2ccccc2C#N)C[C@H](C)N3C(C)=O)c1] |

TABLE 1-continued

| No. | Structure |
|-----|-----------|
| 195 | 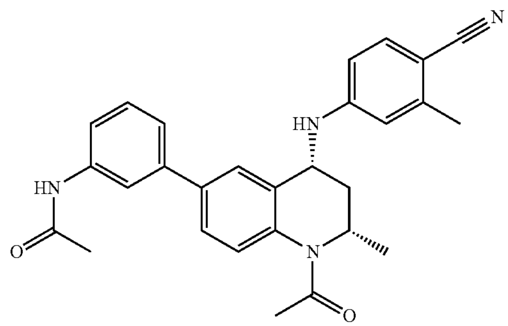 [SMILES: CC(=O)Nc1cccc(-c2ccc3c(c2)[C@H](Nc2ccc(C#N)c(C)c2)C[C@H](C)N3C(C)=O)c1] |
| 196 | 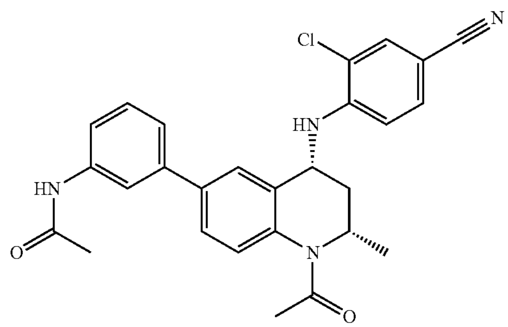 |
| 197 | 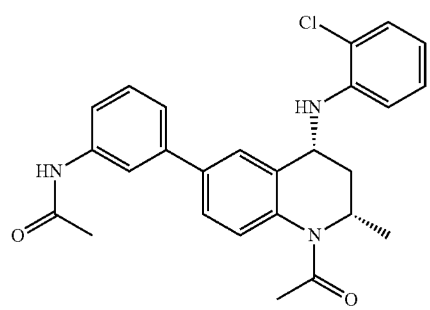 [SMILES: CC(=O)Nc1cccc(-c2ccc3c(c2)[C@H](Nc2ccccc2Cl)C[C@H](C)N3C(C)=O)c1] |
| 198 | 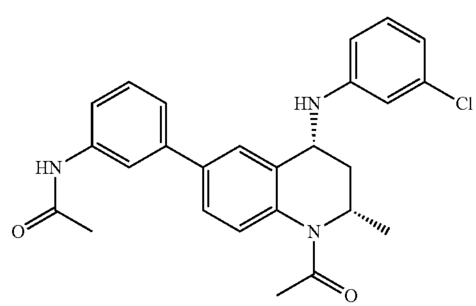 [SMILES: CC(=O)Nc1cccc(-c2ccc3c(c2)[C@H](Nc2cccc(Cl)c2)C[C@H](C)N3C(C)=O)c1] |
| 199 | 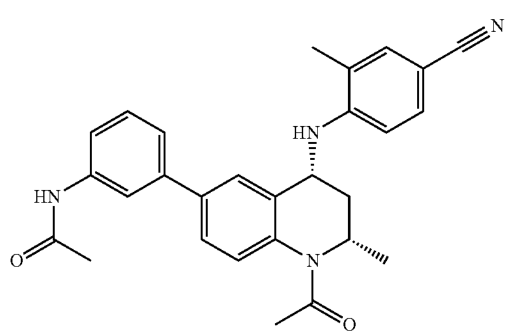 [SMILES: CC(=O)Nc1cccc(-c2ccc3c(c2)[C@H](Nc2ccc(C#N)cc2C)C[C@H](C)N3C(C)=O)c1] |

TABLE 1-continued
| No. | Structure |
|---|---|
| 200 | 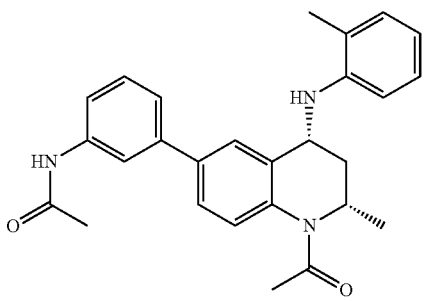 [SMILES: CC(=O)Nc1cccc(-c2ccc3c(c2)[C@H](Nc2ccccc2C)C[C@H](C)N3C(C)=O)c1] |
| 201 | 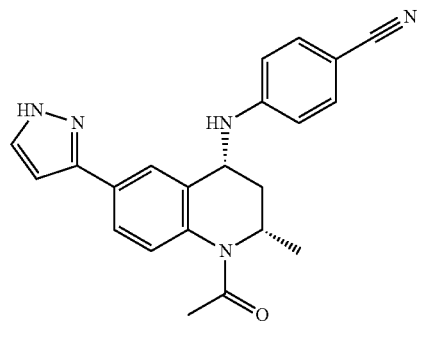 [SMILES: CC(=O)N1c2ccc(-c3cc[nH]n3)cc2[C@H](Nc2ccc(C#N)cc2)C[C@@H]1C] |
| 202 | 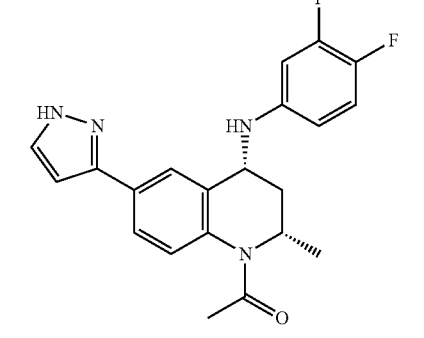 |
| 203 | 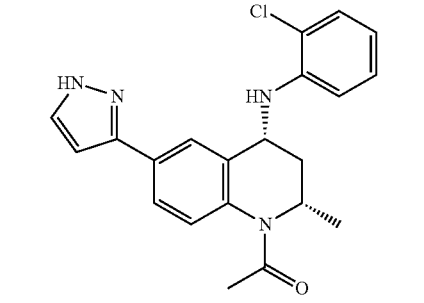 [SMILES: CC(=O)N1c2ccc(-c3cc[nH]n3)cc2[C@H](Nc2ccccc2Cl)C[C@@H]1C] |
| 204 | 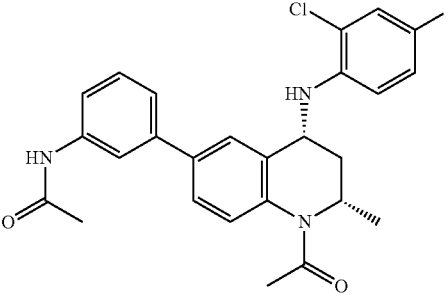 |

TABLE 1-continued

| No. | Structure |
|---|---|
| 205 | 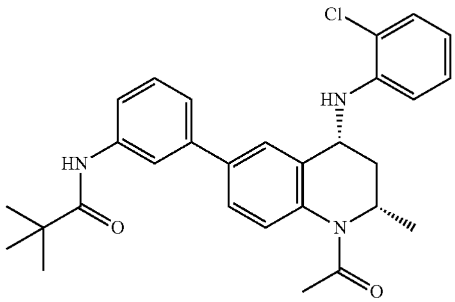 [SMILES: CC(=O)N1c2ccc(-c3cccc(NC(=O)C(C)(C)C)c3)cc2[C@H](Nc2ccccc2Cl)C[C@@H]1C] |
| 206 | 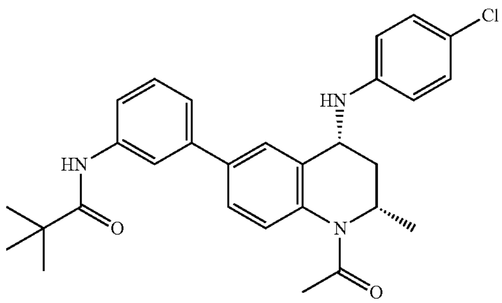 [SMILES: CC(=O)N1c2ccc(-c3cccc(NC(=O)C(C)(C)C)c3)cc2[C@H](Nc2ccc(Cl)cc2)C[C@@H]1C] |
| 207 | 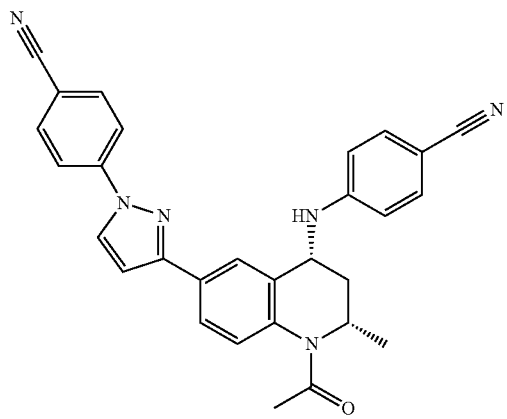 [SMILES: CC(=O)N1c2ccc(-c3ccn(-c4ccc(C#N)cc4)n3)cc2[C@H](Nc2ccc(C#N)cc2)C[C@@H]1C] |
| 208 | 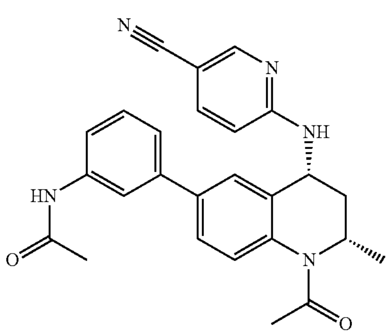 [SMILES: CC(=O)Nc1cccc(-c2ccc3c(c2)[C@H](Nc2ccc(C#N)cn2)C[C@H](C)N3C(C)=O)c1] |

TABLE 1-continued

| No. | Structure |
|-----|-----------|
| 209 | 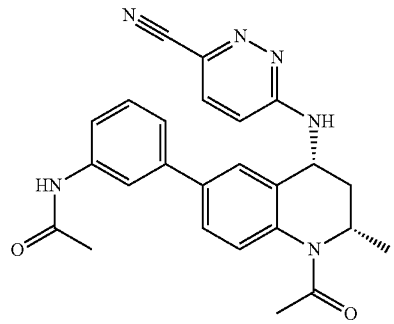 [SMILES: CC(=O)Nc1cccc(-c2ccc3c(c2)[C@H](Nc2ccc(C#N)nn2)C[C@H](C)N3C(C)=O)c1] |
| 210 | 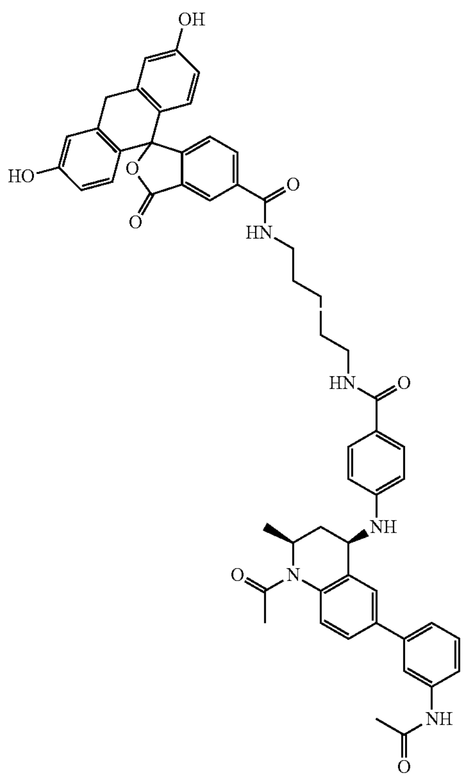 [SMILES: CC(=O)Nc1cccc(-c2ccc3c(c2)[C@H](Nc2ccc(C(=O)NCCCCCNC(=O)c4ccc5c(c4)C(=O)OC54c5ccc(O)cc5Cc5cc(O)ccc54)cc2)C[C@H](C)N3C(C)=O)c1] |

3. Biology Experimentals a. Surface Plasmon Resonance (Biacore) Analysis of Binding to Brd2-BD1 and Brd2-BD2

SPR experiments were conducted at 15° C. using a SensiQ Pioneer optical biosensor (SensiQ Technologies). Poly-His tagged BRD2 constructs were immobilized on polycarboxylate-coated gold chips preimmobilized with nitrilotriacetic acid (His-Cap chips; SensiQ Technologies) by capture-coupling, a hybrid method of capture and amine coupling chemistry (Ref. A). The His-Cap chip was preconditioned and charged with $Ni^{2+}$ in equilibration buffer (10 mM HEPES pH 7.4, 150 mM NaCl, 50 μM EDTA, 0.005% Tween20) at a flow rate of 10 μL/min. The chip was washed with three 60 s injections of regeneration buffer (10 mM HEPES pH 8.3, 150 mM NaCl, 350 mM EDTA, 0.05% Tween20) and one 60 s injection of equilibration buffer and was charged with a 60 s injection of 500 mM $NiCl_2$ in equilibration buffer, which added ~55 RU of $Ni^{2+}$ per channel. The charged chip was primed with binding buffer (20 mM HEPES pH 7.0, 150 mM NaCl, 1 mM TCEP, 0.005% Tween20, 1% DMSO) prior to protein immobilization. Carboxyl groups on the dextran were activated with N-ethyl-N'-(3-dimethylaminopropyl) carbodiimide (EDC) and N-hydroxysuccinimide (NHS), and BRD2 constructs were injected until immobilization levels of ~450-530 RU were achieved. One channel on the chip was charged with $Ni^2$ and activated with EDC/NHS without adding protein to be used as a reference cell. The chip was equilibrated for 1-2 h to allow any remaining active sites to hydrolyze, eliminating the need to apply a blocking agent (e.g. ethanolamine).

Compound 4 was prepared in binding buffer as a 3-fold dilution series starting at 1 μM and was injected in duplicate at each concentration at a flow rate of 150 μL/min. A series of buffer-only (blank) injections was included throughout the experiment to account for instrumental noise. The data were processed, double-referenced, solvent corrected and analyzed using the software package Qdat (version 2.5.3.5, SensiQ Technologies) (Ref B). The kinetic rate constants were determined by globally fitting the data to a 1:1 interaction model. Equilibrium dissociation constants ($K_D$) were calculated as the quotient $k_d/k_a$.

b. Isothermal Titration Calorimetry Analysis of Binding to Brd2-BD1 and Brd2-BD2

Binding of compounds to BRD2 was monitored using an $ITC_{200}$ (Microcal, Piscataway, N.J.). Either Brd2.1 (74-194) or Brd2.2 (348-455) was dialyzed overnight into a solution containing 50 mM HEPES, pH 7.0 and 150 mM NaCl at 15° C. Enzyme concentrations were determined after dialysis by absorbance at 280 nm using a molar extinction coefficient ($\varepsilon_{280}$) of 25,565 $M^{-1}$ $cm^{-1}$ (2.1) or 16,055 $M^{-1}$ $cm^{-1}$ (2.2). Enzyme was diluted in dialysis buffer and 39.6 μL was loaded into the syringe. Compounds were dissolved in the same dialysis buffer and loaded in the cell to a volume of 204 μL. Injections were carried out by serial injections of enzyme; first, 1 injection of 1 μL, followed by 19 incremental injections of 2 μL, at 120 second intervals. Data from the first injection was excluded, due to pre-equilibration mixing between the contents of cell and syringe at the syringe tip. Peak areas were integrated, normalized, and then fitted by non-linear regression using the independent sites model in Origin™ (version 2.3.6, Microcal, Piscataway, N.J.).

c. Cell Culture

Human G3 medulloblastoma or mouse SHH medulloblastoma cells were grown as neurospheres in supplemented neurobasal medium, as previously described (Kawauchi et al., 2012.)

d. High Throughput Screening Using CellTiter-Glo 2000 human G3 medulloblastoma or 1000 mouse SHH medulloblastoma cells per well were plated into 384-well plates (8408BC, Corning) in 30 μL of supplemented neurobasal medium using a Wellmate automated dispenser (Thermo Matrix). After 24 hours, 125 nL of compound was transferred via pin-tool, resulting in a final drug concentration from 2 nM to 40 μM. After 7 days of treatment, an equal volume of CellTiter-Glo reagent (G7572, Promega) was added and the luminescence signal was measured using an automated Envision plate reader (Perkin-Elmer). Luminescence data were normalized by $log_{10}$ transformation prior to calculating the percent inhibition using the following equation:

100*(negative control mean −compound value)/(negative control mean −positive control mean). The negative control represents cells treated with 0.1% DMSO and 0% inhibition. Cells treated with 10 μM JQ1 represent the positive control with 100% inhibition. The $EC_{50}$ represents the drug concentration inducing 50% inhibition.

High-throughput assay data were analyzed using Robust Interpretation of Screening Experiments (RISE) application written in Pipeline Pilot (Accelrys, v. 8.5) and the R program (R Development Core Team).

Dose-response curves were calculated by regressing the median percent inhibition obtained over triplicate experiments to log 10-transformed concentrations. Non-linear regression was then performed using the R drc package with the four parameter log-logistic function (LL2.4) (Ritz and Streibig, 2009). Curves were fit under three different constraints: (1) all parameters free, (2) high response fixed to 100, (3) low response fixed to 0; and the best fit from these three nested models was selected using the anova.drc function.

e. HCM 3000 human G3 medulloblastoma or 2000 mouse SHH medulloblastoma cells per well were plated into 384-well plates (6007710, Perkin Elmer) in 30 μL of supplemented neurobasal medium using a Wellmate automated dispenser (Thermo Matrix). After 24 hours, 125 nl of compound was transferred via pin tool, resulting in a final drug concentration from 2 nM to 40 μM. 72 hours after adding the drug, the plates were fixed with 4% formaldehyde for 20 min. After fixation the cells were then washed 3 times with 75 μl of PBS. The cells were then permeabilized with 0.1% Triton-X 100 for 15 minutes at 25° C. and blocked using 1% BSA in PBS for 1 hour at 25° C. The primary antibody against c-Myc Ab (#9402, Cell Signaling) at a 1:400 dilution was diluted in 1% BSA in PBS. This mixture was added to each well before incubation overnight at 4° C. Each well was then washed 3 times with PBS using a Biotek ELX405 Select plate washer, and incubated for 1 hour at 25° C. with a solution containing 1/400 goat α-rabbit-Alexa-488 (4412S, Cell Signaling) and 1 μM Hoechst 33342 to detect nuclear material (H3570, Molecular Probes). Two images were captured of each well at 10× using a GE Healthcare InCell 6000 at 405 nM to detect nuclear staining and 488 nM to detect c-Myc. All data were analyzed using the multi-target analysis algorithm of the GE InCell Analyzer Workstation software. The number of nuclear objects in each well, as well as all nuclear measurements, was determined through nuclear masks over the Hoechst staining. C-Myc staining was then measured using top-hat segmentation in the entire cell.

f. Washout Experiment 3000 human G3 medulloblastoma and 2000 mouse SHH medulloblastoma cells per well were plated in 96-well plates (8804BC, Corning) in 100 μL of supplemented neurobasal medium using Wellmate dispenser. After 24 hours, 128 nL of a dilution series of compounds were transferred using a pin-tool resulting in a final drug concentration from 0.5 nM to 9.3 μM. In order to assess the optimal exposure time of the compound, the medium was replaced at 1, 3, 6, 10, or 72 hours. The level of c-Myc protein in each well was determined either by high content microscopy after 72 hours, or the cell number in each well using CellTiter-Glo after 7 days of compound treatment.

4. Structure-Activity Relationship (SAR) Analysis

The N-acyl tetrahydroquinoline (THQ) scaffold was selected as a starting point based on analysis of established synthetically-tractable BET inhibitor scaffolds that would permit targeting the ZA channel (Atkinson et al. (2014) *MedChemComm* 5: 342). This scaffold has been reported as a fragment that blocks p53-CREB association (Sachchidanand et al. (2006) *Chemistry & Biology* (Cambridge, Mass., United States) 110: 19754) and BET inhibitors based on this scaffold have been reported in several GSK patents (Amans et al. WO 2014/140076 A1; Amans et al. WO 2012/143415 A1; Amans et al. WO 2012/143413 A1; Demont et al. WO 2011/054841 A1; Demont et al. WO 2011/054848 A1). GSK1324726A (Gosmini et al. (2014) *J. Med. Chem.* 57: 8111) has been shown to potently inhibit all BET proteins, up-regulate ApoA1, and block expression of N-myc and BCL-2, resulting in tumor growth inhibition in neuroblastoma tumor models (Wyce et al. (2013) *PLoS One* 8: e72967). Most of the biochemical results in these publications did not discuss binding domain selectivity within the BET family. Using a modified version of the reported route (Demont et al. WO 2011/054841 A1), isopropyl ((2S,4R)-1-acetyl-6-bromo-2-methyl-1,2,3,4-tetrahydroquinolin-4-yl)carbamate was synthesized in four steps (see above). This compound was used to generate inhibitors containing substituted aryl rings at the 4-position using Suzuki conditions.

Inhibitor potency was determined using a competitive TR-FRET assay as detailed herein, measuring interaction of the respective BET-BD with an acetylated peptide ligand (Table 2). The 2-furanyl analog (50) inhibited BD2 with potency similar to JQ1 and exhibited 7:1 selectivity (BD2: BD1). The closely related 3-furanyl analog (51) was 10-fold less potent than 50 and its selectivity was much lower, close to that of (+)-JQ1.

inhibitor RVX-208 revealed that RVX-208 did not inhibit c-Myc oncogene expression. The authors concluded that either the BD1 or both domains needed to be blocked in order to cause reduced c-Myc levels (Picaud et al. (2013) *Proceedings of the National Academy of Sciences of the United States of America* 110: 19754. Here, compounds 50,

TABLE 2

| Cmpd | BRD2-BD1 (µM) | BRD2-BD2 (µM) | BD1/BD2 | BRD3-BD1 (µM) | BRD4-BD1 (µM) | BRD4-BD2 (µM) | BRDT (µM) |
|---|---|---|---|---|---|---|---|
| (+)-JQ1 | 0.76 | 0.22 | 3 | | | | |
| 50 | 5.1 | 0.30 | 17 | 1.1 | 4.6 | 2.6 | |
| 51 | 7.23 | 1.42 | 5 | 2.3 | 5.8 | 4.3 | 23 |
| 52 | 1.68 | 0.34 | 5 | 1.2 | >77.79 | 3.0 | |
| 53 | 7.21 | 0.97 | 7 | 3.1 | 14 | 4.6 | |
| 54 | 1.55 | >48.58 | NA | 5.6 | 1.7 | 8.5 | |
| 55 | 1.71 | 0.37 | 5 | 0.26 | 1.3 | 1.2 | 49 |

Next, the thermodynamics of inhibitor binding to individual BRD2 domains was explored using isothermal calorimetry (ITC, Table 3). ITC confirmed that the compounds bind preferentially to BD2 relative to BD1. When the ring oxygen is moved from the 2-position (50) to the 3-position (51), selective binding is functionally abolished. Binding of 50 to BD1 appears to be almost completely driven by enthalpy ($\Delta H$), with a very small negative entropic ($\Delta S$) component. In the binding of 50 to BD2, there is a large negative change in $\Delta H$, countered by a negative change in $\Delta S$. This phenomenon can be explained by formation of a large number of specific interactions resulting in a large negative $\Delta H$, with the negative $\Delta S$ coming from a decrease in conformational flexibility upon binding. The thermodynamics of binding of 51 change slightly between BD2 and BD1, with binding to BD1 almost completely driven by enthalpy, while BD2 binding shows more conventional contributions of $\Delta H$ and $\Delta S$ to total binding energy. The more lipophilic thiophene analogs (52, 53) exhibit a moderate selectivity towards BD2, and their respective binding affinities are guided by changes in $\Delta S$. With the pyrrole analogs (54, 55), the preference is not clearly driven by either $\Delta H$ or $\Delta S$.

51, and (+)-JQ1 were tested. Exposure of HDMB03 cells to compounds 50, 51, and (+)-JQ1 resulted in a dose-dependent decline in cellular viability and c-Myc expression. As predicted by the biochemical data, compound 50 inhibited cell viability ($EC_{50}$=0.17 µM) with potency close to that exhibited by (+)-JQ1 ($EC_{50}$=0.21 µM). Compound 51, less potent according to TR-FRET data, was ~10-fold less active ($EC_{50}$=3.3 µM). In concordance with the cell proliferation inhibition data, 50 inhibits c-Myc expression in this cell line with an $EC_{50}$=0.33 µM. (+)-JQ1 exhibits greater potency ($EC_{50}$=0.02 µM) and 51 is least potent ($EC_{50}$=1.0 µM).

5. Evaluation of $R^{4a}$

Although GSK-726 offers minimal selective (~15:1, BD2:BD1) within the BET family, the disclosed analogs demonstrated greater selectivity (>50:1, BD2:BD1 in some cases) without a precipitous drop in potency (see Table 4). Some analogs also show negligible inhibition of BRDT (the BET family member involved in spermatogenesis). The selectivity of compound 4 was also confirmed using other biochemical assays including isothermal titration calorimetry (ITC) and surface plasmon resonance (SPR). According to ITC, compound 4 binds more potently to BRD2(2) ($K_D$<1 nM) than BRD2(1) ($K_D$=25 nM). (+)-JQ1 demonstrated no selec-

TABLE 3

| | Compound | | | | | | |
|---|---|---|---|---|---|---|---|
| | (+)-JQ1 (1) | 50 | 51 | 52 | 53 | 54 | 55 |
| BRD2-BD1 | | | | | | | |
| average $K_d$, nM | 88.99 | 2188.61 | 162.47 | 61.26 | 71.65 | 131.22 | 91.53 |
| $\Delta G$, kcal/mol | −9.29 | −7.47 | −8.96 | −9.52 | −9.43 | −9.08 | −9.28 |
| $\Delta H$, kcal/mol | −4.90 | −7.27 | −9.90 | −8.27 | −7.69 | −6.90 | −7.33 |
| −T$\Delta S$, kcal/mol | −4.39 | −0.20 | 0.94 | −1.25 | −1.74 | −2.18 | −1.95 |
| BRD2-BD2 | | | | | | | |
| average $K_d$, nM | 112.14 | 280.44 | 299.51 | 20.87 | 17.12 | 35.86 | 19.94 |
| $\Delta G$, kcal/mol | −9.30 | −8.62 | −8.61 | −10.12 | −10.25 | −9.82 | −10.15 |
| $\Delta H$, kcal/mol | −1.47 | −15.27 | −6.31 | −7.18 | −6.92 | −6.89 | −7.01 |
| −T$\Delta S$, kcal/mol | −7.83 | 6.65 | −2.29 | −2.94 | −3.33 | −2.92 | −3.32 |
| Selectivity (2-1/2-2) | 0.8 | 7.8 | 0.5 | 2.9 | 4.2 | 3.7 | 4.6 |

Average of 3 experiments each; N values ranged from 0.95-1.08.

Next, the ability of this BD2-selective probe to inhibit myc-expression and induce cell cytotoxicity in HDMB03, a myc-dependent medulloblastoma cell line, was evaluated (Northcott et al. (2012) *Nature* (London. United Kingdom) 488: 49). A previous study with the BD2-selective BET tivity in ITC (BRD2(1) $K_D$=89 nM; BRD2(2) $K_D$=112 nM). In SPR, a similar trend was observed; compound 4 has a $K_D$=13 nM for BRD2(2) and a $K_D$=132 nM for MRD2(1). The $K_D$ values for (+)-JQ1 were 239 nM and 311 nM, respectively.

TABLE 4

| No. | EC$_{50}$ (µM) BRD2(1) | BRD2(2) | [2(1)/ 2(2)] | EC$_{50}$ (µM) BRD4(1) | BRD4(2) | [4(1)/ 4(2)] | BRD3(1) | BRDT EC$_{50}$ (µM) |
|---|---|---|---|---|---|---|---|---|
| (+)-JQ1 | 0.7 | 0.27 | 2.6 | 0.45 | 0.47 | 1.0 | — | 2.2 |
| GSK-726 | 1.0 | 0.057 | 17.5 | 1.2 | 0.088 | 13.6 | — | 5.3 |
| 4 | 0.43 | 0.022 | 19.5 | 0.43 | 0.021 | 20.5 | 1.1 | 4.0 |
| 19 | 8.3 | 0.16 | 52 | 8.3 | 0.14 | 59 | 5.4 | 10 |
| 10 | 2.6 | 0.08 | 33 | 3.1 | 0.21 | 15 | 1.9 | 3.7 |
| 39 | 5.6 | 0.11 | 51 | 5.7 | 0.09 | 63 | 2.7 | 10 |
| 40 | 4.2 | 0.060 | 75 | 6.0 | 0.10 | 52.9 | 2.0 | 9.1 |
| 41 | 70 | 0.35 | 57 | — | — | — | 20 | 53 |
| 42 | 13 | 0.14 | >100 | — | — | — | >14 | >14 |

None of the THQ compounds exhibit cytotoxicity in healthy, mammalian cell lines (HEK239, BJ, and HEPG2). The selected disclosed compounds display anti-proliferative properties against several cancer cell lines such as HDBM03 (medulloblastoma group 3), NALM-16 (haemopoietic), Loucy (ETP-ALL, leukemia) and SEM (β-ALCL) similar to promiscuous BET inhibitors such as (+)-JQ1. Compounds 4 and 40 have activity versus several neural crest tumor cell lines with IC$_{50}$ ranges from 50 to 200 nM. Additionally, these compounds can block the formation of oncogenic proteins, such as c-Myc (in HDMB03), N-myc, and Lmo2 (both in ETP-ALL cell lines, concentration=1 µM after 48 hour exposure).

TABLE 5

| No. | EC$_{50}$ (µM) HDMB03 | NALM-16 | Loucy | SEM | Myc-inhibition |
|---|---|---|---|---|---|
| (+)-JQ1 | 0.69 | 0.16 | 0.23 | 0.03 | 0.12 |
| GSK-726 | 5.77 | 0.23 | 0.33 | 0.02 | 0.17 |
| 4 | 0.31 | 0.35 | 0.39 | 0.02 | 0.03 |
| 19 | 1.14 | >1.7 | NA | 0.04 | 0.11 |
| 10 | 1.18 | 0.33 | NA | NA | 0.68 |
| 39 | 1.68 | NA | NA | NA | 0.04 |
| 40 | 17.64 | 0.26 | 0.32 | 0.02 | 0.49 |
| 41 | 1.6 | NA | NA | NA | 6.2 |
| 42 | 0.76 | NA | NA | NA | >10 |

6. Evaluation of R$^{3a}$

Replacing the acetamide of compound 4 with alkyl groups retains the selectivity observed with compound 4 without dampening efficacy in anti-proliferation or blocking Myc expression (see Table 6 and Table 7).

TABLE 6

| No. | EC$_{50}$ (µM) BRD2(1) | BRD2(2) | [2(1)/2(2)] | EC$_{50}$ (µM) | BRD3(1) |
|---|---|---|---|---|---|
| (+)-JQ1 | 0.44 | 0.49 | 0.9 | 2.6 | — |
| GSK-726 | 1.3 | 0.19 | 6.8 | 5.5 | — |
| 4 | 1.56 | 0.11 | 14.2 | 4.0 | 1.1 |
| 43 | 0.51 | 0.05 | 10 | 1.2 | 0.41 |
| 44 | 2.7 | 0.12 | 22.5 | 7.4 | 2.1 |
| 45 | 2.6 | 0.16 | 16.25 | 7.3 | 2.1 |
| 46 | 1.3 | 0.17 | 7.6 | 2.6 | 1.0 |
| 47 | 2.3 | 0.32 | 7.2 | 5.8 | 1.9 |

TABLE 7

| No. | EC$_{50}$ (µM) HDMB03 | MV-4-11 | Myc-inhibition |
|---|---|---|---|
| (+)-JQ1 | 0.69 | 0.032 | 0.71 |
| GSK-726 | 0.95 | NA | 1.5 |
| 4 | 0.75 | 0.016 | 1.3 |
| 43 | 1.5 | 0.007 | 0.88 |
| 44 | 0.39 | 0.035 | 0.3 |
| 45 | 0.56 | 0.083 | 0.38 |
| 46 | 0.35 | 0.018 | 0.34 |
| 47 | 0.35 | 0.008 | 0.25 |

7. Evaluation of Ar$^3$

The effect of replacing the aryl moiety at Ar$^3$ was evaluated as shown in Table 8 below.

TABLE 8

| No. | EC$_{50}$ (µM) BRD2(1) | BRD2(2) | EC$_{50}$ (µM) | BRD3(1) |
|---|---|---|---|---|
| (+)-JQ1 | 0.44 | 0.49 | 2.6 | — |
| GSK-726 | 1.3 | 0.19 | 5.5 | — |
| 4 | 1.56 | 0.11 | 4.0 | 1.1 |
| 49 | 1.4 | 0.14 | 4.4 | 0.9 |

Cancer cell proliferation inhibition and c-Myc expression inhibition in HDMB03 cells is illustrated in Table 9 below.

TABLE 9

| No. | EC$_{50}$ (µM) HDMB03 | Myc-inhibition |
|---|---|---|
| (+)-JQ1 | 0.69 | 0.71 |
| GSK-726 | 0.95 | 1.5 |
| 4 | 0.75 | 1.3 |
| 49 | 1.6 | 5.1 |

8. BROMOscan

Figure 4B:
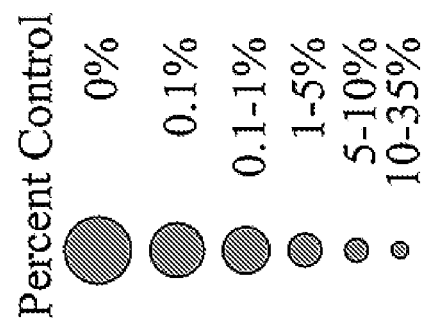
FIG. 4A-C show representative images illustrating the selectivity of (+)-JQ1 (4A), GSK-726 (4B), and compound 4 (4C) within various bromodomains.
Figure 4B:
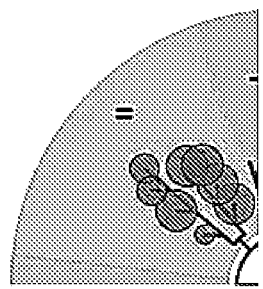
Figure 4A:
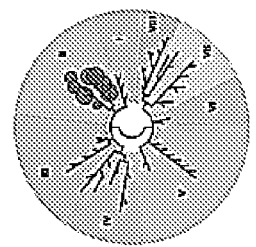
Figure 4C:
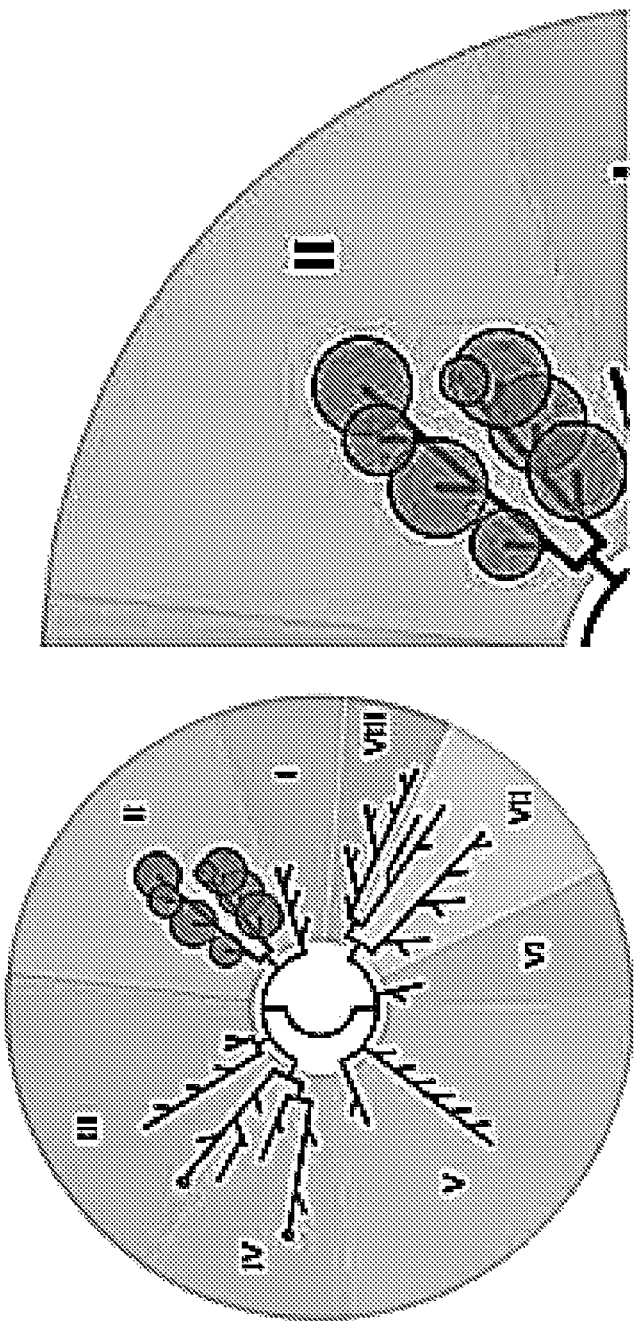
Figure 5:
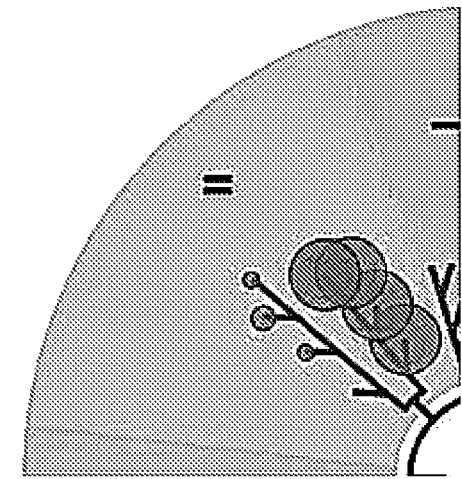
FIG. 5 shows representative images illustrating the selectivity of compounds 19 (left), 41 (middle), and 56 (right) within the BET family.
Figure 5:
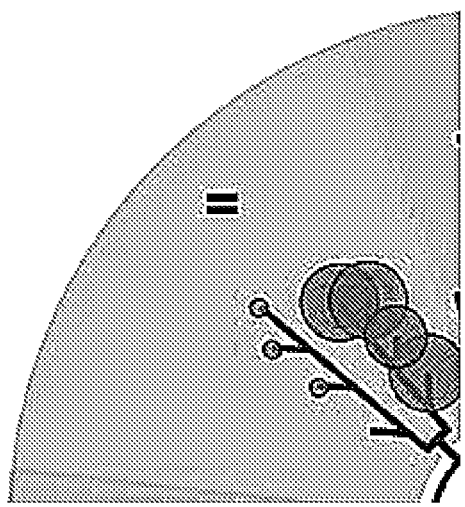
Figure 5:
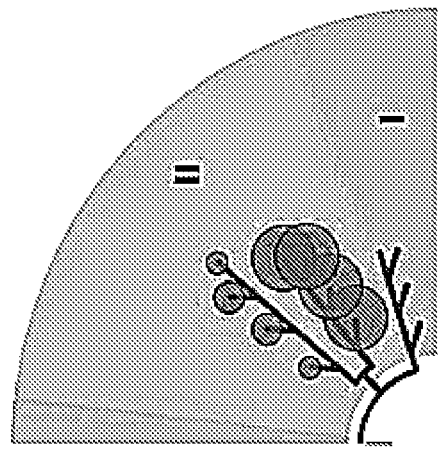

DiscoverX® can screen compounds against all ~42 bromodomains (a service called BROMOscan) and perform follow-up K$_D$ determination. This service is considered the industrial standard for bromodomain inhibitor comparisons. FIG. 4A-C illustrate the results of a competitive binding experiment between (+)-JQ1 (FIG. 4A), GSK-726 (FIG. 4B), and compound 4 (FIG. 4C) (at a single concentration, 1 µM) and a control for each of the bromodomains. Dots are symbolic of inhibition of the compound at this concentration; the larger the size of the dot, the greater the activity of the compound. (+)-JQ1 and GSK-726 exhibit activity only versus the BET family (family II). Though these compounds are selective for the BET family, the selectivity within the BET family is poor. The results of a competitive binding experiment between compounds 19 (left), 41 (center), and 56 (right) (at a single concentration, 1 µM) and a control for each of the bromodomains are shown in FIG. 5.

The $K_D$ value of each compound versus each of the BET family members is illustrated in Table 10 below.

TABLE 10

| No. | BRD2 (1) | BRD2 (2) | 2(1)/2(2) | BRD3 (1) | BRD3 (2) | 3(1)/3(2) | BRD4 (1) | BRD4 (2) | 4(1)/4(2) | BRDT (1) | BRDT (2) | T(1)/T(2) |
|---|---|---|---|---|---|---|---|---|---|---|---|---|
| (+)-JQ1 | 27 | 18 | 1.5 | 14 | 19 | 0.7 | 14 | 8.2 | 1.7 | 47 | 35 | 1.3 |
| GSK 726 | 4.7 | 0.2 | 23.5 | 3.1 | 0.2 | 15.5 | 4.8 | 0.21 | 22.9 | 4.5 | 0.89 | 5.1 |
| 56 | 160 | 8.2 | 19.5 | 99 | 4.3 | 23.0 | 140 | 4.4 | 31.8 | 95 | 23 | 4.1 |
| 41 | 790 | 16 | 49.4 | 500 | 3.6 | 138.9 | 410 | 6.4 | 64.1 | 290 | 31 | 9.4 |
| 47 | 41 | 5 | 8.2 | 37 | 2.3 | 16.1 | 32 | 2.8 | 11.4 | 21 | 8.1 | 2.6 |
| 49 | 23 | 1.7 | 13.5 | 11 | 1.6 | 6.9 | 14 | 1.1 | 12.7 | 17 | 2.8 | 6.1 |
| 4 | 24 | 0.65 | 36.9 | 0.72 | 0.39 | 1.8 | 27 | 0.42 | 64.3 | 4.9 | 4.9 | 1.0 |
| 19 | 170 | 3.5 | 48.6 | 110 | 1.3 | 84.6 | 99 | 1.7 | 58.2 | 72 | 11 | 6.5 |
| 136 | 350 | 16 | 21.9 | 220 | 7.5 | 29.3 | 270 | 7.7 | 35.1 | 220 | 66 | 3.3 |
| 13 | 28 | 2 | 14.0 | 22 | 0.78 | 28.2 | 17 | 1.3 | 13.1 | 20 | 6.9 | 2.9 |

Values in nanomolar

9. Additional Modifications

Additional modifications were evaluated as shown in Table 11 below. Values in micromolar.

TABLE 11

| No. | 2.1 EC50 | 2.2 EC50 | 3.1 EC50 | 4.1 EC50 | 4.2 EC50 | BRDT EC50 | 2.1/2.2 |
|---|---|---|---|---|---|---|---|
| 1 | 0.85 | 0.29 | 0.62 | 0.67 | 0.23 | 5.9 | 2.9 |
| 2 | 0.73 | 0.11 | 0.25 | 1.88 | 0.64 | — | 6.6 |
| 3 | 5.8 | 0.85 | 2.3 | >67.85 | >67.85 | — | 6.8 |
| 7 | 81 | 0.080 | 1.6 | 4.8 | 81 | 10 | >1000 |
| 9 | 12 | 14 | 10 | 47 | 15 | 10 | 0.86 |
| 11 | 3.2 | 0.20 | 1.6 | 3.4 | 51 | 4.3 | 16 |
| 12 | 0.93 | 0.030 | 0.59 | 1.5 | 0.040 | 1.8 | 31 |
| 13 | 0.88 | 59 | 1.1 | 1.3 | 60 | 2.5 | 0.015 |
| 14 | 1.8 | 0.090 | 1.19 | 2.0 | 0.060 | 2.6 | 20 |
| 15 | 7.0 | 0.11 | 10 | 7.0 | 0.10 | 0.70 | 64 |
| 16 | 9.8 | 0.98 | 6.4 | 13 | 1.9 | 17 | 10 |
| 17 | 1.1 | 0.07 | — | — | — | 4.6 | 16 |
| 18 | 1.9 | 0.11 | 1.5 | 2.3 | 0.080 | 2.6 | 4.8 |
| 21 | 0.93 | 0.03 | 0.59 | 1.5 | 0.040 | 1.8 | 31 |
| 22 | 26 | 0.79 | 10 | 27 | 1.9 | 10 | 33 |
| 23 | 2.3 | 0.10 | 0.71 | 1.5 | 0.32 | 2.1 | 23 |
| 26 | 0.47 | 0.023 | 0.078 | 1.1 | — | >36 | 20 |
| 27 | 0.22 | 0.035 | 0.31 | 2.1 | — | 0.66 | 6.3 |
| 28 | >52 | 0.010 | >52 | >52 | — | >52 | — |
| 29 | 0.46 | 0.0080 | 0.26 | 1.2 | — | 0.30 | 58 |
| 30 | 2.9 | 0.020 | 9.8 | >70 | — | 4.8 | 145 |
| 31 | 0.88 | 0.02 | 0.29 | 0.59 | — | 1.2 | 44 |
| 32 | >23 | >23 | >23 | >23 | — | >23 | — |
| 33 | >4.9 | 10 | >4.9 | >4.9 | — | >4.9 | — |
| 34 | 0.41 | 0.020 | 0.51 | 5.1 | — | 0.89 | 21 |
| 35 | 0.08 | 0.012 | 0.13 | 2.5 | — | 0.14 | 6.7 |
| 36 | 3.2 | 3.0 | 1.4 | 2.4 | 5.4 | 7.0 | 1.1 |
| 37 | 2.4 | 0.62 | 1.2 | 1.5 | 0.54 | 2.8 | 3.9 |
| 38 | 5.5 | 2.4 | 3.7 | 6.8 | 2.6 | 11 | 2.3 |
| 48 | 1.9 | 0.36 | 1.9 | — | — | 5.3 | 5.3 |
| 56 | 8.2 | 0.50 | 8.1 | >63 | — | 12 | 16 |
| 57 | 1.5 | 0.79 | 1.4 | 2.9 | 0.73 | — | 1.9 |
| 58 | 7.7 | 1.1 | 5.2 | >96 | 6.2 | — | 7.0 |
| 59 | 3.6 | 1.2 | 1.9 | 3.5 | 2.1 | — | 2.9 |
| 60 | 15 | 2.9 | 11 | >50 | 14 | — | 5.3 |
| 61 | 13 | 2.1 | 8.8 | 11 | 14 | — | 6.2 |
| 62 | 77 | 77 | 62 | 77 | 41 | — | 6.0 |
| 63 | 13 | 2.4 | 6.9 | 13 | 7.6 | — | 1.0 |
| 64 | 8.1 | 2.0 | 11 | 7.3 | 10 | — | 4.1 |
| 65 | 5.7 | 4.0 | 2.6 | 5.2 | 7.8 | — | 1.4 |
| 66 | 71 | 36 | 77 | 78 | 78 | — | 2.0 |
| 67 | 24 | 18 | 36 | 60 | 11 | — | 1.4 |
| 68 | 70 | 10 | 41 | 80 | 20 | — | 6.9 |
| 69 | 75 | 2.7 | 75 | 74 | 75 | — | 28 |
| 70 | 16 | 69 | 9.9 | 69 | 26 | — | 0.23 |
| 71 | 86 | 18 | 32 | 86 | 11 | — | 4.9 |
| 72 | 51 | 51 | 27 | 39 | 51 | — | 1.0 |

TABLE 11-continued

| No. | 2.1 EC50 | 2.2 EC50 | 3.1 EC50 | 4.1 EC50 | 4.2 EC50 | BRDT EC50 | 2.1/2.2 |
|---|---|---|---|---|---|---|---|
| 73 | 16 | 83 | 12 | 33 | 19 | — | 0.20 |
| 74 | 11 | 17 | 9.8 | 19 | 77 | — | 0.65 |
| 75 | 53 | 53 | 36 | 53 | 53 | — | 1.0 |
| 76 | 3.4 | 0.27 | 2.3 | 3.2 | 0.65 | — | 12 |
| 77 | 16 | 9.7 | 10 | 15 | 14 | — | 1.6 |
| 78 | 7.7 | 2.9 | 4.0 | 6.1 | 6.7 | — | 2.6 |
| 79 | 7.1 | 2.7 | 2.2 | 8.2 | 8.8 | — | 2.6 |
| 80 | 6.3 | 1.1 | 2.1 | 5.3 | 4.0 | — | 2.0 |
| 81 | 8.0 | 4.7 | 5.9 | 6.6 | 8.1 | — | 2.7 |
| 82 | 4.0 | 1.1 | 2.7 | 3.5 | 2.0 | — | 6.0 |
| 83 | 7.5 | 1.6 | 4.3 | 6.0 | 3.4 | — | 1.7 |
| 84 | 2.5 | 0.46 | 0.99 | 2.1 | 3.5 | — | 2.5 |
| 85 | 13 | 1.2 | 4.8 | 8.5 | 12 | — | 3.6 |
| 86 | 1.8 | 27 | 1.0 | 2.5 | 41 | — | 4.7 |
| 87 | 68 | 13 | 13 | 68 | 7.6 | — | 5.4 |
| 88 | 2.1 | 0.47 | 1.4 | 2.9 | 0.65 | — | 11 |
| 89 | 1.6 | 0.43 | 0.87 | 1.4 | 1.7 | — | 0.067 |
| 90 | 11 | 3.5 | 3.4 | 8.7 | 56 | 14 | 0.84 |
| 91 | 1.3 | 1.1 | 1.1 | 0.86 | 37 | 4.9 | 0.032 |
| 92 | 1.7 | 1.4 | 0.41 | 1.3 | 1.3 | 3.0 | 5.1 |
| 93 | 0.58 | 0.12 | 0.15 | 0.38 | — | 1.2 | 4.6 |
| 94 | 2.0 | 0.17 | 0.43 | 1.4 | — | 84 | 1.2 |
| 95 | 3.1 | 0.42 | 0.38 | 2.0 | — | 0.51 | 1.2 |
| 96 | 2.6 | 0.79 | 0.83 | 1.9 | — | 6.2 | 11 |
| 97 | 100 | 2.5 | 7.80 | 20 | — | 40 | 4.8 |
| 98 | 1.5 | 0.12 | 0.24 | 0.90 | — | 1.2 | 15 |
| 99 | 0.94 | 0.12 | 0.25 | 1.0 | — | 0.73 | 12 |
| 100 | 3.8 | 40 | 0.69 | 6.0 | — | 40 | 7.3 |
| 101 | 1.1 | 0.11 | 0.34 | 0.95 | — | 1.3 | 3.3 |
| 102 | 4.8 | 0.43 | 0.53 | 3.8 | — | 1.2 | 40 |
| 103 | 3.7 | 2.8 | 0.89 | 3.5 | — | 4.8 | 13 |
| 104 | 1.6 | 0.29 | 0.41 | 0.94 | — | 1.6 | 7.8 |
| 105 | 0.4 | 0.03 | 0.10 | 0.20 | — | 1.1 | 0.095 |
| 106 | 3.9 | 43 | 0.98 | 3.3 | — | 7.0 | 10 |
| 107 | 1.2 | 0.16 | 0.17 | 0.81 | — | 0.49 | 11 |
| 108 | 2.5 | 0.36 | 0.37 | 1.7 | — | 59 | 1.3 |
| 109 | 11 | 0.28 | 0.67 | >11 | — | 11 | 5.6 |
| 110 | 1.3 | 0.12 | 0.23 | 1.1 | — | 1.6 | 14 |
| 111 | 1.9 | 0.52 | 0.65 | 1.8 | — | 3.9 | 0.091 |
| 112 | 7.2 | 2.5 | 2.1 | 5.0 | — | 4.4 | 3.6 |
| 113 | 2.2 | 0.11 | 0.41 | 1.4 | — | 7.5 | 4.8 |
| 114 | 0.79 | 0.050 | 0.12 | 0.47 | — | 52 | 9.1 |
| 115 | 0.37 | 0.040 | 0.090 | 0.16 | — | 0.33 | 7.2 |
| 116 | 1.2 | 0.38 | 0.28 | 2.3 | — | 1.2 | 7.0 |
| 117 | 0.60 | 0.10 | 0.23 | 0.52 | — | 1.2 | 39 |
| 118 | 3.6 | 0.11 | 2.1 | 5.1 | 0.21 | 1.6 | 10 |
| 119 | | | | | | | 2.9 |
| 120 | 33 | 0.13 | 4.9 | 13 | 0.17 | — | 3.1 |
| 121 | | | | | | | 33 |
| 122 | | | | | | | 70 |
| 123 | | | | | | | >1000 |
| 124 | | | | | | | 4.0 |
| 127 | 2.3 | 0.11 | 1.2 | 2.9 | 0.06 | 4.1 | 17 |
| 132 | 20 | 0.37 | 10 | 17 | 0.54 | 10 | 16 |
| 134 | 21 | 0.59 | 10 | 21 | 0.90 | 10 | 36 |
| 136 | 17 | 0.19 | 10 | 17 | 0.25 | 10 | 63 |
| 138 | 4.6 | 0.090 | 1.8 | — | — | 8.7 | 36 |
| 139 | 0.79 | 0.23 | 0.69 | — | — | 1.9 | 3.4 |
| 140 | 21 | 1.4 | 31 | — | — | >82 | 22.9 |
| 141 | 2.5 | 0.50 | 1.7 | — | — | 5.2 | 0.015 |
| 142 | 2.5 | 0.23 | 2.5 | — | — | 8.3 | 52 |
| 143 | 8.0 | 1.1 | 11 | — | — | 34 | 93 |
| 144 | 3.8 | 0.29 | 3.1 | — | — | 15 | 7.0 |
| 145 | 19 | 0.39 | 21 | — | — | >58 | 5.0 |
| 146 | 78 | 9.6 | >78 | — | — | >78 | 22 |
| 147 | 7.2 | 1.6 | 9.4 | — | — | 17 | 7.4 |
| 148 | 90 | 34 | >90 | — | — | >90 | 16 |
| 149 | 1.3 | 0.14 | 1.0 | — | — | 3.6 | 10 |
| 150 | 72 | 22 | >72 | — | — | >72 | 13 |
| 151 | 14 | 0.67 | 8.3 | — | — | 26 | 49 |
| 152 | 79 | 8.4 | 78 | — | — | >79 | |
| 153 | 90 | 1.7 | 39 | — | — | >90 | 8.2 |
| 154 | 20 | 1.8 | 27 | — | — | >84 | 4.6 |
| 155 | 17 | 5.7 | 79 | — | — | >84 | 2.6 |
| 156 | | | | | | | 9.4 |
| 157 | | | | | | | 52 |
| 158 | | | | | | | 11 |

TABLE 11-continued

| No. | 2.1 EC50 | 2.2 EC50 | 3.1 EC50 | 4.1 EC50 | 4.2 EC50 | BRDT EC50 | 2.1/2.2 |
|---|---|---|---|---|---|---|---|
| 159 | | | | | | | 2.9 |
| 160 | 2.2 | | 3.0 | >30 | — | 3.3 | 44 |
| 161 | 0.87 | 0.044 | >30 | >30 | — | 0.76 | 20 |
| 162 | | | | | | | 21 |
| 163 | | | | | | | 6.7 |
| 164 | 22 | 0.22 | 30 | 57 | — | 32 | 100 |
| 166 | 0.13 | 0.020 | 0.15 | 0.64 | — | 0.28 | 6.5 |
| 167 | >70 | 2.1 | >70 | >70 | — | >70 | 16 |
| 168 | 35 | 1.2 | 45 | >57 | — | 39 | 99 |
| 169 | >30 | — | >30 | >30 | — | >30 | |
| 170 | 3.1 | 0.14 | 14 | >26 | — | 4.9 | 6.5 |
| 171 | >53 | 0.44 | 23 | 31 | — | >53 | 140 |
| 172 | 8.2 | 0.64 | 12 | 17 | — | 12 | 6.3 |
| 173 | 1.4 | 0.17 | 1.5 | 3.8 | — | 2.0 | 8.2 |
| 174 | 0.90 | 0.040 | 1.1 | >15 | — | 1.2 | 58 |
| 175 | 2.7 | 0.10 | 1.7 | 5.5 | — | 2.9 | 27 |
| 176 | 10 | 0.75 | 8.5 | 16 | — | 13 | 30 |
| 178 | | | | | | | 22 |
| 180 | | | | | | | 13 |
| 181 | 8.0 | 0.17 | — | — | — | — | 8.4 |
| 182 | | | | | | | 23 |
| 183 | | | | | | | 27 |
| 184 | 0.67 | 0.11 | — | — | — | — | 14 |
| 185 | 1.8 | 0.029 | — | — | — | — | |
| 186 | 2.1 | 0.059 | — | — | — | — | |
| 187 | 8.7 | 0.12 | — | — | — | — | |
| 188 | 0.11 | 0.0040 | — | — | — | — | |
| 189 | 0.67 | 0.017 | — | — | — | — | 48 |
| 190 | 2.2 | 0.12 | — | — | — | — | 37 |
| 191 | 1.2 | 0.047 | — | — | — | — | 26 |
| 192 | 4.8 | 0.052 | — | — | — | — | 6.3 |
| 193 | 1.0 | | — | — | — | — | 63 |
| 194 | 2.2 | 0.060 | — | — | — | — | 35 |
| 195 | 0.87 | 0.017 | — | — | — | — | 73 |
| 196 | 2.17 | 0.060 | — | — | — | — | 27 |
| 197 | 3.5 | 0.054 | — | — | — | — | 39 |
| 198 | 3.3 | 0.057 | — | — | — | — | 19 |
| 199 | 0.89 | 0.019 | — | — | — | — | 26 |
| 200 | 2.0 | | | | | | 92 |
| 202 | | | | | | | 36 |
| 203 | | | | | | | 51 |
| 204 | | | | | | | 36 |
| 205 | | | | | | | 64 |
| 206 | | | | | | | 57 |
| 207 | | | | | | | 44 |

I. References

R. L. Rich, J. Errey, F. Marshall, D. G. Myszka, *Anal Biochem* 409, 267 (2011).

D. G. Myszka, *J Mol Recognit* 12, 279 (1999).

Verdin, E.; Ott, M. *Nat Rev Mol Cell Biol* 2015, 16, 258.

Rothbart, S. B.; Strahl, B. D. *Biochimica et biophysica acta* 2014, 1839, 627.

Marushige, K. Proceedings of the National Academy of Sciences of the United States of America 1976, 73, 3937.

Marmorstein, R. Nature Reviews Molecular Cell Biology 2001, 2, 422.

Johnstone, R. W. *Nature Reviews Drug Discovery* 2002, 1, 287.

Wolffe, A. P.; Hayes, J. *J. Nucleic Acids Research* 1999, 27, 711.

Zeng, L.; Zhou, M.-M. *FEBS Letters* 2002, 513, 124.

Sanchez, R.; Meslamani, J.; Zhou, M.-M. Biochimica et Biophysica Acta, Gene Regulatory Mechanisms 2014, 1839, 676.

Filippakopoulos, P.; Knapp, S. *Nature Reviews Drug Discovery* 2014, 13, 337.

Romero, F. A.; Taylor, A. M.; Crawford, T. D.; Tsui, V.; Cote, A.; Magnuson, S. *J. Med. Chem.* 2015, Ahead of Print.

Wu, X.; Qi, J.; Bradner, J. E.; Xiao, G.; Chen, L.-F. *Journal of Biological Chemistry* 2013, 288, 36094.

Belkina, A. C.; Denis, G. V. *Nature Reviews Cancer* 2012, 12, 465.

Xu, Z.; Shi, Y. Zhonghua Fuchanke Zazhi 2011, 46, 636.

Filippakopoulos, P.; Qi, J.; Picaud, S.; Shen, Y.; Smith, W. B.; Fedorov, O.; Morse, E. M.; Keates, T.; Hickman, T. T.; Felletar, I.; Philpott, M.; Munro, S.; McKeown, M. R.; Wang, Y.; Christie, A. L.; West, N.; Cameron, M. J.; Schwartz, B.; Heightman, T. D.; La Thangue, N.; French, C.; Wiest, O.; Kung, A. L.; Knapp, S.; Bradner, J. E. Nature (London, United Kingdom) 2010, 468, 1067.

Muller, S.; Filippakopoulos, P.; Knapp, S. *Expert Reviews in Molecular Medicine* 2011, 13, e29/1.

Shi, J.; Wang, Y.; Zeng, L.; Wu, Y.; Deng, J.; Zhang, Q.; Lin, Y.; Li, J.; Kang, T.; Tao, M.; Rusinova, E.; Zhang, G.; Wang, C.; Zhu, H.; Yao, J.; Zeng, Y.-X.; Evers, B. M.; Zhou, M.-M.; Zhou, B. P. *Cancer Cell* 2014, 25, 210.

Umehara, T.; Nakamura, Y.; Wakamori, M.; Ozato, K.; Yokoyama, S.; Padmanabhan, B. *FEBS Letters* 2010, 584, 3901.

Nicodeme, E.; Jeffrey, K. L.; Schaefer, U.; Beinke, S.; Dewell, S.; Chung, C.-w.; Chandwani, R.; Marazzi, I.;

Wilson, P.; Coste, H.; White, J.; Kirilovsky, J.; Rice, C. M.; Lora, J. M.; Prinjha, R. K.; Lee, K.; Tarakhovsky, A. *Nature* 2010, 468, 1119.

Delmore, J. E.; Issa, G. C.; Lemieux, M. E.; Rahl, P. B.; Shi, J.-W.; Jacobs, H. M.; Kastritis, E.; Gilpatrick, T.; Paranal, R. M.; Qi, J.; Chesi, M.; Schinzel, A. C.; McKeown, M. R.; Heffernan, T. P.; Vakoc, C. R.; Bergsagel, P. L.; Ghobrial, I. M.; Richardson, P. G.; Young, R. A.; Hahn, W. C.; Anderson, K. C.; Kung, A. L.; Bradner, J. E.; Mitsiades, C. S. *Cell* (Cambridge, Mass., United States) 2011, 146, 904.

Shimamura, T.; Chen, Z.; Soucheray, M.; Carretero, J.; Kikuchi, E.; Tchaicha, J. H.; Gao, Y.; Cheng, K. A.; Cohoon, T. J.; Qi, J.; Akbay, E.; Kimmelman, A. C.; Kung, A. L.; Bradner, J. E.; Wong, K.-K. *Clinical Cancer Research* 2013, 19, 6183.

Puissant, A.; Frumm, S. M.; Alexe, G.; Bassil, C. F.; Qi, J.; Chanthery, Y. H.; Nekritz, E. A.; Zeid, R.; Gustafson, W. C.; Greninger, P.; Garnett, M. J.; McDermott, U.; Benes, C. H.; Kung, A. L.; Weiss, W. A.; Bradner, J. E.; Stegmaier, K. *Cancer Discovery* 2013, 3, 308.

Pastori, C.; Daniel, M.; Penas, C.; Volmar, C.-H.; Johnstone, A. L.; Brothers, S. P.; Graham, R. M.; Allen, B.; Sarkaria, J. N.; Komotar, R. J.; Wahlestedt, C.; Ayad, N. G. *Epigenetics* 2014, 9, 611.

Ott, C. J.; Kopp, N.; Bird, L.; Paranal, R. M.; Qi, J.; Bowman, T.; Rodig, S. J.; Kung, A. L.; Bradner, J. E.; Weinstock, D. M. *Blood* 2012, 120, 2843.

Henssen, A.; Thor, T.; Odersky, A.; Heukamp, L.; El-Hindy, N.; Beckers, A.; Speleman, F.; Althoff, K.; Schafers, S.; Schramm, A.; Sure, U.; Fleischhack, G.; Eggert, A.; Schulte Johannes, H. *Oncotarget* 2013, 4, 2080.

Bandopadhayay, P.; Bergthold, G.; Nguyen, B.; Schubert, S.; Gholamin, S.; Tang, Y.; Bolin, S.; Schumacher, S. E.; Zeid, R.; Masoud, S.; Yu, F.; Vue, N.; Gibson, W. J.; Paolella, B. R.; Mitra, S. S.; Cheshier, S. H.; Qi, J.; Liu, K.-W.; Wechsler-Reya, R.; Weiss, W. A.; Swartling, F. J.; Kieran, M. W.; Bradner, J. E.; Beroukhim, R.; Cho, Y.-J. *Clinical Cancer Research* 2014, 20, 912.

Cheng, Z.; Gong, Y.; Ma, Y.; Lu, K.; Lu, X.; Pierce, L. A.; Thompson, R. C.; Muller, S.; Knapp, S.; Wang, J. *Clinical Cancer Research* 2013, 19, 1748.

Fowler, T.; Ghatak, P.; Price, D. H.; Conaway, R.; Conaway, J.; Chiang, C.-M.; Bradner, J. E.; Shilatifard, A.; Roy, A. L. *PLoS One* 2014, 9, e87003/1.

Mertz, J. A.; Conery, A. R.; Bryant, B. M.; Sandy, P.; Balasubramanian, S.; Mele, D. A.; Bergeron, L.; Sims, R. J., III *Proceedings of the National Academy of Sciences of the United States of America* 2011, 108, 16669.

Roderick, J. E.; Tesell, J.; Shultz, L. D.; Brehm, M. A.; Greiner, D. L.; Harris, M. H.; Silverman, L. B.; Sallan, S. E.; Gutierrez, A.; Look, A. T.; Qi, J.; Bradner, J. E.; Kelliher, M. A. *Blood* 2014, 123, 1040.

Wyce, A.; Degenhardt, Y.; Bai, Y.; Le, B.; Korenchuk, S.; Crouthame, M.-C.; McHugh Charles, F.; Vessella, R.; Creasy Caretha, L.; Tummino Peter, J.; Barbash, O. *Oncotarget* 2013, 4, 2419.

Garnier, J.-M.; Sharp, P. P.; Burns, C. J. *Expert Opinion on Therapeutic Patents* 2014, 24, 185.

Gehling, V. S.; Hewitt, M. C.; Vaswani, R. G.; Leblanc, Y.; Cote, A.; Nasveschuk, C. G.; Taylor, A. M.; Harmange, J.-C.; Audia, J. E.; Pardo, E.; Joshi, S.; Sandy, P.; Mertz, J. A.; Sims, R. J.; Bergeron, L.; Bryant, B. M.; Bellon, S.; Poy, F.; Jayaram, H.; Sankaranarayanan, R.; Yellapantula, S.; Bangalore Srinivasamurthy, N.; Birudukota, S.; Albrecht, B. K. *ACS Medicinal Chemistry Letters* 2013, 4, 835.

Hewings, D. S.; Rooney, T. P. C.; Jennings, L. E.; Hay, D. A.; Schofield, C. J.; Brennan, P. E.; Knapp, S.; Conway, S. J. *J. Med. Chem.* 2012, 55, 9393.

Chung, C.-w.; Coste, H.; White, J. H.; Mirguet, O.; Wilde, J.; Gosmini, R. L.; Delves, C.; Magny, S. M.; Woodward, R.; Hughes, S. A.; Boursier, E. V.; Flynn, H.; Bouillot, A. M.; Bamborough, P.; Brusq, J.-M. G.; Gellibert, F. J.; Jones, E. J.; Riou, A. M.; Homes, P.; Martin, S. L.; Uings, I. J.; Toum, J.; Clement, C. A.; Boullay, A.-B.; Grimley, R. L.; Blandel, F. M.; Prinjha, R. K.; Lee, K.; Kirilovsky, J.; Nicodeme, E. *J. Med. Chem.* 2011, 54, 3827.

Mirguet, O.; Gosmini, R.; Toum, J.; Clement, C. A.; Bamathan, M.; Brusq, J.-M.; Mordaunt, J. E.; Grimes, R. M.; Crowe, M.; Pineau, O.; Ajakane, M.; Daugan, A.; Jeffrey, P.; Cutler, L.; Haynes, A. C.; Smithers, N. N.; Chung, C.-w.; Bamborough, P.; Uings, I. J.; Lewis, A.; Witherington, J.; Parr, N.; Prinjha, R. K.; Nicodeme, E. *J. Med. Chem.* 2013, 56, 7501.

Fedorov, O.; Lingard, H.; Wells, C.; Monteiro, O. P.; Picaud, S.; Keates, T.; Yapp, C.; Philpott, M.; Martin, S. J.; Felletar, I.; Marsden, B. D.; Filippakopoulos, P.; Muller, S.; Knapp, S.; Brennan, P. E. *J. Med. Chem.* 2014, 57, 462.

Spiltoir, J. I.; Stratton, M. S.; Cavasin, M. A.; Demos-Davies, K.; Reid, B. G.; Qi, J.; Bradner, J. E.; McKinsey, T. A. *Journal of Molecular and Cellular Cardiology* 2013, 63, 175.

Boehn, D.; Calvanese, V.; Dar, R. D.; Xing, S.; Schroeder, S.; Martins, L.; Aull, K.; Li, P.-C.; Planelles, V.; Bradner, J. E.; Zhou, M.-M.; Siliciano, R. F.; Weinberger, L.; Verdin, E.; Ott, M. *Cell Cycle* 2013, 12, 452.

McBride, A. A.; Jang, M. K. *Viruses* 2013, 5, 1374.

Wang, F.-N.; Liu, H.-S.; Blanton, W. P.; Belkina, A.; Lebrasseur, N. K.; Denis, G. V. *Biochemical Journal* 2010, 425, 71.

Matzuk, M. M.; McKeown, M. R.; Filippakopoulos, P.; Li, Q.; Ma, L.; Agno, J. E.; Lemieux, M. E.; Picaud, S.; Yu, R. N.; Qi, J.; Knapp, S.; Bradner, J. E. *Cell* (Cambridge, Mass., United States) 2012, 150, 673.

Bolden, J. E.; Peart, M. J.; Johnstone, R. W. *Nature Reviews Drug Discovery* 2006, 5, 769.

Zhang, G.; Plotnikov, A. N.; Rusinova, E.; Shen, T.; Morohashi, K.; Joshua, J.; Zeng, L.; Mujtaba, S.; Ohlmeyer, M.; Zhou, M.-M. *J. Med. Chem.* 2013, 56, 9251.

Gacias, M.; Gerona-Navarro, G.; Plotnikov, A. N.; Zhang, G.; Zeng, L.; Kaur, J.; Moy, G.; Rusinova, E.; Rodriguez, Y.; Matikainen, B.; Vincek, A.; Joshua, J.; Casaccia, P.; Zhou, M.-M. *Chemistry & Biology* (Oxford. United Kingdom) 2014, 21, 841.

Baud, M. G. J.; Lin-Shiao, E.; Cardote, T.; Tallant, C.; Pschibul, A.; Chan, K.-H.; Zengerle, M.; Garcia, J. R.; Kwan, T. T. L.; Ferguson, F. M.; Ciulli, A. *Science* (Washington. D.C. United States) 2014, 346, 638.

Baud, M. G. J.; Lin-Shiao, E.; Zengerle, M.; Tallant, C.; Ciulli, A. *J. Med. Chem.* 2015, Ahead of Print.

McLure, K. G.; Gesner, E. M.; Tsujikawa, L.; Kharenko, O. A.; Attwell, S.; Campeau, E.; Wasiak, S.; Stein, A.; White, A.; Fontano, E.; Suto, R. K.; Wong, N. C. W.; Wagner, G. S.; Hansen, H. C.; Young, P. R. *PLoS One* 2013, 8, e83190/1.

Picaud, S.; Wells, C.; Felletar, I.; Brotherton, D.; Martin, S.; Savitsky, P.; Diez-Dacal, B.; Philpott, M.; Bountra, C.; Lingard, H.; Fedorov, O.; Muller, S.; Brennan, P. E.; Knapp, S.; Filippakopoulos, P. *Proceedings of the National Academy of Sciences of the United States of America* 2013, 110, 19754.

Atkinson, S. J.; Soden, P. E.; Angell, D. C.; Bantscheff, M.; Chung, C.-w.; Giblin, K. A.; Smithers, N.; Furze, R. C.; Gordon, L.; Drewes, G.; Rioja, I.; Witherington, J.; Parr, N. J.; Prinjha, R. K. *MedChemComm* 2014, 5, 342.

Sachchidanand; Resnick-Silverman, L.; Yan, S.; Mutjaba, S.; Liu, W.-j.; Zeng, L.; Manfredi, J. J.; Zhou, M.-M. *Chemistry & Biology* (Cambridge, Mass., United States) 2006, 13, 81.

Amans, D.; Atkinson, S. J.; Harrison, L. A.; Hirst, D. J.; Law, R. P.; Lindon, M.; Preston, A.; Seal, J. T.; Wellaway, C. R.; (GlaxoSmithKline Intellectual Property (No. 2) Limited, UK). Application: WO2014140076 A1, 2014, p 479pp.

Amans, D.; Demont, E. H.; Mitchell, D. J.; Seal, J. T.; (GlaxoSmithKline LLC, USA). Application: WO2012143415 A1, 2012, p 129pp.

Amans, D.; Demont, E. H.; Mitchell, D. J.; Watson, R. J.; (GlaxoSmithKline LLC, USA). Application: WO2012143413 A1, 2012, p 70pp.

Demont, E. H.; Garton, N. S.; Gosmini, R. L. M.; Hayhow, T. G. C.; Seal, J.; Wilson, D. M.; Woodrow, M. D.; (GlaxoSmithkline LLC, USA). Application: WO2011054841 A1, 2011, p 205pp.

Demont, E. H.; Gosmini, R. L. M.; (GlaxoSmithkline LLC, USA). Application: WO2011054848 A1, 2011, p 199pp.

Gosmini, R; Nguyen Van, L.; Toum, J.; Simon, C.; Brusq Jean-Marie, G.; Krysa, G.; Mirguet, O.; Riou-Eymard Alizon, M.; Boursier Eric, V.; Trottet, L.; Bamborough, P.; Clark, H.; Chung, C.-W.; Cutler, L.; Demont Emmanuel, H.; Kaur, R; Lewis Antonia, J.; Schilling Mark, B.; Soden Peter, E.; Taylor, S.; Walker Ann, L.; Walker Matthew, D.; Prinjha Rab, K.; Nicodeme, E. *Journal of medicinal chemistry* 2014, 57, 8111.

Wyce, A.; Ganji, G.; Smitheman, K. N.; Chung, C.-W.; Korenchuk, S.; Bai, Y.; Barbash, O.; Le, B. C.; Craggs, P. D.; McCabe, M. T.; Kennedy-Wilson, K. M.; Sanchez, L. V.; Gosmini, R. L.; Parr, N.; McHugh, C. F.; Dhanak, D.; Prinjha, R. K.; Auger, K. R.; Tummino, P. J. *PLoS One* 2013, 8, e72967.

Nobeli, I.; Price, S. L.; Lommerse, J. P. M.; Taylor, R. *Journal of Computational Chemistry* 1997, 18, 2060.

Klebe, G. *Nat Rev Drug Discov* 2015, 14, 95.

Northcott, P. A.; Shih, D. J. H.; Peacock, J.; Garzia, L.; Sorana Morrissy, A.; Zichner, T.; Stuetz, A. M.; Korshunov, A.; Reimand, J.; Schumacher, S. E.; Beroukhim, R.; Ellison, D. W.; Marshall, C. R.; Lionel, A. C.; Mack, S.; Dubuc, A.; Yao, Y.; Ramaswamy, V.; Luu, B.; Rolider, A.; Cavalli, F. M. G.; Wang, X.; Remke, M.; Wu, X.; Chiu, R. Y. B.; Chu, A.; Chuah, E.; Corbett, R. D.; Hoad, G. R.; Jackman, S. D.; Li, Y.; Lo, A.; Mungall, K. L.; Ming Nip, K.; Qian, J. Q.; Raymond, A. G. J.; Thiessen, N.; Varhol, R. J.; Birol, I.; Moore, R. A.; Mungall, A. J.; Holt, R.; Kawauchi, D.; Roussel, M. F.; Kool, M.; Jones, D. T. W.; Witt, H.; Fernandez-L, A.; Kenney, A. M.; Wechsler-Reya, R. J.; Dirks, P.; Aviv, T.; Grajkowska, W. A.; Perek-Polnik, M.; Haberler, C. C.; Delattre, O.; Reynaud, S. S.; Doz, F. F.; Pemet-Fattet, S. S.; Cho, B.-K.; Kim, S.-K.; Wang, K.-C.; Scheurlen, W.; Eberhart, C. G.; Fevre-Montange, M.; Jouvet, A.; Pollack, I. F.; Fan, X.; Muraszko, K. M.; Yancey Gillespie, G.; Di Rocco, C.; Massimi, L.; Michiels, E. M. C.; Kloosterhof, N. K.; French, P. J.; Kros, J. M.; Olson, J. M.; Ellenbogen, R. G.; Zitterbart, K.; Kren, L.; Thompson, R. C.; Cooper, M. K.; Lach, B.; McLendon, R. E.; Bigner, D. D.; Fontebasso, A.; Albrecht, S.; Jabado, N.; Lindsey, J. C.; Bailey, S.; Gupta, N.; Weiss, W. A.; Bognar, L.; Klekner, A.; Van Meter, T. E.; Kumabe, T.; Tominaga, T.; Elbabaa, S. K.; Leonard, J. R.; Rubin, J. B. *Nature* (London. United Kingdom) 2012, 488, 49.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

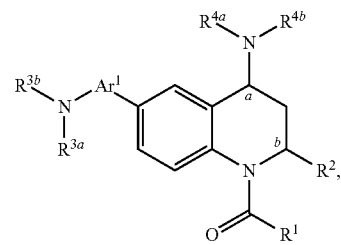

wherein $R^1$ is selected from C1-C4 alkyl, C1-C4 haloalkyl, and C1-C4 deuterated alkyl;

wherein $R^2$ is C1-C4 alkyl;

wherein $R^{3a}$ is selected from hydrogen, C1-C6 alkyl, C1-C6 haloalkyl, $Cy^2$, —(C1-C6 alkyl)$Cy^2$, —(C1-C6 alkyl)$Ar^4$, —C(O)(C1-C6 alkyl), —C(O)(CH$_2$)$_m$Cy$^2$, —C(O)(CH$_2$)$_m$Ar$^4$, —C(O)(C1-C4 alkyl)CCH, —CO$_2$(C1-C6 alkyl), and amine protecting group, and wherein $R^{3b}$ is selected from —C(O)(unsubstituted C1-C6 alkyl), —C(O)(CH$_2$)$_m$Cy$^2$, —C(O)(CH$_2$)$_m$Ar$^4$, —C(O)(C1-C4 alkyl)CCH, and -CO$_2$(C1-C6 alkyl);

wherein m, when present, is selected from 0, 1, 2, and 3;

wherein $Cy^2$, when present, is selected from C3-C6 cycloalkyl and C3-C6 heterocycloalkyl and is substituted with 0-4 non-hydrogen groups independently selected from halogen, —OH, —CN, C1-C4 alkyl, C1-C4 alkoxy, and C1-C4 haloalkyl;

wherein $Ar^4$, when present, is selected from aryl and heteroaryl and is substituted with 0-4 non-hydrogen groups independently selected from halogen, —OH, —CN, C1-C4 alkyl, C1-C4 alkoxy, and C1-C4 haloalkyl;

or wherein each of $R^{3a}$ and $R^{3b}$ are optionally covalently bonded together and, together with the intermediate atoms, comprise a 5- to 7-membered heteroaryl and are substituted with 0-4 non-hydrogen groups independently selected from halogen, —OH, —CN, C1-C4 alkyl, C1-C4 alkoxy, and C1-C4 haloalkyl;

wherein $Ar^1$ is selected from aryl and is substituted with 0-4 non-hydrogen groups independently selected from halogen, —OH, —CN, C1-C4 alkyl, C1-C4 alkoxy, and C1-C4 haloalkyl;

wherein $R^{4a}$ is selected from hydrogen, C1-C4 alkyl, and amine protecting group and wherein $R^{4b}$ is selected from C4-C8 alkyl, —(CH$_2$)$_n$Cy$^1$, —(CH$_2$)$_o$Ar$^2$, and —COR$^6$;

wherein each of n and o, when present, is selected from 0, 1, 2, and 3;

wherein Cy¹, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl;

wherein Ar², when present, is selected from aryl and 5- to 12-membered heteroaryl and is substituted with 0-4 non-hydrogen groups independently selected from halogen, —OH, —CN, —NO₂, C1-C4 alkyl, C1-C4 alkoxy, C1-C4 haloalkyl, C1-C4 haloalkoxy, C1-C4 aminoalkyl, C3-C6 cycloalkyl, —COR²¹, —CO₂R²¹, —CONR²²ᵃR²²ᵇ, —(CH₂)$_q$NR²²ᵃR²²ᵇ, —SO₂NR²²ᵃR²²ᵇ, —NR²³C(O)R²⁴, —NR²³(CH₂)$_q$(C3-C6 cycloalkyl), —NR²³(CH₂)$_q$(heterocycloalkyl), and 3- to 5-membered heterocycloalkyl;

wherein q, when present, is selected from 0, 1, 2, 3, and 4;

wherein each occurrence of R²¹, when present, is independently selected from hydrogen, C1-C6 alkyl, C1-C6 hydroxyalkyl, C3-C6 cycloalkyl, C3-C6 heterocycloalkyl, —COR³⁰, —(C1-C4 alkyl)OC(O)(C1-C4 alkyl), and —(C1-C6 alkyl)NHC(O)A;

wherein A has a structure:

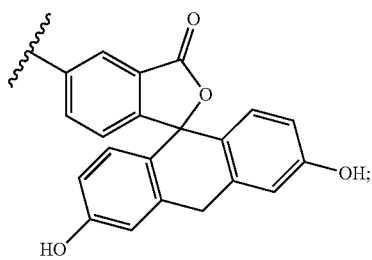

wherein each occurrence of R³⁰, when present, is independently selected from hydrogen, C1-C6 alkyl, C1-C6 alkoxy, C1-C6 aminoalkyl, C3-C6 cycloalkyl, and C3-C6 heterocycloalkyl;

wherein each occurrence of each of R²²ᵃ and R²²ᵇ, when present, is independently selected from hydrogen, C1-C6 alkyl, C3-C6 cycloalkyl, C3-C6 heterocycloalkyl, and —COR³⁰;

wherein R²³, when present, is selected from hydrogen and C1-C4 alkyl;

wherein R²⁴, when present, is selected from C1-C4 alkyl, C1-C4 hydroxyalkyl, C1-C4 alkyl (C1-C4 alkoxy), C1-C4 alkylamino, (C1-C4)(C1-C4) dialkylamino, C1-4 alkylamino(C1-C4 alkyl), (C1-C4)(C1-C4) dialkylamino(C1-C4 alkyl), —(CH₂)$_r$(C3-C6 cycloalkyl), and —(CH₂)$_s$(C3-C6 heterocycloalkyl);

wherein r, when present, is selected from 0, 1, 2, and 3;

wherein R⁶, when present, is selected from C1-C4 alkyl, C1-C4 haloalkyl, C1-C4 alkoxy, and —(CH₂)$_s$Cy³;

wherein s, when present, is selected from 0, 1, and 2; and wherein Cy³, when present, is selected from cycloalkyl, heterocycloalkyl, aryl, and heteroaryl and is substituted with 0-4 non-hydrogen groups independently selected from halogen, —OH, —CN, C1-C4 alkyl, C1-C4 alkoxy, and C1-C4 haloalkyl;

or wherein each of R⁴ᵃ and R⁴ᵇ is hydrogen, provided that when o is 0 and Ar² is monoaryl then Ar² is substituted with at least one non-hydrogen group, or a pharmaceutically acceptable salt thereof.

2. A compound having a structure represented by a formula:

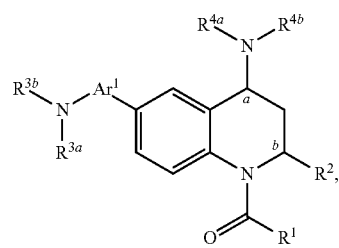

wherein R¹ is selected from C1-C4 alkyl, C1-C4 haloalkyl, and C1-C4 deuterated alkyl;

wherein R² is C1-C4 alkyl;

wherein R³ᵃ is selected from hydrogen, C1-C6 alkyl, C1-C6 haloalkyl, —(C1-C6 alkyl)Cy², —C(O)(C1-C6 alkyl), —C(O)Cy², and amine protecting group; and R³ᵇ is selected from —C(O)(unsubstituted C1-C6 alkyl), and —C(O)Cy²;

wherein Cy², when present, is selected from C3-C6 cycloalkyl and C3-C6 heterocycloalkyl and is substituted with 0-4 non-hydrogen groups independently selected from halogen, —OH, —CN, C1-C4 alkyl, C1-C4 alkoxy, and C1-C4 haloalkyl;

or wherein each of R³ᵃ and R³ᵇ are optionally covalently bonded together and, together with the intermediate atoms, comprise a 5- to 7-membered heteroaryl and are substituted with 0-4 non-hydrogen groups independently selected from halogen, —OH, —CN, C1-C4 alkyl, C1-C4 alkoxy, and C1-C4 haloalkyl;

wherein Ar¹ is selected from aryl and is substituted with 0-4 non-hydrogen groups independently selected from halogen, —OH, —CN, C1-C4 alkyl, C1-C4 alkoxy, and C1-C4 haloalkyl;

wherein R⁴ᵃ is selected from hydrogen, C1-C4 alkyl, and amine protecting group and wherein R⁴ᵇ is selected from Cy¹, Ar², and —COR⁶;

wherein Cy¹, when present, is selected from cycloalkyl, five-membered heterocycle, and six-membered heterocycle and is substituted with 0-4 non-hydrogen groups independently selected from halogen, —OH, —CN, C1-C4 alkyl, C1-C4 alkoxy, and C1-C4 haloalkyl;

wherein Ar², when present, is selected from aryl and 5- to 12-membered heteroaryl and is substituted with 1-4 non-hydrogen groups independently selected from halogen, —OH, —CN, —NO₂, C1-C4 alkyl, C1-C4 alkoxy, C1-C4 haloalkyl, C1-C4 haloalkoxy, C1-C4 aminoalkyl, C3-C6 cycloalkyl, —COR²¹, —CO₂R²¹, —CONR²²ᵃR²²ᵇ, —NR²²ᵃR²²ᵇ, —SO₂NR²²ᵃR²²ᵇ, and 3- to 5-membered heterocycloalkyl;

wherein each occurrence of R²¹, when present, is independently selected from hydrogen, C1-C6 alkyl, C3-C6 cycloalkyl, C3-C6 heterocycloalkyl, and —COR³⁰;

wherein each occurrence of each of R²²ᵃ and R²²ᵇ, when present, is independently selected from hydrogen, C1-C6 alkyl, C3-C6 cycloalkyl, C3-C6 heterocycloalkyl, and —COR³⁰;

wherein each occurrence of $R^{30}$, when present, is independently selected from hydrogen, C1-C6 alkyl, C1-C6 alkoxy, C1-C6 aminoalkyl, C3-C6 cycloalkyl, and C3-C6 heterocycloalkyl; and wherein $R^6$, when present, is selected from C1-C4 alkyl, C1-C4 haloalkyl, and C1-C4 alkoxy, or a pharmaceutically acceptable salt thereof.

3. The compound of claim 2, wherein the substituents on the carbons marked "a" and "b" are in a cis configuration.

4. The compound of claim 2, wherein $R^{4a}$ is hydrogen and $R^{4b}$ is $Ar^2R^5$, wherein $R^5$ is selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^{21}$, —CO$_2$R$^{21}$, —CONR$^{22a}$R$^{22b}$, —NR$^{22a}$R$^{22b}$, —SO$_2$NR$^{22a}$R$^{22b}$, and 3- to 5-membered heterocycloalkyl.

5. The compound of claim 1, wherein $R^{4a}$ is selected from hydrogen, C1-C4 alkyl, and amine protecting group and wherein $R^{4b}$ is selected from $Cy^1$, $Ar^2$, and —COR$^6$.

6. The compound of claim 1, wherein $R^{4b}$ is selected from $Cy^1$, $Ar^2$, and —COR$^6$.

7. The compound of claim 2, wherein $Ar^1$ is aryl substituted with 0 non-hydrogen groups.

8. The compound of claim 2, having a structure represented by a formula:

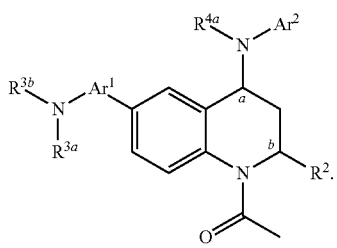

9. The compound of claim 2, having a structure represented by a formula:

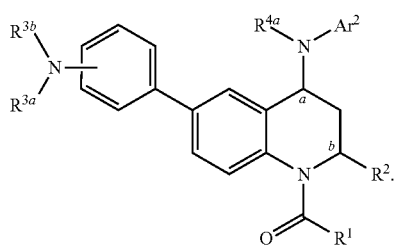

10. The compound of claim 2, having a structure represented by a formula:

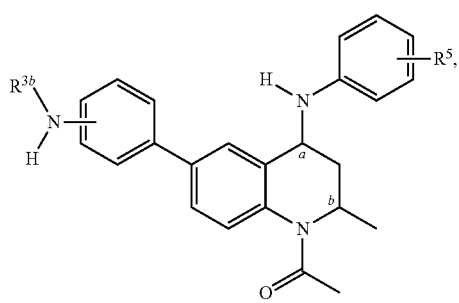

wherein $R^5$ is selected from halogen, —OH, —CN, —NO$_2$, C1-C4 alkyl, C1-C4 alkoxy, C1-C4 haloalkyl, C1-C4 haloalkoxy, C1-C4 aminoalkyl, C3-C6 cycloalkyl, —COR$^M$, —CO$_2$R$^{21}$, —CONR$^{22a}$R$^{22b}$, —NR$^{22a}$R$^{22b}$, —SO$_2$NR$^{22a}$R$^{22b}$, and 3- to 5-membered heterocycloalkyl.

11. A pharmaceutical composition comprising the compound of claim 2.

12. A method of treating a disorder for which a bromodomain is indicated in a subject in need thereof, the method comprising administering a therapeutically effective amount of the compound of claim 2.

13. The method of claim 12, wherein the disorder is selected from an estrogen deficiency, inflammation, a metabolic disorder, adipogenesis, a vascular disease, acute myocardial infarction, addiction, biliary-driven liver regeneration, atherosclerosis, trypanosomiasis, pulmonary arterial hypertension, amyotrophic lateral sclerosis, psoriasis, rheumatoid arthritis, autosomal dominant polycystic kidney disease, acute graft-versus-host disease, a T-cell mediated inflammatory disease, septic shock, diabetic nephropathy, heart failure, moloney murine leukemia, an autoimmune disorder, idiopathic pulmonary fibrosis, respiratory syncytial virus, human immunodeficiency virus, and autoimmune encephalomyelitis.

14. The method of claim 12, wherein the disorder is cancer.

15. The compound of claim 2, wherein the compound has a structure represented by a formula:

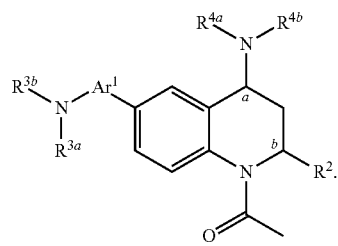

16. A compound selected from:

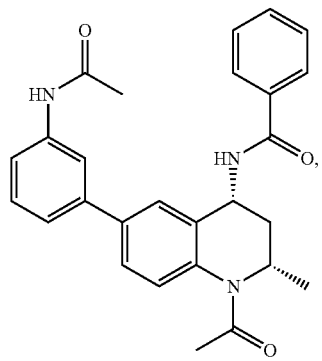

351
-continued
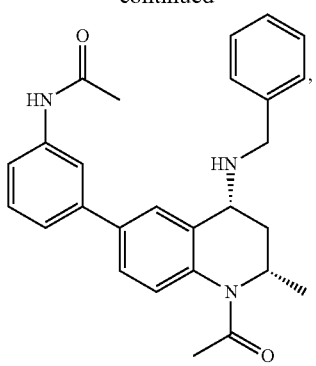
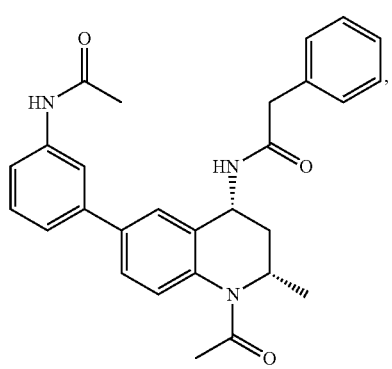
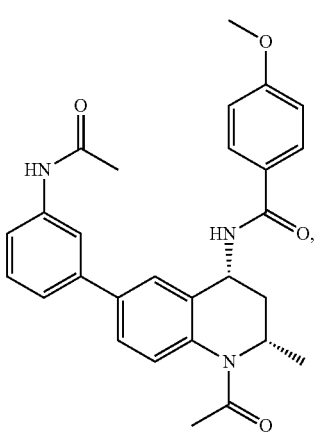
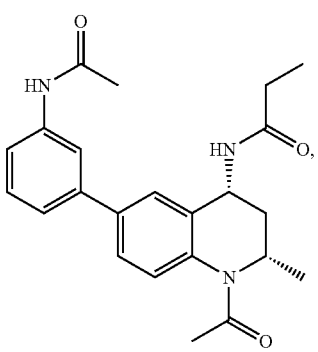
352
-continued
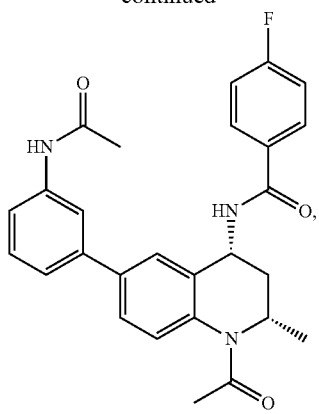
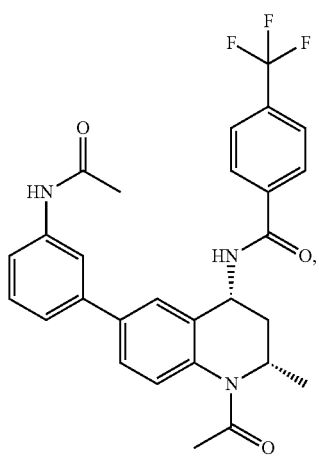
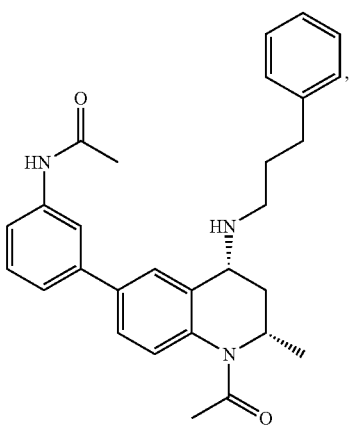
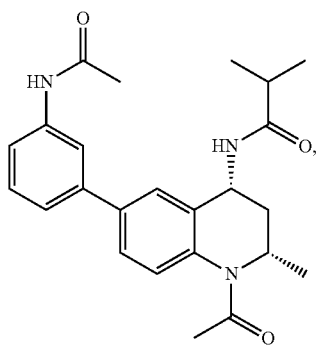

353
-continued
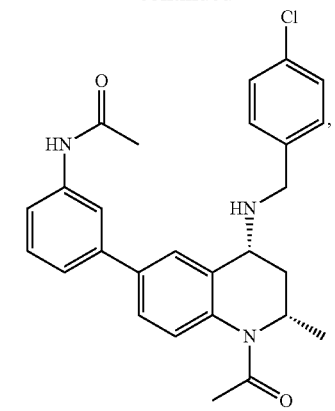
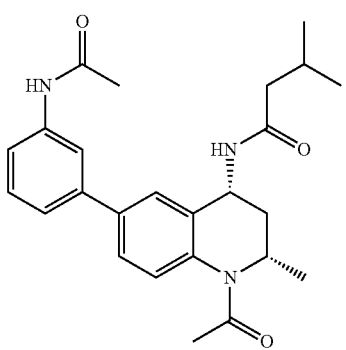
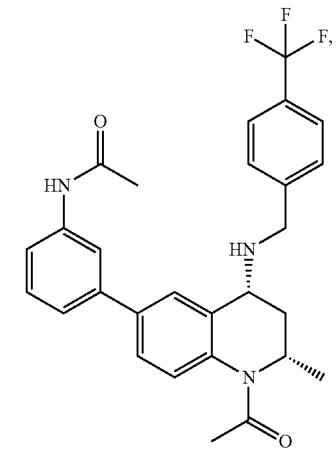
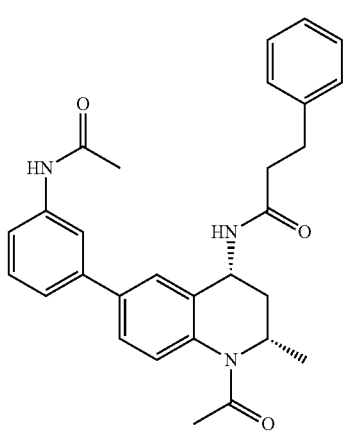
354
-continued
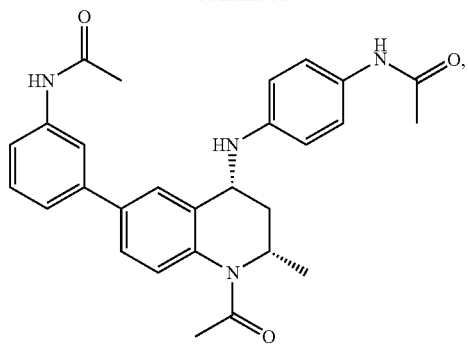
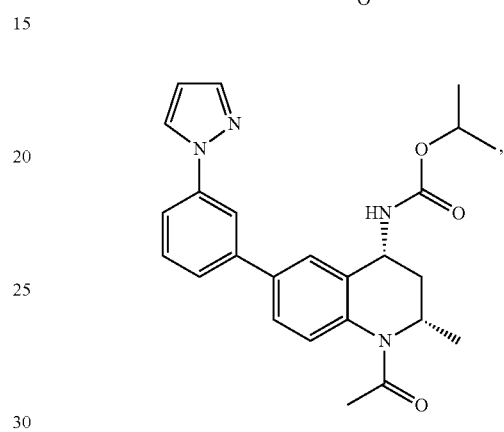
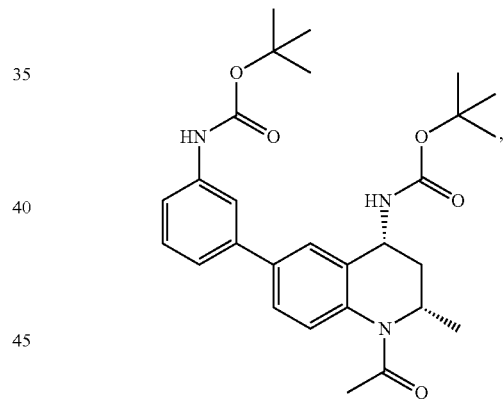
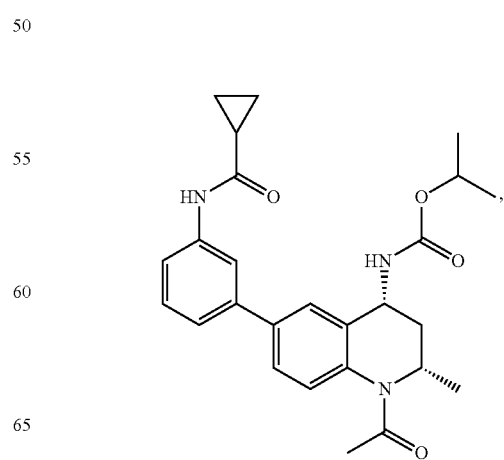

355
-continued
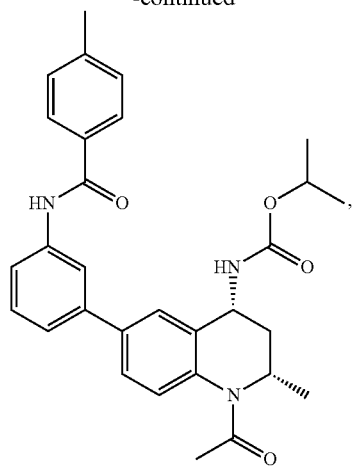
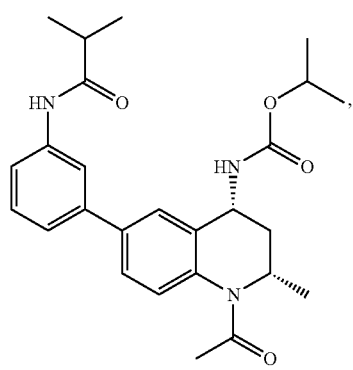
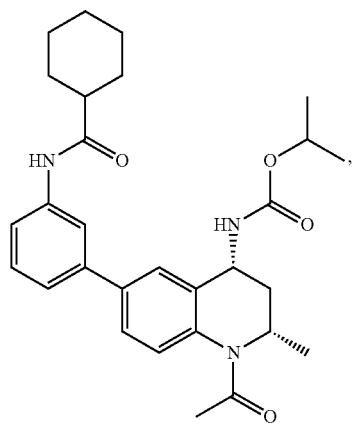
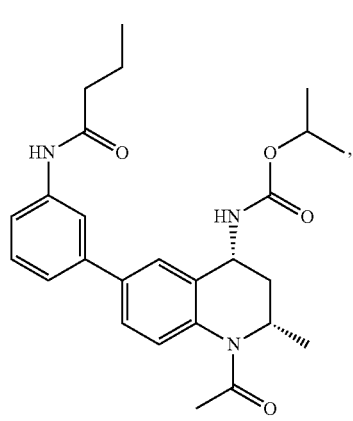
356
-continued
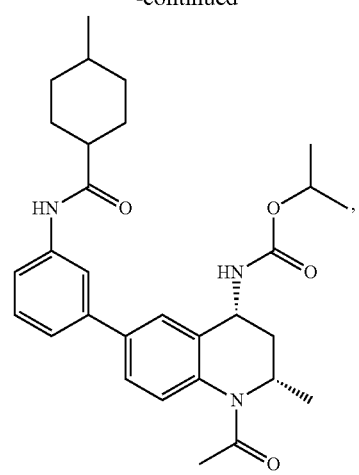
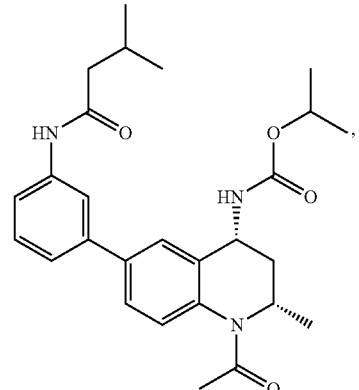
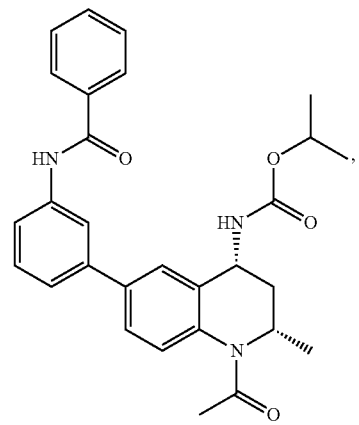
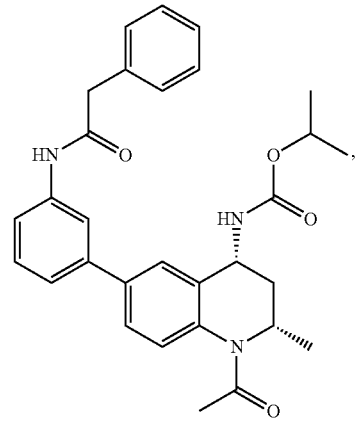

357
-continued
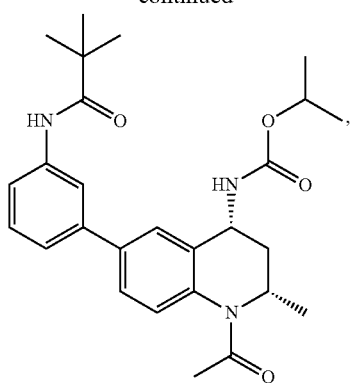
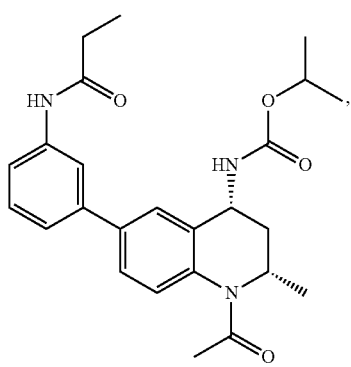
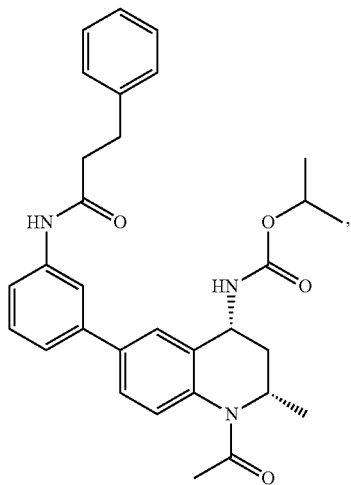
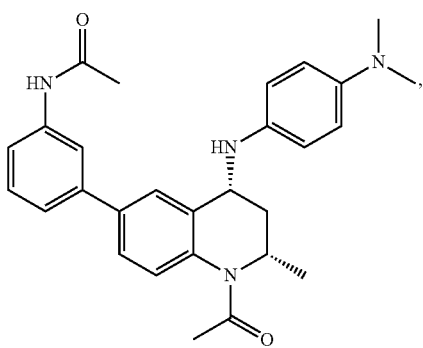
358
-continued
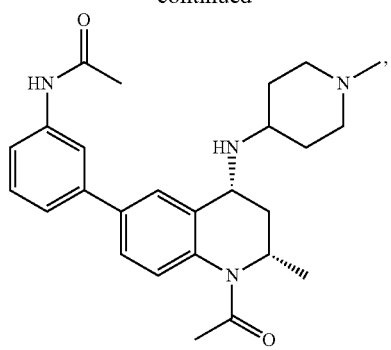
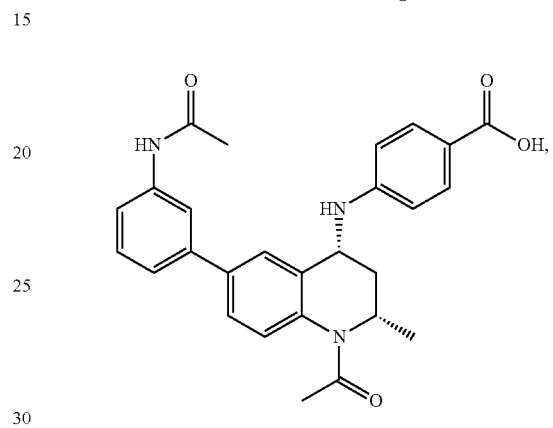
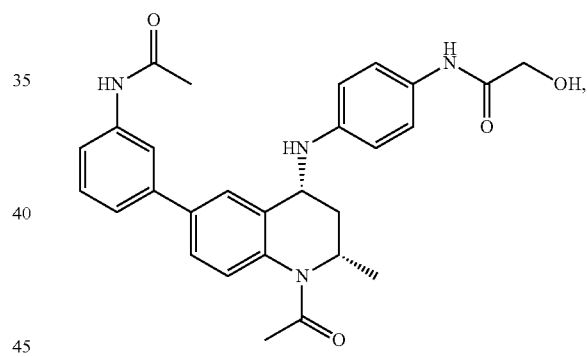
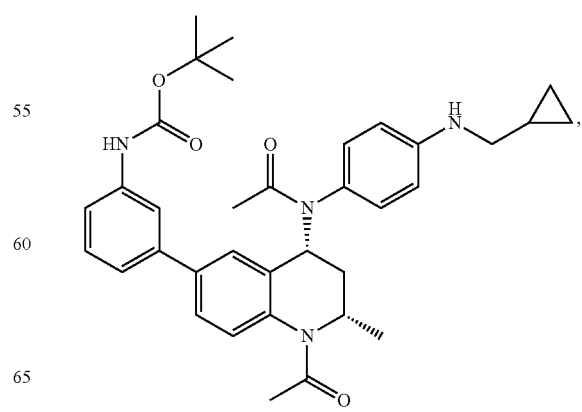

| 359 -continued | 360 -continued |
|---|---|
| 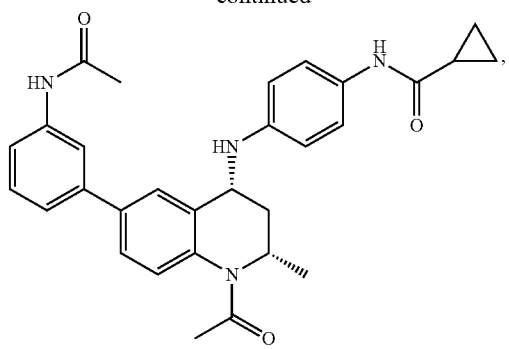 | 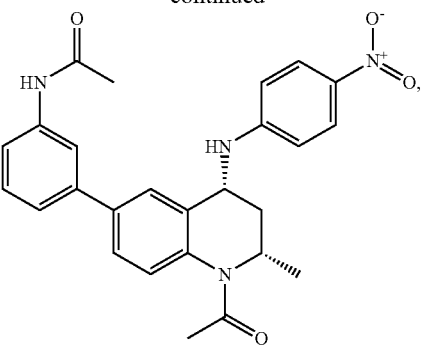 |
| 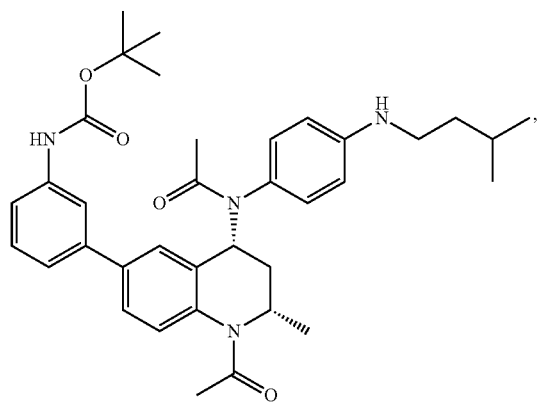 | 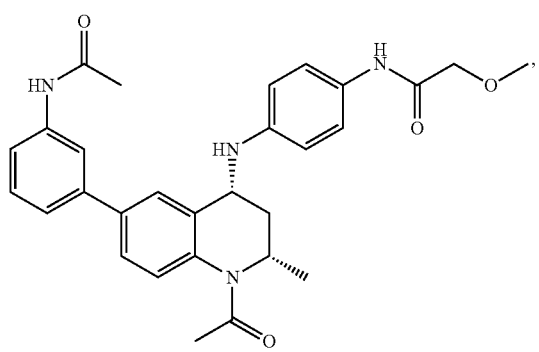 |
| 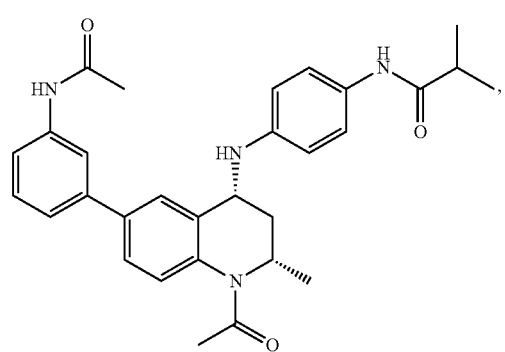 | 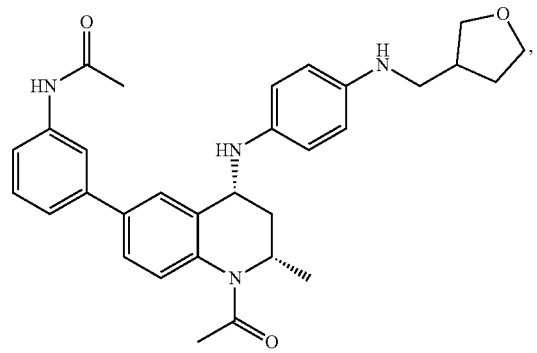 |
| 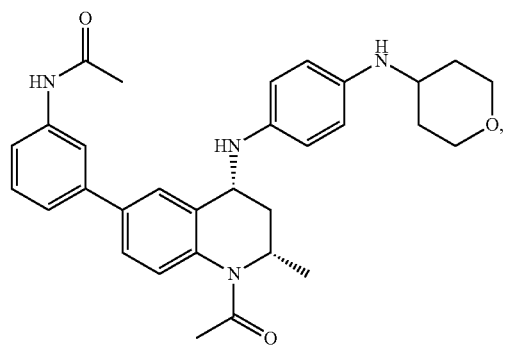 | 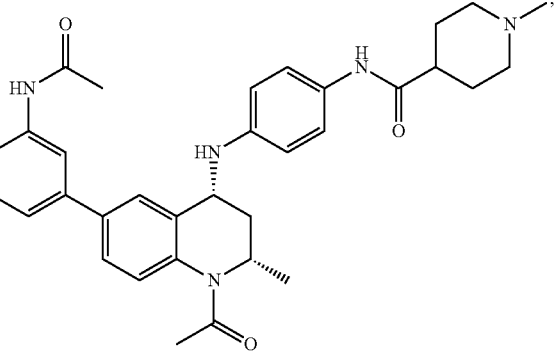 |

361
-continued
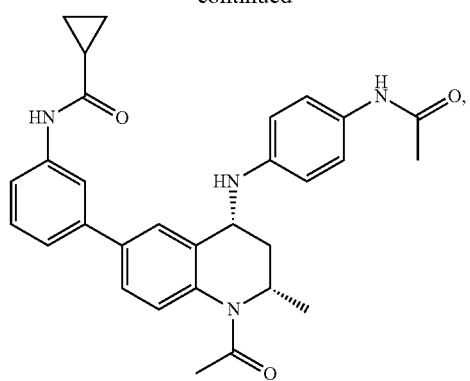
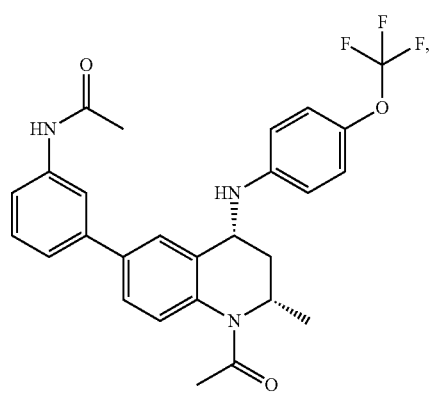
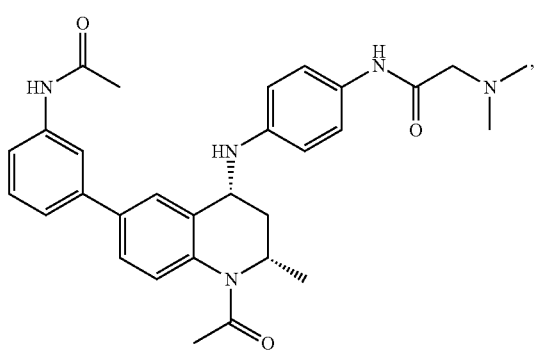
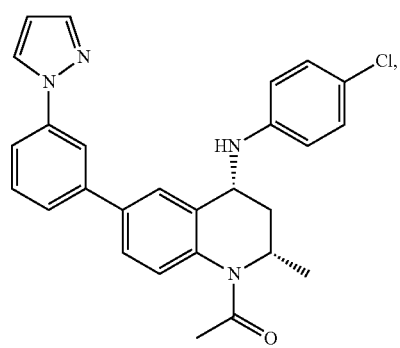
362
-continued
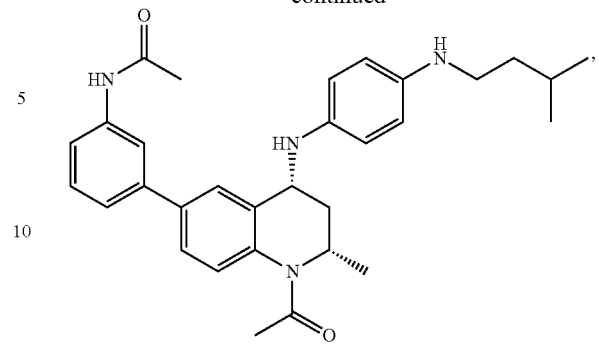
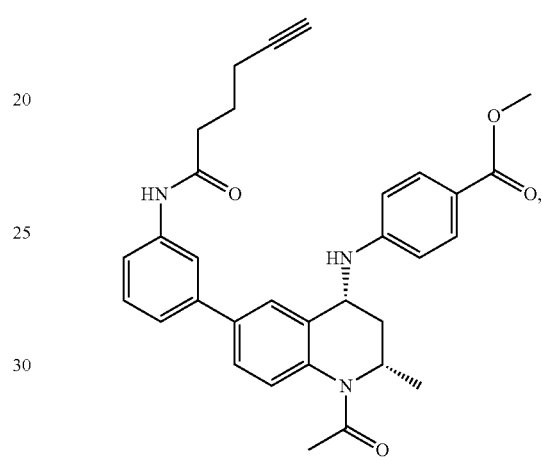
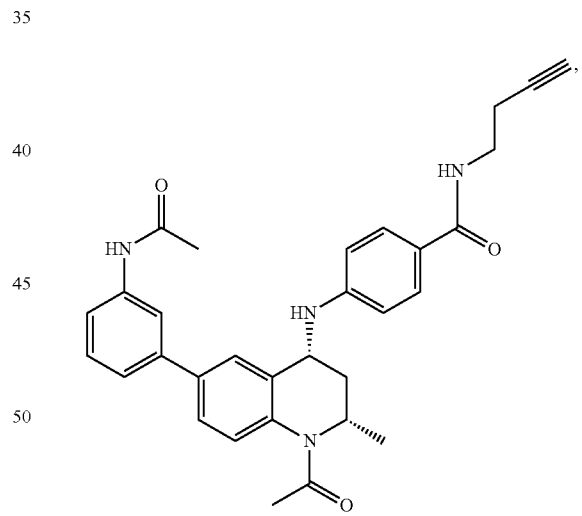
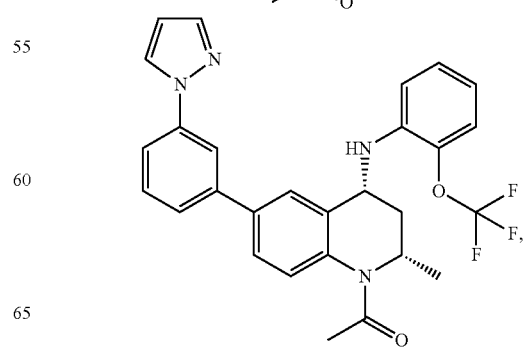

363
-continued

364
-continued

365
-continued
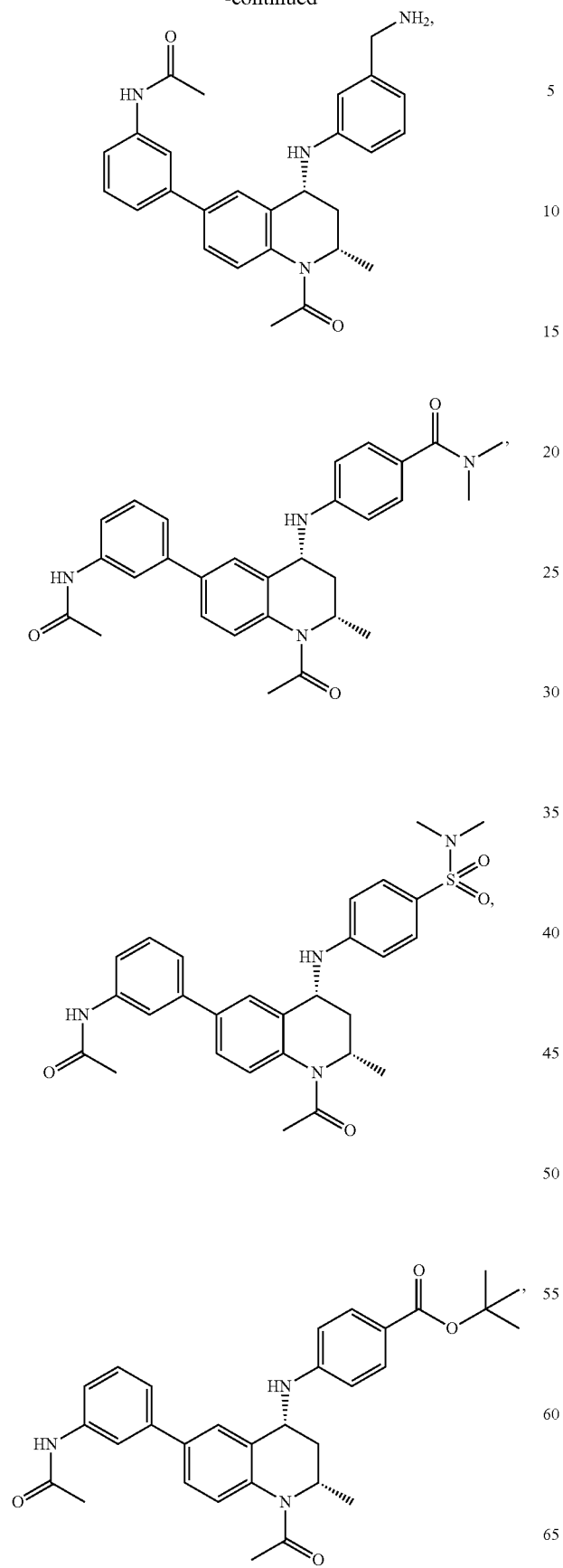
366
-continued
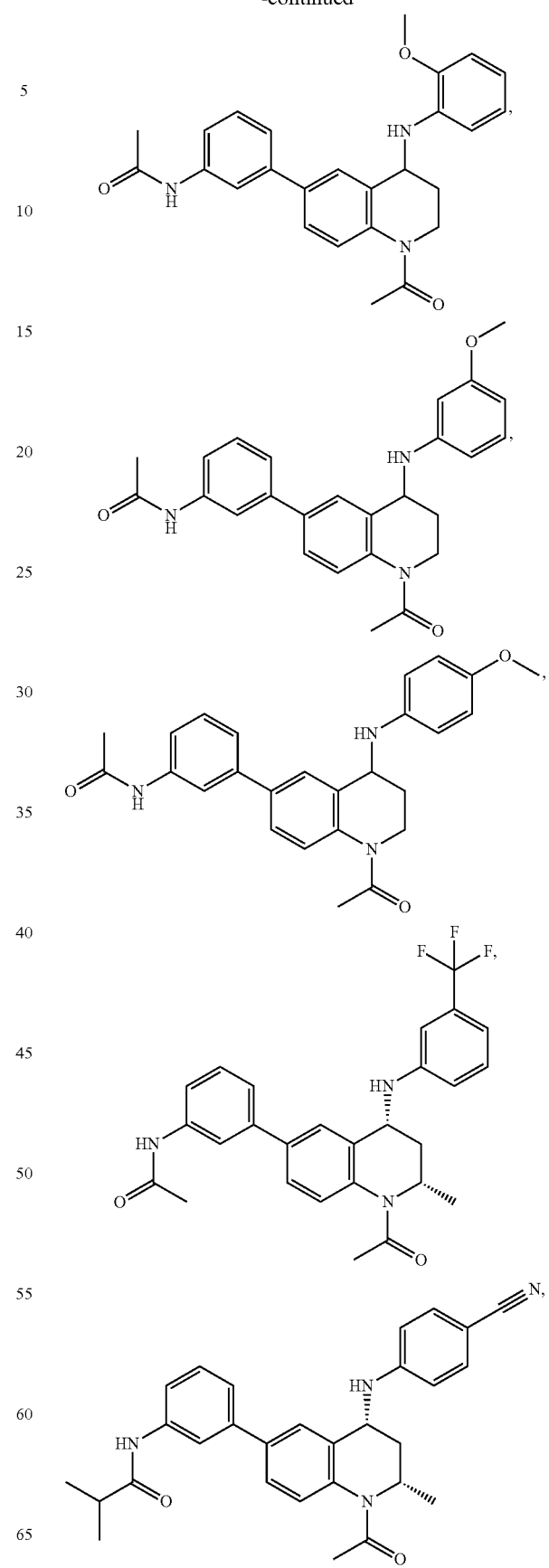

367
-continued
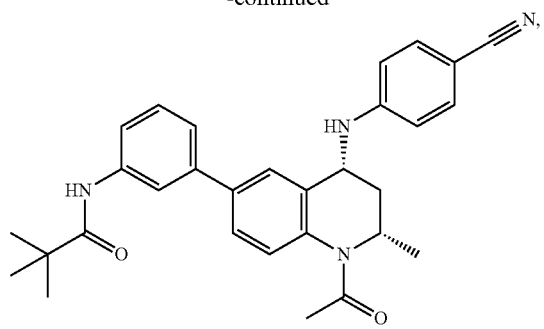
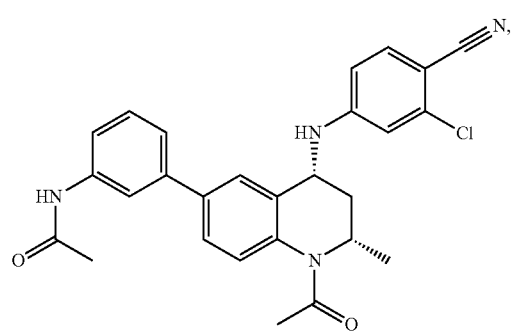
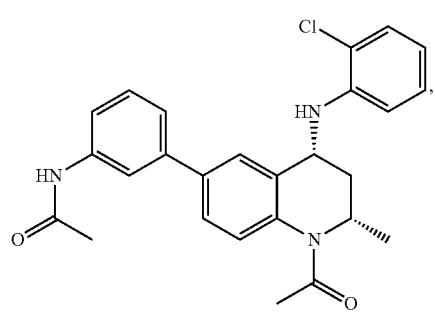
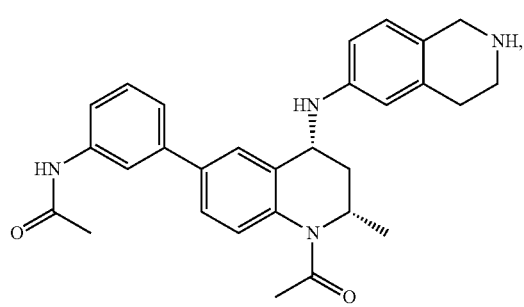
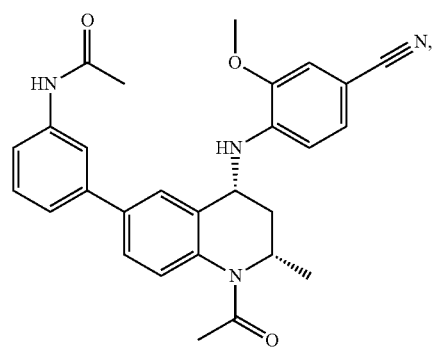
368
-continued
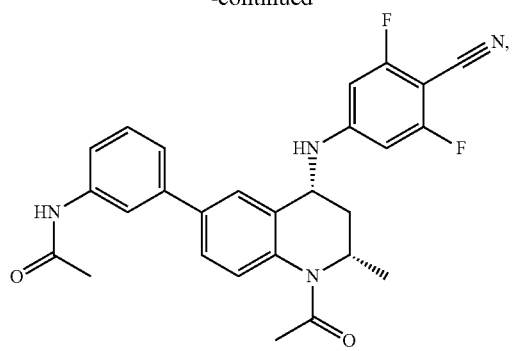
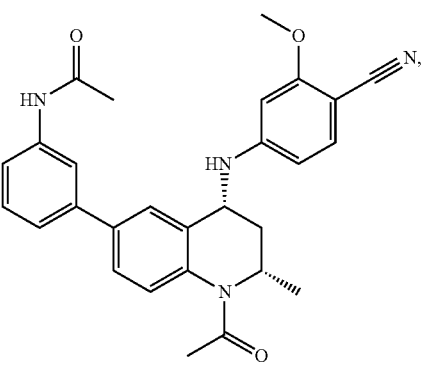
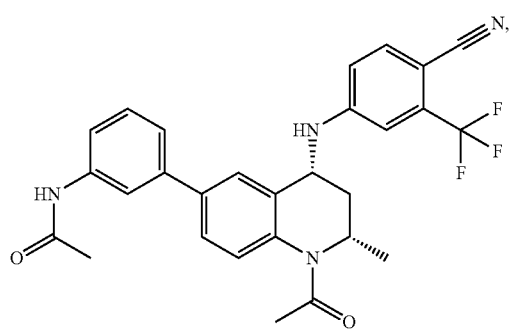
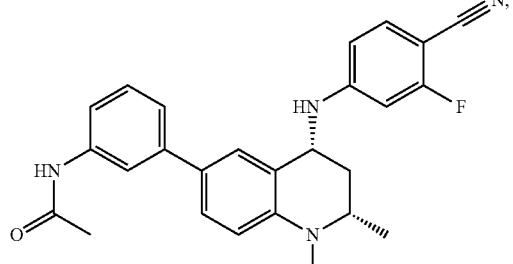
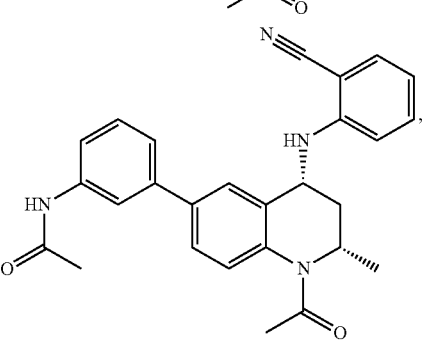

369
-continued
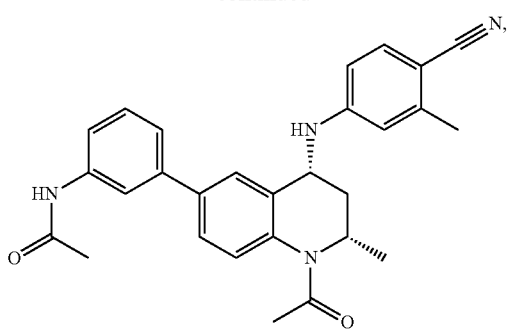
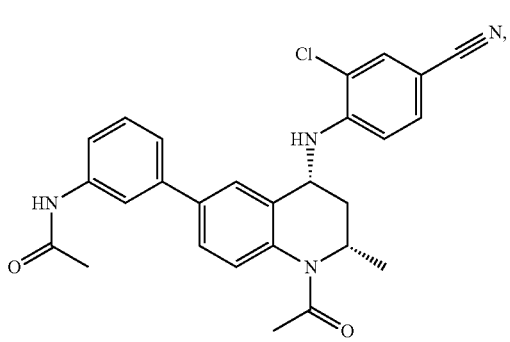
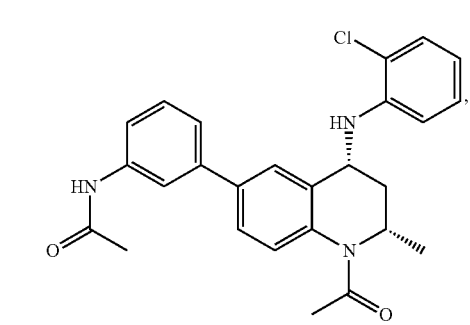
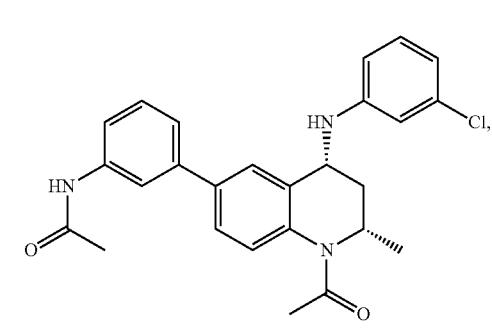
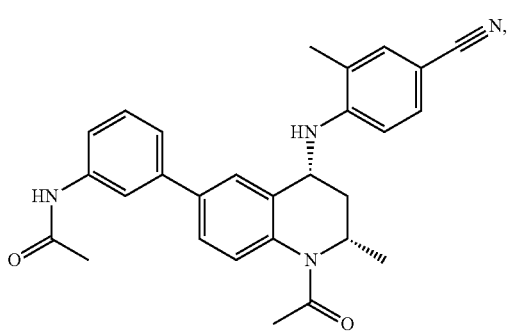
370
-continued
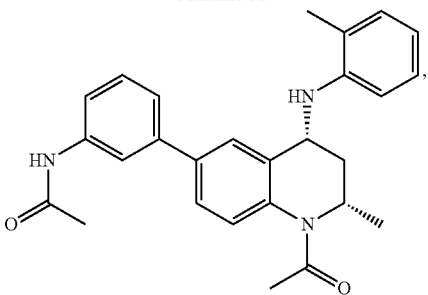
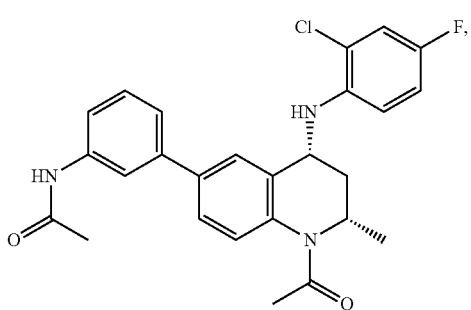
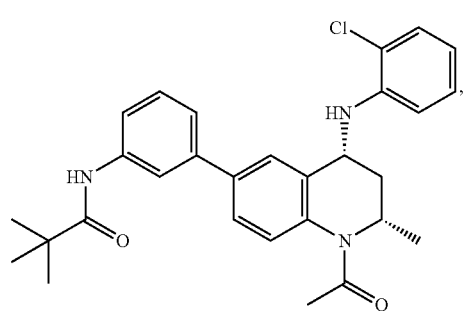
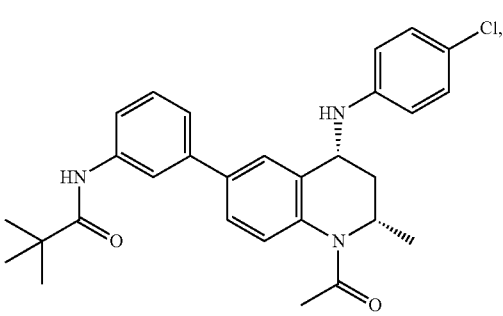
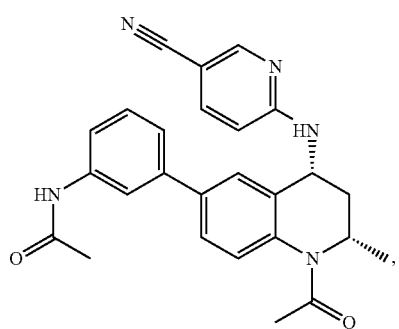

-continued
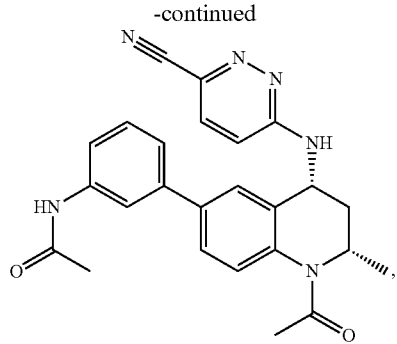
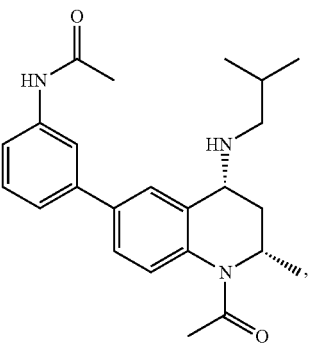
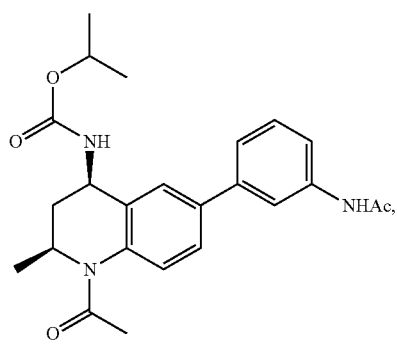
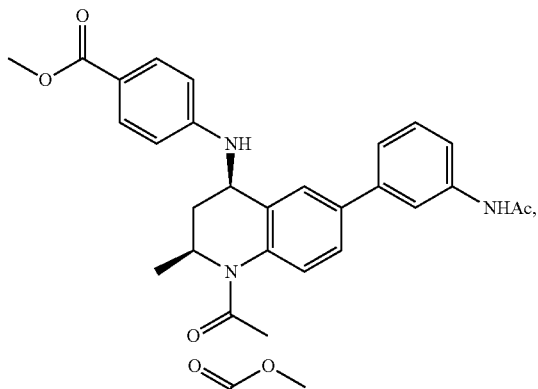
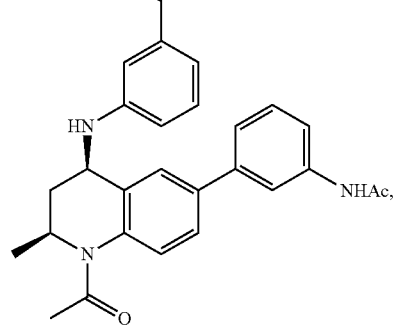
-continued
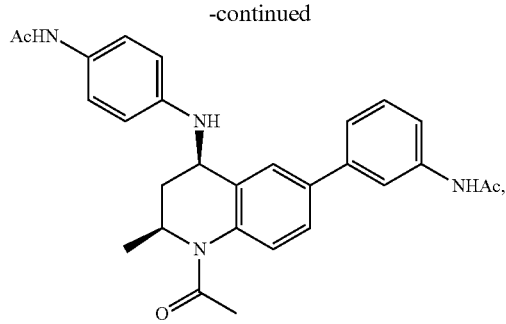
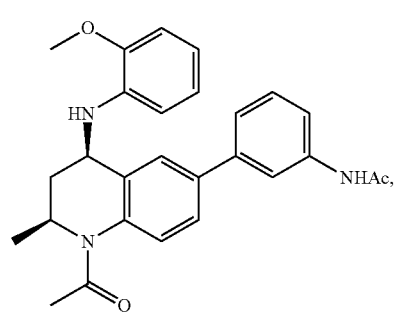
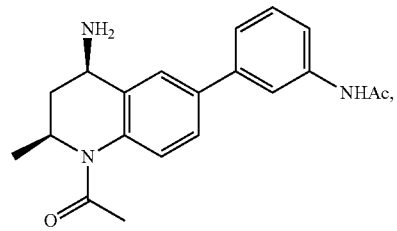
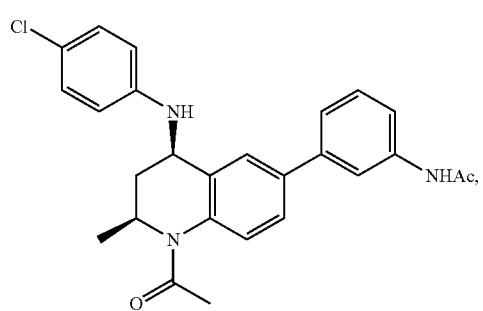
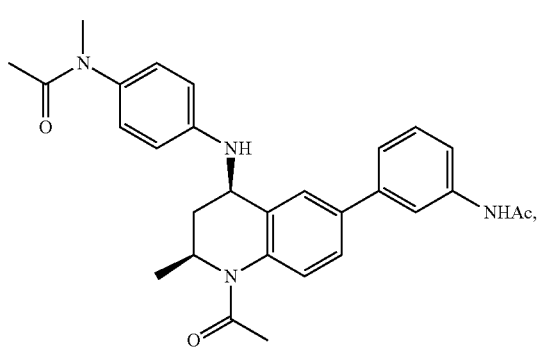

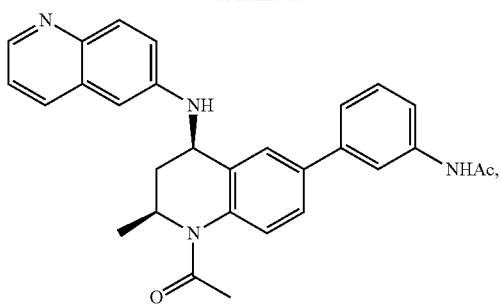
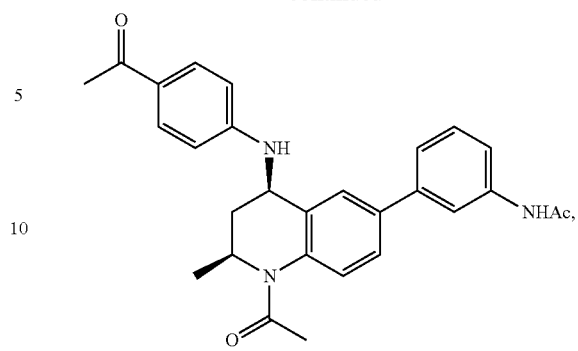
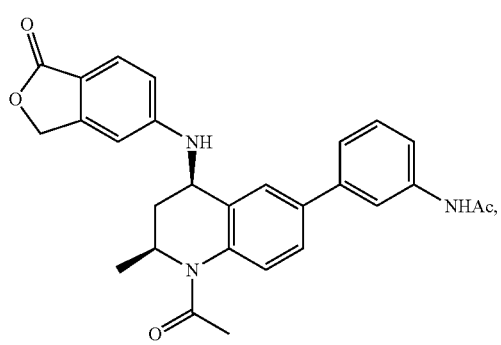
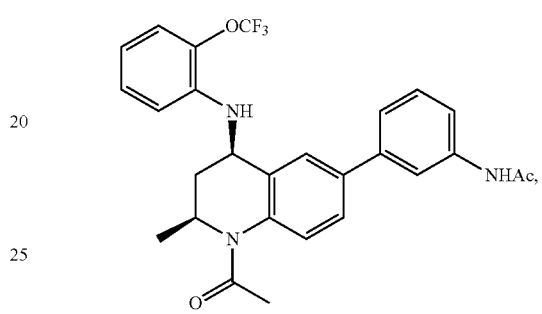
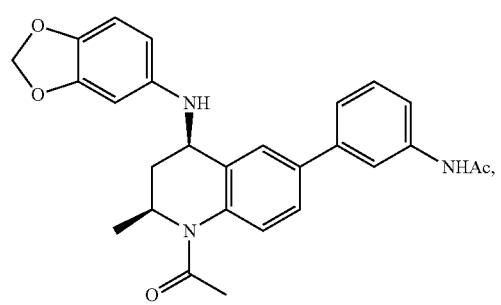
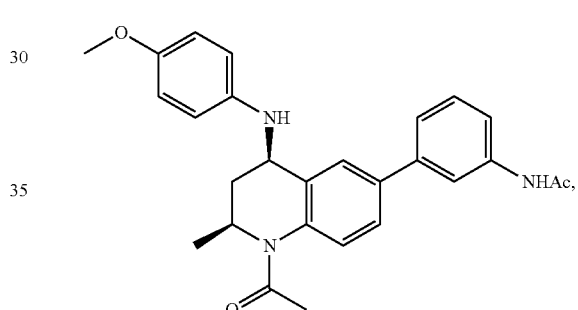
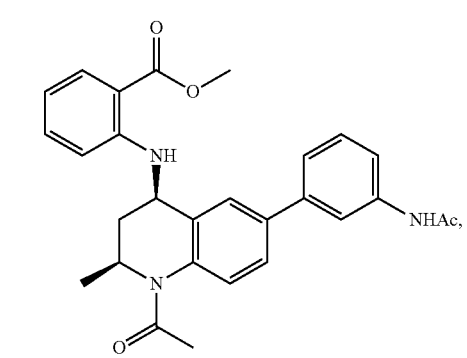
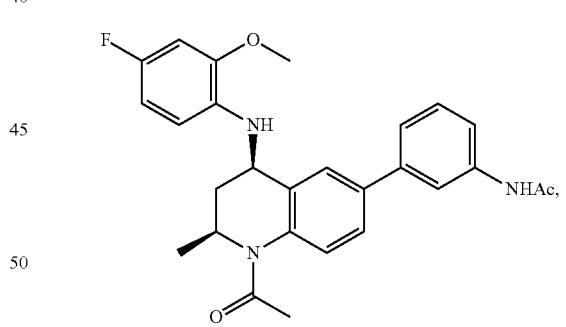
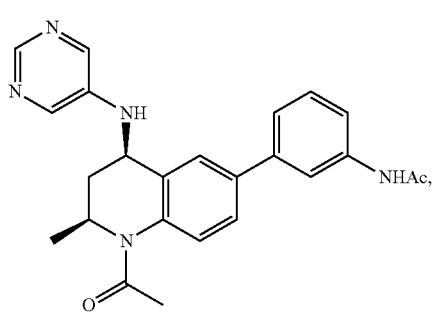
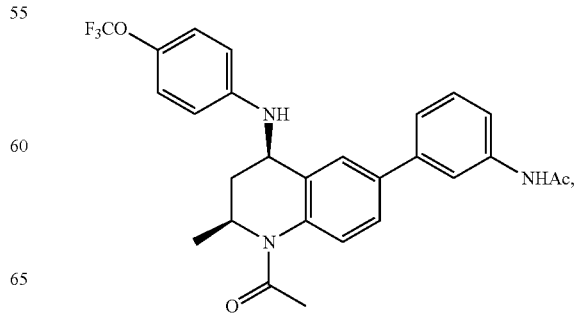

375
-continued
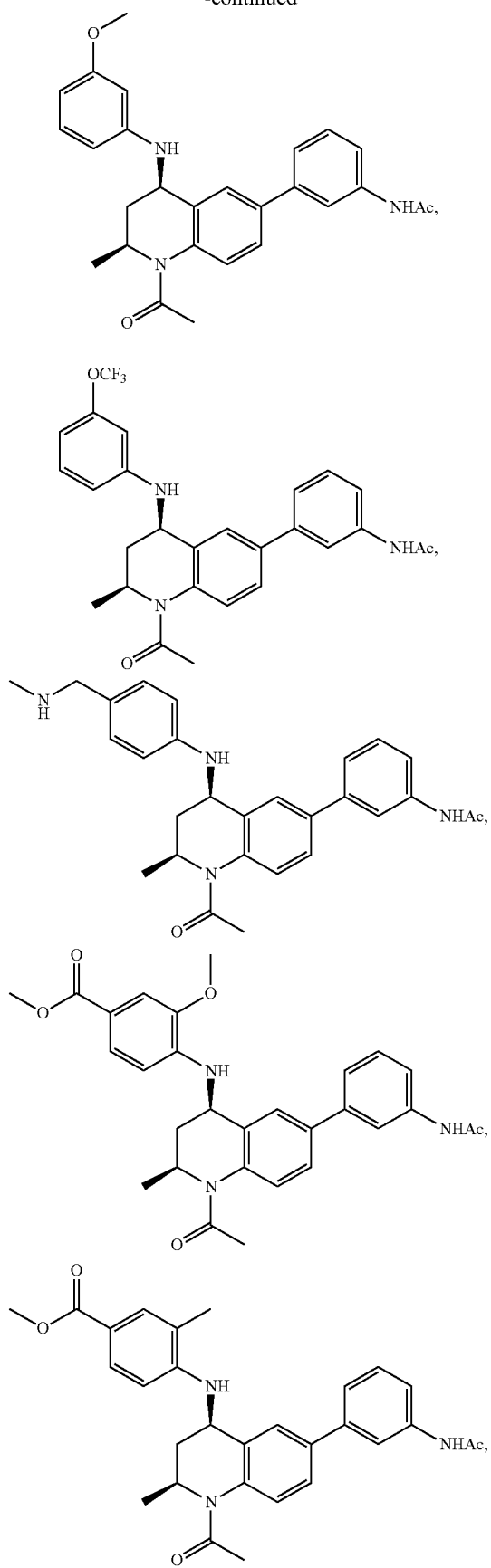
376
-continued
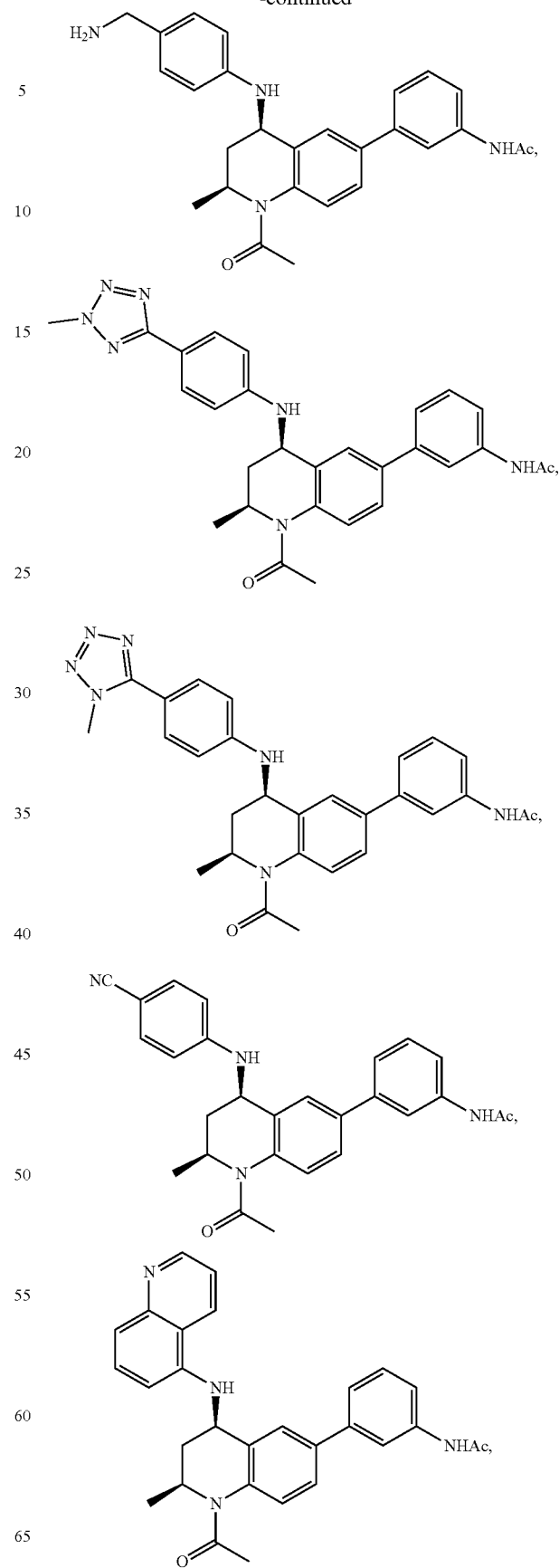

377
-continued
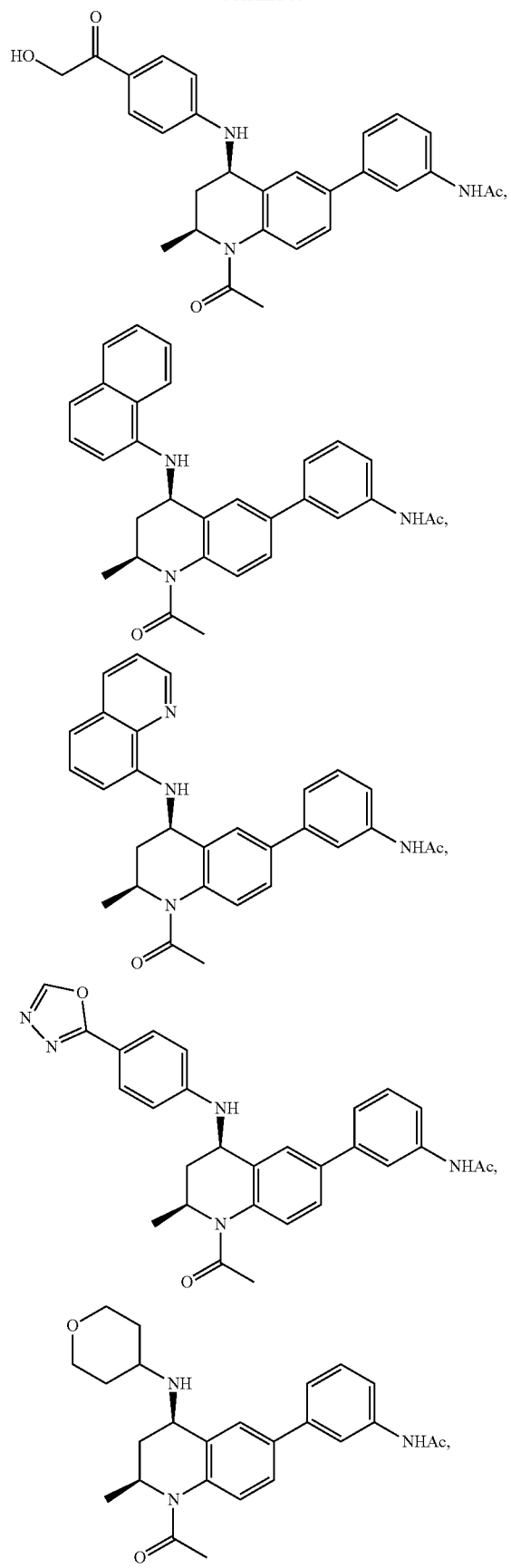
378
-continued
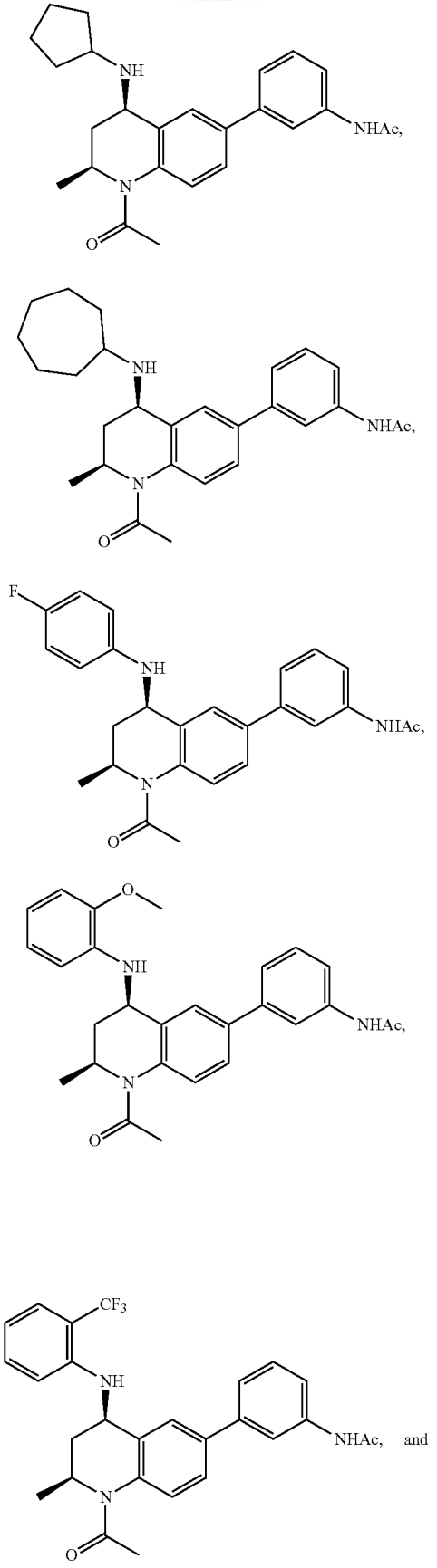

-continued
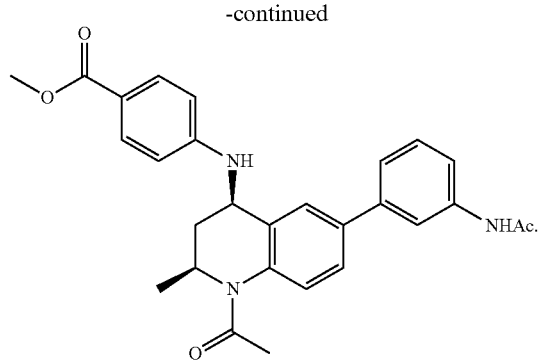
* * * * *